US012479857B2

(12) United States Patent
Matsuyama et al.

(10) Patent No.: US 12,479,857 B2
(45) Date of Patent: Nov. 25, 2025

(54) BAX INHIBITORS AND USES THEREOF

(71) Applicant: CASE WESTERN RESERVE UNIVERSITY, Cleveland, OH (US)

(72) Inventors: Shigemi Matsuyama, Cleveland, OH (US); William Greenlee, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 878 days.

(21) Appl. No.: 17/615,377

(22) PCT Filed: Jun. 1, 2020

(86) PCT No.: PCT/US2020/035564
§ 371 (c)(1),
(2) Date: Nov. 30, 2021

(87) PCT Pub. No.: WO2021/002986
PCT Pub. Date: Jan. 7, 2021

(65) Prior Publication Data

US 2022/0389028 A1 Dec. 8, 2022

Related U.S. Application Data

(60) Provisional application No. 62/855,185, filed on May 31, 2019.

(51) Int. Cl.

| | |
|---|---|
| ***C07D 495/04*** | (2006.01) |
| ***C07C 13/28*** | (2006.01) |
| ***C07D 403/12*** | (2006.01) |
| ***C07D 405/12*** | (2006.01) |
| ***C07D 413/12*** | (2006.01) |
| ***C07D 491/048*** | (2006.01) |
| ***C07D 519/00*** | (2006.01) |

(52) U.S. Cl.
CPC ............ *C07D 495/04* (2013.01); *C07C 13/28* (2013.01); *C07D 403/12* (2013.01); *C07D 405/12* (2013.01); *C07D 413/12* (2013.01); *C07D 491/048* (2013.01); *C07D 519/00* (2013.01)

(58) Field of Classification Search
None
See application file for complete search history.

(56) References Cited

U.S. PATENT DOCUMENTS 6,046,206 A * 4/2000 Pamukcu ............ A61K 31/505 514/266.3
6,770,656 B2 8/2004 Halazy et al.
6,969,720 B2 11/2005 Trova
2015/0190366 A1 7/2015 Housley et al.

FOREIGN PATENT DOCUMENTS

JP 2006-500385 A 1/2006
JP 2016-504365 A 2/2016
JP 2022-534902 A 8/2022
WO 2004/020441 A1 3/2004
WO 2012/079079 A1 6/2012
WO 2016/011394 A1 1/2016
WO 2018/019284 A1 2/2018

OTHER PUBLICATIONS

Japanese Application No. 2021-570180, Office Action dated Jun. 11, 2024.
Japanese Application No. 2021-570180, Office Action dated Sep. 24, 2024.
Read et al., Bioorganic & Medicinal Chemistry, vol. 18, No. 11, Jun. 1, 2010, pp. 3885-3897.
Klittich et al., Pesticide Biochemistry and Physiology, vol. 107, No. 3, Nov. 1, 2013, pp. 351-359.
(Continued)

*Primary Examiner* — Clinton A Brooks
*Assistant Examiner* — Nicola Maria Bauer
(74) *Attorney, Agent, or Firm* — Tarolli, Sundheim, Covell & Tummino LLP

(57) ABSTRACT

A compound having formula (I) or (II) for use inhibiting Bax mediated cell death and/or apoptosis.

(I)

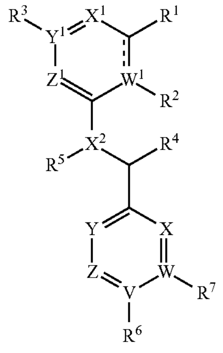

(II)

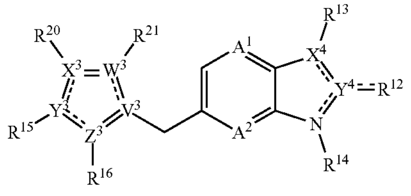

8 Claims, 6 Drawing Sheets

(56) References Cited

OTHER PUBLICATIONS

European Application No. 20835329.2, Extended Search Report dated Jun. 5, 2023.
PUBCHEM-CID: 70352 Create Date: Mar. 26, 2005 (Mar. 26, 2005) pp. 1-23 p. 2, structure.
Australian Application No. 2020299526, Examination Report dated May 29, 2025.
Canadian Application No. 3,142,424, Office Action dated May 29, 2025.
Registry (STN) [online], 2008.3.31 [search date May 20, 2024], CAS registration No. 1011107-28-0.
Japanese Application No. 2025-010128, Office Action dated Jul. 17, 2025.
Registry (STN) [online], 1984.11.16 [search date Jul. 9, 2025], CAS registration No. 31324-44-4.

* cited by examiner

BBI-5 (re-synthesized) Protected MEFs from Bax-induced cell death

BAX INHIBITORS AND USES THEREOF

RELATED APPLICATION

This application claims priority from U.S. Provisional Application No. 62/855,185 filed May 31, 2019, the subject matter of which is incorporated herein by reference in its entirety.

GOVERNMENT FUNDING

This invention was made with government support under Grant No. RO1AG031903 awarded by The National Institutes of Health and National Institute on Aging, and W81XWH-12-1-0331, awarded by the Department of Defense. The United States government has certain rights in the invention.

BACKGROUND

Bax-induced cell death is a major cause of many types of degenerative diseases. Bax is a 21-kDa member of the conserved Bcl-2 family of proteins involved in regulating programmed cell death. Bax plays a key role in the intrinsic pathway of apoptosis. Bcl-2 family proteins are characterized by the presence of four Bcl-2 homology (BH) domains. Antiapoptotic members (e.g., Bcl-2, Bcl-XL and Mcl-1) have all four BH domains (BH1-4). The proapoptotic members are further divided into multi-domain proteins (e.g., Bax, Bak and Bok) containing three BH domains (BH 1-3) or BH3-only proteins (e.g., Bim, Bid and PUMA, etc.), containing just the BH-3 domain. The molecular mechanisms, by which these proteins function and interact is not fully understood, but their role in apoptosis is indisputable.

SUMMARY

Embodiments described herein relate to compounds for use in inhibiting Bax mediated cell death and/or apoptosis and to their use in treating conditions, disorders, and/or diseases associate with Bax mediated cell death and/or apoptosis. The Bax inhibiting compounds described herein suppressed Bax-induced cell death at 1 nM-1000 nM (e.g., Bax-induced death of mouse embryonic fibroblasts (MEFs)) compared to previously reported Bax inhibitors that required at least 200 nM to inhibit Bax-induced death of MEFs, and have Bax binding affinity (Kd) ranging from 1 nM-1000 nM.

In some embodiments, the Bax inhibiting compound can include the following formula (I):

(I)

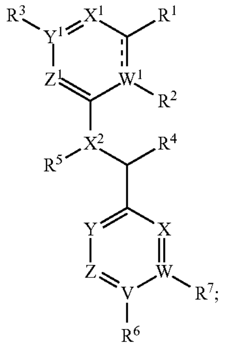

or a pharmaceutically acceptable salt, tautomer, or solvate thereof, wherein:

$R^1$ and $R^2$ are each independently —H, alkyl, —F, —CN, —O-alkyl, cycloalkyl, oxetanyl, or tetrahydrofuranyl, or $R^1$ together with $R^2$ forms a phenyl ring optionally substituted with one or two $R^8$ groups, or $R^1$ together with $R^2$ forms a five or six-membered heteroaromatic ring containing one or two heteroatoms chosen from N, O and S, optionally substituted with one or two $R^8$ groups;

$R^8$ is halo, alkyl, cycloalkyl, oxetanyl, tetrahydrofuranyl, —CN, —O-alkyl, —O-cycloalkyl, —$SO_2$-alkyl, or —$CH_2SO_2$-alkyl;

$R^3$ is absent, —H, -D, —F, —Cl, —$CF_3$, -alkyl, cyclopropyl-O-alkyl, or —CN;

$R^4$ is —H, alkyl, cyclopropyl, or —$CF_3$;

$R^5$ is absent, —H, or alkyl;

alternatively, $R^5$ and the nitrogen atom to which it is attached may be replaced by an oxygen atom;

V, W, X, Y and Z are each independently —CH, or N;

$X^1$ and $Z^1$ are each independently —CH or N;

$W^1$ and $Y^1$ are each independently C or N, and when $Y^1$ is N, $R^3$ is absent;

$X^2$ is O or N, when $X^2$ is O, $R^5$ is absent;

$\overset{---}{---}$ represents a single or double bond;

$R^6$ is —H, halo, alkyl, cycloalkyl, —CN, —O-alkyl, —O-cycloalkyl, —O— heterocyclyl, —$SO_2$-alkyl, —$CH_2SO_2$-alkyl, —$CONH_2$, —CONH-alkyl, or —CON(alkyl)$_2$;

$R^7$ is —H, halo, alkyl, cycloalkyl, —CN, —O-alkyl, —O-cycloalkyl, —O— heterocyclyl, —$SO_2$-alkyl, —$CH_2SO_2$-alkyl, —$CONH_2$, —CONH-alkyl, or —CON(alkyl)$_2$;

alternatively, $R^6$ or $R^7$ can be an aryl optionally substituted with one or two $R^9$ groups;

alternatively, $R^6$ or $R^7$ can be a 4-6 membered ring heterocycle containing one or two heteroatoms chosen from the group consisting of N, O and S, and optionally substituted with one or two $R^9$ groups, excluding unstable heterocycles;

alternatively, $R^6$ or $R^7$ can be a 5-6 membered ring heteroaryl group containing one to four heteroatoms chosen from the group consisting of N, O and S, and optionally substituted with one or two $R^9$ groups, excluding unstable heterocycles;

$R^9$ is H, halo, alkyl, cycloalkyl, alkyl-CO—, oxetanyl, 3-tetrahydrofuranyl, —CN, —O-alkyl, —O-cycloalkyl, —$CONH_2$, —CONH-alkyl, or —CON(alkyl)$_2$;

$R^6$ together with $R^7$ and the phenyl ring or heteroaryl ring to which they are attached, may be a benzimidazole ring, benzotriazole ring, azaindole ring, azaindazole, or benzodioxolane, with N of the rings bearing an optional substituent $R^{10}$, and with Cs of the rings optionally substituted with $R_{11}$;

$R^{10}$ is —H, alkyl, or cycloalkyl; and $R^{11}$ is —H, alkyl, or cycloalkyl.

In other embodiments, the Bax inhibiting compound having formula (I) can include a compound having the following formula:

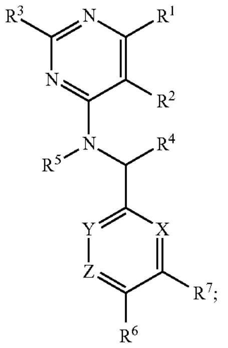

or a pharmaceutically acceptable salt, tautomer, or solvate thereof, wherein:

$R^1$ and $R^2$ are each independently —H, $C_1$-$C_6$-alkyl, —F, —CN, —O—$C_1$-$C_6$-alkyl, $C_3$-$C_7$-cycloalkyl, 3-oxetanyl, or 3-tetrahydrofuranyl, or $R^1$ together with $R^2$ forms a phenyl ring optionally substituted with one or two $R^8$ groups, or $R^1$ together with $R^2$ forms a five or six-membered heteroaromatic ring containing one or two heteroatoms chosen from N, O and S, optionally substituted with one or two $R^8$ groups;

$R^8$ is halo, $C_1$-$C_6$-alkyl, $C_3$-$C_7$-cycloalkyl, 3-oxetanyl, 3-tetrahydrofuranyl, —CN, —O—$C_1$-$C_6$-alkyl, —O—$C_3$-$C_7$-cycloalkyl, —$SO_2$—$C_1$-$C_6$-alkyl, or —$CH_2SO_2$—$C_1$-$C_6$-alkyl;

$R^3$ is —H, -D, —F, —Cl, —$CF_3$, —$C_1$-$C_6$-alkyl, cyclopropyl-O—$C_1$-$C_6$-alkyl, or —CN;

$R^4$ is —H, —$C_1$-$C_6$-alkyl, -cyclopropyl, or —$CF_3$;

$R^5$ is —H, or —$C_1$-$C_6$-alkyl;

alternatively, $R^5$ and the nitrogen atom to which it is attached may be replaced by an oxygen atom;

X, Y and Z are each independently —CH, or N;

$\equiv$ represents a single or double bond;

$R^6$ is —H, halo, $C_1$-$C_6$-alkyl, $C_3$-$C_7$-cycloalkyl, —CN, —O—$C_1$-$C_6$-alkyl, —O—$C_3$-$C_7$-cycloalkyl, —O-heterocyclyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON($C_1$-$C_6$-alkyl)$_2$;

$R^7$ is —H, halo, $C_1$-$C_6$-alkyl, $C_3$-$C_7$-cycloalkyl, —CN, —O—$C_1$-$C_6$-alkyl, —O—$C_3$-$C_7$-cycloalkyl, —O-heterocyclyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON($C_1$-$C_6$-alkyl)$_2$;

alternatively, $R^6$ or $R^7$ can be an aryl optionally substituted with one or two $R^9$ groups;

alternatively, $R^6$ or $R^7$ can be a 4-6 membered ring heterocycle containing one or two heteroatoms chosen from the group consisting of N, O and S, and optionally substituted with one or two $R^9$ groups, excluding unstable heterocycles;

alternatively, $R^6$ or $R^7$ can be a 5-6 membered ring heteroaryl group containing one to four heteroatoms chosen from the group consisting of N, O and S, and optionally substituted with one or two $R^9$ groups, excluding unstable heterocycles;

$R^9$ is halo, $C_1$-$C_6$-alkyl, $C_3$-$C_7$-cycloalkyl, $C_1$-$C_5$-alkyl-CO—, 3-oxetanyl, 3-tetrahydrofuranyl, —CN, —O—$C_1$-$C_6$-alkyl, —O—$C_3$-$C_7$-cycloalkyl, —$CONH_2$, —CONH-alkyl, or —CON(alkyl)$_2$;

$R^6$ together with $R^7$ and the phenyl ring or heteroaryl ring to which they are attached, may be a benzimidazole ring, benzotriazole ring, azaindole ring, azaindazole, or benzodioxolane, with N of the rings bearing an optional substituent $R^{10}$, and with Cs of the rings optionally substituted with $R^{11}$;

$R^{10}$ is —H, $C_1$-$C_6$-alkyl, or $C_3$-$C_7$-cycloalkyl; and $R^{11}$ is —H, $C_1$-$C_6$-alkyl, or $C_3$-$C_7$-cycloalkyl.

In some embodiments, $R^1$ and $R^2$ are each independently —H, $C_1$-$C_6$-alkyl, —F, —CN, —O—$C_1$-$C_6$-alkyl, $C_3$-$C_7$-cycloalkyl, 3-oxetanyl, or 3-tetrahydrofuranyl, or $R^1$ together with $R^2$ forms a phenyl ring optionally substituted with one or two $R^8$ groups, or $R^1$ together with $R^2$ forms a saturated five or six-membered heteroaromatic ring containing one or two heteroatoms chosen from N, O and S, optionally substituted with one or two $R^8$ groups.

In other embodiments, $R^8$ is halo, $C_1$-$C_6$-alkyl, $C_3$-$C_7$-cycloalkyl, 3-oxetanyl, 3-tetrahydrofuranyl, —CN, —O—$C_1$-$C_6$-alkyl, —O—$C_3$-$C_7$-cycloalkyl, —$SO_2$—$C_1$-$C_6$-alkyl, or —$CH_2SO_2$—$C_1$-$C_6$-alkyl.

In other embodiments, $R^3$ is absent, —H, -D, —F, —Cl, —$CF_3$, —$C_1$-$C_6$-alkyl, cyclopropyl-O—$C_1$-$C_6$-alkyl, or —CN.

In some embodiments, $R^4$ is —H, —$C_1$-$C_6$-alkyl, -cyclopropyl, or —$CF_3$.

In other embodiments, $R^5$ is absent, —H, or —$C_1$-$C_6$-alkyl.

In other embodiments, $R^6$ is —H, halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON($C_1$-$C_6$-alkyl)$_2$.

In other embodiments, $R^7$ is —H, halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON($C_1$-$C_6$-alkyl).

In some embodiments, $R^9$ is H, halo, $C_1$-$C_6$-alkyl, $C_3$-$C_7$-cycloalkyl, $C_1$-$C_5$-alkyl-CO—, 3-oxetanyl, 3-tetrahydrofuranyl, —CN, —O—$C_1$-$C_6$-alkyl, or —O—$C_3$-$C_7$-cycloalkyl.

In other embodiments, $R^{10}$ is —H, $C_1$-$C_6$-alkyl, or $C_3$-$C_7$-cycloalkyl.

In still other embodiments, $R^{11}$ is —H, $C_1$-$C_6$-alkyl, or $C_3$-$C_7$-cycloalkyl.

In other embodiments, $R^1$ together with $R^2$ can form a phenyl ring optionally substituted with one or two $R^8$ groups, or $R^1$ together with $R^2$ can form a saturated five or six-membered heteroaromatic ring containing one or two heteroatoms chosen from N, O and S, optionally substituted with one or two $R^8$ groups.

In some embodiments, $R^4$ is —$C_1$-$C_6$-alkyl or —$CF_3$ and $R^5$ is —H.

In other embodiments, X and Y are independently H; and Z is N.

In some embodiments, $R^6$ or $R^7$ is a 4-6 membered ring saturated heterocycle containing one or two heteroatoms chosen from the group consisting of N, O and S, and optionally substituted with one or two $R^9$ groups, excluding unstable heterocycles, or $R^6$ or $R^7$ is a 5-6 membered ring heteroaryl group containing one to three heteroatoms chosen from the group consisting of N, O and S, and optionally substituted with one or two $R^9$ groups, excluding unstable heterocycles.

In other embodiments, $R^6$ is selected from the group consisting of:

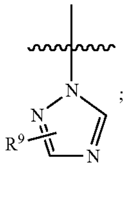 ; 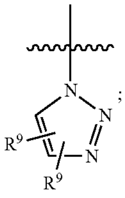 ; 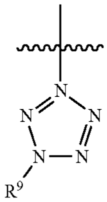 ;

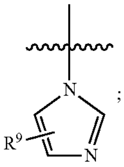 ; 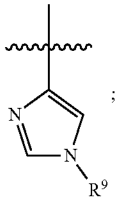 ; 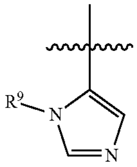 ;

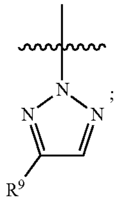 ; 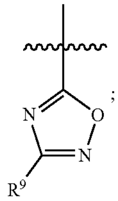 ; 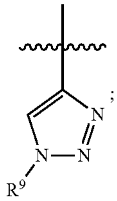 ;

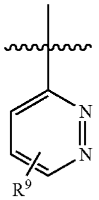 ; 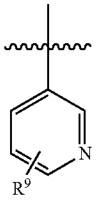 ; and 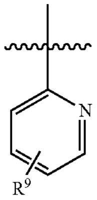 .

In other embodiments, a Bax inhibiting compound can include the following formula (II):

(II)

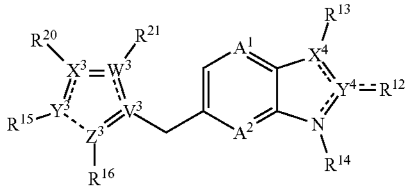

or a pharmaceutically acceptable salt, tautomer, or solvate thereof, wherein:

$R^{12}$ is =O or $R^{17}$; and when $R^{12}$ is =O, $R^{13}$ and $R^{14}$ are independently absent, —H, alkyl, cycloalkyl, oxetanyl, or tetrahydrofuranyl, or when $R^{12}$ is $R^{17}$, $R^{13}$ or $R^{14}$ is absent and the other is —H, alkyl, cycloalkyl, oxetanyl, or tetrahydrofuranyl;

$A^1$ and $A^2$ are independently CH or N;

the heterocycle comprising $V^3$, $W^3$, $X^3$, $Y^3$ and $Z^3$ and its substituents $R^{15}$, $R^{16}$, $R^{20}$, and $R^{21}$ is a heteroaromatic ring with two double bonds, including, for example, pyrrole, imidazole, pyrazole or triazole; $V^3$, $W^3$, $X^3$, $Y^3$ and $Z^3$ can independently be CH or N, with 1-3 of these atoms being N;

$X^4$ is N or O;

$Y^4$ is N or C;

═══ represents a single or double bond;

$R^{15}$, $R^{16}$, $R^{20}$, and $R^{21}$ are independently absent, H, alkyl, cycloalkyl, bicyclyl, phenyl, or heteroaryl each optionally substituted with one or more $R^{18}$, or a heterocyclic ring with one or two heteroatoms chosen from the group consisting of N, O, S;

$R^{17}$ is —H, =NH, alkyl, cycloalkyl, oxetanyl, or tetrahydrofuranyl;

alternatively, $R^{15}$ together with $R^{16}$ and the ring to which they are attached can form a bicyclic ring in which $V^3$ and $X^3$ are N and $W^3$ is CH and $Y^3$ and $Z^3$ are C atoms at the ring fusion; the bicyclic ring being optionally substituted with one or two $R^{19}$ substituents;

$R^{18}$ is halo, alkyl, cycloalkyl, —CN, —O-alkyl, —O-cycloalkyl, —O-alkyl-alkynyl, —$SO_2$-alkyl, —$CH_2SO_2$-alkyl, —$CONH_2$, —CONH-alkyl, or —CON(alkyl)$_2$; and $R^{19}$ is halo, alkyl, cycloalkyl, —CN, —O-alkyl, —O-cycloalkyl, —$SO_2$-alkyl, or —$CH_2SO_2$-alkyl.

In other embodiments, the Bax inhibiting compound have formula (II) can include the following formula:

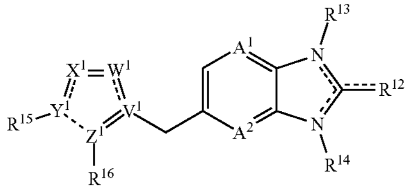

or a pharmaceutically acceptable salt, tautomer, or solvate thereof, wherein:

$R^{12}$ is =O or $R^{17}$; and when $R^{12}$ is =O, $R^{13}$ and $R^{14}$ are independently —H, $C_1$-$C_6$-alkyl, $C_3$-$C_7$-cycloalkyl, 3-oxetanyl, or 3-tetrahydrofuranyl, or when $R^{12}$ is $R^{17}$, $R^{13}$ or $R^{14}$ is absent and the other is —H, $C_1$-$C_6$-alkyl, $C_3$-$C_7$-cycloalkyl, 3-oxetanyl, or 3-tetrahydrofuranyl;

$A^1$ and $A^2$ are independently CH or N;

the heterocycle comprising $V^1$, $W^1$, $X^1$, $Y^1$ and $Z^1$ and its substituents $R^{15}$ and $R^{16}$ is a heteroaromatic ring with two double bonds, including, for example, pyrrole, imidazole, pyrazole or triazole; $V^1$, $W^1$, $X^1$, $Y^1$ and $Z^1$ can independently be CH or N, with 1-3 of these atoms being N;

═══ represents a single or double bond;

$R^{15}$ and $R^{16}$ are independently $C_1$-$C_6$-alkyl, $C_3$-$C_7$-cycloalkyl, phenyl, or $C_5$-$C_6$ heteroaryl each optionally substituted with $R^{18}$, or a $C_4$-$C_6$ heterocyclic ring with one or two heteroatoms chosen from the group consisting of N, O, S;

$R^{17}$ is —H, $C_1$-$C_6$-alkyl, $C_3$-$C_7$-cycloalkyl, 3-oxetanyl, or 3-tetrahydrofuranyl;

alternatively, $R^{15}$ together with $R^{16}$ and the ring to which they are attached can form a benzimidazole ring in which $V^1$ and $X^1$ are N and $W^1$ is CH and $Y^1$ and $Z^1$ are C atoms at the ring fusion; the benzimidazole ring being optionally substituted with one or two $R^{19}$ substituents;

$R^{18}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON($C_1$-$C_6$-alkyl)$_2$; and $R^{19}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, or —$CH_2SO_2$—$C_1$-$C_6$-alkyl.

In some embodiments, $R^{12}$ is =O or $R^{17}$; and when $R^{12}$ is =O, $R^{13}$ and $R^{14}$ are independently absent, —H, $C_1$-$C_6$-alkyl, $C_3$-$C_7$-cycloalkyl, 3-oxetanyl, or 3-tetrahydrofuranyl, or when $R^{12}$ is $R^{17}$, $R^{13}$ or $R^{14}$ is absent and the other is —H, $C_1$-$C_6$-alkyl, $C_3$-$C_7$-cycloalkyl, 3-oxetanyl, or 3-tetrahydrofuranyl;

In other embodiments, $R^{15}$, $R^{16}$, $R^{20}$, and $R^{21}$ are independently $C_1$-$C_6$-alkyl, $C_3$-$C_7$-cycloalkyl, phenyl or $C_5$-$C_6$ heteroaryl optionally substituted with $R^{18}$, or a $C_4$-$C_6$ heterocyclic ring with one or two heteroatoms chosen from the group consisting of N, O, S.

In still other embodiments, $R^{17}$ is —H, =NH, $C_1$-$C_6$-alkyl, $C_3$-$C_7$-cycloalkyl, 3-oxetanyl, or 3-tetrahydrofuranyl.

In some embodiments, $R^{18}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON($C_1$-$C_6$-alkyl)$_2$.

In other embodiments, $R^{19}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, or —$CH_2SO_2$—$C_1$-$C_6$-alkyl.

In some embodiments, $A^1$ and $A^2$ are independently CH.

In other embodiments, $R^{12}$ is =O

In other embodiments, a Bax inhibiting compound having formula (II) can include the following formula:

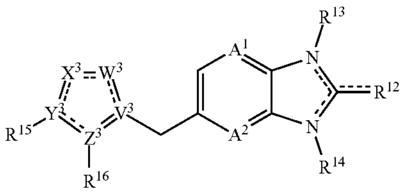

or a pharmaceutically acceptable salt, tautomer, or solvate thereof, wherein:

$R^{12}$ is =O or $R^{17}$; and when $R^{12}$ is =O, $R^{13}$ and $R^{14}$ are independently absent, —H, $C_1$-$C_6$-alkyl, $C_3$-$C_7$-cycloalkyl, 3-oxetanyl, or 3-tetrahydrofuranyl, or when $R^{12}$ is $R^{17}$, $R^{13}$ or $R^{14}$ is absent and the other is —H, $C_1$-$C_6$-alkyl, $C_3$-$C_7$-cycloalkyl, 3-oxetanyl, or 3-tetrahydrofuranyl;

$A^1$ and $A^2$ are independently CH or N;

the heterocycle comprising $V^3$, $W^3$, $X^3$, $Y^3$ and $Z^3$ and its substituents $R^{15}$ and $R^{16}$ is a heteroaromic ring with two double bonds, including, for example, pyrrole, imidazole, pyrazole or triazole; $V^3$, $W^3$, $X^3$, $Y^3$ and $Z^3$ can independently be CH or N, with 1-3 of these atoms being N;

$\overset{---}{---}$ represents a single or double bond;

$R^{15}$ and $R^{16}$ are independently $C_1$-$C_6$-alkyl, $C_3$-$C_7$-cycloalkyl, phenyl or $C_5$-$C_6$ heteroaryl optionally substituted with $R^{18}$, or a $C_4$-$C_6$ heterocyclic ring with one or two heteroatoms chosen from the group consisting of N, O, S;

$R^{17}$ is —H, —NH, $C_1$-$C_6$-alkyl, $C_3$-$C_7$-cycloalkyl, 3-oxetanyl, or 3-tetrahydrofuranyl;

alternatively, $R^{15}$ together with $R^{16}$ and the ring to which they are attached can form a benzimidazole ring in which $V^3$ and $X^3$ are N and $W^3$ is CH and $Y^3$ and $Z^3$ are C atoms at the ring fusion; the benzimidazole ring being optionally substituted with one or two $R^{19}$ substituents;

$R^{18}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON($C_1$-$C_6$-alkyl)$_2$; and $R^{19}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, or —$CH_2SO_2$—$C_1$-$C_6$-alkyl.

In some embodiments, $A^1$ and $A^2$ are independently CH.

In other embodiments, $R^{12}$ is =O

In some embodiments, the Bax inhibiting compound of formula (II) can have the following formula:

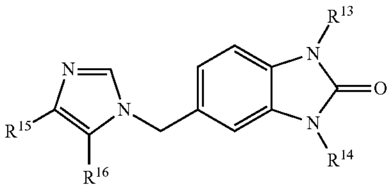

, wherein $R^{13}$ and $R^{14}$ are independently —H, $C_1$-$C_6$-alkyl, $C_3$-$C_7$-cycloalkyl, 3-oxetanyl, 3-tetrahydrofuranyl;

$R^{15}$ and $R^{16}$ are independently $C_1$-$C_6$-alkyl, $C_3$-$C_7$-cycloalkyl, phenyl or $C_5$-$C_6$ heteroaryl optionally substituted with $R^{18}$, or a $C_4$-$C_6$ heterocyclic ring with one or two heteroatoms chosen from the group consisting of N, O, S;

$R^{17}$ is —H, $C_1$-$C_6$-alkyl, $C_3$-$C_7$-cycloalkyl, 3-oxetanyl, or 3-tetrahydrofuranyl;

or $R^{15}$ together with $R^{16}$ and the ring to which they are attached can be a benzimidazole ring; the benzimidazole ring can be optionally substituted with one or two $R^{19}$ substituents;

$R^{18}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON($C_1$-$C_6$-alkyl)$_2$; and $R^{19}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, or —$CH_2SO_2$—$C_1$-$C_6$-alkyl.

In other embodiments, the Bax inhibiting compound having formula (II) can have the following formula:

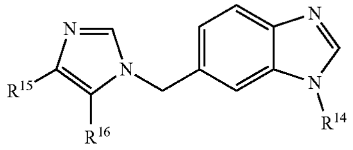

, wherein $R^{14}$ is —H, $C_1$-$C_6$-alkyl, $C_3$-$C_7$-cycloalkyl, 3-oxetanyl, 3-tetrahydrofuranyl $R^{15}$ and $R^{16}$ are independently $C_1$-$C_6$-alkyl, $C_3$-$C_7$-cycloalkyl, phenyl or $C_5$-$C_6$ heteroaryl optionally substituted with $R^{18}$, or a $C_4$-$C_6$ heterocyclic ring with one or two heteroatoms chosen from the group consisting of N, O, S;

$R^{17}$ is —H, $C_1$-$C_6$-alkyl, $C_3$-$C_7$-cycloalkyl, 3-oxetanyl, or 3-tetrahydrofuranyl;

or $R^{15}$ together with $R^{16}$ and the ring to which they are attached can be a benzimidazole ring; the benzimidazole ring being optionally substituted with one or two $R^{19}$ substituents;

$R^{18}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON($C_1$-$C_6$-alkyl)$_2$; and $R^{19}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, or —$CH_2SO_2$—$C_1$-$C_6$-alkyl.

In some embodiments, the Bax inhibiting compounds can be provided in a pharmaceutical composition that includes the Bax inhibiting compound and a pharmaceutically acceptable excipient or a carrier.

In other embodiments, the compound or Bax inhibiting compounds described herein can inhibit the Mouse Embryonic Fibroblasts (MEFs) from Bax-induced cell death Bax at an $IC_{50}$ of less than or equal to 1 μM, an $IC_{50}$ of less than or equal to 250 nM, an $IC_{50}$ of less than or equal to 50 nM, an $IC_{50}$ of less than or equal to 10 nM, an $IC_{50}$ of less than or equal to 5 nM, an $IC_{50}$ of about 2.5 nM to about 10 nM, or an $IC_{50}$ of less than or equal to about 2.5 nM.

In some embodiments, the Bax inhibiting compound can be administered to a subject to inhibit cell death in the eyes associated with the degenerative eye diseases. The degenerative eye disease can include, for example, at least one of Stargardt's disease, cone-rod dystrophy, retinitis-pigmentosis, macular degeneration, geographic atrophy, glaucoma, optic nerve injury, and Fuchs endothelial corneal dystrophy.

In other embodiments, the Bax inhibiting compound can be administered to a subject to inhibit cell death associated with or treat at least one of a disease, disorder, and/or condition of the nervous system. The disease, disorder, and/or condition of the nervous system can include at least one of a neurological disorder, neural injury, neural toxicity disorder, and neural degenerative disorders.

In some embodiments, the neurological disorder can include at least one of traumatic or toxic injuries to peripheral or cranial nerves, spinal cord or to the brain, cranial nerves, traumatic brain injury, stroke, cerebral aneurism, and spinal cord injury.

In other embodiments, the neurological disorder can include at least one of Alzheimer's disease, dementias related to Alzheimer's disease, Parkinson's, Lewy diffuse body diseases, senile dementia, Huntington's disease, Gilles de la Tourette's syndrome, multiple sclerosis, amyotrophic lateral sclerosis, hereditary motor and sensory neuropathy, diabetic neuropathy, progressive supranuclear palsy, epilepsy, or Jakob-Creutzfieldt disease.

In some embodiments, the neural injury can be caused by or associated with at least one of epilepsy, cerebrovascular diseases, autoimmune diseases, sleep disorders, autonomic disorders, urinary bladder disorders, abnormal metabolic states, disorders of the muscular system, infectious and parasitic diseases neoplasms, endocrine diseases, nutritional and metabolic diseases, immunological diseases, diseases of the blood and blood-forming organs, mental disorders, diseases of the nervous system, diseases of the sense organs, diseases of the circulatory system, diseases of the respiratory system, diseases of the digestive system, diseases of the genitourinary system, diseases of the skin and subcutaneous tissue, diseases of the musculoskeletal system and connective tissue, congenital anomalies, or conditions originating in the perinatal period.

In other embodiments, the Bax inhibiting compound can be administered to a subject to inhibit cell death associated with or treat at least one symptom associated with an ischemic tissue or a tissue damaged by ischemia. The ischemia can be associated with at least one of acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

In other embodiments, the Bax inhibiting compound can be administered ex vivo to at least one of cells, tissue, or organs to increase fitness of the cells, tissue, or organs as a donor graft or transplantation, or enhance cell, tissue, or organ engraftment or transplantation.

In some embodiments, the Bax inhibiting compound can be administered to a subject or to a tissue graft of a subject to mitigate graft rejection or enhance graft engraftment.

In other embodiments, the Bax inhibiting compound can be administered to a subject or to a tissue graft of a subject to enhance graft engraftment following treatment of the subject with radiation therapy, chemotherapy, or immunosuppressive therapy.

In other embodiments, the Bax inhibiting compound can be administered to a subject to confer resistance to toxic or lethal effects of exposure to radiation.

In still other embodiments, the Bax inhibiting compound being administered to a subject to confer resistance to the toxic effect of chemotherapy, or the toxic effect of immunosuppressive therapy.

In other embodiments, the Bax inhibiting compound can be administered to a subject to treat stroke, myocardial infarction, degenerative disease, and an infectious agent.

DETAILED DESCRIPTION

Figure 1:
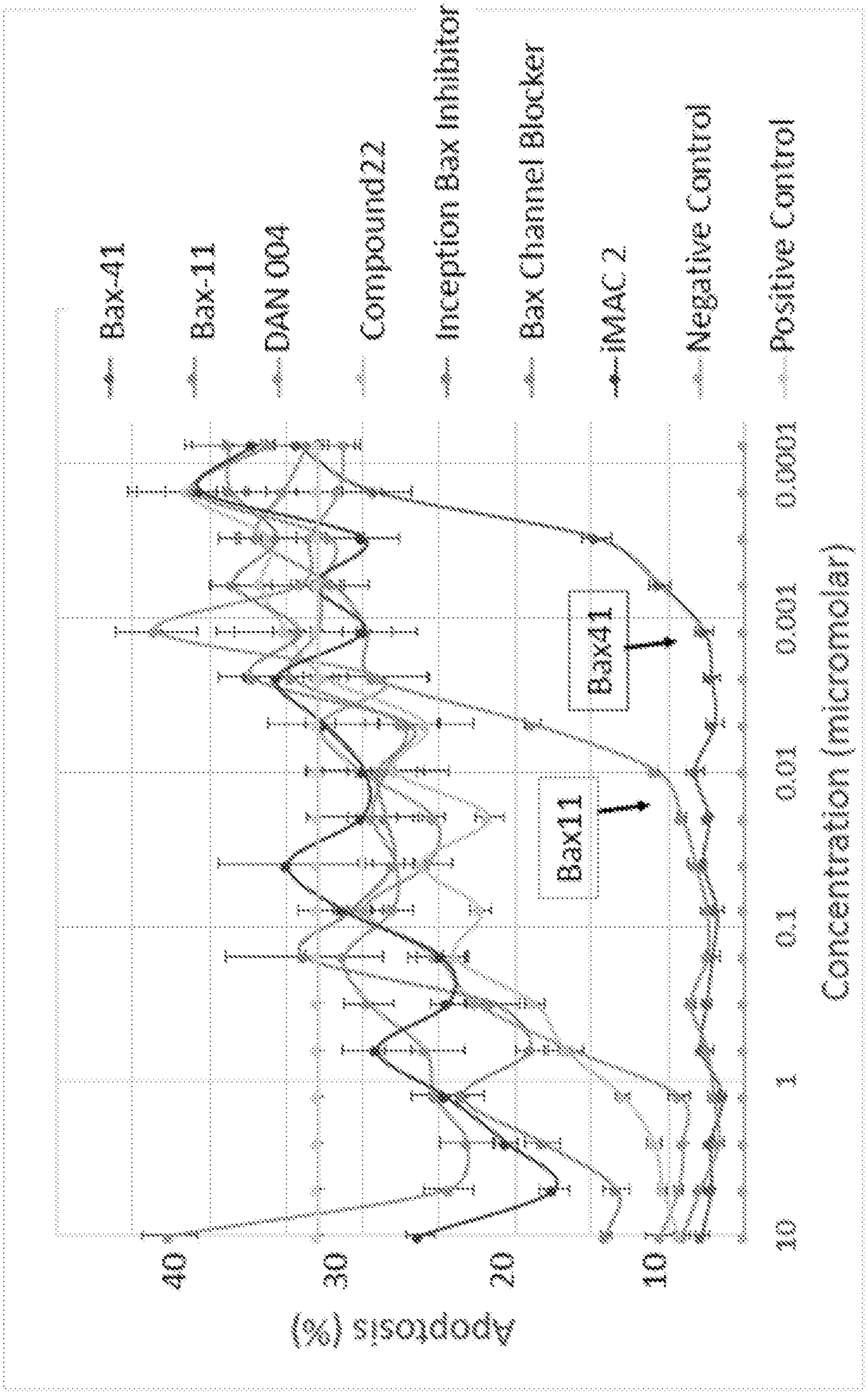
FIG. 1 is a graph illustrating Bax inhibiting compounds described herein (i.e., Bax41S (BBI5/6 analog) and Bax-11 (BBI7 analog)) protected Mouse Embryonic Fibroblasts (MEFs) from Bax-induced cell death at the concentration of 1 and 10 nM, respectively. Bax inhibitors reported by others (DAN004, Compound 22, Inception Bax inhibitor, iMAC2) require at least 200 nM to show protective activities.

While the following terms are believed to be well understood by one of ordinary skill in the art, the following definitions are set forth to facilitate explanation of the presently disclosed subject matter.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods. The term "pharmaceutically acceptable salts" also includes those obtained by reacting the active compound functioning as an acid, with an inorganic or organic base to form a salt, for example salts of ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, and the like. Non-limiting examples of inorganic or metal salts include lithium, sodium, calcium, potassium, magnesium salts and the like.

Additionally, the salts of the compounds described herein, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds and salts described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The terms below, as used herein, have the following meanings, unless indicated otherwise:

"Amino" refers to the $-NH_2$ radical.

"Cyano" refers to the —CN radical.

"Halo" or "halogen" refers to bromo, chloro, fluoro or iodo radical.

"Hydroxy" or "hydroxyl" refers to the —OH radical.

"Imino" refers to the =NH substituent.

"Nitro" refers to the $-NO_2$ radical.

"Oxo" refers to the =O substituent.

"Thioxo" refers to the =S substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl.

Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —$OR_a$ where $R_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula —$NHR_a$ or —$NR_aR_a$ where each $R_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —C(=O)$R_a$ moiety, wherein $R_a$ is an alkyl, alkenyl or alkynyl radical as defined above. A non-limiting example of an alkyl carbonyl is the methyl carbonyl ("acetal") moiety. Alkylcarbonyl groups can also be referred to as "$C_w$-$C_z$ acyl" where w and z depicts the range of the number of carbon in $R_a$, as defined above. For example, "$C_1$-$C_{10}$ acyl" refers to alkylcarbonyl group as defined above, where $R_a$ is $C_1$-$C_{10}$ alkyl, $C_2$-$C_{10}$ alkenyl, or $C_2$-$C_{10}$ alkynyl radical as defined above. Unless stated otherwise specifically in the specification, an alkyl carbonyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from phenyl (benzene), aceanthrylene, acenaphthylene, acephenanthrylene, anthracene, azulene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" or "arylalkyl" refers to a radical of the formula —$R_b$—$R_c$ where $R_b$ is an alkylene group as defined above and $R_c$ is one or more aryl radicals as defined above. Aralkyl radicals include, but are not limited to, benzyl, diphenylmethyl and the like. Unless stated otherwise specifically in the specification, an aralkyl group can be optionally substituted.

"Aralkenyl" or "arylalkenyl" refers to a radical of the formula —$R_b$—$R_c$ where $R_b$ is an alkenylene group as defined above and $R_c$ is one or more aryl radicals as defined above. Unless stated otherwise specifically in the specification, an aralkenyl group can be optionally substituted.

"Aralkynyl" or "arylalkynyl" refers to a radical of the formula —$R_b$—$R_c$ where $R_b$ is an alkynylene group as defined above and $R_c$ is one or more aryl radicals as defined above. Unless stated otherwise specifically in the specification, an aralkynyl group can be optionally substituted.

"Carbocyclyl," "carbocyclic ring" or "carbocycle" refers to a ring structure, wherein the atoms which form the ring are each carbon. Carbocyclic rings can comprise from 3 to 20 carbon atoms in the ring. Carbocyclic rings include aryls and cycloalkyl. Cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused, bridged, or spiral ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused, bridged, or spiral ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cycloctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused, bridged, or spiral ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula —$R_b$—$R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkynyl group can be optionally substituted.

"Heterocyclyl," "heterocyclic ring" or "heterocycle" refers to a stable 3- to 20-membered non-aromatic, partially aromatic, or aromatic ring radical which consists of two to twelve carbon atoms and from one to six heteroatoms selected from the group consisting of nitrogen, oxygen and sulfur. Heterocyclycl or heterocyclic rings include heteroaryls as defined below. Unless stated otherwise specifically in the specification, the heterocyclyl radical can be a monocyclic, bicyclic, tricyclic or tetracyclic ring system, which can include fused, bridged, and spiral ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, aziridinyl, oextanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, pyridine-one, and the like. The point of attachment of the heterocyclyl, heterocyclic ring, or heterocycle to the rest of the molecule by a single bond is through a ring member atom, which can be carbon or nitrogen. Unless stated otherwise specifically in the specification, a heterocyclyl group can be optionally substituted.

"Heterocyclylalkyl" refers to a radical of the formula —$R_b$—$R_e$ where $R_b$ is an alkylene group as defined above and $R_e$ is a heterocyclyl radical as defined above. Unless stated otherwise specifically in the specification, a heterocyclylalkyl group can be optionally substituted.

"Heterocyclylalkenyl" refers to a radical of the formula —$R_b$—$R_e$ where $R_b$ is an alkenylene group as defined above and $R_e$ is a heterocyclyl radical as defined above. Unless stated otherwise specifically in the specification, a heterocyclylalkenyl group can be optionally substituted.

"Heterocyclylalkynyl" refers to a radical of the formula —$R_b$—$R_e$ where $R_b$ is an alkynylene group as defined above and $R_e$ is a heterocyclyl radical as defined above. Unless stated otherwise specifically in the specification, a heterocyclylalkynyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, an N-heterocyclyl group can be optionally substituted.

"Heteroaryl" refers to a 5- to 20-membered ring system radical one to thirteen carbon atoms and one to six heteroatoms selected from the group consisting of nitrogen, oxygen and sulfur, as the ring member. For purposes of this invention, the heteroaryl radical can be a monocyclic, bicyclic, tricyclic or tetracyclic ring system, which can include fused or bridged ring systems, wherein at least one ring containing a heteroatom ring member is aromatic. The nitrogen, carbon or sulfur atoms in the heteroaryl radical can be optionally oxidized and the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrazolopyridine, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula $—R_b—R_f$ where $R_b$ is an alkylene chain as defined above and $R_f$ is a heteroaryl radical as defined above. Unless stated otherwise specifically in the specification, a heteroarylalkyl group can be optionally substituted.

"Heteroarylalkenyl" refers to a radical of the formula $—R_b—R_f$ where $R_b$ is an alkenylene, chain as defined above and $R_f$ is a heteroaryl radical as defined above. Unless stated otherwise specifically in the specification, a heteroarylalkenyl group can be optionally substituted.

"Heteroarylalkynyl" refers to a radical of the formula $—R_b—R_f$ where $R_b$ is an alkynylene chain as defined above and $R_f$ is a heteroaryl radical as defined above. Unless stated otherwise specifically in the specification, a heteroarylalkynyl group can be optionally substituted.

"Thioalkyl" refers to a radical of the formula $—SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (e.g., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl, heteroarylalkyl, heteroarylalkenyl, heteroarylalkynyl, etc) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with: $—NR_gR_h$, $—NR_gC(═O)R_h$, $—NR_gC(═O)NR_gR_h$, $—NR_gC(═O)OR_h$, $—NR_gSO_2R_h$, $—OC(═O)NR_gR_h$, $—OR_g$, $—SR_g$, $—SOR_g$, $—SO_2R_g$, $—OSO_2R_g$, $—SO_2OR_g$, $═NSO_2R_g$, and $—SO_2NR_gR_h$. "Substituted" also means any of the above groups in which one or more hydrogen atoms are replaced with $—C(═O)R_g$, $—C(═O)OR_g$, $—C(═O)NR_gR_h$, $—CH_2SO_2R_g$, $—CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol

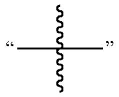

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

indicates that the chemical entity "A" is bonded to another chemical entity via the point of attachment bond. Further-more, the specific point of attachment to the non-depicted chemical entity can be specified by inference. For example, the compound

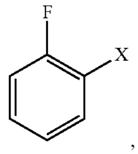

, wherein X is

infers that the point of attachment bond is the bond by which X is depicted as being attached to the phenyl ring at the ortho position relative to fluorine.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

All percentages and ratios used herein, unless otherwise indicated, are by weight.

Embodiments described herein relate to compounds for use in inhibiting Bax mediated cell death and/or apoptosis and to their use in treating conditions, disorders, and/or diseases associate with Bax mediated cell death and/or apoptosis. The Bax inhibiting compounds described herein suppressed Bax-induced cell death at 1 nM-10 nM (in culture medium) compared to previously reported Bax inhibitors that required at least 1 μM (1000 nM in cell culture medium), and have Bax binding affinity (Kd) ranging from 1 nM-100 nM.

As shown in FIGS. 1 to 4, Bax inhibiting compounds described herein showed a dose-dependent effect to rescue cells from Bax, protected mouse embryonic fibroblast (MEF) cells from Bax induced cell death, inhibited Bas-induced apoptosis without significant impact on expression levels of Bax, Bcl-2, Bcl-XL and Mcl-1, and protected ARP19 (Retinal cells) cells from atRAL induced cell death. Advantageously, the Bax inhibiting compounds described herein can be used to help subjects suffering from cell death-related diseases and/or apoptosis including, for example, retinal degenerative diseases, cardiovascular diseases, neurodegenerative diseases, and other diseases caused by unwanted Bax-induced programmed cell death. The Bax inhibiting compounds described herein can also be used as Bax inhibitors to extend the survival of cells, tissues, and/or organs ex vivo and after transplantation and engraftment. Therefore, the Bax inhibiting compounds can be beneficial in improving the efficiency of the storage and transplantation of cells, tissues, and organs.

In some embodiments, the Bax inhibiting compound can include the following formula (I):

(I)

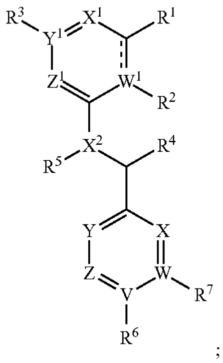

;

or a pharmaceutically acceptable salt, tautomer, or solvate thereof, wherein:

$R^1$ and $R^2$ are each independently —H, alkyl, —F, —CN, —O-alkyl, cycloalkyl, oxetanyl, or tetrahydrofuranyl, or $R^1$ together with $R^2$ forms a phenyl ring optionally substituted with one or two $R^8$ groups, or $R^1$ together with $R^2$ forms a five or six-membered heteroaromatic ring containing one or two heteroatoms chosen from N, O and S, optionally substituted with one or two $R^8$ groups;

$R^8$ is halo, alkyl, cycloalkyl, oxetanyl, tetrahydrofuranyl, —CN, —O-alkyl, —O-cycloalkyl, —$SO_2$-alkyl, or —$CH_2SO_2$-alkyl;

$R^3$ is absent, —H, -D, —F, —Cl, —$CF_3$, -alkyl, cyclopropyl-O-alkyl, or —CN;

$R^4$ is —H, alkyl, cyclopropyl, or —$CF_3$;

$R^5$ is absent, —H, or alkyl;

alternatively, $R^5$ and the nitrogen atom to which it is attached may be replaced by an oxygen atom;

V, W, X, Y and Z are each independently —CH, or N;

$X^1$ and $Z^1$ are each independently —CH or N;

$W^1$ and $Y^1$ are each independently C or N, and when $Y^1$ is N, $R^3$ is absent;

$X^2$ is O or N, when $X^2$ is O, $R^5$ is absent;

=== represents a single or double bond;

$R^6$ is —H, halo, alkyl, cycloalkyl, —CN, —O-alkyl, —O-cycloalkyl, —O— heterocyclyl, —$SO_2$-alkyl, —$CH_2SO_2$-alkyl, —$CONH_2$, —CONH-alkyl, or —CON$(alkyl)_2$;

$R^7$ is —H, halo, alkyl, cycloalkyl, —CN, —O-alkyl, —O-cycloalkyl, —O— heterocyclyl, —$SO_2$-alkyl, —$CH_2SO_2$-alkyl, —$CONH_2$, —CONH-alkyl, or —CON$(alkyl)_2$;

alternatively, $R^6$ or $R^7$ can be an aryl optionally substituted with one or two $R^9$ groups;

alternatively, $R^6$ or $R^7$ can be a 4-6 membered ring heterocycle containing one or two heteroatoms chosen from the group consisting of N, O and S, and optionally substituted with one or two $R^9$ groups, excluding unstable heterocycles;

alternatively, $R^6$ or $R^7$ can be a 5-6 membered ring heteroaryl group containing one to four heteroatoms chosen from the group consisting of N, O and S, and optionally substituted with one or two $R^9$ groups, excluding unstable heterocycles;

$R^9$ is H, halo, alkyl, cycloalkyl, alkyl-CO—, oxetanyl, 3-tetrahydrofuranyl, —CN, —O-alkyl, —O-cycloalkyl, —$CONH_2$, —CONH-alkyl, or —CON$(alkyl)_2$;

$R^6$ together with $R^7$ and the phenyl ring or heteroaryl ring to which they are attached, may be a benzimidazole ring, benzotriazole ring, azaindole ring, azaindazole, or benzodioxolane, with N of the rings bearing an optional substituent $R^{10}$, and with Cs of the rings optionally substituted with $R^{11}$;

$R^{10}$ is —H, alkyl, or cycloalkyl; and $R^{11}$ is —H, alkyl, or cycloalkyl.

In some embodiments, $R^1$ and $R^2$ are each independently —H, $C_1$-$C_6$-alkyl, —F, —CN, —O—$C_1$-$C_6$-alkyl, $C_3$-$C_7$-cycloalkyl, 3-oxetanyl, or 3-tetrahydrofuranyl, or $R^1$ together with $R^2$ forms a phenyl ring optionally substituted with one or two $R^8$ groups, or $R^1$ together with $R^2$ forms a saturated five or six-membered heteroaromatic ring containing one or two heteroatoms chosen from N, O and S, optionally substituted with one or two $R^8$ groups.

In other embodiments, $R^8$ is halo, $C_1$-$C_6$-alkyl, $C_3$-$C_7$-cycloalkyl, 3-oxetanyl, 3-tetrahydrofuranyl, —CN, —O—$C_1$-$C_6$-alkyl, —O—$C_3$-$C_7$-cycloalkyl, —$SO_2$—$C_1$-$C_6$-alkyl, or —$CH_2SO_2$—$C_1$-$C_6$-alkyl.

In other embodiments, $R^3$ is absent, —H, -D, —F, —Cl, —$CF_3$, —$C_1$-$C_6$-alkyl, cyclopropyl-O—$C_1$-$C_6$-alkyl, or —CN.

In some embodiments, $R^4$ is —H, —$C_1$-$C_6$-alkyl, -cyclopropyl, or —$CF_3$.

In other embodiments, $R^5$ is absent, —H, or —$C_1$-$C_6$-alkyl.

In other embodiments, $R^6$ is —H, halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON$(C_1$-$C_6$-alkyl$)_2$.

In other embodiments, $R^7$ is —H, halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON$(C_1$-$C_6$-alkyl$)_2$.

In some embodiments, $R^9$ is H, halo, $C_1$-$C_6$-alkyl, $C_3$-$C_7$-cycloalkyl, $C_1$-$C_5$-alkyl-CO—, 3-oxetanyl, 3-tetrahydrofuranyl, —CN, —O—$C_6$-$C_6$-alkyl, or —O—$C_3$-$C_7$-cycloalkyl.

In other embodiments, $R^{10}$ is —H, $C_1$-$C_6$-alkyl, or $C_3$-$C_7$-cycloalkyl.

In still other embodiments, $R^{11}$ is —H, $C_1$-$C_6$-alkyl, or $C_3$-$C_7$-cycloalkyl.

In other embodiments, $R^1$ together with $R^2$ can form a phenyl ring optionally substituted with one or two $R^8$ groups, or $R^1$ together with $R^2$ can form a saturated five or six-membered heteroaromatic ring containing one or two heteroatoms chosen from N, O and S, optionally substituted with one or two $R^8$ groups.

In some embodiments, $R^4$ is —$C_1$-$C_6$-alkyl or —$CF_3$ and $R^5$ is —H.

In other embodiments, X and Y are independently H; and Z is N.

In some embodiments, $R^6$ or $R^7$ is a 4-6 membered ring saturated heterocycle containing one or two heteroatoms chosen from the group consisting of N, O and S, and optionally substituted with one or two $R^9$ groups, excluding unstable heterocycles, or $R^6$ or $R^7$ is a 5-6 membered ring heteroaryl group containing one to three heteroatoms chosen from the group consisting of N, O and S, and optionally substituted with one or two $R^9$ groups, excluding unstable heterocycles.

In other embodiments, $R^6$ is selected from the group consisting of:

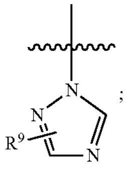 ; 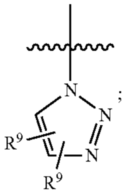 ; 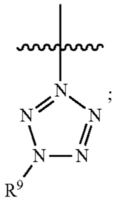 ;

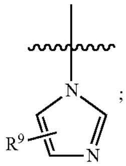 ; 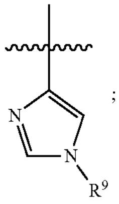 ; 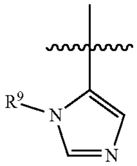 ;

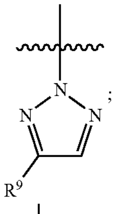 ; 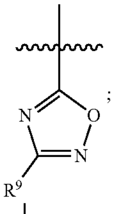 ; 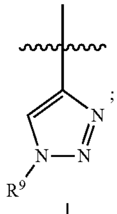 ;

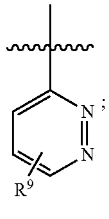 ; 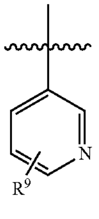 ; and 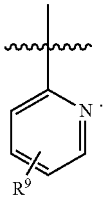 .

In other embodiments, the Bax inhibiting compound having formula (I) can include a compound having the following formula:

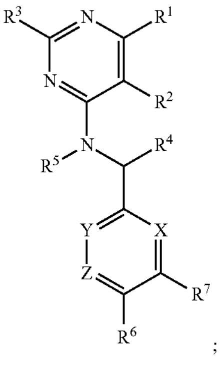

;

or a pharmaceutically acceptable salt, tautomer, or solvate thereof, wherein:

$R^1$ and $R^2$ are each independently —H, $C_1$-$C_6$-alkyl, —F, —CN, —O—$C_1$-$C_6$-alkyl, $C_3$-$C_7$-cycloalkyl, 3-oxetanyl, or 3-tetrahydrofuranyl, or $R^1$ together with $R^2$ forms a phenyl ring optionally substituted with one or two $R^8$ groups, or $R^1$ together with $R^2$ forms a five or six-membered heteroaromatic ring containing one or two heteroatoms chosen from N, O and S, optionally substituted with one or two $R^8$ groups;

$R^8$ is halo, $C_1$-$C_6$-alkyl, $C_3$-$C_7$-cycloalkyl, 3-oxetanyl, 3-tetrahydrofuranyl, —CN, —O—$C_1$-$C_6$-alkyl, —O—$C_3$-$C_7$-cycloalkyl, —$SO_2$—$C_1$-$C_6$-alkyl, or —$CH_2SO_2$—$C_1$-$C_6$-alkyl;

$R^3$ is —H, -D, —F, —Cl, —$CF_3$, —$C_1$-$C_6$-alkyl, cyclopropyl-O—$C_1$-$C_6$-alkyl, or —CN;

$R^4$ is —H, —$C_1$-$C_6$-alkyl, -cyclopropyl, or —$CF_3$;

$R^5$ is —H, or —$C_1$-$C_6$-alkyl;

alternatively, $R^5$ and the nitrogen atom to which it is attached may be replaced by an oxygen atom;

X, Y and Z are each independently —CH, or N;

$\overline{\underline{---}}$ represents a single or double bond;

$R^6$ is —H, halo, $C_1$-$C_6$-alkyl, $C_3$-$C_7$-cycloalkyl, —CN, —O—$C_1$-$C_6$-alkyl, —O—$C_3$-$C_7$-cycloalkyl, —O-heterocyclyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON($C_1$-$C_6$-alkyl)$_2$;

$R^7$ is —H, halo, $C_1$-$C_6$-alkyl, $C_3$-$C_7$-cycloalkyl, —CN, —O—$C_1$-$C_6$-alkyl, —O—$C_3$-$C_7$-cycloalkyl, —O-heterocyclyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON($C_1$-$C_6$-alkyl)$_2$;

alternatively, $R^6$ or $R^7$ can be an aryl optionally substituted with one or two $R^9$ groups;

alternatively, $R^6$ or $R^7$ can be a 4-6 membered ring heterocycle containing one or two heteroatoms chosen from the group consisting of N, O and S, and optionally substituted with one or two $R^9$ groups, excluding unstable heterocycles;

alternatively, $R^6$ or $R^7$ can be a 5-6 membered ring heteroaryl group containing one to four heteroatoms chosen from the group consisting of N, O and S, and optionally substituted with one or two $R^9$ groups, excluding unstable heterocycles;

$R^9$ is halo, $C_1$-$C_6$-alkyl, $C_3$-$C_7$-cycloalkyl, $C_1$-$C_5$-alkyl-CO—, 3-oxetanyl, 3-tetrahydrofuranyl, —CN, —O—$C_1$-$C_6$-alkyl, —O—$C_3$-$C_7$-cycloalkyl, —$CONH_2$, —CONH-alkyl, or —CON(alkyl)$_2$;

$R^6$ together with $R^7$ and the phenyl ring or heteroaryl ring to which they are attached, may be a benzimidazole ring, benzotriazole ring, azaindole ring, azaindazole, or benzodioxolane, with N of the rings bearing an optional substituent $R^{10}$, and with Cs of the rings optionally substituted with $R^{11}$;

$R^{10}$ is —H, $C_1$-$C_6$-alkyl, or $C_3$-$C_7$-cycloalkyl; and $R^{11}$ is —H, $C_1$-$C_6$-alkyl, or $C_3$-$C_7$-cycloalkyl.

In other embodiments, $R^1$ together with $R^2$ can form a phenyl ring optionally substituted with one or two $R^8$ groups, or $R^1$ together with $R^2$ can form a saturated five or six-membered heteroaromatic ring containing one or two heteroatoms chosen from N, O and S, optionally substituted with one or two $R^8$ groups.

In some embodiments, $R^4$ is —$C_1$-$C_6$-alkyl or —$CF_3$ and $R^5$ is —H.

In other embodiments, X and Y are independently H; and Z is N.

In some embodiments, $R^6$ or $R^7$ is a 4-6 membered ring saturated heterocycle containing one or two heteroatoms chosen from the group consisting of N, O and S, and optionally substituted with one or two $R^9$ groups, excluding unstable heterocycles, or $R^6$ or $R^7$ is a 5-6 membered ring heteroaryl group containing one to three heteroatoms chosen from the group consisting of N, O and S, and optionally substituted with one or two $R^9$ groups, excluding unstable heterocycles.

In other embodiments, $R^6$ is selected from the group consisting of:

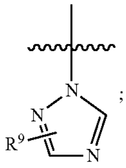 ; 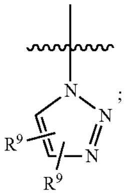 ; 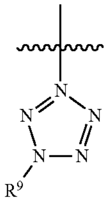 ;

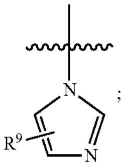 ; 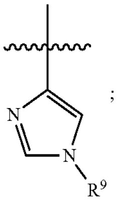 ; 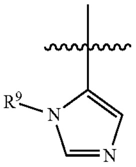 ;

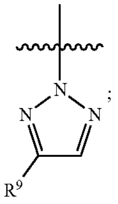 ; 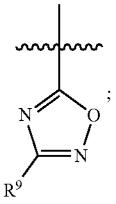 ; 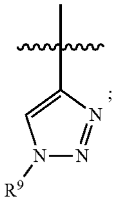 ;

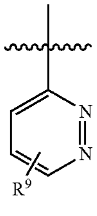 ; 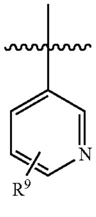 ; and 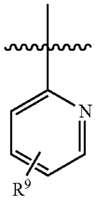 .

In other embodiments, the Bax inhibiting compound having formula (I) can be selected from the group consisting of:

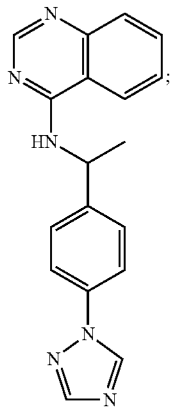 ;

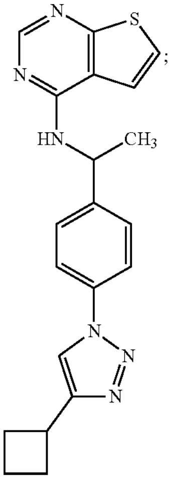 ;

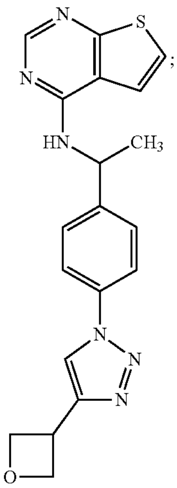 ;

-continued
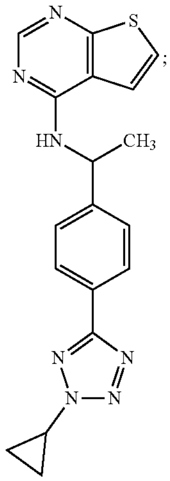
;
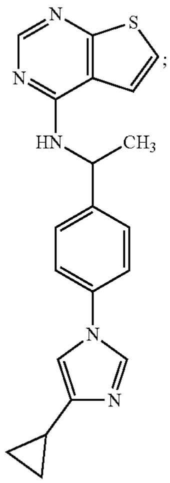
;
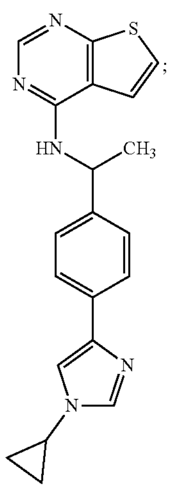
;
-continued
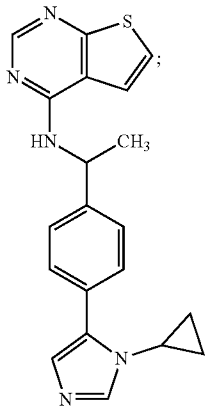
;
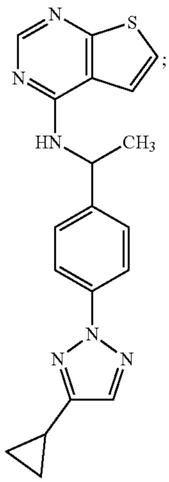
;
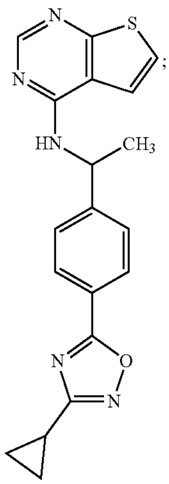
;

-continued
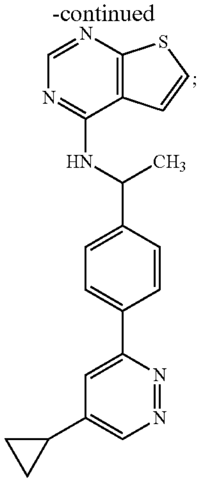
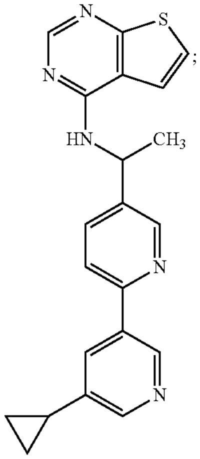
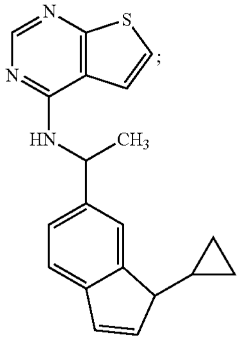
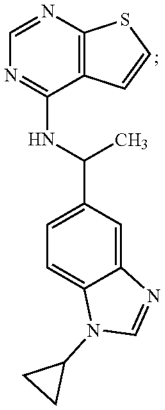
-continued
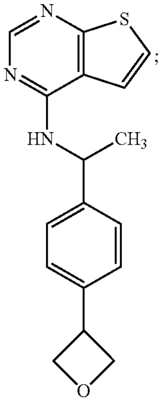
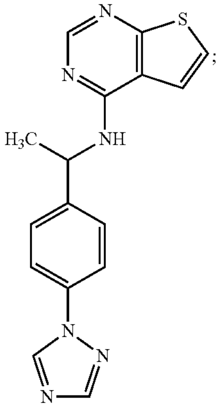
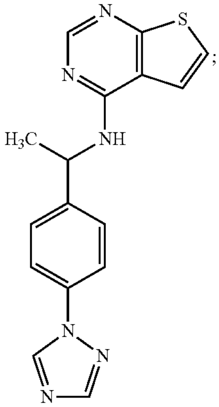
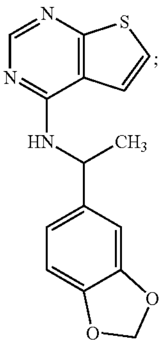

-continued
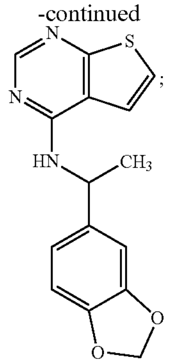
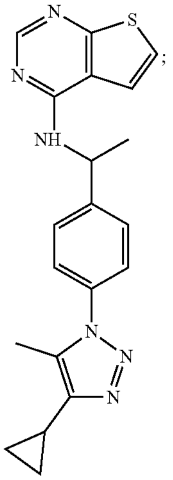
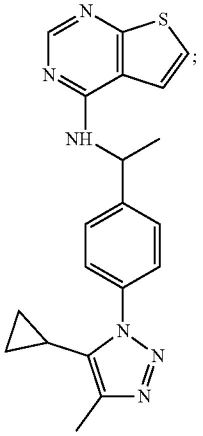
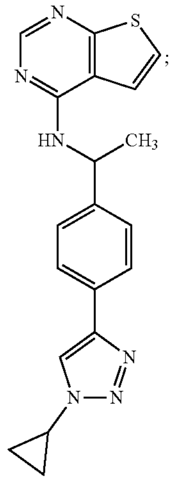
-continued
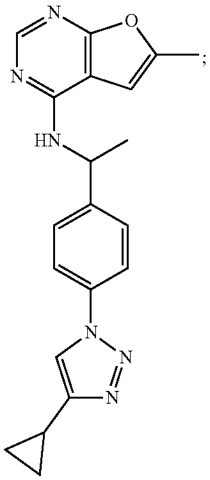
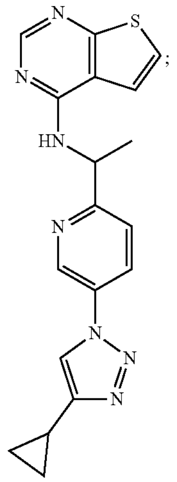
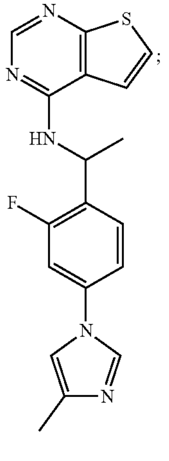

-continued
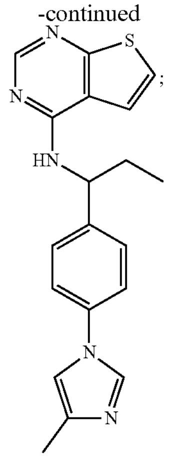
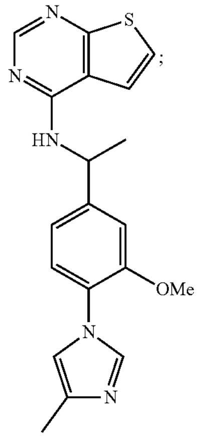
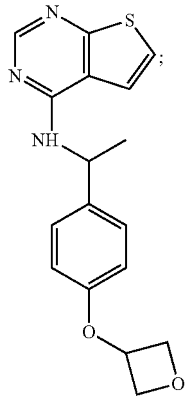
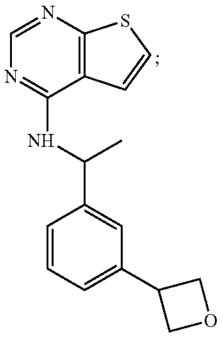
-continued
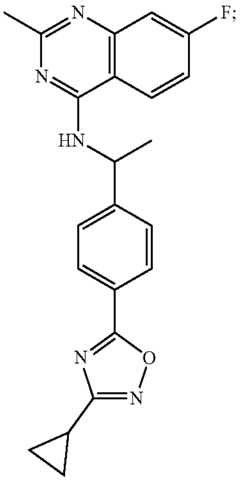
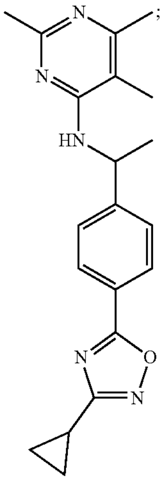
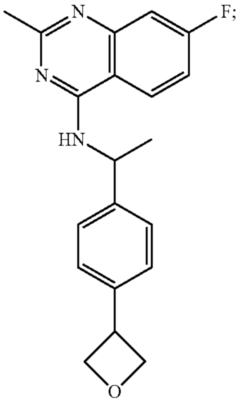

-continued
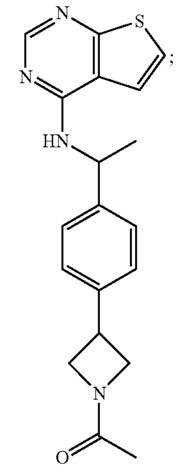
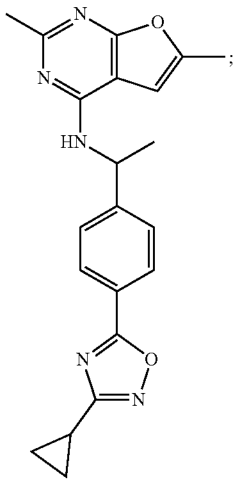
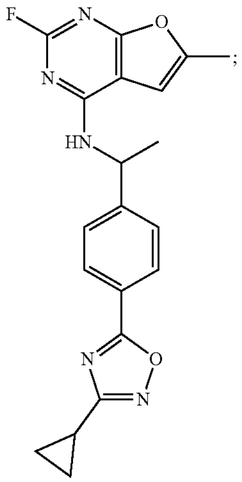
-continued
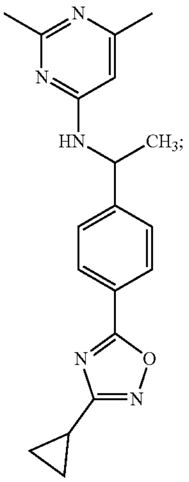
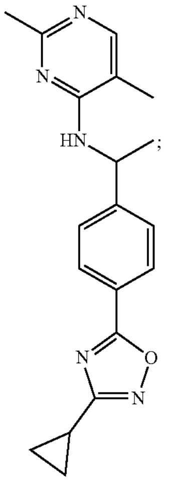
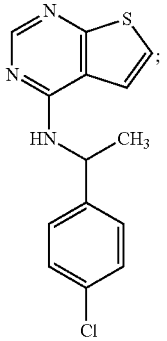
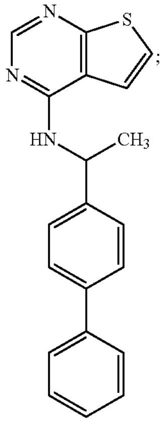

-continued
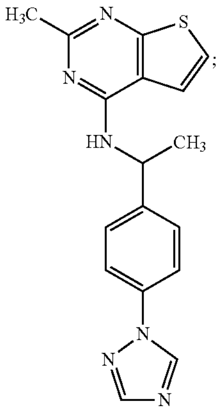
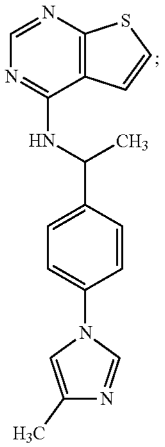
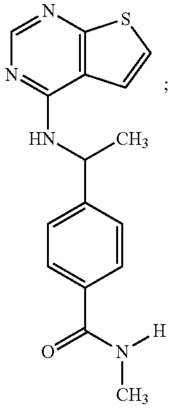
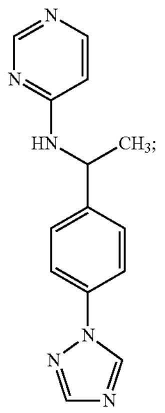
-continued
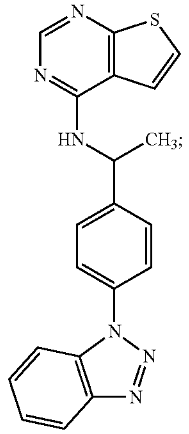
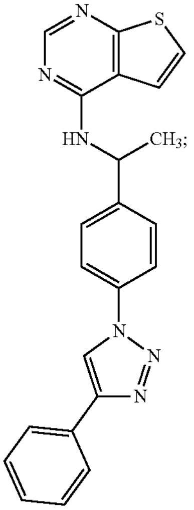
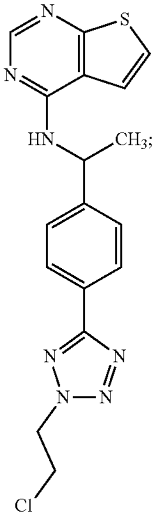

-continued
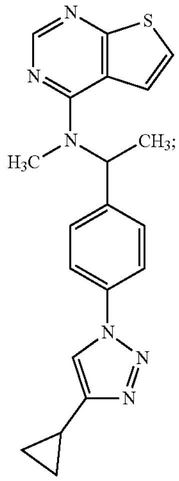
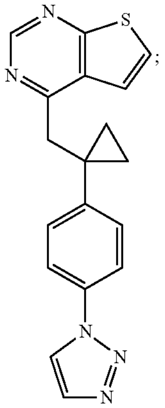
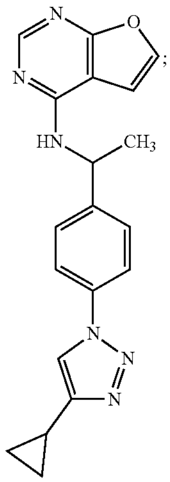
-continued
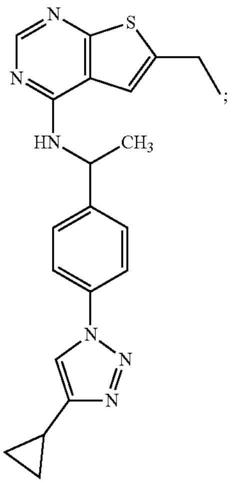
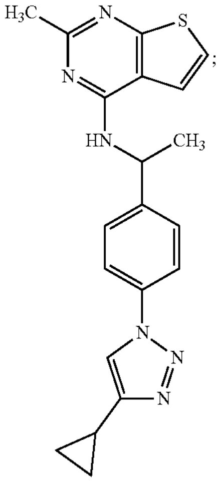
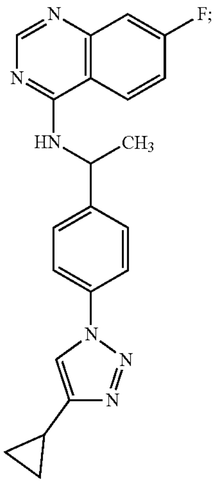

-continued
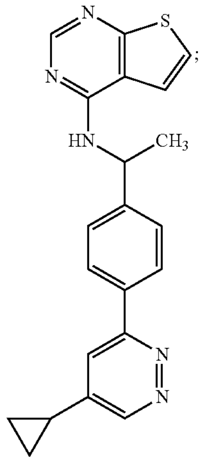
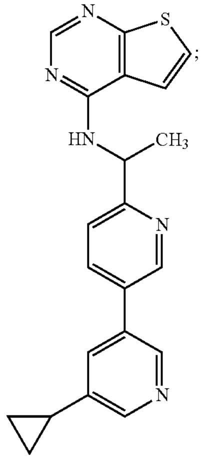
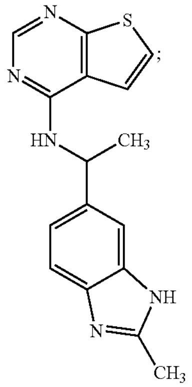
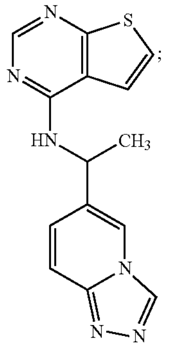
-continued
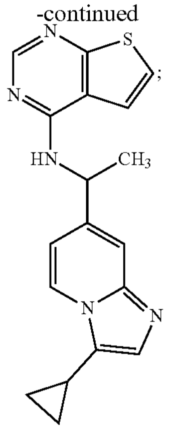
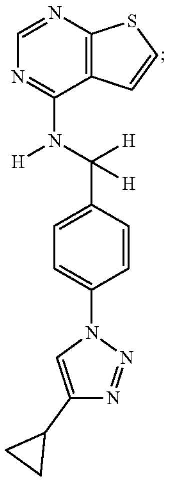
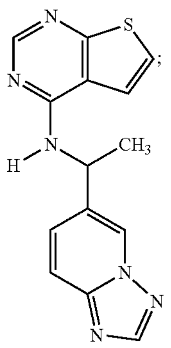
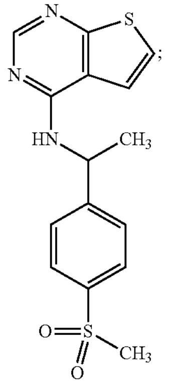

-continued
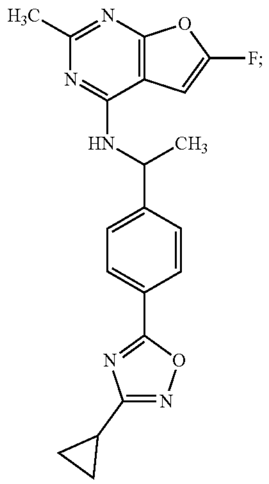
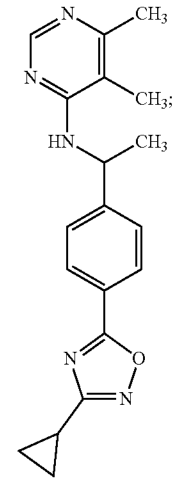
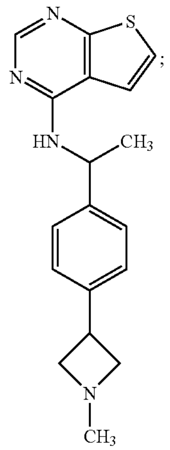
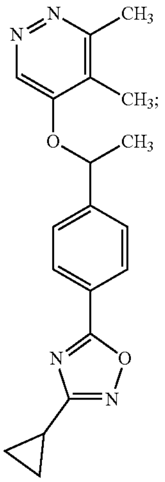
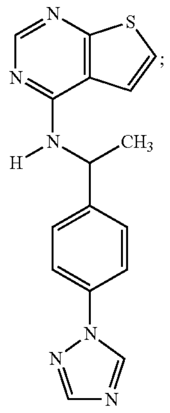
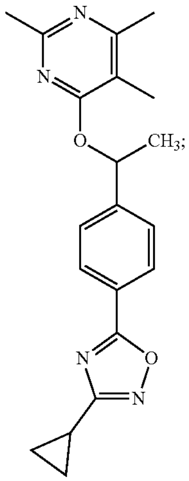

-continued
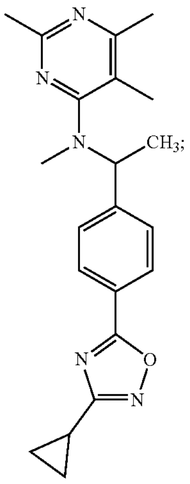
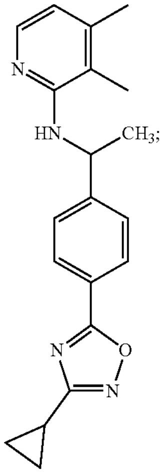
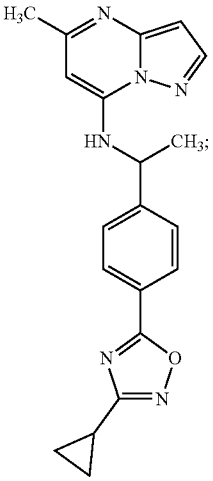
-continued
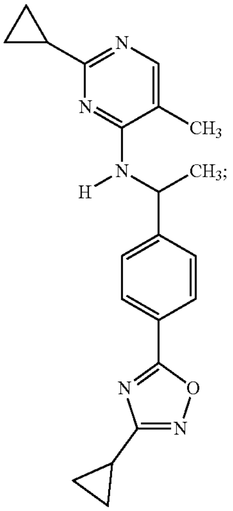
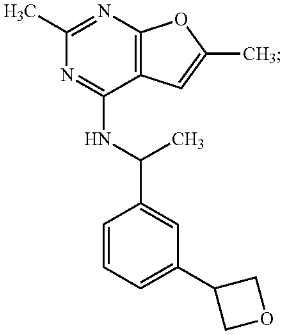
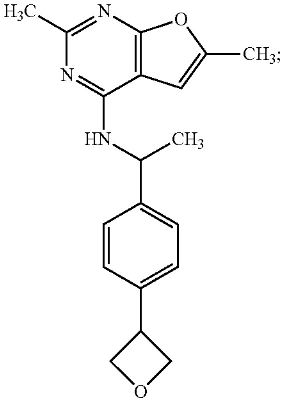
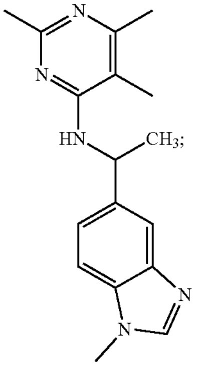

-continued
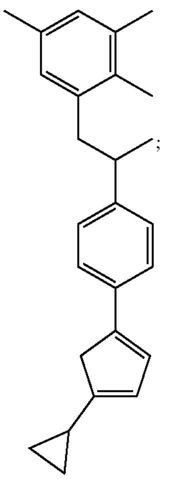
-continued
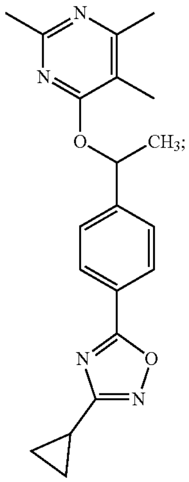
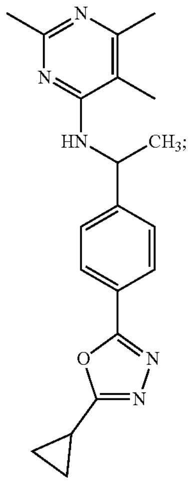
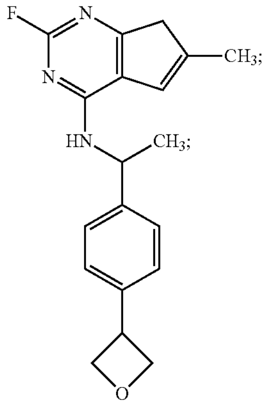
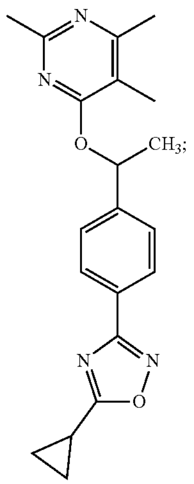
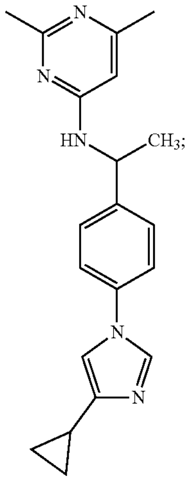

-continued
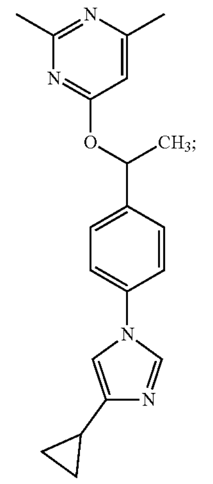
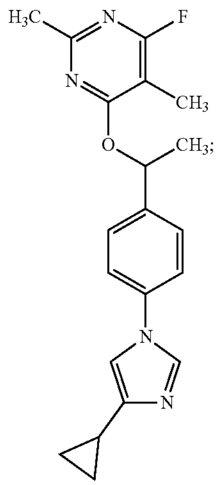
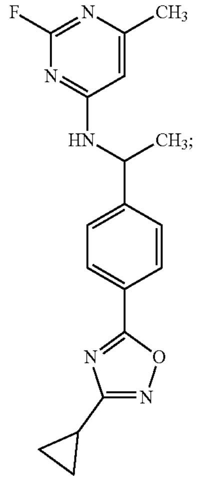
-continued
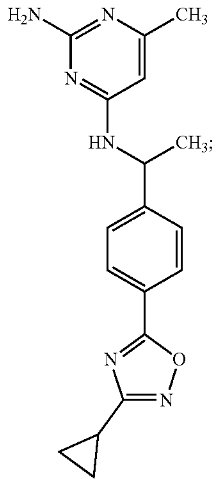
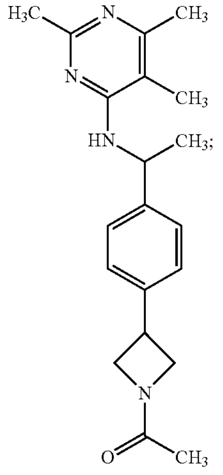
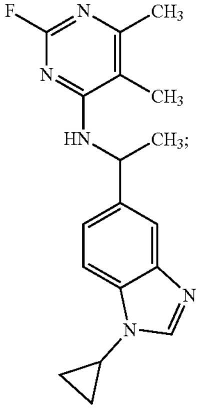

-continued
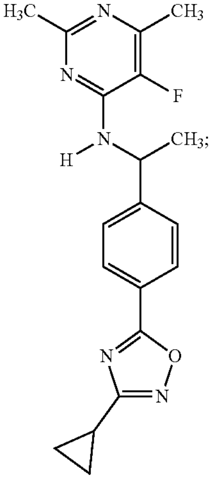
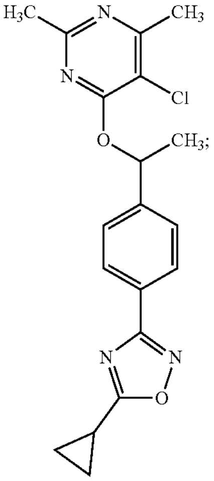
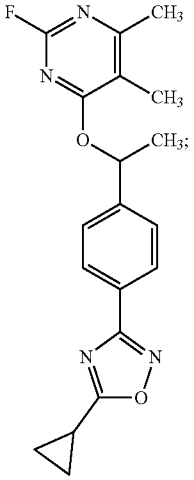
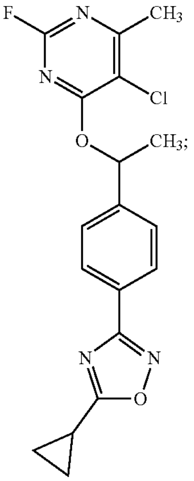
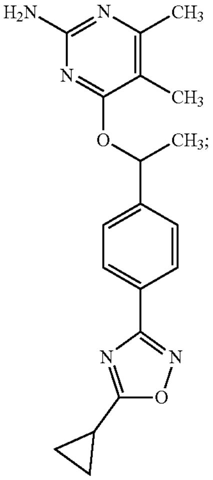
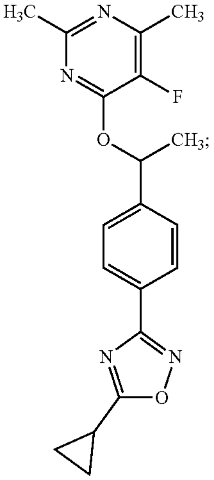

-continued
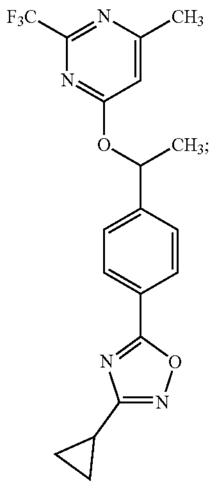
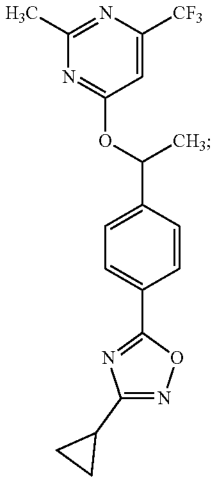
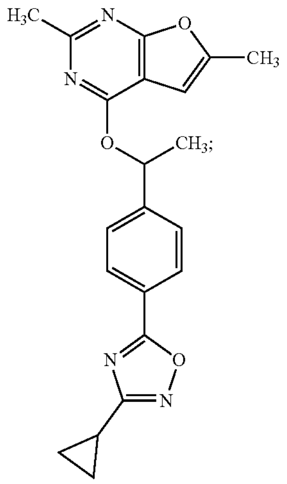
-continued
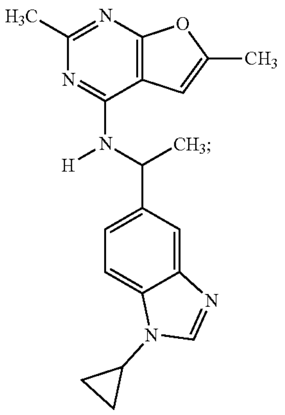
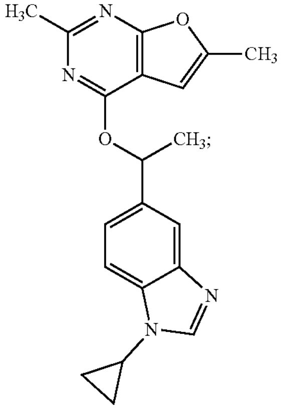
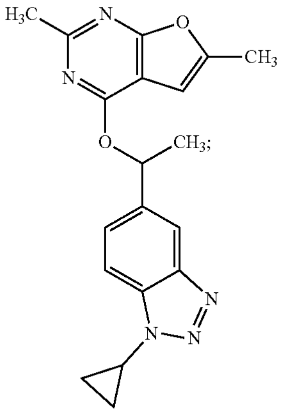
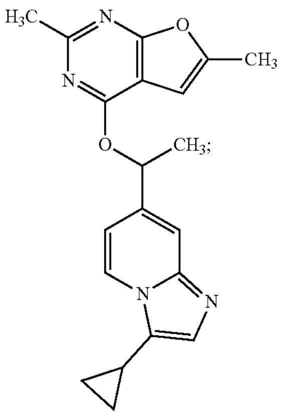

-continued
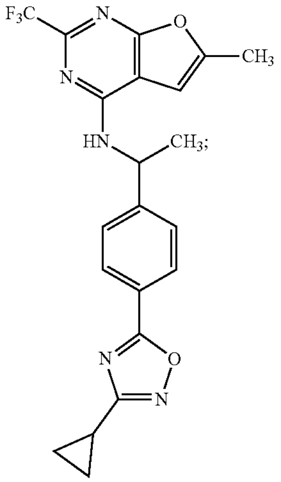
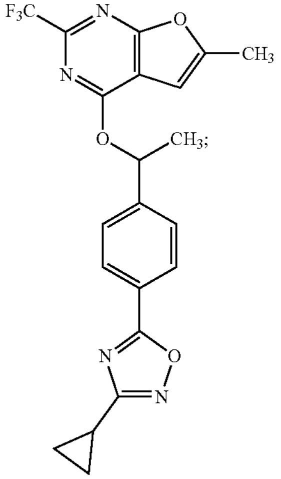
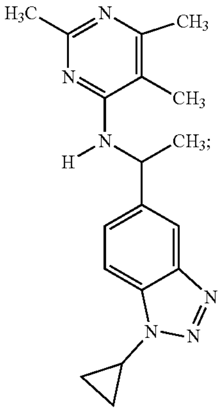
-continued
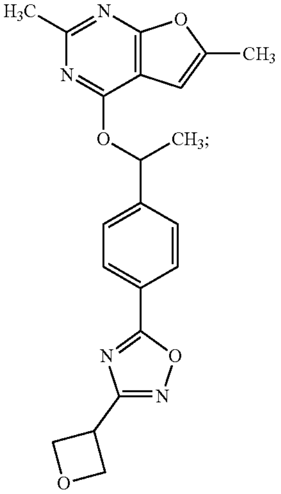
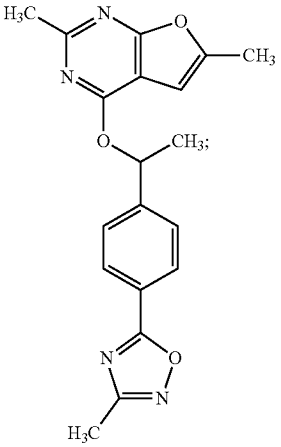
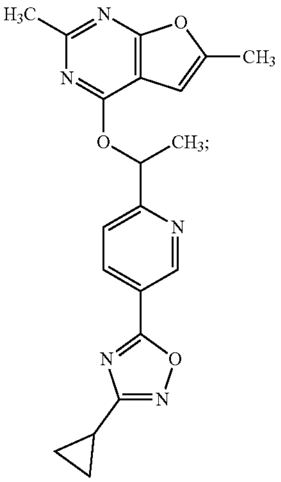

-continued
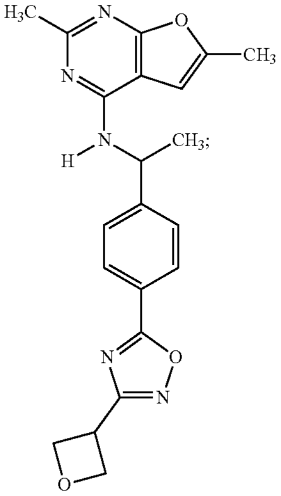
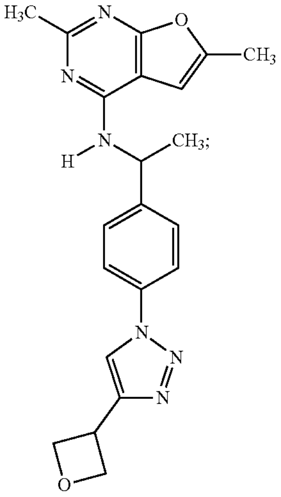
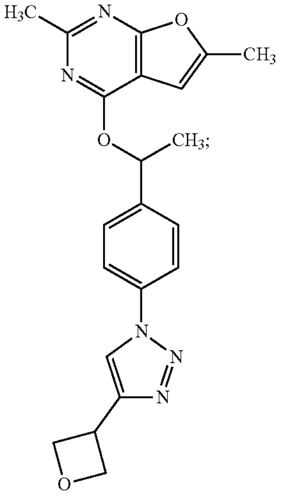
and pharmaceutically acceptable salts thereof.
In still other embodiments, the Bax inhibiting compound having formula (I) can be selected from the group consisting of:
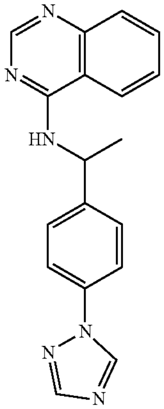
;
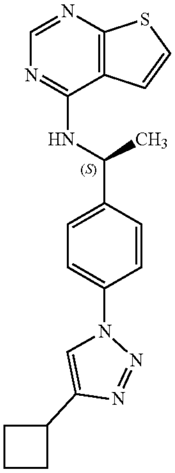
;
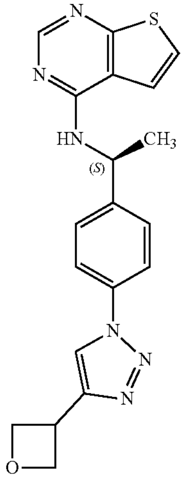
;
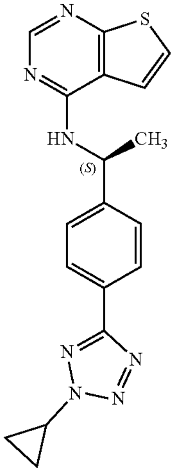
;
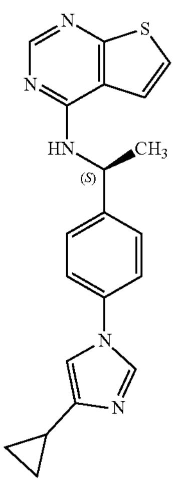
;
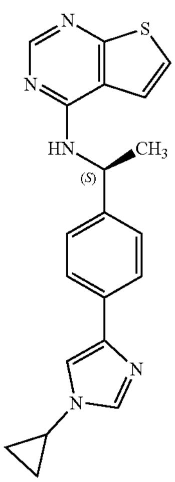
;

-continued
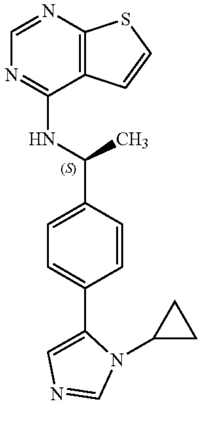 ; 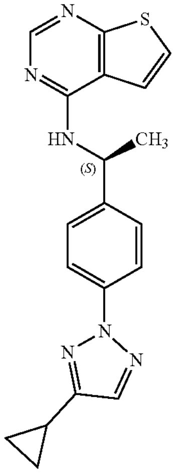 ;
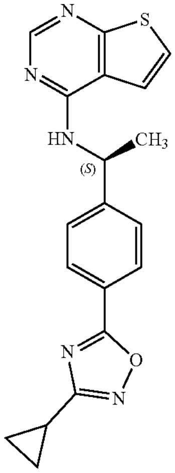 ; 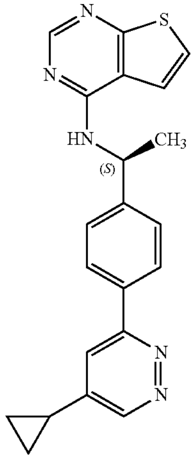 ;
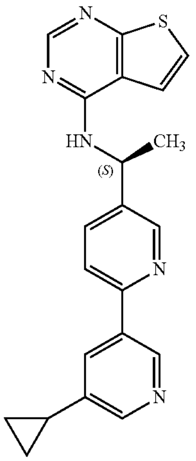 ; 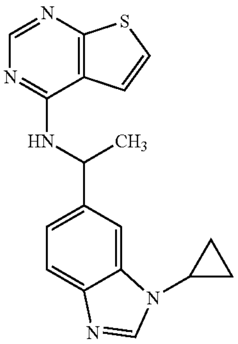 ;
-continued
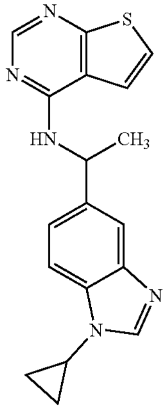 ; 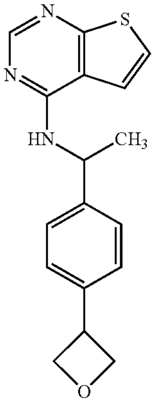 ;
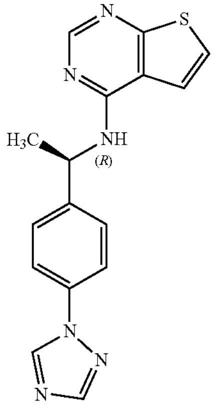 ; 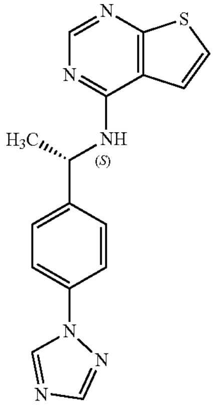 ;
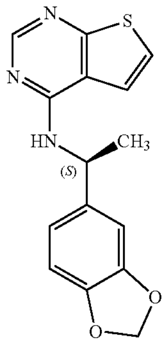 ; 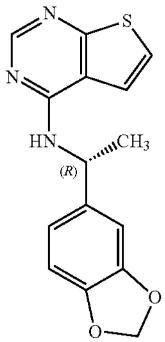 ;
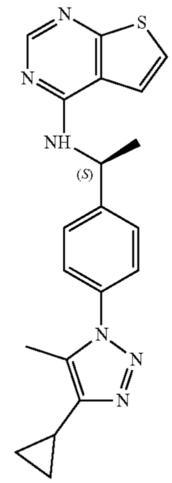 ; 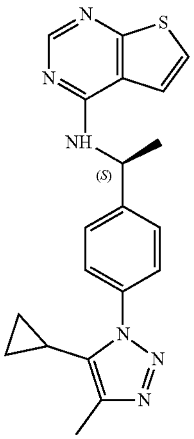 ;

-continued
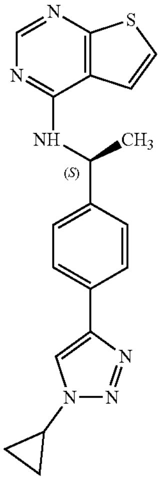
;
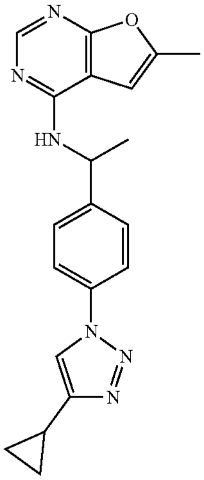
;
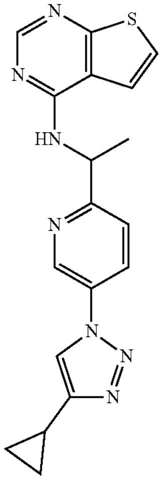
;
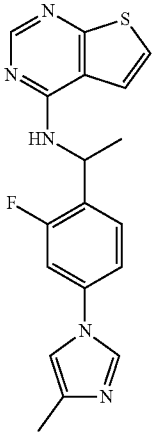
;
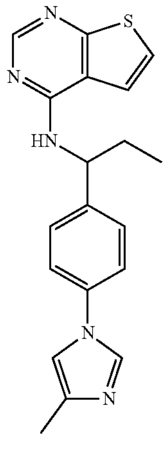
;
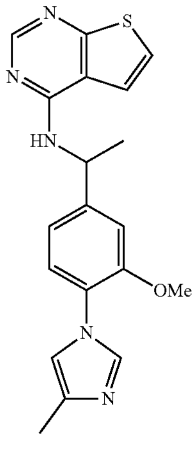
;
-continued
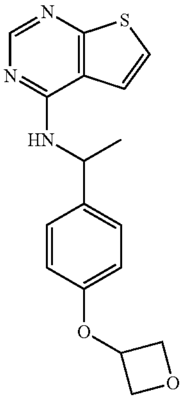
;
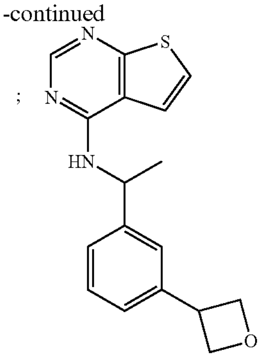
;
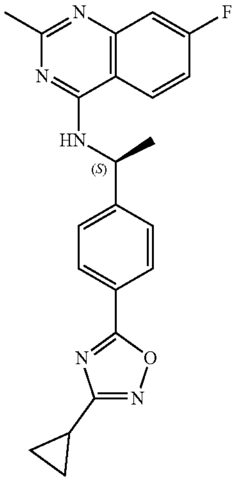
;
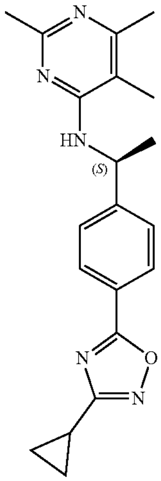
;
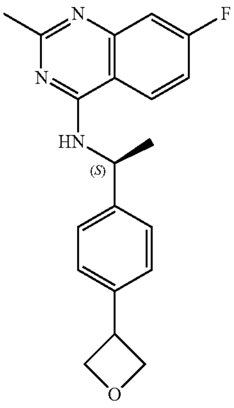
;
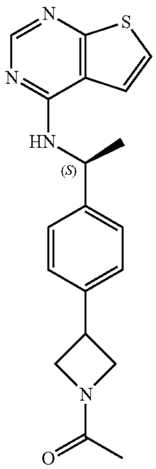
;

-continued

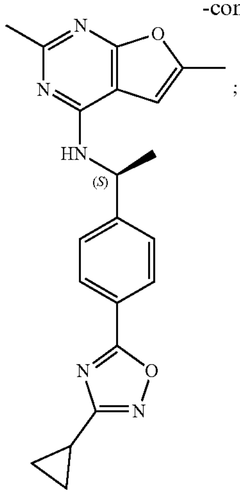

;

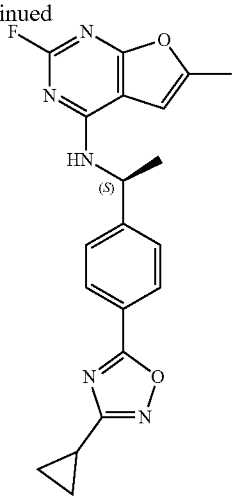

;

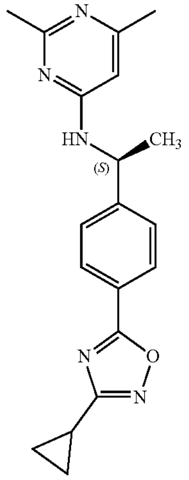

;

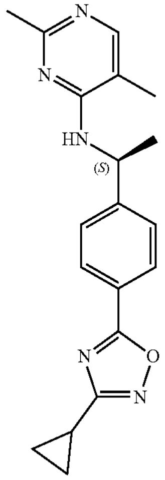

;

and pharmaceutically acceptable salts thereof.

In other embodiments, a Bax inhibiting compound can include the following formula (II):

(II)

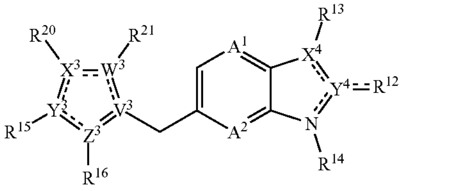

or a pharmaceutically acceptable salt, tautomer, or solvate thereof, wherein:

$R^{12}$ is =O or $R^{17}$; and when $R^{12}$ is =O, $R^{13}$ and $R^{14}$ are independently absent, —H, alkyl, cycloalkyl, oxetanyl, or tetrahydrofuranyl, or when $R^{12}$ is $R^{17}$, $R^{13}$ or $R^{14}$ is absent and the other is —H, alkyl, cycloalkyl, oxetanyl, or tetrahydrofuranyl;

$A^1$ and $A^2$ are independently CH or N;

the heterocycle comprising $V^3$, $W^3$, $X^3$, $Y^3$ and $Z^3$ and its substituents $R^{15}$, $R^{16}$, $R^{20}$, and $R^{21}$ is a heteroaromic ring with two double bonds, including, for example, pyrrole, imidazole, pyrazole or triazole; $V^3$, $W^3$, $X^3$, $Y^3$ and $Z^3$ can independently be CH or N, with 1-3 of these atoms being N;

$X^4$ is N or O;

$Y^4$ is N or C;

$\overline{\underline{---}}$ represents a single or double bond;

$R^{15}$, $R^{16}$, $R^{20}$, and $R^{21}$ are independently alkyl, cycloalkyl, bicyclyl, phenyl or heteroaryl optionally substituted with one or more $R^{18}$, or a heterocyclic ring with one or two heteroatoms chosen from the group consisting of N, O, S;

$R^{17}$ is —H, =NH, alkyl, cycloalkyl, oxetanyl, or tetrahydrofuranyl; alternatively, $R^{15}$ together with $R^{16}$ and the ring to which they are attached can form a bicyclic ring in which $V^3$ and $X^3$ are N and $W^3$ is CH and $Y^3$ and $Z^3$ are C atoms at the ring fusion; the bicyclic ring being optionally substituted with one or two $R^{19}$ substituents;

$R^{18}$ is halo, alkyl, cycloalkyl, —CN, —O-alkyl, —O-cycloalkyl, —O-alkyl-alkynyl, —$SO_2$-alkyl, —$CH_2SO_2$-alkyl, —$CONH_2$, —CONH-alkyl, or —CON(alkyl)$_2$; and $R^{19}$ is halo, alkyl, cycloalkyl, —CN, —O-alkyl, —O-cycloalkyl, —$SO_2$-alkyl, or —$CH_2SO_2$-alkyl.

In some embodiments, $R^{12}$ is =O or $R^{17}$; and when $R^{12}$ is =O, $R^{13}$ and $R^{14}$ are independently absent, —H, $C_1$-$C_6$-alkyl, $C_3$-$C_7$-cycloalkyl, 3-oxetanyl, or 3-tetrahydrofuranyl, or when $R^{12}$ is $R^{17}$, $R^{13}$ or $R^{14}$ is absent and the other is —H, $C_1$-$C_6$-alkyl, $C_3$-$C_7$-cycloalkyl, 3-oxetanyl, or 3-tetrahydrofuranyl;

In other embodiments, $R^{15}$, $R^{16}$, $R^{20}$, and $R^{21}$ are independently $C_1$-$C_6$-alkyl, $C_3$-$C_7$-cycloalkyl, phenyl or $C_5$-$C_6$ heteroaryl optionally substituted with $R^{18}$, or a $C_4$-$C_6$ heterocyclic ring with one or two heteroatoms chosen from the group consisting of N, O, S.

In still other embodiments, $R^{17}$ is —H, =NH, $C_1$-$C_6$-alkyl, $C_3$-$C_7$-cycloalkyl, 3-oxetanyl, or 3-tetrahydrofuranyl.

In some embodiments, $R^{18}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON($C_1$-$C_6$-alkyl)$_2$.

In other embodiments, $R^{19}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, or —$CH_2SO_2$—$C_1$-$C_6$-alkyl.

In some embodiments, $A^1$ and $A^2$ are independently CH.

In other embodiments, $R^{12}$ is =O

In other embodiments, a Bax inhibiting compound having formula (II) can include the following formula:

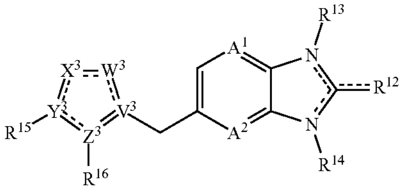

or a pharmaceutically acceptable salt, tautomer, or solvate thereof, wherein:

$R^{12}$ is =O or $R^{17}$; and when $R^{12}$ is =O, $R^{13}$ and $R^{14}$ are independently absent, —H, $C_1$-$C_6$-alkyl, $C_3$-$C_7$-cycloalkyl, 3-oxetanyl, or 3-tetrahydrofuranyl, or when $R^{12}$ is $R^{17}$, $R^{13}$ or $R^{14}$ is absent and the other is —H, $C_1$-$C_6$-alkyl, $C_3$-$C_7$-cycloalkyl, 3-oxetanyl, or 3-tetrahydrofuranyl;

$A^1$ and $A^2$ are independently CH or N;

the heterocycle comprising $V^3$, $W^3$, $X^3$, $Y^3$ and $Z^3$ and its substituents $R^{15}$ and $R^{16}$ is a heteroaromic ring with two double bonds, including, for example, pyrrole, imidazole, pyrazole or triazole; $V^3$, $W^3$, $X^3$, $Y^3$ and $Z^3$ can independently be CH or N, with 1-3 of these atoms being N;

$\overline{---}$ represents a single or double bond;

$R^{15}$ and $R^{16}$ are independently $C_1$-$C_6$-alkyl, $C_3$-$C_7$-cycloalkyl, phenyl or $C_5$-$C_6$ heteroaryl optionally substituted with $R^{18}$, or a $C_4$-$C_6$ heterocyclic ring with one or two heteroatoms chosen from the group consisting of N, O, S;

$R^{17}$ is —H, —NH, $C_1$-$C_6$-alkyl, $C_3$-$C_7$-cycloalkyl, 3-oxetanyl, or 3-tetrahydrofuranyl;

alternatively, $R^{15}$ together with $R^{16}$ and the ring to which they are attached can form a benzimidazole ring in which $V^3$ and $X^3$ are N and $W^3$ is CH and $Y^3$ and $Z^3$ are C atoms at the ring fusion; the benzimidazole ring being optionally substituted with one or two $R^{19}$ substituents;

$R^{18}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON($C_1$-$C_6$-alkyl$)_2$; and $R^{19}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, or —$CH_2SO_2$—$C_1$-$C_6$-alkyl.

In some embodiments, $A^1$ and $A^2$ are independently CH.

In other embodiments, $R^{12}$ is =O

In some embodiments, the Bax inhibiting compound of formula (II) can have the following formula:

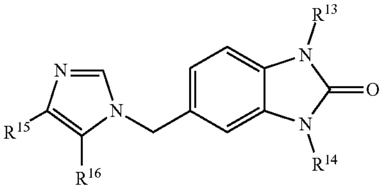

, wherein $R^{13}$ and $R^{14}$ are independently —H, $C_1$-$C_6$-alkyl, $C_3$-$C_7$-cycloalkyl, 3-oxetanyl, 3-tetrahydrofuranyl;

$R^{15}$ and $R^{16}$ are independently $C_1$-$C_6$-alkyl, $C_3$-$C_7$-cycloalkyl, phenyl or $C_5$-$C_6$ heteroaryl optionally substituted with $R^{18}$, or a $C_4$-$C_6$ heterocyclic ring with one or two heteroatoms chosen from the group consisting of N, O, S;

$R^{17}$ is —H, $C_1$-$C_6$-alkyl, $C_3$-$C_7$-cycloalkyl, 3-oxetanyl, or 3-tetrahydrofuranyl;

or $R^{15}$ together with $R^{16}$ and the ring to which they are attached can be a benzimidazole ring; the benzimidazole ring can be optionally substituted with one or two $R^{19}$ substituents;

$R^{18}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON($C_1$-$C_6$-alkyl$)_2$; and $R^{19}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, or —$CH_2SO_2$—$C_1$-$C_6$-alkyl.

In other embodiments, the Bax inhibiting compound having formula (II) can have the following formula:

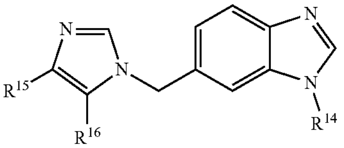

, wherein $R^{14}$ is —H, $C_1$-$C_6$-alkyl, $C_3$-$C_7$-cycloalkyl, 3-oxetanyl, 3-tetrahydrofuranyl $R^{15}$ and $R^{16}$ are independently $C_1$-$C_6$-alkyl, $C_3$-$C_7$-cycloalkyl, phenyl or $C_5$-$C_6$ heteroaryl optionally substituted with $R^{18}$, or a $C_4$-$C_6$ heterocyclic ring with one or two heteroatoms chosen from the group consisting of N, O, S;

$R^{17}$ is —H, $C_1$-$C_6$-alkyl, $C_3$-$C_7$-cycloalkyl, 3-oxetanyl, or 3-tetrahydrofuranyl; or $R^{15}$ together with $R^{16}$ and the ring to which they are attached can be a benzimidazole ring; the benzimidazole ring being optionally substituted with one or two $R^{19}$ substituents;

$R^{18}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, —$CH_2SO_2$—$C_1$-$C_6$-alkyl, —$CONH_2$, —CONH—$C_1$-$C_6$-alkyl, or —CON($C_1$-$C_6$-alkyl$)_2$; and $R^{19}$ is halo, $C_1$-$C_6$-alkyl, $C_3$-$C_7$-cycloalkyl, —CN, —O—$C_1$-$C_6$-alkyl, —O—$C_3$-$C_7$-cycloalkyl, —$SO_2$—$C_1$-$C_6$-alkyl, or —$CH_2SO_2$—$C_1$-$C_6$-alkyl.

In some embodiments, the Bax inhibiting compound having formula (II) can be selected from the group consisting of:

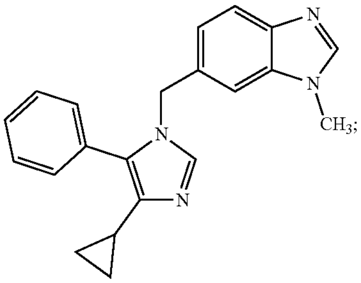

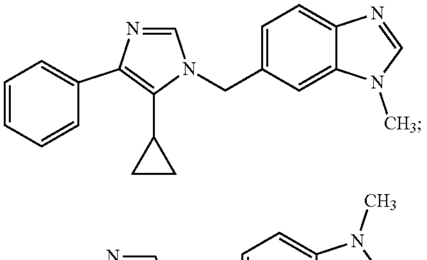

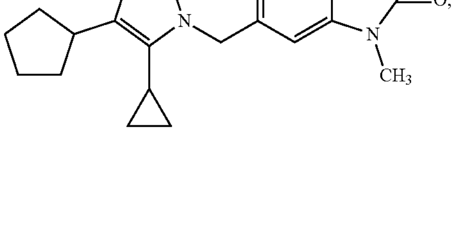

-continued
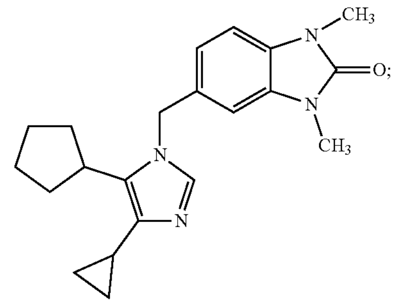
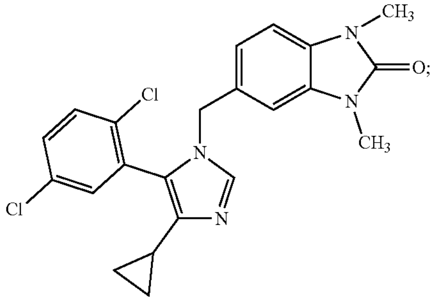
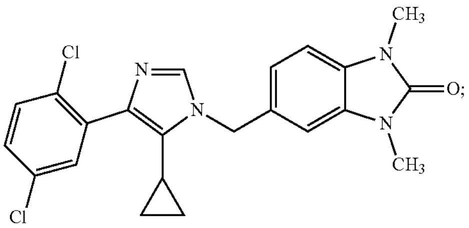
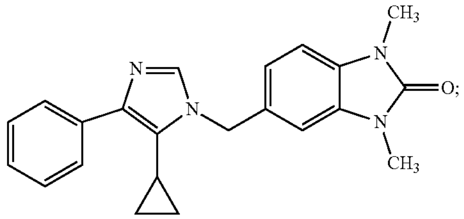
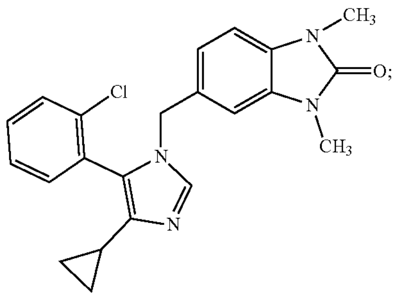
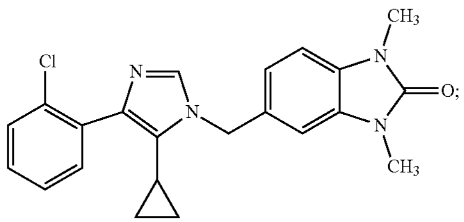
-continued
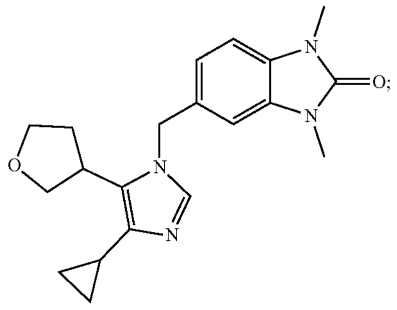
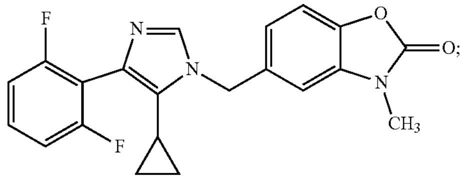
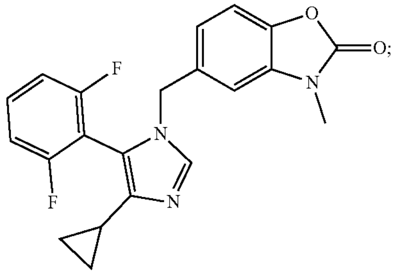
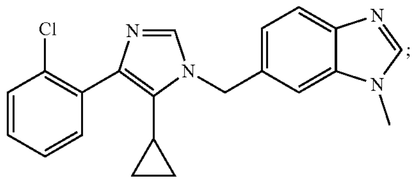
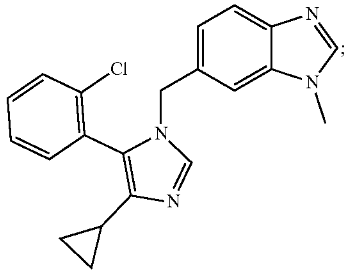
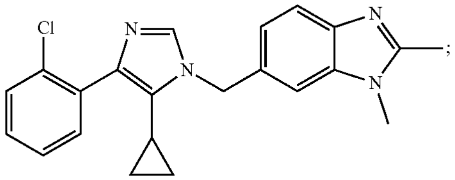
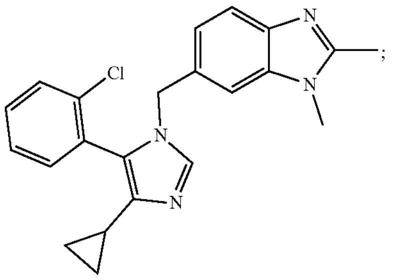

-continued
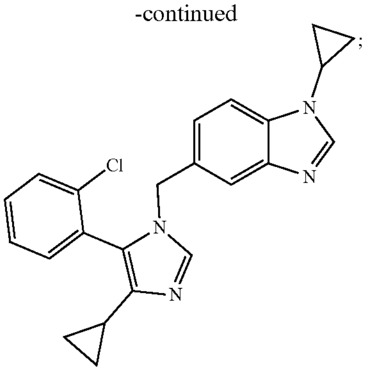
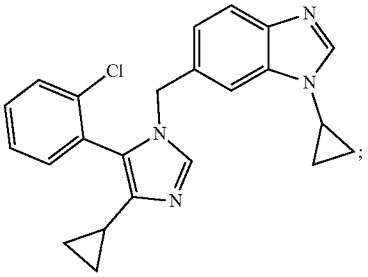
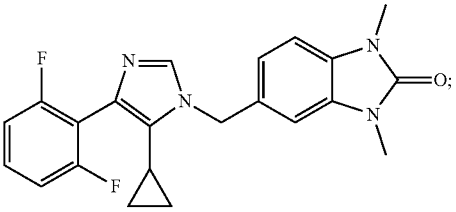
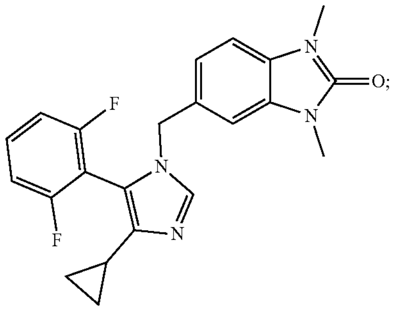
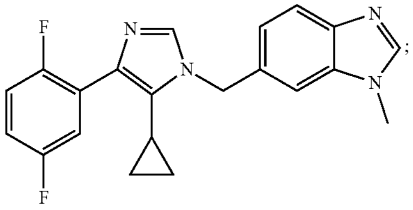
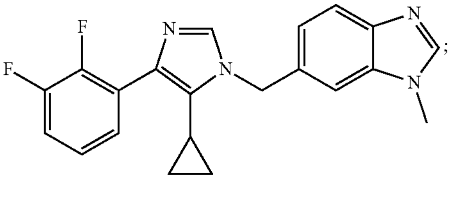
-continued
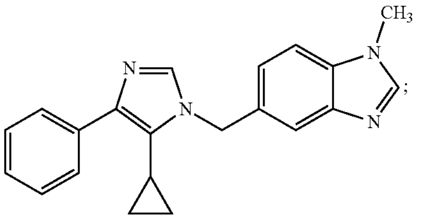
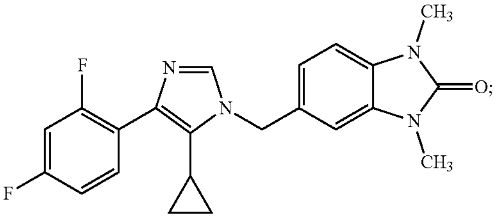
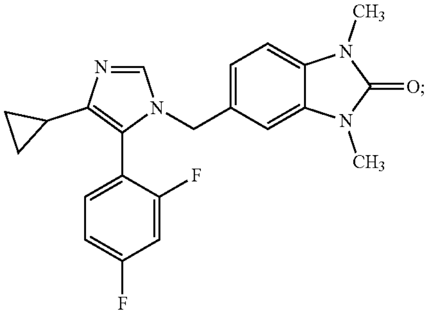
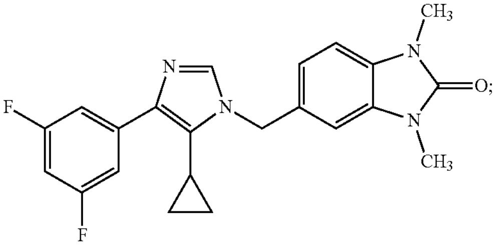
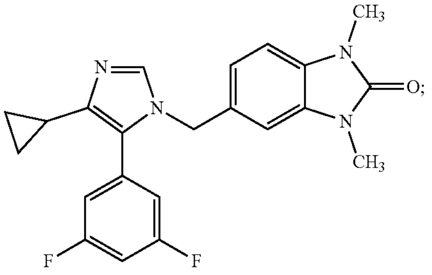
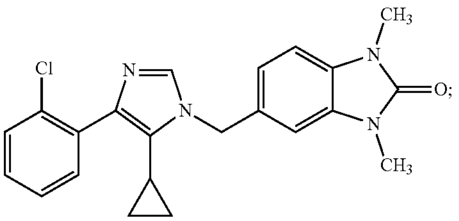

-continued
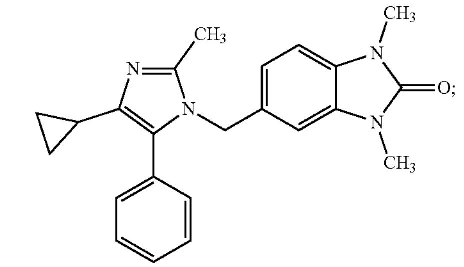
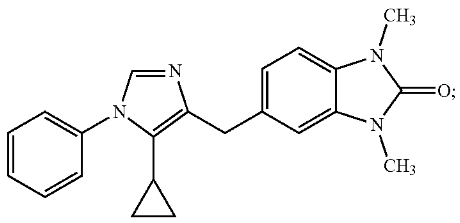
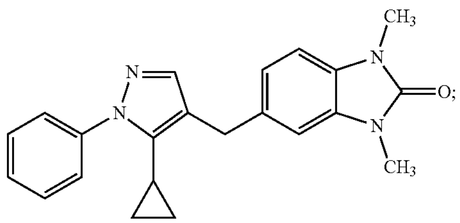
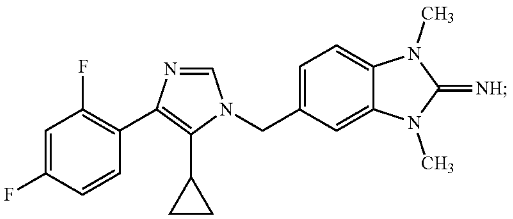
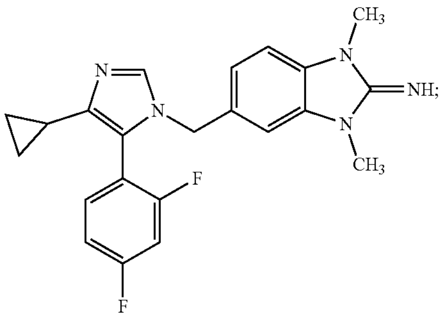
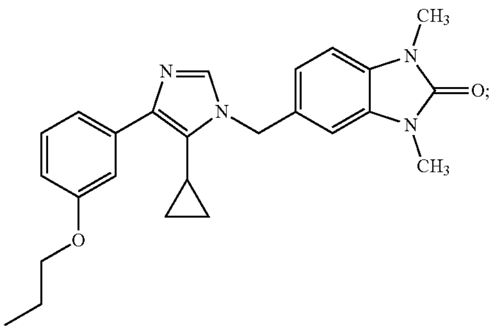
-continued
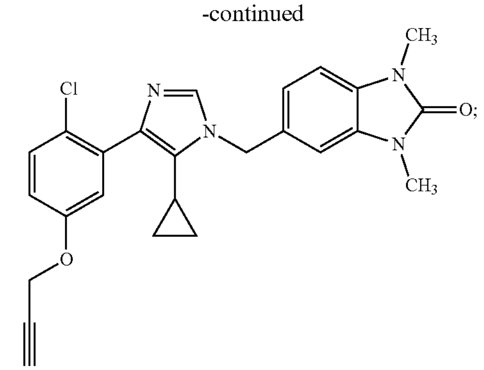
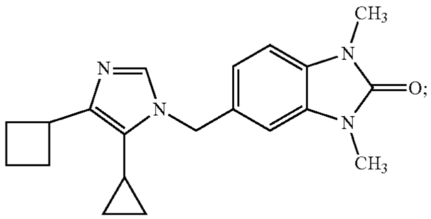
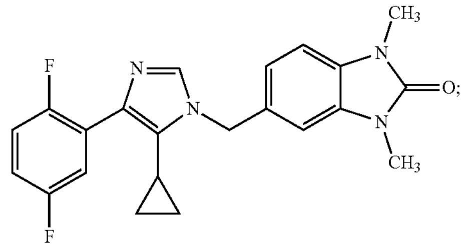
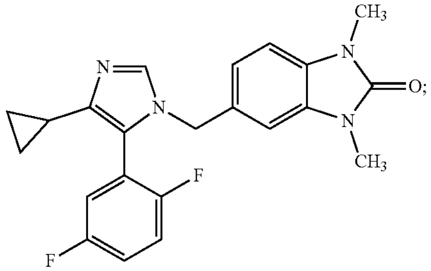
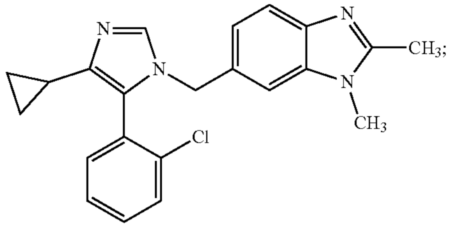
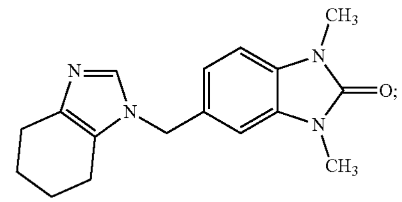
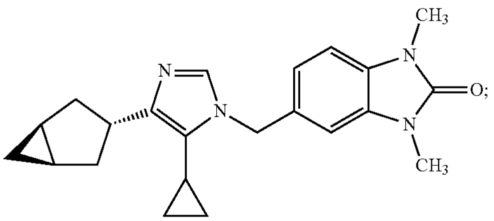

-continued
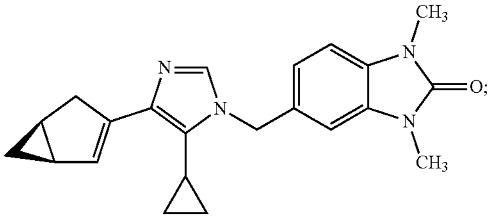
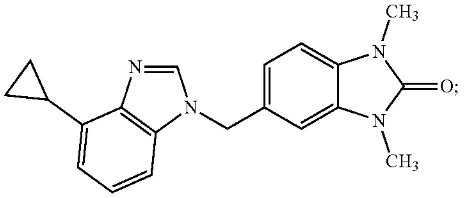
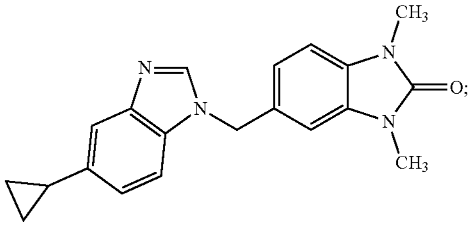
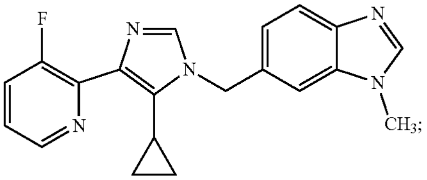
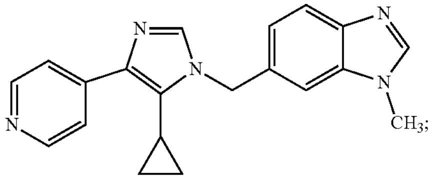
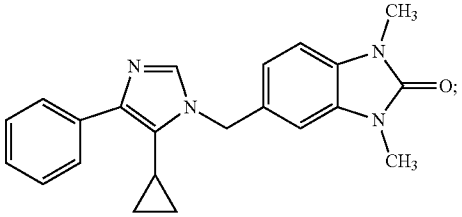
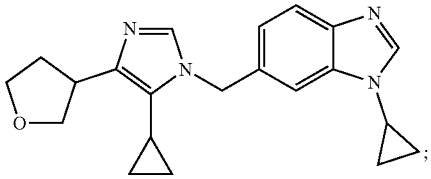
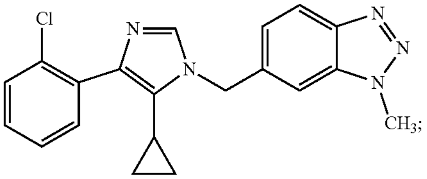
-continued
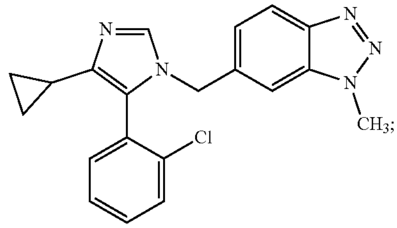
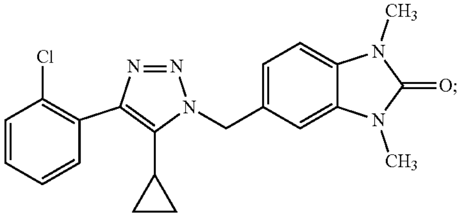
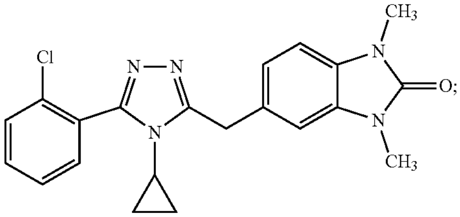
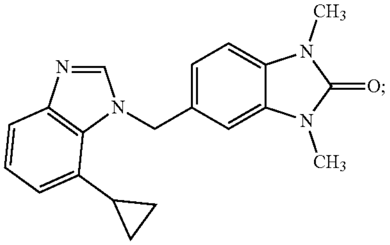
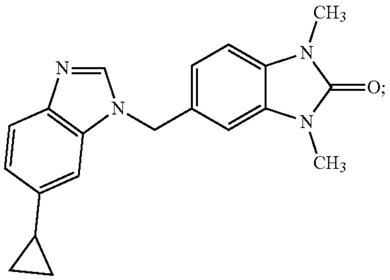
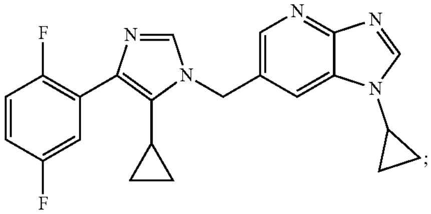
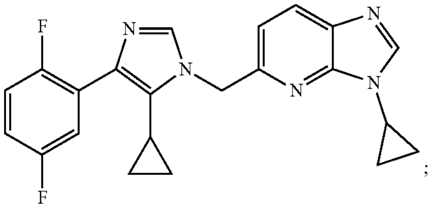

-continued
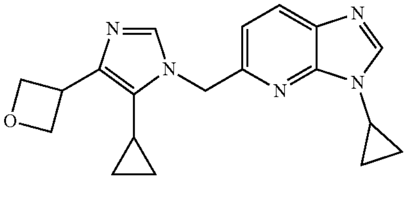
;
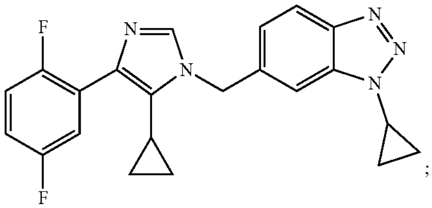
;
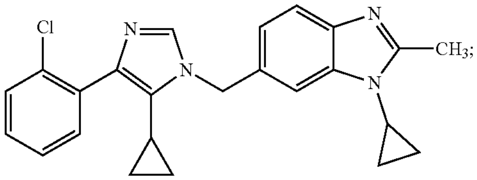
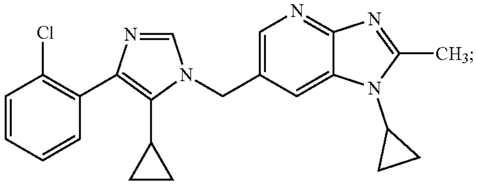
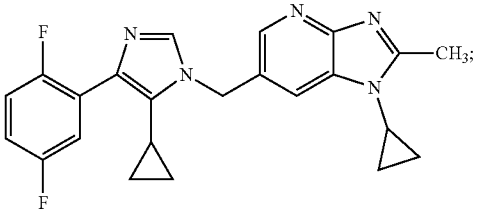
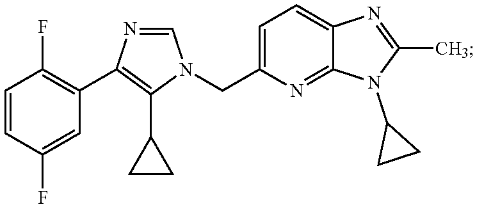
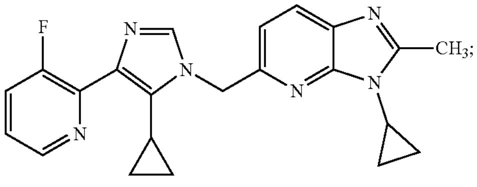
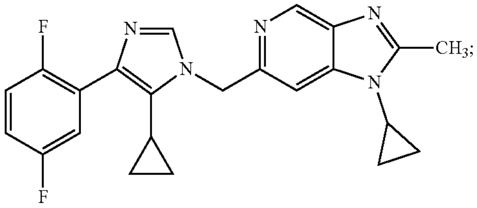
-continued
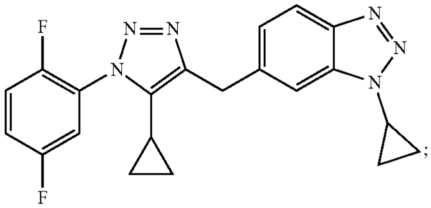
;
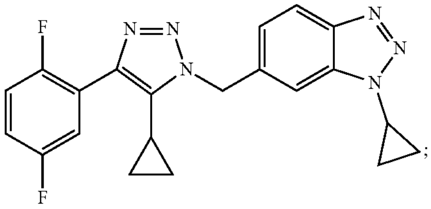
;
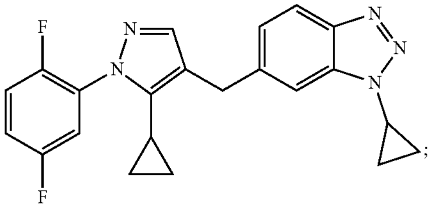
;
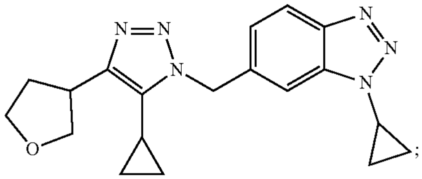
;
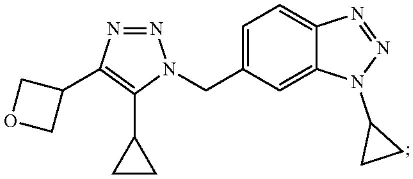
;
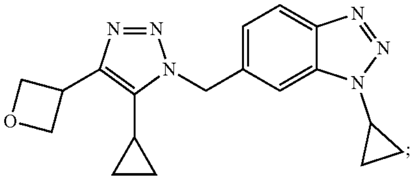
;
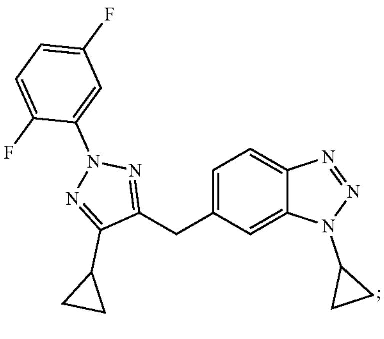
;

-continued

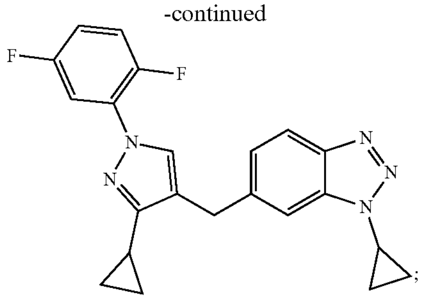

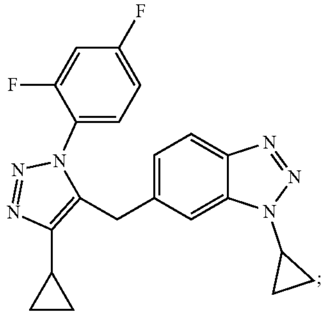

and pharmaceutically acceptable salts thereof.

In some embodiments, the Bax inhibiting compounds can be provided in a pharmaceutical composition that includes the Bax inhibiting compound and a pharmaceutically acceptable excipient or a carrier.

In other embodiments, the compound or Bax inhibiting compounds described herein can inhibit the Mouse Embryonic Fibroblasts (MEFs) from Bax-induced cell death Bax at an $IC_{50}$ of less than or equal to 1 μM, an $IC_{50}$ of less than or equal to 250 nM, an $IC_{50}$ of less than or equal to 50 nM, an $IC_{50}$ of less than or equal to 10 nM, an $IC_{50}$ of less than or equal to 5 nM, an $IC_{50}$ of about 2.5 nM to about 10 nM, or an $IC_{50}$ of less than or equal to about 2.5 nM.

In some embodiments, the Bas inhibiting compounds (e.g., formula I-II) have a human or mouse microsome stability $T_{1/2}$ of greater than 50 minutes, greater than 60 minute, greater than 70 minutes, greater than 80 minutes, greater than 90 minutes, or greater than 100 minutes, including all values and ranges there between. In embodiments, the Bax inhibiting compounds described herein have a human or mouse microsome stability $T_{1/2}$ of greater than 110 minutes, greater than 120 minutes, greater than 130 minutes, or greater than 145 minutes, including all values and ranges therebetween. In embodiments the Bax inhibiting compounds described herein have a human or mouse microsome stability $T_{1/2}$ ranging from 65 to at least 145 (e.g., 65, 70, 80, 90, 100, 110, 120, 130, 140, 150, 160, 170, 180, 190, 200, or more, including all values and ranges therebetween). In embodiments, the Bax inhibiting compounds described herein have a human or mouse microsome stability $T_{1/2}$ of greater than 145 minutes.

The Bax inhibiting compounds described herein can be used in a method of inhibiting apoptosis in a cell by administering to the cell a therapeutically effective amount of the Bax inhibiting compound. An "effective amount" or "therapeutically effective amount" of the Bax inhibiting compound administered to a cell is the amount of the Bax inhibiting compound effective to mitigate Bax mediated apoptosis in the cell. In some embodiments, the Bax mediated apoptosis is induced by, for example, cell injury, a degenerative disorder or disease, or cytotoxic stresses elicited, for example, by chemo- and radiotherapy delivered to the cell.

It is well known that apoptosis, and particularly Bax mediated apoptosis, is centrally involved in the pathogenesis of many human illnesses and injury states. The following references describe the Bax protein playing a key role in various diseases: Injury-induced neuron death-Deckwerth, et al. Neuron. 17:401-411, 1996; Martin, et al., J. Compo Neurol. 433:299-311, 2001; Kirkland, et al., J. Neurosci. 22:6480-90, 2002; Alzheimer disease-MacGibbon, et al., Brain Res. 750:223-234, 1997; Selznick, et al., J. Neuropathol. Exp. Neurol. 59:271-279, 2000; Cao, et al., J. Cereb. Blood Flow Metab. 21:321-333, 2001; Zhang, et al., J. Cell Biol. 156:519-529, 2002; Ischemia induced cell damage-Kaneda, et al., Brain Res. 815: 11-20, 1999; Gibson, et al., Mol. Med. 7:644-655, 2001; HIV (AIDS) and Bax: Castedo, et al., J. Exp. Med. 45 194:1097-1110, 2001; Drug-induced neuron death-Dargusch, et al., J. Neurochem. 76:295-301, 2001; Parkinson's disease-Ploix and Spier, Trends Neurosci. 24:255, 2001; Huntington's disease-Antonawich, et al., Brain Res. Bull. 57:647-649, 2002.

Therefore, in another embodiment, a pharmaceutical composition comprising a compound described herein can be administered to a subject for the treatment of an apoptotic disease. The method includes administering a therapeutically effective amount of a pharmaceutical composition comprising the Bax inhibiting compound to the subject. For example, a therapeutically effective amount of a pharmaceutical composition including a Bax inhibiting compound described herein encompasses the reduction of Bax mediated cell or tissue death in a subject.

Apoptotic diseases and related disorders as contemplated herein, can include, for example, stroke, heart attack, ischemia, degenerative diseases (neuron and muscle, e.g., Alzheimer disease, Parkinson's disease, cardiomyocyte degeneration, etc), macular degeneration, hypoxia induced apoptosis, ischemia, atrophy, infection by parasitic organisms (virus, bacteria, yeast, or protozoa, etc), side effects of other drugs (e.g., anti-cancer drugs), UV/X-ray irradiation, and several other pathological conditions triggering cell death signals.

As described above, the compositions described herein can be used to inhibit Bax mediated cell death wherein Bax overexpression in the cell is induced by chemo- and radiotherapy. In one exemplary embodiment, a pharmaceutical composition described above can protect megakaryocytes from chemotherapy induced apoptosis without substantially affecting the ability of megakaryocytes to produce and release platelets.

It is further contemplated that the pharmaceutical compositions described herein can be used in a combination therapy or adjunctive therapy with antiproliferative agents or chemotherapeutic agents for the treatment of proliferative disorders, such as neoplastic disorders or cancer. The phrase "combination therapy" embraces the administration of the pharmaceutical compositions including the Bax inhibiting compounds described herein and a therapeutic agent as part of a specific treatment regimen intended to provide a beneficial effect from the co-action of these therapeutic agents.

Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The apoptotic disease treated by the combination therapy can include proliferative diseases, such as neoplastic disorders (e.g., leukemia) and cancer. Besides being useful for human treatment, the combination therapy is also useful for veterinary treatment of companion animals, exotic and farm animals, including rodents, horses, dogs, and cats.

In another embodiment of the invention, the therapeutic agents administered in combination therapy with the Bax inhibiting compounds described herein or pharmaceutical compositions thereof can comprise at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

Other embodiments described herein relate to a method of preserving tissues and organs for transfusions or transplantation. In some embodiments, the cells, tissue, or organ can be stored in and/or contacted with a composition including a Bax inhibiting compound described herein. The effective amount of the Bax inhibiting compound is an amount effective to mitigate Bax mediated apoptosis of the cells, tissue, or organ of interest. In some embodiments, a composition for storing cells or organs can include an effective amount of the Bax inhibiting compound and an organ preservation solution.

Typically, the tissue or organ has been separated from its usual nutrient sources, e.g., the blood circulation of a living animal or person. Organ preservation solutions depend on contacting, storing and/or perfusing the organ with a supportive preservation solution designed to provide pH buffering, osmotic balance and/or some minimal nutritional support, e.g., in the form of glucose and a limited set of other basic nutrients. This approach is typically combined with reduction in organ temperature to just above the freezing point of water. This is intended to reduce the metabolic rate of organ tissues, thus slowing the consumption of nutrients and the production of waste products. Thus, in some embodiments, a pharmaceutical composition containing the Bax inhibiting compound described herein can be employed at the hypothermic ranges commonly used in the art, which can range from below 20° C. to about 4° C. These art-known preservative solutions include, for example, isotonic saline solutions, that may contain, in various proportions, salts, sugars, osmotic agents, local anesthetic, buffers, and other such agents, as described, simply by way of example, by Berdyaev et al., U.S. Pat. No. 5,432,053; Belzer et al., described by U.S. Pat. Nos. 4,798,824, 4,879,283; and 4,873,230; Taylor, U.S. Pat. No. 5,405,742; Dohi et al., U.S. Pat. No. 5,565,317; Stern et al., U.S. Pat. Nos. 5,370,989 and 5,552,267.

The term, "organ" as used herein encompasses both solid organs, e.g., kidney, heart, liver, lung, pancreas, as well as functional parts of organs, e.g., segments of skin, sections of artery, transplantable lobes of a liver, kidney, lung, and other organs. The term, "tissue" refers herein to viable cellular materials in an aggregate form, e.g., small portions of an organ, as well as dispersed cells, e.g., cells dispersed, isolated and/or grown from heart muscle, liver or kidney, including bone marrow cells and progeny cells, blood born stem cells and progeny, and the various other art-known blood elements, unless otherwise specified.

Other embodiments described herein relate for localized or systemic circulatory or perfusion support for organs or tissues acutely deprived of normal blood circulation caused by trauma, e.g., infusions or temporary circulation of the Bax inhibiting compounds described herein to support a partially severed limb, or analogous conditions, until surgical repair of damaged vasculature is achieved.

Syndromic conditions, traumatic injuries, chronic conditions, medical interventions, or other conditions that cause or are associated with tissue damage and a need for tissue repair, and thus, suitable for treatment or amelioration using the methods described herein, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetes, diabetic neuropathy, diabetes induced ischemia, disseminated intravascular coagulation (DIC), embolic brain ischemia, graft-versus-host disease, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other illustrative examples of genetic disorders, syndromic conditions, traumatic injuries, chronic conditions, medical interventions, or other conditions that cause or are associated with tissue damage and a need for tissue repair suitable for treatment or amelioration using the Bax inhibiting compounds described herein, include, ischemia resulting from surgery, chemotherapy, radiation therapy, or cell, tissue, or organ transplant or graft.

In various embodiments, the Bax inhibiting compounds described herein can be used for treating ischemia, such as cerebrovascular ischemia, myocardial ischemia, limb ischemia (CLI), myocardial ischemia (especially chronic myocardial ischemia), ischemic Zcardiomyopathy, cerebrovascular ischemia, renal ischemia, pulmonary ischemia, intestinal ischemia, and the like.

In some embodiments, the ischemia is associated with at least one of acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

In some embodiments, the Bax inhibiting compounds described herein can be administered to a preparation of hematopoietic stem cells, such as peripheral blood hematopoietic stem cells or umbilical cord stem cells of the subject, to increase the fitness of the stem cell preparation as a donor graft or to decrease the number of units of umbilical cord blood required for transplantation.

In some embodiments, the hematopoietic stem cells can be administered or contacted ex vivo with one or more Bax inhibiting compounds described herein to provide a therapeutic composition. In one embodiment, the therapeutic compositions of the can include a population of hematopoietic stem cells treated ex vivo with a one or more of the Bax inhibiting compounds described herein. In certain embodiments, the therapeutic composition comprising the enhanced HSPCs is whole bone marrow, umbilical cord blood, or mobilized peripheral blood.

Preparations of hematopoietic stem cells administered one or more of the Bax inhibiting Bax inhibiting compounds described herein and/or therapeutic compositions that include hematopoietic stem cells and one or more Bax inhibiting compounds described herein can be used for improving hematopoietic stem cell transplants and in treating ischemia or ischemia-damaged tissue, and in reducing further damage to ischemic tissue and/or repairing damage to ischemic tissue through cell recruitment, improving vascularization in ischemic tissue, improving tissue regeneration at sites of ischemia, decreasing ischemic tissue necrosis or apoptosis, and/or increasing cell survival at sites of ischemia. In particular embodiments, the preparations of the Bax inhibiting compound treated hematopoietic stem cells and/or therapeutic compositions of Bax inhibiting compounds and hematopoietic stem cells are useful to subjects in need of hematopoietic reconstitution, such as subjects that have undergone or are scheduled to undergo myeloablative therapy.

Subjects, which can be treated with the preparations of Bax inhibiting compound treated hematopoietic stem cells and/or therapeutic compositions of Bax inhibiting compounds and hematopoietic stem cells, can include subjects that have or that have been diagnosed with various types of leukemias, anemias, lymphomas, myelomas, immune deficiency disorders, and solid tumors. A subject also includes a human who is a candidate for stem cell transplant or bone marrow transplantation, such as during the course of treatment for a malignant disease or a component of gene therapy. Subjects may also include individuals or animals that donate stem cells or bone marrow for allogeneic transplantation. In certain embodiments, a subject may have undergone myeloablative irradiation therapy or chemotherapy, or may have experienced an acute radiation or chemical insult resulting in myeloablation. In certain embodiments, a subject may have undergone irradiation therapy or chemotherapy, such as during various cancer treatments. Typical subjects include animals that exhibit aberrant amounts (lower or higher amounts than a "normal" or "healthy" subject) of one or more physiological activities that can be modulated by an agent or a stem cell or marrow transplant.

Subjects, which can be treated with the preparations of Bax inhibiting compound treated hematopoietic stem cells and/or therapeutic compositions of Bax inhibiting compounds and hematopoietic stem cells, can also include subjects undergoing chemotherapy or radiation therapy for cancer, as well as subjects suffering from (e.g., afflicted with) non malignant blood disorders, particularly immunodeficiencies (e.g. SCID, Fanconi's anemia, severe aplastic anemia, or congenital hemoglobinopathies, or metabolic storage diseases, such as Hurler's disease, Hunter's disease, mannosidosis, among others) or cancer, particularly hematological malignancies, such as acute leukemia, chronic leukemia (myeloid or lymphoid), lymphoma (Hodgkin's or non-Hodgkin's), multiple myeloma, myelodysplastic syndrome, or non-hematological cancers such as solid tumors (including breast cancer, ovarian cancer, brain cancer, prostate cancer, lung cancer, colon cancer, skin cancer, liver cancer, or pancreatic cancer).

Subjects may also include subjects suffering from aplastic anemia, an immune disorder (severe combined immune deficiency syndrome or lupus), myelodysplasia, thalassemaia, sickle-cell disease or Wiskott-Aldrich syndrome. In some embodiments, the subject suffers from a disorder that is the result of an undesired side effect or complication of another primary treatment, such as radiation therapy, chemotherapy, or treatment with a bone marrow suppressive drug, such as zidovadine, chloramphenical or gangciclovir. Such disorders include neutropenias, anemias, thrombocytopenia, and immune dysfunction. Other subjects may have disorders caused by an infection (e.g., viral infection, bacterial infection or fungal infection) which causes damage to stem or progenitor cells of the bone marrow.

In other embodiments, the Bax inhibiting compounds described herein can be administered to a recipient of a bone marrow transplant, of a hematopoietic stem cell transplant, or of an umbilical cord blood stem cell transplant, in order to decrease the administration of other treatments or growth factors.

In some embodiments, the Bax inhibiting compounds described herein can be administered to a subject to enhance recovery of neutrophils following bone marrow transplantation, following umbilical cord blood transplantation, following transplantation with hematopoietic stem cells, following conventional chemotherapy, following radiation treatment, and in individuals with neutropenias from diseases that include but are not limited to aplastic anemia, myelodysplasia, myelofibrosis, neutropenias from other bone marrow diseases, drug induced neutropenia, immune neutropenias, idiopathic neutropenia, and following infections with viruses that include, but are not limited to, HIV, CMV, and parvovirus.

In other embodiments, the Bax inhibiting compounds described herein can be administered to a subject to enhance recovery of platelets following bone marrow transplantation, following umbilical cord blood transplantation, following transplantation with hematopoietic stem cells, following conventional chemotherapy, following radiation treatment, and in individuals with neutropenias from diseases that include but are not limited to aplastic anemia, myelodysplasia, myelofibrosis, thrombocytopenias from other bone marrow diseases, drug induced thrombocytopenia, immune thrombocytopenia, idiopathic thrombocytopenic purpura, idiopathic thrombocytopenia, and following infections with viruses that include, but are not limited to, HIV, CMV, and parvovirus.

In still other embodiments, the Bax inhibiting compounds described herein can be administered to a subject to enhance recovery of hemoglobin following bone marrow transplantation, following umbilical cord blood transplantation, following transplantation with hematopoietic stem cells, following conventional chemotherapy, following radiation treatment, and in individuals with anemias from diseases that include but are not limited to aplastic anemia, myelodysplasia, myelofibrosis, anemia from other bone marrow diseases, drug induced anemia, immune mediated anemias, anemia of chronic disease, idiopathic anemia, and following infections with viruses that include, but are not limited to, HIV, CMV, and parvovirus.

In some embodiments, the Bax inhibiting compounds described herein can be administered to a subject to enhance numbers of bone marrow stem cell numbers following bone marrow transplantation, following umbilical cord blood transplantation, following transplantation with hematopoietic stem cells, following conventional chemotherapy, following radiation treatment, in individuals with other bone marrow diseases, in individuals with cytopenias following viral infections, and in individuals with cytopenias.

In further embodiments, the Bax inhibiting compounds described herein can be administered to a subject or to a tissue graft of a subject to mitigate graft rejection, to enhance graft engraftment, to enhance graft engraftment following treatment of the subject or the marrow of the subject with radiation therapy, chemotherapy, or immunosuppressive therapy, to confer resistance to toxic or lethal effects of exposure to radiation, confer resistance to the toxic effect of Cytoxan, the toxic effect of fludarabine, the toxic effect of chemotherapy, or the toxic effect of immunosuppressive therapy, to decrease infection, and/or to decrease pulmonary toxicity from radiation.

In other embodiments, the Bax inhibiting compounds described herein can be administered to a recipient of a tissue stem cell transplant, including but not limited to a transplant with hematopoietic stem cells, neural stem stems, mesenchymal stem cells, or stem cells for other tissues, so as to accelerate tissue regeneration and repair following the transplant.

The Bax inhibiting compounds described herein can be provided in a pharmaceutical composition or cosmetic composition depending on the pathological or cosmetic condition or disorder being treated. A pharmaceutical composition containing the Bax inhibiting compounds described herein as an active ingredient may be manufactured by mixing the derivative with a pharmaceutically acceptable carrier(s) or an excipient(s) or diluting the Bax inhibiting compounds described herein with a diluent in accordance with conventional methods. The pharmaceutical composition may further contain fillers, anti-cohesives, lubricants, wetting agents, flavoring agents, emulsifying agents, preservatives and the like. The pharmaceutical composition may be formulated into a suitable formulation in accordance with the methods known to those skilled in the art so that it can provide an immediate, controlled or sustained release of the Bax inhibiting compounds described herein after being administered into a mammal.

In some embodiments, the pharmaceutical composition may be formulated into a parenteral or oral dosage form. The solid dosage form for oral administration may be manufactured by adding excipient, if necessary, together with binder, disintegrants, lubricants, coloring agents, and/or flavoring agents, to the Bax inhibiting compounds and shaping the resulting mixture into the form of tablets, sugar-coated pills, granules, powder or capsules. The additives that can be added in the composition may be ordinary ones in the art. For example, examples of the excipient include lactose, sucrose, sodium chloride, glucose, starch, calcium carbonate, kaolin, microcrystalline cellulose, silicate and the like. Exemplary binders include water, ethanol, propanol, sweet syrup, sucrose solution, starch solution, gelatin solution, carboxymethylcellulose, hydroxypropyl cellulose, hydroxypropyl starch, methylcellulose, ethylcellulose, shellac, calcium phosphonate and polypyrrolidone. Examples of the disintegrant include dry starch, sodium arginate, agar powder, sodium bicarbonate, calcium carbonate, sodium lauryl sulfate, stearic monoglyceride and lactose. Further, purified talc, stearates, sodium borate, and polyethylene glycol may be used as a lubricant; and sucrose, bitter orange peel, citric acid, tartaric acid, may be used as a flavoring agent. In some embodiments, the pharmaceutical composition can be made into aerosol formulations (e.g., they can be nebulized) to be administered via inhalation.

The Bax inhibiting compounds described herein may be combined with flavoring agents, buffers, stabilizing agents, and the like and incorporated into oral liquid dosage forms such as solutions, syrups or elixirs in accordance with conventional methods. One example of the buffers may be sodium citrate. Examples of the stabilizing agents include tragacanth, acacia and gelatin.

In some embodiments, the Bax inhibiting compounds described herein described herein may be incorporated into an injection dosage form, for example, for a subcutaneous, intramuscular or intravenous route by adding thereto pH adjusters, buffers, stabilizing agents, relaxants, topical anesthetics. Examples of the pH adjusters and the buffers include sodium citrate, sodium acetate and sodium phosphate. Examples of the stabilizing agents include sodium pyrosulfite, EDTA, thioglycolic acid and thiolactic acid. The topical anesthetics may be procaine HCl, lidocaine HCl and the like. The relaxants may be sodium chloride, glucose and the like.

In other embodiments, the Bax inhibiting compounds described herein may be incorporated into suppositories in accordance with conventional methods by adding thereto pharmaceutically acceptable carriers that are known in the art, for example, polyethylene glycol, lanolin, cacao butter or fatty acid triglycerides, if necessary, together with surfactants such as Tween.

The pharmaceutical composition may be formulated into various dosage forms as discussed above and then administered through various routes including an oral, inhalational, transdermal, subcutaneous, intravenous or intramuscular route. The dosage can be a pharmaceutically effective amount. The pharmaceutically effective amount can be an amount of the Bax inhibiting compounds described herein to treat or inhibit cell death associated with a disease or disorder. The pharmaceutically effective amount of the compound will be appropriately determined depending on the kind and the severity of the disease to be treated, age, sex, body weight and the physical condition of the patients to be treated, administration route, duration of therapy and the like. Generally, the effective amount of the compound may be in the range of about 1 to 1,000 mg in the oral administration, about 0.1 to 500 mg in the intravenous administration, about 5 to 1,000 mg in the rectal administration. Generally, the daily dosage for adults is in the range of about 0.1 to 5,000 mg, preferably about to 1,000 mg but cannot be determined uniformly because it depends on age, sex, body weight and the physical condition of the patients to be treated. The formulation may be administered once a day or several times a day with a divided dose.

Cosmetic compositions containing the Bax inhibiting compounds described herein can include any substance or preparation intended to be brought into contact with the various superficial parts of the human body (epidermis, body hair and hair system, nails, lips and external genital organs) or with the teeth or the buccal mucous membranes for the purpose, exclusively or mainly, of cleansing them, of giving them a fragrance, of modifying their appearance and/or of correcting body odors and/or protecting them or of maintaining them in good condition.

The cosmetic composition can comprise a cosmetically acceptable medium that may be water or a mixture of water and at least one solvent selected from among hydrophilic organic solvents, lipophilic organic solvents, amphiphilic organic solvents, and mixtures thereof.

For topical application, the cosmetic composition can be administered in the form of aqueous, alcoholic, aqueous-alcoholic or oily solutions or suspensions, or of a dispersion of the lotion or serum type, of emulsions that have a liquid or semi-liquid consistency or are pasty, obtained by dispersion of a fatty phase in an aqueous phase (O/W) or vice versa (W/O) or multiple emulsions, of a free or compacted powder to be used as it is or to be incorporated into a physiologically acceptable medium, or else of microcapsules or microparticles, or of vesicular dispersions of ionic and/or nonionic type. It may thus be in the form of a salve, a tincture, milks, a cream, an ointment, a powder, a patch, an impregnated pad, a solution, an emulsion or a vesicular dispersion, a lotion, aqueous or anhydrous gels, a spray, a suspension, a shampoo, an aerosol or a foam. It may be anhydrous or aqueous. It may also comprise solid preparations constituting soaps or cleansing cakes.

The cosmetic compositions may in particular comprise a hair care composition, and in particular a shampoo, a setting lotion, a treating lotion, a styling cream or gel, restructuring lotions for the hair, a mask, etc. The cosmetic compositions can be a cream, a hair lotion, a shampoo or a conditioner. These can be used in particular in treatments using an application that may or may not be followed by rinsing, or else in the form of a shampoo. A composition in the form of a foam, or else in the form of spray or an aerosol, then comprising propellant under pressure, is also intended. It can thus be in the form of a lotion, serum, milk, cream, gel, salve, ointment, powder, balm, patch, impregnated pad, cake or foam.

In a known manner, the cosmetic compositions may also contain adjuvants that are normal in the cosmetics field, such as hydrophilic or lipophilic gelling agents, hydrophilic or lipophilic additives, preservatives, antioxidants, solvents, fragrances, fillers, UV-screening agents, odor absorbers and dyestuffs. The amounts of these various adjuvants are those conventionally used in the cosmetics field, and are for example from 0.1% to 20%, in particular less than or equal to 10%, of the total weight of the composition. According to their nature, these adjuvants can be introduced into the fatty phase, into the aqueous phase and/or into the lipid spherules.

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

The following examples describes the synthesis of novel Bax inhibitors.

Example 1

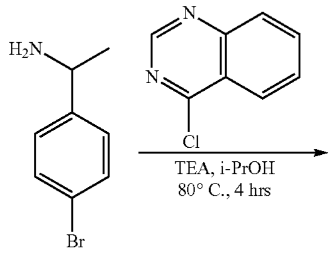

1

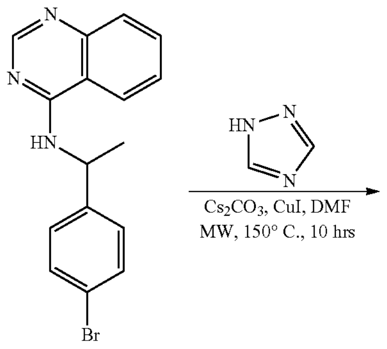

2

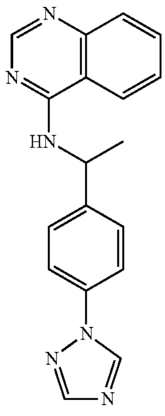

BAX-29

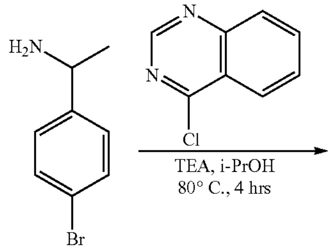

-continued

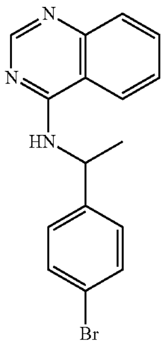

2

To a mixture of 1-(4-bromophenyl)ethanamine (100 mg, 422.77 umol, 1 eq, HCl) and TEA (171 mg, 1.69 mmol, 4 eq) in i-PrOH (2 mL) was added 4-chloroquinazoline (77 mg, 465.04 umol, 1.1 eq) and the mixture was stirred at 80° C. for 4 hours. The reaction was concentrated in vacuo. The residue was purified by column chromatography ($SiO_2$, Petroleum ether/Ethyl acetate=10/1 to 2:1) to give N-[1-(4-bromophenyl)ethyl]quinazolin-4-amine (250 mg, 761.72 umol, 90.09% yield, 2 batches in parallel) as a white solid. ESI [M+H]=328.3/330.3.

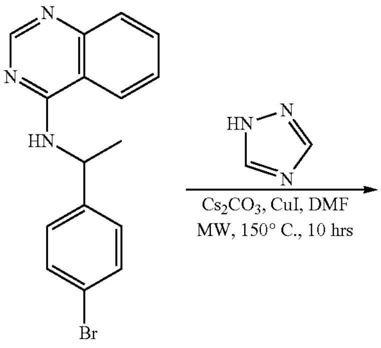

2

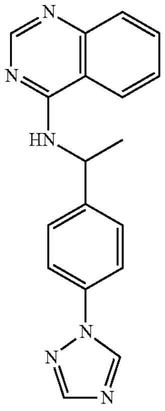

BAX-29

N-[1-(4-bromophenyl)ethyl]quinazolin-4-amine (100.00 mg, 304.69 umol, 1 eq), 1H-1,2,4-triazole (42 mg, 609.37 umol, 2 eq) and $Cs_2CO_3$ (199 mg, 609.37 umol, 2 eq), CuI (12 mg, 60.94 umol, 0.2 eq) were taken up into a microwave tube in DMF (2 mL). The sealed tube was heated at 150° C.

for 10 hours under microwave. The reaction was added water (20 mL) and extracted with EtOAc (10 mL×3). The organic layer was washed with brine (20 mL), dried over $MgSO_4$ and concentrated in vacuo. The residue was purified by prep-HPLC (column: Kromasil 250*50 mm*10 um; mobile phase: [water (10 mM NH4HCO3)-ACN]; B %: 10%-40%, 10 min) to give N-[1-[4-(1,2,4-triazol-1-yl)phenyl]ethyl]quinazolin-4-amine (43.65 mg, 137.81 umol, 45.23% yield, 99.882% purity) as a white solid.

$^1$H NMR (400 MHz, CHLOROFORM-d) δ 8.67 (s, 1H), 8.56 (s, 1H), 8.12 (s, 1H), 7.89 (d, J=8.6 Hz, 1H), 7.84-7.76 (m, 2H), 7.72-7.66 (m, 2H), 7.64-7.57 (m, 2H), 7.57-7.50 (m, 1H), 5.90 (br d, J=6.4 Hz, 1H), 5.70 (quin, J=6.9 Hz, 1H), 1.76 (d, J=7.0 Hz, 3H). ESI [M+H]=317.1.

Example 2

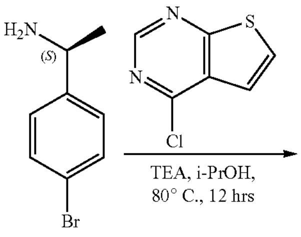

1

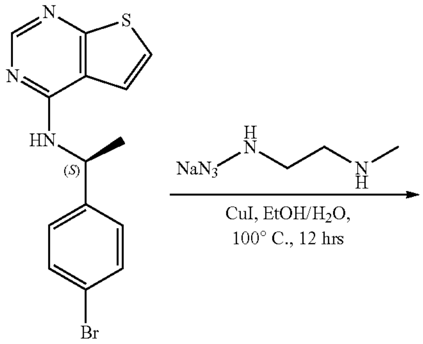

2

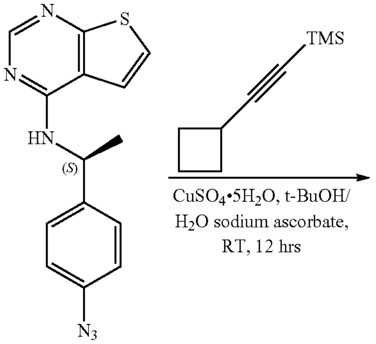

3

-continued

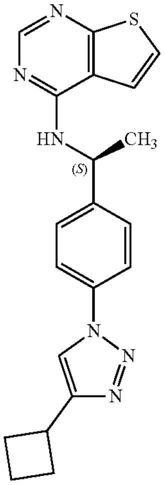

BAX-32 (S)

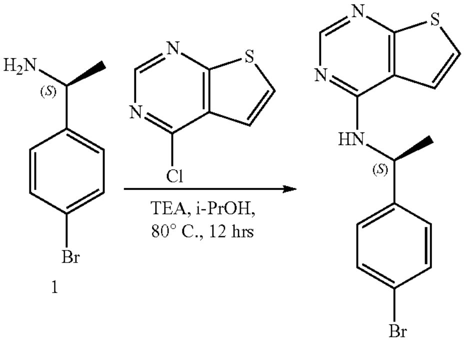

1 2

A mixture of (1S)-1-(4-bromophenyl)ethanamine (6 g, 29.99 mmol, 4.32 mL, 1 eq), 4-chlorothieno[2,3-d]pyrimidine (5.88 g, 34.49 mmol, 1.15 eq) and TEA (6.07 g, 59.98 mmol, 8.35 mL, 2 eq) in i-PrOH (200 mL) was stirred at 80° C. for 12 hours. The reaction mixture was concentrated in vacuo. The residue was purified by column chromatography ($SiO_2$, Petroleum ether:THF=20:1 to 5:1) to give N-[(1S)-1-(4-bromophenyl)ethyl]thieno[2,3-d]pyrimidin-4-amine (7.8 g, 23.34 mmol, 77.82% yield) as a white solid.

$^1$H NMR (400 MHz, CHLOROFORM-d) δ 8.50 (s, 1H), 7.53-7.46 (m, 2H), 7.36-7.30 (m, 3H), 7.18 (d, J=6.0 Hz, 1H), 5.55 (quin, J=7.0 Hz, 1H), 5.36 (br d, J=7.0 Hz, 1H), 1.66 (d, J=6.8 Hz, 3H). ESI [M+H]=334.2/336.2.

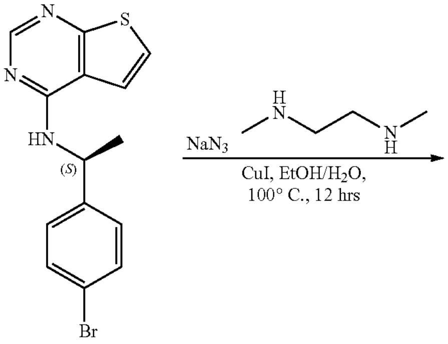

2

-continued

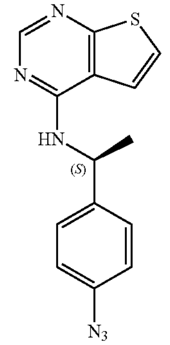

3

A mixture of N-[(1S)-1-(4-bromophenyl)ethyl]thieno[2,3-d]pyrimidin-4-amine (1 g, 2.99 mmol, 1 eq), $NaN_3$ (233 mg, 3.59 mmol, 1.2 eq), CuI (57 mg, 299.19 umol, 0.1 eq) and N1,N2-dimethylethane-1,2-diamine (53 mg, 598.38 umol, 64.40 uL, 0.2 eq) in EtOH (10 mL) and $H_2O$ (5 mL) was stirred at 100° C. for 12 hours under $N_2$. The reaction was added sat.aq. $NaHCO_3$ (20 mL) and extracted with EtOAc (10 mL×3). The organic layer was dried over $MgSO_4$ and blow-dried by N2 to give N-[(1S)-1-(4-azidophenyl)ethyl]thieno[2,3-d]pyrimidin-4-amine (1 g, crude) which was used into the next step without further purification. ESI [M+H]=297.3.

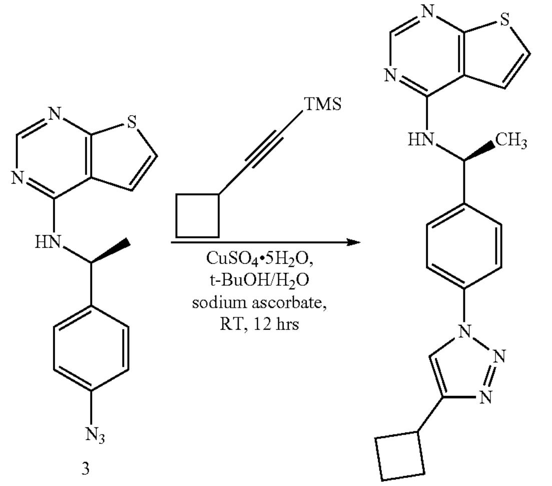

3

BAX-32 (S)

A mixture of N-[(1S)-1-(4-azidophenyl)ethyl]thieno[2,3-d]pyrimidin-4-amine (100 mg, 337.44 umol, 1 eq), 2-cyclobutylethynyl(trimethyl)silane (62 mg, 404.93 umol, 1.2 eq), $CuSO_4.5H_2O$ (17 mg, 67.49 umol, 0.2 eq) and sodium ascorbate (13 mg, 67.49 umol, 0.2 eq) in t-BuOH (2 mL) and $H_2O$ (2 mL) was stirred at 25° C. for 12 hours. The mixture was added water (10 mL) and extracted with EtOAc (10 mL×3). The organic layer was washed with brine (10 mL), dried over $MgSO_4$ and concentrated in vacuo. The residue was purified by prep-HPLC (column: HUAPU C8 Extreme BDS 150*30 5u; mobile phase: [water (10 mM $NH_4HCO_3$)-ACN]; B %: 40%-60%, 10 min) to give N-[(1S)-1-[4-(4-cyclobutyltriazol-1-yl)phenyl]ethyl]thieno[2,3-d]pyrimidin-4-amine (45.06 mg, 116.48 umol, 34.52% yield, 97.322% purity) as a white solid.

$^1H$ NMR (400 MHz, CHLOROFORM-d) δ 8.50 (s, 1H), 7.74-7.67 (m, 3H), 7.57 (d, J=8.4 Hz, 2H), 7.33 (d, J=6.0 Hz, 1H), 7.20 (d, J=6.0 Hz, 1H), 5.64 (quin, J=6.9 Hz, 1H), 5.37 (br d, J=7.5 Hz, 1H), 3.71 (quin, J=8.5 Hz, 1H), 2.50-2.39 (m, 2H), 2.37-2.23 (m, 2H), 2.15-2.04 (m, 1H), 2.03-1.93 (m, 1H), 1.71 (d, J=6.8 Hz, 3H). ESI [M+H]=377.1.

Example 3

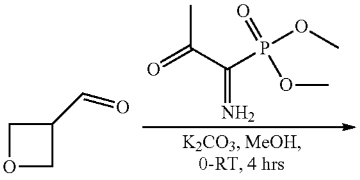

1

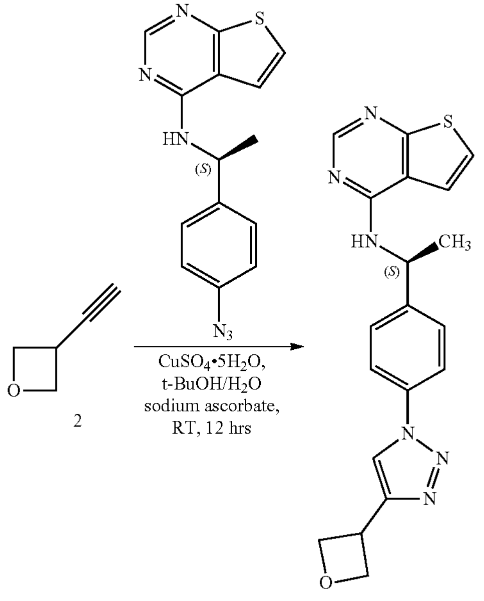

2

BAX-33 (S)

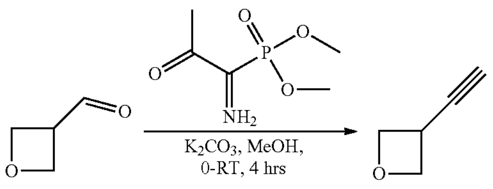

1 2

To a solution of oxetane-3-carbaldehyde (0.3 g, 3.48 mmol, 1 eq) in MeOH (3 mL) was added 1-diazo-1-dimethoxyphosphoryl-propan-2-one (1 g, 5.23 mmol, 1.5 eq) and $K_2CO_3$ (963 mg, 6.97 mmol, 2 eq) at 0° C. Then the mixture was stirred at 25° C. for 4 hours. After filtration, the filtrate was added water (3 mL) and MTBE (1 mL×2). The crude product 3-ethynyloxetane (289 mg, crude) (in 3 mL $H_2O$) was used into the next step without further purification.

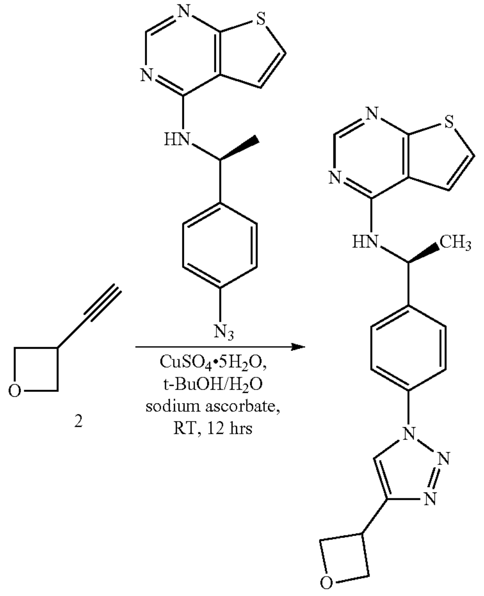

2

BAX-33 (S)

A mixture of N-[(1S)-1-(4-azidophenyl)ethyl]thieno[2,3-d]pyrimidin-4-amine (100 mg, 337.44 umol, 1 eq), 3-ethynyloxetane (139 mg, 1.69 mmol, 5 eq) (a solution in 3 mL $H_2O$), $CuSO_4.5H_2O$ (17 mg, 67.49 umol, 0.2 eq) and sodium ascorbate (13 mg, 67.49 umol, 0.2 eq) in t-BuOH (3 mL) was stirred at 25° C. for 12 hours. The mixture was added water (10 mL) and extracted with EtOAc (10 mLx3). The organic layer was washed with brine (10 mL), dried over $MgSO_4$ and concentrated in vacuo. The residue was purified by prep-HPLC (column: Kromasil 250*50 mm*10 um; mobile phase: [water (10 mM NH4HCO3)-ACN]; B %: 20%-50%, 10 min) to give N-[(1S)-1-[4-[4-(oxetan-3-yl)triazol-1-yl]phenyl]ethyl]thieno[2,3-d]pyrimidin-4-amine (90.64 mg, 234.94 umol, 69.62% yield, 98.093% purity) as a white solid.

$^1$H NMR (400 MHz, CHLOROFORM-d) δ 8.51 (br s, 1H), 7.95 (s, 1H), 7.73 (d, J=8.6 Hz, 2H), 7.61 (d, J=8.4 Hz, 2H), 7.36 (d, J=6.0 Hz, 1H), 7.23 (d, J=5.9 Hz, 1H), 5.66 (quin, J=7.0 Hz, 1H), 5.41 (br d, J=7.5 Hz, 1H), 5.11 (dd, J=5.9, 8.4 Hz, 2H), 4.92 (t, J=6.4 Hz, 2H), 4.59-4.46 (m, 1H), 1.73 (d, J=7.0 Hz, 3H). ESI [M+H]=379.1.

Example 4

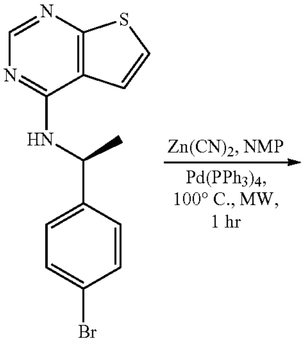

1

-continued

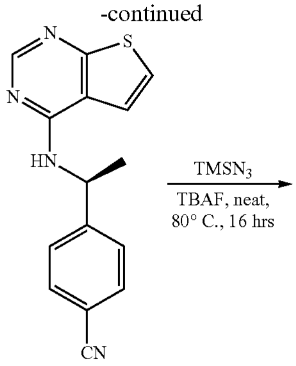

2

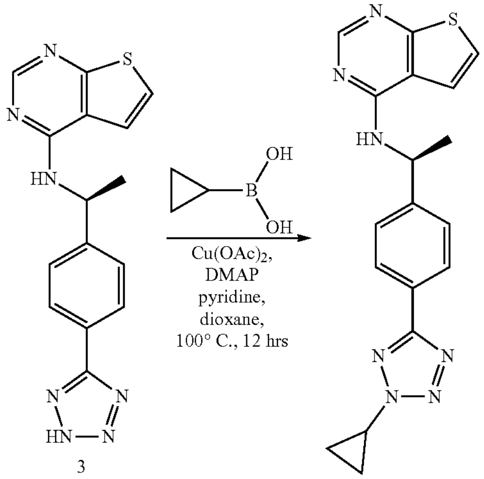

3

BAX-37(S)

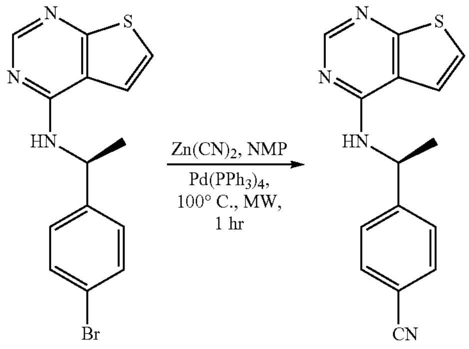

1 2

N-[(1S)-1-(4-bromophenyl)ethyl]thieno[2,3-d]pyrimidin-4-amine (0.5 g, 1.50 mmol, 1 eq), $Zn(CN)_2$ (193 mg, 1.65 mmol, 104.45 uL, 1.1 eq) and $Pd(PPh_3)_4$ (173 mg, 149.60 umol, 74.80 uL, 0.1 eq) were taken up into a microwave tube in NMP (10 mL) under $N_2$. The sealed tube was heated at 100° C. for 1 hr under microwave. The reaction was added water (20 mL) and extracted with EtOAc (10 mLx3). The organic layer was washed with brine (20 mLx2), dried over $MgSO_4$ and concentrated in vacuo. The residue was purified by column chromatography ($SiO_2$, Petroleum ether/Ethyl acetate=20/1 to 3:1) to give 4-[(1S)-1-(thieno[2,3-d]pyrimidin-4-ylamino)ethyl]benzonitrile (0.4 g, 1.43 mmol, 95.38% yield) as a yellow oil. ESI [M+H]=281.1.

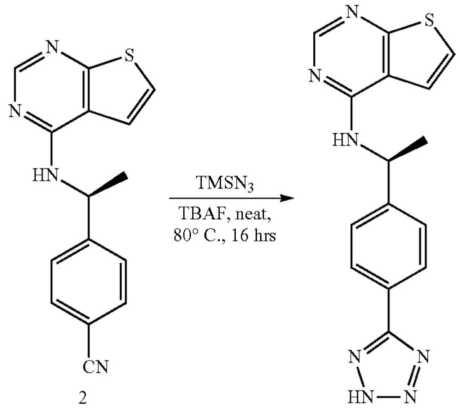

2

3

A mixture of 4-[(1S)-1-(thieno[2,3-d]pyrimidin-4-ylamino)ethyl]benzonitrile (0.4 g, 1.43 mmol, 1 eq) in TBAF (2 mL, 1M) and $TMSN_3$ (0.4 mL) was stirred at 80° C. for 16 hours. The reaction was concentrated in vacuo. The residue was purified by reversed-phase HPLC (0.1% TFA condition) to give N-[(1S)-1-[4-(2H-tetrazol-5-yl)phenyl]ethyl]thieno[2,3-d]pyrimidin-4-amine (0.39 g, 1.21 mmol, 84.53% yield) as a yellow oil. ESI [M+H]=324.2.

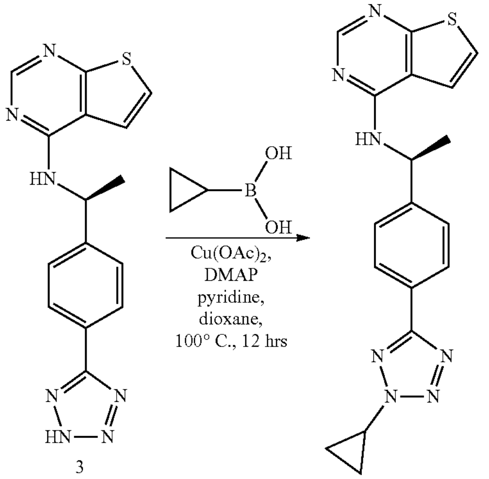

3

BAX-37(S)

To a mixture of N-[(1S)-1-[4-(2H-tetrazol-5-yl)phenyl]ethyl]thieno[2,3-d]pyrimidin-4-amine (200 mg, 618.48 umol, 1 eq), cyclopropylboronic acid (106 mg, 1.24 mmol, 2 eq), $Cu(OAc)_2$ (112 mg, 618.48 umol, 1 eq) and DMAP (227 mg, 1.86 mmol, 3 eq) in dioxane (4 mL) was added PYRIDINE (59 mg, 742.17 umol, 1.2 eq) and the mixture was stirred at 100° C. for 12 hours under 02. The reaction was added water (10 mL) and extracted with EtOAc (5 mL×3). The organic layer was dried over $MgSO_4$ and concentrated in vacuo. The residue was purified by prep-HPLC twice, then purified again by SFC (column: DAICEL CHIRALCEL OJ (250 mm*30 mm, 10 um); mobile phase: [0.1% $NH_3H_2O$ MEOH]; B %: 40%-40%, 15 min) to give N-[(1S)-1-[4-(2-cyclopropyltetrazol-5-yl)phenyl]ethyl]thieno[2,3-d]pyrimidin-4-amine (18.3 mg, 49.60 umol, 8.02% yield, 98.504% purity) as a white solid.

$^1$H NMR (400 MHz, METHANOL-d4) δ 8.26 (s, 1H), 8.02 (d, J=8.4 Hz, 2H), 7.66 (d, J=6.0 Hz, 1H), 7.56 (d, J=8.4 Hz, 2H), 7.47 (d, J=6.0 Hz, 1H), 5.59 (q, J=7.1 Hz, 1H), 4.36 (tt, J=3.7, 7.5 Hz, 1H), 1.66 (d, J=7.1 Hz, 3H), 1.49-1.42 (m, 2H), 1.33-1.24 (m, 2H). ESI [M+H]=364.1.

Example 5

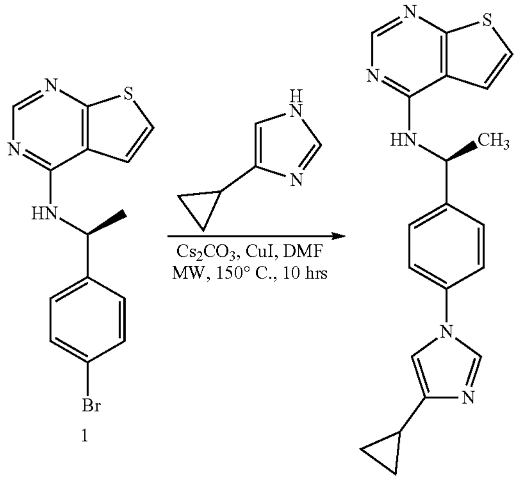

1

BAX-38 (S)

N-[(1S)-1-(4-bromophenyl)ethyl]thieno[2,3-d]pyrimidin-4-amine (60 mg, 179.52 umol, 1 eq), 4-cyclopropyl-1H-imidazole (29 mg, 269.27 umol, 1.5 eq) and CuI (7 mg, 35.90 umol, 0.2 eq), $Cs_2CO_3$ (117 mg, 359.03 umol, 2 eq) were taken up into a microwave tube in DMF (1 mL). The sealed tube was heated at 150° C. for 10 hours under microwave under N2. The reaction mixture was added water (5 mL) and extracted with EtOAc (5 mL×3). The combined organic layers were dried over $Na_2SO_4$, filtered and concentrated under reduced pressure to give a residue. The residue was purified by prep-HPLC (column: Xtimate C18 150*25 mm*5 um; mobile phase: [water (10 mM NH4HCO3)-ACN]; B %: 25%-50%, 10 min) to give N-[(1S)-1-[4-(4-cyclopropylimidazol-1-yl)phenyl]ethyl]thieno[2,3-d]pyrimidin-4-amine (13.85 mg, 36.76 umol, 20.48% yield, 95.938% purity) as white solid.

$^1$H NMR (400 MHz, METHANOL-d4) δ 8.28 (s, 1H), 7.94 (d, J=1.2 Hz, 1H), 7.67 (d, J=6.0 Hz, 1H), 7.57 (d, J=8.6 Hz, 2H), 7.52-7.46 (m, 3H), 7.26 (s, 1H), 5.60 (q, J=7.0 Hz, 1H), 1.94-1.82 (m, 1H), 1.68 (d, J=7.0 Hz, 3H), 0.91-0.83 (m, 2H), 0.77-0.69 (m, 2H1). ESI [M+H]=362.1.

Example 6

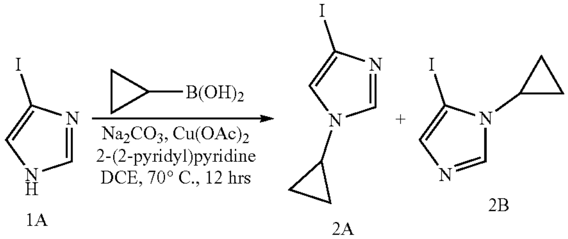

1A 2A 2B

-continued

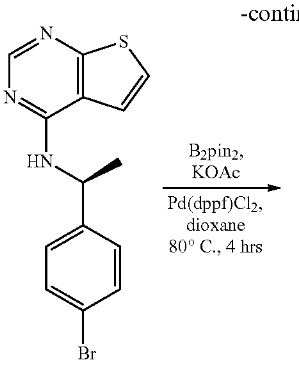

1

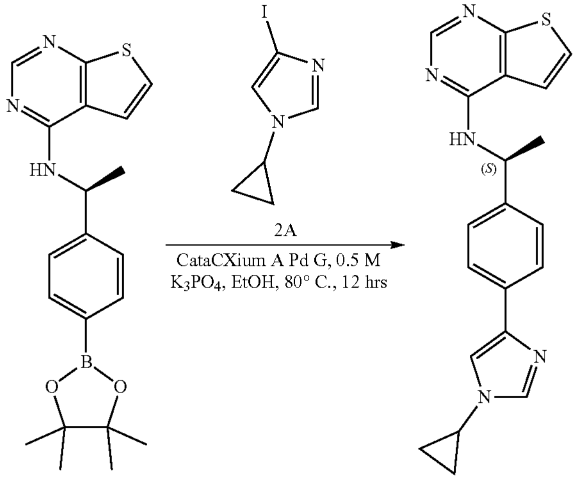

2

BAX-39 (S)

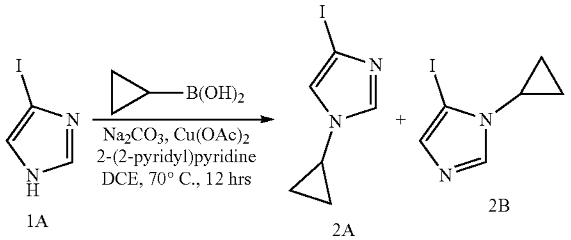

1A

2A

2B

To a solution of 4-iodo-1H-imidazole (1 g, 5.16 mmol, 1 eq) in DCE (60 mL) was added cyclopropylboronic acid (1.33 g, 15.47 mmol, 3 eq) and $Na_2CO_3$ (1.28 g, 15.47 mmol, 3 eq). Then the mixture was heated to 70° C., 2-(2-pyridyl)pyridine (966 mg, 6.19 mmol, 1.2 eq) and $Cu(OAc)_2$ (1.12 g, 6.19 mmol, 1.2 eq) was added and the mixture was stirred at 70° C. for 12 hours. The reaction was added water (100 mL) and extracted with DCM (30 mL×3). The organic layer was dried over $MgSO_4$ and concentrated in vacuo. The residue was purified by column chromatography ($SiO_2$, Petroleum ether/THF=10/1 to 3:1) to give 1 g mixture of regio-isomers, then 400 mg mixture regio-isomers was purified by prep-TLC ($SiO_2$, Petroleum ether: Ethyl acetate=1:1) to give 1-cyclopropyl-4-iodo-imidazole (330 mg) and 1-cyclopropyl-5-iodo-imidazole (40 mg) as a yellow oil.

2A: $^1H$ NMR (400 MHz, CHLOROFORM-d) δ 7.45 (d, J=1.0 Hz, 1H), 7.07 (d, J=1.3 Hz, 1H), 3.40-3.31 (m, 1H), 1.04-0.92 (m, 4H).

2B: $^1H$ NMR (400 MHz, CHLOROFORM-d) δ 7.55 (s, 1H), 7.04 (s, 1H), 3.07 (tt, J=3.7, 7.2 Hz, 1H1), 1.10-1.03 (m, 2H1), 0.96-0.88 (m, 2H1).

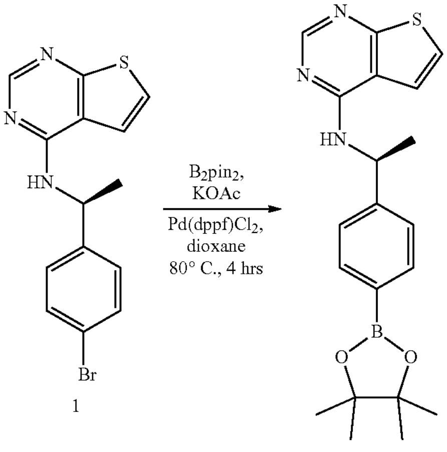

1

2

A mixture of N-[(1S)-1-(4-bromophenyl)ethyl]thieno[2,3-d]pyrimidin-4-amine (500 mg, 1.50 mmol, 1 eq), 4,4,5,5-tetramethyl-2-(4,4,5,5-tetramethyl-1,3,2-dioxaborolan-2-yl)-1,3,2-dioxaborolane (418 mg, 1.65 mmol, 1.1 eq), KOAc (440 mg, 4.49 mmol, 3 eq), $Pd(dppf)Cl_2$ (109 mg, 149.60 umol, 0.1 eq) in dioxane (10 mL) was degassed and purged with $N_2$ for 3 times, and then the mixture was stirred at 80° C. for 4 hour under N2 atmosphere. The reaction mixture was concentrated under reduced pressure to give a residue. The residue was purified by column chromatography ($SiO_2$, Petroleum ether/Ethyl acetate=1/0 to 5:1) to give N-[(1S)-1-[4-(4,4,5,5-tetramethyl-1,3,2-dioxaborolan-2-yl)phenyl] ethyl]thieno[2,3-d]pyrimidin-4-amine (600 mg, crude) as colorless oil.

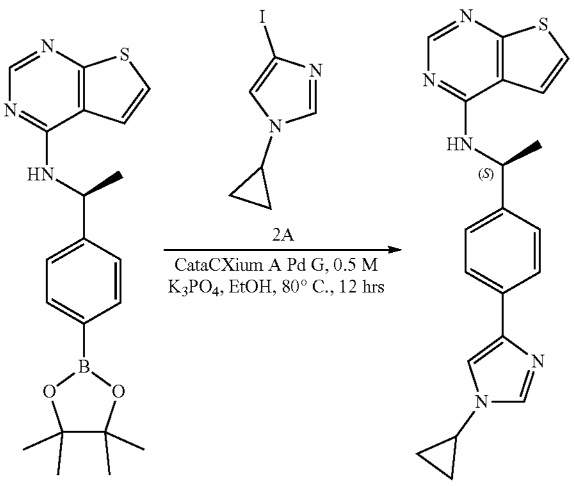

2

BAX-39 (S)

A mixture of N-[(1S)-1-[4-(4,4,5,5-tetramethyl-1,3,2-dioxaborolan-2-yl)phenyl]ethyl]thieno[2,3-d]pyrimidin-4-amine (80 mg, 209.81 umol, 1 eq), 1-cyclopropyl-4-iodo-imidazole (98 mg, 419.62 umol, 2 eq), $K_3PO_4$ (0.5 M, 839.24 uL, 2 eq), [2-(2-aminophenyl)phenyl]-chloro-palladium; bis(1-adamantyl)-butyl-phosphane (14 mg, 20.98 umol, 0.1 eq) in EtOH (3 mL) was stirred at 80° C. under N2 for 12 hours. The reaction was concentrated in vacuo. The residue was purified by prep-HPLC (column: Waters Xbridge 150*25 5u; mobile phase: [water (10 mM $NH_4HCO_3$)-ACN]; B %: 25%-55%, 10 min) to give N-[(1S)-1-[4-(1-cyclopropylimidazol-4-yl)phenyl]ethyl]thieno[2,3-d]pyrimidin-4-amine (33.17 mg, 90.88 umol, 43.31% yield, 99.033% purity) as a white solid.

$^1$H NMR (400 MHz, CHLOROFORM-d) δ 8.54 (s, 1H), 7.76 (d, J=8.3 Hz, 2H), 7.60 (d, J=0.7 Hz, 1H), 7.44 (d, J=8.3 Hz, 2H), 7.31 (s, 1H), 7.28 (d, J=1.2 Hz, 1H), 7.17 (d, J=6.0 Hz, 1H), 5.62 (quin, J=7.0 Hz, 1H), 5.41 (br d, J=7.7 Hz, 1H), 3.44-3.36 (m, 1H), 1.70 (d, J=6.7 Hz, 3H), 1.09-1.01 (m, 4H). ESI [M+H]=362.1.

Example 7

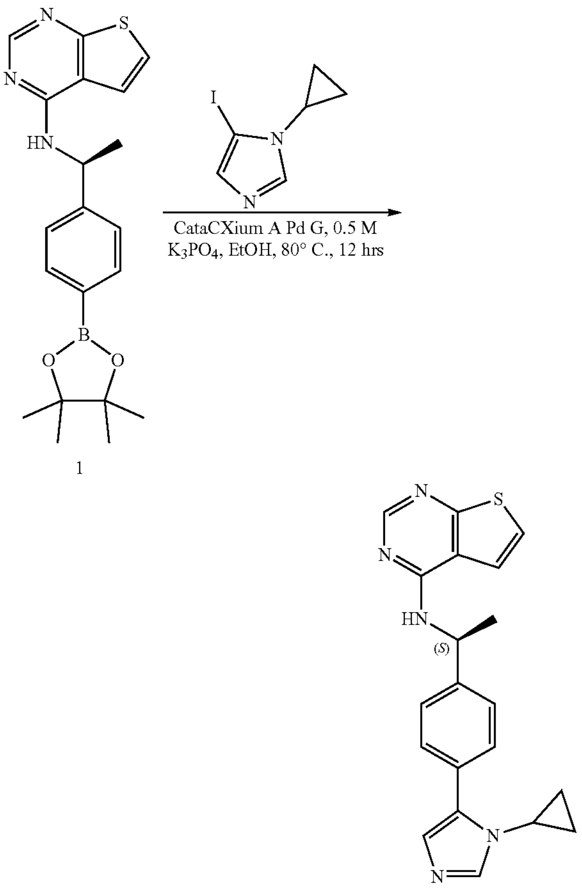

1

BAX-39A (S)

A mixture of N-[(1S)-1-[4-(4,4,5,5-tetramethyl-1,3,2-dioxaborolan-2-yl)phenyl]ethyl]thieno[2,3-d]pyrimidin-4-amine (60 mg, 157.36 umol, 1 eq), 1-cyclopropyl-5-iodo-imidazole (39 mg, 165.22 umol, 1.05 eq), $K_3PO_4$ (0.5 M, 629.43 uL, 2 eq), [2-(2-aminophenyl)phenyl]-chloro-palladium; bis(1-adamantyl)-butyl-phosphane (11 mg, 15.74 umol, 0.1 eq) in EtOH (3 mL) was stirred at 80° C. under N2 for 12 hours. The reaction was concentrated in vacuo. The residue was purified by prep-HPLC (column: HUAPU C8 Extreme BDS 150*30 5u; mobile phase: [water (10 mM $NH_4HCO_3$)-ACN]; B %: 40%-60%, 10 min) to give N-[(1S)-1-[4-(3-cyclopropylimidazol-4-yl)phenyl]ethyl]thieno[2,3-d]pyrimidin-4-amine (29.62 mg, 80.10 umol, 50.90% yield, 97.745% purity) as a white solid.

$^1$H NMR (400 MHz, CHLOROFORM-d) δ 8.45 (s, 1H), 7.52-7.44 (m, 3H), 7.43-7.38 (m, 2H), 7.24 (d, J=6.0 Hz, 1H), 7.10 (d, J=6.0 Hz, 1H), 7.01 (s, 1H), 5.58 (quin, J=7.0 Hz, 1H), 5.28 (br d, J=7.3 Hz, 1H), 3.28 (tt, J=3.7, 7.1 Hz, 1H), 1.64 (d, J=6.8 Hz, 3H), 0.94-0.88 (m, 2H1), 0.86-0.79 (m, 2H1). ESI [M+H]=362.1.

Example 8

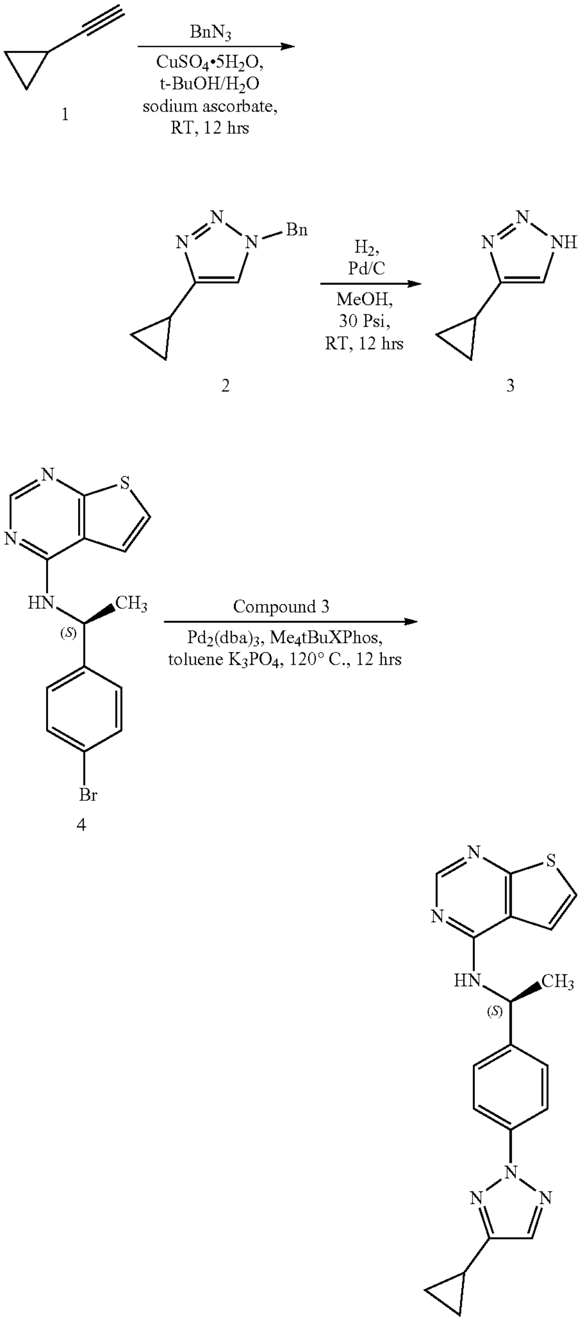

1

2

3

4

BAX-40 (S)

-continued

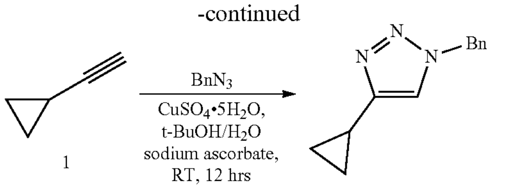

1

2

To a mixture of azidomethylbenzene (0.3 g, 2.25 mmol, 1 eq) and ethynylcyclopropane (298 mg, 4.51 mmol, 2 eq) in t-BuOH (3 mL) and $H_2O$ (3 mL) was added sodium ascorbate (89 mg, 450.62 umol, 0.2 eq) and $CuSO_4.5H_2O$ (113 mg, 450.62 umol, 0.2 eq) and the mixture was stirred at 25° C. for 12 hours. The reaction was added water (10 mL) and extracted with EtOAc (5 mL×3). The organic layer was washed with brine (10 mL), dried over $MgSO_4$ and concentrated in vacuo. The residue was purified by column chromatography ($SiO_2$, Petroleum ether/Ethyl acetate=20/1 to 5/1) to give 1-benzyl-4-cyclopropyl-triazole (430 mg, 2.16 mmol, 95.78% yield) as a white solid.

$^1H$ NMR (400 MHz, CHLOROFORM-d) δ 7.34-7.26 (m, 3H), 7.19-7.15 (m, 2H), 7.06 (s, 1H), 5.39 (s, 2H), 1.84 (tt, J=5.0, 8.4 Hz, 1H), 0.89-0.81 (m, 2H), 0.77-0.71 (m, 2H). ESI [M+H]=200.3.

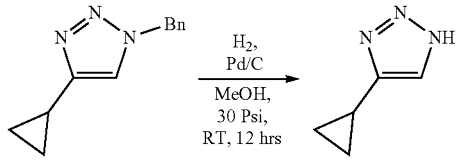

2

3

To a solution of 1-benzyl-4-cyclopropyl-triazole (360 mg, 1.81 mmol, 1 eq) in MeOH (10 mL) was added Pd/C (20 mg, 10% purity) under N2 atmosphere. The suspension was degassed and purged with $H_2$ for 3 times. The mixture was stirred under $H_2$ (30 Psi) at 25° C. for 12 hours. The reaction mixture was filtered, the filtrate was concentrated in vacuo to give 4-cyclopropyl-1H-triazole (150 mg, 1.37 mmol, 76.08% yield) which was used into the next step without further purification. ESI [M+H]=110.1.

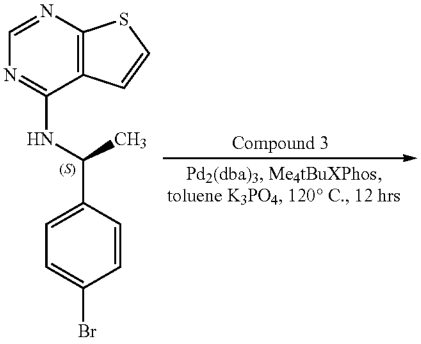

4

-continued

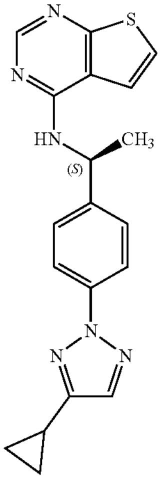

BAX-40 (S)

A mixture of $Pd_2(dba)_3$ (27 mg, 29.92 umol, 0.1 eq) and ditert-butyl-[2,3,4,5-tetramethyl-6-(2,4,6-triisopropylphenyl)phenyl]phosphane (29 mg, 59.84 umol, 0.2 eq) in 8 mL oven-dried vial under $N_2$, toluene (1 mL) was added to the vial via syringe. The resulting mixture was stirred at 120° C. for 3 minutes. Then the premixed catalyst solution was added to a mixture of N-[(1S)-1-(4-bromophenyl)ethyl]thieno[2,3-d]pyrimidin-4-amine (100 mg, 299.19 umol, 1 eq), 4-cyclopropyl-1H-triazole (49 mg, 448.79 umol, 1.5 eq) and $K_3PO_4$ (127 mg, 598.38 umol, 2 eq) in toluene (1 mL) under N2. The mixture was stirred at 120° C. for 12 hours. The reaction was concentrated in vacuo. The residue was purified by prep-HPLC (column: Waters Xbridge 150*25 5u; mobile phase: [water (10 mM $NH_4HCO_3$)-ACN]; B %: 40%-70%, 10 min) to give N-[(1S)-1-[4-(4-cyclopropyltriazol-2-yl)phenyl]ethyl]thieno[2,3-d]pyrimidin-4-amine (99 mg, 273.42 umol, 91.39% yield, 100% purity) as a white solid.

$^1H$ NMR (400 MHz, CHLOROFORM-d) δ 8.50 (s, 1H), 7.97 (d, J=8.6 Hz, 2H), 7.49 (d, J=7.3 Hz, 3H), 7.30 (d, J=6.0 Hz, 1H), 7.17 (d, J=6.2 Hz, 1H), 5.61 (quin, J=7.1 Hz, 1H), 5.38 (br d, J=7.5 Hz, 1H), 2.07-1.96 (m, 1H), 1.69 (d, J=6.8 Hz, 3H), 1.08-0.99 (m, 2H), 0.91-0.85 (m, 2H1). ESI [M+H]=363.1.

Example 9

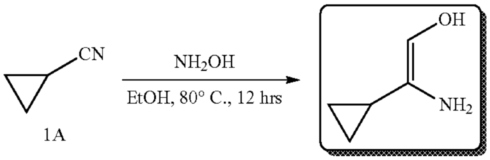

1A

2A

-continued

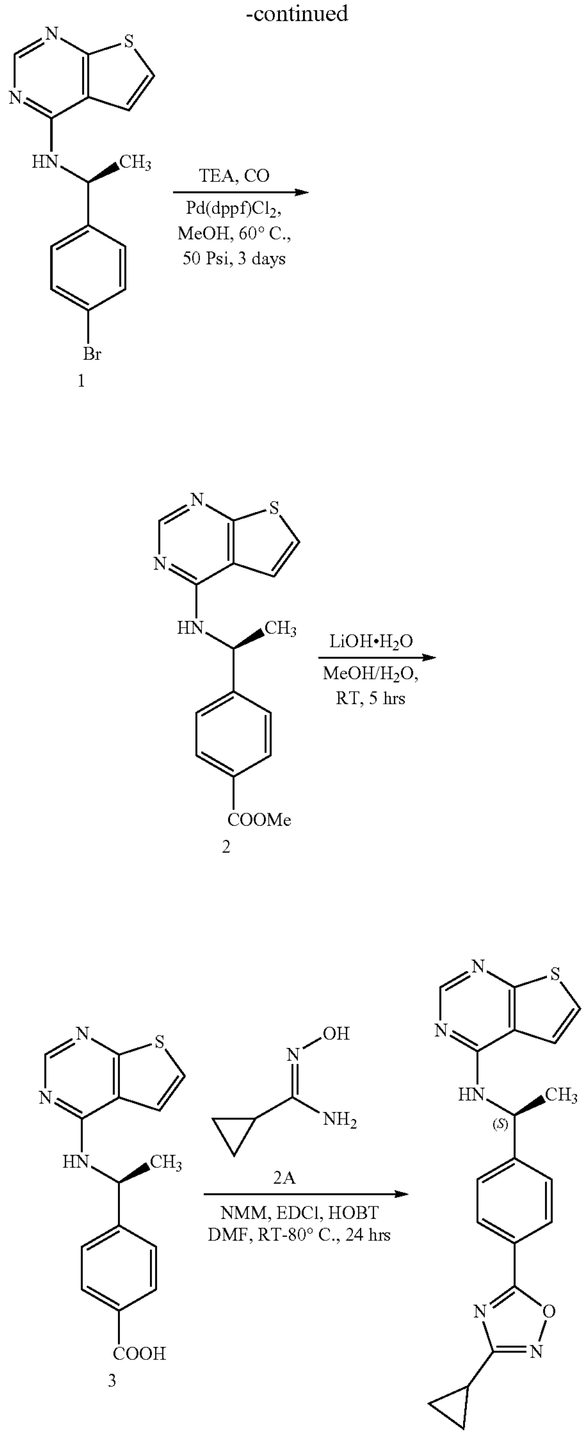

1

2

3

2A

BAX-41 (S)

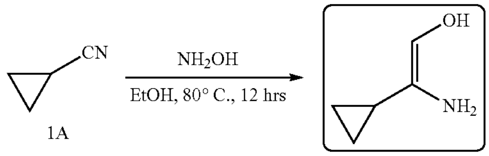

1A

2A

Cyclopropanecarbonitrile (500 mg, 7.45 mmol, 548.85 uL, 1 eq), hydroxylamine (591 mg, 8.94 mmol, 50% purity, 1.2 eq) in EtOH (2 mL) was stirred at 80° C. for 12 hours. The reaction mixture was concentrated under reduced pressure to give N'-hydroxycyclopropanecarboxamidine (820 mg, crude) as colorless oil.

$^1$H NMR (400 MHz, DMSO-d6) δ 8.68 (s, 1H), 5.37-5.02 (m, 2H), 3.31 (s, 1H), 0.65-0.59 (m, 2H), 0.59-0.52 (m, 2H).

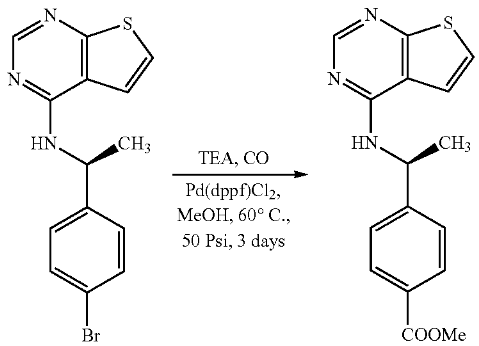

1

2

To a solution of N-[(1S)-1-(4-bromophenyl)ethyl]thieno[2,3-d]pyrimidin-4-amine (0.3 g, 897.57 umol, 1 eq) in MeOH (10 mL) was added TEA (454 mg, 4.49 mmol, 5 eq) and Pd(dppf)$Cl_2$ (66 mg, 89.76 umol, 0.1 eq) under $N_2$ atmosphere. The suspension was degassed and purged with CO for 3 times. The mixture was stirred under CO (50 Psi) at 60° C. for 72 hours. The reaction was concentrated in vacuo. The residue was purified by prep-TLC (Petroleum ether:Ethyl acetate=2:1) to give methyl 4-[(1S)-1-(thieno[2,3-d]pyrimidin-4-ylamino)ethyl]benzoate (230 mg, 733.95 umol, 81.77% yield) as a yellow solid. ESI [M+H]=314.1.

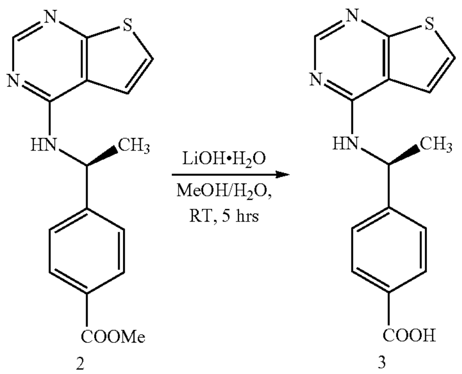

2

3

To a solution of methyl 4-[(1S)-1-(thieno[2,3-d]pyrimidin-4-ylamino)ethyl]benzoate (230 mg, 733.95 umol, 1 eq) in MeOH (3 mL) and $H_2O$ (1 mL) was added LiOH·$H_2O$ (62 mg, 1.47 mmol, 2 eq) and the mixture was stirred at 25° C. for 5 hours. MeOH was removed, and the aqueous was extracted with EtOAc (10 mL×1), the aqueous was adjust to pH=2 with 1N HCl and extracted with EtOAc (5 mL×5). The organic layer was dried over $MgSO_4$ and concentrated in vacuo to give 4-[(1S)-1-(thieno[2,3-d]pyrimidin-4-ylamino)ethyl]benzoic acid (190 mg, 634.71 umol, 86.48% yield) as a white solid. ESI [M+H]=300.1

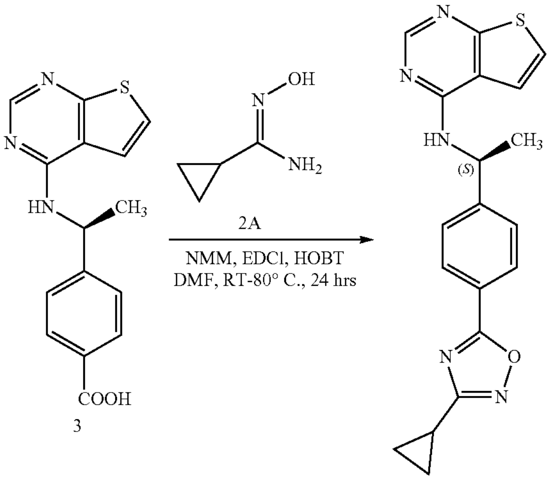

3

BAX-41 (S)

To a solution of 4-[(1S)-1-(thieno[2,3-d]pyrimidin-4-ylamino)ethyl]benzoic acid (180 mg, 601.31 umol, 1 eq) in DMF (3 mL) was added N'-hydroxycyclopropanecarboxamidine (120 mg, 1.20 mmol, 2 eq), HOBt (114 mg, 841.83 umol, 1.4 eq), NMM (184 mg, 1.80 mmol, 198.33 uL, 3 eq) and EDCI (161 mg, 841.83 umol, 1.4 eq) and the mixture was stirred at 25° C. for 12 hours. Then the mixture was stirred at 80° C. for 12 hours. The reaction was concentrated in vacuo. The residue was purified by prep-HPLC (column: Xtimate C18 150*25 mm*5 μm; mobile phase: [water (10 mM $NH_4HCO_3$)-ACN]; B %: 25%-75%, 10 min) to give N-[(1S)-1-[4-(3-cyclopropyl-1,2,4-oxadiazol-5-yl)phenyl]ethyl]thieno[2,3-d]pyrimidin-4-amine (50.05 mg, 137.71 umol, 22.90% yield, 100% purity) as a white solid.

$^1$H NMR (400 MHz, CHLOROFORM-d) δ 8.49 (s, 1H), 8.08 (d, J=8.4 Hz, 2H), 7.57 (d, J=8.3 Hz, 2H), 7.35 (d, J=6.0 Hz, 1H), 7.22 (d, J=6.0 Hz, 1H), 5.64 (quin, J=6.9 Hz, 1H), 5.42 (br d, J=5.9 Hz, 1H), 2.16 (tt, J=5.1, 8.1 Hz, 1H), 1.72 (d, J=7.0 Hz, 3H), 1.17-1.07 (m, 4H). ESI [M+H]=364.1.

Example 10

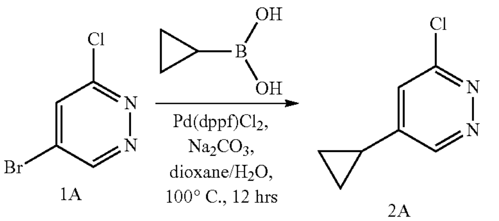

1A 2A

-continued

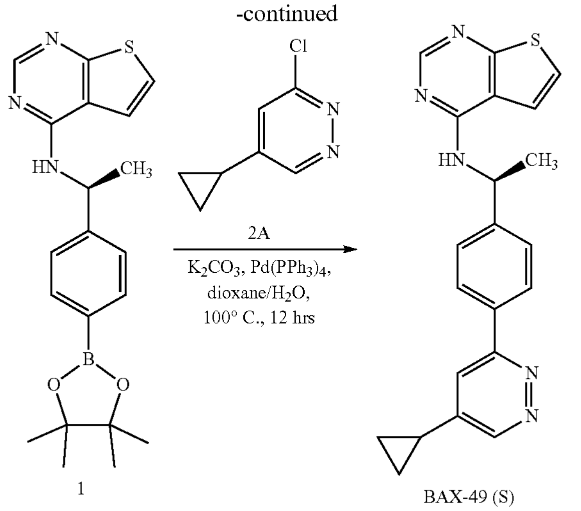

1 BAX-49 (S)

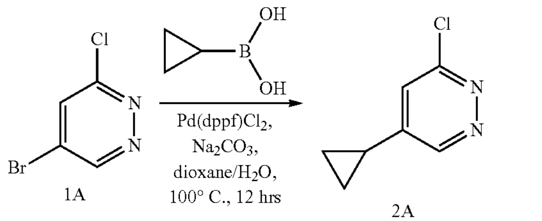

1A 2A

A mixture of 5-bromo-3-chloro-pyridazine (0.2 g, 1.03 mmol, 1 eq), cyclopropylboronic acid (133 mg, 1.55 mmol, 1.5 eq), $Na_2CO_3$ (219 mg, 2.07 mmol, 2 eq) and Pd(dppf)$Cl_2$ (76 mg, 103.40 umol, 0.1 eq) in dioxane (5 mL) and $H_2O$ (1 mL) was stirred at 100° C. for 12 hours under N2. The reaction was concentrated in vacuo. The residue was purified by prep-TLC ($SiO_2$, Petroleum ether:Ethyl acetate=1:1) to give 3-chloro-5-cyclopropyl-pyridazine (120 mg, 776.21 umol, 75.07% yield) as a yellow oil.

$^1$H NMR (400 MHz, CHLOROFORM-d) δ 8.87 (d, J=1.8 Hz, 1H), 7.10 (d, J=1.8 Hz, 1H), 1.98-1.84 (m, 1H), 1.37-1.24 (m, 2H), 0.99-0.90 (m, 2H). ESI [M+H]=155.2.

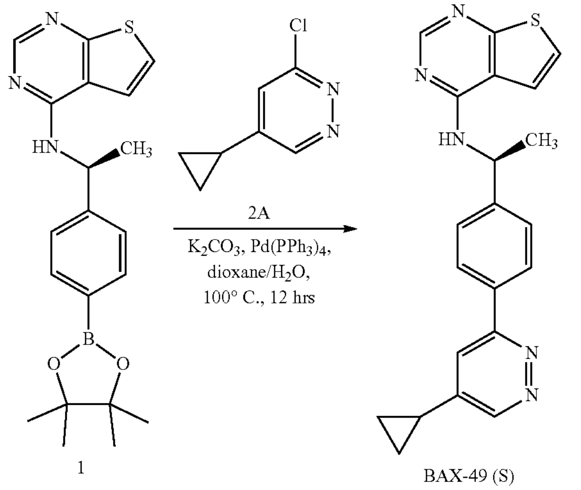

1 BAX-49 (S)

A mixture of N-[(1S)-1-[4-(4,4,5,5-tetramethyl-1,3,2-dioxaborolan-2-yl)phenyl]ethyl]thieno[2,3-d]pyrimidin-4-amine (80 mg, 209.81 umol, 1 eq), 3-chloro-5-cyclopropyl-pyridazine (36 mg, 230.79 umol, 1.1 eq), $K_2CO_3$ (58 mg, 419.62 umol, 2 eq) and $Pd(PPh_3)_4$ (24 mg, 20.98 umol, 0.1 eq) in dioxane (2 mL) and $H_2O$ (0.5 mL) was stirred at 100° C. under N2 for 12 hours. The reaction was concentrated in vacuo. The residue was purified by prep-HPLC (column: HUAPU C8 Extreme BDS 150*30 5u; mobile phase: [water (0.04% HCl)-ACN]; B %: 10%-40%, 11 min) to give N-[(1S)-1-[4-(5-cyclopropylpyridazin-3-yl)phenyl]ethyl]thieno[2,3-d]pyrimidin-4-amine (25.48 mg, 61.68 umol, 29.40% yield, 99.236% purity, HCl) as a white solid.

$^1$H NMR (400 MHz, METHANOL-d4) δ 9.27 (d, J=2.1 Hz, 1H), 8.70 (s, 1H), 8.46 (d, J=2.1 Hz, 1H), 8.14-8.08 (m, 2H), 7.95 (d, J=5.9 Hz, 1H), 7.84 (d, J=5.9 Hz, 1H), 7.79 (d, J=8.3 Hz, 2H), 5.85 (q, J=7.0 Hz, 1H), 2.43-2.34 (m, 1H), 1.81 (d, J=7.1 Hz, 3H), 1.61-1.52 (m, 2H1), 1.39-1.33 (m, 2H1). ESI [M+H]=374.1.

Example 11

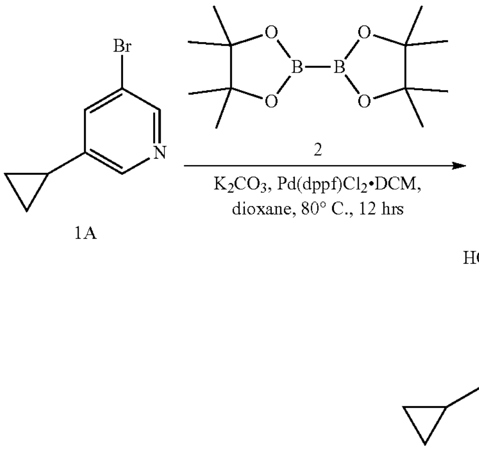

1A

2

2A

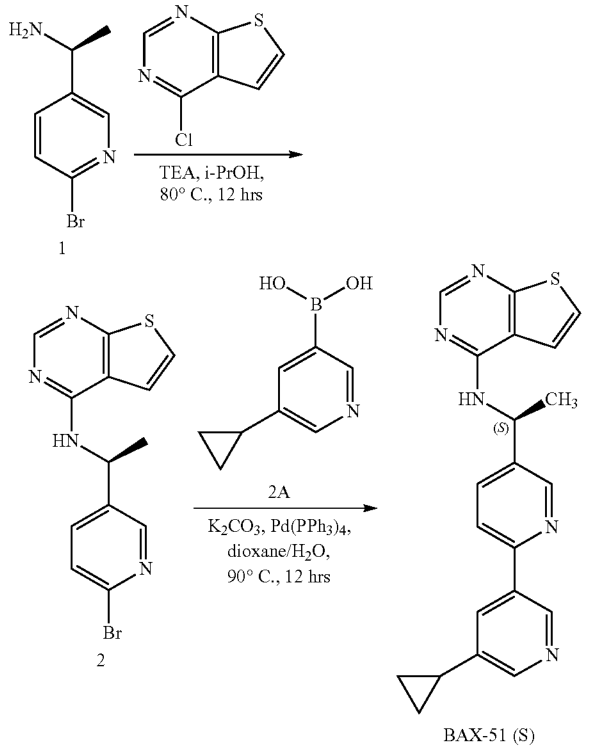

1

2

2A

BAX-51 (S)

-continued

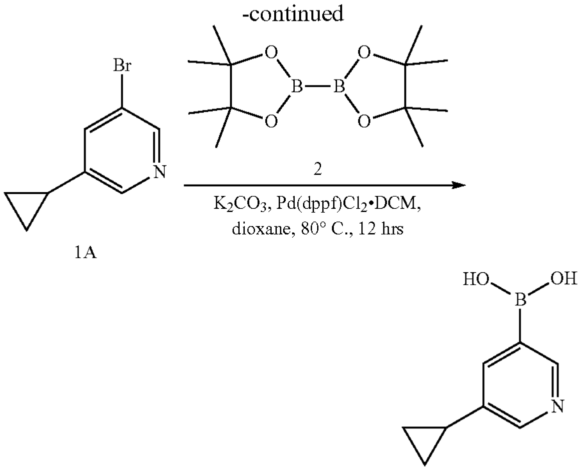

1A

2

2A

A mixture of 3-bromo-5-cyclopropyl-pyridine (100 mg, 504.90 umol, 1 eq), 4,4,4',4',5,5,5',5'-octamethyl-2,2'-bi(1,3,2-dioxaborolane) (769 mg, 3.03 mmol, 6 eq), KOAc (99 mg, 1.01 mmol, 2 eq), $Pd(dppf)Cl_2{\cdot}CH_2Cl_2$ (41 mg, 50.49 umol, 0.1 eq) in dioxane (5 mL) was degassed and purged with N2 for 3 times, and then the mixture was stirred at 80° C. for 12 hours under N2 atmosphere. The reaction mixture was concentrated under reduced pressure to remove solvent. The residue was purified by prep-HPLC (column: Waters Xbridge Prep OBD C18 150*30 5u; mobile phase: [water (0.1% TFA)-ACN]; B %: 1%-30%, 13 min) to give (5-cyclopropyl-3-pyridyl)boronic acid (60 mg, 216.60 umol, 42.90% yield, TFA) as a colorless oil. ESI [M+H]=164.1.

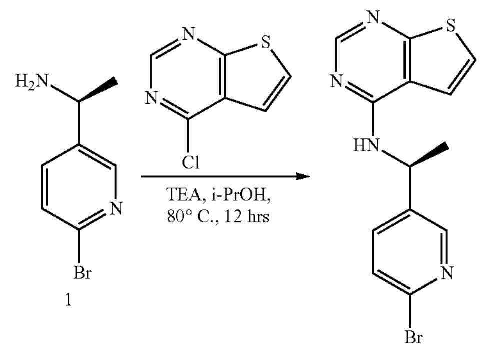

1

2

To a solution of (1S)-1-(6-bromo-3-pyridyl)ethanamine (0.3 g, 1.49 mmol, 1 eq) in i-PrOH (6 mL) was added TEA (303 mg, 2.98 mmol, 2 eq) and 4-chlorothieno[2,3-d]pyrimidine (306 mg, 1.79 mmol, 1.2 eq) and the mixture was stirred at 80° C. for 12 hours. The reaction was concentrated in vacuo. The residue was purified by column choursomatography ($SiO_2$, Petroleum ether/Ethyl acetate=10/1 to 3/1) to give N-[(1S)-1-(6-bromo-3-pyridyl)ethyl]thieno[2,3-d]pyrimidin-4-amine (0.38 g, 1.13 mmol, 75.97% yield) as a yellow solid.

$^1$H NMR (400 MHz, CHLOROFORM-d) δ 8.50-8.42 (m, 2H), 7.59 (dd, J=2.4, 8.2 Hz, 1H), 7.43 (d, J=8.2 Hz, 1H), 7.33 (d, J=6.0 Hz, 1H), 7.18 (d, J=6.2 Hz, 1H), 5.54 (quin, J=7.0 Hz, 1H), 5.39 (br d, J=6.8 Hz, 1H), 1.68 (d, J=7.1 Hz, 3H). ESI [M+H]=335.2/337.2.

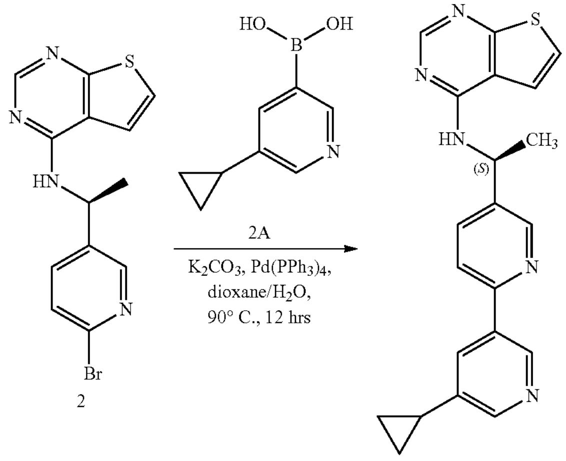

BAX-51 (S)

A mixture of N-[(1S)-1-(6-bromo-3-pyridyl)ethyl]thieno[2,3-d]pyrimidin-4-amine (60 mg, 178.99 umol, 1 eq), (5-cyclopropyl-3-pyridyl)boronic acid (50 mg, 178.99 umol, 1 eq, TFA), $K_2CO_3$ (74 mg, 536.96 umol, 3 eq), $Pd(PPh_3)_4$ (21 mg, 17.90 umol, 0.1 eq) in dioxane (2 mL) and $H_2O$ (0.5 mL) was degassed and purged with N2 for 3 times, and then the mixture was stirred at 90° C. for 12 hours under N2 atmosphere. The reaction was concentrated in vacuo. The residue was purified by prep-HPLC (HCl condition; column: Luna C18 100*30 5u; mobile phase: [water (0.04% HCl)-ACN]; B %: 5%-35%, 11 min) to give N-[(1S)-1-[6-(5-cyclopropyl-3-pyridyl)-3-pyridyl]ethyl]thieno[2,3-d]pyrimidin-4-amine (34.67 mg, 84.53 umol, 47.23% yield, 99.946% purity, HCl) as a white solid.

$^1H$ NMR (400 MHz, METHANOL-d4) δ 9.30 (d, J=1.2 Hz, 1H), 8.96 (s, 1H), 8.90 (t, J=1.7 Hz, 1H), 8.77-8.72 (m, 1H), 8.57-8.56 (m, 1H), 8.24 (d, J=1.3 Hz, 2H), 7.98 (d, J=5.9 Hz, 1H), 7.86 (d, J=5.7 Hz, 1H), 5.90 (q, J=7.0 Hz, 1H), 2.38-2.29 (m, 1H), 1.86 (d, J=7.0 Hz, 3H), 1.38-1.30 (m, 2H), 1.15-1.07 (m, 2H). ESI [M+H]=374.1.

Example 12

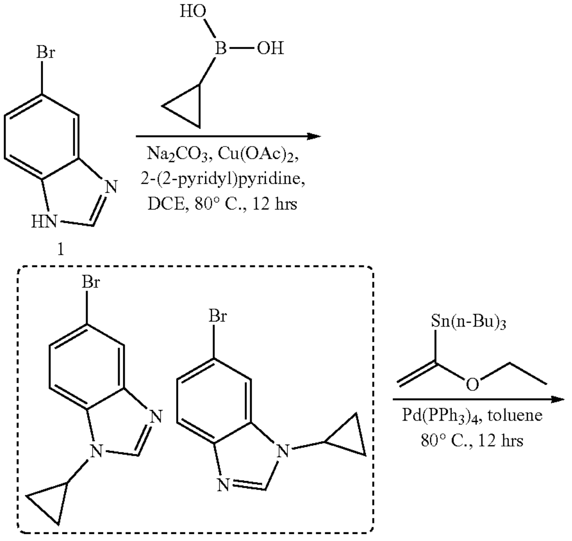

2A 2B

-continued

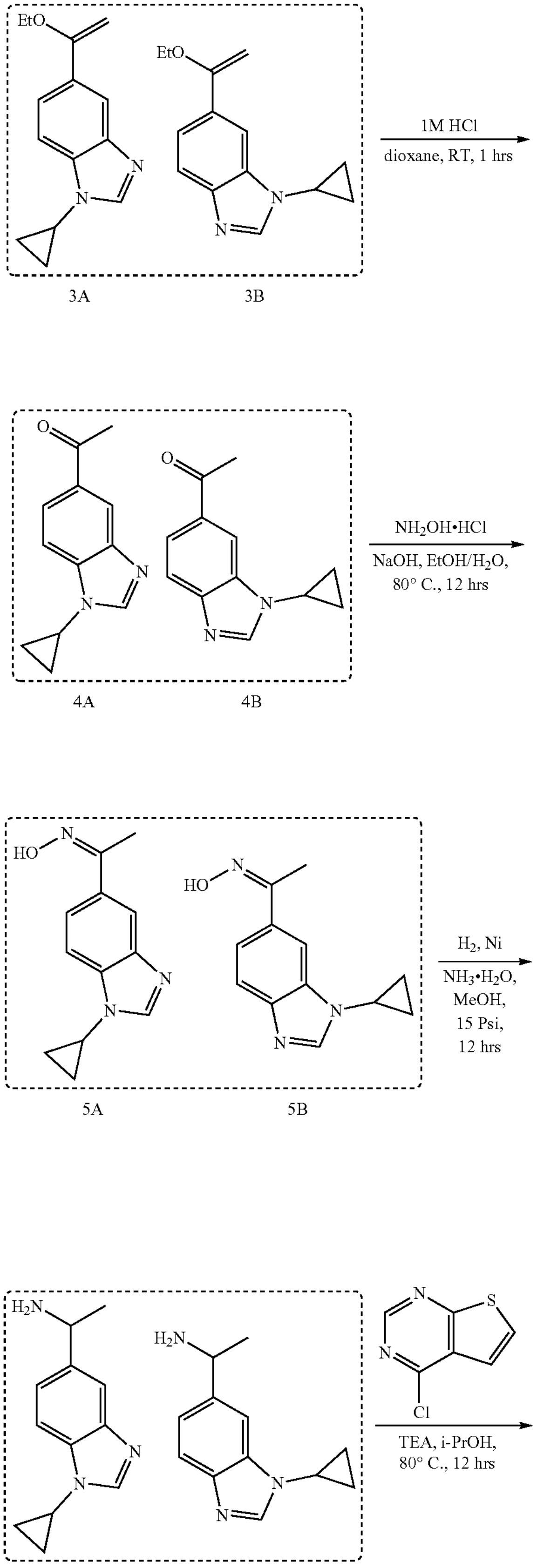

6A 6B

-continued

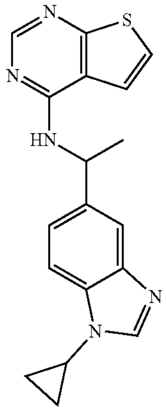

BAX-54 (RS)

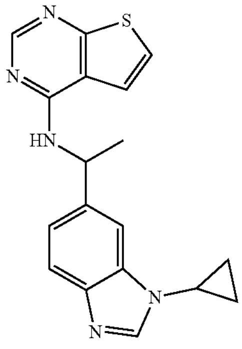

BAX-54A (RS)

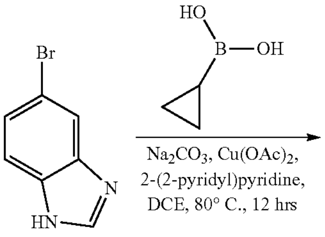

1

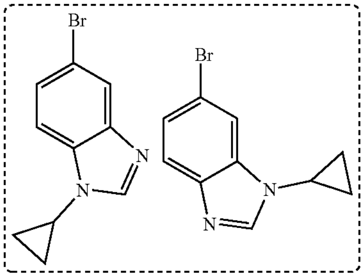

2A 2B

A mixture of 5-bromo-1H-benzimidazole (2 g, 10.15 mmol, 1 eq), cyclopropylboronic acid (2.62 g, 30.45 mmol, 3 eq), $Na_2CO_3$ (3.23 g, 30.45 mmol, 3 eq), $Cu(OAc)_2$ (2.21 g, 12.18 mmol, 1.2 eq) and 2-(2-pyridyl)pyridine (1.90 g, 12.18 mmol, 1.2 eq) in DCE (40 mL) was degassed and purged with 02 for 3 times, and then the mixture was stirred at 80° C. for 12 hours under 02 atmosphere. The reaction was added water (40 mL) and extracted with DCM (30 mL×5). The organic phase dried over drying $Na_2SO_4$, and then concentrated in vacuo. The residue was purified by column chromatography ($SiO_2$, Petroleum ether/Ethyl acetate=20/1 to 3/1) to give a mixture of 5-bromo-1-cyclopropyl-benzimidazole and 6-bromo-1-cyclopropyl-benzimidazole total 980 mg as a brown oil. ESI [M+H]=237.1/239.1.

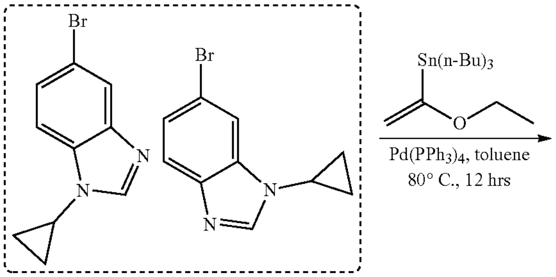

2A 2B

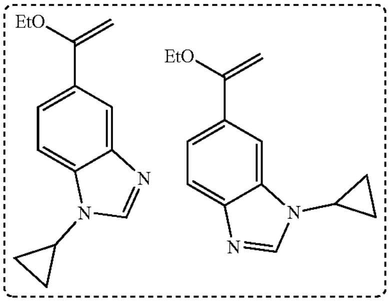

3A 3B

A mixture of 5-bromo-1-cyclopropyl-benzimidazole and 6-bromo-1-cyclopropyl-benzimidazole (total 940 mg, 3.96 mmol), tributyl(1-ethoxyvinyl)stannane (1.72 g, 4.76 mmol, 1.61 mL, 1.2 eq) and $Pd(PPh_3)_4$ (458 mg, 396.46 umol, 0.1 eq) in toluene (30 mL) was stirred at 80° C. for 12 hours. The reaction was concentrated in vacuo to give crude product 1-cyclopropyl-5-(1-ethoxyvinyl)benzimidazole and 1-cyclopropyl-6-(1-ethoxyvinyl)benzimidazole total 900 mg as a black brown oil which was used into the next step without further purification. ESI [M+H]=229.2.

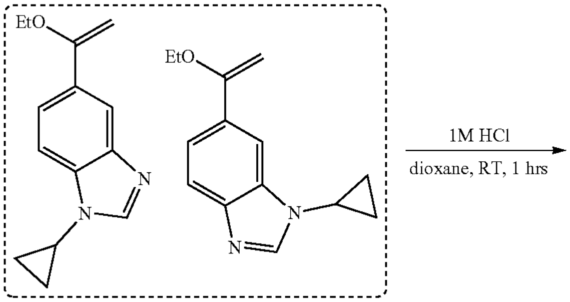

3A 3B

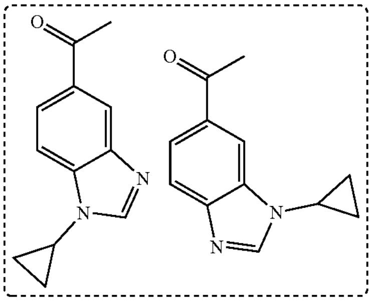

4A 4B

To a solution of 1-cyclopropyl-5-(1-ethoxyvinyl)benzimidazole and 1-cyclopropyl-6-(1-ethoxyvinyl)benzimidazole (total 0.9 g, 3.94 mmol) in dioxane (20 mL) was added HCl (1 M, 20 mL, 5.07 eq) and the mixture was stirred at 25° C. for 1 hours. The reaction was adjusted to pH=8 with sat.aq·$Na_2CO_3$, extracted with EtOAc (20 mL×3). The organic layer was washed with brine (50 mL), dried over $MgSO_4$ and concentrated in vacuo. The residue was purified by column chromatography ($SiO_2$, Petroleum ether/Ethyl acetate=10/1 to 3/1) to give a mixture of 1-(1-cyclopropylbenzimidazol-5-yl)ethanone and 1-(3-cyclopropylbenzimidazol-5-yl)ethanone total 0.3 g as a yellow oil. ESI [M+H]=201.2.

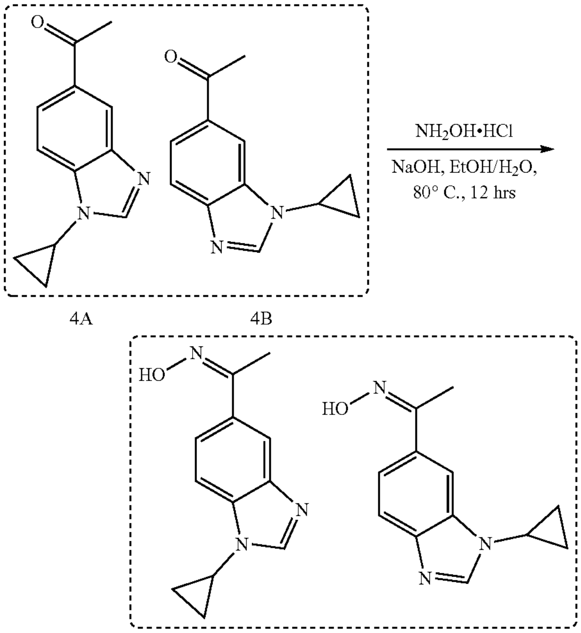

4A 4B 5A 5B

To a solution of 1-(1-cyclopropylbenzimidazol-5-yl)ethanone and 1-(3-cyclopropylbenzimidazol-5-yl)ethanone (total 300 mg, 1.50 mmol) in $H_2O$ (3 mL) and EtOH (9 mL) was added NaOH (539 mg, 13.48 mmol, 9 eq) and $NH_2OH{\cdot}HCl$ (312 mg, 4.49 mmol, 3 eq). The mixture was stirred at 25-80° C. for 12 hours. The reaction was added water (40 mL) and extracted with EtOAc (30 mL×3). The organic phase dried over drying $Na_2SO_4$, and then concentrated in vacuo to give a mixture of 1-(1-cyclopropylbenzimidazol-5-yl)ethanone oxime (crude) and 1-(3-cyclopropylbenzimidazol-5-yl)ethanone oxime (crude) total 330 mg which was used into the next step without further purification. ESI [M+H]=216.1.

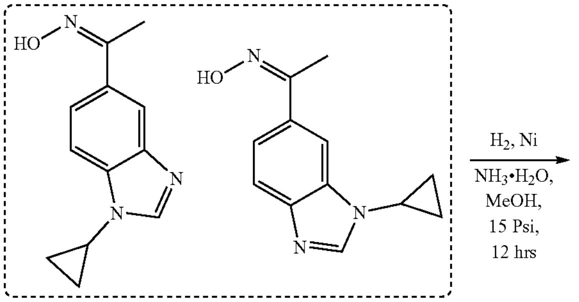

5A 5B

-continued

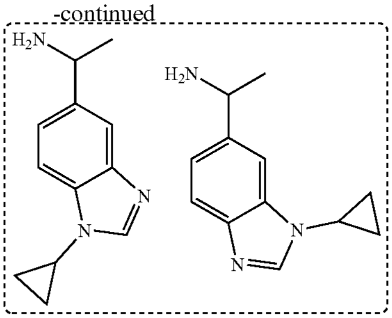

6A 6B

To a solution of 1-(1-cyclopropylbenzimidazol-5-yl)ethanone oxime and 1-(3-cyclopropylbenzimidazol-5-yl)ethanone oxime (total 300 mg, 1.53 mmol) in MeOH (10 mL) was added Ni (100 mg, 1.70 mmol, 1.11 eq) and $NH_3{\cdot}H_2O$ (455 mg, 3.25 mmol, 25% purity, 2.12 eq) under N2 atmosphere. The suspension was degassed and purged with $H_2$ for 3 times. The mixture was stirred at 25° C. for 12 hours under $H_2$ (15 Psi) atmosphere. The reaction was filtered and then concentrated in vacuo. The residue was purified by prep-HPLC (column: Nano-micro Kromasil C18 100*30 mm 5 um; mobile phase: [water (0.1% TFA)-ACN]; B %: 5%-25%, 10 min) to give 1-(3-cyclopropylbenzimidazol-5-yl)ethanamine (0.14 g, 444.04 umol, 28.96% yield, TFA) as a white solid and 1-(1-cyclopropylbenzimidazol-5-yl) ethanamine (0.14 g, 444.04 umol, 28.96% yield, TFA) as a white solid.

6A: $^1H$ NMR (400 MHz, METHANOL-d4) δ 9.08 (s, 1H), 8.01 (d, J=8.6 Hz, 1H), 7.92 (d, J=1.3 Hz, 1H), 7.69 (dd, J=1.6, 8.6 Hz, 1H), 4.70 (q, J=6.9 Hz, 1H), 3.75 (tt, J=3.7, 7.1 Hz, 1H), 1.73 (d, J=7.0 Hz, 3H), 1.37-1.28 (m, 2H), 1.25-1.16 (m, 2H).

6B: $^1H$ NMR (400 MHz, METHANOL-d4) δ 9.13 (s, 1H), 8.07 (s, 1H), 7.89 (d, J=8.4 Hz, 1H), 7.67 (dd, J=1.6, 8.6 Hz, 1H), 4.74 (q, J=6.7 Hz, 1H), 3.76 (tt, J=3.7, 7.2 Hz, 1H), 1.76 (d, J=7.0 Hz, 3H), 1.39-1.31 (m, 2H), 1.28-1.18 (m, 2H).

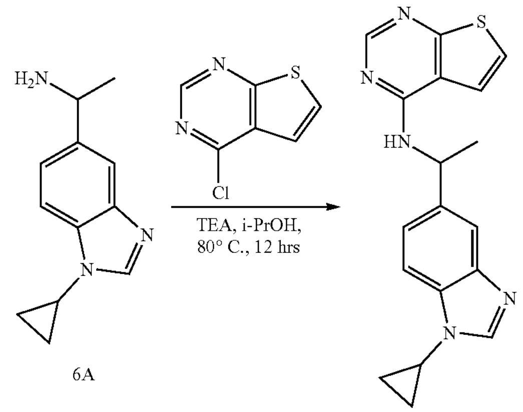

6A

BAX-54 (RS)

To a solution of 1-(1-cyclopropylbenzimidazol-5-yl) ethanamine (140 mg, 444.04 umol, 1 eq, TFA) in i-PrOH (3 mL) was added 4-chlorothieno[2,3-d]pyrimidine (91 mg, 532.84 umol, 1.2 eq) and TEA (225 mg, 2.22 mmol, 5 eq). The mixture was stirred a 80° C. for 12 hours. The reaction was concentrated in vacuo. The residue was purified by prep-HPLC (column: HUAPU C8 Extreme BDS 150*30 5u; mobile phase: [water (10 mM $NH_4HCO_3$)-ACN]; B %: 45%-65%, 10 min) to give N-[1-(1-cyclopropylbenzimidazol-5-yl)ethyl]thieno[2,3-d]pyrimidin-4-amine (19.45 mg, 57.99 umol, 13.06% yield, 100% purity) as a yellow solid. ESI [M+H]=336.1.

$^1$H NMR (400 MHz, METHANOL-d4) δ 8.24 (s, 1H), 8.11 (s, 1H), 7.70 (s, 1H), 7.65 (d, J=6.0 Hz, 1H), 7.61 (d, J=8.4 Hz, 1H), 7.46-7.44 (m, 1H), 7.43 (s, 1H), 5.67 (q, J=7.2 Hz, 1H), 3.46 (tt, J=3.6, 7.1 Hz, 1H), 1.68 (d, J=6.8 Hz, 3H), 1.18-1.12 (m, 2H), 1.05-1.01 (m, 2H).

Example 13

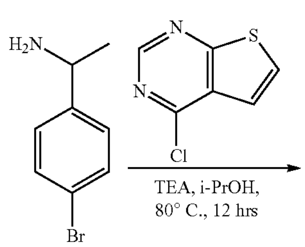

1

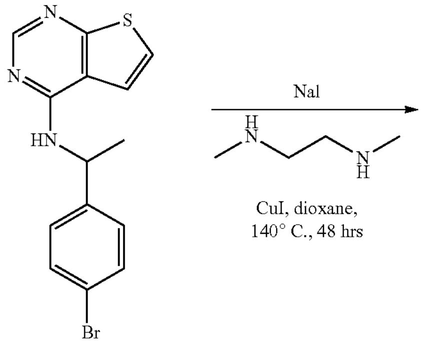

2

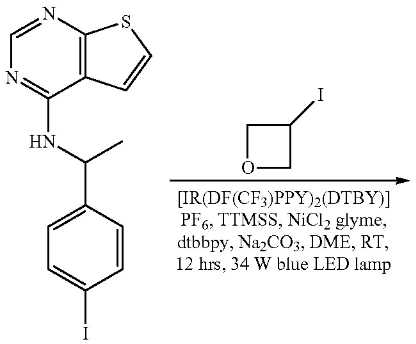

3

-continued

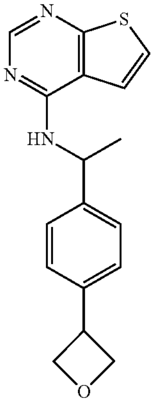

BAX-56 (RS)

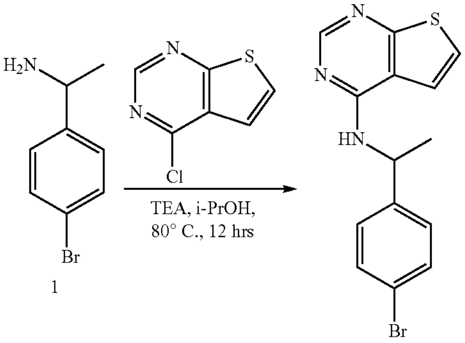

1

2

A mixture of 1-(4-bromophenyl)ethanamine (1 g, 4.23 m mol, 1 eq HCl), 4-chlorothieno[2,3-d]pyrimidine (794 mg, 4.65 mmol, 1.1 eq) and TEA (1.71 g, 16.91 mmol, 4 eq) in i-PrOH (20 mL) was stirred at 80° C. for 12 hours. The reaction was concentrated in vacuo. The residue was purified by column chromatography ($SiO_2$, Petroleum ether/THF=30/1 to 3/1) to give N-[1-(4-bromophenyl)ethyl]thieno[2,3-d]pyrimidin-4-amine (1.4 g, 4.19 mmol, 99.08% yield) as a white solid.

$^1$H NMR (400 MHz, CHLOROFORM-d) δ 8.41 (s, 1H), 7.43-7.36 (m, 2H), 7.25-7.19 (m, 3H), 7.09 (d, J=6.0 Hz, 1H), 5.46 (quin, J=7.0 Hz, 1H), 5.28 (br d, J=7.1 Hz, 1H), 1.57 (d, J=6.8 Hz, 3H). ESI [M+H]=334.2/336.2.

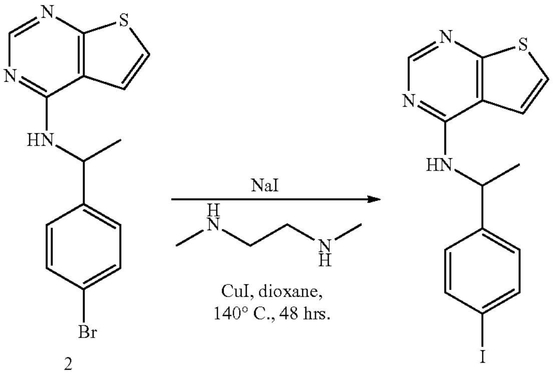

2

3

To a solution of N-[1-(4-bromophenyl)ethyl]thieno[2,3-d]pyrimidin-4-amine (0.2 g, 598.38 umol, 1 eq) in dioxane (8 mL) was added NaI (269.1 mg, 1.80 mmol, 3 eq), CuI (11.4 mg, 59.84 umol, 0.1 eq) and N,N'-dimethylethylendiamine (13.2 mg, 149.60 umol, 16.10 uL, 0.25 eq) under N2. The mixture was stirred at 140° C. for 48 hours in a 30 mL of sealed tube. The reaction was concentrated in vacuo. The residue was purified by pre-TLC ($SiO_2$, Petroleum ether: Ethyl acetate=2:1) to give N-[1-(4-iodophenyl)ethyl]thieno[2,3-d]pyrimidin-4-amine (180 mg, 472.15 umol, 78.90% yield) as a white solid. ESI [M+H]=382.2

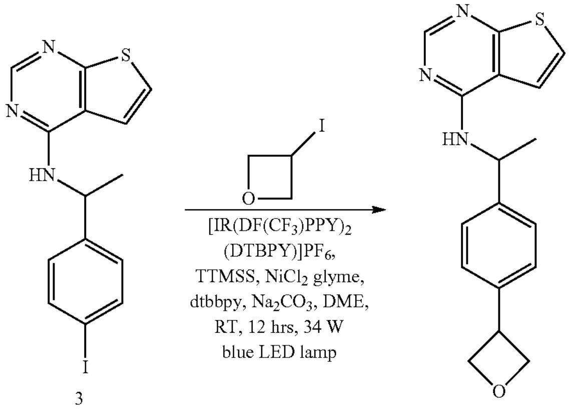

3

BAX-56
(RS)

A mixture of N-[l-(4-iodophenyl)ethyl]thieno[2,3-d]pyrimidin-4-amine (180 mg, 472.15 umol, 1 eq), 3-iodooxetane (261 mg, 1.42 mmol, 3 eq), bis[3,5-difluoro-2-[5-(trifluoromethyl)-2-pyridyl]phenyl]iridium(1+); 4-tert-butyl-2-(4-tert-butyl-2-pyridyl)pyridine; hexafluorophosphate (16 mg, 14.16 umol, 0.03 eq), TTMSS (117 mg, 472.15 umol, 1 eq), $Na_2CO_3$ (100 mg, 944.30 umol, 2 eq), dichloronickel; 1,2-dimethoxyethane (5 mg, 23.61 umol, 0.05 eq) and 4,4'-di-tert-butyl-2,2'-bipyridine (8 mg, 28.33 umol, 0.06 eq) in DME (6 mL) was stirred and irradiated with a 34 W blue LED lamp at 25° C. for 12 hours under N2. The reaction was concentrated in vacuo. The residue was purified by prep-HPLC (column: Xtimate C18 150*25 mm*5 um; mobile phase: [water (10 mM $NH_4HCO_3$)-ACN]; B %: 30%-60%, 10 min) to give N-[1-[4-(oxetan-3-yl)phenyl]ethyl]thieno[2,3-d]pyrimidin-4-amine (54 mg, 172.72 umol, 36.58% yield, 99.656% purity) as a white solid.

$^1$H NMR (400 MHz, CHLOROFORM-d) δ 8.53 (s, 1H), 7.44 (q, J=8.3 Hz, 4H), 7.32 (d, J=6.0 Hz, 1H), 7.17 (d, J=6.0 Hz, 1H), 5.62 (quin, J=7.1 Hz, 1H), 5.36 (br d, J=7.3 Hz, 1H), 5.09 (dd, J=6.0, 8.4 Hz, 2H), 4.84-4.74 (m, 2H), 4.32-4.19 (m, 1H), 1.70 (d, J=6.8 Hz, 3H) ESI [M+H]=312.1.

Example 14

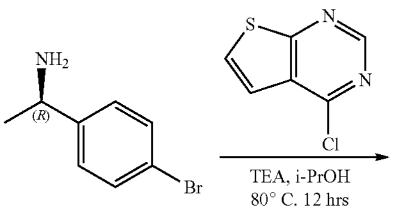

1

-continued

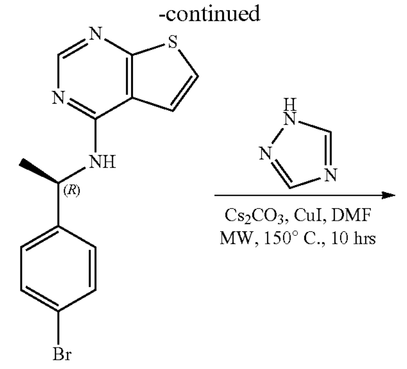

2

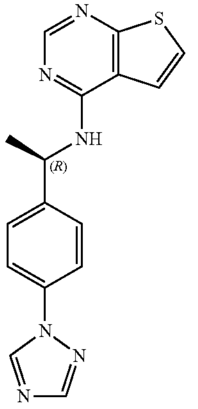

BBI-5-R

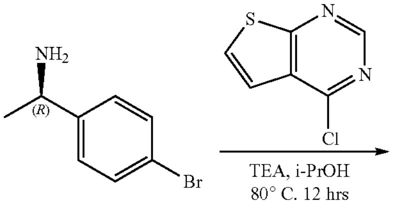

1

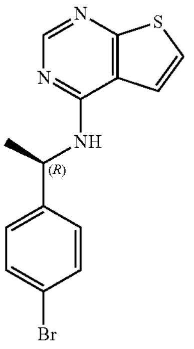

2

A mixture of (1R)-1-(4-bromophenyl)ethanamine (0.5 g, 2.50 mmol, 1 eq), 4-chlorothieno[2,3-d]pyrimidine (469 mg, 2.75 mmol, 1.1 eq) and TEA (506 mg, 5.0 mmol, 2 eq) in i-PrOH (10 mL) was stirred at 80° C. for 12 hours. The reaction mixture was concentrated in vacuum and the residue was purified by column chromatography ($SiO_2$, Petroleum ether:THF=20:1 to 5:1) to give N-[(1R)-1-(4-bromophenyl)ethyl]thieno[2,3-d]pyrimidin-4-amine (0.7 g, 2.09 mmol, 83.81% yield) as a white solid. ESI [M+H]=334.2/336.2.

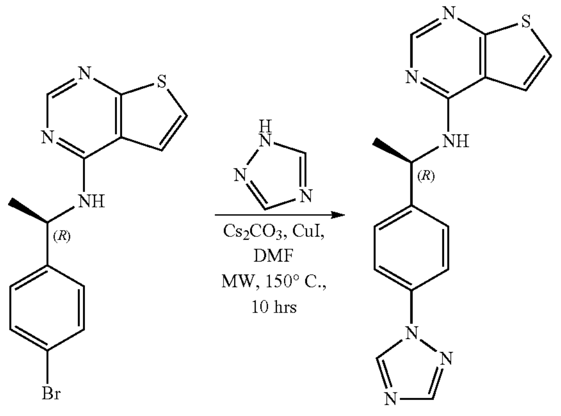

2 BBI-5-R

N-[(1R)-1-(4-bromophenyl)ethyl]thieno[2,3-d]pyrimidin-4-amine (400 mg, 1.2 mmol, 1 eq), 1H-1,2,4-triazole (124 mg, 1.8 mmol, 1.5 eq) and $Cs_2CO_3$ (780 mg, 2.39 mmol, 2 eq), CuI (46 mg, 240 umol, 0.2 eq) were taken up into a microwave tube in DMF (8 mL). The sealed tube was heated at 150° C. for 12 hours under microwave. The reaction was added water (30 mL) and extracted with EtOAc (15 mL×3). The organic layer was washed with brine (20 mL), dried over $MgSO_4$ and concentrated in vacuo. The residue was purified by prep-HPLC (Column: Waters Xbridge Prep OBD C18 150*40 10u; mobile phase: [water (10 mM NH4HCO3)-ACN]; B %: 15%-45%, 11 min) to give (R)—N-(1-(4-(1H-1,2,4-triazol-1-yl)phenyl)ethyl) thieno[2,3-d]pyrimidin-4-amine (279.27 mg, 864.78 umol, 72.26% yield, 99.829% purity) as a white solid.

$^1H$ NMR (400 MHz, CHLOROFORM-d) δ 8.50 (d, J=15.2 Hz, 2H), 8.09 (s, 1H), 7.69-7.62 (m, 2H1), 7.59-7.53 (m, 2H1), 7.32 (d, J=6.0 Hz, 1H1), 7.19 (d, J=6.0 Hz, 1H), 5.62 (quin, J=7.0 Hz, 1H), 5.42 (br d, J=7.3 Hz, 1H), 1.70 (d, J=7.1 Hz, 3H). ESI [M+H]=323.1. ee %=90.7%.

Example 15

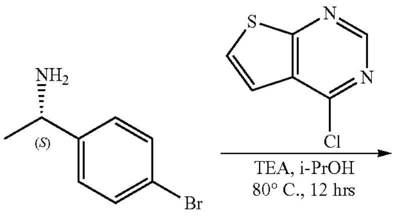

1

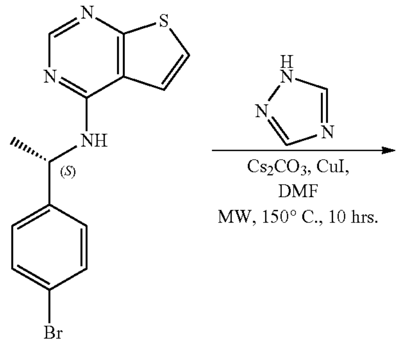

2

-continued

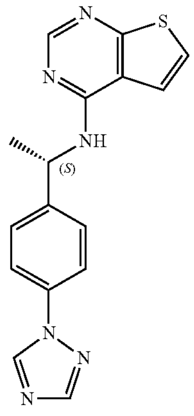

BBI-5-S

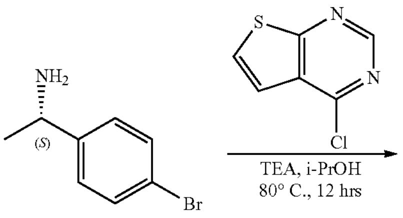

1

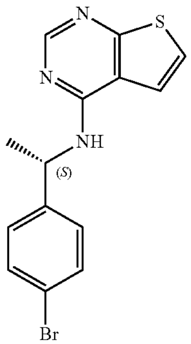

2

A mixture of (1S)-1-(4-bromophenyl)ethanamine (500 mg, 2.50 mmol, 1 eq), 4-chlorothieno[2,3-d]pyrimidine (469 mg, 2.75 mmol, 1.1 eq) and TEA (506 mg, 5.00 mmol, 2 eq) in i-PrOH (10 mL) was stirred at 80° C. for 12 hours. The reaction mixture was concentrated in vacuo. The residue was purified by column chromatography ($SiO_2$, Petroleum ether: THF=20:1 to 5:1) to give N-[(1S)-1-(4-bromophenyl)ethyl] thieno[2,3-d]pyrimidin-4-amine (0.7 g, 2.09 mmol, 83.81% yield) as a white solid. ESI [M+H]=334.2/336.2.

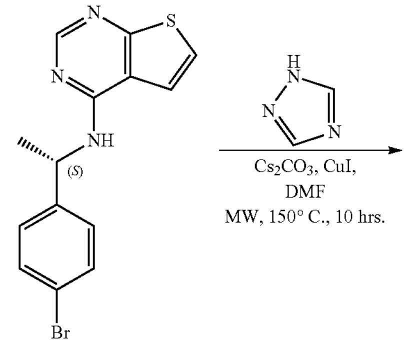

2

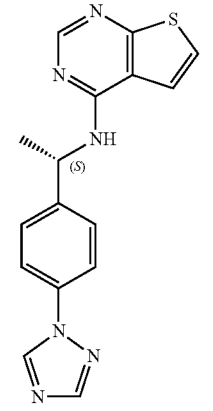

BBI-5-S

N-[(1S)-1-(4-bromophenyl)ethyl]thieno[2,3-d]pyrimidin-4-amine (400 mg, 1.20 mmol, 1 eq), 1H-1,2,4-triazole (124 mg, 1.80 mmol, 1.5 eq) and $Cs_2CO_3$ (780 mg, 2.39 mmol, 2 eq), CuI (46 mg, 239.35 umol, 0.2 eq) were taken up into a microwave tube in DMF (8 mL). The sealed tube was heated at 150° C. for 10 hours under microwave. The reaction was added water (30 mL) and extracted with EtOAc (15 mL×3). The organic layer was washed with brine (20 mL), dried over $MgSO_4$ and concentrated in vacuo. The residue was purified by prep-HPLC (column: Waters Xbridge Prep OBD C18 150*40 10u; mobile phase: [water (10 mM $NH_4HCO_3$)-ACN]; B %: 15%-45%, 11 min) to give N-[(1S)-1-[4-(1,2,4-triazol-1-yl)phenyl]ethyl]thieno[2,3-d]pyrimidin-4-amine (222.06 mg, 687.12 umol, 57.41% yield, 99.756% purity) as a white solid.

$^1H$ NMR (400 MHz, CHLOROFORM-d) δ 8.50 (d, J=14.8 Hz, 2H), 8.09 (s, 1H), 7.68-7.61 (m, 2H), 7.59-7.52 (m, 2H), 7.32 (d, J=6.2 Hz, 1H), 7.20 (d, J=6.0 Hz, 1H), 5.62 (quin, J=7.0 Hz, 1H), 5.43 (br d, J=7.1 Hz, 1H), 1.70 (d, J=7.1 Hz, 3H). ESI [M+H]=323.1. ee %=97.9%.

Example 16

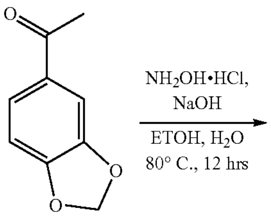

1

-continued

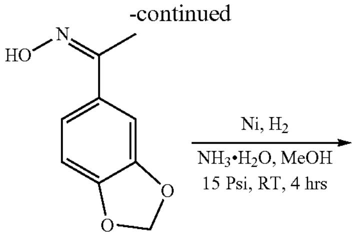

2

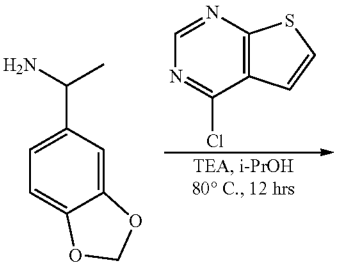

3

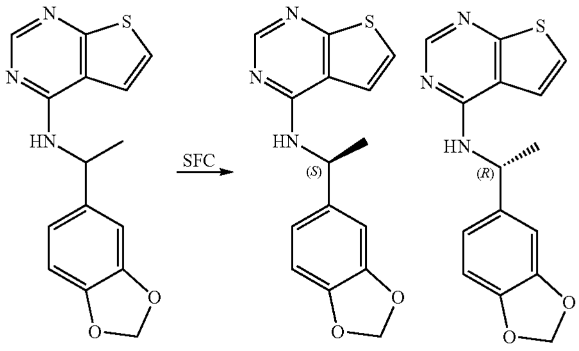

4 CLE-27A CLE-27B

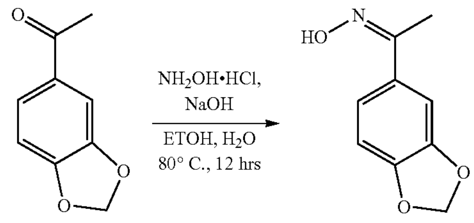

1 2

To a suspension of 1-(1,3-benzodioxol-5-yl)ethanone (1 g, 6.09 mmol, 1 eq) in EtOH (15 mL) and $H_2O$ (5 mL) was added NaOH (2.19 g, 54.83 mmol, 9 eq) and $NH_2OH·HCl$ (1.27 g, 18.28 mmol, 3 eq) at 20° C. and the mixture was stirred at 80° C. for 12 hours. The reaction was added water (30 mL) and extracted with DCM/i-PrOH (3/1, 20 mL×3). The organic layer was dried over $MgSO_4$ and concentrated in vacuo to give 1-(1,3-benzodioxol-5-yl)ethanone oxime (1.1 g, crude) as a white solid.

$^1H$ NMR (400 MHz, CHLOROFORM-d) δ 7.10 (d, J=1.7 Hz, 1H), 7.03 (dd, J=1.7, 8.2 Hz, 1H), 6.74 (d, J=8.1 Hz, 1H), 5.92 (s, 2H), 2.18 (s, 3H). ESI [M+H]=180.1.

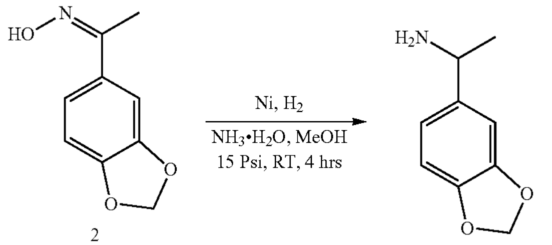

2 3

To a solution of 1-(1,3-benzodioxol-5-yl)ethanone oxime (0.2 g, 1.12 mmol, 1 eq) in MeOH (10 mL) was added Ni (100 mg, 1.70 mmol, 1.53 eq) and $NH_3 \cdot H_2O$ (1.00 mL, 30% purity, 6.98 eq) under N2. The suspension was degassed under vacuum and purged with $H_2$ several times. The mixture was stirred under $H_2$ (15 psi) at 25° C. for 4 hours. The mixture was filtered, and the filtrate was concentrated in vacuo to give 1-(1,3-benzodioxol-5-yl)ethanamine (190 mg, crude) as a white solid.

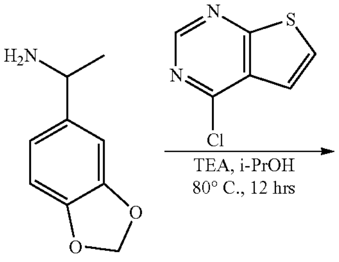

3

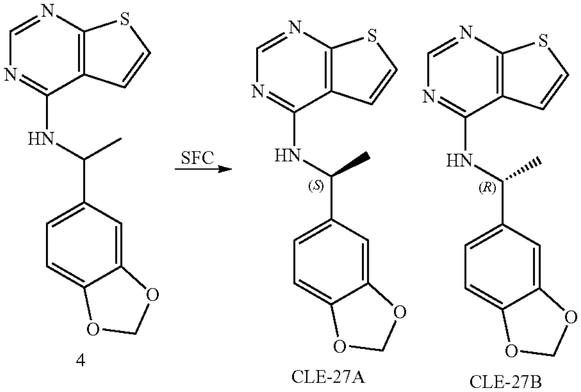

4 CLE-27A CLE-27B

A mixture of 1-(1,3-benzodioxol-5-yl)ethanamine (190 mg, 1.15 mmol, 1 eq), 4-chlorothieno[2,3-d]pyrimidine (216 mg, 1.27 mmol, 1.1 eq) and TEA (232.78 mg, 2.30 mmol, 320.19 uL, 2 eq) in i-PrOH (4 mL) was stirred at 80° C. for 12 hours. The reaction was concentrated under reduced pressure. The residue was purified by prep-TLC ($SiO_2$, PE:EtOAc=2:1) to give desired compound, which was further separated by SFC (Instrument: Waters prep-SFC 80Q; Column: Chiralpak AD-H, 250*25 mm i.d. 5u; Mobile phase: A for $C_{02}$ and B for MEOH (0.1% $NH_3 \cdot H_2O$); Gradient: B %=40%; Flow rate: 70 g/min; Column temperature: 40° C.; System back pressure: 100 bar) to give N-[(1S)-1-(1,3-benzodioxol-5-yl)ethyl]thieno[2,3-d]pyrimidin-4-amine (110.72 mg, 368.53 umol, 32.04% yield, 99.638% purity) as white solid and N-[(1R)-1-(1,3-benzodioxol-5-yl)ethyl]thieno[2,3-d]pyrimidin-4-amine (83.25 mg, 277.59 umol, 24.13% yield, 99.816% purity) as white solid. (The stereochemistry was assigned as R or S randomly since no standard data in reference. The peak with shorter (Rt=3.290) was assigned as S, the peak with longer (Rt=3.791) was assigned as R).

CLE-27A: $^1$HNMR (400 MHz, CHLOROFORM-d) δ 8.52 (s, 1H), 7.31 (d, J=6.0 Hz, 1H), 7.16 (d, J=6.0 Hz, 1H), 6.97-6.90 (m, 2H), 6.81 (d, J=8.2 Hz, 1H), 5.97 (s, 2H), 5.72-5.08 (m, 2H), 1.66 (d, J=6.7 Hz, 3H). ESI [M+H]=300.0.

CLE-27B: $^1$HNMR (400 MHz, CHLOROFORM-d) δ 8.52 (s, 1H), 7.30-7.27 (m, 1H), 7.29 (d, J=3.1 Hz, 1H), 7.16 (d, J=6.0 Hz, 1H), 6.95-6.88 (m, 2H), 6.83-6.77 (m, 1H), 6.07-5.91 (m, 2H), 5.51 (quin, J=7.0 Hz, 1H), 5.35 (br d, J=7.3 Hz, 1H), 1.65 (d, J=6.8 Hz, 3H). ESI [M+H]=300.1.

Example 17

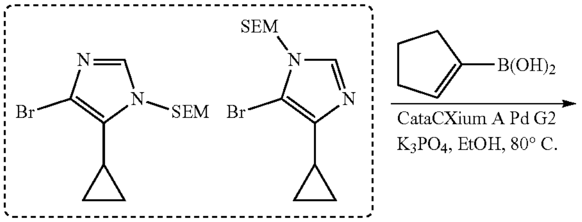

1

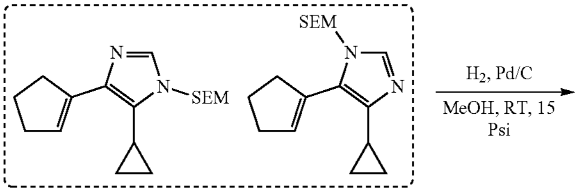

2

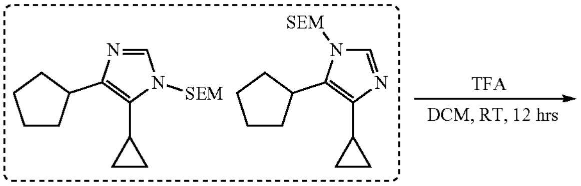

3

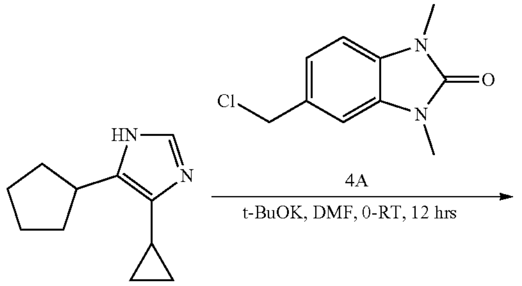

4

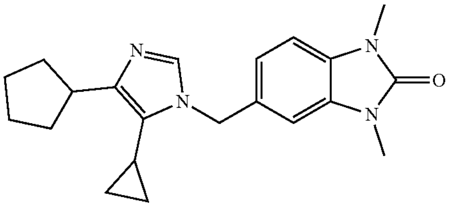

CWRU-WuXi-03

-continued

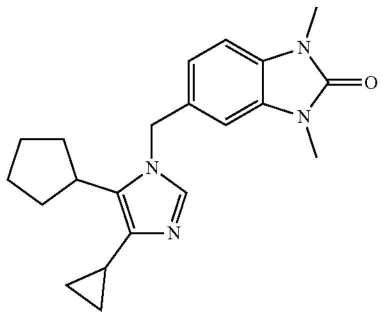

CWRU-WuXi-03A

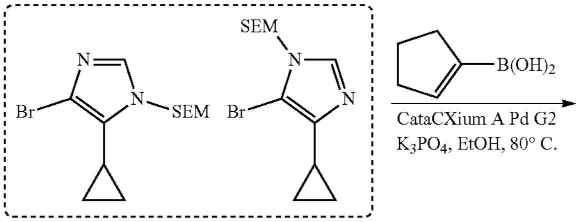

1

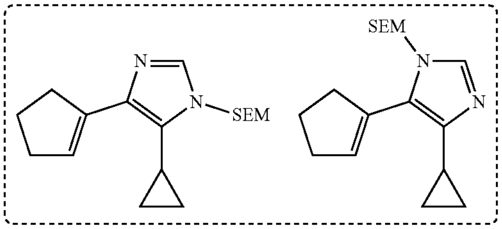

2

A mixture of 2-[(4-bromo-5-cyclopropyl-imidazol-1-yl)methoxy]ethyl-trimethyl-silane and 2-[(5-bromo-4-cyclopropyl-imidazol-1-yl)methoxy]ethyl-trimethyl-silane (total 200 mg), cyclopenten-1-ylboronic acid (141 mg, 1.26 mmol, 2 eq), $K_3PO_4$ (0.5 M, 2.5 mL, 2 eq) and [2-(2-aminophenyl)phenyl]-chloro-palladium; bis(1-adamantyl)-butyl-phosphane (42 mg, 63.03 umol, 0.1 eq) in EtOH (6 mL) was stirred at 80° C. for 12 hours under N2. The reaction was concentrated in vacuo. The residue was purified by prep-TLC (Petroleum ether:Ethyl acetate=1:5) to give 2-[[4-(cyclopenten-1-yl)-5-cyclopropyl-imidazol-1-yl]methoxy]ethyl-trimethyl-silane and 2-[[5-(cyclopenten-1-yl)-4-cyclopropyl-imidazol-1-yl]methoxy]ethyl-trimethyl-silane (total 180 mg) as a yellow oil. ESI [M+H]=305.2

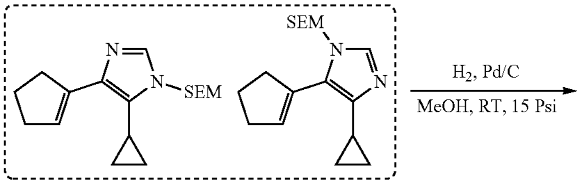

2

-continued

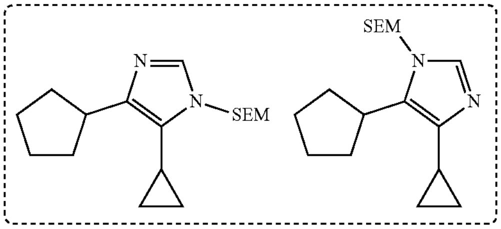

3

To a solution of 2-[[4-(cyclopenten-1-yl)-5-cyclopropyl-imidazol-1-yl]methoxy]ethyl-trimethyl-silane and 2-[[5-(cyclopenten-1-yl)-4-cyclopropyl-imidazol-1-yl]methoxy]ethyl-trimethyl-silane (total 180 mg) in MeOH (10 mL) was added Pd/C (50 mg, 10% purity) under N2 atmosphere. The suspension was degassed and purged with $H_2$ for 3 times. The mixture was stirred under $H_2$ (15 Psi) at 25° C. for 1 hour. The mixture was filtered and the filtrate was concentrated in vacuo to give 2-[(4-cyclopentyl-5-cyclopropyl-imidazol-1-yl)methoxy]ethyl-trimethyl-silane and 2-[(5-cyclopentyl-4-cyclopropyl-imidazol-1-yl)methoxy]ethyl-trimethyl-silane (total 150 mg) as a yellow oil. ESI [M+H]=307.2.

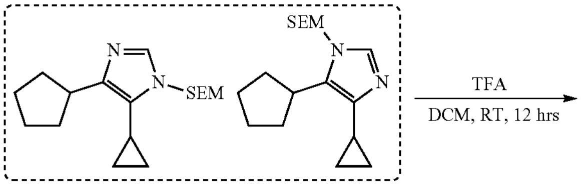

3

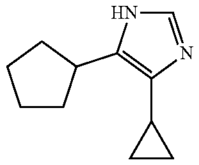

4

A solution of 2-[(4-cyclopentyl-5-cyclopropyl-imidazol-1-yl)methoxy]ethyl-trimethyl-silane and 2-[(5-cyclopentyl-4-cyclopropyl-imidazol-1-yl)methoxy]ethyl-trimethyl-silane (total 150 mg) in DCM (3 mL) and TFA (1 mL) was stirred at 25° C. for 12 hours. The reaction was concentrated in vacuo. The residue was added water (10 mL) and adjusted to pH=8 with sat.aq. $NaHCO_3$, extracted with EtOAc (5 mL×3). The organic layer was dried over $MgSO_4$ and concentrated in vacuo. The residue was purified by prep-TLC ($SiO_2$, Ethyl acetate:Methanol=30:1) to give 4-cyclopentyl-5-cyclopropyl-1H-imidazole (70 mg, 397.15 umol, 81.15% yield) as a yellow oil. ESI [M+H]=177.1.

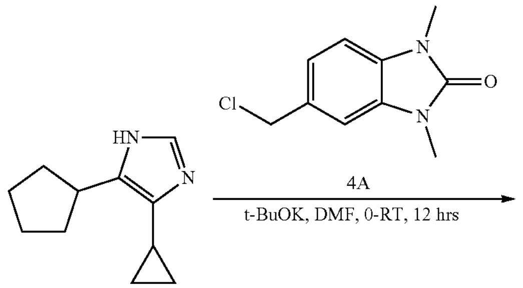

4

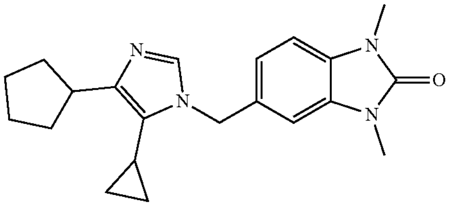

CWRU-WuXi-03

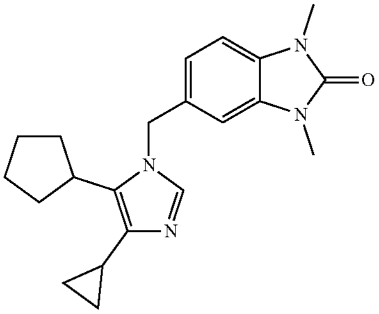

CWRU-WuXi-03A

To a solution of t-BuOK (1 M, 596 uL, 1.5 eq) in DMF (2 mL) was added dropwise 5-cyclopentyl-4-cyclopropyl-1H-imidazole (70 mg, 397.15 umol, 1 eq) in DMF (1 mL) at 0° C. under N2. After 15 minutes, 5-(chloromethyl)-1,3-dimethyl-benzimidazol-2-one (100.4 mg, 476.57 umol, 1.2 eq) in DMF (1 mL) was added at 0° C. under N2. The mixture was stirred at 20° C. for 12 hours. The reaction was added water (10 mL) and extracted with EtOAc (5 mL×3). The organic layer was dried over $MgSO_4$ and concentrated in vacuo. The residue was purified by prep-HPLC (column: Xamide 150*30 mm 5 um; mobile phase: [water (10 mM NH4HCO3)-ACN]; B %: 30%-50%, 10 min) to give 5-[(4-cyclopentyl-5-cyclopropyl-imidazol-1-yl)methyl]-1,3-dimethyl-benzimidazol-2-one (14.75 mg, 40.24 umol, 10.13% yield, 95.610% purity) (yellow gum) and 5-[(5-cyclopentyl-4-cyclopropyl-imidazol-1-yl)methyl]-1,3-dimethyl-benzimidazol-2-one (11.06 mg, 31.13 umol, 7.84% yield, 98.628% purity) as a white solid.

CWRU-WuXi-03: $^1$H NMR (400 MHz, CHLOROFORM-d) δ 7.44 (s, 1H), 6.96-6.88 (m, 2H), 6.72 (s, 1H), 5.19 (s, 2H), 3.41 (d, J=12.8 Hz, 6H), 3.15 (quin, J=8.4 Hz, 1H), 1.94-1.81 (m, 6H), 1.69-1.60 (m, 2H), 1.36 (tt, J=5.3, 8.1 Hz, 1H), 0.93-0.84 (m, 2H), 0.65-0.58 (m, 2H). ESI [M+H]=351.1.

CWRU-WuXi-03A: $^1$H NMR (400 MHz, CHLOROFORM-d) δ 7.32 (s, 1H), 6.92 (d, J=7.9 Hz, 1H), 6.82 (dd, J=1.5, 7.9 Hz, 1H), 6.65 (s, 1H), 5.10 (s, 2H), 3.42 (s, 3H), 3.38 (s, 3H), 3.02-2.91 (m, 1H), 1.87-1.74 (m, 8H), 1.59-1.52 (m, 1H), 0.99-0.92 (m, 2H1), 0.88-0.80 (m, 2H1). ESI [M+H]=351.2.

Example 18

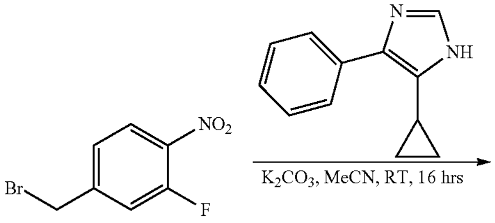

1

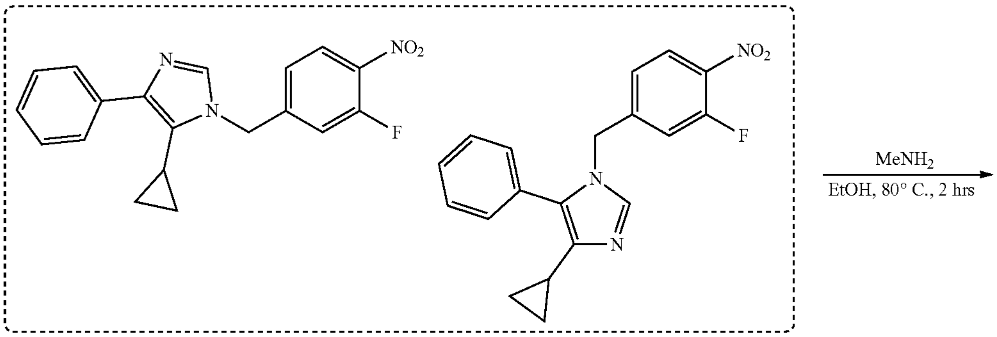

2

-continued
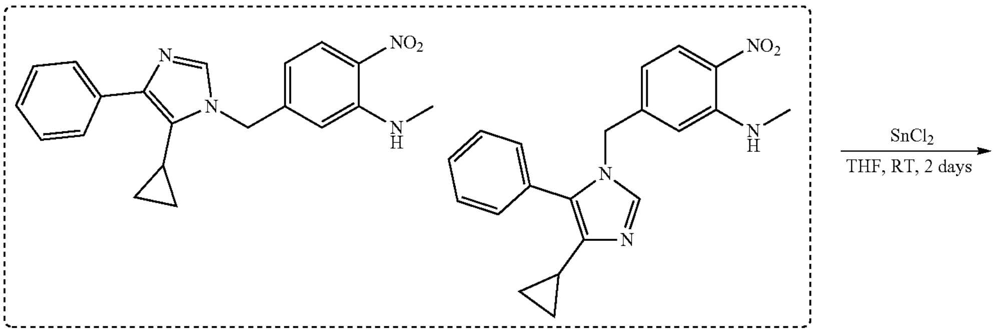
3
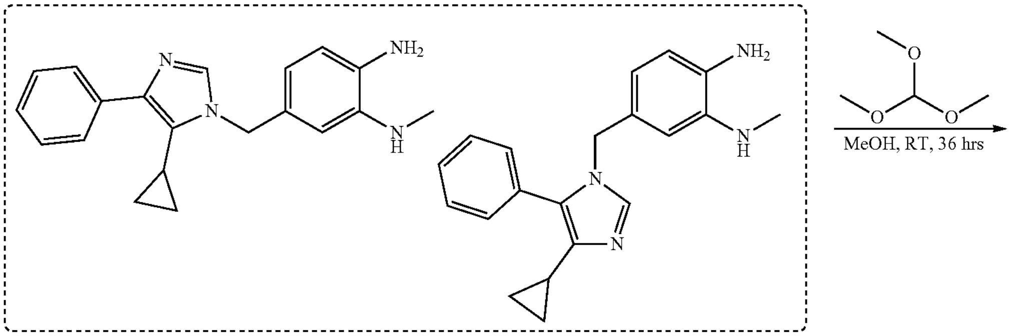
4
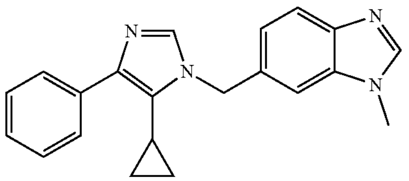
CWRU-WuXi-08
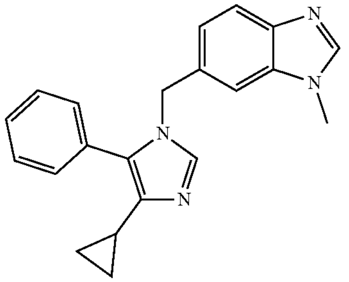
CWRU-WuXi-08A
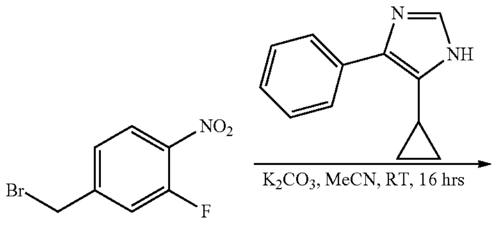
1
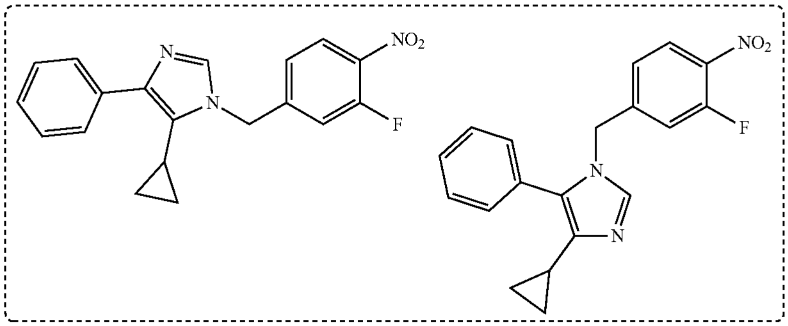
2

A mixture of 4-(bromomethyl)-2-fluoro-1-nitro-benzene (286 mg, 1.22 mmol, 1.5 eq), 5-cyclopropyl-4-phenyl-1H-imidazole (150 mg, 814.17 umol, 1 eq) and $K_2CO_3$ (225 mg, 1.63 mmol, 2 eq) in MeCN (4 mL) was stirred at 20° C. for 16 hours. The reaction was added water (10 mL) and extracted with EtOAc (5 mL×3). The organic layer was dried over $MgSO_4$ and concentrated in vacuo. The residue was purified by prep-TLC ($SiO_2$, Ethyl acetate:Methanol=20:1) to give a mixture of regioisomers 5-cyclopropyl-1-[(3-fluoro-4-nitro-phenyl)methyl]-4-phenyl-imidazole and 4-cyclopropyl-1-[(3-fluoro-4-nitro-phenyl)methyl]-5-phenyl-imidazole (total 100 mg) as a yellow oil. ESI [M+H]=338.1.

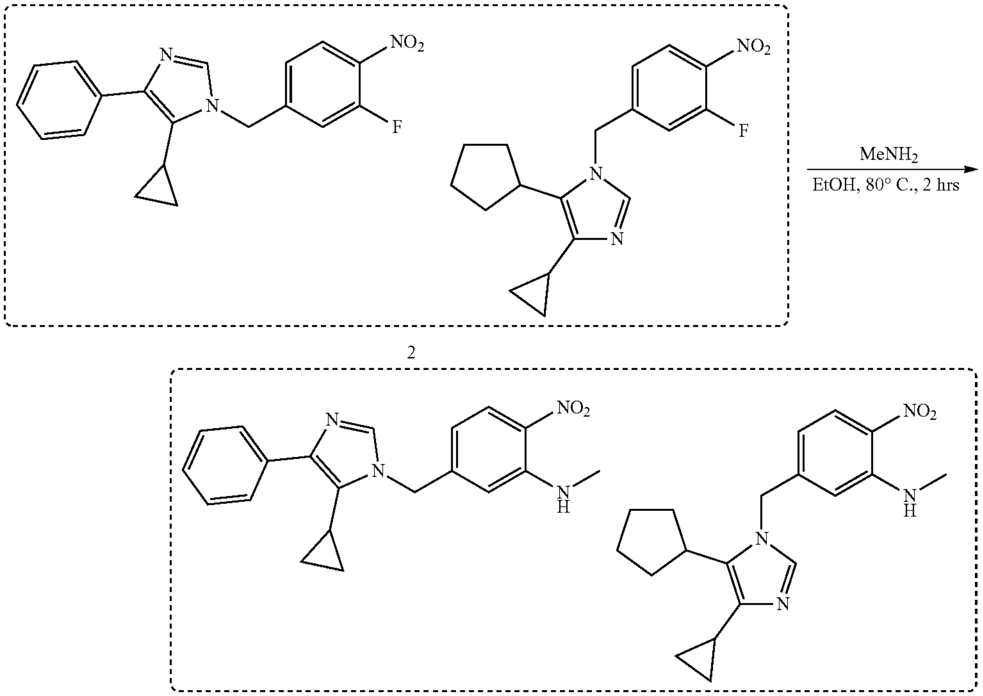

2

3

A solution of 5-cyclopropyl-1-[(3-fluoro-4-nitro-phenyl)methyl]-4-phenyl-imidazole and 4-cyclopropyl-1-[(3-fluoro-4-nitro-phenyl)methyl]-5-phenyl-imidazole (total 100 mg) in $MeNH_2$ (0.5 mL, 33% in EtOH), EtOH (1 mL) was stirred at 80° C. for 2 hours. The reaction mixture was concentrated under reduced pressure to give a residue. The residue was purified by prep-TLC ($SiO_2$, EtAOc/MeOH=30/1) to give a mixture of regioisomers 5-[(5-cyclopropyl-4-phenyl-imidazol-1-yl)methyl]-N-methyl-2-nitro-aniline and 5-[(4-cyclopropyl-5-phenyl-imidazol-1-yl)methyl]-N-methyl-2-nitro-aniline (total 110 mg) as yellow oil. ESI [M+H]=349.1.

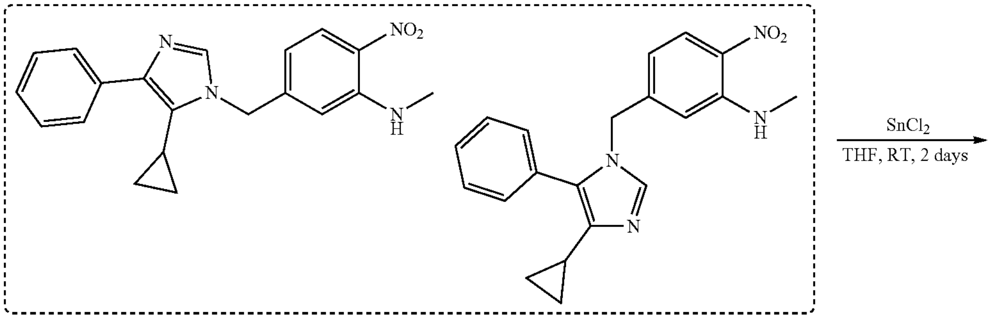

3

-continued

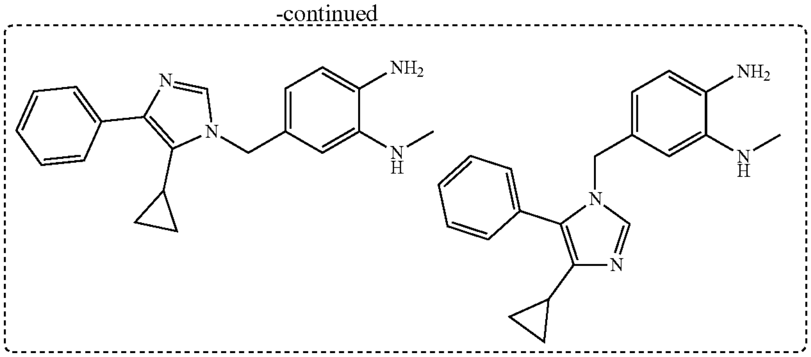

4

To a solution of 5-[(5-cyclopropyl-4-phenyl-imidazol-1-yl)methyl]-N-methyl-2-nitro-aniline] and 5-[(4-cyclopropyl-5-phenyl-imidazol-1-yl)methyl]-N-methyl-2-nitro-aniline (total 110 mg) in THF (1 mL) was added $SnCl_2 \cdot 2H_2O$ (214 mg, 947.19 umol, 3 eq). The mixture was stirred at 20° C. for 48 hours. The reaction mixture was quenched by addition sat.aq.$NaHCO_3$ (10 mL) at 0° C., filtered, and then extracted with EtOAc (10 mL×3). The combined organic layers were dried over $Na_2SO_4$, filtered and concentrated under reduced pressure to give the crude product 4-[(5-cyclopropyl-4-phenyl-imidazol-1-yl)methyl]-N2-methyl-benzene-1,2-diamine and 4-[(4-cyclopropyl-5-phenyl-imidazol-1-yl)methyl]-N2-methyl-benzene-1,2-diamine (total 100 mg) as brown oil. ESI [M+H]=319.1.

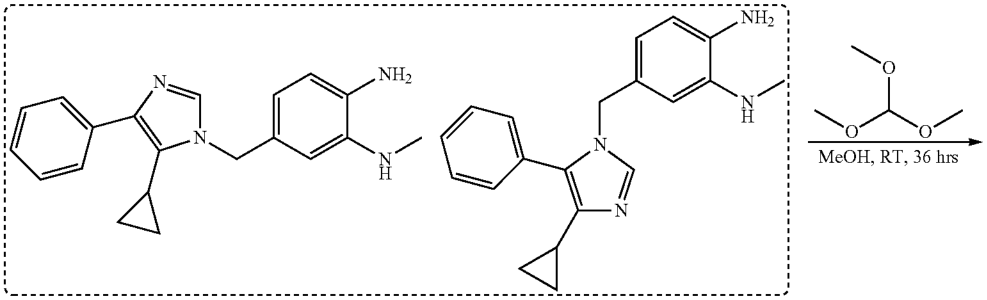

4

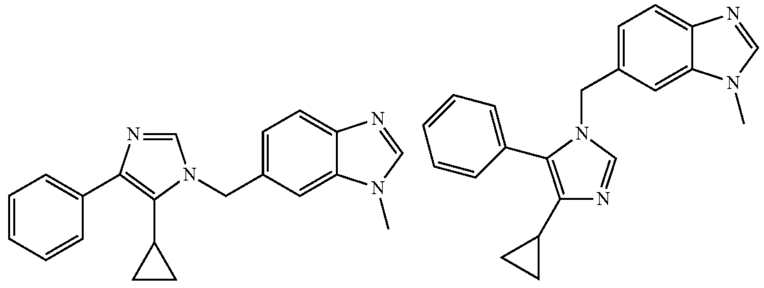

CWRU—WuXi-08 CWRU—WuXi-08A

A mixture of 4-[(5-cyclopropyl-4-phenyl-imidazol-1-yl)methyl]-N2-methyl-benzene-1,2-diamine and 4-[(4-cyclopropyl-5-phenyl-imidazol-1-yl)methyl]-N2-methyl-benzene-1,2-diamine (total 100 mg, 314.06 umol, 1 eq) in trimethoxymethane (4 mL) and MeOH (4 mL) was degassed and purged with N2 for 3 times, and then the mixture was stirred at 20° C. for 36 hours under N2 atmosphere. The reaction mixture was concentrated under reduced pressure to give a residue. The residue was purified by prep-HPLC (column: Waters Xbridge 150*25 5u; mobile phase: [water (10 mM $NH_4HCO_3$)-ACN]; B %: 20%-40%, 10 min) to give a mixture of regioisomer 6-[(5-cyclopropyl-4-phenyl-imidazol-1-yl)methyl]-1-methyl-benzimidazole and 6-[(4-cyclopropyl-5-phenyl-imidazol-1-yl)methyl]-1-methyl-benzimidazole (Purity: 99.772%, 23.18 mg) as white soild. ESI [M+H]=329.1.

Example 19

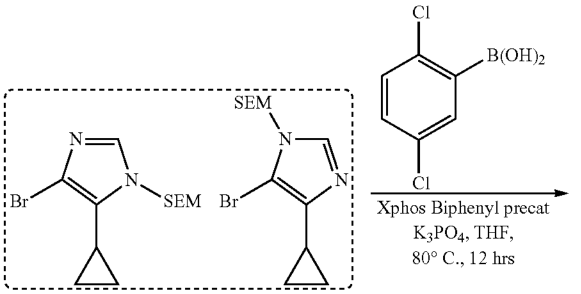

1

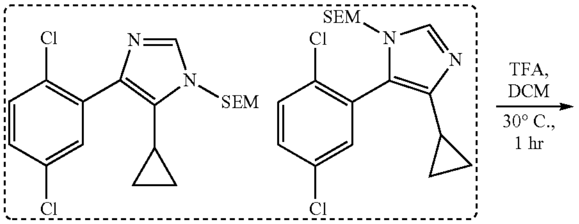

2

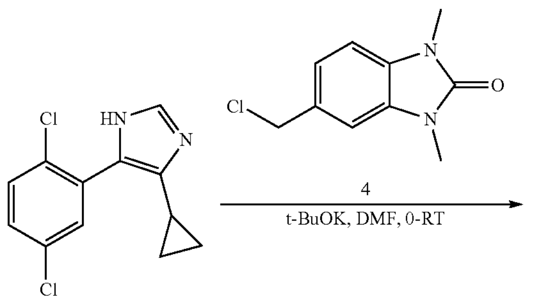

4

3

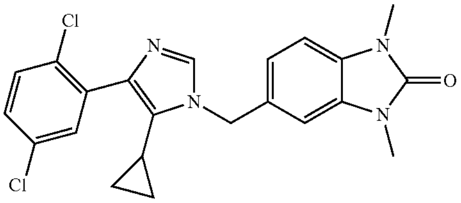

CWRU—WuXi-12

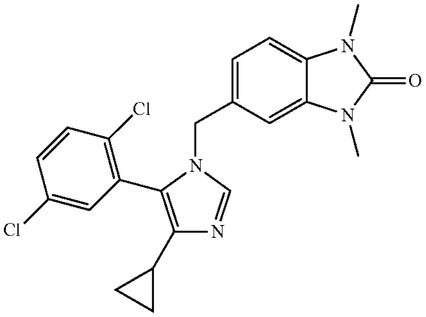

CWRU—WuXi-12A

-continued

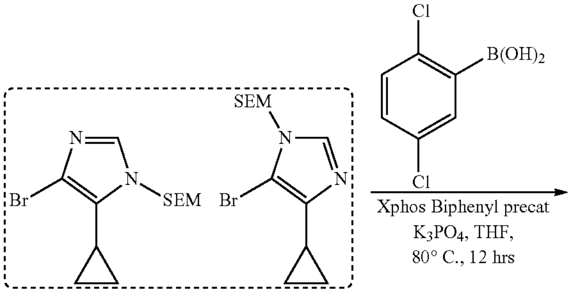

1

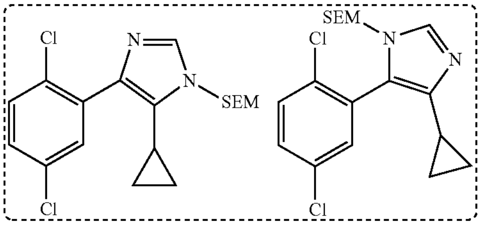

2

A mixture of 2-[(4-bromo-5-cyclopropyl-imidazol-1-yl)methoxy]ethyl-trimethyl-silane and 2-[(5-bromo-4-cyclopropyl-imidazol-1-yl)methoxy]ethyl-trimethyl-silane (total 0.4 g, 1.26 mmol, 1 eq), (2,5-dichlorophenyl)boronic acid (481 mg, 2.52 mmol, 2 eq), $K_3PO_4$ (0.5 M, 5 mL, 2 eq) and [2-(2-aminophenyl)phenyl]-chloro-palladium; dicyclohexyl-[3-(2,4,6-triisopropylphenyl)phenyl]phosphane (50 mg, 63.03 umol, 0.05 eq) in THF (10 mL) was stirred at 80° C. for 12 hours under N2. The reaction was added water (10 mL) and extracted with EtOAc (10 mL×3). The organic layer was washed with brine (20 mL), dried over $MgSO_4$ and concentrated in vacuo. The residue was purified by column chromatography ($SiO_2$, Petroleum ether/Ethyl acetate=20/1 to 1/1) to give 2-[[5-cyclopropyl-4-(2,5-dichlorophenyl)imidazol-1-yl]methoxy]ethyl-trimethyl-silane and 2-[[4-cyclopropyl-5-(2,5-dichlorophenyl)imidazol-1-yl]methoxy]ethyl-trimethyl-silane (total 500 mg, crude) as a yellow oil. ESI [M+H]=383.1.

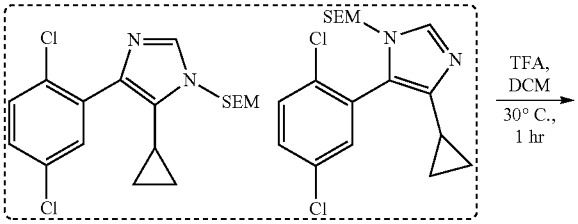

2

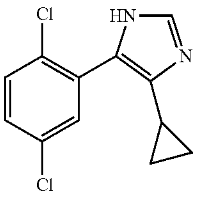

3

A solution of 2-[[5-cyclopropyl-4-(2,5-dichlorophenyl)imidazol-1-yl]methoxy]ethyl-trimethyl-silane and 2-[[4-cyclopropyl-5-(2,5-dichlorophenyl)imidazol-1-yl]methoxy] ethyl-trimethyl-silane (total 500 mg, 1.30 mmol, 1 eq) in DCM (10 mL) and TFA (4 mL) was stirred at 30° C. for 1 hour. The reaction was concentrated in vacuo. The residue was dissolved in EtOAc (5 mL) and water (10 mL), adjusted to pH=8 with sat.aq·$Na_2CO_3$. The mixture was partitioned between EtOAc (5 mL×3) and water (10 mL). The organic phase was separated, dried over $MgSO_4$, filtered and concentrated under reduced pressure to give a residue. The residue was purified by prep-TLC ($SiO_2$, Petroleum ether: Ethyl acetate=0:1) to give 5-cyclopropyl-4-(2,5-dichlorophenyl)-1H-imidazole (150 mg, 592.59 umol, 45.44% yield) as a yellow oil. ESI [M+H]=253.1.

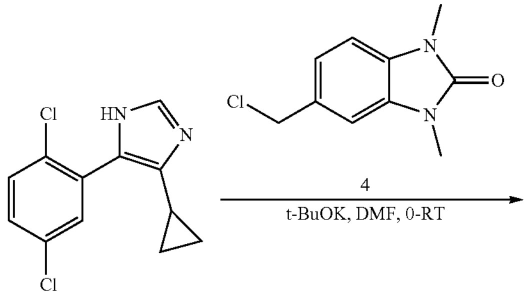

3

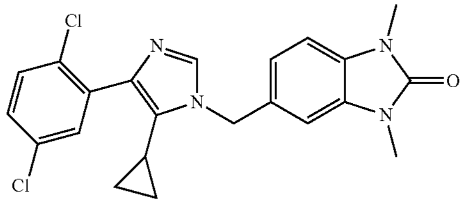

CWRU—WuXi-12

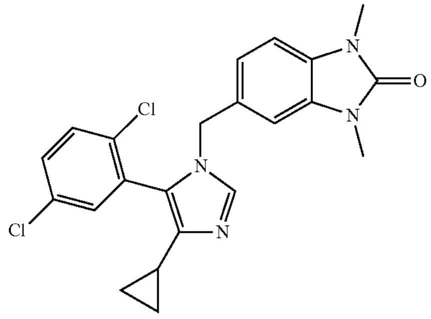

CWRU—WuXi-12A

To a solution of t-BuOK (1 M, 474 uL, 1.5 eq) in DMF (2 mL) was added dropwise 4-cyclopropyl-5-(2,5-dichlorophenyl)-1H-imidazole (80 mg, 316.05 umol, 1 eq) in DMF (0.5 mL) at 0° C. under N2. After 15 minutes, 5-(chloromethyl)-1,3-dimethyl-benzimidazol-2-one (80 mg, 379.26 umol, 1.2 eq) in DMF (0.5 mL) was added at 0° C. under N2. The mixture was stirred at 20° C. for 12 hours. The reaction was added water (10 mL) and extracted with EtOAc (5 mL×3). The organic layer was dried over $MgSO_4$ and concentrated in vacuo. The residue was purified by prep-HPLC (column: Xtimate C18 150*25 mm*5 um; mobile phase: [water (10 mM NH4HCO3)-ACN]; B %: 40%-60%, 10 min) to give 5-[[5-cyclopropyl-4-(2,5-dichlorophenyl) imidazol-1-yl]methyl]-1,3-dimethyl-benzimidazol-2-one (12.16 mg, 28.01 umol, 8.86% yield, 98.422% purity) and 5-[[4-cyclopropyl-5-(2,5-dichlorophenyl)imidazol-1-yl] methyl]-1,3-dimethyl-benzimidazol-2-one (30.81 mg, 71.24 umol, 22.54% yield, 98.805% purity) as a white solid.

CWRU-WuXi-12: $^1$H NMR (400 MHz, CHLOROFORM-d) δ 7.27 (s, 1H), 7.22 (d, J=2.4 Hz, 1H), 7.10 (d, J=8.6 Hz, 1H), 6.98 (dd, J=2.5, 8.5 Hz, 1H), 6.70 (d, J=0.7 Hz, 2H), 6.47 (s, 1H), 5.04 (s, 2H), 3.18 (s, 3H), 3.13 (s, 3H), 1.30-1.23 (m, 1H), 0.52-0.46 (m, 2H), 0.05-0.01 (m, 2H). ESI [M+H]=427.1.

CWRU-WuXi-12A: $^1$H NMR (400 MHz, CHLOROFORM-d) δ 7.48 (s, 1H), 7.42-7.37 (m, 1H), 7.32-7.27 (m, 1H), 7.09 (d, J=2.4 Hz, 1H), 6.81 (d, J=7.9 Hz, 1H), 6.68 (d, J=7.9 Hz, 1H), 6.45 (s, 1H), 5.05-4.96 (m, 1H), 4.83 (d, J=15.0 Hz, 1H), 3.39 (s, 3H), 3.32 (s, 3H), 1.56-1.49 (m, 1H), 0.89-0.81 (m, 2H), 0.78-0.71 (m, 2H). ESI [M+H]=427.2.

Example 20

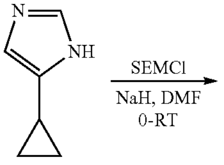

1

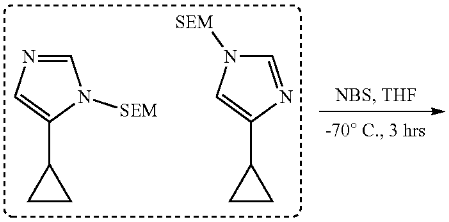

2

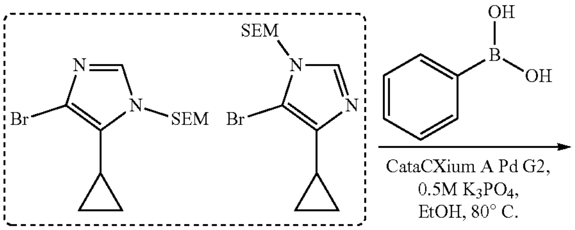

3

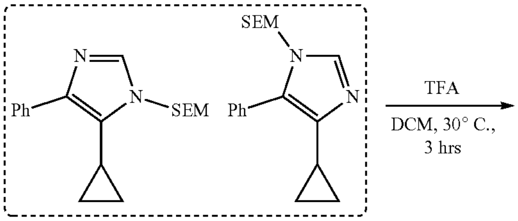

4

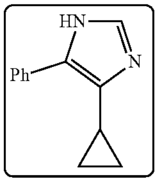

5

-continued

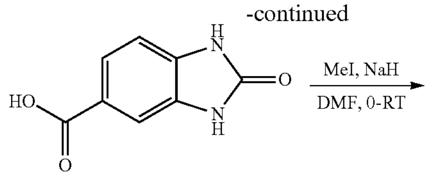

6

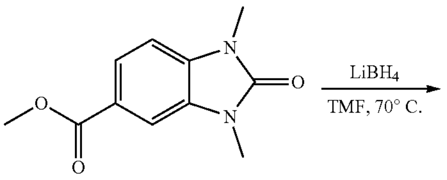

7

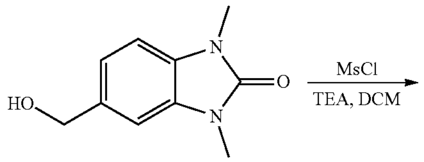

8

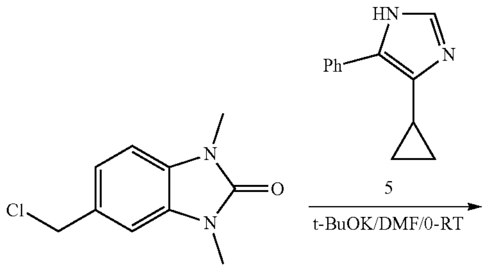

9

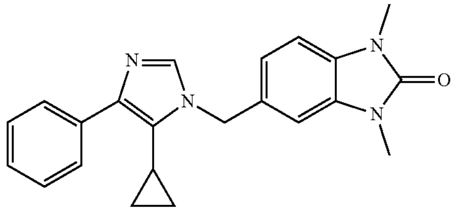

BBI-7

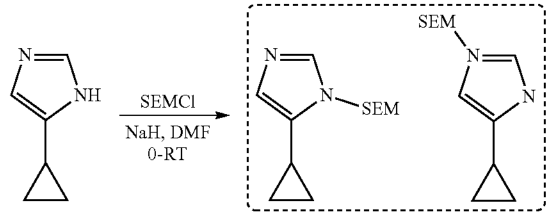

1 2

To a solution of 5-cyclopropyl-1H-imidazole (3.9 g, 36.06 mmol, 1 eq) in DMF (80 mL) was added NaH (1.4 g, 36.06 mmol, 1 eq) at 0° C. The mixture was stirred at 20° C. for 30 minutes, then SEM-Cl (6.6 g, 39.67 mmol, 1 eq) was added at 0° C. and the mixture was stirred at 20° C. for 12 hours. The reaction mixture was quenched with cold sat.aq. $NH_4Cl$ (100 mL), and extracted with EtOAc (50 mL×3). The organic layer was washed with brine (100 mL), dried over $MgSO_4$ and concentrated in vacuo. The residue was purified by column chromatography ($SiO_2$, Petroleum ether:Ethyl acetate=10:1 to 1:1) to give a mixture of regioisomers 2-[(5-cyclopropylimidazol-1-yl)methoxy]ethyl-trimethyl-silane and 2-[(4-cyclopropylimidazol-1-yl)methoxy]ethyl-trimethyl-silane, total 7.3 g as a yellow oil. ESI [M+H]=239.2.

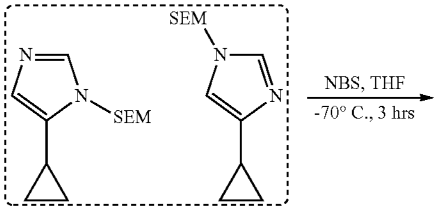

2

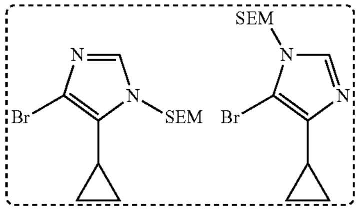

3

To a solution of 2-[(5-cyclopropylimidazol-1-yl)methoxy]ethyl-trimethyl-silane and 2-[(4-cyclopropylimidazol-1-yl)methoxy]ethyl-trimethyl-silane (total 3 g, 12.58 mmol, 1 eq) in THF (90 mL) was added NBS (2.24 g, 12.58 mmol, 1 eq) at −70° C. Then the mixture was stirred at −70° C. for 3 hours. The reaction was added water (60 mL) and extracted with EtOAc (20 mL×3). The organic layer was washed with brine (50 mL), dried over $MgSO_4$ and concentrated in vacuo. The residue was purified by column chromatography ($SiO_2$, Petroleum ether/Ethyl acetate=1/0 to 10/1) to give a mixture of regioisomers 2-[(4-bromo-5-cyclopropyl-imidazol-1-yl)methoxy]ethyl-trimethyl-silane and 2-[(5-bromo-4-cyclopropyl-imidazol-1-yl)methoxy]ethyl-trimethyl-silane total 2.8 g as a yellow oil. ESI [M+H]=317.3/319.3.

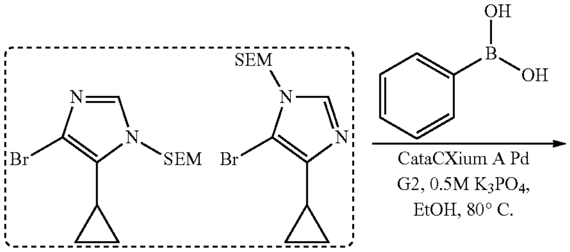

3

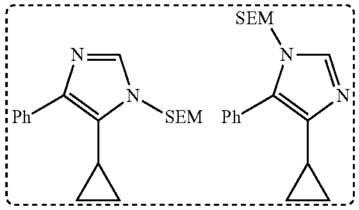

4

A mixture of 2-[(4-bromo-5-cyclopropyl-imidazol-1-yl)methoxy]ethyl-trimethyl-silane and 2-[(5-bromo-4-cyclopropyl-imidazol-1-yl)methoxy]ethyl-trimethyl-silane (total 2.8 g, 8.82 mol, 1 eq), phenylboronic acid (1.3 g, 10.59 mmol, 1.2 eq), $K_3PO_4$ (0.5 M, 35.30 mL, 2 eq) and [2-(2-aminophenyl)phenyl]-chloro-palladium; bis(1-adamantyl)-butyl-phosphane (354 mg, 529.47 umol, 0.06 eq) in EtOH (70 mL) was stirred at 80° C. for 12 hours under N2. The mixture was concentrated under reduced pressure to remove EtOH and the aqueous layer was extracted with EtOAc (20 mL×3). The organic layer was washed with brine (50 mL), dried over $MgSO_4$ and concentrated in vacuo. The residue was purified by column chromatography ($SiO_2$, Petroleum ether/Ethyl acetate=10/1 to 1/1) to give a mixture of regioisomers 2-[(5-cyclopropyl-4-phenyl-imidazol-1-yl)methoxy]ethyl-trimethyl-silane and 2-[(4-cyclopropyl-5-phenyl-imidazol-1-yl)methoxy]ethyl-trimethyl-silane (total 2.6 g, 93.5% yield) as a black brown oil. ESI [M+H]=315.2.

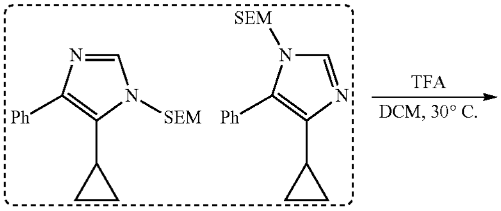

4

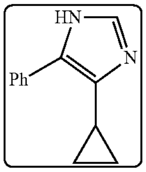

5

A mixture of 2-[(5-cyclopropyl-4-phenyl-imidazol-1-yl)methoxy]ethyl-trimethyl-silane and 2-[(4-cyclopropyl-5-phenyl-imidazol-1-yl)methoxy]ethyl-trimethyl-silane (total 2.6 g, 8.27 mmol) in TFA (10 mL) and DCM (30 mL) was stirred at 30° C. for 3 hour. The reaction was concentrated in vacuo. The residue was dissolved in EtOAc (20 mL) and water (10 mL), adjusted to pH=8 with sat.aq·$Na_2CO_3$. Then the mixture was partitioned between EtOAc (10 mL×3) and water (20 mL). The organic layer was dried over $MgSO_4$ and concentrated in vacuo. The residue was purified by column chromatography ($SiO_2$, Petroleum ether/Ethyl acetate=10/1 to 1/2) to give 5-cyclopropyl-4-phenyl-1H-imidazole (1.8 g) as a yellow solid.

$^1$H NMR (400 MHz, CHLOROFORM-d) δ 7.74 (br s, 2H), 7.51 (s, 1H), 7.42 (t, J=7.7 Hz, 2H), 7.32-7.27 (m, 1H), 2.05 (tt, J=5.2, 8.3 Hz, 1H), 1.03-0.92 (m, 2H), 0.80 (br s, 2H). ESI [M+H]=185.2.

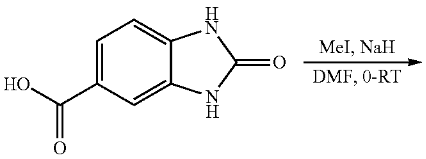

6

-continued

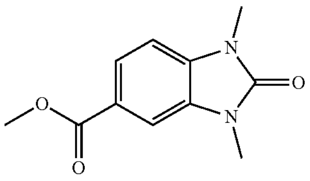

7

To a solution of 2-oxo-1,3-dihydrobenzimidazole-5-carboxylic acid (8 g, 44.91 mmol, 1 eq), in DMF (200 mL) was added NaH (6.3 g, 157.18 mmol, 60% purity, 3.5 eq) at 0° C. After 30 minutes, MeI (22.3 g, 157.18 mmol, 3.5 eq) was added at 0° C. Then the mixture was stirred at 20° C. for 16 hours. The reaction was quenched with sat.aq.$NH_4Cl$ (500 mL) and extracted with EtOAc (200 mL×3). The organic layer was washed with brine (500 mL×2), dried over $MgSO_4$ and concentrated in vacuo. The residue was triturated with PE/MTBE (50 mL/5 mL), and solid precipitate was collected via filtration, dried in vacuo to give methyl 1,3-dimethyl-2-oxo-benzimidazole-5-carboxylate (8.9 g, 40.41 mmol, 89.99% yield) as a brown solid.

$^1$H NMR (400 MHz, CHLOROFORM-d) δ 7.90 (dd, J=1.5, 8.3 Hz, 1H), 7.69 (d, J=1.3 Hz, 1H), 7.01 (d, J=8.2 Hz, 1H), 3.95 (s, 3H), 3.48 (d, J=4.0 Hz, 6H). ESI [M+H]=221.2.

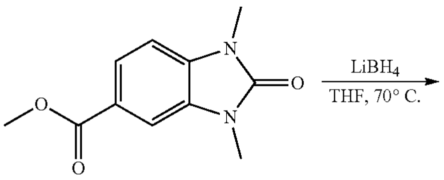

7

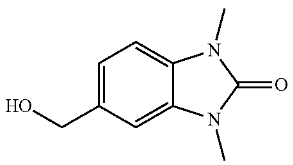

8

To a solution of methyl 1,3-dimethyl-2-oxo-benzimidazole-5-carboxylate (8.9 g, 40.41 mmol, 1 eq) in THF (160 mL) was added $LiBH_4$ (1.76 g, 80.83 mmol, 2 eq) at 20° C. Then the mixture was stirred at 70° C. for 16 hours. The reaction was quenched with cold sat.aq. $NH_4Cl$ (200 mL), extracted with EtOAc (100 mL×3). The organic layer was washed with brine (200 mL), dried over $MgSO_4$ and concentrated in vacuo to give 5-(hydroxymethyl)-1,3-dimethyl-benzimidazol-2-one (7 g, crude) as a light red solid.

$^1$H NMR (400 MHz, CHLOROFORM-d) δ 7.08 (d, J=7.9 Hz, 1H), 7.02 (s, 1H), 6.91 (d, J=8.2 Hz, 1H1), 4.73 (s, 2H1), 3.40 (s, 6H1). ESI [M+H]=193.1.

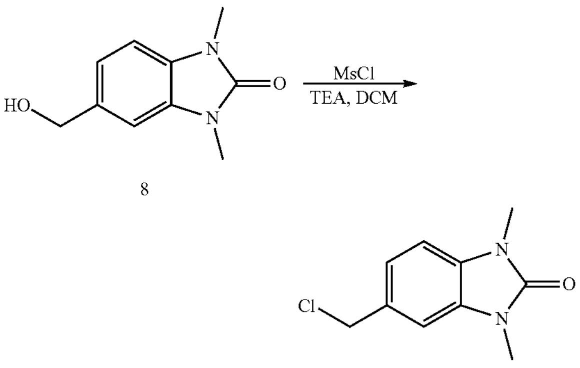

8

9

To a mixture of 5-(hydroxymethyl)-1,3-dimethyl-benzimidazol-2-one (2 g, 10.41 mmol, 1 eq) and TEA (3.2 g, 31.22 mmol, 3 eq) in DCM (40 mL) was added MsCl (2.4 g, 20.81 mmol, 2 eq) at −10° C. The mixture was stirred at −10-0° C. for 2 hours. The reaction was concentrated in vacuo. The residue was purified by column chromatography ($SiO_2$, Petroleum ether/Ethyl acetate=10/1 to 1/1) to give 5-(chloromethyl)-1,3-dimethyl-benzimidazol-2-one (1 g, 4.75 mmol, 45.62% yield) as a white solid.

$^1$H NMR (400 MHz, CHLOROFORM-d) δ 7.12 (dd, J=1.5, 7.9 Hz, 1H), 7.02 (d, J=1.3 Hz, 1H), 6.93 (d, J=7.9 Hz, 1H), 4.67 (s, 2H), 3.43 (d, J=4.4 Hz, 6H).

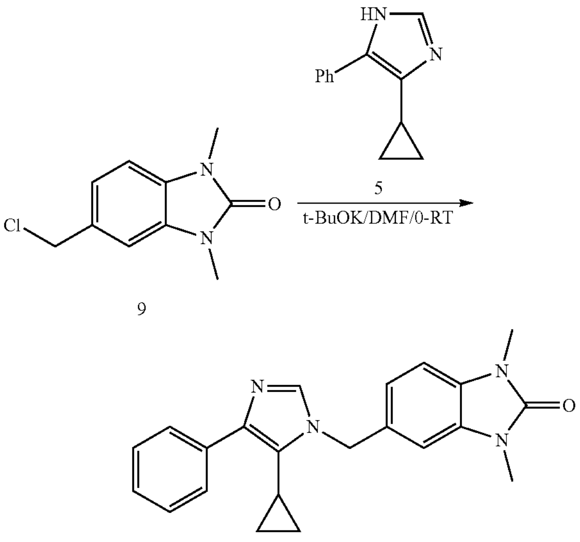

5

9

BBI-7

To a solution of t-BuOK (1 M, 2.44 mL, 1.5 eq) in DMF (10 mL) was added dropwise 4-cyclopropyl-5-phenyl-1H-imidazole (0.3 g, 1.63 mmol, 1 eq) in DMF (2 mL) at 0° C. under N2. After 15 min, 5-(chloromethyl)-1,3-dimethyl-benzimidazol-2-one (377 mg, 1.79 mmol, 1.1 eq) in DMF (5 mL) was added at 0° C. under N2. The mixture was stirred at 20° C. for 2 hours. The reaction was added water (20 mL) and extracted with EtOAc (10 mL×3). The organic layer was dried over $MgSO_4$ and concentrated in vacuo. The residue was purified by column chromatography ($SiO_2$, Petroleum ether/Ethyl acetate=10/1 to 1/2) to give desired compound (560 mg) as a yellow oil, which was further separated by SFC (condition: Instrument: Waters prep-SFC 80Q; Column: Chiralpak OJ-H, 250*25 mm i.d. 10u; Mobile phase: A for $C_{02}$ and B for MEOH (0.1% $NH_3 \cdot H_2O$); Gradient: B %=50%; Flow rate: 70 g/min; Column temperature: 40° C.; System back pressure: 100 bar) to give 5-[(5-cyclopropyl-4-phenyl-imidazol-1-yl)methyl]-1,3-dimethyl-benzimidazol-2-one (188 mg, 520.46 umol, 31.96% yield, 99.225% purity, Rt=3.56 min on SFC) as a white solid.

BBI-7: $^1$H NMR (400 MHz, CHLOROFORM-d) δ 7.80 (d, J=7.2 Hz, 2H), 7.55 (s, 1H), 7.40 (t, J=7.7 Hz, 2H), 7.28-7.23 (m, 1H), 7.01-6.93 (m, 2H), 6.79 (s, 1H), 5.30 (s, 2H), 3.43 (d, J=15.2 Hz, 6H), 1.63-1.55 (m, 1H), 1.04-0.95 (m, 2H), 0.52-0.45 (m, 2H). ESI [M+H]=359.1.

Example 21

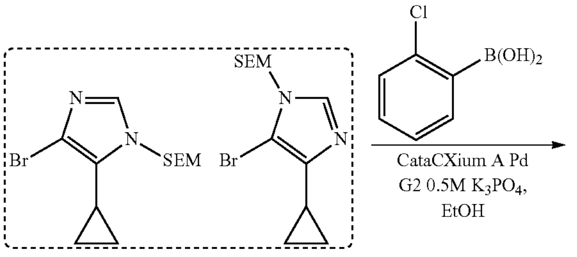

1

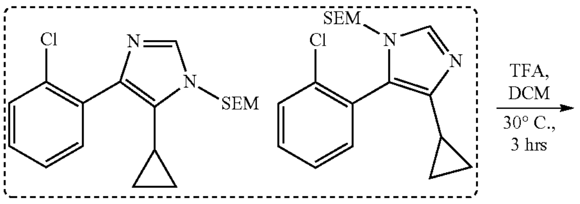

2

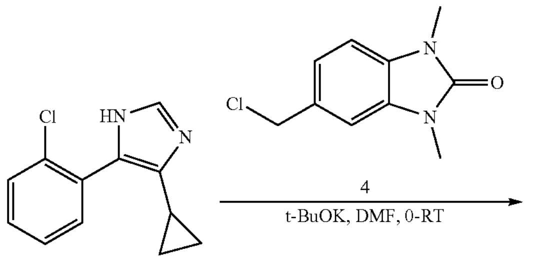

4

3

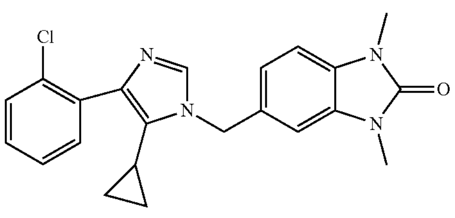

CWRU—WuXi-11

-continued

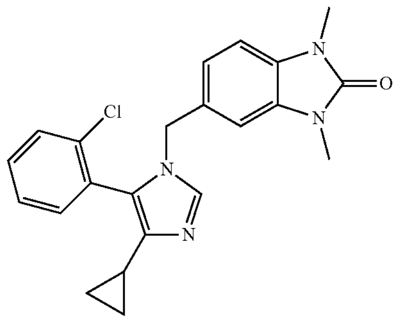

CWRU—WuXi-11A

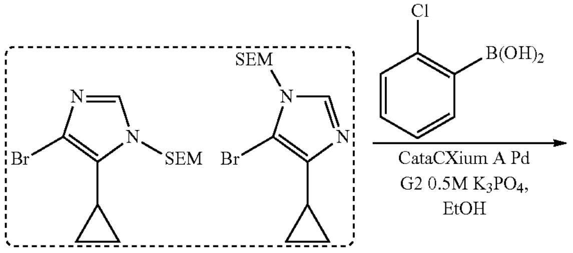

1

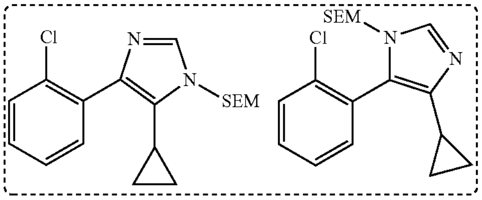

2

A mixture of 2-[(4-bromo-5-cyclopropyl-imidazol-1-yl)methoxy]ethyl-trimethyl-silane and 2-[(5-bromo-4-cyclopropyl-imidazol-1-yl)methoxy]ethyl-trimethyl-silane (total 150 mg, 472.74 ummol, 1 eq), (2-chlorophenyl)boronic acid (110 mg, 709.12 umol, 1.5 eq), $K_3PO_4$ (0.5 M, 1.9 mL, 2 eq) and [2-(2-aminophenyl)phenyl]-chloro-palladium; bis(1-adamantyl)-butyl-phosphane (32 mg, 47.27 umol, 0.1 eq) in EtOH (3 mL) was stirred at 70° C. for 12 hours under N2. The reaction was concentrated in vacuo. The residue was purified by prep-TLC ($SiO_2$, Petroleum ether:Ethyl acetate=0:1) to give 2-[[4-(2-chlorophenyl)-5-cyclopropyl-imidazol-1-yl]methoxy]ethyl-trimethyl-silane and 2-[[5-(2-chlorophenyl)-4-cyclopropyl-imidazol-1-yl]methoxy]ethyl-trimethyl-silane (total 90 mg) as a yellow oil. ESI [M+H]-349.1.

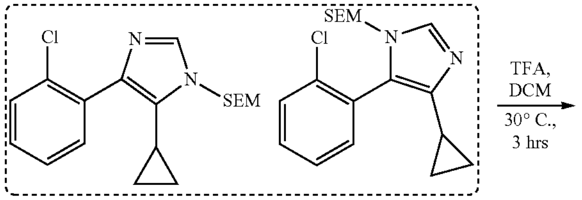

2

-continued

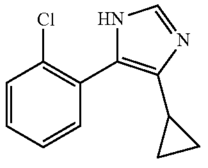

3

A solution of 2-[[4-(2-chlorophenyl)-5-cyclopropyl-imidazol-1-yl]methoxy]ethyl-trimethyl-silane and 2-[[5-(2-chlorophenyl)-4-cyclopropyl-imidazol-1-yl]methoxy]ethyl-trimethyl-silane (total 90 mg, 257.92 umol) in TFA (1 mL) and DCM (3 mL) was stirred at 30° C. for 3 hours. The reaction was concentrated in vacuo. The residue was dissolved in EtOAc (10 mL×2) and washed with sat.aq. $NaHCO_3$ (10 mL). The organic layer was dried over $MgSO_4$ and concentrated in vacuo.

The residue was purified by prep-TLC ($SiO_2$, Petroleum ether:Ethyl acetate=0:1), then purified again by prep-HPLC (column: Waters Xbridge 150*25 5u; mobile phase: [water (10 mM NH4HCO3)-ACN]; B %: 30%-60%, 10 min) to give 4-(2-chlorophenyl)-5-cyclopropyl-1H-imidazole (44 mg, 201.21 umol, 78.01% yield) as a white solid. ESI [M+H]=219.1.

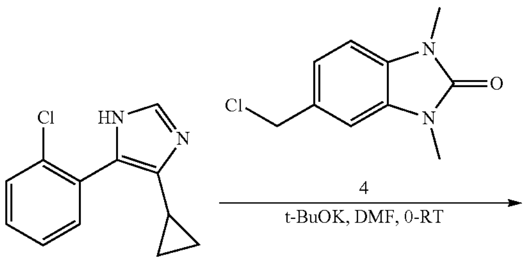

3

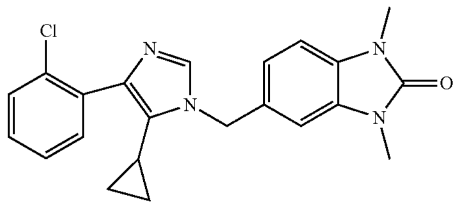

CWRU—WuXi-11

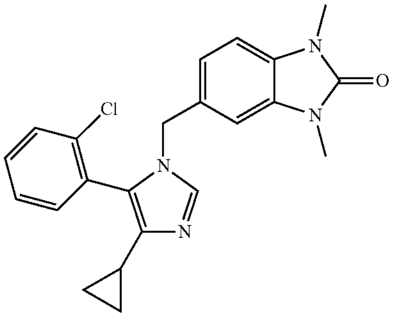

CWRU—WuXi-11A

To a solution of t-BuOK (1 M, 617 uL, 1.5 eq) in DMF (1 mL) was added 5-(2-chlorophenyl)-4-cyclopropyl-1H-imidazole (90 mg, 411.56 umol, 1 eq) in DMF (1 mL) at 0° C. under N2 atmosphere. After 15 minutes, the mixture was added 5-(chloromethyl)-1,3-dimethyl-benzimidazol-2-one (95.4 mg, 452.71 umol, 1.1 eq) in DMF (1 mL) at 0° C., then the mixture was stirred at 20° C. for 1 hour 45 minutes under N2 atmosphere. The reaction mixture was diluted with $H_2O$ (5 mL) and extracted with EtOAc (5 mL×3). The combined organic layers were dried over $Na_2SO_4$, filtered and concentrated under reduced pressure to give a residue. The residue was purified by prep-HPLC (column: Xtimate C18 150*25 mm*5 μm; mobile phase: [water (10 mM NH4HCO3)-ACN]; B %: 35%-55%, 10 min) to give 5-[[5-(2-chlorophenyl)-4-cyclopropyl-imidazol-1-yl]methyl]-1,3-dimethyl-benzimidazol-2-one (44.3 mg, 111.58 umol, 27.11% yield, 98.953% purity) as white solid and 5-[[4-(2-chlorophenyl)-5-cyclopropyl-imidazol-1-yl]methyl]-1,3-dimethyl-benzimidazol-2-one (19.45 mg, 45.97 umol, 11.17% yield, 92.865% purity) as white solid.

CWRU-WuXi-11A: $^1H$ NMR (400 MHz, CHLOROFORM-d) δ 7.48-7.36 (m, 2H), 7.27 (dt, J=1.8, 7.7 Hz, 1H), 7.19-7.15 (m, 1H), 7.14-7.09 (m, 1H), 6.72 (d, J=7.9 Hz, 1H), 6.64-6.58 (m, 1H), 6.38 (s, 1H), 4.99-4.87 (m, 1H), 4.83-4.74 (m, 1H), 3.31 (s, 3H), 3.24 (s, 3H), 1.52-1.46 (m, 1H), 0.80-0.75 (m, 2H), 0.71-0.62 (m, 2H). ESI [M+H]=393.2.

CWRU-WuXi-11: $^1H$ NMR (400 MHz, CHLOROFORM-d) δ 7.56 (s, 1H), 7.50-7.43 (m, 2H), 7.32-7.28 (m, 2H), 7.02-6.95 (m, 2H), 6.74 (s, 1H), 5.32 (s, 2H), 3.45 (s, 3H), 3.42-3.39 (m, 3H), 1.61-1.48 (m, 1H), 0.74-0.64 (m, 2H), 0.35-0.21 (m, 2H). ESI [M+H]=393.1.

Example 22

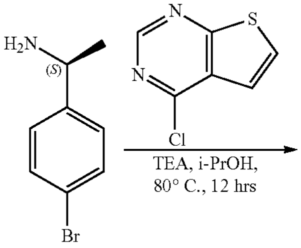

1

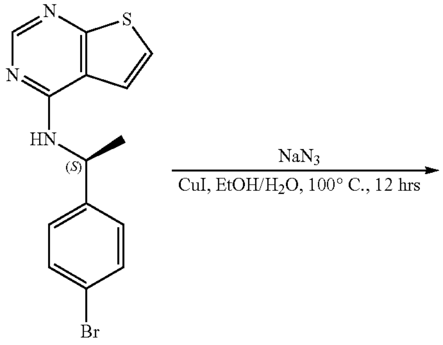

2

-continued

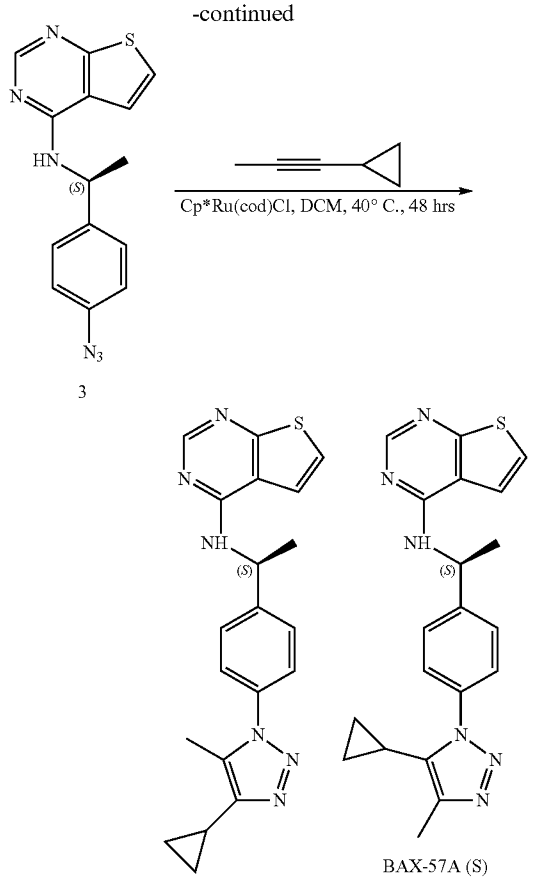

3

BAX-57 (S)

BAX-57A (S)

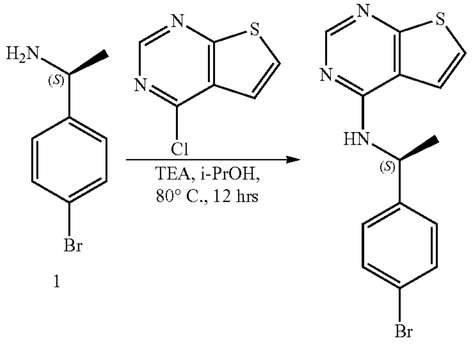

1

2

A mixture of (1S)-1-(4-bromophenyl)ethanamine (6 g, 29.99 mmol, 4.32 mL, 1 eq), 4-chlorothieno[2,3-d]pyrimidine (5.88 g, 34.49 mmol, 1.15 eq) and TEA (6.07 g, 59.98 mmol, 8.35 mL, 2 eq) in i-PrOH (200 mL) was stirred at 80° C. for 12 hrs. The reaction mixture was concentrated in vacuo. The residue was purified by column chromatography (SiO2, Petroleum ether:THF=20:1 to 5:1) to give N-[(1S)-1-(4-bromophenyl)ethyl]thieno[2,3-d]pyrimidin-4-amine (7.8 g, 23.34 mmol, 77.82% yield) as a white solid.

$^1H$-NMR (400 MHz, CHLOROFORM-d) δ 8.50 (s, 1H), 7.53-7.46 (m, 2H), 7.36-7.30 (m, 3H), 7.18 (d, J=6.0 Hz, 1H), 5.55 (quin, J=7.0 Hz, 1H), 5.36 (br d, J=7.0 Hz, 1H), 1.66 (d, J=6.8 Hz, 3H). ESI [M+H]=336.2.

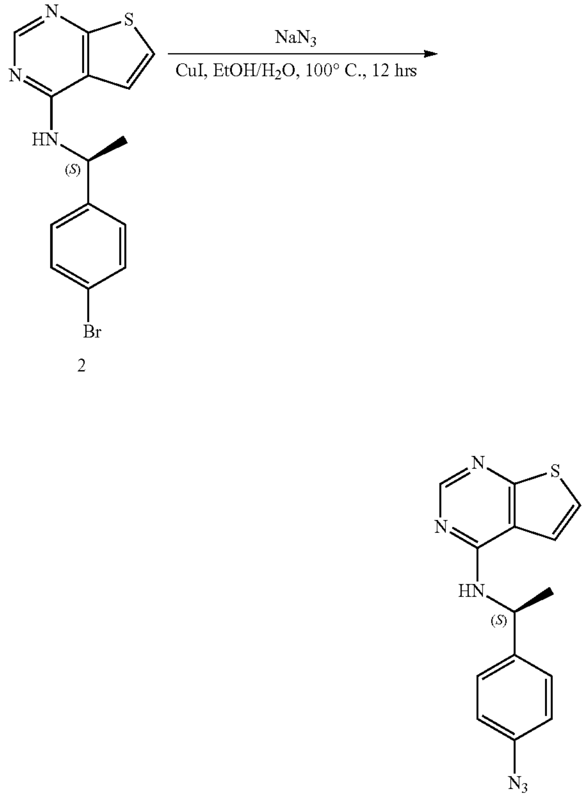

2

3

A mixture of N-[(1S)-1-(4-bromophenyl)ethyl]thieno[2,3-d]pyrimidin-4-amine (1 g, 2.99 mmol, 1 eq), $NaN_3$ (233.40 mg, 3.59 mmol, 1.2 eq), CuI (56.98 mg, 299.19 umol, 0.1 eq) and N1,N2-dimethylethane-1,2-diamine (52.75 mg, 598.38 umol, 64.40 uL, 0.2 eq) in EtOH (10 mL) and $H_2O$ (5 mL) was stirred at 100° C. for 12 hrs under $N_2$. To the reaction mixture was added sat.aq.$NaHCO_3$ (20 mL) and extracted with EtOAc (10 mL*3). The organic layer was dried over $MgSO_4$ and blow-dried by N2 to give N-[(1S)-1-(4-azidophenyl)ethyl]thieno[2,3-d]pyrimidin-4-amine (1 g, crude) as yellow solid, it was used into the next step without further purification. ESI [M+H]=297.3.

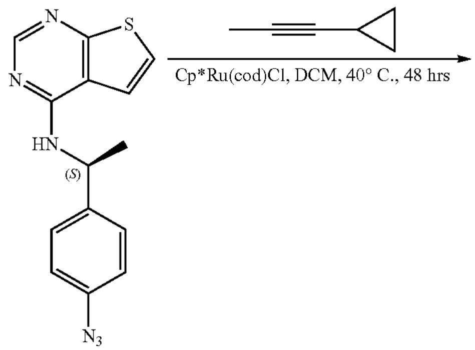

3

-continued

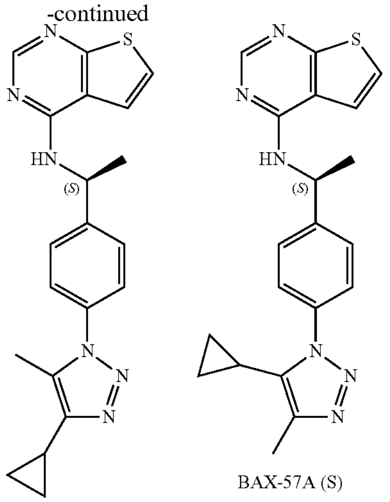

BAX-57 (S)

BAX-57A (S)

To a solution of N-[(1S)-1-(4-azidophenyl)ethyl]thieno[2,3-d]pyrimidin-4-amine (100 mg, 337.44 μmol, 1 eq) in DCM (3 mL) was added prop-1-ynylcyclopropane (40.56 mg, 506.16 umol, 1.5 eq) and chlororuthenium;(1Z,5Z)-cycloocta-1,5-diene; 1,2,3,4,5-pentamethylcyclopentane (12.99 mg, 33.74 umol, 0.1 eq), and the mixture was stirred at 40° C. for 48 hrs. The reaction was concentrated in vacuo. The residue was purified by prep-HPLC (column: Waters Xbridge 150*25 5u; mobile phase: [water (10 mM NH4HCO3)-ACN]; B %: 30%-40%, 10 min) to give N-[(1S)-1-[4-(4-cyclopropyl-5-methyl-triazol-1-yl)phenyl]ethyl]thieno[2,3-d]pyrimidin-4-amine (11.4 mg, 29.67 umol, 8.79% yield, 97.992% purity) and N-[(1S)-1-[4-(5-cyclopropyl-4-methyl-triazol-1-yl)phenyl]ethyl]thieno[2,3-d]pyrimidin-4-amine (24.95 mg, 66.27 umol, 19.64% yield, 100% purity) as a white solid.

BAX-57 (S): 1H-NMR (400 MHz, CHLOROFORM-d) δ 8.51 (s, 1H), 7.58 (d, J=8.3 Hz, 2H), 7.43 (d, J=8.4 Hz, 2H), 7.34 (d, J=6.0 Hz, 1H), 7.20 (d, J=6.0 Hz, 1H), 5.72-5.62 (m, 1H), 5.36 (br d, J=6.6 Hz, 1H), 2.33 (s, 3H), 1.85-1.76 (m, 1H), 1.72 (d, J=6.8 Hz, 3H), 1.06-0.94 (m, 4H). ESI [M+H]=377.1.

BAX-57A (S): 1H-NMR (400 MHz, CHLOROFORM-d) δ 8.43 (s, 1H), 7.49 (s, 4H), 7.26 (d, J=6.0 Hz, 1H), 7.13 (d, J=6.0 Hz, 1H), 5.60 (quin, J=7.0 Hz, 1H), 5.32 (br d, J=7.5 Hz, 1H), 2.30 (s, 3H), 1.65 (d, J=7.0 Hz, 4H), 0.87-0.79 (m, 2H), 0.55-0.48 (m, 2H). ESI [M+H]=377.0.

Example 23

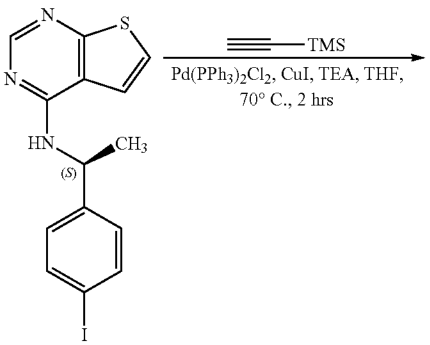

1

-continued

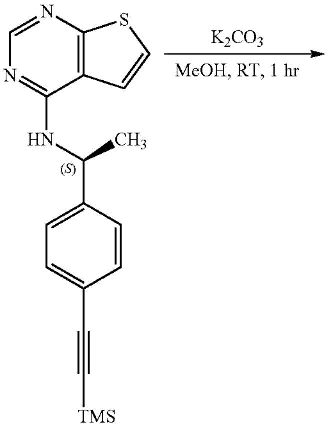

2

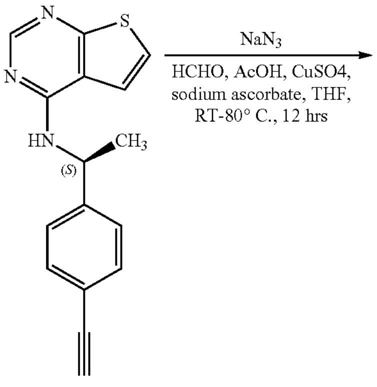

3

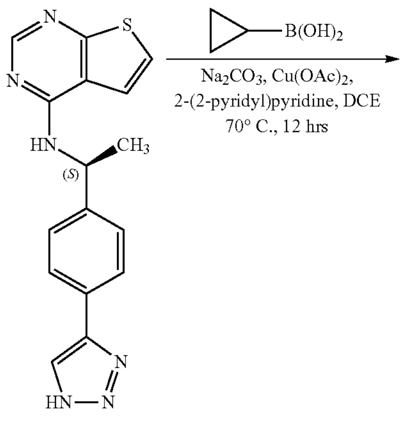

4

-continued

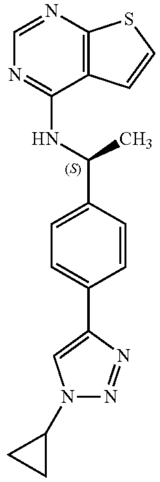

BAX-58 (S)

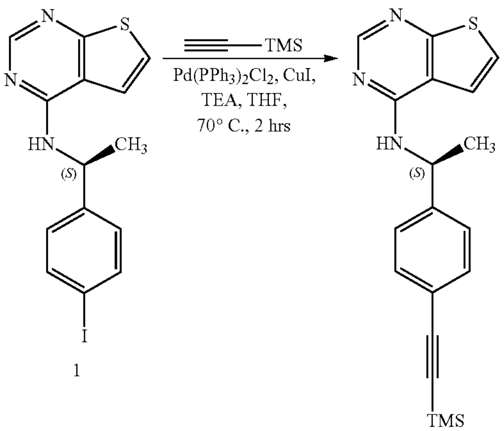

1

2

A mixture of N-[(1S)-1-(4-iodophenyl)ethyl]thieno[2,3-d]pyrimidin-4-aminutese (500 mg, 1.31 mmol, 1 eq), ethynyl(trimethyl)silane (257.6 mg, 2.62 mmol, 363.37 μL, 2 eq), TEA (2.18 g, 21.55 mmol, 3 mL, 16.43 eq) and $Pd(PPh_3)_2Cl_2$ (92 mg, 131.15 umol, 0.1 eq), CuI (25 mg, 131.15 umol, 0.1 eq) in THF (9 mL) was stirred at 70° C. for 2 hour under N2. The reaction mixture was concentrated in vacuo. The residue was purified by column chouromatography (plate 1, SiO2, Petroleum ether:Ethyl acetate=10:1 to 3:1) to give N-[(1S)-1-[4-(2-trimethylsilylethynyl)phenyl]ethyl]thieno[2,3-d]pyrimidin-4-aminutese (460 mg, 1.31 mmol, 99.77% yield) as a yellow oil. ESI [M+H]=351.9.

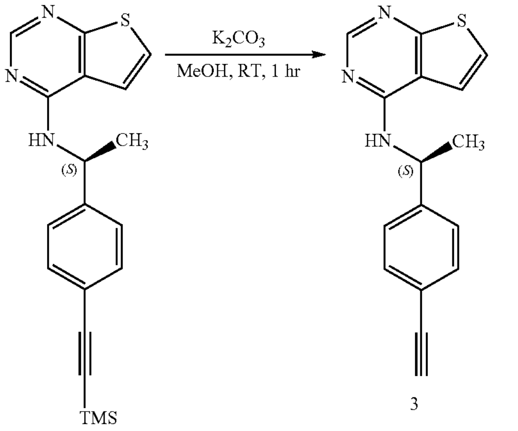

2 3

To a solution of N-[(1S)-1-[4-(2-trimethylsilylethynyl)phenyl]ethyl]thieno[2,3-d]pyrimidin-4-aminutese (460 mg, 1.31 mmol, 1 eq) in MeOH (5 mL) was added $K_2CO_3$ (361.7 mg, 2.62 mmol, 2 eq) and the mixture was stirred at 25° C. for 1 hour. To the reaction mixture was added water (10 mL) and extracted with EtOAc (5 mL*3). The organic layer was dried over $MgSO_4$ and concentrated in vacuo to give N-[(1S)-1-(4-ethynylphenyl)ethyl]thieno[2,3-d]pyrimidin-4-aminutese (240 mg, 859.11 umol, 65.65% yield) as a yellow solid. It was used into the next step without further purification. ESI [M+H]=280.3.

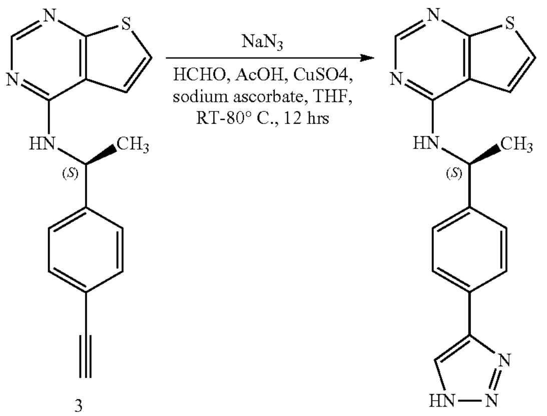

3 4

A mixture of HCHO (290 mg, 3.58 mmol, 266.51 uL, 37% purity, 10 eq), AcOH (32 mg, 536.94 umol, 30.71 uL, 1.5 eq) in THF (2 mL) was stirred for 15 minutes. $NaN_3$ (35 mg, 536.94 umol, 1.5 eq) was added, followed by N-[(1S)-1-(4-ethynylphenyl)ethyl]thieno[2,3-d]pyrimidin-4-aminutese (100 mg, 357.96 umol, 1 eq). The mixture was stirred for 10 minutes and sodium ascorbate (14 mg, 71.59 umol, 0.2 eq) was added, followed by $CuSO_4$ (17 mg, 17.90 umol, 16.45 uL, 16.7% purity, 0.05 eq) at 25° C. The reaction was stirred for 12 hours at 80° C. To the reaction mixture was added sat.aq.$NaHCO_3$ (5 mL) and extracted with EtOAc (3 mL). The organic layer was dried over $MgSO_4$ and concentrated in vacuo. The residue was purified by prep-TLC ($SiO_2$, Petroleum ether:Ethyl acetate=1:1) to give N-[(1S)-1-[4-(1H-triazol-4-yl)phenyl]ethyl]thieno[2,3-d]pyrimidin-4-aminutese (75 mg, 232.64 umol, 64.99% yield) as a white solid. ESI [M+H]=323.1.

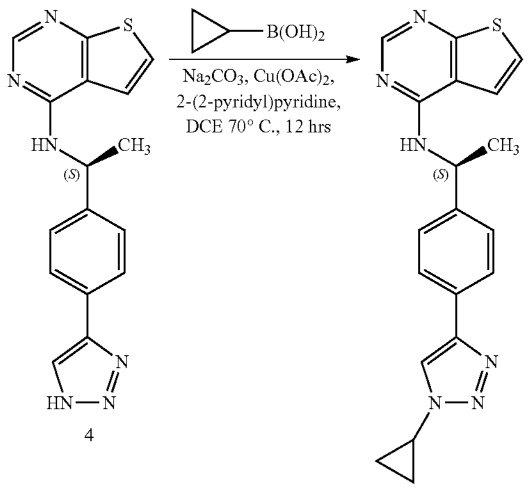

4

BAX-58 (S)

A mixture of 2-(2-pyridyl)pyridine (55 mg, 353.61 umol, 1.2 eq) and $Cu(OAc)_2$ (64 mg, 353.61 umol, 1.2 eq) in DCE (6 mL) was heated to 70° C., and to this mixture was added a mixture of N-[(1S)-1-[4-(1H-triazol-4-yl)phenyl]ethyl]thieno[2,3-d]pyrimidin-4-aminutese (95 mg, 294.68 umol, 1 eq), cyclopropylboronic acid (76 mg, 884.03 umol, 3 eq) and $Na_2CO_3$ (94 mg, 884.03 umol, 3 eq), followed by stirring at 70° C. for 12 hour under 02. To the reaction mixture was added water (20 mL) and extracted with DCM (10 mL*3). The organic layer was dried over $MgSO_4$ and concentrated in vacuo. The residue was purified by prep-HPLC (column: HUAPU C8 Extreme BDS 150*30 5u; mobile phase: [water (10 mM NH4HCO3)-ACN]; B %: 45%-65%, 10 minutes) to give N-[(1S)-1-[4-(1-cyclopropyltriazol-4-yl)phenyl]ethyl]thieno[2,3-d]pyrimidin-4-aminutese (36.09 mg, 98.10 μmol, 33.29% yield, 98.524% purity) as a white solid.

$^1$H-NMR (400 MHz, CHLOROFORM-d) δ 8.53 (s, 1H), 7.85-7.75 (m, 3H), 7.50 (d, J=8.1 Hz, 2H), 7.33 (d, J=6.0 Hz, 1H), 7.18 (d, J=6.0 Hz, 1H), 5.63 (quin, J=7.0 Hz, 1H), 5.36 (br d, J=7.5 Hz, 1H), 4.05 (tt, J=3.8, 7.5 Hz, 1H), 1.72 (d, J=6.8 Hz, 3H), 1.45-1.38 (m, 2H1), 1.19-1.11 (m, 2H1). ESI [M+H]=363.1.

Example 24

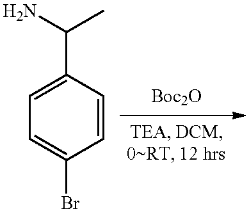

1

-continued

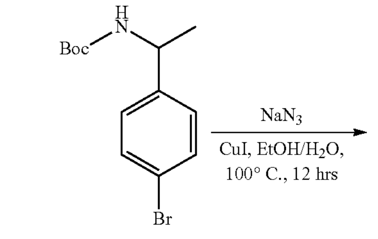

2

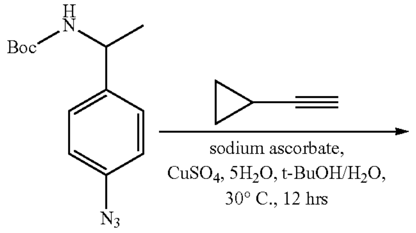

3

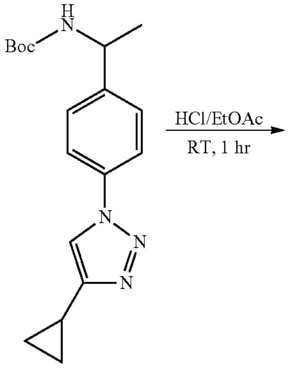

4

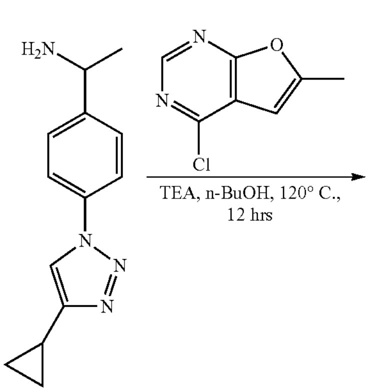

5

-continued

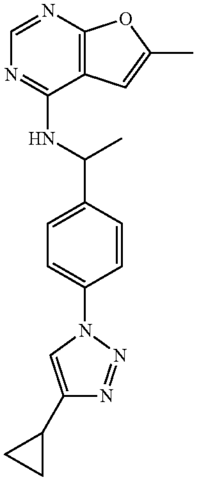

Bax-68 (RS)

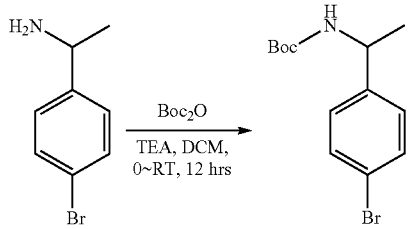

1 2

To a solution of 1-(4-bromophenyl)ethanamine (2 g, 8.46 mmol, 1.43 mL, 1 eq, HCl) in DCM (60 mL) was added TEA (2.57 g, 25.37 mmol, 3.53 mL, 3 eq) and cooled to 0° C. with an ice bath, then $Boc_2O$ (2.21 g, 10.15 mmol, 2.33 mL, 1.2 eq) was added. The mixture was stirred at 0-25° C. for 12 hrs. The reaction mixture was concentrated in vacuo. The residue was purified by column chromatography (SiO2, Petroleum ether/Ethyl acetate=20/1 to 3:1) to give tert-butyl N-[1-(4-bromophenyl)ethyl]carbamate (2.5 g, 8.33 mmol, 98.49% yield) as a white solid.

$^1$H-NMR (400 MHz, METHANOL-d4) δ 7.50-7.43 (m, 2H), 7.29-7.19 (m, 2H), 4.70-4.57 (m, 1H), 4.72-4.57 (m, 1H), 4.72-4.52 (m, 1H), 1.50-1.29 (m, 12H). ESI [M+H]=285.0.

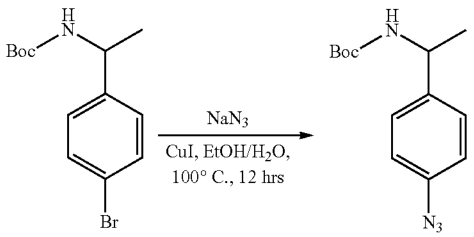

2 3

A mixture of tert-butyl N-[1-(4-bromophenyl)ethyl]carbamate (2.5 g, 8.33 mmol, 1 eq), $NaN_3$ (649.68 mg, 9.99 mmol, 1.2 eq), CuI (158.61 mg, 832.80 umol, 0.1 eq) and N1,N2-dimethylethane-1,2-diamine (146.82 mg, 1.67 mmol, 179.27 uL, 0.2 eq) in EtOH (20 mL) and $H_2O$ (10 mL) was stirred at 100° C. for 12 hrs under N2. To the reaction mixture was added sat.aq.$NaHCO_3$ (20 mL) and extracted with EtOAc (10 mL*3). The organic layer was dried over $MgSO_4$ and blow-dried by N2 to give tert-butyl N-[1-(4-azidophenyl)ethyl]carbamate (2.2 g, crude) as a yellow solid. It was used into the next step without further purification. ESI [M+H]=207.1.

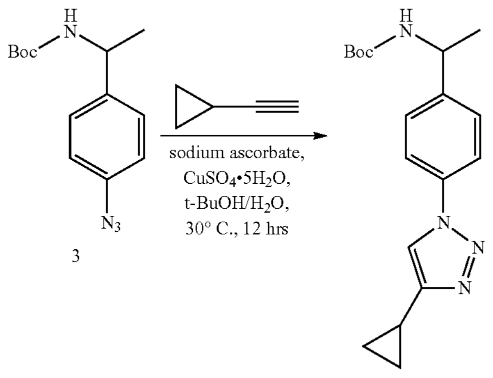

3

4

A mixture of tert-butyl N-[1-(4-azidophenyl)ethyl]carbamate (2.2 g, 8.39 mmol, 1 eq), ethynylcyclopropane (1.11 g, 16.77 mmol, 1.39 mL, 2 eq), $CuSO_4.5H_2O$ (418.84 mg, 1.68 mmol, 0.2 eq) and SODIUM ASCORBATE (332.31 mg, 1.68 mmol, 0.2 eq) in t-BuOH (20 mL) and $H_2O$ (20 mL) was stirred at 30° C. for 12 hrs. The reaction mixture was concentrated in vacuo. The residue was purified by column chromatography ($SiO_2$, Petroleum ether/Ethyl acetate=20/1 to 0:1) to give tert-butyl N-[1-[4-(4-cyclopropyltriazol-1-yl)phenyl]ethyl]carbamate (2.4 g, 7.31 mmol, 87.13% yield) as a white solid. ESI [M−56+H]=279.3 and [M−100+H]=229.2.

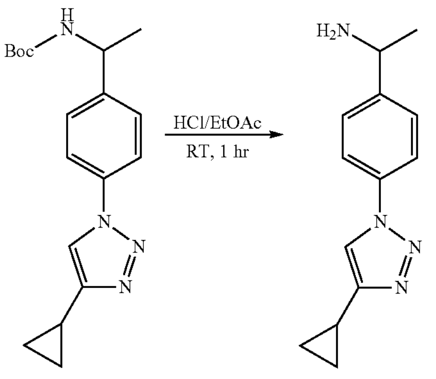

4

5

A mixture of tert-butyl N-[1-[4-(4-cyclopropyltriazol-1-yl)phenyl]ethyl]carbamate (2.4 g, 7.31 mmol, 1 eq) in HCl/EtOAc (15 mL) and EtOAc (15 mL) was stirred at 25° C. for 1 hr. The reaction mixture was adjusted to pH=8 with $NH_3 \cdot H_2O$ and concentrated in vacuo. The residue was purified by prep-HPLC (column: Waters Xbridge Prep OBD C18 150*40 10u; mobile phase: [water (10 mM $NH_4HCO_3$)-ACN]; B %: 5%-45%, 11 min) to give 1-[4-(4-cyclopropyltriazol-1-yl)phenyl]ethanamine (500 mg, 2.19 mmol, 29.97% yield) as a brown solid. ESI [M+H]=229.1.

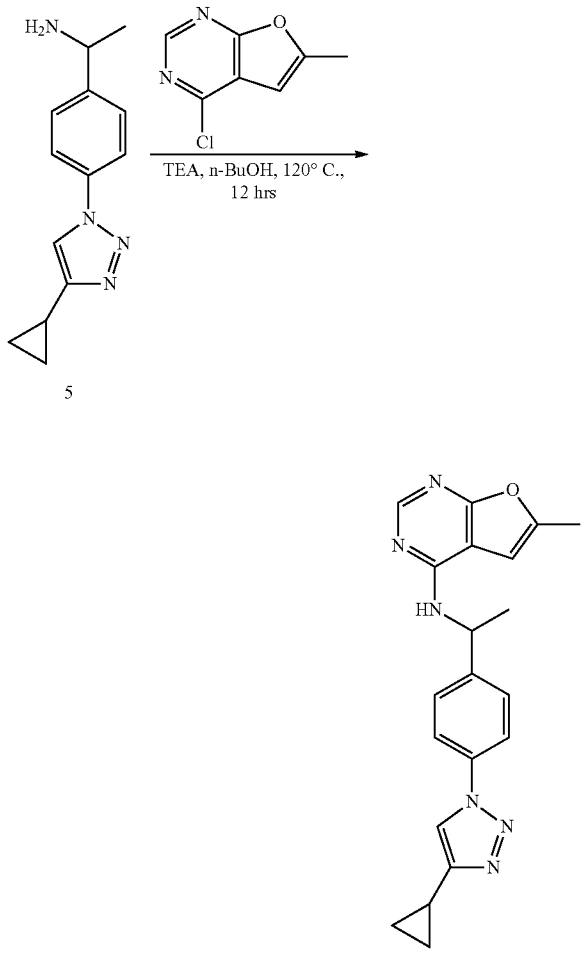

5

Bax-68 (RS)

To a solution of 1-[4-(4-cyclopropyltriazol-1-yl)phenyl]ethanamine (50 mg, 219.02 umol, 1 eq) in n-BuOH (2 mL) was added TEA (44.32 mg, 438.03 umol, 60.97 μL, 2 eq) and 4-chloro-6-methyl-furo[2,3-d]pyrimidine (40.61 mg, 240.92 umol, 1.1 eq). The mixture was stirred at 120° C. for 12 hrs. The reaction mixture was concentrated in vacuo. The residue was purified by prep-HPLC (column: Luna C18 100*30 5u; mobile phase: [water (0.04% HCl)-ACN]; B %: 25%-55%, 11 min) to give N-[l-[4-(4-cyclopropyltriazol-1-yl)phenyl]ethyl]-6-methyl-furo[2,3-d]pyrimidin-4-amine (52.28 mg, 138.42 umol, 63.20% yield, 95.425% purity) as a orange solid. ESI [M+H]=361.1.

$^1$H-NMR (400 MHz, METHANOL-d4) δ 8.21-8.16 (m, 1H), 8.15-8.07 (m, 1H), 7.79-7.70 (m, 2H), 7.62-7.51 (m, 2H), 6.67-6.61 (m, 1H), 5.51-5.39 (m, 1H), 2.46-2.40 (m, 3H), 2.06-1.96 (m, 1H), 1.66-1.58 (m, 3H), 1.04-0.95 (m, 2H), 0.87-0.79 (m, 2H).

Example 25

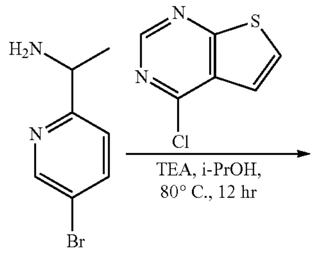

1

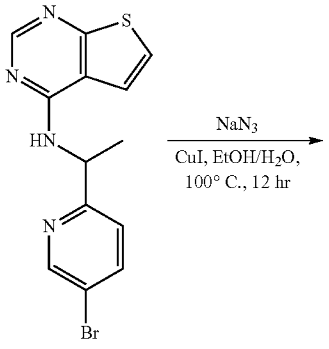

2

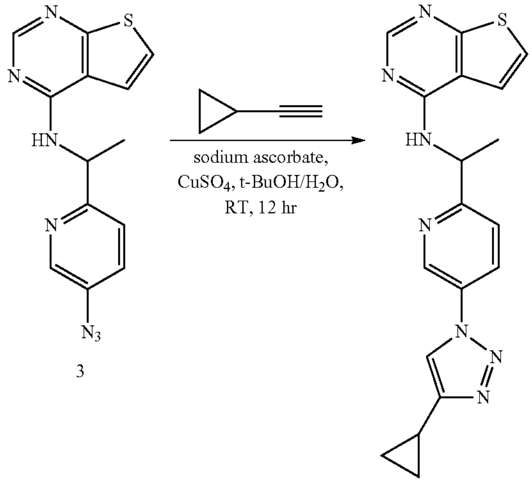

3

Bax-75 (RS)

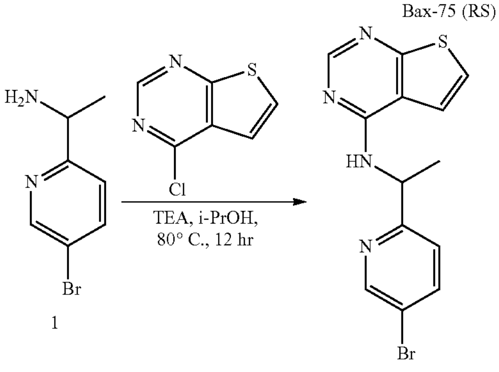

1

2

To a solution of 1-(5-bromo-2-pyridyl)ethanamine (200 mg, 994.71 μmol, 204.08 μL, 1 eq) in i-PrOH (5 mL) was added TEA (202 mg, 1.99 mmol, 276.90 uL, 2 eq) and 4-chlorothieno[2,3-d]pyrimidine (187 mg, 1.09 mmol, 1.1 eq). The mixture was stirred at 80° C. for 12 hours. The reaction mixture was concentrated in vacuo. The residue was purified by column chouromatography ($SiO_2$, Petroleum ether/Ethyl acetate=20/1 to 2:1) to give N-[1-(5-bromo-2-pyridyl)ethyl]thieno[2,3-d]pyrimidin-4-amine (340 mg) as a yellow solid. ESI [M+H]=335.0.

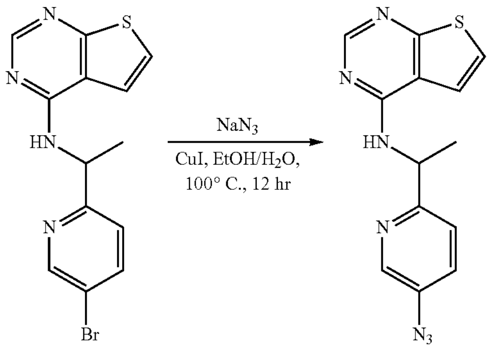

2

3

A mixture of N-[1-(5-bromo-2-pyridyl)ethyl]thieno[2,3-d]pyrimidin-4-amine (100 mg, 298.31 umol, 1 eq), $NaN_3$ (23 mg, 357.97 umol, 1.2 eq), CuI (6 mg, 29.83 μmol, 0.1 eq) and N1,N2-dimethylethane-1,2-diamine (5 mg, 59.66 umol, 6.42 uL, 0.2 eq) in EtOH (2 mL) and $H_2O$ (1 mL) was stirred at 100° C. for 12 hours under N2. To the reaction mixture was added sat.aq.$NaHCO_3$ (10 mL) and extracted with EtOAc (5 mL*3). The organic layer was dried over $MgSO_4$ and blow-dried by N2 to give N-[1-(5-azido-2-pyridyl) ethyl]thieno[2,3-d]pyrimidin-4-amine (90 mg, crude) as a yellow oil. It was used into the next step without further purification. ESI [M+H]=298.1.

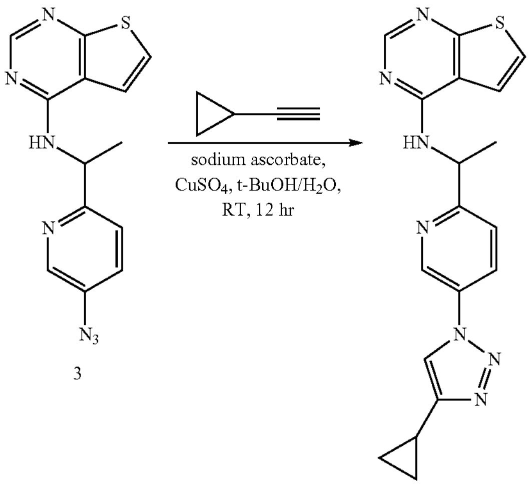

3

Bax-75 (RS)

To a solution of N-[l-(5-azido-2-pyridyl)ethyl]thieno[2,3-d]pyrimidin-4-amine (90 mg, 302.69 μmol, 1 eq) in t-BuOH (2 mL) and $H_2O$ (2 mL) was added ethynylcyclopropane (40 mg, 605.37 umol, 50.21 uL, 2 eq) and $CuSO_4.5H_2O$ (15 mg, 60.54 umol, 0.2 eq), SODIUM ASCORBATE (12 mg, 60.54 μmol, 0.2 eq) and the mixture was stirred at 25° C. for 12 hours. To the reaction mixture was added water (10 mL) and extracted with EtOAc (5 mL*3). The organic layer was washed with brine (10 mL), dried over $MgSO_4$ and concentrated in vacuo. The residue was purified by prep-HPLC (column: Waters Xbridge 150*25 5u; mobile phase: [water (10 mM $NH_4HCO_3$)-ACN]; B %: 20%-50%, 10 min) to give N-[1-[5-(4-cyclopropyltriazol-1-yl)-2-pyridyl]ethyl]thieno[2,3-d]pyrimidin-4-amine (21.6 mg, 58.23 umol, 19.24% yield, 97.977% purity) as a white solid.

$^1$H-NMR (400 MHz, METHANOL-d4) δ 8.98 (d, J=2.3 Hz, 1H), 8.30 (s, 1H), 8.24 (s, 1H), 8.17 (dd, J=2.6, 8.5 Hz, 1H), 7.68 (d, J=6.0 Hz, 1H), 7.63 (d, J=8.6 Hz, 1H), 7.49 (d, J=6.0 Hz, 1H), 5.61 (q, J=7.1 Hz, 1H), 2.10-2.00 (m, 1H), 1.70 (d, J=7.1 Hz, 3H), 1.06-0.98 (m, 2H), 0.90-0.83 (m, 2H). ESI [M+H]=364.1.

Example 26

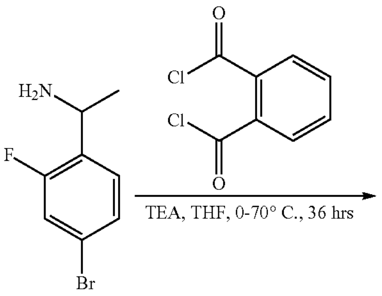

1

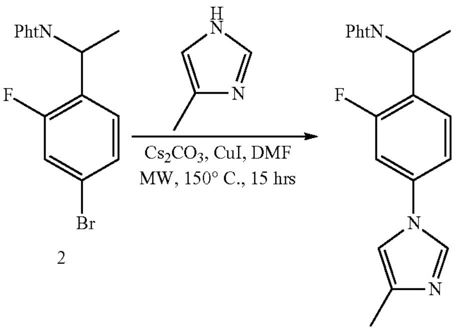

2

3

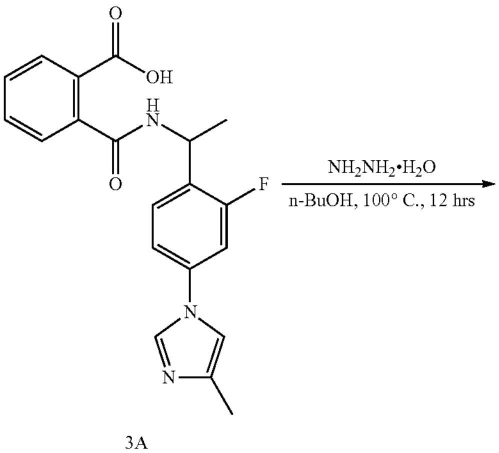

3A

-continued

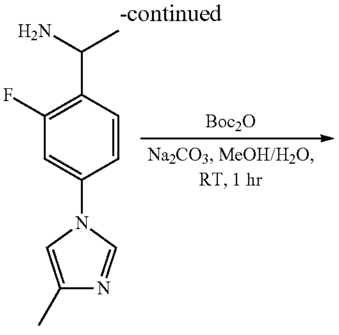

4

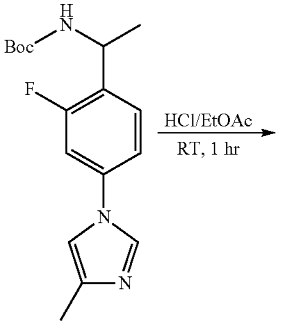

5

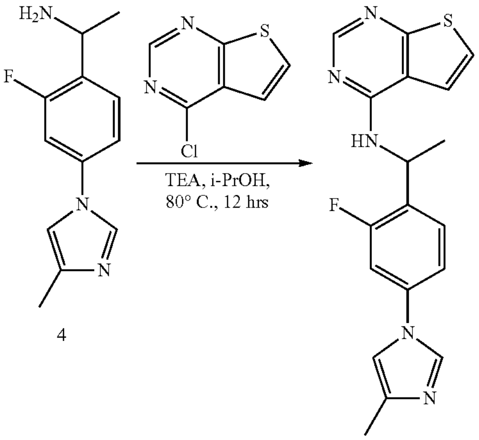

4

Bax-76 (RS)

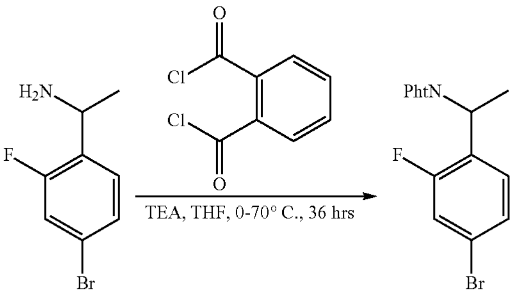

1 2

To a solution of 1-(4-bromo-2-fluoro-phenyl)ethanamine (250 mg, 982.21 μmol, 1 eq, HCl) in THF (6 mL) was added TEA (397.56 mg, 3.93 mmol, 546.85 μL, 4 eq) and benzene-1,2-dicarbonyl chloride (239.29 mg, 1.18 mmol, 169.71 μL, 1.2 eq) at 0° C. The mixture was stirred at 25° C. for 12 hrs, then it was heated to 70° C. and stirred for another 24 hrs. To the reaction mixture was add water (10 mL), extracted with EtOAc (10 mL*4). The organic phase was dried over drying $Na_2SO_4$ and concentrated in vacuo. The residue was purified by column chromatography ($SiO_2$, Petroleum ether/Ethyl acetate=20/1 to 5:1) to give 2-[1-(4-bromo-2-fluoro-phenyl)ethyl]isoindoline-1,3-dione (150 mg, 430.83 μmol, 43.86% yield) as a yellow oil. ESI [M+H]=350.0.

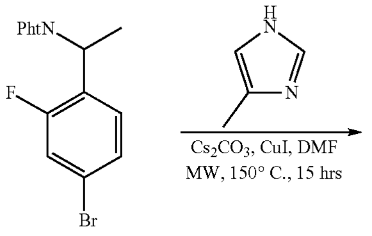

2

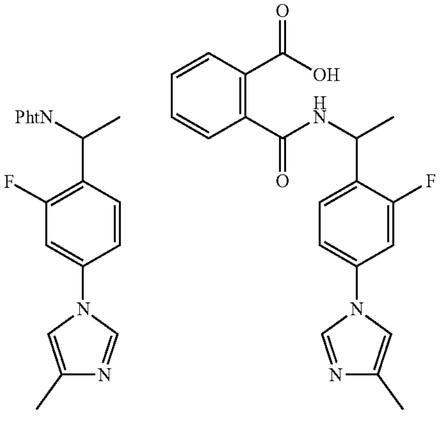

3 3A

2-[1-(4-bromo-2-fluoro-phenyl)ethyl]isoindoline-1,3-dione (150 mg, 430.83 umol, 1 eq), 4-methyl-1H-imidazole (70.75 mg, 861.66 umol, 2 eq), $Cs_2CO_3$ (280.75 mg, 861.66 umol, 2 eq), CuI (16.41 mg, 86.17 umol, 0.2 eq) were taken up into a microwave tube in DMF (4 mL). The sealed tube was heated at 150° C. for 15 hrs under microwave under N2. To the reaction mixture was add water (10 mL), extracted with DCM/i-PrOH (3/1, 20 mL*5). The organic phase was dried over drying $Na_2SO_4$, and concentrated in vacuo. The aqueous phase was vacuum freeze dehydration. The residue was purified by prep-HPLC (column: Luna C18 100*30 5u; mobile phase: [water (0.04% HCl)-ACN]; B %: 15%-45%, 11 min) to give 2-[1-[2-fluoro-4-(4-methylimidazol-1-yl)phenyl]ethyl]isoindoline-1,3-dione (15 mg, 38.88 umol, 9.02% yield, HCl) as a white solid and 2-[1-[2-fluoro-4-(4-methylimidazol-1-yl)phenyl]ethylcarbamoyl]benzoic acid (140 mg, 346.68 umol, 80.47% yield, HCl) as a yellow oil. ESI [M+H]=368.1.

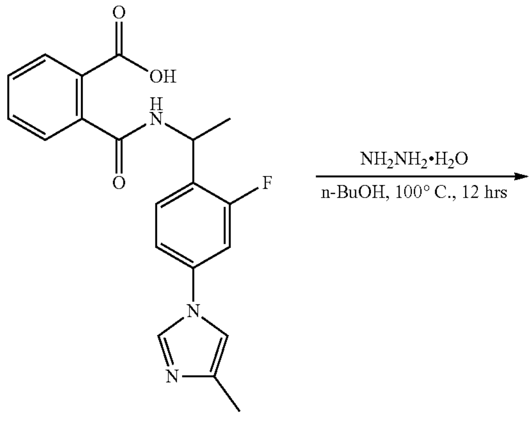

3A

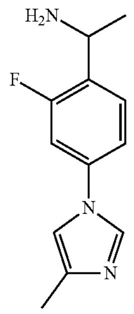

4

To a solution of 2-[1-[2-fluoro-4-(4-methylimidazol-1-yl)phenyl]ethylcarbamoyl]benzoic acid (130 mg, 321.91 umol, 1 eq, HCl) in n-BuOH (3 mL) was added $NH_2NH_2 \cdot H_2O$ (98.66 mg, 1.93 mmol, 95.79 uL, 98% purity, 6 eq). The mixture was stirred at 100° C. for 12 hrs. The reaction mixture was concentrated in vacuo. To the residue was add $H_2O$ (15 mL), extracted with EtOAc (20 mL*4). The combined organic layers were dried over drying $Na_2SO_4$, filtered and concentrated under reduced pressure to give 1-[2-fluoro-4-(4-methylimidazol-1-yl)phenyl]ethanamine (80 mg) as a yellow oil. ESI [M+H]=220.1. It was combined with the other batch of ET22082-126.

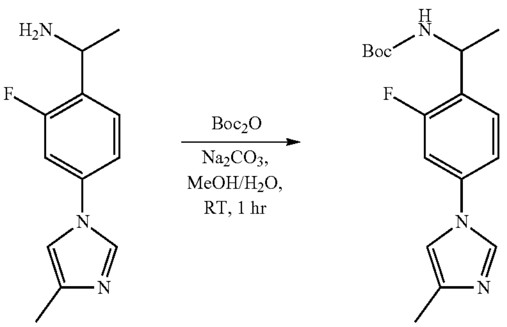

4 5

To a solution of 1-[2-fluoro-4-(4-methylimidazol-1-yl)phenyl]ethanamine (60 mg, 273.65 umol, 1 eq) in MeOH (2 mL) and $H_2O$ (1 mL) was added $Na_2CO_3$ (58.01 mg, 547.30 μmol, 2 eq) and $Boc_2O$ (179.17 mg, 820.95 umol, 188.60 μL, 3 eq). The mixture was stirred at 25° C. for 1 hr. The reaction mixture was concentrated in vacuo. To the residue was add water (15 mL), extracted with EtOAc (20 mL*4). The organic phase was dried over drying $Na_2SO_4$ and concentrated in vacuo. The residue was purified by prep-TLC ($SiO_2$, Petroleum ether:Ethyl acetate=0:1) to give tert-butyl N-[1-[2-fluoro-4-(4-methylimidazol-1-yl)phenyl]ethyl]carbamate (80 mg, 250.49 umol, 91.54% yield) as a yellow oil. ESI [M+H]=320.2.

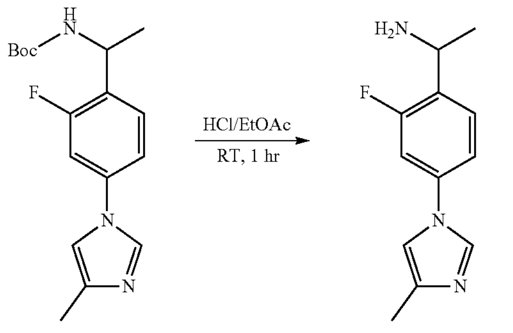

5 6

To a solution of tert-butyl N-[1-[2-fluoro-4-(4-methylimidazol-1-yl)phenyl]ethyl]carbamate (80 mg, 250.49 umol, 1 eq) in EtOAc (3 mL) was added HCl/EtOAc (4 mL) (4M). The mixture was stirred at 25° C. for 1 hr. The reaction mixture was concentrated in vacuo to give 1-[2-fluoro-4-(4-methylimidazol-1-yl)phenyl]ethanamine (60 mg, 234.63 umol, 93.67% yield, HCl) as a white solid. It was used into the next step without further purification. ESI [M+H]=220.3.

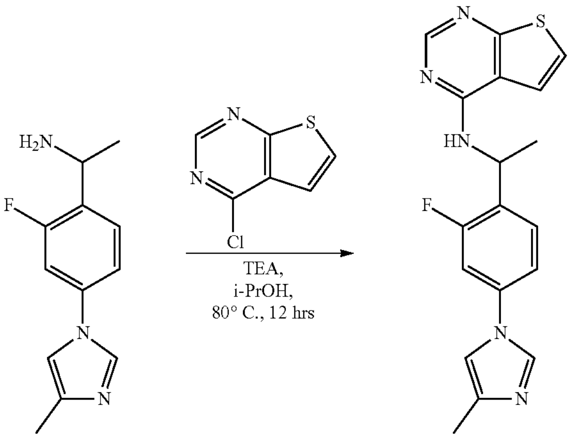

6 Bax-76 (RS)

To a solution of 1-[2-fluoro-4-(4-methylimidazol-1-yl)phenyl]ethanamine (60 mg, 234.63 umol, 1 eq, HCl) in i-PrOH (2 mL) was added TEA (94.97 mg, 938.53 umol, 130.63 uL, 4 eq) and 4-chlorothieno[2,3-d]pyrimidine (44.04 mg, 258.10 μmol, 1.1 eq). The mixture was stirred at 80° C. for 12 hrs. The reaction mixture was concentrated in vacuo. The residue was purified by prep-HPLC (column: Luna C18 100*30 5u; mobile phase: [water (0.04% HCl)-ACN]; B %: 5%-30%, 11 min) to give N-[l-[2-fluoro-4-(4-methylimidazol-1-yl)phenyl]ethyl]thieno[2,3-d]pyrimidin-4-amine (15.36 mg, 39.07 umol, 16.65% yield, 99.174% purity, HCl) as a white solid.

$^1$H-NMR (400 MHz, METHANOL-d4) δ 9.41 (s, 1H), 8.70 (s, 1H), 7.98 (d, J=5.7 Hz, 1H), 7.90-7.74 (m, 3H), 7.67 (br d, J=10.6 Hz, 1H), 7.59 (br d, J=7.5 Hz, 1H), 5.97 (q, J=6.9 Hz, 1H), 2.46 (s, 3H), 1.80 (br d, J=7.0 Hz, 3H). ESI [M+H]=354.1 and [M/2+H]=177.6.

Example 27

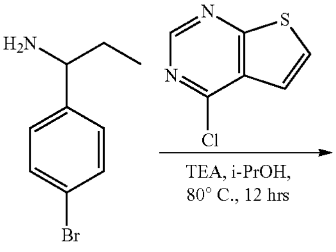

1

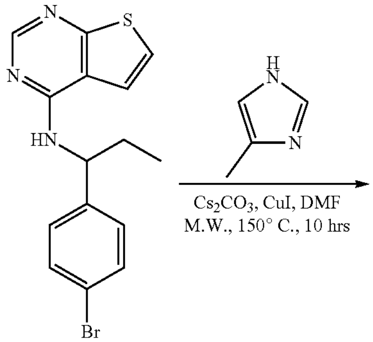

2

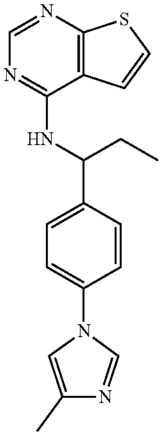

BAX-77 (RS)

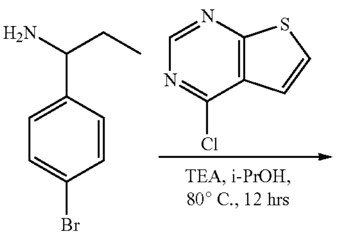

1

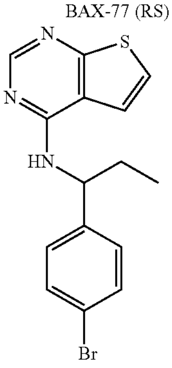

2

To a solution of 1-(4-bromophenyl)propan-1-amine (100 mg, 467.07 umol, 1 eq) in i-PrOH (3 mL) was added TEA (95 mg, 934.14 umol, 130.02 uL, 2 eq) and 4-chlorothieno [2,3-d]pyrimidine (88 mg, 513.77 umol, 1.1 eq). The mixture was stirred at 80° C. for 12 hours. The reaction was concentrated in vacuo. The residue was purified by column chouromatography ($SiO_2$, Petroleum ether:Ethyl acetate=1:1) to give N-[1-(4-bromophenyl)propyl]thieno[2,3-d]pyrimidin-4-amine (160 mg, 459.43 umol, 98.36% yield) as a yellow oil. ESI [M+H]=350.0.

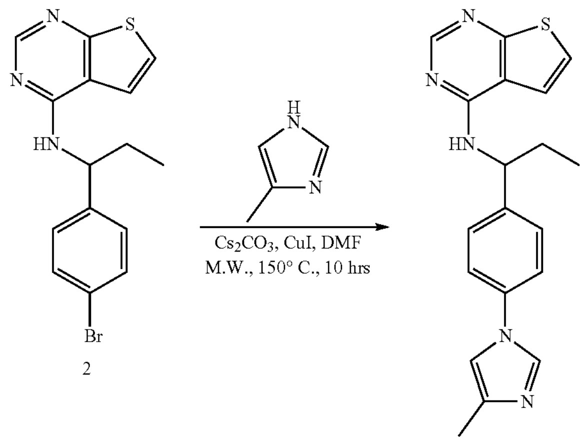

2

Bax-77 (RS)

N-[1-(4-bromophenyl)propyl]thieno[2,3-d]pyrimidin-4-amine (80 mg, 229.71 umol, 1 eq), 4-methyl-1H-imidazole (38 mg, 459.43 umol, 2 eq) and $Cs_2CO_3$ (150 mg, 459.43 μmol, 2 eq), CuI (9 mg, 45.94 umol, 0.2 eq) were taken up into a microwave tube in DMF (2 mL). The sealed tube was heated at 150° C. for 10 hours under microwave under N2. To the mixture was added water (10 mL) and extracted with EtOAc (5 mL*3). The organic layer was dried over $MgSO_4$ and concentrated in vacuo. The residue was purified by prep-HPLC (column: Xtimate C18 150*25 mm*5 μm; mobile phase: [water (10 mM NH4HCO3)-ACN]; B %: 37%-57%, 10 min), then the residue was purified again by prep-TLC (Ethyl acetate:Methanol=10:1) to give N-[1-[4-(4-methylimidazol-1-yl)phenyl]propyl]thieno[2,3-d]pyrimidin-4-amine (27.11 mg, 76.05 umol, 33.11% yield, 98.032% purity) as a white solid.

$^1$H-NMR (400 MHz, CHLOROFORM-d) δ 8.47 (s, 1H), 7.73 (s, 1H), 7.48 (d, J=8.4 Hz, 2H), 7.36-7.28 (m, 3H), 7.20 (d, J=6.2 Hz, 1H), 6.97 (s, 1H), 5.46-5.32 (m, 2H), 2.29 (s, 3H), 2.10-1.93 (m, 2H), 1.02 (t, J=7.3 Hz, 3H). ESI [M+H]=350.1.

Example 28

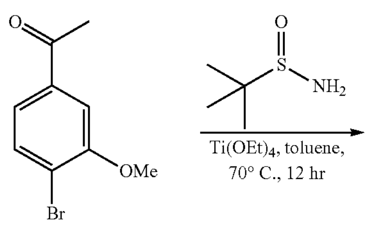

1

-continued

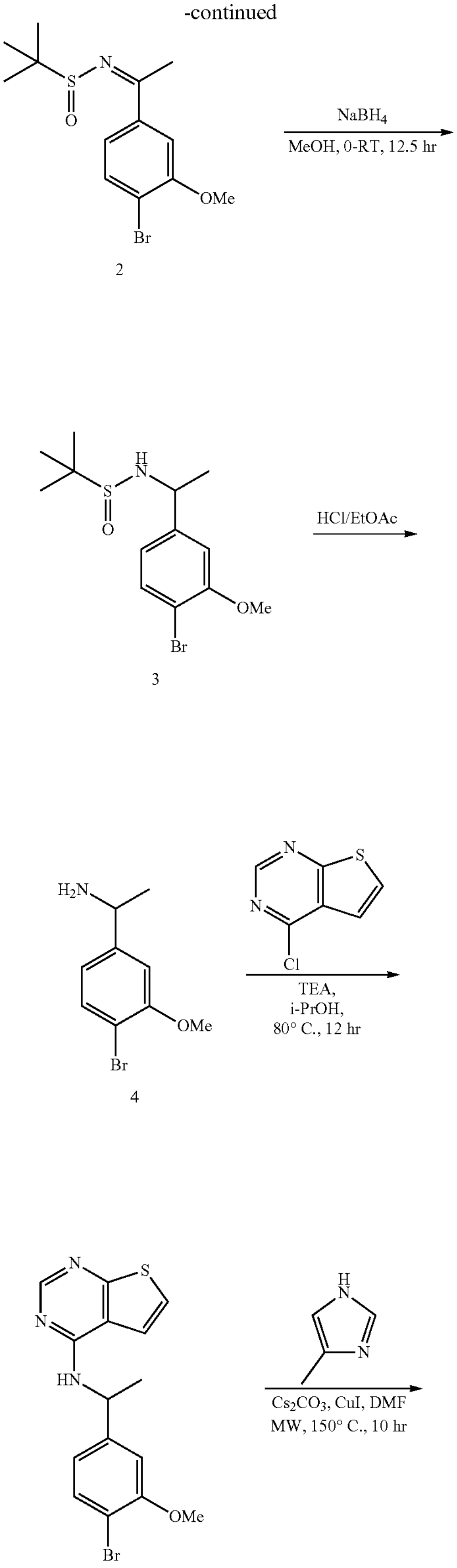

2

3

4

5

-continued

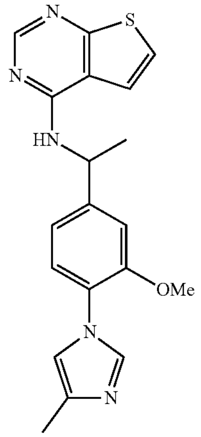

Bax-78 (RS)

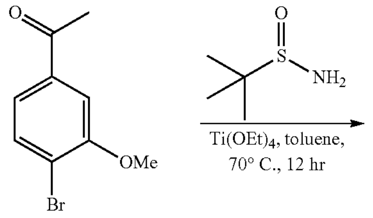

1

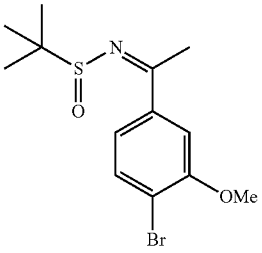

2

To a solution of 1-(4-bromo-3-methoxy-phenyl)ethanone (90 mg, 392.89 umol, 1 eq) and 2-methylpropane-2-sulfinamide (72 mg, 589.34 umol, 1.5 eq) in toluene (1 mL) was added $Ti(OEt)_4$ (179 mg, 785.79 umol, 162.95 uL, 2 eq) and the mixture was stirred at 70° C. for 12 hours. To the reaction mixture was added water (10 mL), the precipitate was formed, filtered, and the filtrate was extracted with EtOAc (5 mL*3). The organic layer was washed with brine (10 mL), dried over $MgSO_4$ and concentrated in vacuo to give (NZ)-N-[1-(4-bromo-3-methoxy-phenyl)ethylidene]-2-methyl-propane-2-sulfinamide (0.13 g, crude) as a yellow oil, it was used into the next step without further purification. ESI [M+H]=334.0.

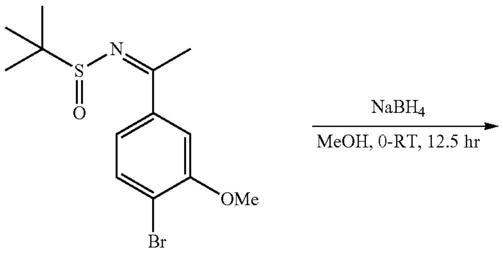

2

-continued

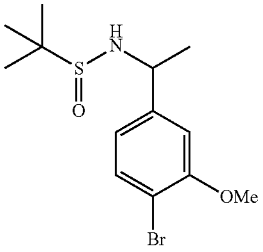

3

To a solution of (NZ)-N-[1-(4-bromo-3-methoxy-phenyl) ethylidene]-2-methyl-propane-2-sulfinamide (130 mg, 391.26 umol, 1 eq) in MeOH (3 mL) was added $NaBH_4$ (30 mg, 782.53 umol, 2 eq) at 0° C. for 30 mins. Then the mixture was stirred at 25° C. for 12 hrs. The reaction mixture was quenched by water (10 mL) and extracted with EtOAc (5 mL*3). The organic layer was washed with brine (10 mL), dried over $MgSO_4$ and concentrated in vacuo to give N-[1-(4-bromo-3-methoxy-phenyl)ethyl]-2-methyl-propane-2-sulfinamide (130 mg, crude) as a yellow oil, it was used into the next step without further purification. ESI [M+H]=336.1.

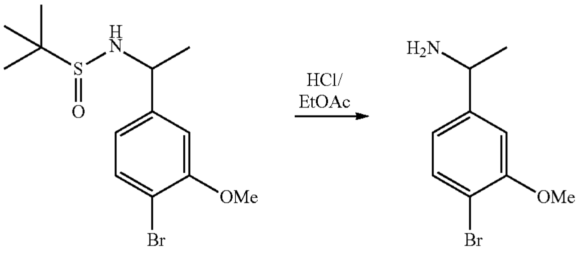

3 4

To a solution of N-[l-(4-bromo-3-methoxy-phenyl)ethyl]-2-methyl-propane-2-sulfinamide (130 mg, 388.91 umol, 1 eq) in EtOAc (1 mL) was added HCl/EtOAc (4M, 5 mL) and the mixture was stirred at 25° C. for 30 mins. The reaction mixture was concentrated in vacuo to give 1-(4-bromo-3-methoxy-phenyl)ethanaminutese (100 mg, crude, HCl) as a yellow solid, it was used into the next step without further purification.

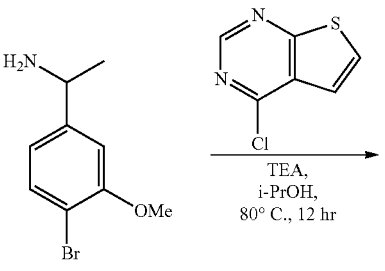

4

-continued

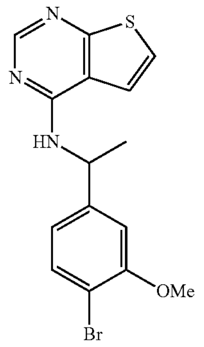

5

To a solution of 1-(4-bromo-3-methoxy-phenyl)ethanaminutese (100 mg, 375.15 umol, 1 eq, HCl) in i-PrOH (2 mL) was added TEA (114 mg, 1.13 mmol, 156.65 uL, 3 eq) and 4-chlorothieno[2,3-d]pyrimidine (77 mg, 450.18 umol, 1.2 eq). Then the mixture was stirred at 80° C. for 12 hour. The reaction mixture was concentrated in vacuo. The residue was purified by prep-TLC ($SiO_2$, Petroleum ether:Ethyl acetate=1:1) to give N-[1-(4-bromo-3-methoxy-phenyl)ethyl]thieno[2,3-d]pyrimidin-4-aminutese (100 mg, 274.53 μmol, 73.18% yield) as a yellow solid. ESI [M+H]=364.0, ESI [M+3H]=365.9.

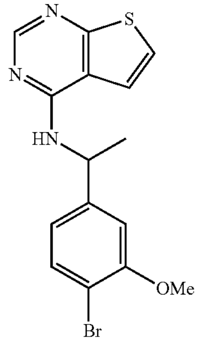

5

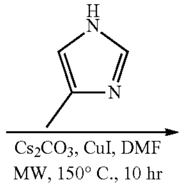

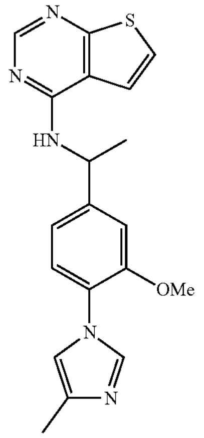

Bax-78 (RS)

N-[1-(4-bromo-3-methoxy-phenyl)ethyl]thieno[2,3-d]pyrimidin-4-aminutese (60 mg, 164.72 umol, 1 eq), 4-methyl-1H-imidazole (27 mg, 329.44 μmol, 2 eq) and $Cs_2CO_3$ (107 mg, 329.44 umol, 2 eq), CuI (6 mg, 32.94 umol, 0.2 eq) were taken up into a microwave tube in DMF (2 mL). The sealed tube was heated at 150° C. for 10 hrs under microwave under N2. To the reaction mixture was added water (10 mL) and extracted with EtOAc (5 mL*3). The organic layer was dried over $MgSO_4$ and concentrated in vacuo. The residue was purified by prep-HPLC (column: Xtimate C18 150*25 mm*5 μm; mobile phase: [water (10 mM $NH_4HCO_3$)-ACN]; B %: 38%-48%, 10 minutes) to give N-[1-[3-methoxy-4-(4-methylimidazol-1-yl)phenyl]ethyl]thieno[2,3-d]pyrimidin-4-aminutese (21.3 mg, 56.20 umol, 34.12% yield, 96.427% purity) as a white solid.

$^1$H-NMR (400 MHz, CHLOROFORM-d) δ 8.49 (s, 1H), 7.65 (br s, 1H), 7.40 (dd, J=2.1, 8.5 Hz, 1H), 7.32-7.27 (m, 2H), 7.20 (d, J=6.0 Hz, 1H), 7.00 (d, J=8.4 Hz, 1H), 6.90 (br s, 1H), 5.68-5.62 (m, 1H), 5.62-5.53 (m, 1H), 3.83 (s, 3H), 2.27 (s, 3H), 1.66 (d, J=6.8 Hz, 3H1). ESI [M+H]=366.1.

Example 29

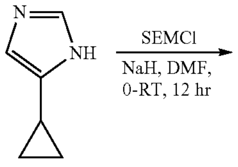

1

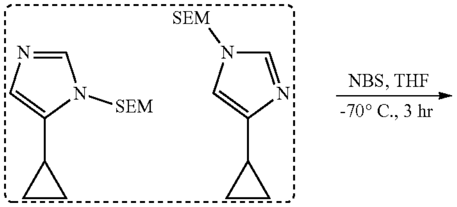

2

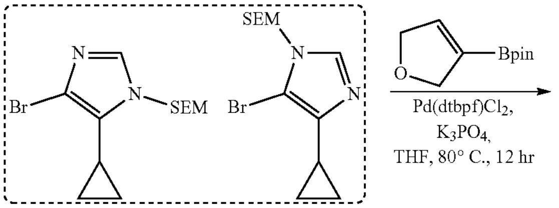

Common intermediate A
3

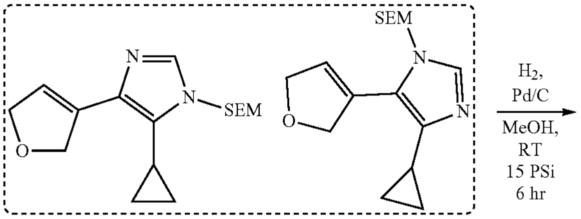

4

-continued

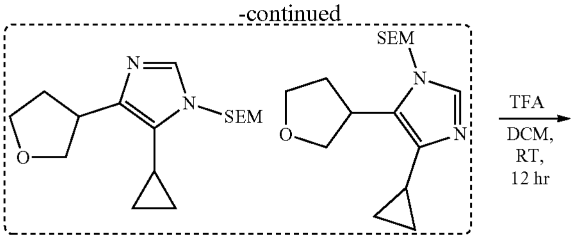

5

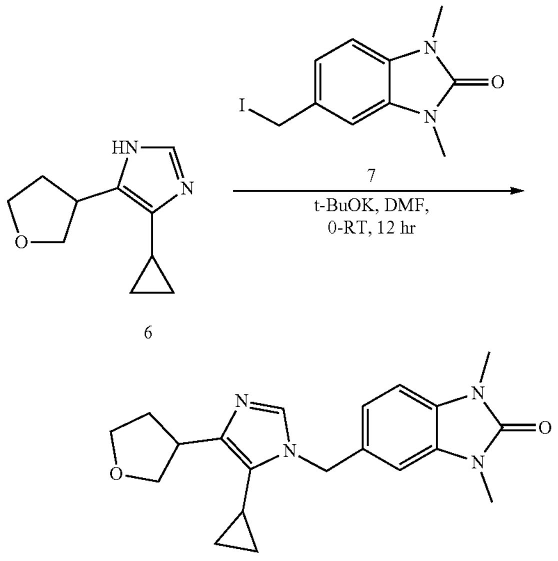

Bax-81 (RS)

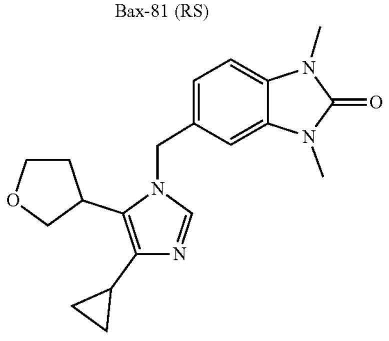

Bax-81A (RS)

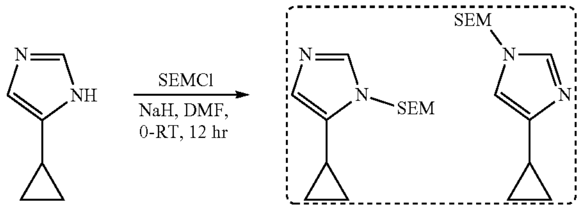

1 2

To a solution of 5-cyclopropyl-1H-imidazole (2 g, 18.49 mmol, 1 eq) in DMF (40 mL) was added NaH (740 mg, 18.49 mmol, 60% purity, 1 eq) at 0° C. The mixture was stirred at 20° C. for 30 minutes, then SEM-Cl (3.39 g, 20.34 mmol, 3.60 mL, 1.1 eq) was added at 0° C. and the mixture was stirred at 20° C. for 12 hours. The reaction mixture was quenched with cold sat.aq.$NH_4Cl$ (30 mL), extracted with EtOAc (15 mL*3). The organic layer was washed with brine (30 mL*1), dried over $MgSO_4$ and concentrated in vacuo. The residue was purified by column chromatography ($SiO_2$, Petroleum ether:Ethyl acetate=10:1 to 1:1) to give a mixture of region-isomer 2-[(5-cyclopropylimidazol-1-yl)methoxy]ethyl-trimethyl-silane and 2-[(4-cyclopropylimidazol-1-yl)methoxy]ethyl-trimethyl-silane total 3.3 g (74.8% yield) as a yellow oil. ESI [M+H]=239.1.

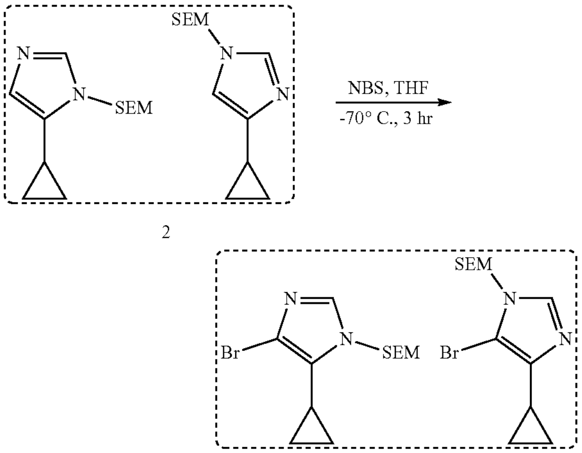

Common intermediate A
3

To a solution of 2-[(5-cyclopropylimidazol-1-yl)methoxy]ethyl-trimethyl-silane and 2-[(4-cyclopropylimidazol-1-yl)methoxy]ethyl-trimethyl-silane (total 3.3 g, 13.84 mmol, 1 eq) in THF (100 mL) was added NBS (2.46 g, 13.84 mmol, 1 eq) at −70° C. Then the mixture was stirred at −70° C. for 3 hours. TLC (Petroleum ether:Ethyl acetate=0:1) showed the reaction was complete. To the reaction mixture was added water (60 mL) and extracted with EtOAc (20 mL*3). The organic layer was washed with brine (50 mL), dried over $MgSO_4$ and concentrated in vacuo. The residue was purified by column chromatography ($SiO_2$, Petroleum ether/Ethyl acetate=1/0 to 10:1) to give a mixture of region-isomer 2-[(4-bromo-5-cyclopropyl-imidazol-1-yl)methoxy]ethyl-trimethyl-silane and 2-[(5-bromo-4-cyclopropyl-imidazol-1-yl)methoxy]ethyl-trimethyl-silane total 2.3 g as a yellow oil. ESI [M+H]=317.0.

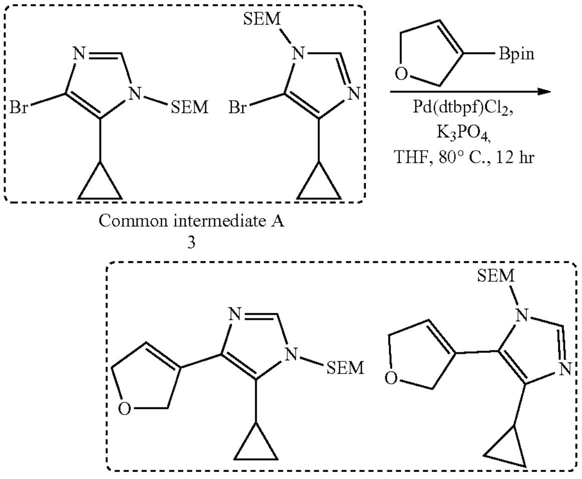

4

A mixture of 2-[(4-bromo-5-cyclopropyl-imidazol-1-yl)methoxy]ethyl-trimethyl-silane and 2-[(5-bromo-4-cyclopropyl-imidazol-1-yl)methoxy]ethyl-trimethyl-silane (total 100 mg), 2-(2,5-dihydrofuran-3-yl)-4,4,5,5-tetramethyl-1,3,2-dioxaborolane (74 mg, 378.20 umol, 1.2 eq) and $K_3PO_4$ (134 mg, 630.33 umol, 2 eq) and ditert-butyl(cyclopentyl)phosphane; dichloropalladium; iron (21 mg, 31.52 μmol, 0.1 eq) in THF (2 mL) and $H_2O$ (0.5 mL) was stirred at 80° C. for 12 hours under N2. The reaction mixture was concentrated in vacuo. The residue was purified by column chromatography ($SiO_2$, Petroleum ether/Ethyl acetate=10/1 to 3:1) to give 2-[[5-cyclopropyl-4-(2,5-dihydrofuran-3-yl)imidazol-1-yl]methoxy]ethyl-trimethyl-silane and 2-[[4-cyclopropyl-5-(2,5-dihydrofuran-3-yl)imidazol-1-yl]methoxy]ethyl-trimethyl-silane total 0.3 g as a yellow oil. ESI [M+H]=307.2.

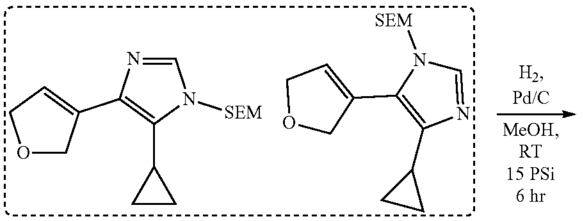

4

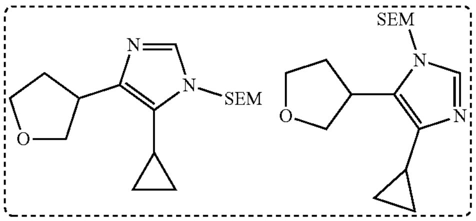

5

To a solution of 2-[[5-cyclopropyl-4-(2,5-dihydrofuran-3-yl)imidazol-1-yl]methoxy]ethyl-trimethyl-silane and 2-[[4-cyclopropyl-5-(2,5-dihydrofuran-3-yl)imidazol-1-yl]methoxy]ethyl-trimethyl-silane (total 0.3 g, 0.98 mmol) in MeOH (10 mL) was added Pd/C (0.1 g, 978.87 umol, 10% purity) under N2 atmosphere. The suspension was degassed and purged with $H_2$ for 3 times. The mixture was stirred under $H_2$ (15 psi) at 15° C. for 6 hours. The reaction mixture was filtered, the filtrate was concentrated in vacuo to give 2-[(5-cyclopropyl-4-tetrahydrofuran-3-yl-imidazol-1-yl)methoxy]ethyl-trimethyl-silane and 2-[(4-cyclopropyl-5-tetrahydrofuran-3-yl-imidazol-1-yl)methoxy]ethyl-trimethyl-silane total 280 mg as a yellow oil. ESI [M+H]=309.3.

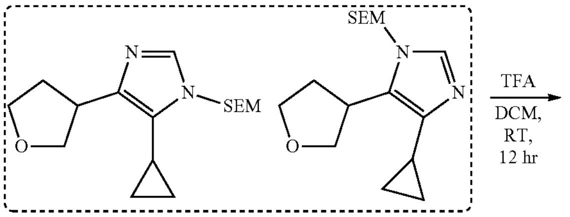

5

-continued

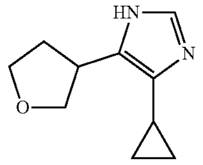

6

To a solution of 2-[(5-cyclopropyl-4-tetrahydrofuran-3-yl-imidazol-1-yl)methoxy]ethyl-trimethyl-silane and 2-[(4-cyclopropyl-5-tetrahydrofuran-3-yl-imidazol-1-yl)methoxy]ethyl-trimethyl-silane (total 280 mg) in DCM (6 mL) was added TFA (2 mL) and the mixture was stirred at 15° C. for 12 hours. The reaction mixture was concentrated in vacuo. To the residue was added DCM (5 mL) and water (10 mL), adjusted to pH=8 with sat.aq.$NaHCO_3$, then extracted with DCM (5 mL*3). The organic layer was dried over $MgSO_4$ and concentrated in vacuo. The residue was purified by prep-TLC ($SiO_2$, Ethyl acetate:Methanol=10:1) to give 5-cyclopropyl-4-tetrahydrofuran-3-yl-1H-imidazole (100 mg, 561.07 umol, 61.82% yield) as a yellow solid. ESI [M+H]=179.3.

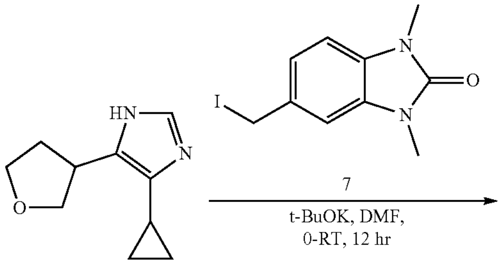

6

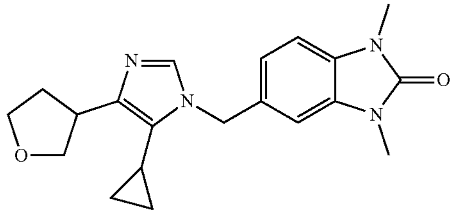

Bax-81 (RS)

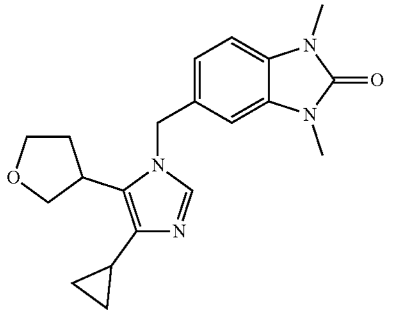

Bax-81A (RS)

To a solution of t-BuOK (1 M, 757.45 uL, 1.5 eq) in DMF (1 mL) was added dropwise 4-cyclopropyl-5-tetrahydrofuran-3-yl-1H-imidazole (90 mg, 504.96 umol, 1 eq) in DMF (0.5 mL) at 0° C. under N2. After 15 minutes, 5-(iodomethyl)-1,3-dimethyl-benzimidazol-2-one (198 mg, 656.45 umol, 1.3 eq) in DMF (0.5 mL) was added at 0° C. under N2. The mixture was stirred at 20° C. for 12 hours. The reaction was added water (10 mL) and extracted with EtOAc (5 mL*3). The organic layer was dried over $MgSO_4$ and concentrated in vacuo. The residue was purified by prep-HPLC (column: Waters Xbridge 150*25 5u; mobile phase: [water (10 mM $NH_4HCO_3$)-ACN]; B %: 20%-40%, 7 min) to give 5-[(5-cyclopropyl-4-tetrahydrofuran-3-yl-imidazol-1-yl)methyl]-1,3-dimethyl-benzimidazol-2-one (40.59 mg, 111.53 umol, 22.09% yield, 96.842% purity) and 5-[(4-cyclopropyl-5-tetrahydrofuran-3-yl-imidazol-1-yl)methyl]-1,3-dimethyl-benzimidazol-2-one (24.44 mg, 67.61 umol, 13.39% yield, 97.501% purity) as a white solid.

Bax-81 (RS)_HNMR: $^1$H-NMR (400 MHz, CHLOROFORM-d) δ 7.33 (s, 1H), 6.88-6.79 (m, 2H), 6.64 (s, 1H), 5.11 (s, 2H), 4.03-3.96 (m, 2H), 3.87 (q, J=7.6 Hz, 1H), 3.69 (t, J=8.4 Hz, 1H), 3.47 (quin, J=8.4 Hz, 1H), 3.33 (d, J=12.0 Hz, 6H), 2.25-2.06 (m, 2H), 1.29 (tt, J=5.4, 8.1 Hz, 1H), 0.86-0.79 (m, 1H), 0.87-0.79 (m, 1H), 0.55-0.49 (m, 2H). ESI [M+H]=353.1.

Bax-81A (RS)_HNMR: $^1$H-NMR (400 MHz, CHLOROFORM-d) δ 7.28 (s, 1H), 6.84 (d, J=8.1 Hz, 1H), 6.71 (dd, J=1.3, 8.0 Hz, 1H), 6.56 (s, 1H), 5.04 (s, 2H), 3.93 (dt, J=4.5, 8.4 Hz, 1H), 3.82-3.75 (m, 1H), 3.73-3.64 (m, 2H), 3.32 (d, J=15.7 Hz, 7H), 2.07-1.89 (m, 2H), 1.80-1.71 (m, 1H), 0.89-0.83 (m, 2H), 0.81-0.73 (m, 2H). ESI [M+H]=353.1.

Example 30

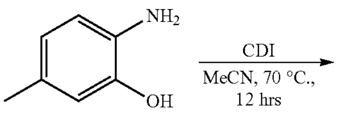

1A

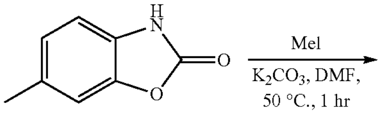

2A

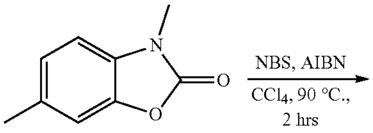

3A

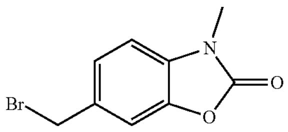

4A

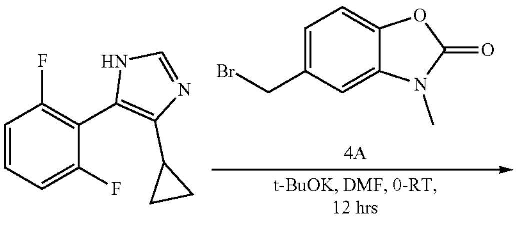

7

-continued

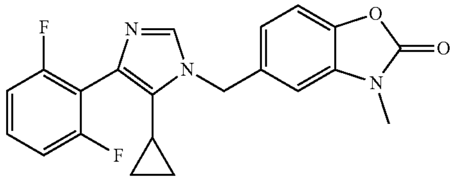

Bax-84

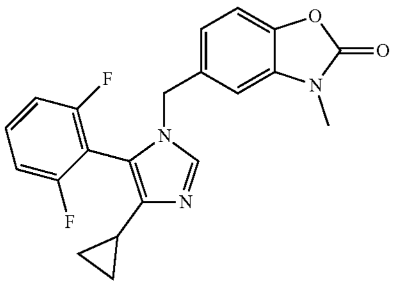

Bax-84A

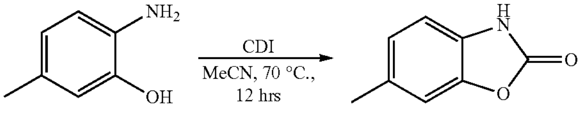

1A 2A

To a solution of 2-amino-4-methyl-phenol (1 g, 8.12 mmol, 1 eq) in MeCN (30 mL) was added CDI (3.95 g, 24.36 mmol, 3 eq) and the mixture was stirred at 70° C. for 12 hrs. The reaction mixture was concentrated in vacuo. The residue was purified by column chromatography (plate 1, $SiO_2$, Petroleum ether/Ethyl acetate=10/1 to 2:1) to give 5-methyl-3H-1,3-benzoxazol-2-one (1.2 g, 8.05 mmol, 99.09% yield) as a white solid. ESI [M+H]=150.1.

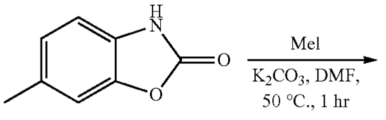

2A

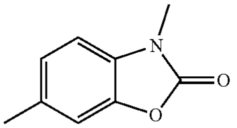

3A

A mixture of 5-methyl-3H-1,3-benzoxazol-2-one (1.14 g, 7.64 mmol, 1 eq), $K_2CO_3$ (2.11 g, 15.29 mmol, 2 eq) and MeI (1.63 g, 11.47 mmol, 713.75 uL, 1.5 eq) in DMF (10 mL) was stirred at 50° C. for 1 hr. To the reaction mixture was added water (30 mL) and extracted with EtOAc (10 mL*3). The organic layer was washed with brine (20 mL*3), dried over $MgSO_4$ and concentrated in vacuo to give 3,5-dimethyl-1,3-benzoxazol-2-one (1.2 g, 7.35 mmol, 96.21% yield) as a white solid. ESI [M+H]=164.2.

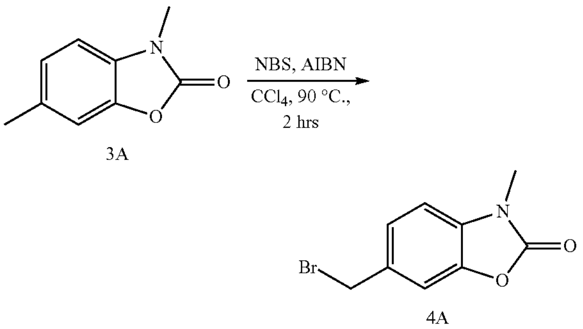

3A
4A

A mixture of 3,5-dimethyl-1,3-benzoxazol-2-one (1.17 g, 7.17 mmol, 1 eq), NBS (1.40 g, 7.89 mmol, 1.1 eq) and AIBN (117.74 mg, 717.03 μmol, 0.1 eq) in $CCl_4$ (20 mL) was stirred at 90° C. for 2 hrs under N2. The mixture was filtered, the filtrate was concentrated in vacuo. The residue was purified by column chromatography (plate 1, $SiO_2$, Petroleum ether/Ethyl acetate=20/1 to 3:1) to give 5-(bromomethyl)-3-methyl-1,3-benzoxazol-2-one (1.9 g, crude). 300 mg of the crude product was purified by prep-TLC (Petroleum ether:Ethyl acetate=2:1) to give 5-(bromomethyl)-3-methyl-1,3-benzoxazol-2-one (200 mg. pure).

$^1$H-NMR (400 MHz, CHLOROFORM-d) δ 7.08 (d, J=1.1 Hz, 2H), 6.95 (s, 1H), 4.48 (s, 2H), 3.35 (s, 3H). ESI [M+H]=243.9.

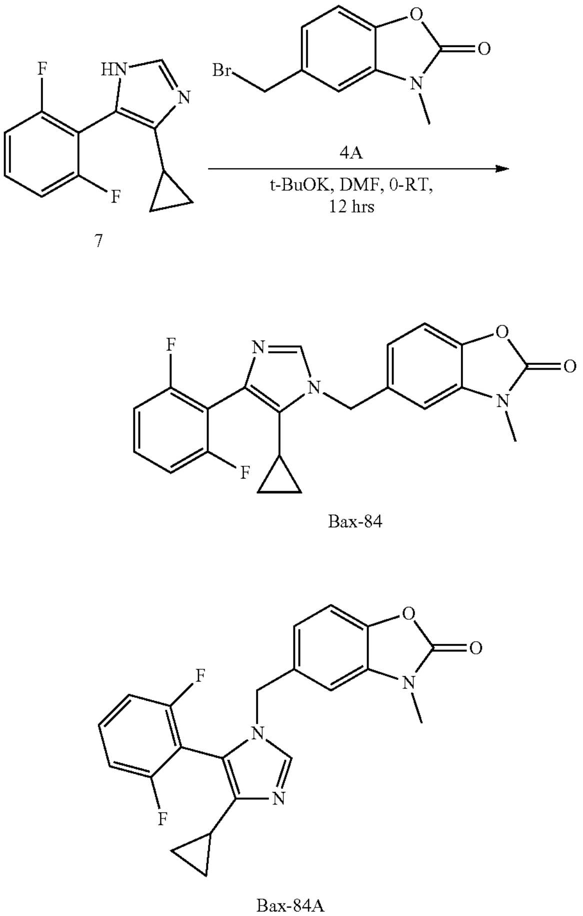

4A
7
Bax-84
Bax-84A

To a solution of t-BuOK (1 M, 681.14 uL, 1.5 eq) in DMF (1 mL) (under N2) was added 4-cyclopropyl-5-(2,6-difluorophenyl)-1H-imidazole (100 mg, 454.10 umol, 1 eq) in DMF (1 mL) drop-wise at 0° C. under N2. After 15 mins, 5-(bromomethyl)-3-methyl-1,3-benzoxazol-2-one (164.88 mg, 681.14 μmol, 1.5 eq) in DMF (1 mL) was added at 0° under N2. The mixture was stirred at 25° C. for 12 hrs. To the reaction mixture was added water (15 mL), extracted with EtOAc 200 mL (40 mL*5). The organic phase was dried over drying $Na_2SO_4$, and then concentrated in vacuo. The residue was purified by prep-HPLC (column: Luna C18 100*30 5u; mobile phase: [water (0.04% HCl)-ACN]; B %: 20%-33%, 10 min) to give 5-[[5-cyclopropyl-4-(2,6-difluorophenyl)imidazol-1-yl]methyl]-3-methyl-1,3-benzoxazol-2-one (15.31 mg, 34.70 umol, 7.64% yield, 86.440% purity) and 5-[[4-cyclopropyl-5-(2,6-difluorophenyl)imidazol-1-yl]methyl]-3-methyl-1,3-benzoxazol-2-one (67.01 mg, 170.12 umol, 37.46% yield, 96.821% purity) were obtained as a white solid.

Bax-84_HNMR: 1H-NMR (400 MHz, METHANOL-d4) δ 9.21 (s, 1H), 7.76-7.54 (m, 1H), 7.22-7.02 (m, 3H), 6.89-6.65 (m, 2H), 5.32 (s, 2H), 3.31-3.30 (m, 2H), 1.87-1.70 (m, 1H), 1.04-0.88 (m, 2H), 0.81-0.67 (m, 2H). ESI [M+H]=382.1.

Bax-84A_HNMR: 1H-NMR (400 MHz, METHANOL-d4) δ 9.08 (s, 1H), 7.72-7.58 (m, 1H), 7.41-7.30 (m, 2H), 7.28-7.17 (m, 3H), 5.62 (s, 2H), 3.42 (s, 3H), 1.82-1.68 (m, 1H), 1.31 (t, J=7.3 Hz, 1H), 1.02-0.90 (m, 2H), 0.51-0.36 (m, 2H). ESI [M+H]=382.1.

Example 31

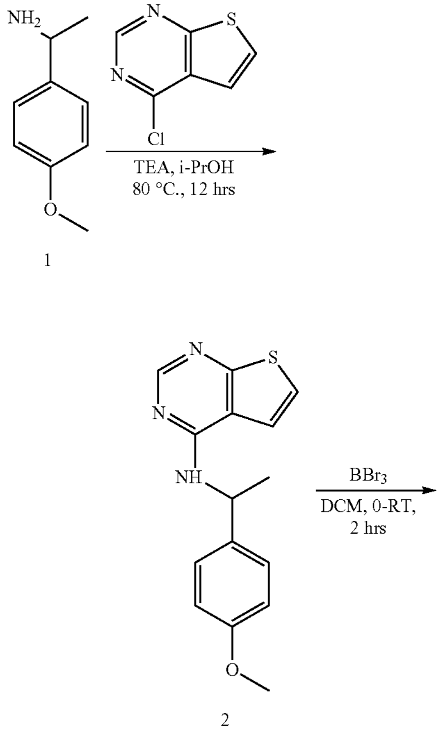

1
2

-continued

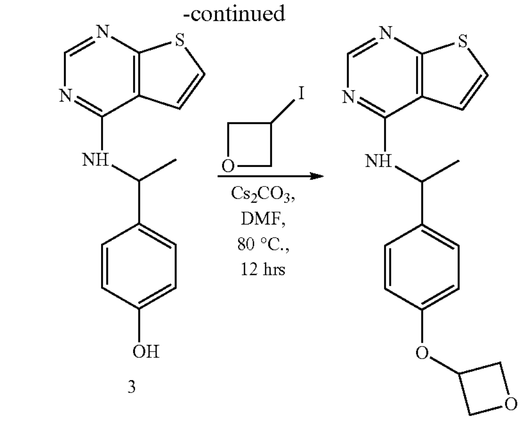

3

Bax-85 (RS)

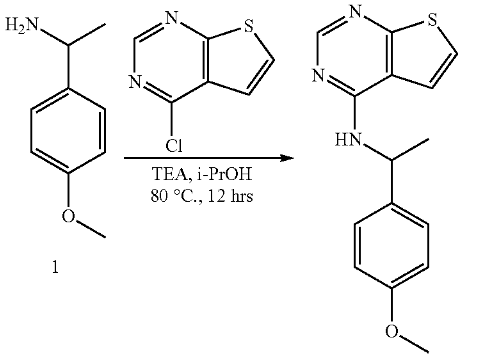

1

2

To a solution of 1-(4-methoxyphenyl)ethanamine (300 mg, 1.98 mmol, 1 eq) in i-PrOH (7 mL) was added TEA (401.53 mg, 3.97 mmol, 552.31 μL, 2 eq) and 4-chlorothieno [2,3-d]pyrimidine (406.22 mg, 2.38 mmol, 1.2 eq). The mixture was stirred at 80° C. for 12 hrs. The reaction mixture was concentrated in vacuo. The residue was purified by prep-TLC ($SiO_2$, Petroleum ether:Ethyl acetate=1:1) to give N-[1-(4-methoxyphenyl)ethyl]thieno[2,3-d]pyrimidin-4-amine (566 mg, 1.98 mmol, 99.97% yield) as a white solid. ESI [M+H]=286.1.

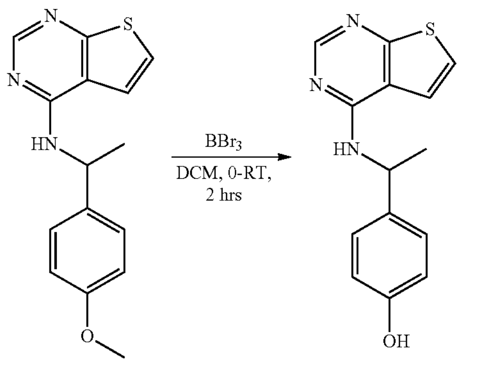

2

3

To a solution of N-[l-(4-methoxyphenyl)ethyl]thieno[2,3-d]pyrimidin-4-amine (300 mg, 1.05 mmol, 1 eq) in DCM (3 mL) was added $BBr_3$ (526.75 mg, 2.10 mmol, 2.10 mL, 100% purity, 2 eq) at 0° C. The mixture was stirred at 15° C. for 2 hrs. The reaction system was poured into ice water (15 mL) and then extracted with DCM (10 mL*5). The organic phase was dried over drying $Na_2SO_4$, and then concentrated in vacuo. The residue was purified by prep-TLC ($SiO_2$, DCM:MeOH=10:1) to give 4-[1-(thieno[2,3-d] pyrimidin-4-ylamino)ethyl]phenol (170 mg, 626.53 umol, 59.60% yield) as a yellow solid. ESI [M+H]=272.2.

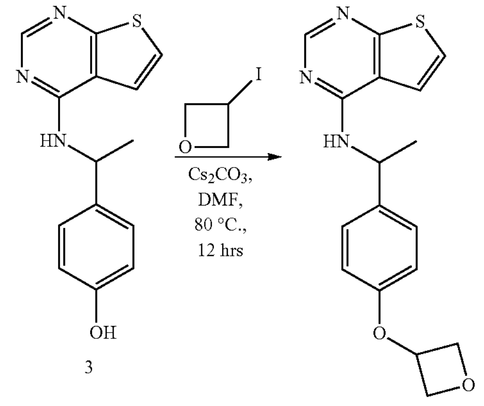

3

Bax-85 (RS)

To a solution of 4-[1-(thieno[2,3-d]pyrimidin-4-ylamino) ethyl]phenol (80 mg, 294.84 μmol, 1 eq) in DMF (2 mL) was added 3-iodooxetane (86.79 mg, 471.74 μmol, 1.6 eq) and $Cs_2CO_3$ (192.13 mg, 589.67 umol, 2 eq). The mixture was stirred at 80° C. for 12 hrs. To the reaction mixture was add water (10 mL), extracted with EtOAc (25 mL*3). The organic phase was dried over drying $Na_2SO_4$, and then concentrated in vacuo. The residue was purified by prep-HPLC (column: Xtimate C18 150*25 mm*5 μm; mobile phase: [water (10 mM NH4HCO3)-ACN]; B %: 25%-55%, 10 min) to give N-[l-[4-(oxetan-3-yloxy)phenyl]ethyl] thieno[2,3-d]pyrimidin-4-amine (37.64 mg, 114.29 umol, 38.76% yield, 99.410% purity) as a white solid. ESI [M+H]=328.1.

$^1$H-NMR (400 MHz, CHLOROFORM-d) δ 8.49 (s, 1H), 7.34 (d, J=8.6 Hz, 2H), 7.26 (s, 1H), 7.30-7.21 (m, 1H), 6.68 (d, J=8.6 Hz, 2H), 5.54 (quin, J=7.0 Hz, 1H), 5.32 (br d, J=7.3 Hz, 1H), 5.18 (quin, J=5.6 Hz, 1H), 4.95 (t, J=6.7 Hz, 2H), 4.75 (dd, J=5.5, 7.1 Hz, 2H), 1.66-1.64 (m, 1H), 1.64-1.60 (m, 1H).

Example 32

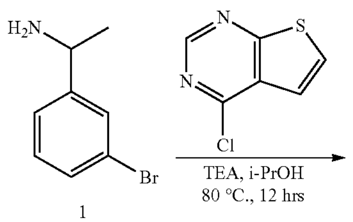

1

-continued

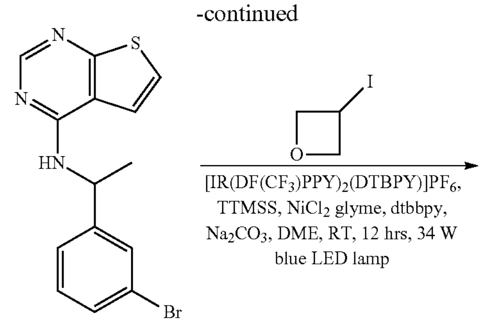

2

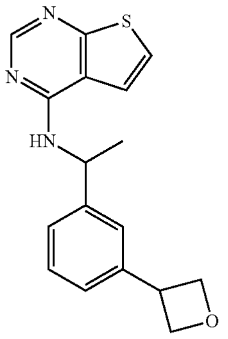

Bax-87 (RS)

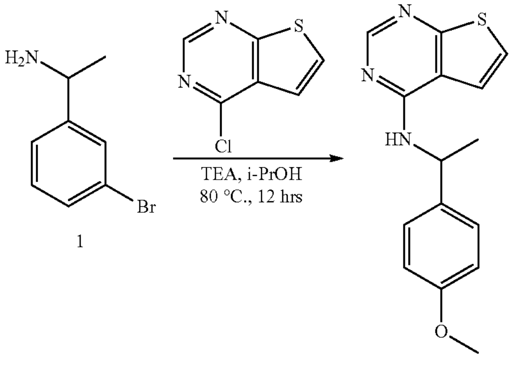

1

2

To a solution of 1-(3-bromophenyl)ethanamine (300 mg, 1.27 mmol, 142.86 μL, 1 eq, HCl) in i-PrOH (7 mL) was added TEA (385.02 mg, 3.80 mmol, 529.60 μL, 3 eq) and 4-chlorothieno[2,3-d]pyrimidine (259.68 mg, 1.52 mmol, 1.2 eq). The mixture was stirred at 80° C. for 12 hrs. The reaction mixture was concentrated in vacuo. The residue was purified by prep-TLC ($SiO_2$, Petroleum ether:Ethyl acetate=1:1) to give N-[1-(3-bromophenyl)ethyl]thieno[2,3-d]pyrimidin-4-amine (360 mg, 1.08 mmol, 84.92% yield) as a white solid. ESI [M+H]=334.1 and [M+3H]=336.1.

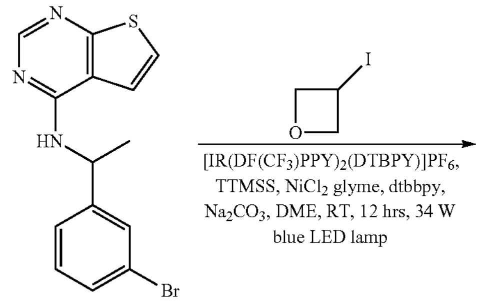

2

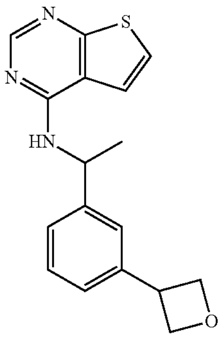

Bax-87 (RS)

A mixture of N-[1-(3-bromophenyl)ethyl]thieno[2,3-d]pyrimidin-4-amine (200 mg, 598.38 umol, 1 eq), 3-iodooxetane (330.26 mg, 1.80 mmol, 3 eq), TTMSS (148.79 mg, 598.38 umol, 184.61 uL, 1 eq), $Na_2CO_3$ (126.84 mg, 1.20 mmol, 2 eq), dichloronickel; 1,2-dimethoxyethane (6.57 mg, 29.92 umol, 0.05 eq), 4-tert-butyl-2-(4-tert-butyl-2-pyridyl)pyridine (9.64 mg, 35.90 umol, 0.06 eq) and bis[3,5-difluoro-2-[5-(trifluoromethyl)-2-pyridyl]phenyl]iridium(1+); 4-tert-butyl-2-(4-tert-butyl-2-pyridyl)pyridine; hexafluorophosphate (20.14 mg, 17.95 umol, 0.03 eq) in DME (1 mL) was stirred and irradiated with a 34 W blue LED lamp at 25° C. for 12 hrs under N2. To the reaction mixture was add water (10 mL), extracted with EtOAc 80 mL (20 mL*4). The organic phase was dried over drying $Na_2SO_4$, and then concentrated in vacuo. The residue was purified by prep-HPLC (column: Waters Xbridge 150*25 5u; mobile phase: [water (10 mM NH4HCO3)-ACN]; B %: 20%-50%, 7 min) to give N-[1-[3-(oxetan-3-yl)phenyl]ethyl]thieno[2,3-d]pyrimidin-4-amine (57.51 mg, 184.68 umol, 30.86% yield, 100% purity) as a white solid. ESI [M+H]=312.0.

$^1$H-NMR (400 MHz, METHANOL-d4) δ 8.28 (s, 1H), 7.67 (d, J=6.0 Hz, 1H), 7.54-7.41 (m, 2H), 7.40-7.25 (m, 3H), 5.57 (q, J=7.1 Hz, 1H), 5.15-5.02 (m, 2H), 4.75 (td, J=6.3, 9.2 Hz, 2H), 4.35-4.17 (m, 1H), 1.66 (d, J=7.1 Hz, 3H).

Example 33

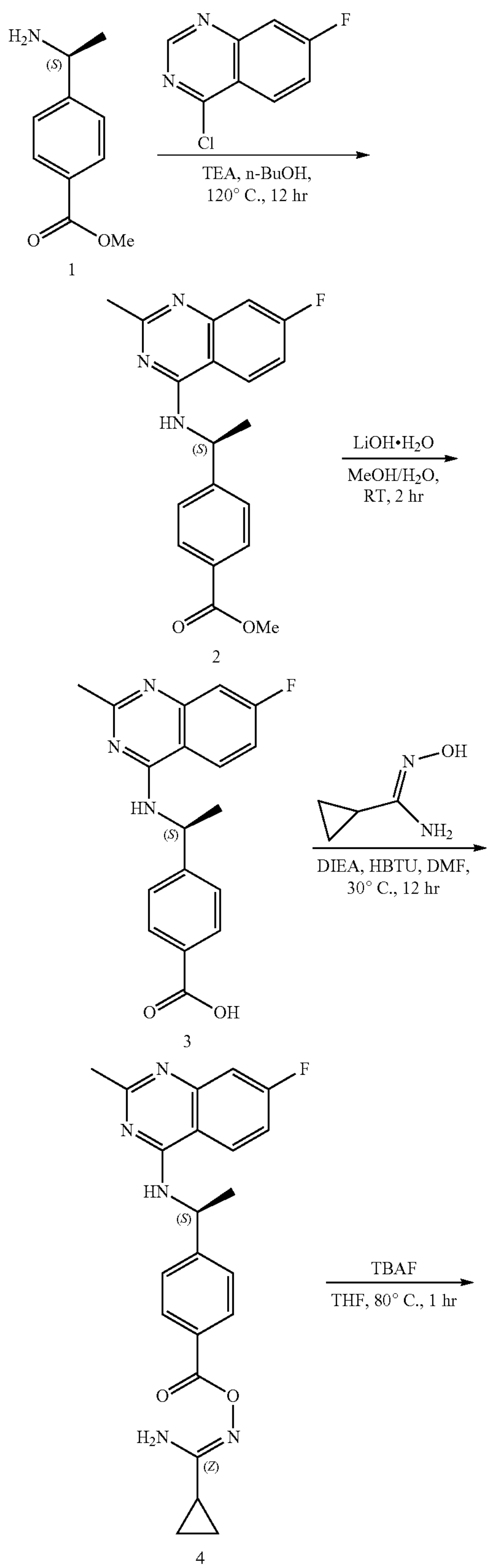

1

2

3

4

-continued

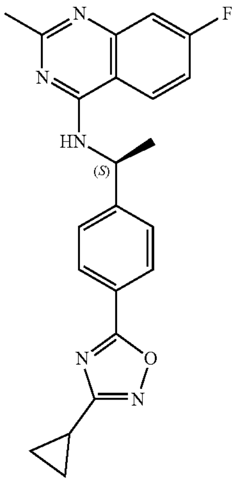

Bax-88 S

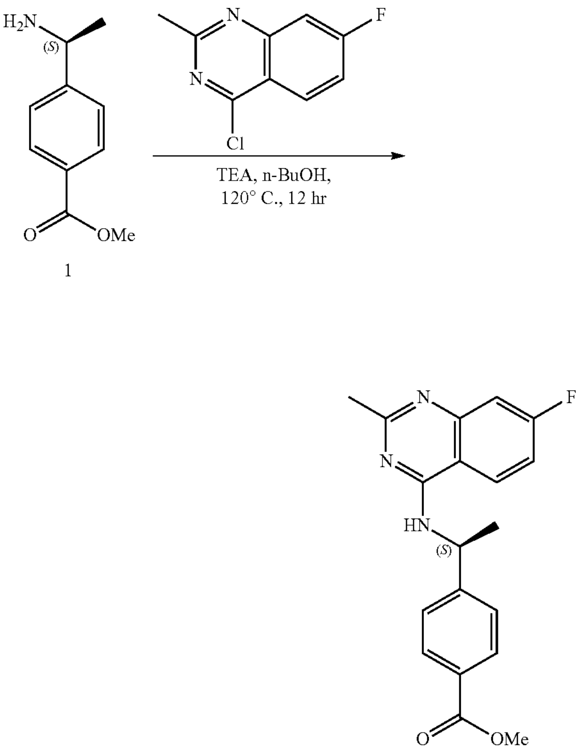

1

2

To a solution of methyl 4-[(1S)-1-aminoethyl]benzoate (200 mg, 1.12 mmol, 1 eq) in n-BuOH (4 mL) was added TEA (339 mg, 3.35 mmol, 465.99 uL, 3 eq) and 4-chloro-7-fluoro-2-methyl-quinazoline (241 mg, 1.23 mmol, 1.1 eq), and the mixture was stirred at 120° C. for 12 hours. The reaction mixture was concentrated in vacuo. The residue was purified by column chouromatography ($SiO_2$, Petroleum ether/Ethyl acetate=10/1 to 3:1) to give methyl 4-[(1S)-1-[(7-fluoro-2-methyl-quinazolin-4-yl)amino]ethyl]benzoate (0.26 g, 766.14 umol, 68.65% yield) as a yellow solid. ESI [M+H]=340.0.

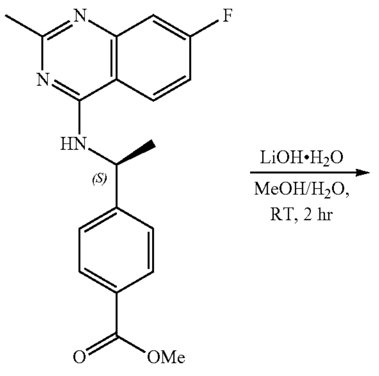

2

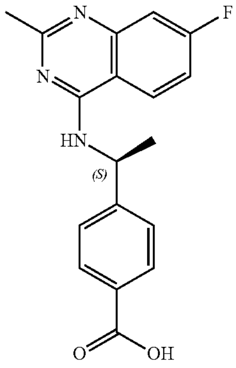
3

To a solution of methyl 4-[(1S)-1-[(7-fluoro-2-methyl-quinazolin-4-yl)amino]ethyl]benzoate (260 mg, 766.14 umol, 1 eq) in MeOH (6 mL) and $H_2O$ (2 mL) was added $LiOH{\cdot}H_2O$ (64 mg, 1.53 mmol, 2 eq), and the mixture was stirred at 15° C. for 12 hour. MeOH was removed, the aqueous layer was extracted with MTBE (2 mL), then adjusted to pH=2 with 1N HCl, the precipitate was formed, filtered, the filter cake was collected and concentrated in vacuo to give 4-[(1S)-1-[(7-fluoro-2-methyl-quinazolin-4-yl)amino]ethyl]benzoic acid (0.2 g, 614.75 umol, 80.24% yield) as a yellow solid. ESI [M+H]=326.1.

-continued

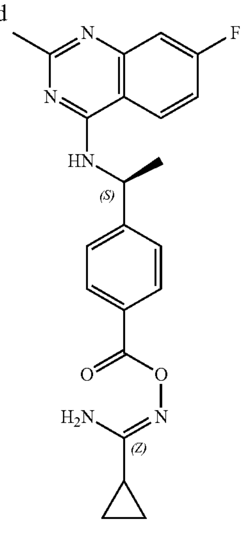
4

To a solution of 4-[(1S)-1-[(7-fluoro-2-methyl-quinazolin-4-yl)amino]ethyl]benzoic acid (100 mg, 307.37 umol, 1 eq) in DMF (2 mL) was added DIEA (119 mg, 922.12 umol, 160.62 uL, 3 eq), N'-hydroxycyclopropanecarboxamidine (46 mg, 461.06 umol, 1.5 eq) and HBTU (140 mg, 368.85 umol, 1.2 eq). Then the mixture was stirred at 30° C. for 12 hours. To the reaction mixture was added water (5 mL) and extracted with EtOAc (5 mL*3). The organic layer was washed with brine (10 mL*2), dried over $MgSO_4$ and concentrated in vacuo to give the crude product [(Z)-[amino (cyclopropyl)methylene]amino]4-[(1S)-1-[(7-fluoro-2-methyl-quinazolin-4-yl)amino]ethyl]benzoate (0.15 g, crude) as a yellow oil. It was used into the next step without further purification. ESI [M+H]=408.1.

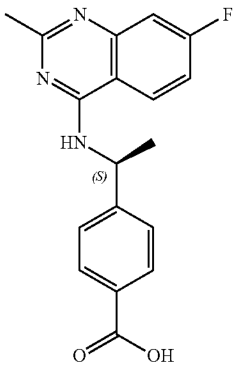
3

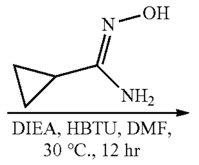

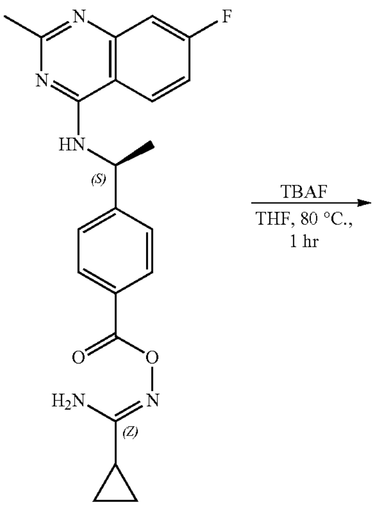

4

-continued

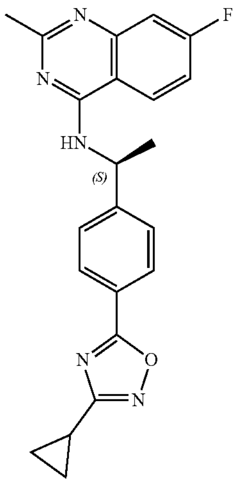

Bax-88 S

To a solution of [(Z)-[amino(cyclopropyl)methylene] amino] 4-[(1S)-1-[(7-fluoro-2-methyl-quinazolin-4-yl) amino]ethyl]benzoate (150 mg, 368.15 umol, 1 eq) in THF (3 mL) as added TBAF (1 M, 1.10 mL, 3 eq, THF solution) and the mixture was stirred at 80° C. for 1 hour. The reaction was concentrated in vacuo. The reaction was purified by prep-TLC (Petroleum ether:Ethyl acetate=1:1), then purified again by prep-HPLC (column: Xtimate C18 150*25 mm*5 μm; mobile phase: [water (10 mM NH4HCO3)-ACN]; B %: 45%-75%, 8 min) to give N-[(1S)-1-[4-(3-cyclopropyl-1,2,4-oxadiazol-5-yl)phenyl]ethyl]-7-fluoro-2-methyl-quinazolin-4-amine (41.4 mg, 105.89 umol, 28.76% yield, 99.602% purity) as a white solid.

Bax-88 S_HNMR: $^1$H-NMR (400 MHz, CHLOROFORM-d) δ 8.06 (d, J=8.1 Hz, 2H), 7.72 (dd, J=5.6, 8.9 Hz, 1H), 7.57 (d, J=8.3 Hz, 2H), 7.40 (dd, J=2.5, 10.1 Hz, 1H), 7.17 (dt, J=2.4, 8.6 Hz, 1H), 5.80-5.73 (m, 1H), 5.73-5.65 (m, 1H), 2.56 (s, 3H), 2.19-2.10 (m, 1H), 1.71 (d, J=6.7 Hz, 3H), 1.15-1.05 (m, 4H). ESI [M+H]=390.2.

Example 34

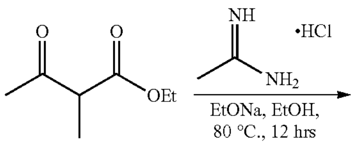

1A

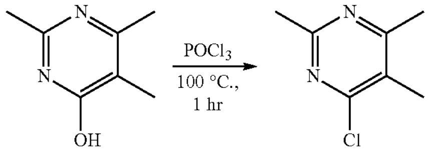

2A

3A

-continued

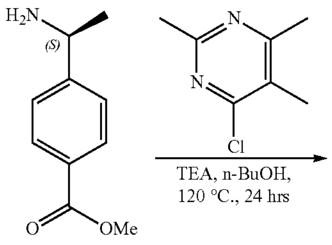

1

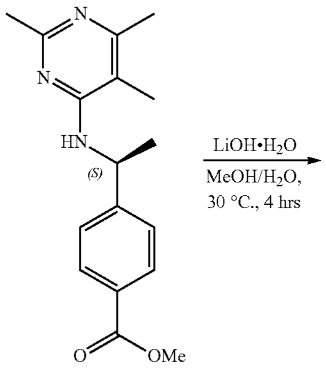

2

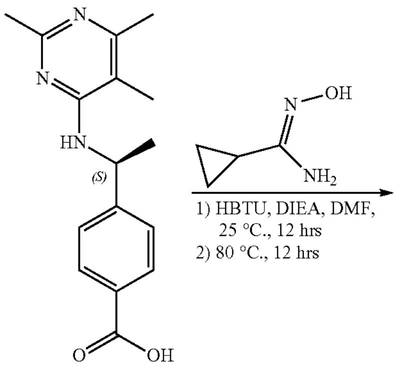

3

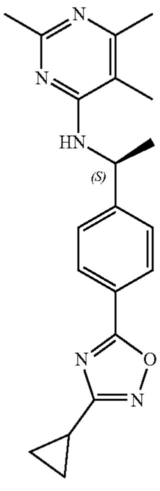

Bax-90 S

-continued

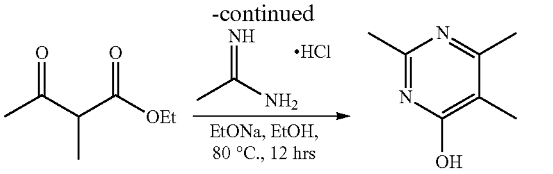

1A 2A

To a solution of acetamidine (655.78 mg, 6.94 mmol, 1 eq, HCl) in EtOH (20 mL) was added EtONa (944.04 mg, 13.87 mmol, 2 eq) and the mixture was stirred at 80° C. for 10 mins, then ethyl 2-methyl-3-oxo-butanoate (1 g, 6.94 mmol, 980.39 μL, 1 eq) was added and the mixture was stirred at 80° C. for 12 hrs. The reaction mixture was concentrated in vacuo. To the residue was added water (10 mL) and adjusted to pH=5-6 with 1N HCl, extracted with DCM/i-PrOH (3/1, 10 mL*5) The organic layer was dried over $MgSO_4$ and concentrated in vacuo to give 2,5,6-trimethylpyrimidin-4-ol (800 mg, 5.79 mmol, 83.47% yield) as a white solid. ESI [M+H]=139.1.

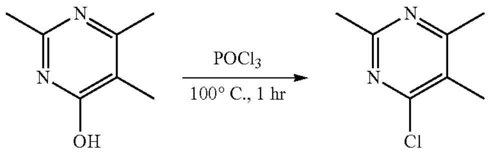

2A 3A

A mixture of 2,5,6-trimethylpyrimidin-4-ol (300 mg, 2.17 mmol, 1 eq) in $POCl_3$ (5 mL) was stirred at 100° C. for 1 hr. The reaction mixture was concentrated in vacuo to give 4-chloro-2,5,6-trimethyl-pyrimidine (330 mg, crude) as a yellow oil. ESI [M+H]=157.1.

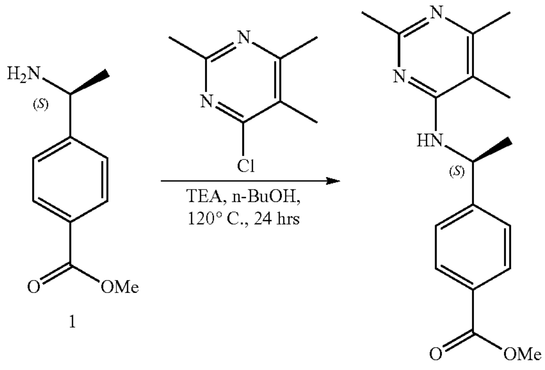

1 2

To a solution of 4-chloro-2,5,6-trimethyl-pyrimidine (314.60 mg, 2.01 mmol, 1.2 eq) in n-BuOH (5 mL) was added TEA (846.94 mg, 8.37 mmol, 1.16 mL, 5 eq) and methyl 4-[(1S)-1-aminoethyl]benzoate (300 mg, 1.67 mmol, 1 eq). The mixture was stirred at 120° C. for 24 hrs. The reaction mixture was concentrated in vacuo. The residue was purified by column chromatography ($SiO_2$, PE/THF=30/1 to 0:1) to give methyl 4-[(1S)-1-[(2,5,6-trimethylpyrimidin-4-yl)amino]ethyl]benzoate (400 mg, crude) as a yellow oil. ESI [M+H]=300.1.

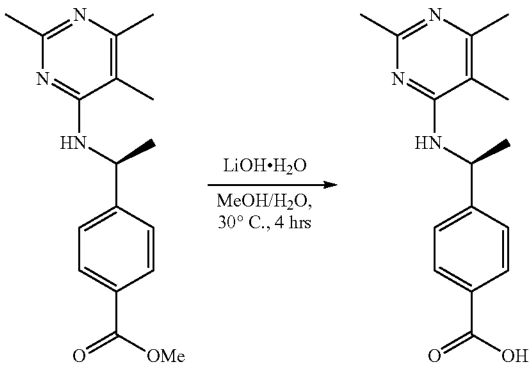

2 3

To a solution of methyl 4-[(1S)-1-[(2,5,6-trimethylpyrimidin-4-yl)amino]ethyl]benzoate (350 mg, 1.17 mmol, 1 eq) in MeOH (12 mL) and $H_2O$ (4 mL) was added $LiOH{\cdot}H_2O$ (98.12 mg, 2.34 mmol, 2 eq). The mixture was stirred at 30° C. for 4 hrs. The reaction mixture was concentrated under reduced pressure to remove MeOH, and extracted with MTBE 60 mL (20 mL*3). The aqueous phase was adjusted to pH=2 with 1N aq.HCl (cooled water), and extracted with EtOAc 60 mL (20*3). The combined organic layers were dried over $Na_2SO_4$, filtered and concentrated under reduced pressure to give a residue. Then the aqueous phase was lyophilization. All of the residue was purified by prep-HPLC (column: Phenomenex Luna C18 200*40 mm*10 μm; mobile phase: [water (0.05% HCl)-ACN]; B %: 1%-30%, 10 min) to give 4-[(1S)-1-[(2,5,6-trimethylpyrimidin-4-yl)amino]ethyl]benzoic acid (140 mg, 490.64 umol, 41.97% yield) as a yellow solid. ESI [M+H]=286.1.

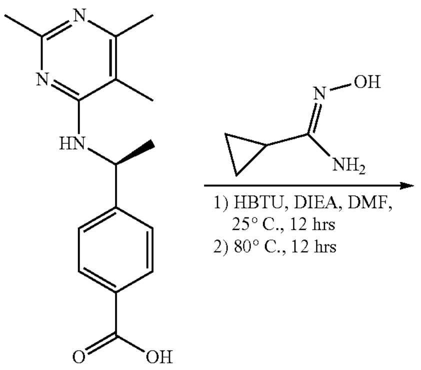

3

-continued

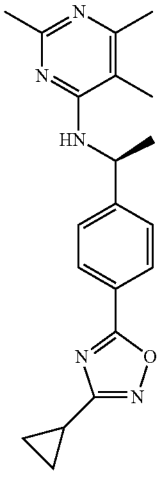

Bax-90 S

To a solution of 4-[(1S)-1-[(2,5,6-trimethylpyrimidin-4-yl)amino]ethyl]benzoic acid (60 mg, 210.28 umol, 1 eq) in DMF (3 mL) was added HBTU (95.69 mg, 252.33 umol, 1.2 eq), DIEA (81.53 mg, 630.83 umol, 109.88 uL, 3 eq) and N'-hydroxycyclopropanecarboxamidine (31.58 mg, 315.41 umol, 1.5 eq), and the mixture was stirred at 25° C. for 12 hrs. Then the mixture was stirred at 80° C. for 12 hrs. The reaction was concentrated in vacuo. The residue was purified by prep-HPLC (column: Waters Xbridge 150*25 5u; mobile phase: [water (10 mM $NH_4HCO_3$)-ACN]; B %: 15%-75%, 10 min) to give N-[(1S)-1-[4-(3-cyclopropyl-1,2,4-oxadiazol-5-yl)phenyl]ethyl]-2,5,6-trimethyl-pyrimidin-4-amine (26.93 mg, 76.32 umol, 36.30% yield, 99.031% purity) as a white solid. ESI [M+H]=350.1.

$^1$H-NMR (400 MHz, METHANOL-d4) δ 8.02 (d, J=8.3 Hz, 2H), 7.59 (d, J=8.3 Hz, 2H), 5.51 (q, J=7.0 Hz, 1H), 2.30 (d, J=7.6 Hz, 6H), 2.12-2.09 (m, 1H), 2.19-2.07 (m, 3H), 1.60 (d, J=7.1 Hz, 3H), 1.16-1.03 (m, 4H).

Example 35

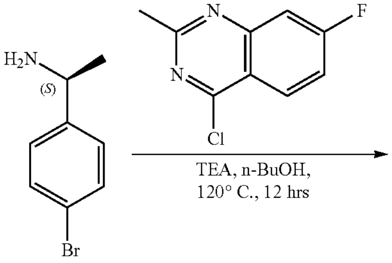

1

-continued

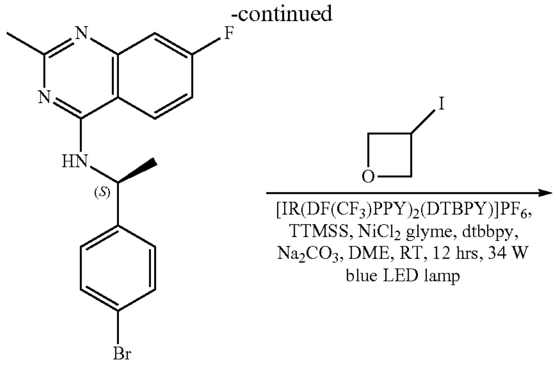

2

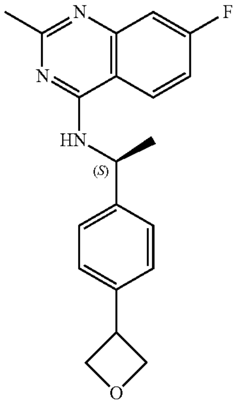

Bax-91 S

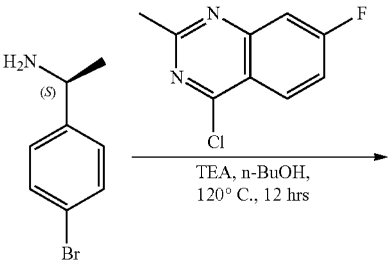

1

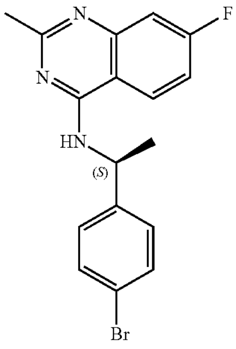

2

To a solution of (1S)-1-(4-bromophenyl)ethanamine (100 mg, 499.81 umol, 71.94 uL, 1 eq) in n-BuOH (3 mL) was added TEA (151.73 mg, 1.50 mmol, 208.70 μL, 3 eq) and 4-chloro-7-fluoro-2-methyl-quinazoline (108.09 mg, 549.79 μmol, 1.1 eq), and the mixture was stirred at 120° C. for 12 hrs. The reaction was concentrated in vacuo. The residue was purified by prep-TLC ($SiO_2$, Petroleum ether:Ethyl acetate=3:1) to give N-[(1S)-1-(4-bromophenyl)ethyl]-7-fluoro-2-methyl-quinazolin-4-amine (100 mg, 277.61 μmol, 55.54% yield) as a yellow solid. ESI [M+H]=359.9 and [M+3H]=361.9.

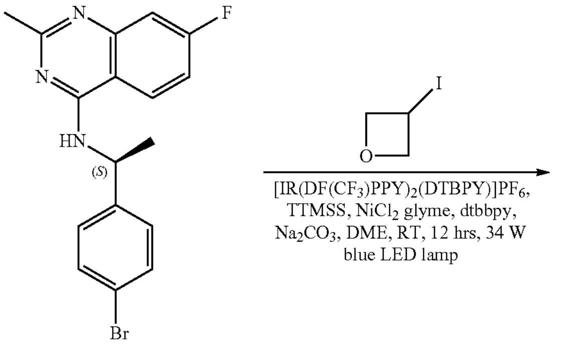

2

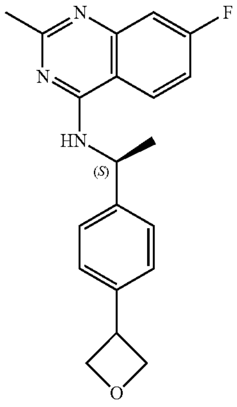

Bax-91 S

A mixture of N-[(1S)-1-(4-bromophenyl)ethyl]-7-fluoro-2-methyl-quinazolin-4-amine (100 mg, 277.61 umol, 1 eq), 3-iodooxetane (153.22 mg, 832.82 umol, 3 eq), TTMSS (69.03 mg, 277.61 umol, 85.64 uL, 1 eq), $Na_2CO_3$ (58.85 mg, 555.21 umol, 2 eq), dichloronickel; 1,2-dimethoxy-ethane (3.05 mg, 13.88 umol, 0.05 eq), 4-tert-butyl-2-(4-tert-butyl-2-pyridyl)pyridine (4.47 mg, 16.66 umol, 0.06 eq) and bis[3,5-difluoro-2-[5-(trifluoromethyl)-2-pyridyl]phenyl]iridium(1+); 4-tert-butyl-2-(4-tert-butyl-2-pyridyl)pyridine; hexafluorophosphate (9.34 mg, 8.33 umol, 0.03 eq) in DME (4 mL) was stirred and irradiated with a 34 W blue LED lamp at 15° C. for 12 hrs under N2. To the reaction mixture was add water (5 mL), extracted with EtOAc 30 mL (10 mL*3). The organic phase was dried over drying $Na_2SO_4$, and then concentrated in vacuo. The residue was purified by prep-HPLC (column: Xtimate C18 150*25 mm*5 um; mobile phase: [water (10 mM NH4HCO3)-ACN]; B %: 35%-65%, 8 min) to give 7-fluoro-2-methyl-N-[(1S)-1-[4-(oxetan-3-yl)phenyl]ethyl]quinazolin-4-amine (25.29 mg, 74.96 umol, 27.00% yield, 100% purity) as a white solid. ESI [M+H]=338.1

$^1$H-NMR (400 MHz, METHANOL-d4) δ 8.30 (dd, J=6.0, 9.9 Hz, 1H), 7.48-7.42 (m, 2H), 7.39-7.34 (m, 2H), 7.27-7.20 (m, 2H), 5.68 (d, J=7.1 Hz, 1H), 5.05 (dd, J=6.0, 8.4 Hz, 2H), 4.72 (dt, J=2.2, 6.3 Hz, 2H), 4.29-4.17 (m, 1H), 2.45 (s, 3H), 1.64 (d, J=7.3 Hz, 3H).

Example 36

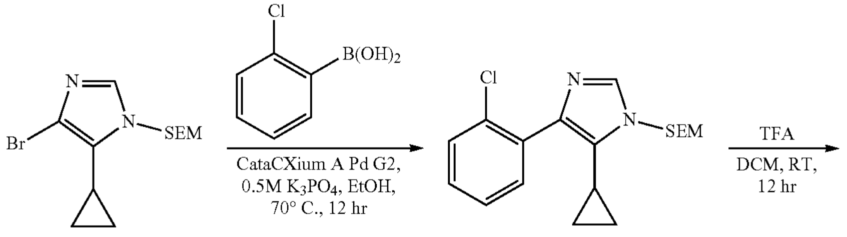

1 2

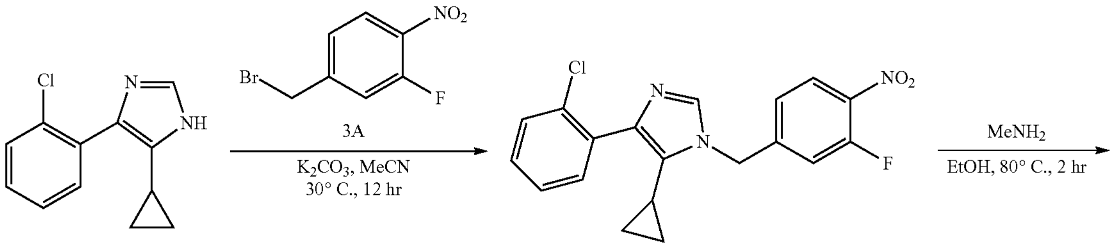

3 4

-continued

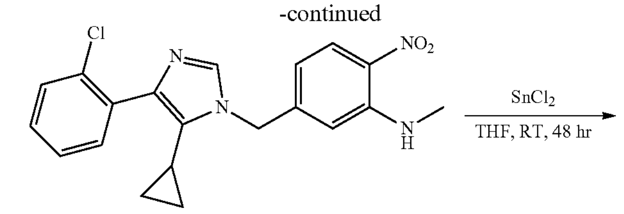

5

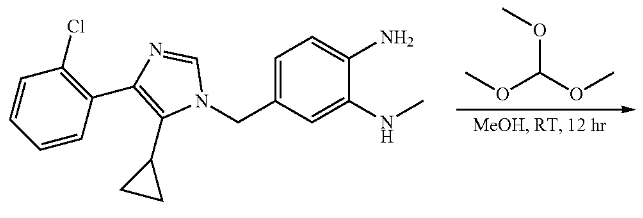

6

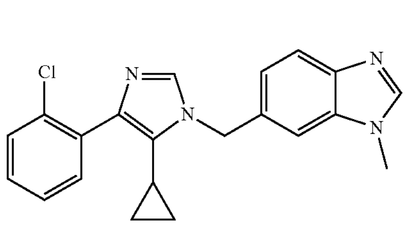

Bax-93

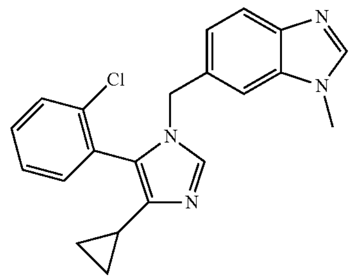

Bax-93A

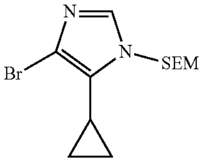

1

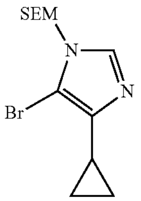

1A

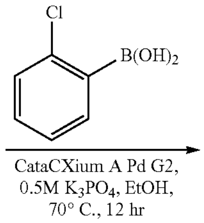

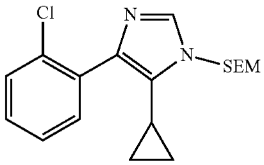

2

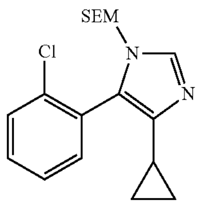

2A

A mixture of 2-[(4-bromo-5-cyclopropyl-imidazol-1-yl) methoxy]ethyl-trimethyl-silane and 2-[(5-bromo-4-cyclopropyl-imidazol-1-yl)methoxy]ethyl-trimethyl-silane (total 2 g), (2-chlorophenyl)boronic acid (1.48 g, 9.45 mmol, 1.5 eq), $K_3PO_4$ (0.5 M, 25.21 mL, 2 eq) and [2-(2-aminophenyl) phenyl]-chloro-palladium; bis(1-adamantyl)-butyl-phosphane (422 mg, 630.33 umol, 0.1 eq) in EtOH (60 mL) was stirred at 70° C. for 12 hours under N2. EtOH was removed, the mixture was added water (30 mL) and extracted with EtOAc (30 mL*3). The organic layer was washed with brine (40 mL), dried over $MgSO_4$ and concentrated in vacuo. The residue was purified by column chromatography ($SiO_2$, Petroleum ether/Ethyl acetate=1/0 to 4:1) to give 2-[[4-(2-chlorophenyl)-5-cyclopropyl-imidazol-1-yl]methoxy]ethyl-trimethyl-silane and 2-[[5-(2-chlorophenyl)-4-cyclopropyl-imidazol-1-yl]methoxy]ethyl-trimethyl-silane total 1.5 g as a yellow oil. ESI [M+H]=349.1

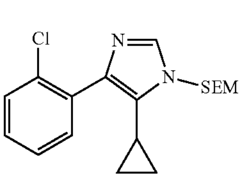

2

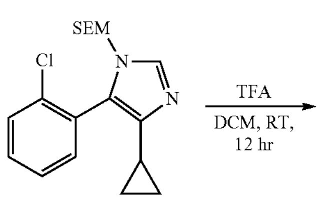

2A

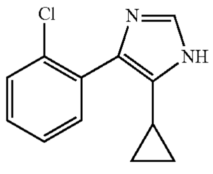

3

To a solution of 2-[[4-(2-chlorophenyl)-5-cyclopropyl-imidazol-1-yl]methoxy]ethyl-trimethyl-silane and 2-[[5-(2-chlorophenyl)-4-cyclopropyl-imidazol-1-yl]methoxy]ethyl-trimethyl-silane total 1.5 g in DCM (24 mL) was added TFA (8 mL) and the mixture was stirred at 15° C. for 12 hours. The reaction mixture was concentrated in vacuo. To the residue was added water (20 mL) and adjusted to pH=8 with sat.aq·$Na_2CO_3$, extracted with EtOAc (10 mL*3). The organic layer was dried over $MgSO_4$ and concentrated in vacuo. The residue was purified by column chromatography ($SiO_2$, Petroleum ether/THF=10/1 to 2:1) to give 4-(2-chlorophenyl)-5-cyclopropyl-1H-imidazole (0.78 g, 3.57 mmol, 82.97% yield) as a yellow solid. ESI [M+H]=219.0.

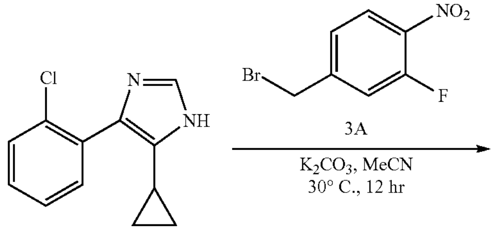

3

-continued

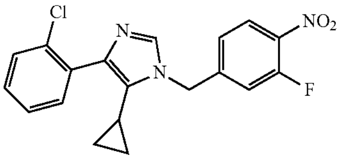

4

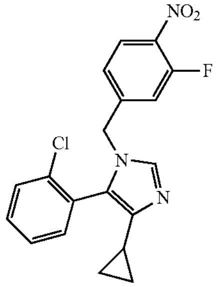

4A

To a solution of 4-(2-chlorophenyl)-5-cyclopropyl-1H-imidazole (500 mg, 2.29 mmol, 1 eq) in MeCN (10 mL) was added $K_2CO_3$ (632 mg, 4.57 mmol, 2 eq) and 4-(bromomethyl)-2-fluoro-1-nitro-benzene (535 mg, 2.29 mmol, 1 eq) and the mixture was stirred at 30° C. for 12 hours. Then the mixture was added 4-(bromomethyl)-2-fluoro-1-nitro-benzene (300 mg) and stirred at 30° C. for 12 hour. The reaction was added water (30 mL) and extracted with EtOAc (10 mL*3). The organic layer was washed with brine (30 mL), dried over $MgSO_4$ and concentrated in vacuo. The residue was purified by column chromatography ($SiO_2$, Petroleum ether/Ethyl acetate=10/1 to 1:2) to give 4-(2-chlorophenyl)-5-cyclopropyl-1-[(3-fluoro-4-nitro-phenyl)methyl]imidazole and 5-(2-chlorophenyl)-4-cyclopropyl-1-[(3-fluoro-4-nitro-phenyl)methyl]imidazole total 380 mg as a yellow oil. ESI [M+H]=372.0.

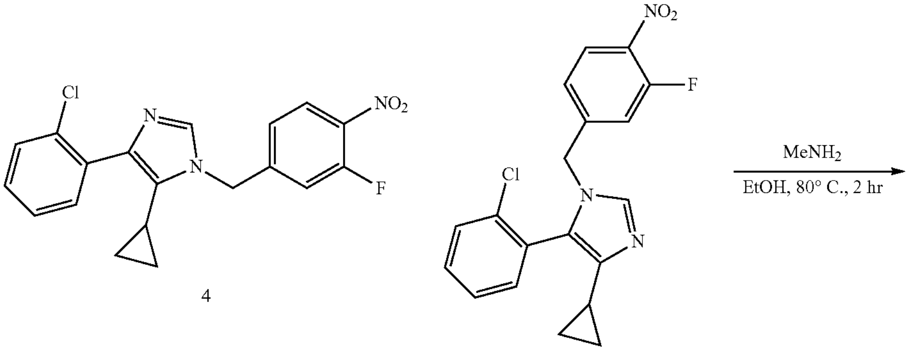

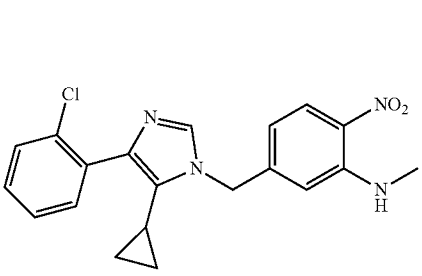

5

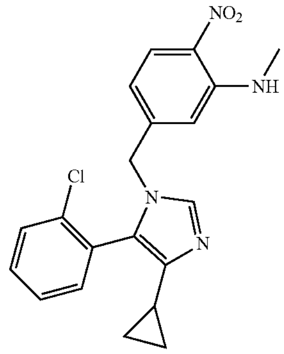

5A

A solution of 4-(2-chlorophenyl)-5-cyclopropyl-1-[(3-fluoro-4-nitro-phenyl)methyl]imidazole and 5-(2-chloro-phenyl)-4-cyclopropyl-1-[(3-fluoro-4-nitro-phenyl)methyl] imidazole total (230 mg, 618.63 umol) in EtOH (3 mL) and MeNH2 (1 mL) (33% purity in EtOH) was stirred at 80° C. for 2 hours. The reaction mixture was concentrated in vacuo to give a crude product 5-[[4-(2-chlorophenyl)-5-cyclopropyl-imidazol-1-yl]methyl]-N-methyl-2-nitro-aniline and 5-[[5-(2-chlorophenyl)-4-cyclopropyl-imidazol-1-yl] methyl]-N-methyl-2-nitro-aniline total 210 mg as a yellow solid. It was used into the next step without further purification. ESI [M+H]=383.0.

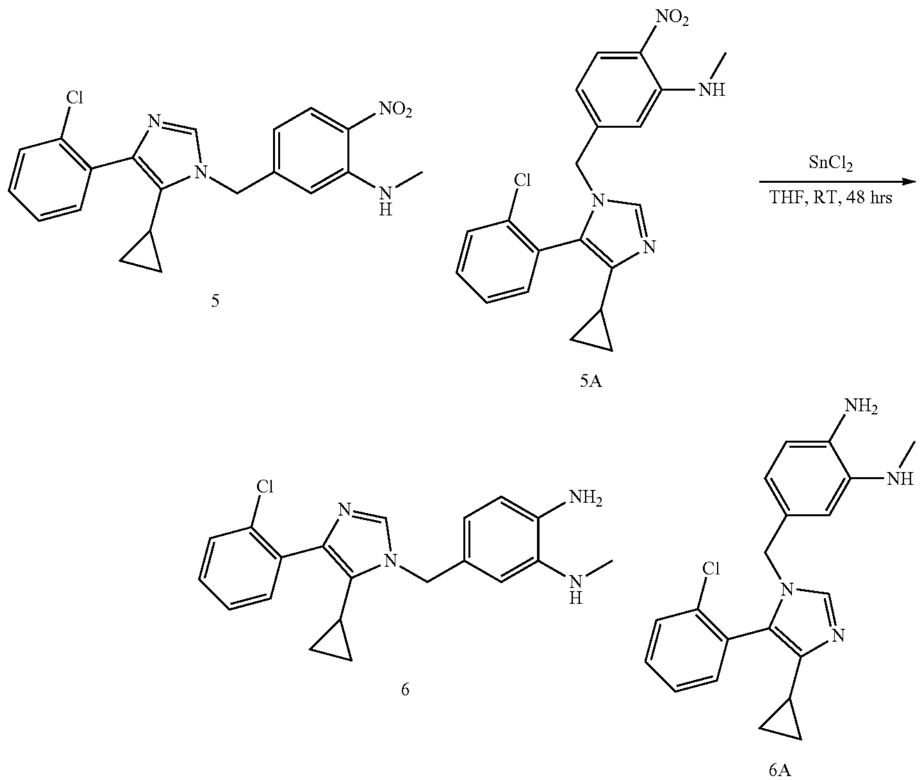

5 5A 6 6A

To a solution of 5-[[4-(2-chlorophenyl)-5-cyclopropyl-imidazol-1-yl]methyl]-N-methyl-2-nitro-aniline and 5-[[5-(2-chlorophenyl)-4-cyclopropyl-imidazol-1-yl]methyl]-N-methyl-2-nitro-aniline (total 210 mg, 548.53 umol, 1 eq) in THF (3 mL) was added $SnCl_2.2H_2O$ (372 mg, 1.65 mmol, 3 eq) and the reaction was stirred at 25° C. for 48 hours. The reaction was quenched with cold sat.aq. $NaHCO_3$ (10 mL) and filtered, the filtrate was extracted with EtOAc (5 mL*3). The organic layer was dried over $MgSO_4$ and concentrated in vacuo to give crude product 4-[[4-(2-chlorophenyl)-5-cyclopropyl-imidazol-1-yl]methyl]-N2-methyl-benzene-1,2-diamine and 4-[[5-(2-chlorophenyl)-4-cyclopropyl-imidazol-1-yl]methyl]-N2-methyl-benzene-1,2-diamine total 200 mg as a yellow oil. It was used into the next step without further purification. ESI [M+H]=353.0.

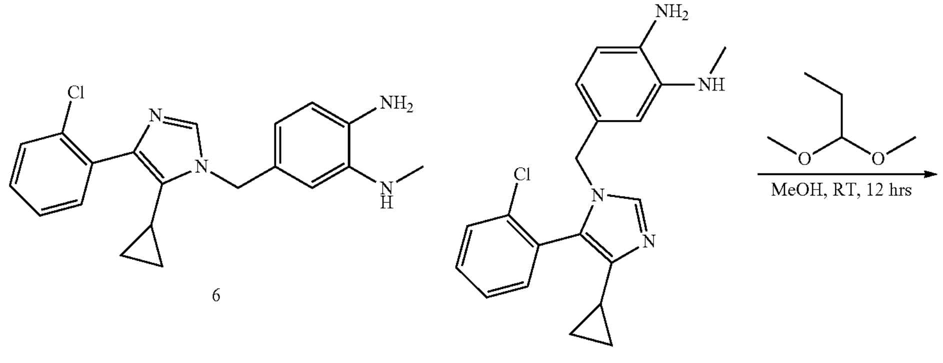

6 6A

-continued

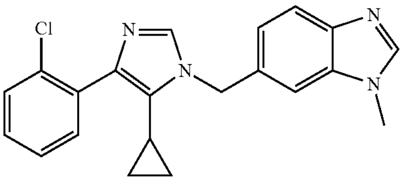

Bax-93

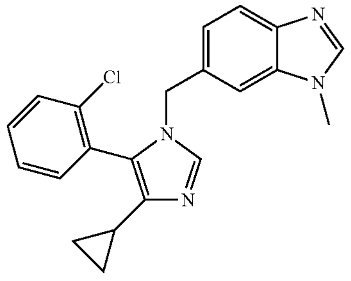

Bax-93A

To a solution of 4-[[4-(2-chlorophenyl)-5-cyclopropyl-imidazol-1-yl]methyl]-N2-methyl-benzene-1,2-diamine and 4-[[5-(2-chlorophenyl)-4-cyclopropyl-imidazol-1-yl] methyl]-N2-methyl-benzene-1,2-diamine (total 100 mg, 283.40 umol) in MeOH (2.5 mL) was added trimethoxymethane (2.42 g, 22.80 mmol, 2.5 mL, 80.47 eq), and the mixture was stirred at 25° C. for 12 hours. The reaction mixture was concentrated in vacuo. The residue was purified by prep-HPLC (column: Kromasil 150*25 mm*10 um; mobile phase: [water (0.04% NH3H2O+10 mM NH4HCO3)-ACN]; B %: 30%-50%, 20 min) to give 6-[[5-(2-chlorophenyl)-4-cyclopropyl-imidazol-1-yl]methyl]-1-methyl-benzimidazole (44.76 mg, 122.62 umol, 43.27% yield, 99.405% purity) as a white solid. Then product 2 was purified again by prep-HPLC (column: Luna C18 100*30 5u; mobile phase: [water (0.04% HCl)-ACN]; B %: 1%-30%, 10 min) to give 6-[[4-(2-chlorophenyl)-5-cyclo-propyl-imidazol-1-yl]methyl]-1-methyl-benzimidazole (4.75 mg, 11.37 umol, 4.01% yield, 95.557% purity, HCl) as a white solid.

Bax-93_HNMR: $^1$H-NMR (400 MHz, METHANOL-d4) δ 9.50 (s, 1H), 9.18 (s, 1H), 8.13 (s, 1H), 7.97 (d, J=8.6 Hz, 1H), 7.77 (br d, J=8.4 Hz, 1H), 7.67-7.61 (m, 1H), 7.60-7.47 (m, 3H), 5.85 (s, 2H), 4.20 (s, 3H), 1.77-1.67 (m, 1H), 0.88 (q, J=6.2 Hz, 2H), 0.37 (q, J=5.2 Hz, 2H).

Bax-93A_HNMR: $^1$H-NMR (400 MHz, CHLOROFORM-d) δ 7.83 (s, 1H), 7.67-7.61 (m, 1H), 7.52-7.44 (m, 2H), 7.32 (dt, J=1.8, 7.6 Hz, 1H), 7.24-7.13 (m, 2H), 6.92-6.84 (m, 2H), 5.17-4.94 (m, 2H), 3.75 (s, 3H), 1.59 (tt, J=5.0, 8.4 Hz, 1H), 0.90-0.82 (m, 2H), 0.79-0.68 (m, 2H). ESI [M+H]=363.1

Example 37

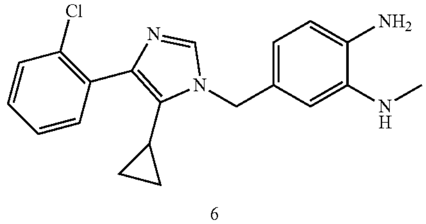

6

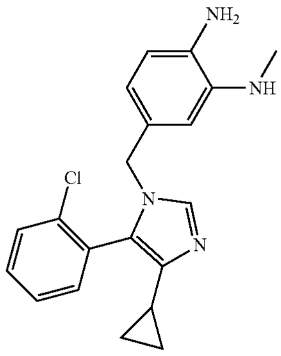

6A

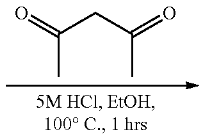

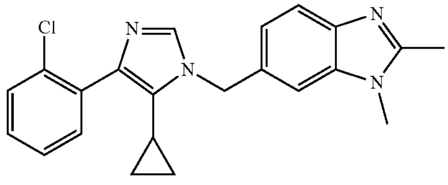

Bax-94

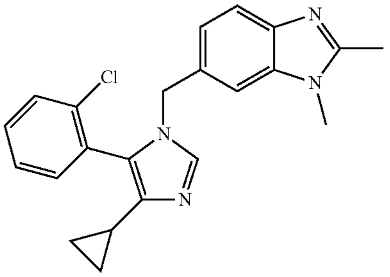

Bax-94A

A mixture of 4-[[4-(2-chlorophenyl)-5-cyclopropyl-imidazol-1-yl]methyl]-N2-methyl-benzene-1,2-diamine and 4-[[5-(2-chlorophenyl)-4-cyclopropyl-imidazol-1-yl] methyl]-N2-methyl-benzene-1,2-diamine (total 90 mg, 255.06 umol) in EtOH (3 mL) and 5M HCl (0.5 mL) was heated to 100° C. and pentane-2,4-dione (51 mg, 510.12 umol, 52.38 uL, 2 eq) was added. Then the mixture was stirred at 100° C. for 1 hour. The reaction mixture was adjusted to pH=8 with sat.aq.$NaHCO_3$, added water (10 mL) and extracted with EtOAc (5 mL*3). The organic layer was dried over $MgSO_4$ and concentrated in vacuo. The residue was purified by prep-HPLC (column: Kromasil 150*25 mm*10 μm; mobile phase: [water (0.04% $NH_3H_2O$+10 mM NH4HCO3)-ACN]; B %: 30%-50%, 20 min) to give 6-[[5-(2-chlorophenyl)-4-cyclopropyl-imidazol-1-yl]methyl]-1,2-dimethyl-benzimidazole (36.85 mg, 95.04 umol, 37.26% yield, 97.201% purity) as a white solid. Then product 2 was purified again by prep-HPLC (column: Luna C18 100*30 5u; mobile phase: [water (0.04% HCl)-ACN]; B %: 1%-30%, 10 min) to give 6-[[4-(2-chlorophenyl)-5-cyclopropyl-imidazol-1-yl]methyl]-1,2-dimethyl-benzimidazole (3.33 mg, 7.50 umol, 2.94% yield, 93.037% purity, HCl) as a white solid.

Bax-94_HNMR: 1H-NMR (400 MHz, METHANOL-d4) δ 9.17 (br s, 1H), 8.05 (s, 1H), 7.85 (br d, J=8.4 Hz, 1H), 7.69 (br d, J=8.3 Hz, 1H), 7.65-7.61 (m, 1H), 7.60-7.47 (m, 3H), 5.82 (s, 2H), 4.04 (s, 3H), 2.90 (s, 3H), 1.71 (br s, 1H), 0.87 (br d, J=7.0 Hz, 2H), 0.36 (br d, J=4.6 Hz, 2H)

Bax-94A_HNMR: $^1$H-NMR (400 MHz, CHLOROFORM-d) δ 7.53-7.45 (m, 3H), 7.32 (dt, J=1.8, 7.6 Hz, 1H), 7.25-7.14 (m, 2H), 6.85-6.77 (m, 2H), 5.14-4.91 (m, 2H), 3.63 (s, 3H), 2.58 (s, 3H), 1.59 (tt, J=5.0, 8.4 Hz, 1H), 0.89-0.82 (m, 2H), 0.78-0.68 (m, 1H1), 0.78-0.68 (m, 1H1). ESI [M+H]=377.1

Example 38

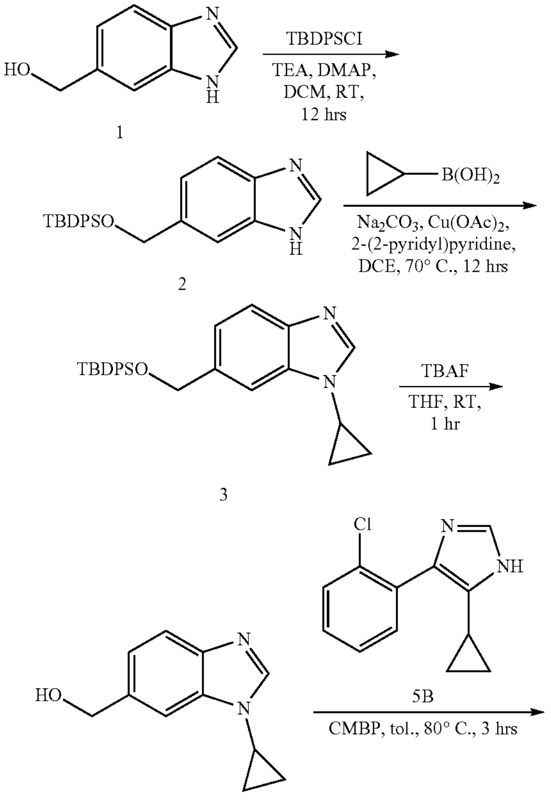

1
2
3
4
5B

-continued

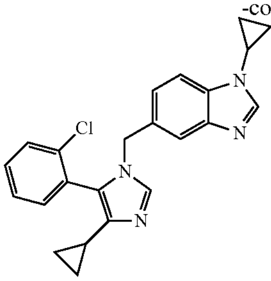
Bax-95 C

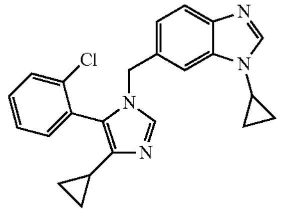
Bax-95 B

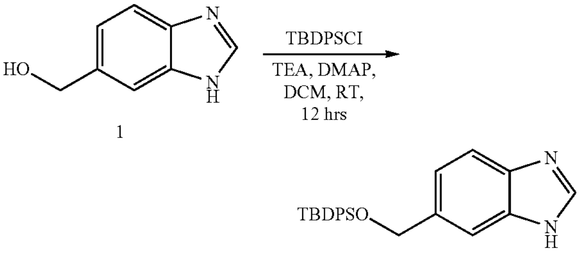

1
2

To a solution of 3H-benzimidazol-5-ylmethanol (400 mg, 2.70 mmol, 1 eq) in DCM (12 mL) was added TEA (546.38 mg, 5.40 mmol, 751.55 uL, 2 eq), TBDPSCl (890.46 mg, 3.24 mmol, 832.21 uL, 1.2 eq) and DMAP (32.98 mg, 269.98 umol, 0.1 eq). The mixture was stirred at 30° C. for 12 hr. To the reaction mixture was added water (15 mL) and extracted with DCM (20 mL*3). The organic layer was dried over $MgSO_4$ and concentrated in vacuo. The residue was purified by column chromatography ($SiO_2$, Petroleum ether/Ethyl acetate=10/1 to 0/1) to give 3H-benzimidazol-5-ylmethoxy-tert-butyl-diphenyl-silane (910 mg, 2.35 mmol, 87.20% yield) as a colorless oil. ESI [M+H]=387.1.

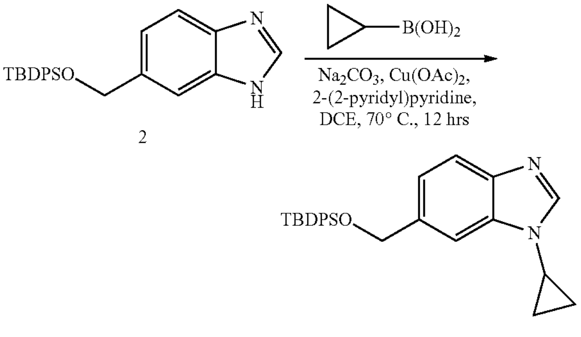

2
3

A mixture of 3H-benzimidazol-5-ylmethoxy-tert-butyl-diphenyl-silane (910 mg, 2.35 mmol, 1 eq), cyclopropylboronic acid (404.42 mg, 4.71 mmol, 2 eq), $Cu(OAc)_2$ (427.57 mg, 2.35 mmol, 1 eq), 2-(2-pyridyl)pyridine (367.66 mg, 2.35 mmol, 1 eq) and $Na_2CO_3$ (748.53 mg, 7.06 mmol, 3 eq) in DCE (30 mL) was stirred at 70° C. for 12 hrs under 02 atmosphere (15 psi). To the reaction mixture was added water (30 mL) and extracted with DCM (40 mL*4). The organic layer was dried over $MgSO_4$ and concentrated in vacuo. The residue was purified by column chromatography ($SiO_2$, Petroleum ether/Ethyl acetate=20/1 to 0/1) to give tert-butyl-[(3-cyclopropylbenzimidazol-5-yl)methoxy]-diphenyl-silane and tert-butyl-[(1-cyclopropylbenzimidazol-5-yl)methoxy]-diphenyl-silane total 697 mg as a yellow oil. ESI [M+H]=427.2.

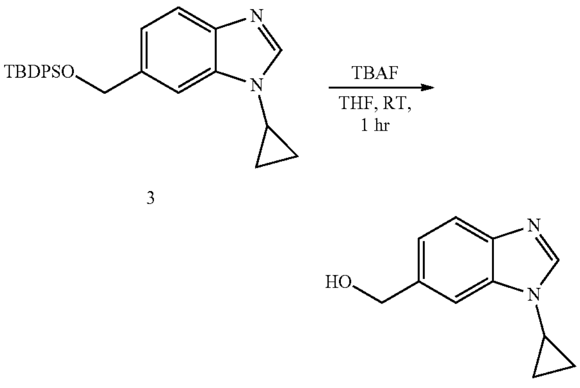

3

4

To a solution of tert-butyl-[(3-cyclopropylbenzimidazol-5-yl)methoxy]-diphenyl-silane and tert-butyl-[(1-cyclopropylbenzimidazol-5-yl)methoxy]-diphenyl-silane total 697 mg in THF (10 mL) was added TBAF (1 M, 3.13 mL, 2 eq) (in THF). The mixture was stirred at 30° C. for 1 hr. The reaction mixture was concentrated in vacuo. The residue was purified by column chromatography ($SiO_2$, Petroleum ether: Ethyl acetate=10/1 to 0/1) to give (3-cyclopropylbenzimidazol-5-yl)methanol and (1-cyclopropylbenzimidazol-5-yl) methanol total 290 mg as a white solid. ESI [M+H]=189.1.

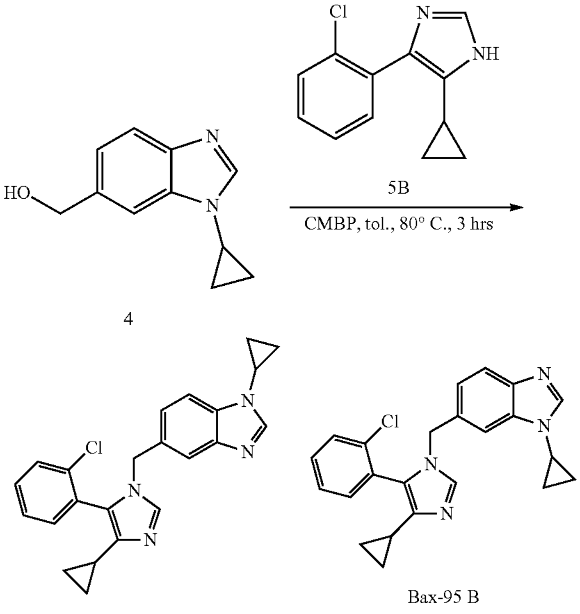

4

5B

Bax-95 C

Bax-95 B

To a solution of (3-cyclopropylbenzimidazol-5-yl)methanol and (1-cyclopropylbenzimidazol-5-yl)methanol total 51.64 mg in Tol. (2 mL) was added (1-cyclopropylbenzimidazol-5-yl)methanol (50 mg, 228.64 umol, 1 eq) and 2-(tributyl-phosphanylidene)acetonitrile (110.37 mg, 457.28 umol, 2 eq). The mixture was stirred at 80° C. for 3 hrs under N2. To the reaction mixture was added water (20 mL) and extracted with EtOAc (15 mL*3). The organic layer was dried over $MgSO_4$ and concentrated in vacuo. The residue was purified by prep-HPLC (column: Waters Xbridge BEH C18 100*25 mm*5 um; mobile phase: [water (10 mM $NH_4HCO_3$)-ACN]; B %: 35%-55%, 10 min) to give 5-[[5-(2-chlorophenyl)-4-cyclopropyl-imidazol-1-yl]methyl]-1-cyclopropyl-benzimidazole (14.8 mg, 35.12 umol, 15.36% yield, 92.274% purity) as a white solid.

Bax-95 C_HNMR: 1H-NMR (400 MHz, CHLOROFORM-d) δ 7.83 (s, 1H), 7.44-7.34 (m, 3H), 7.30-7.23 (m, 2H), 7.17 (d, J=4.2 Hz, 2H), 6.88 (dd, J=1.3, 8.3 Hz, 1H), 5.03-4.96 (m, 1H), 4.87-4.79 (m, 1H), 3.28 (qd, J=3.5, 7.1 Hz, 1H), 1.55-1.46 (m, 1H), 1.11-1.04 (m, 2H), 0.99-0.90 (m, 2H), 0.80-0.73 (m, 2H), 0.68-0.62 (m, 2H). ESI [M+H] =389.2.

The product of ET22082-326-P2 was re-purified by prep-HPLC (column: Phenomenex Luna C18 150*30 mm*5 um; mobile phase: [water (0.04% HCl)-ACN]; B %: 5%-35%, 10 min) to give 6-[[5-(2-chlorophenyl)-4-cyclopropyl-imidazol-1-yl]methyl]-1-cyclopropyl-benzimidazole (9.03 mg, 15.48 umol, 6.77% yield, 72.911% purity, HCl) as a white solid.

Bax-95 B_HNMR: 1H-NMR (400 MHz, CHLOROFORM-d) δ 10.24 (br s, 1H), 9.84 (br s, 1H), 7.92 (br s, 1H), 7.71 (br d, J=7.8 Hz, 1H), 7.53-7.41 (m, 2H), 7.34 (br s, 1H), 7.16 (br d, J=4.4 Hz, 1H), 6.92 (br d, J=7.8 Hz, 1H), 5.64-5.31 (m, 2H), 3.63 (br s, 1H), 1.64-1.53 (m, 1H), 1.31 (br s, 4H), 1.03 (br d, J=4.5 Hz, 2H), 0.89 (br d, J=8.1 Hz, 2H). ESI [M+H]=389.1.

Example 39

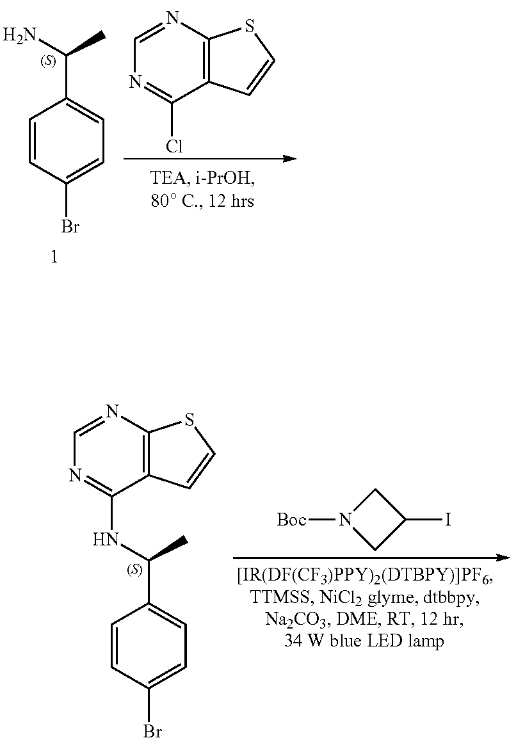

1

2

-continued

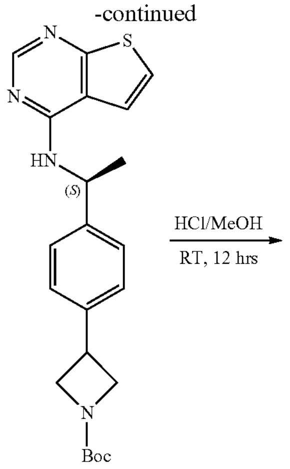

3

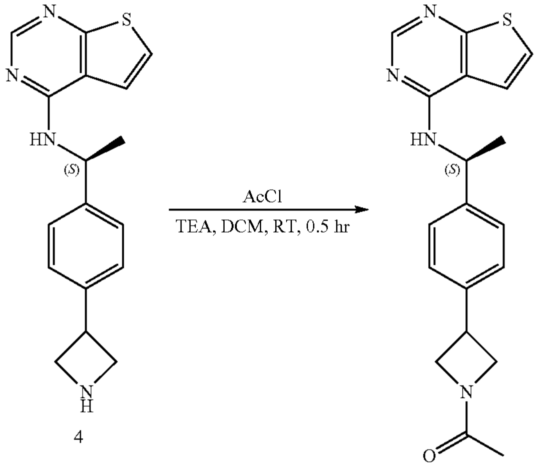

4

Bax-97 S

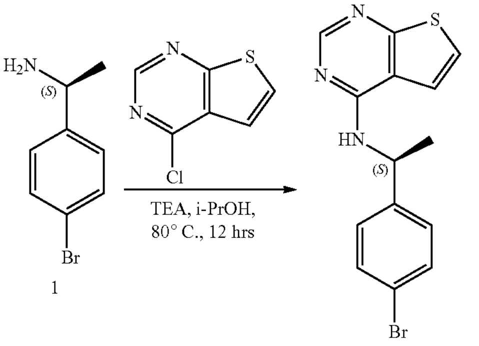

1

2

To a solution of (1S)-1-(4-bromophenyl)ethanamine (500 mg, 2.50 mmol, 359.71 μL, 1 eq) in i-PrOH (15 mL) was added TEA (506 mg, 5.00 mmol, 695.68 μL, 2 eq) and 4-chlorothieno[2,3-d]pyrimidine (512 mg, 3.00 mmol, 1.2 eq). The mixture was stirred at 80° C. for 12 hours. The reaction was concentrated in vacuo. The residue was purified by column chouromatography ($SiO_2$, Petroleum ether/Ethyl acetate=0/1 to 3:1) to give N-[(1S)-1-(4-bromophenyl)ethyl]thieno[2,3-d]pyrimidin-4-amine (700 mg, 2.09 mmol, 83.81% yield) as a yellow solid. ESI [M+H]=335.9.

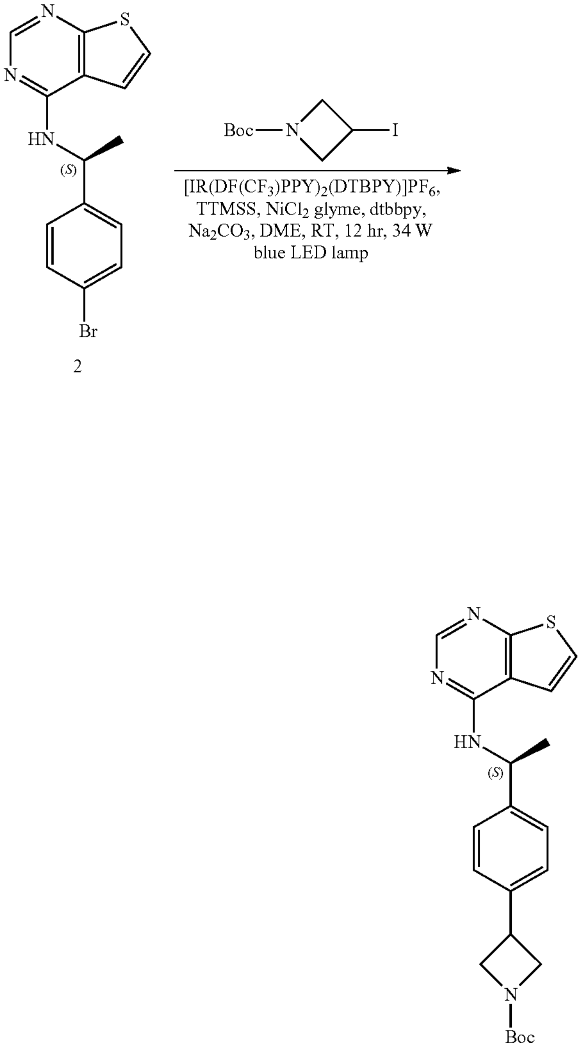

2

3

A mixture of N-[(1S)-1-(4-bromophenyl)ethyl]thieno[2,3-d]pyrimidin-4-amine (660 mg, 1.97 mmol, 1 eq), tert-butyl 3-iodoazetidine-1-carboxylate (1.68 g, 5.92 mmol, 3 eq), TTMSS (491 mg, 1.97 mmol, 609.21 μL, 1 eq), $Na_2CO_3$ (419 mg, 3.95 mmol, 2 eq), dichloronickel; 1,2-dimethoxyethane (22 mg, 98.73 umol, 0.05 eq), 4-tert-butyl-2-(4-tert-butyl-2-pyridyl)pyridine (32 mg, 118.48 umol, 0.06 eq) and bis[3,5-difluoro-2-[5-(trifluoromethyl)-2-pyridyl]phenyl]iridium(1+); 4-tert-butyl-2-(4-tert-butyl-2-pyridyl)pyridine; hexafluorophosphate (66 mg, 59.24 umol, 0.03 eq) in DME (16 mL) was stirred and irradiated with a 34 W blue LED lamp at 15° C. for 12 hours under N2. The reaction was added water (10 mL) and extracted with EtOAc (10 mL*3). The organic phase was dried over drying $Na_2SO_4$, and then concentrated in vacuo. The residue was purified by prep- TLC ($SiO_2$, Petroleum ether:Ethyl acetate=1:1), to give a tert-butyl 3-[4-[(1S)-1-(thieno[2,3-d]pyrimidin-4-ylamino) ethyl]phenyl]azetidine-1-carboxylate (360 mg, 876.91 umol, 44.41% yield) as a yellow oil. ESI [M+H]=411.1.

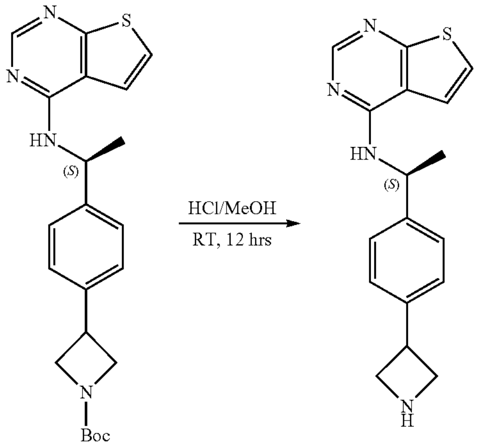

3

4

To a solution of tert-butyl 3-[4-[(1S)-1-(thieno[2,3-d] pyrimidin-4-ylamino)ethyl]phenyl]azetidine-1-carboxylate (350 mg, 852.55 umol, 1 eq) in MeOH (4 mL) was added HCl/MeOH (4M, 4 mL). The mixture was stirred at 15° C. for 12 hours. The reaction mixture was concentrated in vacuo to give N-[(1S)-1-[4-(azetidin-3-yl)phenyl]ethyl] thieno[2,3-d]pyrimidin-4-amine (190 mg, 547.74 umol, 64.25% yield, HCl) as a yellow solid. ESI [M+H]=311.0.

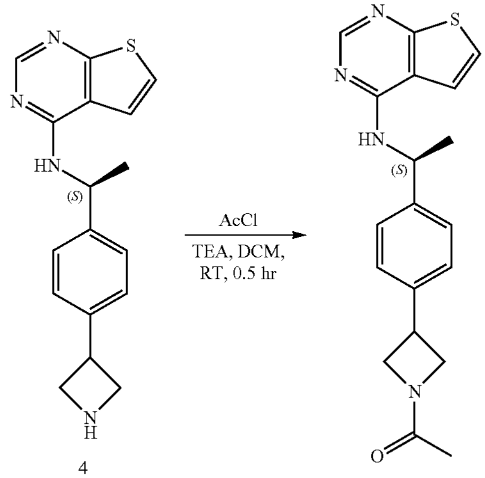

4

Bax-97 S

To a solution of N-[(1S)-1-[4-(azetidin-3-yl)phenyl]ethyl] thieno[2,3-d]pyrimidin-4-amine (50 mg, 144.14 umol, 1 eq, HCl) in DCM (2 mL) was added TEA (44 mg, 432.43 μmol, 60.19 μL, 3 eq) and acetyl chloride (9 mg, 115.31 μmol, 8.23 μL, 0.8 eq) and the mixture was stirred at 15° C. for 30 mins. The reaction was quenched with water (5 mL) and extracted with DCM (5 mL*3). The organic layer was dried over $MgSO_4$ and concentrated in vacuo. The residue was purified by prep-HPLC (column: Waters Xbridge 150*25 5u; mobile phase: [water (10 mM $NH_4HCO_3$)-ACN]; B %: 15%-45%, 10 min) to give 1-[3-[4-[(1S)-1-(thieno[2,3-d]pyrimidin-4-ylamino)ethyl]phenyl]azetidin-1-yl]ethanone (18.33 mg, 52.01 umol, 36.08% yield, 100% purity) as a white solid. $^1$H-NMR (400 MHz, CHLOROFORM-d) δ 8.50 (s, 1H), 7.44 (d, J=7.5 Hz, 2H), 7.34-7.28 (m, 3H), 7.17 (dd, J=1.1, 6.1 Hz, 1H), 5.59 (quin, J=7.0 Hz, 1H), 5.37 (br d, J=7.3 Hz, 1H), 4.52 (t, J=8.6 Hz, 1H), 4.41 (t, J=9.4 Hz, 1H), 4.16-4.03 (m, 2H), 3.85-3.75 (m, 1H), 1.92 (d, J=2.6 Hz, 3H), 1.68 (d, J=6.8 Hz, 3H). ESI [M+H]=353.1.

Example 40

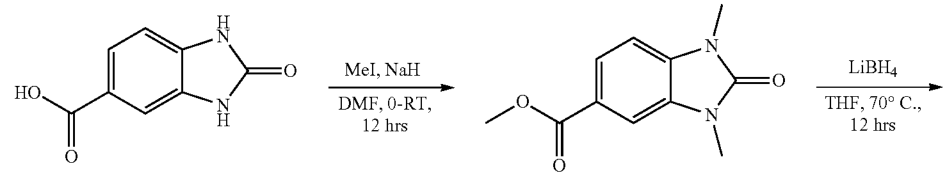

1A
5 g

2A

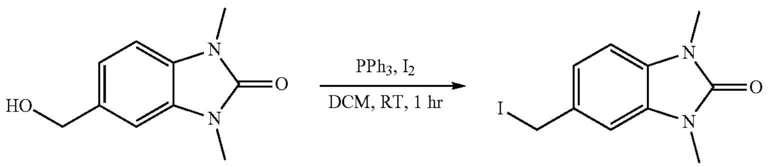

3A

4A

-continued
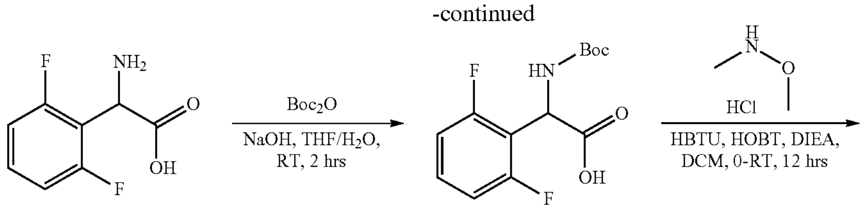
1 2
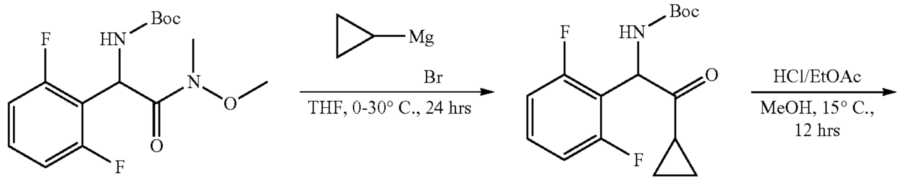
3 4
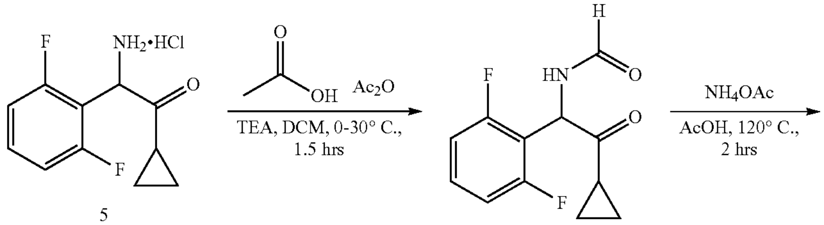
5 6
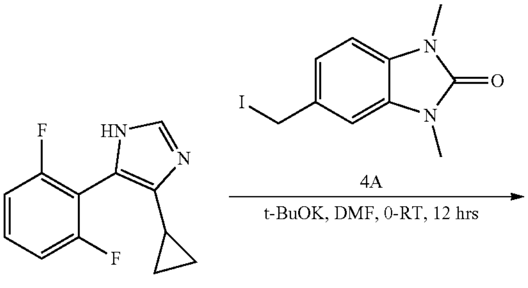
7
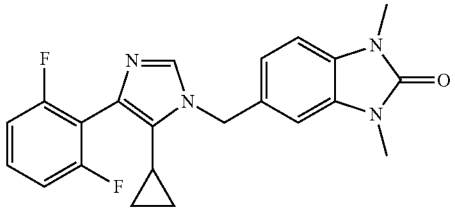
Bax-100
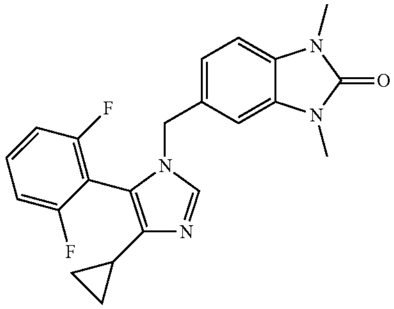
Bax-100A
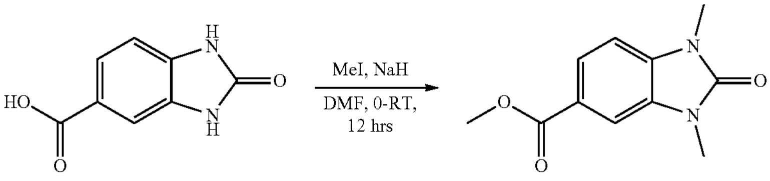
1A 2A
To a solution of 2-oxo-1,3-dihydrobenzimidazole-5-carboxylic acid (5 g, 28.07 mmol, 1 eq) in DMF (120 mL) was added NaH (3.93 g, 98.23 mmol, 60% purity, 3.5 eq) at 0° C. After 30 mins, MeI (13.94 g, 98.23 mmol, 6.12 mL, 3.5 eq) was added at 0° C. Then the mixture was stirred at 25° C. for 16 hrs. The reaction was quenched with sat.aq.$NH_4Cl$ (500 mL) and extracted with EtOAc (200 mL*3). The organic layer was washed with brine (500 mL*2), dried over $MgSO_4$ and concentrated in vacuo. The residue was triturated with PE/MTBE (50 mL/5 mL), and solid precipitate was collected via filtration, dried in vacuo to give methyl 1,3-dimethyl-2-oxo-benzimidazole-5-carboxylate (5.5 g, 24.97 mmol, 88.98% yield) as a brown solid. ESI [M+H]=221.1.

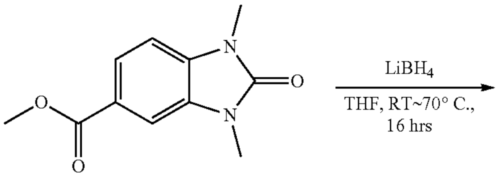

2A

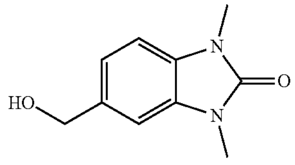

3A

To a solution of methyl 1,3-dimethyl-2-oxo-benzimidazole-5-carboxylate (5.5 g, 24.97 mmol, 1 eq) in THF (100 mL) was added $LiBH_4$ (1.09 g, 49.95 mmol, 2 eq) at 20° C. Then the mixture was stirred at 70° C. for 16 hrs. The reaction was quenched with cold sat.aq. $NH_4Cl$ (200 mL), extracted with EtOAc (100 mL*3). The organic layer was washed with brine (200 mL), dried over $MgSO_4$ and concentrated in vacuo. The residue was triturated with EtOAc/MTBE (1:1, 50 mL) to give 5-(hydroxymethyl)-1,3-dimethyl-benzimidazol-2-one (4.5 g, 23.41 mmol, 93.74% yield) as a light red solid. ESI [M+H]=193.1.

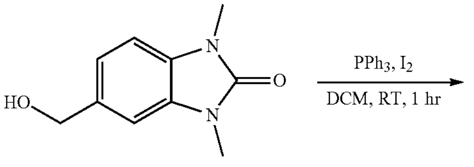

3A

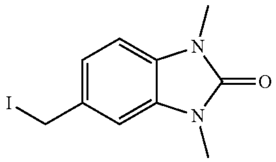

4A

To a solution of $PPh_3$ (702.74 mg, 2.68 mmol, 1.03 eq) in DCM (6 mL) was added $I_2$ (680.03 mg, 2.68 mmol, 539.71 uL, 1.03 eq) at 20° C. under N2. After 5 mins, 5-(hydroxymethyl)-1,3-dimethyl-benzimidazol-2-one (0.5 g, 2.60 mmol, 1 eq) in DCM (2 mL) was added and the mixture was stirred at 20° C. for 1 hr. The mixture was purified by column chromatography (Petroleum ether:Ethyl acetate=10:1 to 2:1) to give 5-(iodomethyl)-1,3-dimethyl-benzimidazol-2-one (670 mg, 2.22 mmol, 85.26% yield) as a yellow solid. ESI [M+H]=382.1.

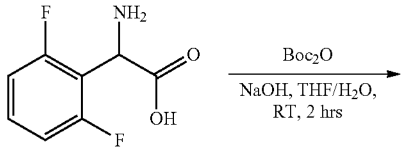

1

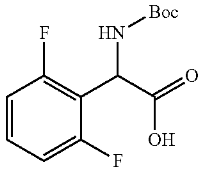

2

To a solution of 2-amino-2-(2,6-difluorophenyl)acetic acid (900 mg, 4.81 mmol, 1 eq) in THF (16 mL) was added NaOH (577.06 mg, 14.43 mmol, 3 eq) in $H_2O$ (16 mL) and then was added dropwise tert-butoxycarbonyl tert-butyl carbonate (2.10 g, 9.62 mmol, 2.21 mL, 2 eq) at 0° C. over 10 mins. The mixture was stirred at 15° C. for 2 hrs. The reaction mixture was concentrated under reduced pressure to remove THF, and extracted with MTBE 60 mL (20 mL*3). The aqueous phase was adjusted to pH=3 with 1N aq.HCl (cooled water) and extracted with EtOAc 60 mL (20*3). The combined organic layers were dried over $Na_2SO_4$, filtered and concentrated under reduced pressure to give 2-(tert-butoxycarbonylamino)-2-(2,6-difluorophenyl)acetic acid (1.03 g, 3.59 mmol, 74.56% yield) as a white solid and it was used into the next step without further purification. ESI [M−56+H]=232.1 and [M−100+H]=188.1.

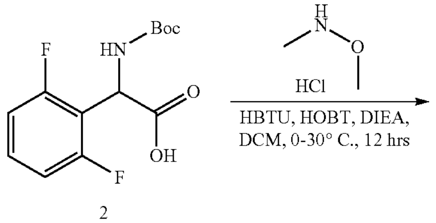

2

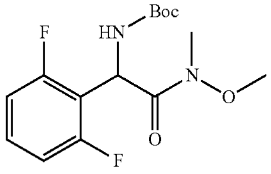

3

A mixture of 2-(tert-butoxycarbonylamino)-2-(2,6-difluorophenyl)acetic acid (1.03 g, 3.59 mmol, 1 eq), HBTU (1.36 g, 3.59 mmol, 1 eq), HOBt (484.49 mg, 3.59 mmol, 1 eq) and DIEA (463.41 mg, 3.59 mmol, 624.54 uL, 1 eq) in DCM (30 mL) was cooled to 0° C. A mixture of N,O-dimethylhydroxylamine hydrochloride (384.73 mg, 3.94 mmol, 1.1 eq) and DIEA (509.75 mg, 3.94 mmol, 686.99 μL, 1.1 eq) in DCM (10 mL) was added slowly degassed and purged with N2 for 3 times, and then the mixture was stirred at 30° C. for 12 hrs under $N_2$ atmosphere. To the reaction mixture was add $H_2O$ (30 mL), extracted with DCM 80 mL (20 mL*4). The combined organic layers were dried over $Na_2SO_4$, filtered and concentrated under reduced pressure to give a residue.

The residue was purified by column chromatography (SiO2, Petroleum ether/Ethyl acetate=20/1 to 2:1) to give tert-butyl N-[1-(2,6-difluorophenyl)-2-[methoxy(methyl)amino]-2-oxo-ethyl]carbamate (1.1 g, 3.33 mmol, 92.87% yield) as a white solid. ESI [M+H]=331.2.

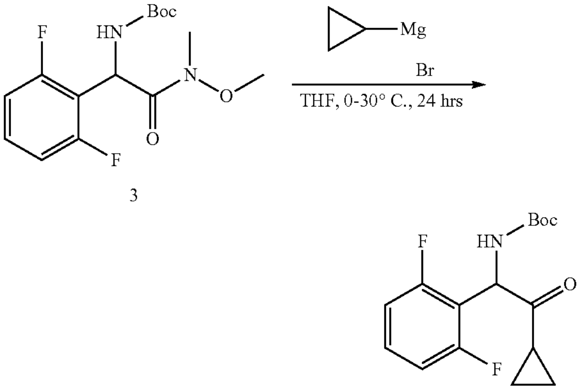

3

4

To a solution of tert-butyl N-[1-(2,6-difluorophenyl)-2-[methoxy(methyl)amino]-2-oxo-ethyl]carbamate (1.1 g, 3.33 mmol, 1 eq) in THF (30 mL) was added dropwise bromo(cyclopropyl)magnesium (1 M, 26.64 mL, 8 eq) at 0° C., it was degassed and purged with N2 for 3 times, and then the mixture was stirred at 30° C. for 24 hrs under N2 atmosphere. The reaction mixture was quenched by addition cold sat.aq.$NH_4Cl$ (100 mL) and $H_2O$ (50 mL), extracted with EtOAc 280 mL (70 mL*4). The combined organic layers were dried over $MgSO_4$, filtered and concentrated under reduced pressure to give a residue. The residue was purified by column chromatography ($SiO_2$, Petroleum ether: Ethyl acetate=20:1 to 3:1) to give the crude product and the crude product was purified by prep-HPLC (column: Waters Xbridge 150*25 5u; mobile phase: [water (10 mM $NH_4HCO_3$)-ACN]; B %: 45%-65%, 7 min) to give tert-butyl N-[2-cyclopropyl-1-(2,6-difluorophenyl)-2-oxo-ethyl]-arbamate (400 mg, 1.28 mmol, 38.58% yield) as a white solid. ESI [M+H]=212.0.

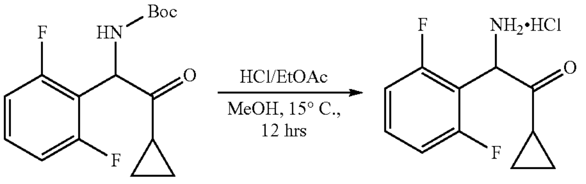

4

5

To a solution of tert-butyl N-[2-cyclopropyl-1-(2,6-difluorophenyl)-2-oxo-ethyl]carbamate (200 mg, 642.42 μmol, 1 eq) in MeOH (2 mL) was added HCl/EtOAc (4 M, 2.41 mL, 15 eq). The mixture was stirred at 15° C. for 12 hrs. The reaction was concentrated in vacuo to give the crude product 2-amino-1-cyclopropyl-2-(2,6-difluorophenyl)ethanone (135 mg, crude, HCl) as a yellow oil, it was used into the next step without further purification. ESI [M+H]=212.1.

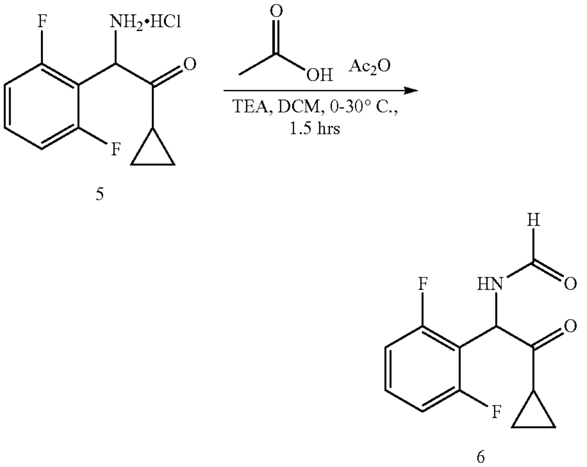

5

6

A mixture of acetyl acetate (111.29 mg, 1.09 mmol, 102.10 uL, 2 eq), formic acid (100.35 mg, 2.18 mmol, 82.25 μL, 4 eq) was stirred at 15° C. for 30 mins, and then it was added to a solution of 2-amino-1-cyclopropyl-2-(2,6-difluorophenyl)ethanone (135 mg, 545.08 μmol, 1 eq, HCl) and TEA (551.57 mg, 5.45 mmol, 758.69 uL, 10 eq) in DCM (3 mL) at 0° C., then the mixture was stirred at 30° C. for 1 hr. To the reaction mixture was add water (10 mL), extracted with DCM (20 mL*4). The organic phase was dried over drying $Na_2SO_4$, and then concentrated in vacuo to give N-[2-cyclopropyl-1-(2,6-difluorophenyl)-2-oxo-ethyl]formamide (120 mg, crude) as a yellow oil. It was used into the next step without further purification. ESI [M+H]=240.0.

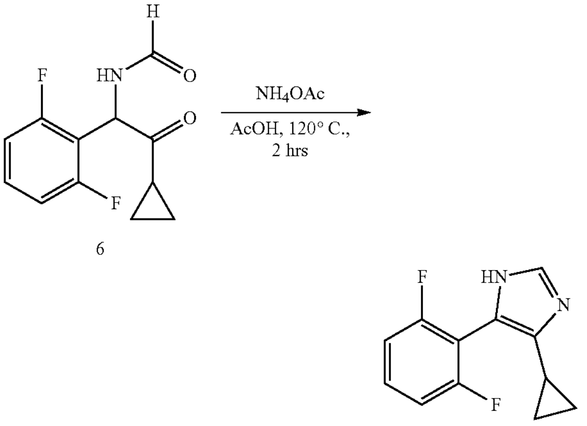

6

7

To a solution of N-[2-cyclopropyl-1-(2,6-difluorophenyl)-2-oxo-ethyl]formamide (120 mg, 501.64 umol, 1 eq) in AcOH (2 mL) was added acetic acid; ammonia (1.16 g, 15.05 mmol, 30 eq). The mixture was stirred at 120° C. for 2 hrs. To the reaction mixture was add $H_2O$ (5 mL)(cold), diluted with sat.aq $Na_2CO_3$ at 0° C. and adjusted pH to 8, and then extracted with EtAOc 80 mL (20 mL*4). The combined organic layers were dried over $Na_2SO_4$, filtered and concentrated under reduced pressure to give a residue. The residue was purified by prep-TLC (SiO2, Ethyl acetate: Methanol=30:1) to give the crude product 4-cyclopropyl-5-(2,6-difluorophenyl)-1H-imidazole (55 mg, 249.75 umol, 49.79% yield) as a brown solid. It was used into the next step without further purification. ESI [M+H]=221.2.

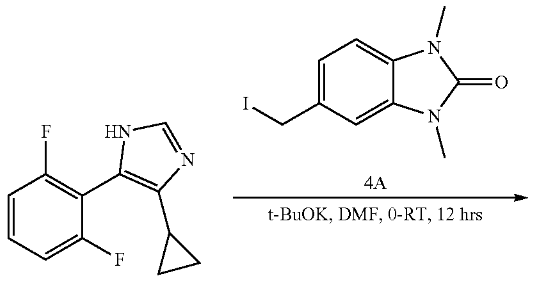

7

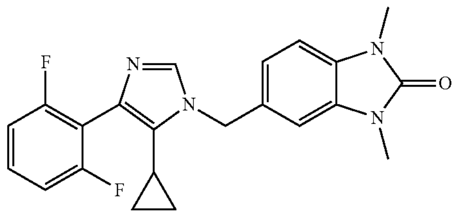

Bax-100

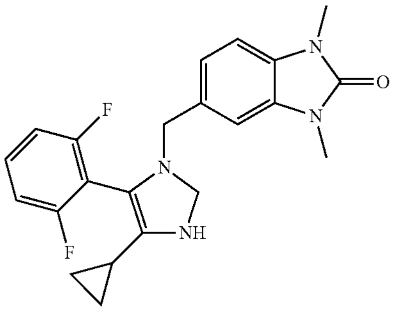

Bax-100A

To a solution of t-BuOK (1 M, 681.14 uL, 1.5 eq) in DMF (1 mL) under $N_2$ was added dropwise 4-cyclopropyl-5-(2,6-difluorophenyl)-1H-imidazole (100 mg, 454.10 umol, 1 eq) in DMF (1 mL) at 0° C. under N2. After 15 mins, 5-(iodomethyl)-1,3-dimethyl-benzimidazol-2-one (178.34 mg, 590.33 umol, 1.3 eq) in DMF (1 mL) was added at 0° C. under $N_2$. The mixture was stirred at 25° C. for 12 hrs. To the reaction mixture was add water (15 mL), extracted with EtOAc 200 mL (40 mL*5). The organic phase was dried over drying $Na_2SO_4$, and then concentrated in vacuo. The residue was purified by prep-HPLC (column: Luna C18 100*30 5u; mobile phase: [water (0.05% HCl)-ACN]; B %: 1%-40%, 12 min) to give desired compound as a white solid, which was further separated by SFC (column: DAICEL CHIRALPAK AD (250 mm*50 mm, 10 μm); mobile phase: [0.1% $NH_3H_2O$ ETOH]; B %: 35%-35%, 10 min) to give 5-[[5-cyclopropyl-4-(2,6-difluorophenyl)imidazol-1-yl]methyl]-1,3-dimethyl-benzimidazol-2-one (14.01 mg, 35.17 umol, 7.75% yield, 99.019% purity) and 5-[[4-cyclopropyl-5-(2,6-difluorophenyl)imidazol-1-yl]methyl]-1,3-dimethyl-benzimidazol-2-one (33.61 mg, 85.21 umol, 18.77% yield) as a white solid.

Bax-100A_HNMR: 1H-NMR (400 MHz, CHLOROFORM-d) δ 7.49 (s, 1H), 7.39-7.29 (m, 1H), 6.98-6.88 (m, 2H), 6.81-6.66 (m, 2H), 6.50 (s, 1H), 4.96 (s, 2H), 3.38-3.34 (m, 3H), 3.32-3.28 (m, 3H), 1.59-1.54 (m, 1H), 0.90-0.83 (m, 2H), 0.79-0.69 (m, 2H). ESI [M+H]=395.1.

Bax-100_HNMR: 1H-NMR (400 MHz, CHLOROFORM-d) б=7.57 (s, 1H), 7.26-7.11 (m, 1H), 6.93-6.82 (m, 4H), 6.68 (s, 1H), 5.23 (s, 2H), 3.37-3.34 (m, 3H), 3.33-3.31 (m, 3H), 1.48 (ddd, J=2.9, 5.2, 8.2 Hz, 1H), 0.69-0.61 (m, 2H), 0.29-0.22 (m, 2H). ESI [M+H]=395.1.

Example 41

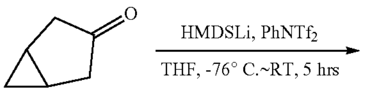

1

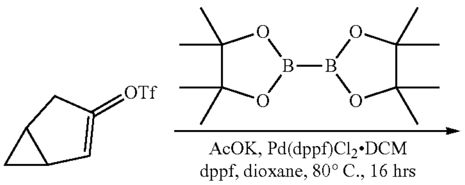

2

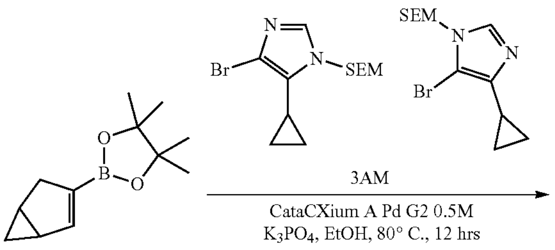

3

-continued

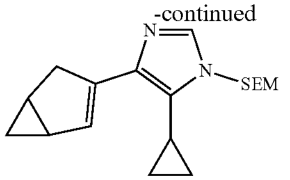

4

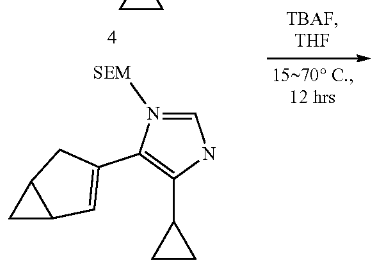

4A

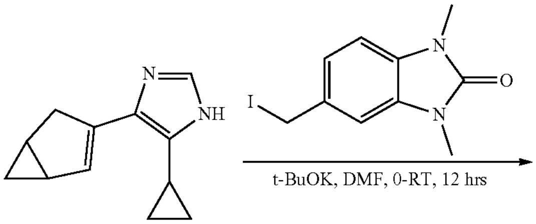

5

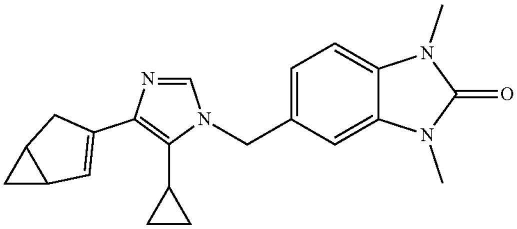

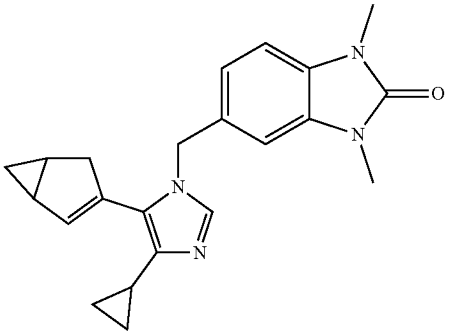

Bax-102 AM

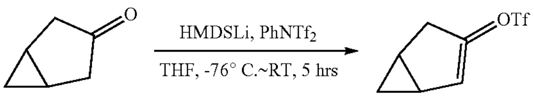

1 2

To a −76° C. stirred mixture of bicyclo[3.1.0]hexan-3-one (620 mg, 6.45 mmol, 1 eq) in THF (10 mL) under N2 was added LiHMDS (1 M, 12.90 mL, 2.0 eq) (in THF) dropwise. After 1 hr, 1,1,1-trifluoro-N-phenyl-N(trifluoromethylsulfonyl) methanesulfonamide (2.53 g, 7.09 mmol, 1.1 eq) in THF (10 mL) was added to the mixture dropwise at −70° C. The resulting mixture was stirred at 20° C. under N2 for 4 hrs. The reaction mixture was quenched by addition saturated $NaHCO_3$ solution (50 mL), and then diluted with EtOAc (10 mL) and extracted with EtOAc (50 mL*3). The combined organic layers were washed with brine (30 mL), dried over $Na_2SO_4$, filtered and concentrated under reduced pressure to give a residue. The residue was purified by column chromatography ($SiO_2$, PE) to give 3-bicyclo[3.1.0]hex-2-enyl trifluoromethanesulfonate (1.19 g, 5.21 mmol, 80.85% yield) as a colorless oil. (Spectrum of 1H-NMR was cited the pilot batch).

$^1$H-NMR (400 MHz, CHLOROFORM-d) δ 5.69 (d, J=1.8 Hz, 1H), 2.69 (br dd, J=7.5, 17.2 Hz, 1H), 2.36 (br d, J=17.1 Hz, 1H), 1.64-1.51 (m, 1H), 1.43-1.33 (m, 1H), 0.78 (dt, J=4.8, 7.4 Hz, 1H1), 0.83-0.74 (m, 1H1), 0.04-0.05 (m, 1H1).

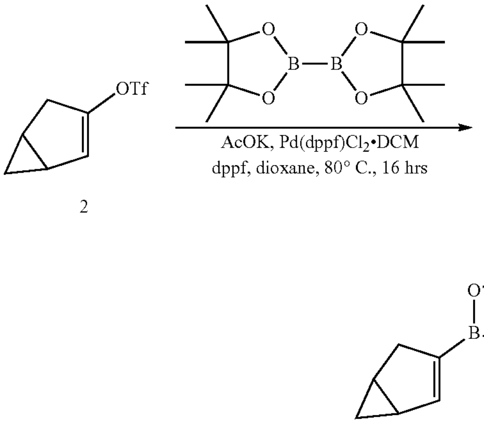

3

A mixture of 3-bicyclo[3.1.0]hex-2-enyl trifluoromethanesulfonate (1.19 g, 5.21 mmol, 1 eq), 4,4,5,5-tetramethyl-2-(4,4,5,5-tetramethyl-1,3,2-dioxaborolan-2-yl)-1,3,2-dioxaborolane (1.99 g, 7.82 mmol, 1.5 eq), AcOK (1.02 g, 10.43 mmol, 2 eq), DPPF (173.46 mg, 312.90 umol, 0.06 eq) and $Pd(dppf)Cl_2{\cdot}CH_2Cl_2$ (255.52 mg, 312.90 umol, 0.06 eq) in dioxane (20 mL) was stirred at 80° C. under N2 for 16 hrs. The reaction mixture was concentrated under reduced pressure to give a residue. The residue was purified by column chromatography ($SiO_2$, PE) to give 2-(3-bicyclo[3.1.0]hex-2-enyl)-4,4,5,5-tetramethyl-1,3,2-dioxaborolane (650 mg, 3.15 mmol, 60.48% yield) as a light yellow oil. (Spectrum of 1H-NMR was cited the pilot batch).

$^1$H-NMR (400 MHz, CHLOROFORM-d) δ 6.85 (br d, J=2.0 Hz, 1H), 2.88-2.73 (m, 1H), 2.58 (br d, J=17.4 Hz, 1H), 2.07-1.95 (m, 1H), 1.84-1.75 (m, 1H), 1.38 (s, 12H), 1.01 (dt, J=3.5, 7.7 Hz, 1H), 0.06-0.04 (m, 1H).

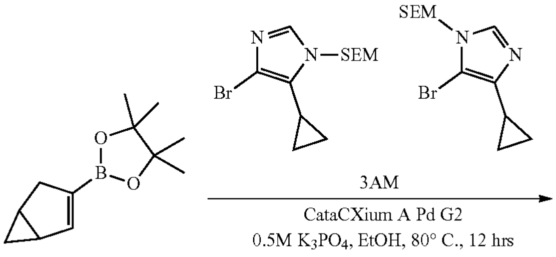

3

-continued

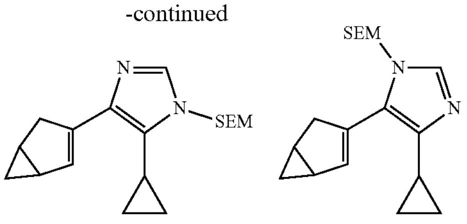

4 4A

A mixture of 2-(3-bicyclo[3.1.0]hex-2-enyl)-4,4,5,5-tetramethyl-1,3,2-dioxaborolane (150 mg, 727.84 umol, 1.2 eq), 2-[(4-bromo-5-cyclopropyl-imidazol-1-yl)methoxy]ethyl-trimethyl-silane (96.23 mg, 303.27 umol, 0.5 eq), 2-[(5-bromo-4-cyclopropyl-imidazol-1-yl)methoxy]ethyl-trimethyl-silane (96.23 mg, 303.27 umol, 0.5 eq) (regio-mixture, total 193 mg, 1 eq), $K_3PO_4$ (0.5 M, 2.43 mL, 2.0 eq) (in $H_2O$) and [2-(2-aminophenyl)phenyl]-chloro-palladium; bis(1-adamantyl)-butyl-phosphane (40.55 mg, 60.65 μmol, 0.1 eq) in EtOH (3 mL) under N2 was stirred at 80° C. for 12 hrs. The reaction mixture was concentrated to give a residue. The residue was purified by prep-TLC (PE:EtOAc=1:1, Plate 1) to give 2-[[4-(3-bicyclo[3.1.0]hex-2-enyl)-5-cyclopropyl-imidazol-1-yl]methoxy]ethyl-trimethyl-silane and 2-[[5-(3-bicyclo[3.1.0]hex-2-enyl)-4-cyclopropyl-imidazol-1-yl]methoxy]ethyl-trimethyl-silane (region-mixture, total 130 mg) as a light yellow oil. ESI [M+H]=317.2.

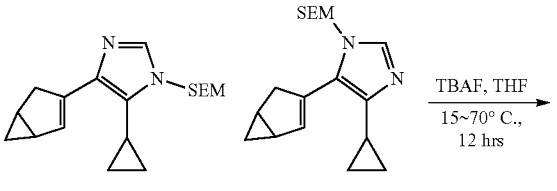

4 4A

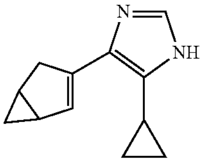

5

To a mixture of 2-[[4-(3-bicyclo[3.1.0]hex-2-enyl)-5-cyclopropyl-imidazol-1-yl]methoxy]ethyl-trimethyl-silane (60 mg, 189.57 umol, 0.5 eq) and 2-[[5-(3-bicyclo[3.1.0]hex-2-enyl)-4-cyclopropyl-imidazol-1-yl]methoxy]ethyl-trimethyl-silane (60.00 mg, 189.57 μmol, 0.5 eq) (region-mixture, total 120 mg, 1 eq) in THF (3 mL) was added TBAF (1 M, 1.52 mL, 4 eq) (in THF) at 15° C., and the resulting mixture was stirred at 70° C. for 12 hrs. The reaction mixture was concentrated in vacuo to give a residue. The residue was purified by prep-TLC ($SiO_2$, EtOAc/MeOH=10/1, Plate 1) to give 4-(3-bicyclo[3.1.0]hex-2-enyl)-5-cyclopropyl-1H-imidazole (50 mg, 268.45 umol, 70.81% yield) as a yellow oil. ESI [M+H]=187.2.

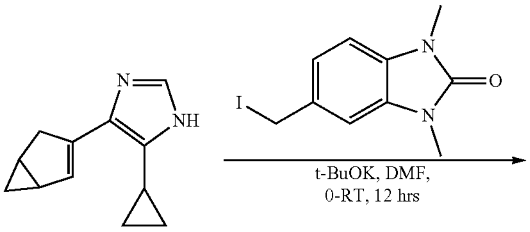

5

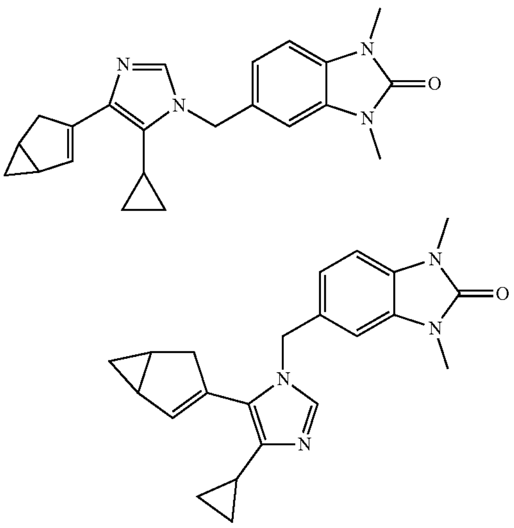

Bax-102 AM

To a 0° C. stirred solution of t-BuOK (1 M, 322.14 uL, 1.5 eq) (in THF) in DMF (0.5 mL) under N2 was added 4-(3-bicyclo[3.1.0]hex-2-enyl)-5-cyclopropyl-1H-imidazole (40 mg, 214.76 μmol, 1 eq) in DMF (0.5 mL) dropwise. After 15 mins, 5-(iodomethyl)-1,3-dimethyl-benzimidazol-2-one (77.86 mg, 257.71 μmol, 1.2 eq) in DMF (1.5 mL) was added dropwise under N2. The resulting mixture was stirred at 15° C. for 12 hrs. The reaction mixture was concentrated under reduced pressure to give a residue. The residue was purified by prep-HPLC (column: Waters Xbridge Prep OBD C18 150*40 mm*10 μm; mobile phase: [water (0.04% $NH_3H_2O$+10 mM $NH_4HCO_3$)-ACN]; B %: 15%-45%, 10 min) to give 5-[[4-(3-bicyclo[3.1.0]hex-2-enyl)-5-cyclopropyl-imidazol-1-yl]methyl]-1,3-dimethyl-benzimidazol-2-one and 5-[[5-(3-bicyclo[3.1.0]hex-2-enyl)-4-cyclopropyl-imidazol-1-yl]methyl]-1,3-dimethyl-benzimidazol-2-one (regio-mixture, total 14.38 mg, purity: 96.935%) as a white solid. ESI [M+H]=361.1.

$^1$H-NMR (400 MHz, METHANOL-d4) δ 7.56 (s, 1H), 7.50 (s, 1H), 7.13-7.04 (m, 2H), 7.03-6.95 (m, 2H), 6.85 (s, 1H), 6.78 (d, J=8.1 Hz, 1H), 6.11 (d, J=1.8 Hz, 1H), 5.98 (d, J=1.8 Hz, 1H), 5.30 (s, 1H), 5.17 (s, 2H), 3.43-3.34 (m, 12H), 3.01 (br dd, J=6.7, 17.4 Hz, 1H), 2.86 (br dd, J=7.2, 17.2 Hz, 1H), 2.68 (br d, J=17.2 Hz, 1H), 2.42 (br d, J=17.2 Hz, 1H), 1.87 (br d, J=7.1 Hz, 2H), 1.81-1.71 (m, 1H), 1.66-1.55 (m, 1H), 1.66-1.55 (m, 1H), 1.44-1.34 (m, 1H), 1.00 (dd, J=1.7, 8.0 Hz, 2H), 0.91-0.68 (m, 7H), 0.57-0.44 (m, 2H), −0.06 (q, J=3.5 Hz, 1H), −0.21 (q, J=3.7 Hz, 1H).

Example 42
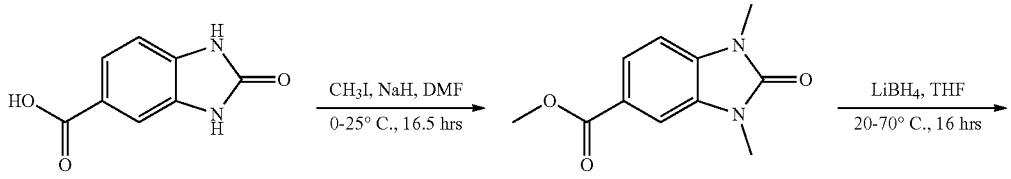
1A 2A
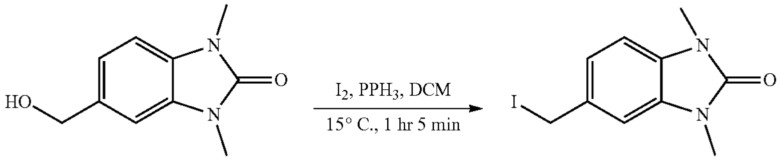
3A 4A
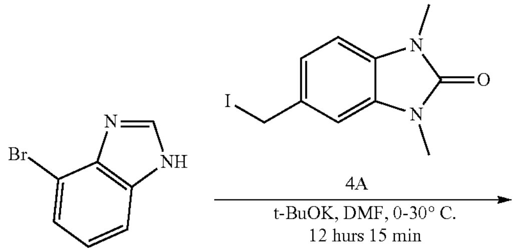
1
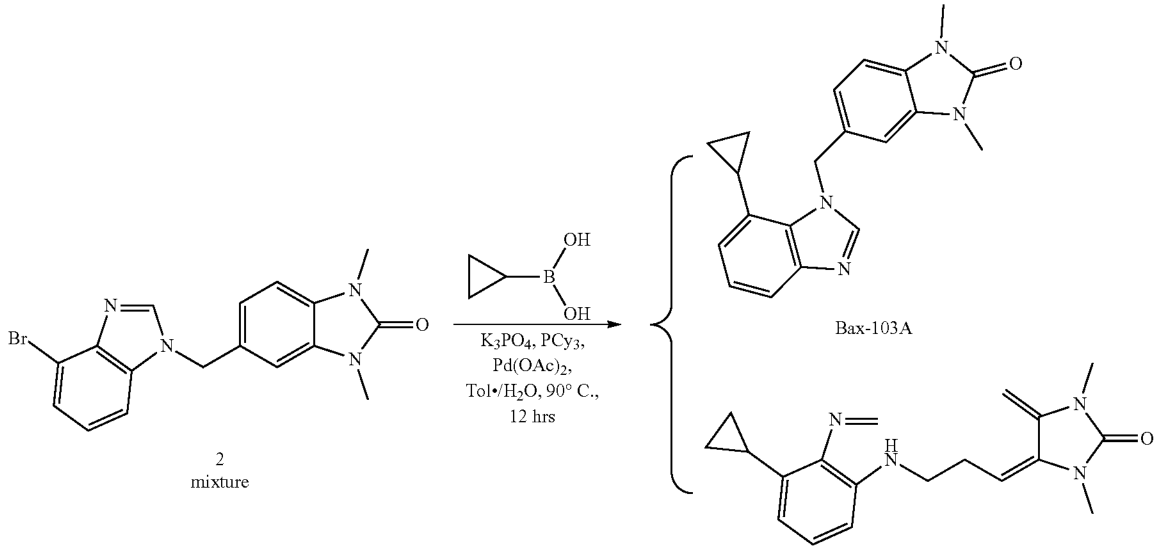
2
mixture
Bax-103
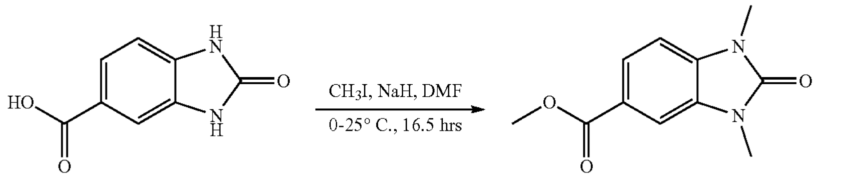
1A 2A To a solution of 2-oxo-1,3-dihydrobenzimidazole-5-carboxylic acid (5 g, 28.07 mmol, 1 eq) in DMF (120 mL) was added NaH (3.93 g, 98.23 mmol, 60% purity, 3.5 eq) at 0° C. After 30 min, MeI (13.94 g, 98.23 mmol, 6.12 mL, 3.5 eq) was added at 0° C. Then the mixture was stirred at 25° C. for 16 hrs. The reaction was quenched with sat.aq.$NH_4Cl$ (500 mL) and extracted with EtOAc (200 mL*3). The organic layer was washed with brine (500 mL*2), dried over $MgSO_4$ and concentrated in vacuo. The residue was triturated with PE/MTBE (50 mL/5 mL), and solid precipitate was collected via filtration, dried in vacuo to give methyl 1,3-dimethyl-2-oxo-benzimidazole-5-carboxylate (5.5 g, 24.97 mmol, 88.98% yield) was obtained as a brown solid. ESI [M+H]=221.1.

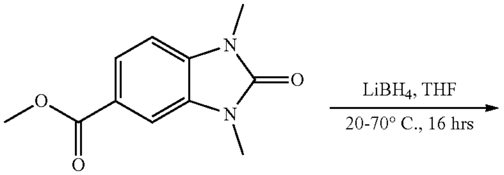

2A

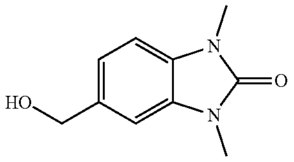

3A

To a solution of methyl 1,3-dimethyl-2-oxo-benzimidazole-5-carboxylate (5.5 g, 24.97 mmol, 1 eq) in THF (100 mL) was added $LiBH_4$ (1.09 g, 49.95 mmol, 2 eq) at 20° C. Then the mixture was stirred at 70° C. for 16 hrs. The reaction was quenched with cold sat.aq.$NH_4Cl$ (200 mL), extracted with EtOAc (100 mL*3). The organic layer was washed with brine (200 mL), dried over $MgSO_4$ and concentrated in vacuo. The residue was triturated with EtOAc/MTBE (1:1, 50 mL) to give 5-(hydroxymethyl)-1,3-dimethyl-benzimidazol-2-one (4.5 g, 23.41 mmol, 93.74% yield) was obtained as a light red solid. ESI [M+H]=193.1.

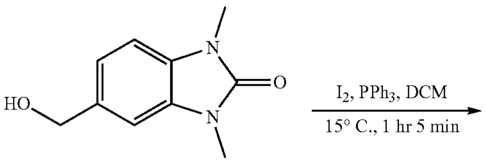

3A

-continued

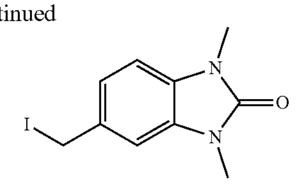

4A

To a solution of $PPh_3$ (429.83 mg, 1.64 mmol, 1.05 eq) in DCM (5 mL) was added $I_2$ (415.94 mg, 1.64 mmol, 330.11 uL, 1.05 eq) at 15° C. under N2. After 5 min, 5-(hydroxymethyl)-1,3-dimethyl-benzimidazol-2-one (300 mg, 1.56 mmol, 1 eq) in DCM (3 mL) was added and the mixture was stirred at 15° C. for 1 hr. The reaction was concentrated in vacuo. The residue was purified by column chromatography ($SiO_2$, Petroleum ether/Ethyl acetate=10:1 to 0:1) to give 5-(iodomethyl)-1,3-dimethyl-benzimidazol-2-one (440 mg, 1.46 mmol, 93.31% yield) was obtained as a yellow solid.

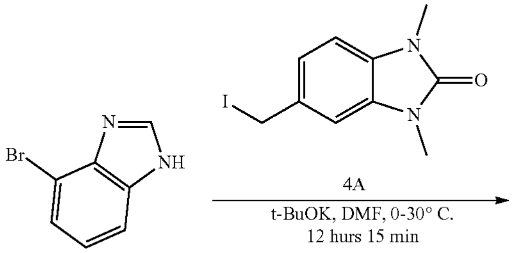

1

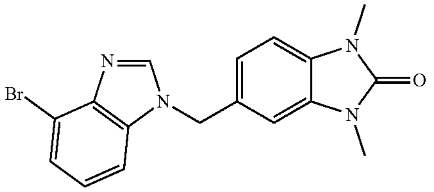

2
mixture

To a solution of t-BuOK (1 M, 1.09 mL, 1.5 eq) in DMF (1 mL) (under N2) was added dropwise 4-bromo-1H-benzimidazole (143 mg, 725.77 umol, 1 eq) in DMF (1 mL) at 0° C. under N2. After 15 min, 5-(iodomethyl)-1,3-dimethyl-benzimidazol-2-one (219.26 mg, 725.77 umol, 1 eq) in DMF (1 mL) was added at 0° C. under N2. The mixture was stirred at 30° C. for 12 hrs. The reaction was add water (20 mL) extracted with DCM/i-PrOH (3/1, 30 mL*5). The organic phase was dried over drying $Na_2SO_4$, and then concentrated in vacuo. The residue was purified by prep-TLC ($SiO_2$, Ethyl acetate:Methanol=10:1) to give 5-[(4-bromobenzimidazol-1-yl)methyl]-1,3-dimethyl-benzimidazol-2-one and 5-[(7-bromobenzimidazol-1-yl)methyl]-1,3-dimethyl-benzimidazol-2-one total 136 mg were obtained as a yellow solid. ESI [M+H and M+3H]=371.1 and 373.1.

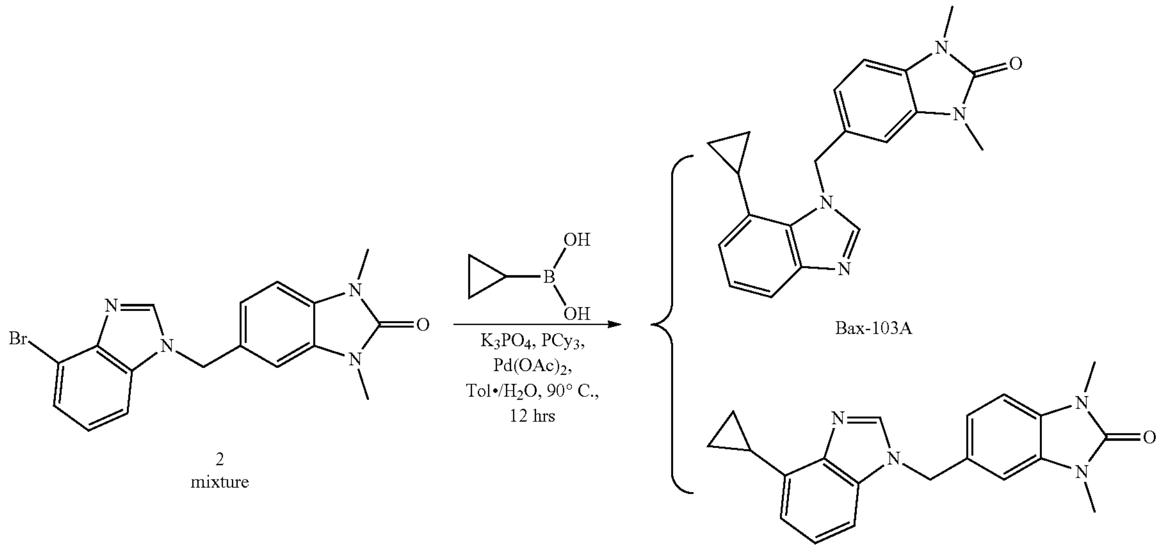

2
mixture

Bax-103A

Bax-103

A mixture of 5-[(4-bromobenzimidazol-1-yl)methyl]-1,3-dimethyl-benzimidazol-2-one and 5-[(7-bromobenzimidazol-1-yl)methyl]-1,3-dimethyl-benzimidazol-2-one total 130 mg, $K_3PO_4$ (223.00 mg, 1.05 mmol, 3 eq), $P(Cy)_3$ (19.64 mg, 70.04 umol, 22.71 uL, 0.2 eq), cyclopropyl boronic acid (60.16 mg, 700.37 umol, 2 eq) and $Pd(OAc)_2$ (7.86 mg, 35.02 umol, 0.1 eq) in toluene (3 mL) and $H_2O$ (1 mL) under $N_2$, and then the mixture was stirred at 90° C. for 12 hrs under N2 atmosphere. The reaction was add water (10 mL) and extracted with EtOAc (20 mL*3). The organic phase was dried over drying $Na_2SO_4$, and then concentrated in vacuo. The residue was purified by prep-HPLC (column: Waters Xbridge 150*25 5u; mobile phase: [water (10 mM NH4HCO3)-ACN]; B %: 10%-40%, 10 min), purified again by prep-HPLC (column: Luna C18 100*30 5u; mobile phase: [water (0.04% HCl)-ACN]; B %: 10%-40%, 10 min) to give 5-[(4-cyclopropylbenzimidazol-1-yl)methyl]-1,3-dimethyl-benzimidazol-2-one (99.694% purity) and 5-[(7-cyclopropylbenzimidazol-1-yl)methyl]-1,3-dimethyl-benzimidazol-2-one (99.694% purity) total 16.24 mg was obtained as a white solid. ESI [M+H]=333.1.

$^1H$ NMR (400 MHz, METHANOL-d4) δ 9.58 (s, 1H), 9.24 (s, 1H), 7.70 (dd, J=8.3, 14.3 Hz, 2H), 7.61-7.49 (m, 2H), 7.41-7.29 (m, 3H), 7.26-7.18 (m, 4H), 7.09 (d, J=8.1 Hz, 1H), 6.19 (s, 2H), 5.79 (s, 2H), 3.46-3.40 (m, 12H), 2.43-2.13 (m, 2H), 1.23-1.16 (m, 2H), 1.12-1.05 (m, 2H), 0.98-0.93 (m, 2H), 0.93-0.88 (m, 2H).

Example 43

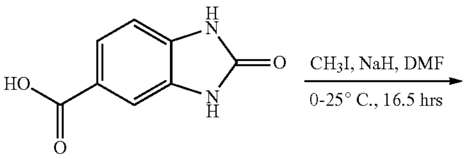

1A

-continued

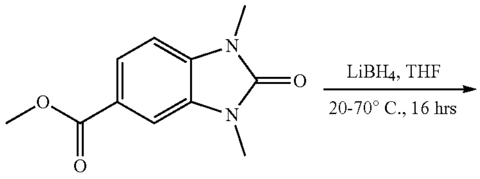

2A

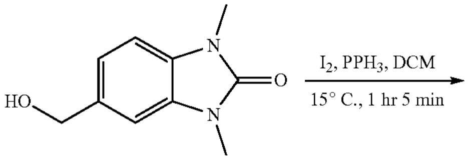

3A

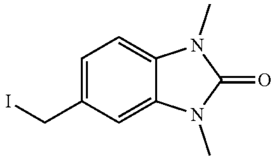

4A

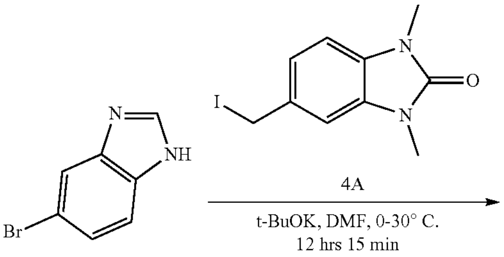

1

-continued

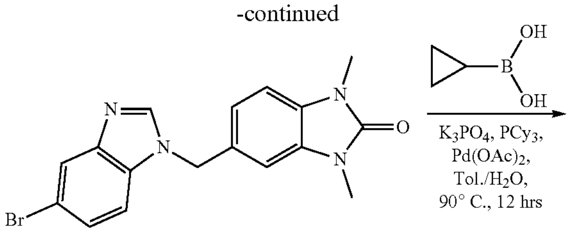

2
mixture

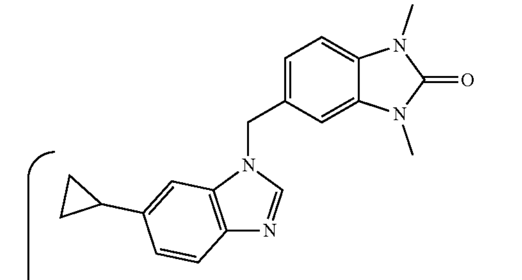

Bax-104A

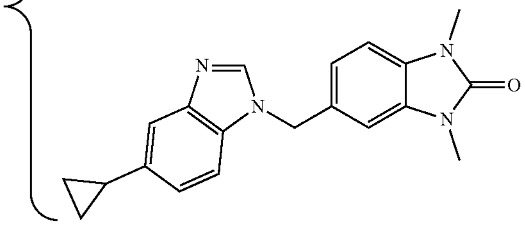

Bax-104

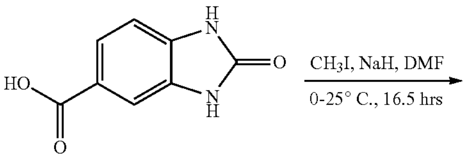

1A

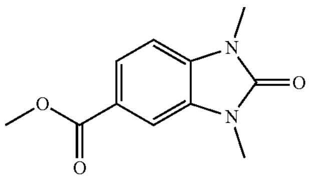

2A

To a solution of 2-oxo-1,3-dihydrobenzimidazole-5-carboxylic acid (5 g, 28.07 mmol, 1 eq) in DMF (120 mL) was added NaH (3.93 g, 98.23 mmol, 60% purity, 3.5 eq) at 0° C. After 30 min, MeI (13.94 g, 98.23 mmol, 6.12 mL, 3.5 eq) was added at 0° C. Then the mixture was stirred at 25° C. for 16 hrs. The reaction was quenched with sat.aq.$NH_4Cl$ (500 mL) and extracted with EtOAc (200 mL*3). The organic layer was washed with brine (500 mL*2), dried over $MgSO_4$ and concentrated in vacuo. The residue was triturated with PE/MTBE (50 mL/5 mL), and solid precipitate was collected via filtration, dried in vacuo to give methyl 1,3-dimethyl-2-oxo-benzimidazole-5-carboxylate (5.5 g, 24.97 mmol, 88.98% yield) was obtained as a brown solid. ESI [M+H]=221.1.

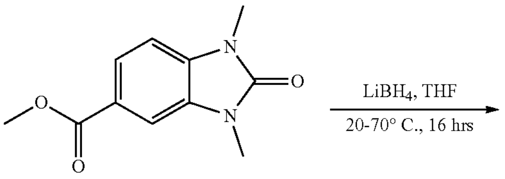

2A

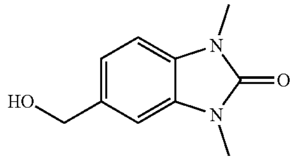

3A

To a solution of methyl 1,3-dimethyl-2-oxo-benzimidazole-5-carboxylate (5.5 g, 24.97 mmol, 1 eq) in THF (100 mL) was added $LiBH_4$ (1.09 g, 49.95 mmol, 2 eq) at 20° C. Then the mixture was stirred at 70° C. for 16 hrs. The reaction was quenched with cold sat.aq.$NH_4Cl$ (200 mL), extracted with EtOAc (100 mL*3). The organic layer was washed with brine (200 mL), dried over $MgSO_4$ and concentrated in vacuo. The residue was triturated with EtOAc/MTBE (1:1, 50 mL) to give 5-(hydroxymethyl)-1,3-dimethyl-benzimidazol-2-one (4.5 g, 23.41 mmol, 93.74% yield) was obtained as a light red solid. ESI [M+H]=193.1.

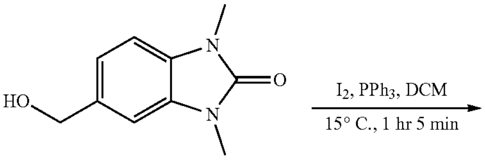

3A

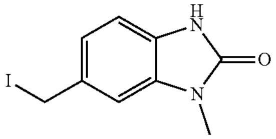

4A

To a solution of $PPh_3$ (573.11 mg, 2.19 mmol, 1.05 eq) in DCM (3 mL) was added $I_2$ (554.59 mg, 2.19 mmol, 440.15 uL, 1.05 eq) at 15° C. under N2. After 5 min, 5-(hydroxymethyl)-1,3-dimethyl-benzimidazol-2-one (400 mg, 2.08 mmol, 1 eq) in DCM (2 mL) was added and the mixture was stirred at 15° C. for 1 hr. The reaction was concentrated in vacuo. The residue was purified by column chromatography ($SiO_2$, Petroleum ether/Ethyl acetate=10:1 to 0:1) to give 5-(iodomethyl)-1,3-dimethyl-benzimidazol-2-one (550 mg, 1.82 mmol, 87.48% yield) was obtained as a yellow solid.

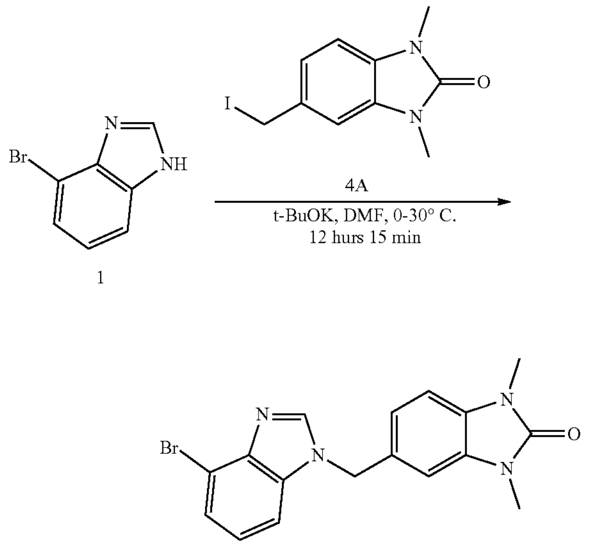

1

4A 2
mixture

To a solution of t-BuOK (1 M, 913.56 uL, 1.5 eq) in DMF (1 mL) (under N2) was added dropwise 5-bromo-1H-benzimidazole (120 mg, 609.04 umol, 1 eq) in DMF (1 mL) at 0° C. under N2. After 15 min, 5-(iodomethyl)-1,3-dimethyl-benzimidazol-2-one (184.00 mg, 609.04 umol, 1 eq) in DMF (1 mL) was added at 0° C. under $N_2$. The mixture was stirred at 30° C. for 12 hrs. The reaction was add water (20 mL) extracted with DCM/i-PrOH (3/1, 30 mL*5). The organic phase was dried over drying $Na_2SO_4$, and then concentrated in vacuo. The residue was purified by prep-TLC ($SiO_2$, Ethyl acetate:Methanol=15:1) to give 5-[(5-bromobenzimidazol-1-yl)methyl]-1,3-dimethyl-benzimidazol-2-one and 5-[(6-bromobenzimidazol-1-yl)methyl]-1,3-dimethyl-benzimidazol-2-one total 135 mg were obtained as a yellow oil. ESI [M+H and M+3H]=370.9 and 372.9.

A mixture of 5-[(5-bromobenzimidazol-1-yl)methyl]-1,3-dimethyl-benzimidazol-2-one and 5-[(6-bromobenzimidazol-1-yl)methyl]-1,3-dimethyl-benzimidazol-2-one total 135 mg, $K_3PO_4$ (231.58 mg, 1.09 mmol, 3 eq), $P(Cy)_3$ (20.40 mg, 72.73 umol, 23.58 uL, 0.2 eq), cyclopropylboronic acid (93.71 mg, 1.09 mmol, 3 eq) and $Pd(OAc)_2$ (8.16 mg, 36.37 umol, 0.1 eq) in toluene (3 mL) and $H_2O$ (1 mL) was stirred at 90° C. for 12 hrs under N2 atmosphere. The reaction was added water (10 mL) and extracted with EtOAc (15 mL*4). The organic layer was dried over $Na_2SO_4$ and concentrated in vacuo. The residue was purified by prep-HPLC (column: Xtimate C18 150*25 mm*5 μm; mobile phase: [water (10 mM $NH_4HCO_3$)-ACN]; B %: 30%-60%, 8 min) to give 5-[(5-cyclopropylbenzimidazol-1-yl)methyl]-1,3-dimethyl-benzimidazol-2-one (99.664% purity) and 5-[(6-cyclopropyl benzimidazol-1-yl)methyl]-1,3-dimethyl-benzimidazol-2-one (99.664% purity) total 20.93 mg (99.664% purity) was obtained as a white solid. ESI [M+H]=333.1.

$^1$H NMR (400 MHz, METHANOL-d4) δ 8.23 (s, 1H), 8.20 (s, 1H), 7.54 (d, J=8.4 Hz, 1H), 7.40-7.31 (m, 2H), 7.21 (s, 1H), 7.15-7.09 (m, 6H), 7.02 (dt, J=1.5, 8.3 Hz, 2H), 5.51 (s, 4H), 3.41-3.40 (m, 6H), 3.38 (d, J=2.8 Hz, 6H), 2.01 (ddd, J=3.0, 5.3, 8.3 Hz, 2H), 1.01-0.91 (m, 4H), 0.68 (dt, J=1.8, 5.7 Hz, 4H).

Example 44

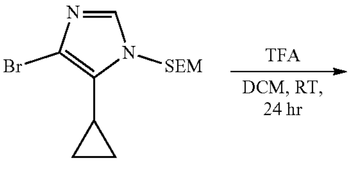

1

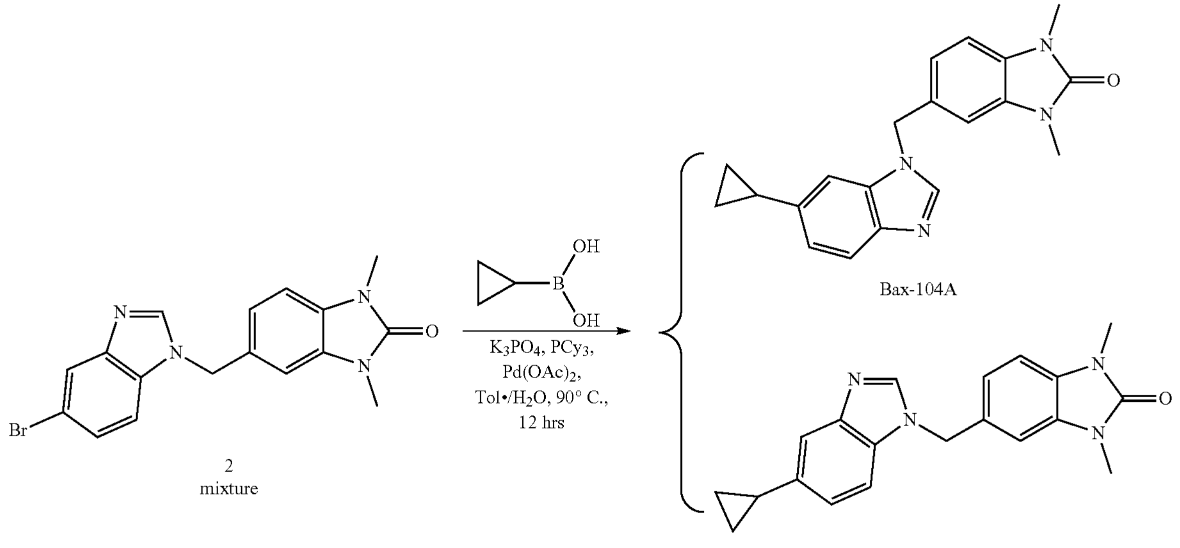

2
mixture

Bax-104A

Bax-104

-continued

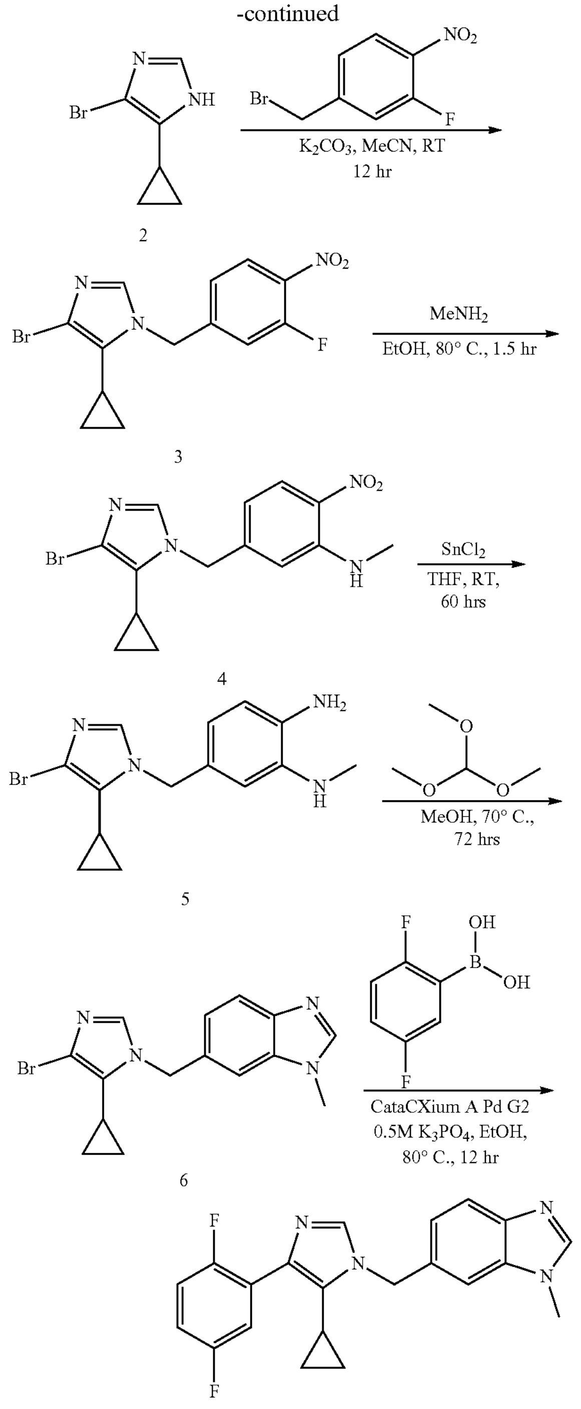

2

3

4

5

6

Bax-105

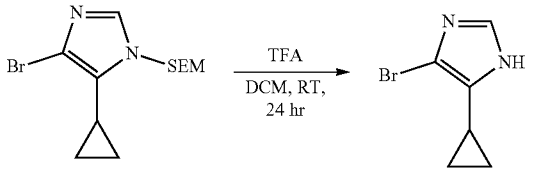

1

2

2-[(4-bromo-5-cyclopropyl-imidazol-1-yl)methoxy]ethyl-trimethyl-silane and 2-[(5-bromo-4-cyclopropyl-imidazol-1-yl)methoxy]ethyl-trimethyl-silane total 2 g in DCM (18 mL) was added TFA (9.24 g, 81.04 mmol, 6 mL, 12.86 eq). The mixture was stirred at 25° C. for 24 hours. The reaction mixture was concentrated in vacuo to give a residue. To the residue was added water (30 mL), adjusted to pH=8 with sat.aq. $NaHCO_3$, then extracted with DCM (50 mL*5). The organic phase was dried over drying $Na_2SO_4$, and then concentrated in vacuo to give a residue. The residue was purified by column chromatography ($SiO_2$, Petroleum ether/Ethyl acetate/THF=10:1:0 to 1:2:1) to give 4-bromo-5-cyclopropyl-1H-imidazole (1.07 g, 5.72 mmol, 90.76% yield) as a white solid. ESI [M+H]=187.1, [M+3H]=189.1.

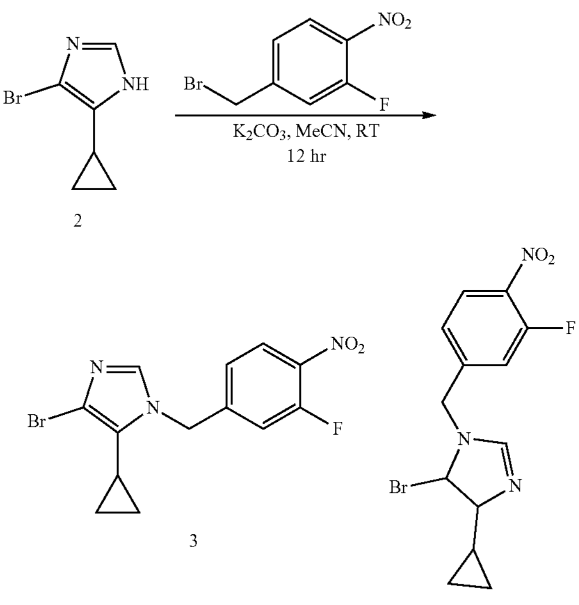

2

3

3A

To a solution of 4-bromo-5-cyclopropyl-1H-imidazole (1.07 g, 5.72 mmol, 1 eq) in MeCN (40 mL) was added $K_2CO_3$ (1.58 g, 11.44 mmol, 2 eq) and 4-(bromomethyl)-2-fluoro-1-nitro-benzene (1.34 g, 5.72 mmol, 1 eq), and the mixture was stirred at 30° C. for 12 hrs. To the reaction mixture was added water (30 mL) and extracted with EtOAc (30 mL*5). The organic layer was dried over $MgSO_4$ and concentrated in vacuo to give a residue. The residue was purified by column chromatography ($SiO_2$, Petroleum ether/Ethyl acetate=20/1 to 0:1), and then the residue was purified again by prep-HPLC (column: Ximate C18 10μ 250 mm*50 mm; mobile phase: [water (10 mM NH4HCO3)-ACN]; B %: 30%-60%, 20 min) to give 4-bromo-5-cyclopropyl-1-[(3-fluoro-4-nitro-phenyl)methyl]imidazole (330 mg, 970.17 umol, 16.96% yield) as a white solid, and 5-bromo-4-cyclopropyl-1-[(3-fluoro-4-nitro-phenyl)methyl]imidazole (870 mg, 2.56 mmol, 44.71% yield) as a yellow solid.

$^1$H-NMR of 3A: $^1$H-NMR (400 MHz, METHANOL-d4) δ 8.10 (t, J=8.1 Hz, 1H), 7.87 (s, 1H), 7.19 (d, J=11.7 Hz, 1H), 7.14-7.08 (m, 1H), 5.35 (s, 2H), 1.87-1.77 (m, 1H), 0.92-0.86 (m, 2H), 0.85-0.80 (m, 2H).

$^1$H-NMR of 3: $^1$H-NMR (400 MHz, METHANOL-d4) δ 8.11 (t, J=8.1 Hz, 1H), 7.74 (s, 1H), 7.24 (br d, J=11.7 Hz, 1H), 7.16-7.11 (m, 1H), 5.44 (s, 2H), 1.34 (tt, J=5.2, 8.2 Hz, 1H), 0.93-0.85 (m, 2H), 0.77-0.71 (m, 2H). ESI [M+H]=340.0, [M+3H]=342.0.

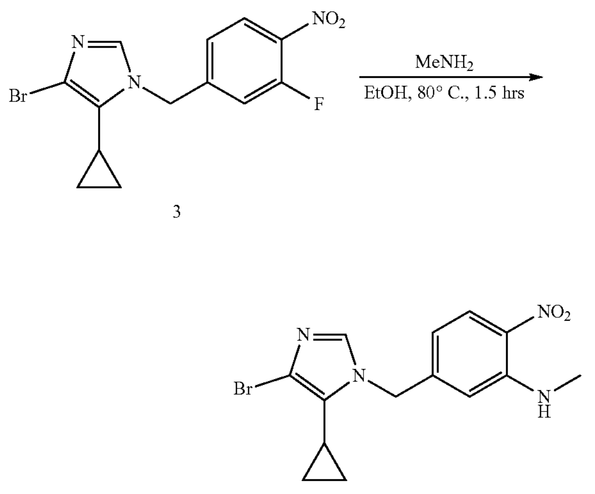

3

4

To a solution of 4-bromo-5-cyclopropyl-1-[(3-fluoro-4-nitro-phenyl)methyl]imidazole (330 mg, 970.17 umol, 1 eq) in EtOH (4 mL) was added $MeNH_2$ (1.38 g, 14.61 mmol, 2 mL, 15.06 eq, 33%, in EtOH). The mixture was stirred at 80° C. for 1.5 hrs. The reaction was concentrated in vacuo to give 5-[(4-bromo-5-cyclopropyl-imidazol-1-yl)methyl]-N-methyl-2-nitro-aniline (340 mg, crude) as yellow solid. It was used into the next step without further purification. ESI [M+H]=351.1, [M+3H]=353.1

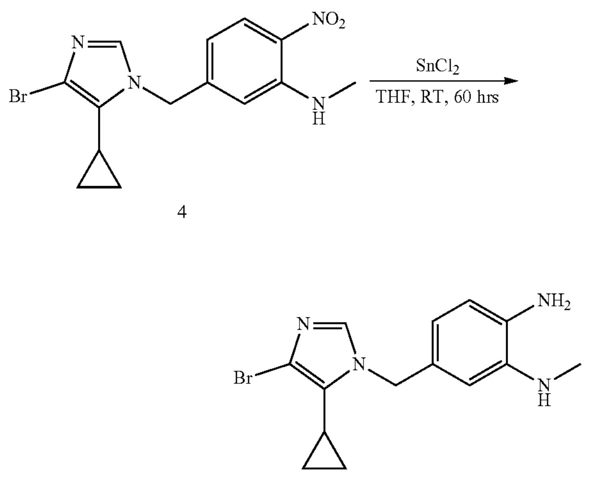

4

5

To a solution of 5-[(4-bromo-5-cyclopropyl-imidazol-1-yl)methyl]-N-methyl-2-nitro-aniline (340 mg, 968.12 umol, 1 eq) in THF (10 mL) was added $SnCl_2.2H_2O$ (655 mg, 2.90 mmol, 3 eq). The mixture was stirred at 30° C. for 60 hrs under N2 atmosphere. The reaction was quenched with cold sat.aq. $NaHCO_3$ (15 mL) and filtered, the filtrate was added water (10 mL), extracted with EtOAc (20 mL*4). The organic layer was dried over $MgSO_4$ and concentrated in vacuo to give 4-[(4-bromo-5-cyclopropyl-imidazol-1-yl)methyl]-N2-methyl-benzene-1,2-diamine (290 mg, 902.82 μmol, 93.26% yield) as a yellow solid. ESI [M+H]=321.1, [M+H]=323.1.

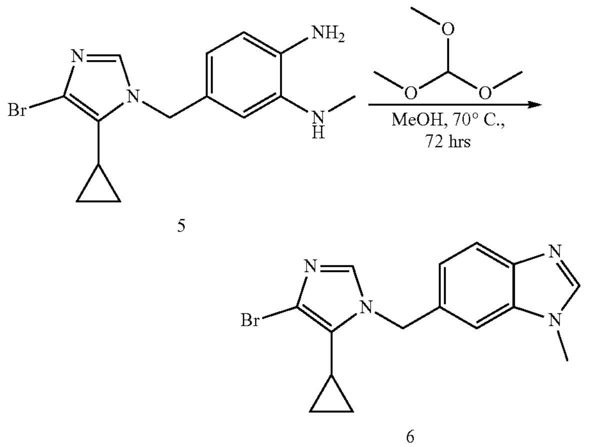

5

6

To a solution of 4-[(4-bromo-5-cyclopropyl-imidazol-1-yl)methyl]-N2-methyl-benzene-1,2-diamine (280 mg, 871.69 umol, 1 eq) in MeOH (7 mL) was added trimethoxymethane (6.78 g, 63.85 mmol, 7 mL, 73.25 eq). The mixture was stirred at 70° C. for 72 hrs. The reaction mixture was concentrated in vacuo to give a residue. The residue was purified by column chromatography ($SiO_2$, Petroleum ether/THF=10/1 to 0/1) to give 6-[(4-bromo-5-cyclopropyl-imidazol-1-yl)methyl]-1-methyl-benzimidazole (280 mg, 845.39 umol, 96.98% yield) as a yellow oil. ESI [M+H]=331.0, [M+H]=332.9.

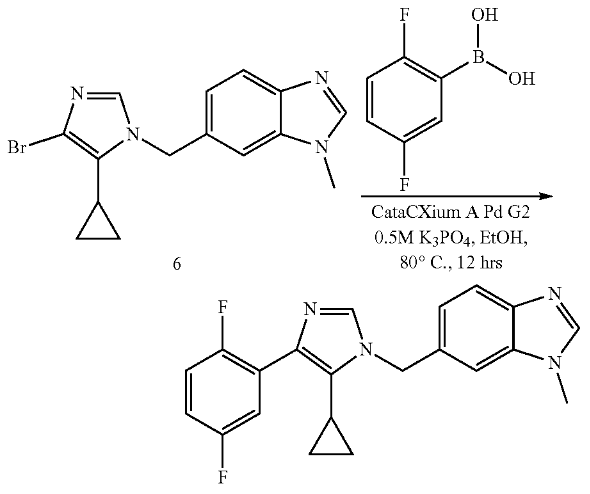

6

Bax-105

A mixture of 6-[(4-bromo-5-cyclopropyl-imidazol-1-yl)methyl]-1-methyl-benzimidazole (40 mg, 120.77 umol, 1 eq), (2,5-difluorophenyl)boronic acid (38 mg, 241.54 umol, 2 eq), [2-(2-aminophenyl)phenyl]-chloro-palladium; bis(1-adamantyl)-butyl-phosphane (8 mg, 12.08 μmol, 0.1 eq), $K_3PO_4$ (0.5 M, 483.08 μL, 2 eq) in EtOH (2 mL) was stirred at 80° C. for 12 hrs under N2 atmosphere. The reaction was concentrated in vacuo to give a residue. The residue was purified by prep-HPLC (column: mobile phase: [water (10 mM $NH_4HCO_3$)-ACN]; B %: 45%-65%, 10 min) to give 6-[[5-cyclopropyl-4-(2,5-difluorophenyl)imidazol-1-yl]methyl]-1-methyl-benzimidazole (20.97 mg, 54.82 umol, 45.39% yield, 95.251% purity) as a white solid.

$^1$H-NMR (400 MHz, CHLOROFORM-d) δ 7.57 (s, 1H), 7.49 (d, J=8.4 Hz, 1H), 6.99 (ddd, J=3.1, 5.7, 9.0 Hz, 1H), 6.95-6.94 (m, 1H), 6.89 (dd, J=1.4, 8.3 Hz, 1H), 6.78 (s, 1H), 6.76-6.69 (m, 1H), 6.67-6.60 (m, 1H), 5.09 (s, 2H), 3.49 (s, 3H), 1.27 (tt, J=5.3, 8.2 Hz, 1H), 0.54-0.45 (m, 2H), 0.07--0.03 (m, 2H). ESI [M+H]=365.1.

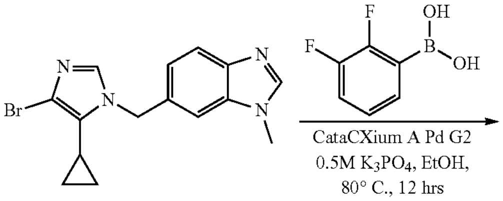

6

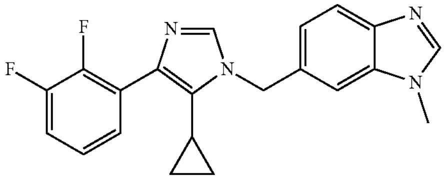

Bax-107

A mixture of 6-[(4-bromo-5-cyclopropyl-imidazol-1-yl)methyl]-1-methyl-benzimidazole (40 mg, 120.77 umol, 1 eq), (2,3-difluorophenyl)boronic acid (38 mg, 241.54 umol, 2 eq), [2-(2-aminophenyl)phenyl]-chloro-palladium; bis(1-adamantyl)-butyl-phosphane (8 mg, 12.08 umol, 0.1 eq), and $K_3PO_4$ (0.5 M, 483.08 uL, 2 eq) in EtOH (2 mL) was stirred at 80° C. for 12 hrs under N2 atmosphere. The reaction was concentrated in vacuo to give a residue. The residue was purified by prep-HPLC (column: mobile phase: [water (10 mM $NH_4HCO_3$)-ACN]; B %: 45%-65%, 10 min) to give 6-[[5-cyclopropyl-4-(2,3-difluorophenyl)imidazol-1-yl]methyl]-1-methyl-benzimidazole (20.06 mg, 51.43 umol, 42.58% yield, 93.420% purity) as a white solid.

$^1$H-NMR (400 MHz, CHLOROFORM-d) δ 7.58 (s, 1H), 7.50 (d, J=8.2 Hz, 1H), 7.08-7.02 (m, 1H), 6.96 (s, 1H), 6.90 (dd, J=1.2, 8.3 Hz, 1H), 6.83-6.75 (m, 3H), 5.10 (s, 2H), 3.50 (s, 3H), 1.33-1.25 (m, 2H), 0.54-0.46 (m, 2H), 0.05--0.01 (m, 2H). ESI [M+H]=365.1.

Example 45

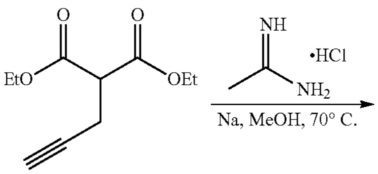

1

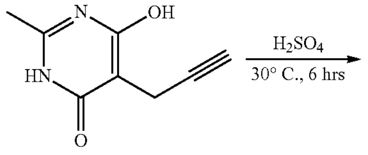

2

-continued

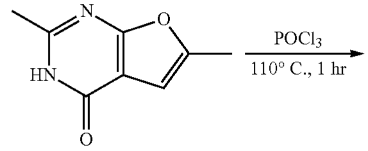

3

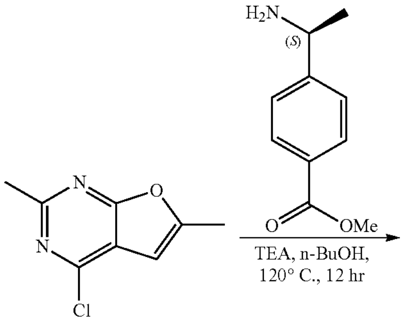

4

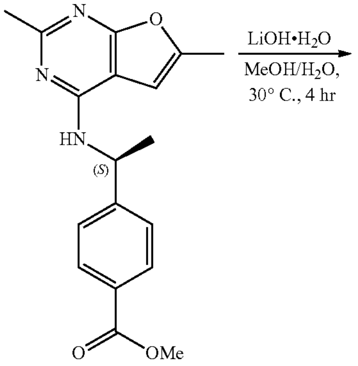

5

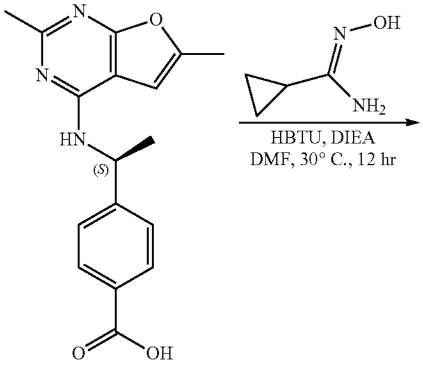

6

-continued

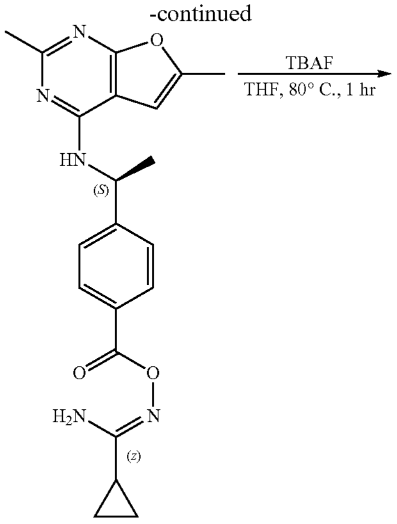

7

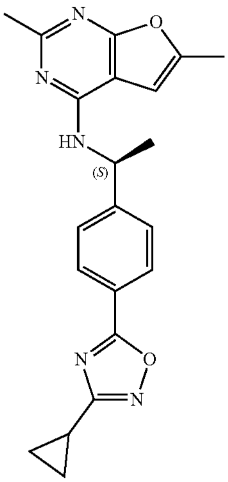

Bax-109 S

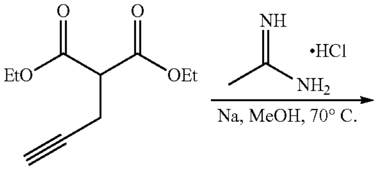

1

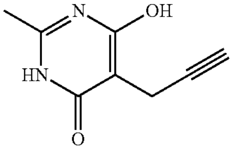

2

A solution of Na (116 mg, 5.05 mmol, 119.57 uL, 1 eq) in MeOH (20 mL) was stirred 20 mins, then diethyl 2-prop-2-ynylpropanedioate (1 g, 5.05 mmol, 1 eq) and acetamidine; hydrochloride (477 mg, 5.05 mmol, 1 eq) was added. The mixture was stirred at 70° C. for 12 hrs. The precipitate was formed and collected by filtration and dissolved in 20 mL of water. This solution was adjusted to pH=3 with 1N HCl and then the mixture was filtered and collection of filter cake to give 4-hydroxy-2-methyl-5-prop-2-ynyl-1H-pyrimidin-6-one (150 mg, 913.74 umol, 18.11% yield) as a white solid. ESI [M+H]=165.2.

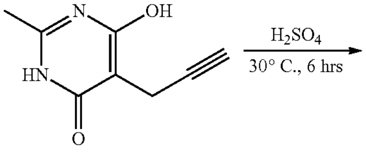

2

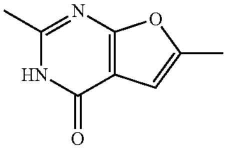

3

A solution of 4-hydroxy-2-methyl-5-prop-2-ynyl-1H-pyrimidin-6-one (150 mg, 913.74 umol, 1 eq) in $H_2SO_4$ (1.5 mL) was stirred at 30° C. for 6 hrs. The reaction mixture was quenched by cold water (20 mL), and extracted with DCM (30 mL*5). The combined organic layers were dried over $Na_2SO_4$, filtered and concentrated under reduced pressure to give 2,6-dimethyl-3H-furo[2,3-d]pyrimidin-4-one (116 mg, crude) as a white solid.

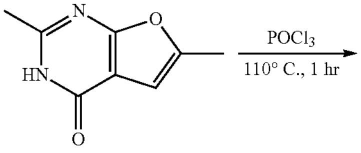

3

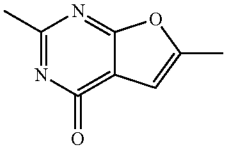

4

A solution of 2,6-dimethyl-3H-furo[2,3-d]pyrimidin-4-one (100 mg, 609.16 umol, 1 eq) in $POCl_3$ (2 mL) was stirred at 110° C. for 1 hr. The reaction was concentrated in vacuo to give crude product 4-chloro-2,6-dimethyl-furo[2,3-d]pyrimidine (110 mg, brown oil). It was used into the next step without further purification.

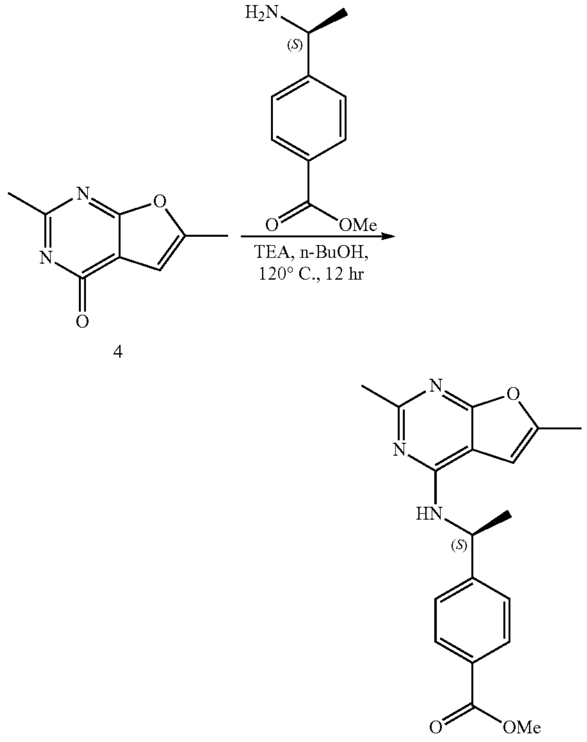

4

5

To a solution of 4-chloro-2,6-dimethyl-furo[2,3-d]pyrimidine (110 mg, 602.39 umol, 1 eq) in n-BuOH (3 mL) was added TEA (244 mg, 2.41 mmol, 335.38 uL, 4 eq) and methyl 4-[(1S)-1-aminoethyl]benzoate (162 mg, 903.58 umol, 1.5 eq). The mixture was stirred at 120° C. for 12 hrs. The reaction was concentrated in vacuo to give a residue. The residue was purified by prep-TLC ($SiO_2$, Petroleum ether:Ethyl acetate=1:1) to give methyl 4-[(1S)-1-[(2,6-dimethylfuro[2,3-d]pyrimidin-4-yl)amino]ethyl]benzoate (130 mg, 399.56 umol, 66.33% yield) as a yellow oil. ESI [M+H]=326.2.

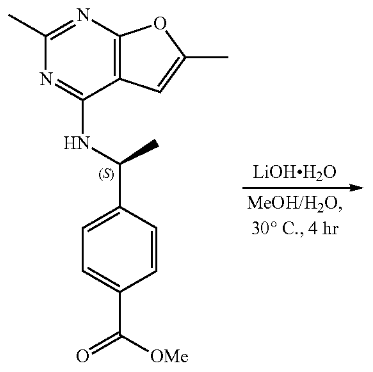

5

-continued

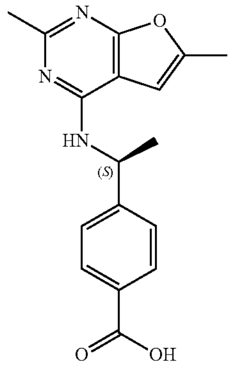

6

To a solution of methyl 4-[(1S)-1-[(2,6-dimethylfuro[2,3-d]pyrimidin-4-yl)amino]ethyl]benzoate (130 mg, 399.56 umol, 1 eq) in MeOH (3 mL) and $H_2O$ (1 mL) was added $LiOH·H_2O$ (34 mg, 799.11 umol, 2 eq). The mixture was stirred at 30° C. for 4 hr. The reaction mixture was concentrated under reduced pressure to remove MeOH, and extracted with MTBE (20 mL*2). The aqueous phase was adjusted to pH=2 with 1N aq. HCl, and extracted with DCM/i-PrOH (3/1, 20 mL*5). The combined organic layers were dried over $Na_2SO_4$, filtered and concentrated under reduced pressure to give 4-[(1S)-1-[(2,6-dimethylfuro[2,3-d]pyrimidin-4-yl)amino]ethyl]benzoic acid (120 mg, 385.44 umol, 96.47% yield) as a yellow solid. ESI [M+H]=312.2.

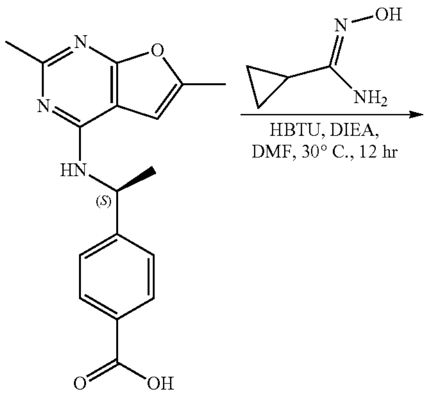

6

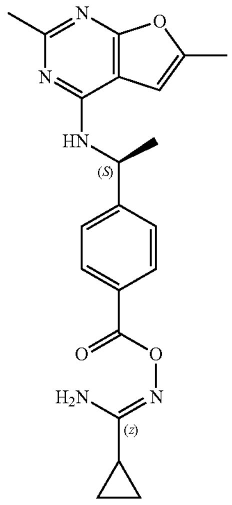

7

To a solution of 4-[(1S)-1-[(2,6-dimethylfuro[2,3-d]pyrimidin-4-yl)amino]ethyl]benzoic acid (80 mg, 256.96 umol, 1 eq) in DMF (3 mL) was added DIEA (100 mg, 770.88 umol, 134.27 uL, 3 eq), HBTU (117 mg, 308.35 umol, 1.2 eq), and N'-hydroxycyclopropanecarboxamidine (39 mg, 385.44 umol, 1.5 eq) and the mixture was stirred at 30° C. for 12 hours. To the reaction mixture was added water (10 mL) and extracted with EtOAc (10 mL*4). The organic layer was washed with brine (30 mL), dried over $MgSO_4$ and concentrated in vacuo to give [(Z)-[amino(cyclopropyl) methylene]amino]4-[(1S)-1-[(2,6-dimethylfuro[2,3-d]pyrimidin-4-yl)amino]ethyl]benzoate (100 mg, crude) as a brown oil. ESI [M+H]=394.1

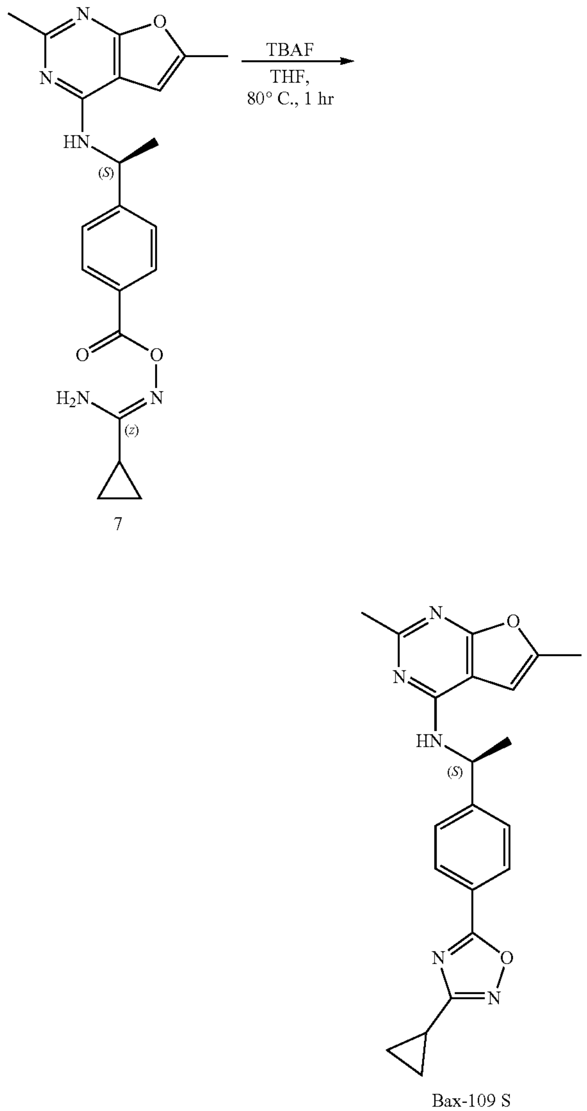

7

Bax-109 S

To a solution of [(Z)-[amino(cyclopropyl)methylene] amino] 4-[(1S)-1-[(2,6-dimethylfuro[2,3-d]pyrimidin-4-yl) amino]ethyl]benzoate (100 mg, 254.17 umol, 1 eq) in THF (3 mL) was added TBAF (1 M, 762.51 uL, 3 eq) (in THF). The mixture was stirred at 80° C. for 1 hr. The reaction mixture was concentrated in vacuo to give a residue. The residue was purified by prep-TLC ($SiO_2$, Petroleum ether: Ethyl acetate=0:1), and then the residue was purified again by prep-HPLC (column: Waters Xbridge 150*25 5u; mobile phase: [water (10 mM NH4HCO3)-ACN]; B %: 35%-65%, 10 min) to give N-[(1S)-1-[4-(3-cyclopropyl-1,2,4-oxadiazol-5-yl)phenyl]ethyl]-2,6-dimethyl-furo[2,3-d]pyrimidin-4-amine (43.04 mg, 114.64 umol, 45.11% yield, 100% purity) as a white solid.

$^1$H-NMR (400 MHz, CHLOROFORM-d) δ 8.05 (d, J=8.4 Hz, 2H), 7.52 (d, J=8.4 Hz, 2H), 6.05 (s, 1H), 5.45-5.31 (m, 1H), 5.19 (br d, J=5.1 Hz, 1H), 2.52 (s, 3H), 2.35 (s, 3H), 2.19-2.04 (m, 1H), 1.64 (d, J=6.8 Hz, 3H), 1.13-1.05 (m, 4H). ESI [M+H]=376.1.

Example 46

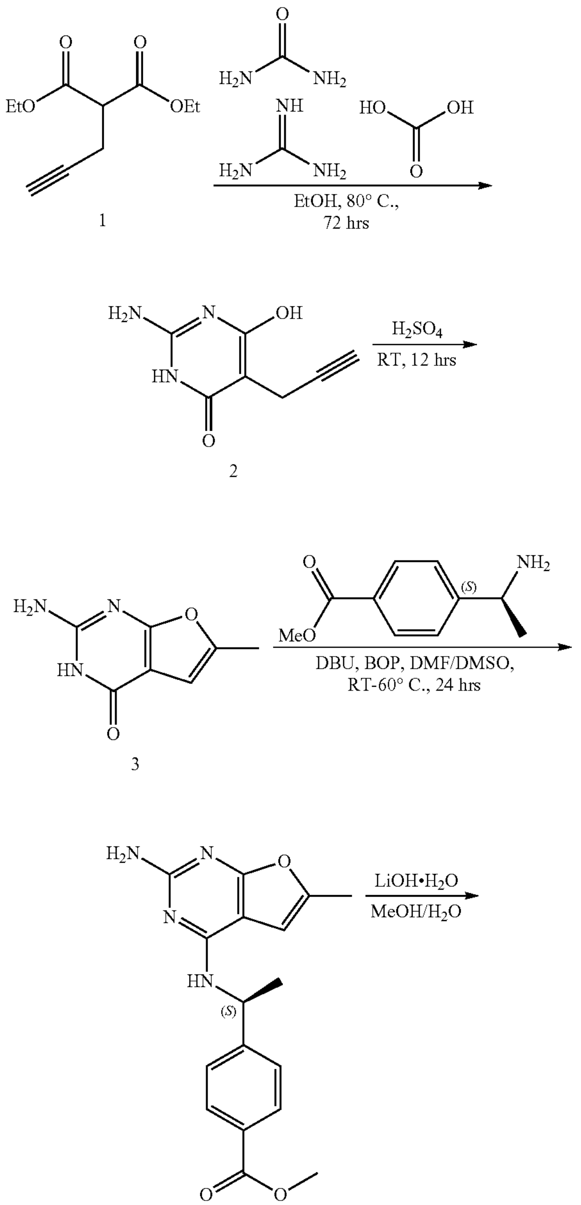

1

2

3

4

-continued

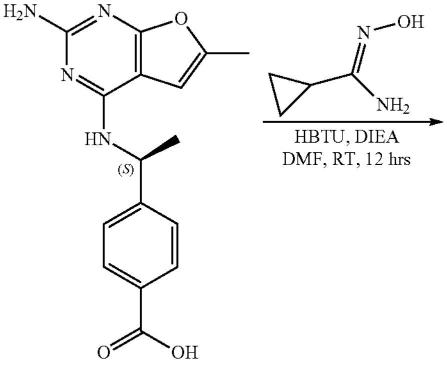

5

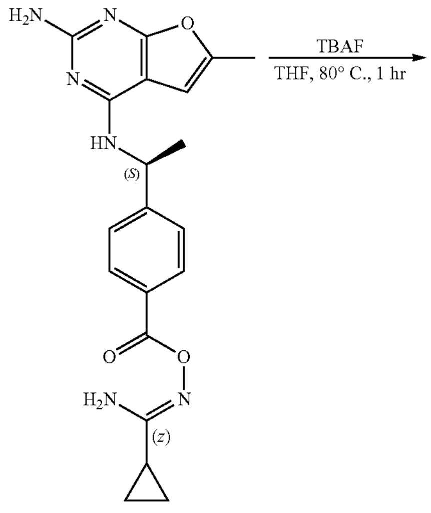

6

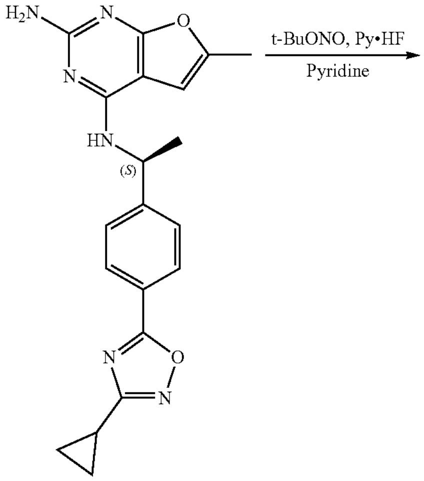

7

-continued

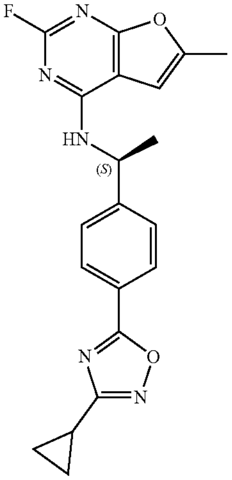

Bax-110 S

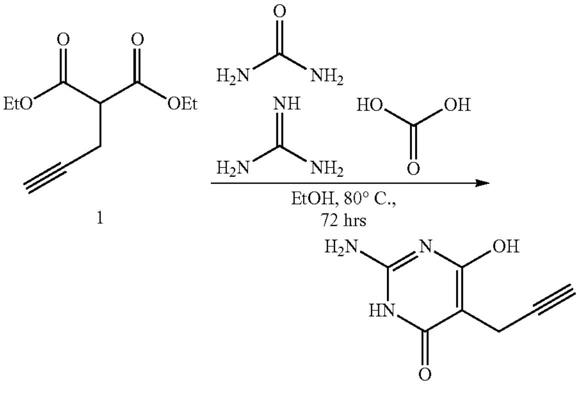

1

2

A mixture of diethyl 2-prop-2-ynylpropanedioate (5 g, 25.23 mmol, 1 eq) and guanidine carbonate (2.50 g, 13.88 mmol, 0.55 eq) in EtOH (50 mL) was stirred at 80° C. for 72 hrs under N2. The reaction mixture was cooled to 15° C., filtered, the filter cake was collected and then dissolved in water (10 mL). The aqueous layer was adjusted to pH=3 with 0.5M HCl, the precipitate was formed, and filtered, the filter cake was collected and concentrated in vacuo to give 2-amino-4-hydroxy-5-prop-2-ynyl-1H-pyrimidin-6-one (1 g, 6.06 mmol, 24.00% yield) as a light red solid. ESI [M+H]=166.2.

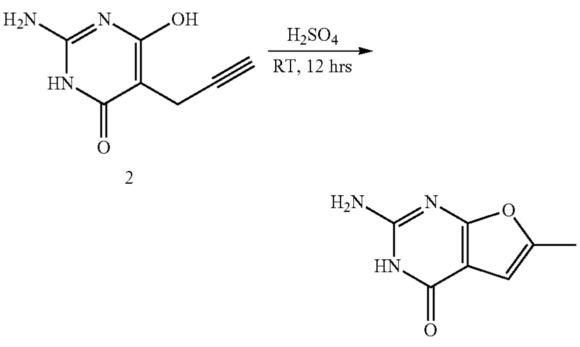

2

3

A solution of 2-amino-4-hydroxy-5-prop-2-ynyl-1H-pyrimidin-6-one (1.2 g, 7.27 mmol, 1 eq) in conc·$H_2SO_4$ (10 mL) was stirred at 25° C. for 12 hrs. The reaction mixture was added dropwise to cold water (20 mL). Then the mixture was added dropwise 5N NaOH solution until the precipitate was formed. The precipitate was filtered, the filter cake was collected and concentrated in vacuo. The crude product 2-amino-6-methyl-3H-furo[2,3-d]pyrimidin-4-one (0.4 g, crude) as a red solid was used into the next step without further purification. ESI [M+H]=166.1.

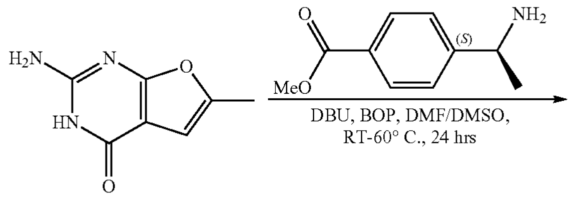

3

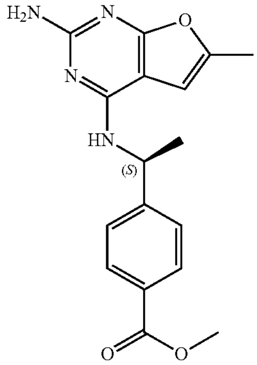

4

To a mixture of 2-amino-6-methyl-3H-furo[2,3-d]pyrimidin-4-one (0.4 g, 2.42 mmol, 1 eq), DBU (737.45 mg, 4.84 mmol, 730.15 uL, 2 eq) and BOP (1.29 g, 2.91 mmol, 1.2 eq) in DMF (10 mL) and DMSO (10 mL) was added methyl 4-[(1S)-1-aminoethyl]benzoate (1.30 g, 7.27 mmol, 3 eq) and the mixture was stirred at 30° C. for 12 hrs. Then the mixture was heated to 60° C. for 12 hrs. To the reaction mixture was added water (30 mL) and extracted with EtOAc (20 mL*3). The organic layer was washed with brine (50 mL), dried over $MgSO_4$ and concentrated in vacuo. The residue was purified by column chromatography (plate 1, $SiO_2$, Petroleum ether/Ethyl acetate=10/1 to 3/1) to give methyl 4-[(1S)-1-[(2-amino-6-methyl-furo[2,3-d]pyrimidin-4-yl)amino]ethyl]benzoate (0.6 g, 1.84 mmol, 75.91% yield) as a yellow oil. ESI [M+H]=327.2.

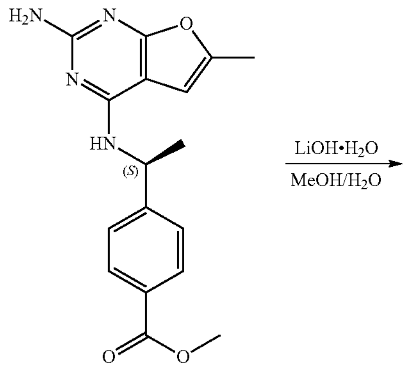

5

-continued

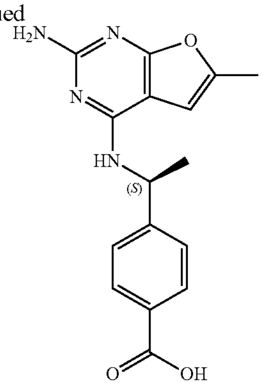

6

To a solution of methyl 4-[(1S)-1-[(2-amino-6-methyl-furo[2,3-d]pyrimidin-4-yl)amino]ethyl]benzoate (0.6 g, 1.84 mmol, 1 eq) in MeOH (15 mL) and $H_2O$ (5 mL) was added $LiOH{\cdot}H_2O$ (154.30 mg, 3.68 mmol, 2 eq), and the mixture was stirred at 30° C. for 12 hrs. MeOH was removed, the aqueous layer was washed with MTBE (5 mL*2), then adjusted to pH~2 with 1N HCl, and extracted with EtOAc (10 mL*3). The organic layer was dried over $MgSO_4$ and concentrated in vacuo to give 4-[(1S)-1-[(2-amino-6-methyl-furo[2,3-d]pyrimidin-4-yl)amino]ethyl] benzoic acid (0.4 g, 1.28 mmol, 69.66% yield) as a yellow solid. ESI [M+H]=313.1.

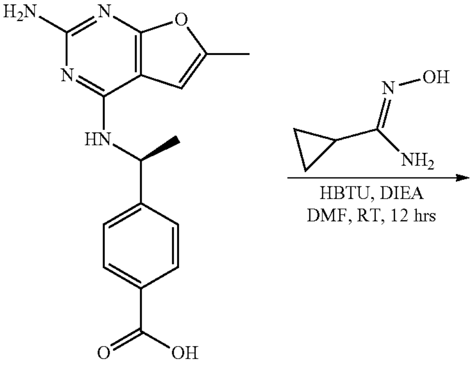

6

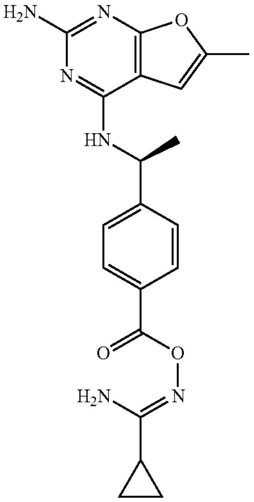

7

To a mixture of 4-[(1S)-1-[(2-amino-6-methyl-furo[2,3-d]pyrimidin-4-yl)amino]ethyl]benzoic acid (170 mg, 544.31 umol, 1 eq), DIEA (211.04 mg, 1.63 mmol, 284.43 μL, 3 eq) and N'-hydroxycyclopropanecarboxamidine (81.74 mg, 816.46 umol, 1.5 eq) in DMF (5 mL) was added HBTU (247.71 mg, 653.17 umol, 1.2 eq). Then the mixture was stirred at 30° C. for 12 hrs. To the reaction mixture was added water (20 mL) and extracted with EtOAc (20 mL*5). The organic layer was washed with brine (20 mL*2), dried over $MgSO_4$ and concentrated in vacuo to give [(Z)-[amino(cyclopropyl)methylene]amino]4-[(1S)-1-[(2-amino-6-methyl-furo[2,3-d]pyrimidin-4-yl)amino]ethyl]benzoate (0.4 g, crude) as a yellow solid, it was used into the next step without further purification. ESI [M+H]=395.1.

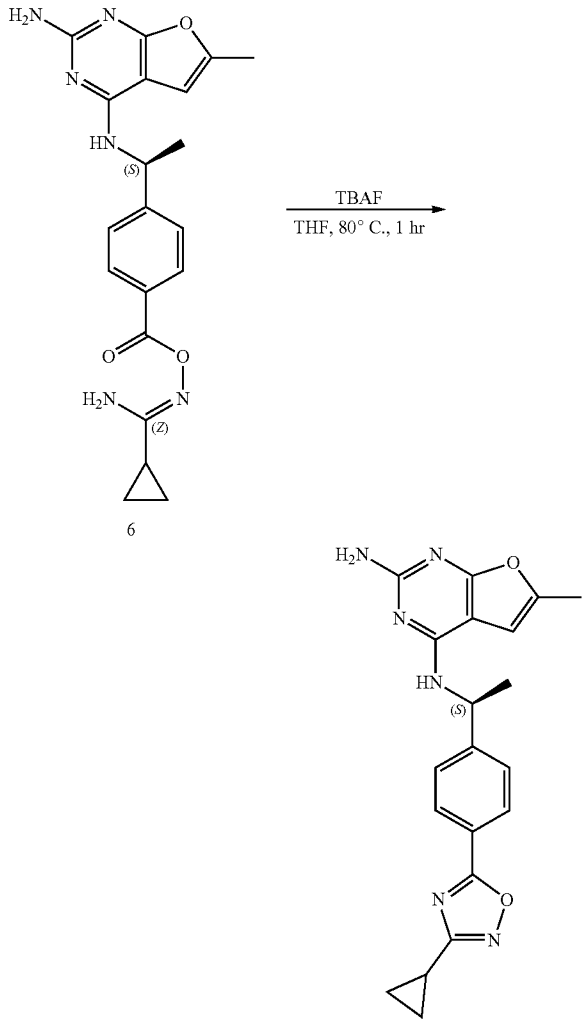

6

7

To a solution of [(Z)-[amino(cyclopropyl)methylene]amino] 4-[(1S)-1-[(2-amino-6-methyl-furo[2,3-d]pyrimidin-4-yl)amino]ethyl]benzoate (0.4 g, 1.01 mmol, 1 eq) in THF (6 mL) was added TBAF (1 M, 2.03 mL, 2 eq), and the mixture was stirred at 80° C. for 1 hr. The reaction was concentrated in vacuo. The residue was purified by prep-TLC ($SiO_2$, Petroleum ether:Ethyl acetate=0:1) to give N4-[(1S)-1-[4-(3-cyclopropyl-1,2,4-oxadiazol-5-yl)phenyl]ethyl]-6-methyl-furo[2,3-d]pyrimidine-2,4-diamine (200 mg, 531.33 μmol, 52.39% yield) as a yellow oil. ESI [M+H]=377.1.

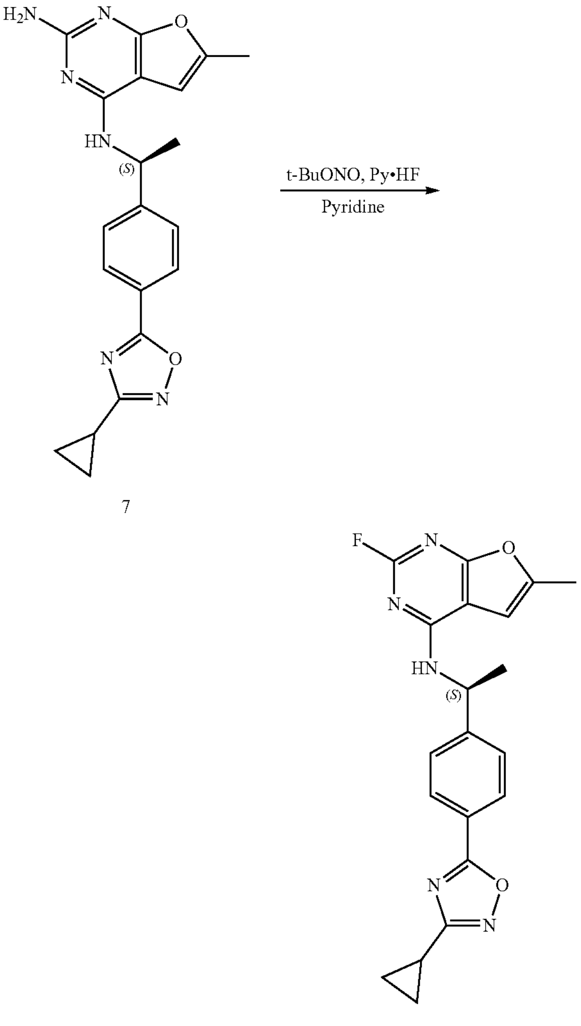

7

Bax-110 S

To a solution of N4-[(1S)-1-[4-(3-cyclopropyl-1,2,4-oxadiazol-5-yl)phenyl]ethyl]-6-methyl-furo[2,3-d]pyrimidine-2,4-diamine (70 mg, 185.97 umol, 1 eq) in Pyridine (0.3 mL) was added pyridine; hydrofluoride (660.00 mg, 6.66 mmol, 0.6 mL, 35.81 eq) at −50° C., the mixture was stirred at −25° C. for 15 mins. Then tert-butyl nitrite (38.35 mg, 371.93 umol, 44.24 uL, 2 eq) was added at −25° C. The mixture was stirred at 15° C. for 1 hr. Cold water (15 mL) was added, then the reaction mixture was adjusted to pH=8 with sat.aq $NaHCO_3$ and extracted with DCM (15 mL*4). The combined organic layers were dried over drying $Na_2SO_4$, filtered and concentrated under reduced pressure to give a residue. The residue was purified by prep-HPLC (column: Phenomenex Luna C18 150*30 mm*5 um; mobile phase: [water (0.04% HCl)-ACN]; B %: 45%-80%, 10 min) to give N-[(1S)-1-[4-(3-cyclopropyl-1,2,4-oxadiazol-5-yl)phenyl]ethyl]-2-fluoro-6-methyl-furo[2,3-d]pyrimidin-4-amine (16.18 mg, 42.65 umol, 22.93% yield, 100% purity) as a white solid.

$^1$H-NMR (400 MHz, CHLOROFORM-d) δ 8.09 (br d, J=8.2 Hz, 2H), 7.54 (br d, J=8.2 Hz, 2H), 6.18 (br s, 1H), 5.51-5.28 (m, 2H), 2.41 (s, 3H), 2.21-2.11 (m, 1H), 1.69 (br d, J=6.6 Hz, 3H), 1.16-1.07 (m, 4H). ESI [M+H]=380.2.

Example 47

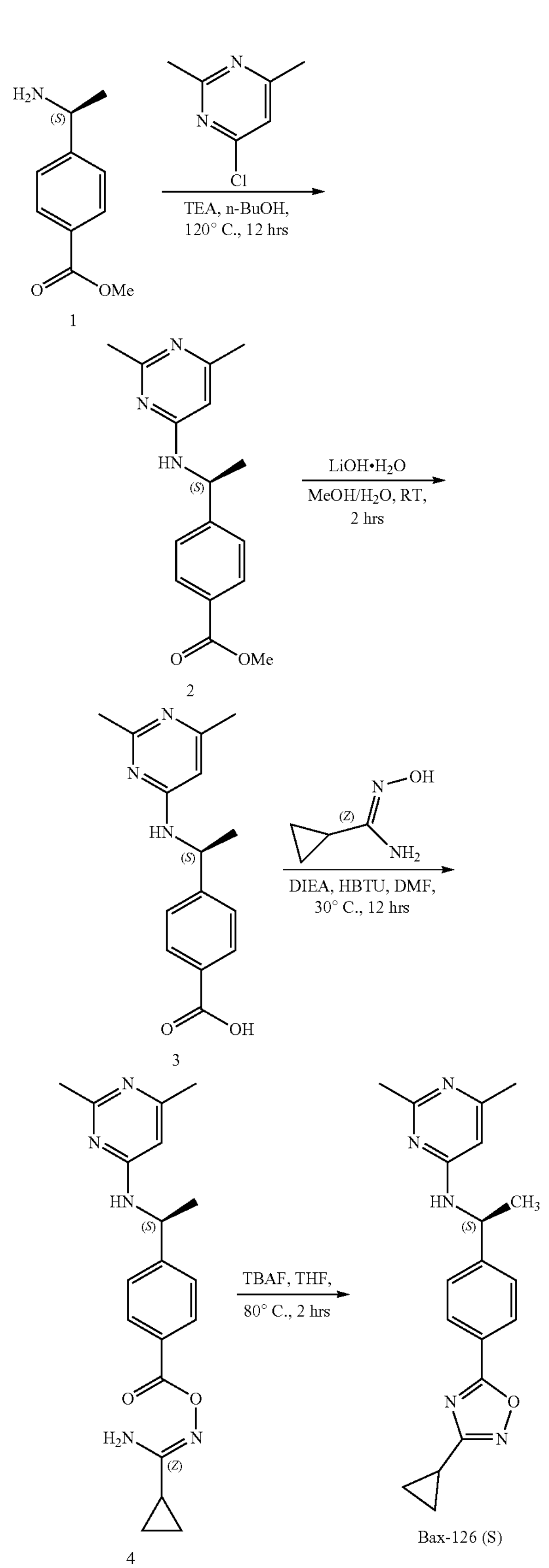

1

2

3

4

Bax-126 (S)

-continued

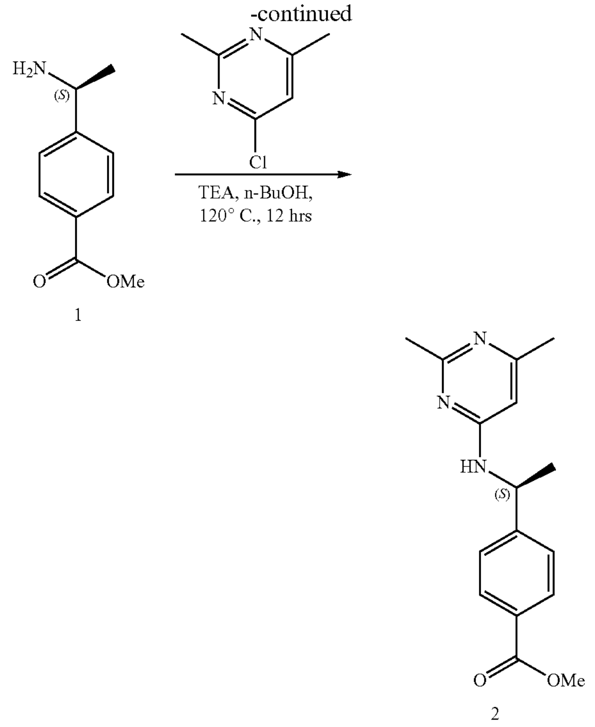

1

2

To a solution of methyl 4-[(1S)-1-aminoethyl]benzoate (300 mg, 1.67 mmol, 1 eq) in n-BuOH (7 mL) was added TEA (338.78 mg, 3.35 mmol, 465.99 uL, 2 eq) and 4-chloro-2,6-dimethyl-pyrimidine (238.68 mg, 1.67 mmol, 1 eq). The mixture was stirred at 120° C. for 12 hrs. The reaction was concentrated in vacuo to give a residue. The residue was purified by column chromatography ($SiO_2$, Petroleum ether/THF=10/1 to 1/1) to give methyl 4-[(1S)-1-[(2,6-dimethylpyrimidin-4-yl)amino]ethyl]benzoate (330 mg, 1.16 mmol, 69.09% yield) as a yellow solid. ESI [M+H]=286.2.

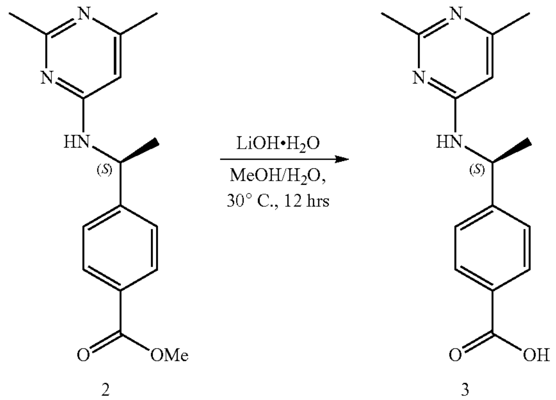

2

3

To a solution of methyl 4-[(1S)-1-[(2,6-dimethylpyrimidin-4-yl)amino]ethyl]benzoate (330.00 mg, 1.16 mmol, 1 eq) in MeOH (3 mL) and $H_2O$ (1 mL) was added $LiOH{\cdot}H_2O$ (97.06 mg, 2.31 mmol, 2 eq). The mixture was stirred at 30° C. for 12 hrs. MeOH was removed, the aqueous layer was washed with MTBE (15 mL*2), then adjusted pH=2 with 1N HCl, and extracted with DCM/i-PrOH (3/1, 15 mL*5). The organic layer was dried over $MgSO_4$ and concentrated in vacuo to give 4-[(1S)-1-[(2,6-dimethylpyrimidin-4-yl)

amino]ethyl]benzoic acid (165 mg, 608.15 umol, 52.58% yield) as a white solid. ESI [M+H]=272.1.

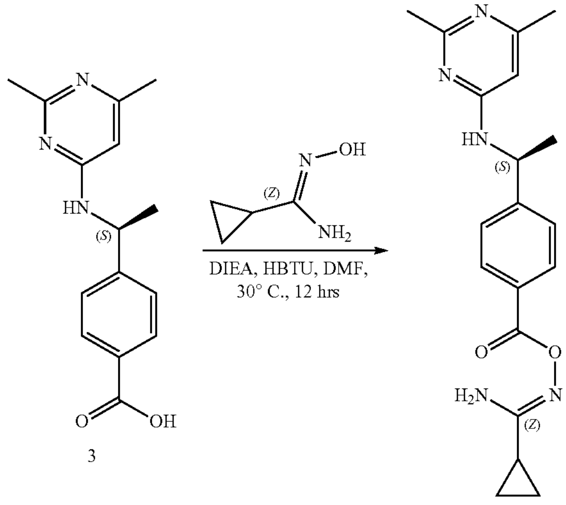

3

4

To a solution of 4-[(1S)-1-[(2,6-dimethylpyrimidin-4-yl) amino]ethyl]benzoic acid (165.00 mg, 608.15 umol, 1 eq) in DMF (3 mL) was added DIEA (235.80 mg, 1.82 mmol, 317.79 uL, 3 eq), N'-hydroxycyclopropanecarboxamidine (91.33 mg, 912.23 umol, 1.5 eq) and HBTU (276.76 mg, 729.78 umol, 1.2 eq). The mixture was stirred at 30° C. for 12 hrs. To the reaction mixture was added water (20 mL) and extracted with DCM/i-PrOH (3/1, 20 mL*5). The organic layer was washed with brine (20 mL*2), dried over $MgSO_4$ and concentrated in vacuo to give [(Z)-[amino(cyclopropyl) methylene]amino]4-[(1S)-1-[(2,6-dimethylpyrimidin-4-yl) amino]ethyl]benzoate (0.4 g, crude) as a brown oil, it was used into the next step without further purification. ESI [M+H]=354.1.

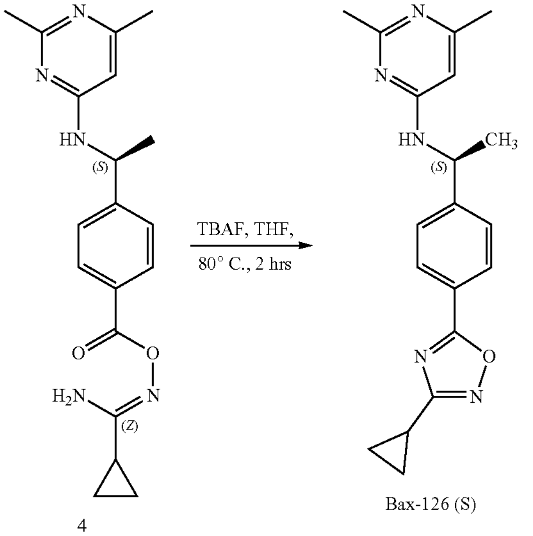

4

Bax-126 (S)

To a solution of [(Z)-[amino(cyclopropyl)methylene] amino] 4-[(1S)-1-[(2,6-dimethylpyrimidin-4-yl)amino] ethyl]benzoate (200 mg, 565.90 umol, 1 eq) in THF (3 mL) was added TBAF (1 M, 1.13 mL, 2 eq), the mixture was stirred at 80° C. for 2 hrs. The mixture was concentrated to give a residue. The residue was purified by prep-TLC (EtOAc:MeOH=10:1) to give the crude product. The crude product was purified by prep-HPLC (column: Phenomenex Luna C18 150*30 mm*5 um; mobile phase: [water (0.04% HCl)-ACN]; B %: 15%-45%, 10 min) to give N-[(1S)-1-[4-(3-cyclopropyl-1,2,4-oxadiazol-5-yl)phenyl]ethyl]-2,6-dimethyl-pyrimidin-4-amine (34.88 mg, 93.71 umol, 16.56% yield, 99.903% purity, HCl) as a white solid.

$^1$H-NMR (400 MHz, CHLOROFORM-d) δ 14.13 (br s, 1H), 9.93 (br s, 1H), 7.90 (d, J=7.8 Hz, 2H), 7.50 (d, J=8.1 Hz, 2H), 6.91 (br s, 1H), 5.36 (br t, J=6.7 Hz, 1H), 2.52 (s, 3H), 2.35 (s, 3H), 2.10-2.00 (m, 1H), 1.59 (br d, J=6.8 Hz, 3H), 1.05-0.98 (m, 4H). ESI [M+H]=336.2.

Example 48

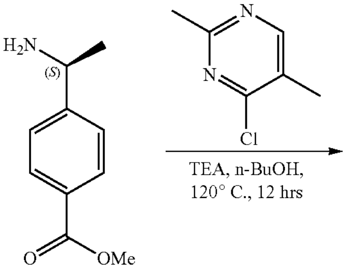

1

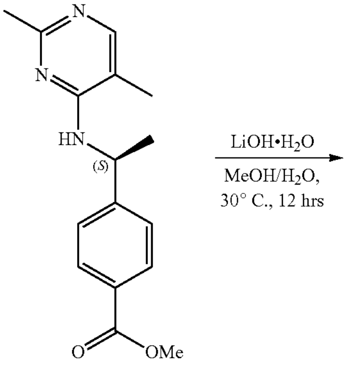

2

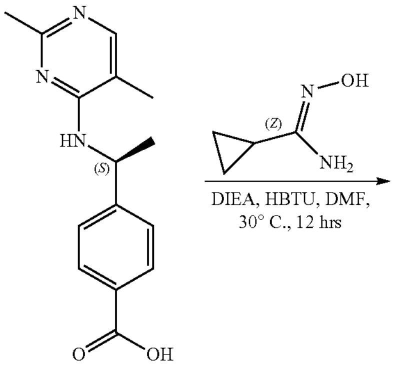

3

-continued

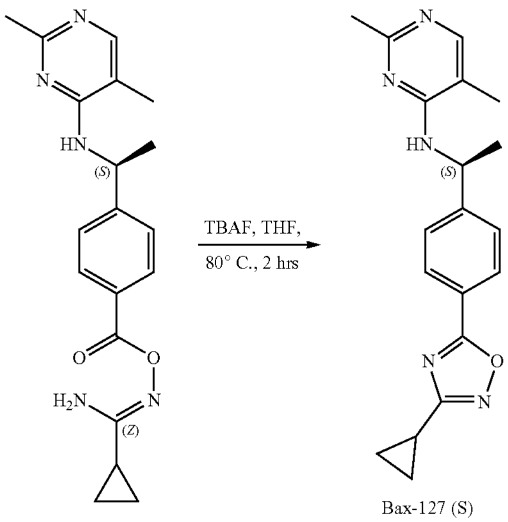

4

Bax-127 (S)

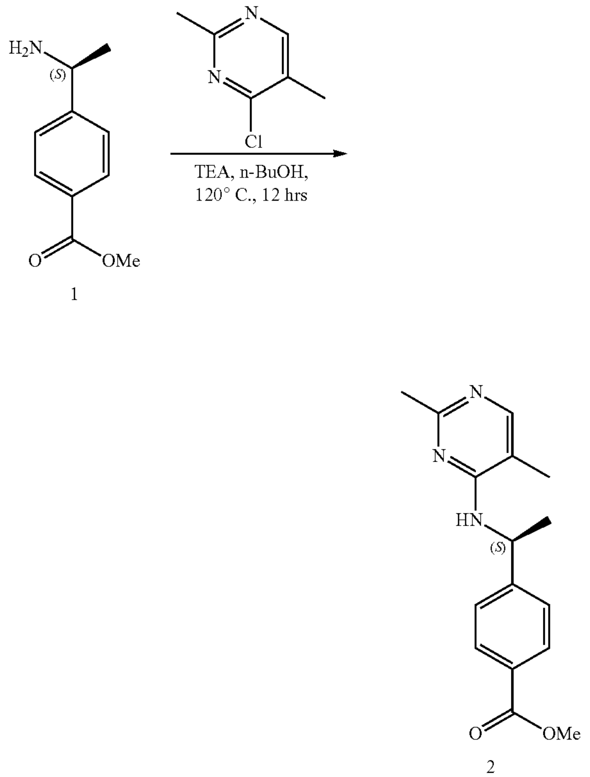

1

2

To a solution of methyl 4-[(1S)-1-aminoethyl]benzoate (300 mg, 1.67 mmol, 1 eq) in n-BuOH (7 mL) was added TEA (338.78 mg, 3.35 mmol, 465.99 uL, 2 eq) and 4-chloro-2,5-dimethyl-pyrimidine (286.42 mg, 2.01 mmol, 1.2 eq). The mixture was stirred at 120° C. for 12 hrs. The reaction mixture was concentrated in vacuo to give a residue. The residue was purified by column chromatography ($SiO_2$, Petroleum ether/THF=10/1 to 1/1) to give methyl 4-[(1S)-1-[(2,5-dimethylpyrimidin-4-yl)amino]ethyl]benzoate (250 mg, 876.15 umol, 52.34% yield) as a yellow solid. ESI [M+H]=286.2.

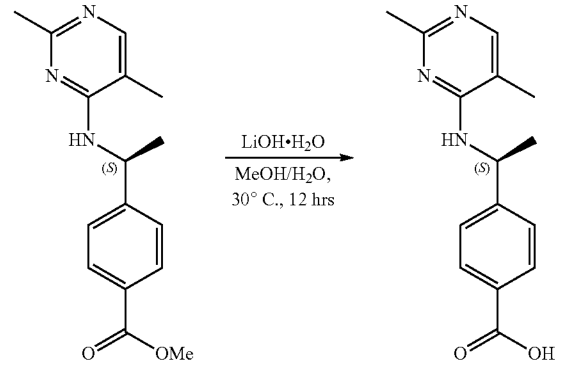

2

3

To a solution of methyl 4-[(1S)-1-[(2,5-dimethylpyrimidin-4-yl)amino]ethyl]benzoate (250 mg, 876.15 umol, 1 eq) in MeOH (3 mL) and $H_2O$ (1 mL) was added LiOH·$H_2O$ (73.53 mg, 1.75 mmol, 2 eq). The mixture was stirred at 30° C. for 12 hrs. MeOH was removed, the aqueous layer was washed with MTBE (20 mL*2), then adjusted pH=2 with 1N HCl, and extracted with DCM/i-PrOH (3/1, 20 mL*5). The organic layer was dried over $MgSO_4$ and concentrated in vacuo to give 4-[(1S)-1-[(2,5-dimethylpyrimidin-4-yl)amino]ethyl]benzoic acid (100 mg, 368.58 umol, 42.07% yield) as a white solid. ESI [M+H]=272.0.

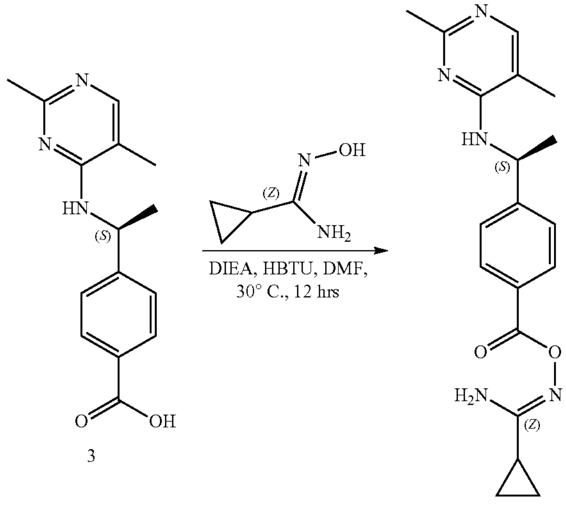

3

4

To a solution of 4-[(1S)-1-[(2,5-dimethylpyrimidin-4-yl)amino]ethyl]benzoic acid (100 mg, 368.58 umol, 1 eq) in DMF (3 mL) was added N'-hydroxycyclopropanecarboxamidine (55.35 mg, 552.87 umol, 1.5 eq), DIPEA (142.91 mg, 1.11 mmol, 192.60 μL, 3 eq) and HBTU (167.74 mg, 442.29 μmol, 1.2 eq). The mixture was stirred at 30° C. for 16 hrs. To the reaction mixture was added $H_2O$ (10 mL) and extracted with DCM/i-PrOH (10 mL*5, 3:1). The combined organic layers were washed with brine (10 mL*2), dried over $Na_2SO_4$, filtered and concentrated under reduced pressure to give [(Z)-[amino(cyclopropyl)methylene]amino] 4-[(1S)-1-[(2,5-dimethylpyrimidin-4-yl)amino]ethyl]benzoate (120 mg, crude) as a brown oil. ESI [M+H]=354.1.

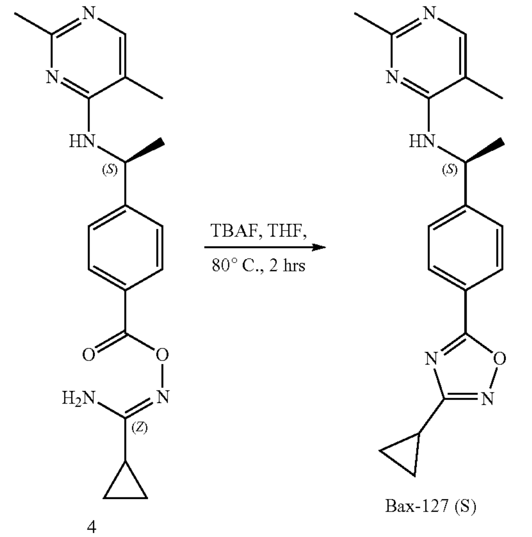

4 Bax-127 (S)

To a solution of [(Z)-[amino(cyclopropyl)methylene] amino] 4-[(1S)-1-[(2,5-dimethylpyrimidin-4-yl)amino] ethyl]benzoate (120.00 mg, 339.54 umol, 1 eq) in THF (2 mL) was added TBAF (1 M, 679.08 uL, 2 eq), the mixture was stirred at 80° C. for 2 hrs. The mixture was concentrated to give a residue. The residue was purified by prep-TLC (EtOAc:MeOH=10:1) and prep-HPLC (column: Phenomenex Luna C18 150*30 mm*5 µm; mobile phase: [water (0.04% HCl)-ACN]; B %: 15%-45%, 10 min) to give N-[(1S)-1-[4-(3-cyclopropyl-1,2,4-oxadiazol-5-yl)phenyl] ethyl]-2,5-dimethyl-pyrimidin-4-amine (24.13 mg, 63.44 umol, 18.68% yield, 97.759% purity, HCl) as a white solid.

$^1$H-NMR (400 MHz, CHLOROFORM-d) δ 15.17 (br s, 1H), 7.95 (d, J=7.9 Hz, 2H), 7.74 (br s, 1H), 7.63 (br s, 1H), 7.56 (br d, J=7.9 Hz, 2H), 5.53 (br t, J=6.7 Hz, 1H), 2.57 (s, 3H), 2.24 (s, 3H), 2.10-2.01 (m, 1H), 1.72 (br d, J=6.8 Hz, 3H), 1.05-0.99 (m, 4H). ESI [M+H]=336.2.

Example 49

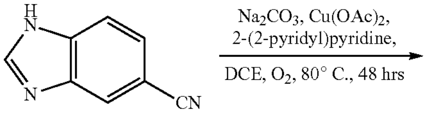

9

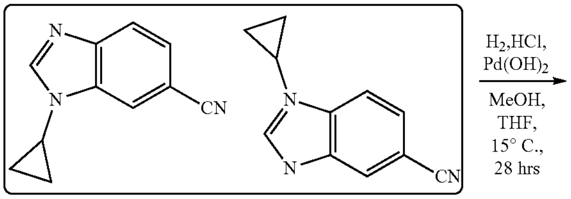

10A 10B

-continued

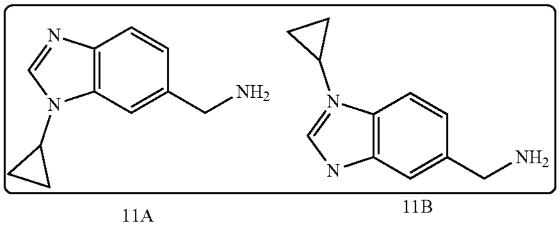

11A 11B

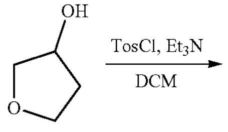

1

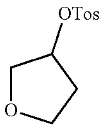

2

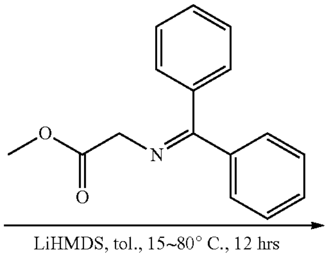

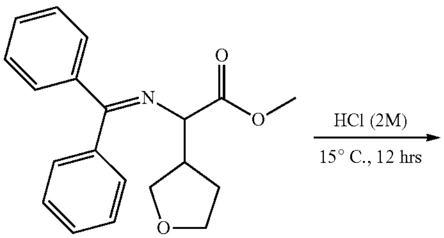

3

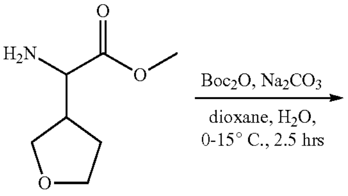

4

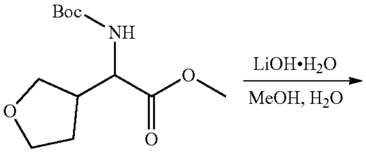

5

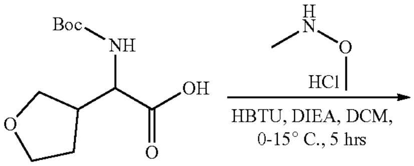

6

-continued

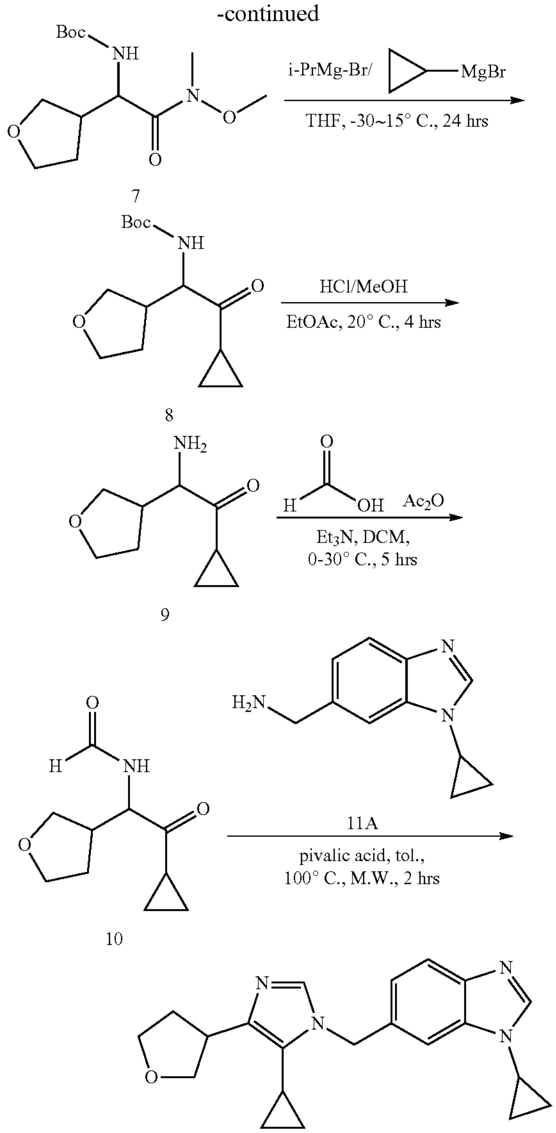

7, 8, 9, 10

Bax-131 RS

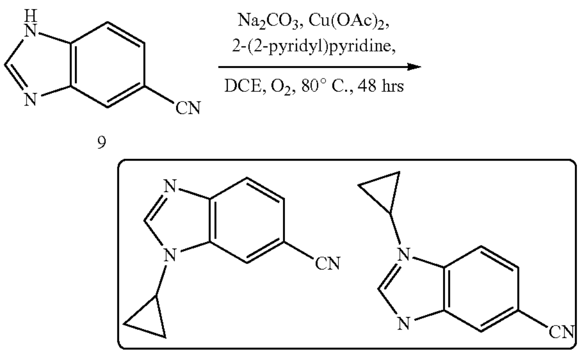

9

10A 10B

A mixture of 3H-benzimidazole-5-carbonitrile (0.5 g, 3.49 mmol, 1 eq), cyclopropylboronic acid (600.07 mg, 6.99 mmol, 2 eq), 2-(2-pyridyl)pyridine (545.53 mg, 3.49 mmol, 1 eq), $Cu(OAc)_2$ (634.43 mg, 3.49 mmol, 1 eq) and $Na_2CO_3$ (1.11 g, 10.48 mmol, 3 eq) in DCE (60 mL) was stirred at 80° C. for 12 hrs under $O_2$ (15 psi). LCMS showed a part of 3H-benzimidazole-5-carbonitrile was remained, so the mixture was stirred at 80° C. for another 36 hrs under 02 (15 psi). TLC (PE:EtOAc=0:1) showed 3H-benzimidazole-5-carbonitrile was consumed and a main spot with the lower polarity was detected. LCMS showed 3H-benzimidazole-5-carbonitrile was consumed and the main peaks with desired MS were detected. The reaction mixture was filtered, the filtrate was concentrated to give a residue. The residue was purified by column chromatography ($SiO_2$, Petroleum ether/Ethyl acetate=1/0 to 0/1) and prep-HPLC (column: Phenomenex Luna C18 150*30 mm*5 um; mobile phase: [water (0.04% HCl)-ACN]; B %: 5%-40%, 10 min) to give 3-cyclopropylbenzimidazole-5-carbonitrile (140 mg, 764.16 umol, 21.88% yield) and 1-cyclopropylbenzimidazole-5-carbonitrile (200 mg, 1.09 mmol, 31.25% yield) as white solid. P1 was the desired product and confirmed by $^1$H-NMR. ESI [M+H]=188.1.

$^1$H-NMR (400 MHz, METHANOL-d4) δ 9.75 (s, 1H), 8.61 (s, 1H), 8.07-7.99 (m, 2H), 3.90 (td, J=3.4, 7.2 Hz, 1H), 1.44-1.37 (m, 2H), 1.37-1.31 (m, 2H).

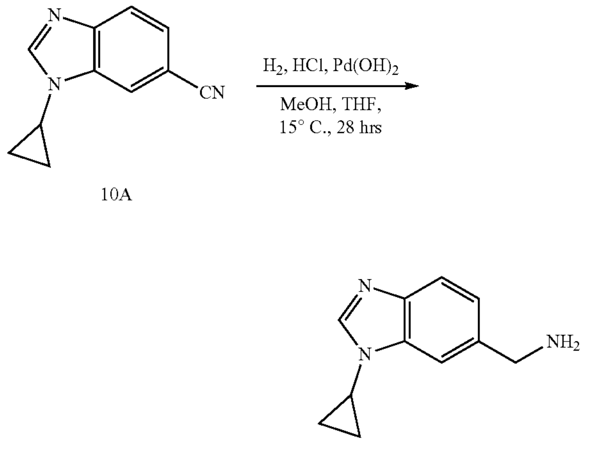

10A

11A

To a solution of 3-cyclopropylbenzimidazole-5-carbonitrile (140 mg, 764.16 umol, 1 eq) in MeOH (10 mL) and THF (5 mL) was added $Pd(OH)_2$ (107.31 mg, 764.16 umol, 1.00 eq) and HCl (12 M, 63.68 uL, 1 eq) under N2. The suspension was degassed under vacuum and purged with $H_2$ several times. The mixture was stirred under $H_2$ (15 psi) at 15° C. for 12 hrs. LCMS showed most of 3-cyclopropylbenzimidazole-5-carbonitrile was remained and the desired MS was detected. So to the mixture was added $Pd(OH)_2$ (214.63 mg, 1.53 mmol, 2.00 eq) and the mixture was stirred at 15° C. under $H_2$ (15 psi) for 16 hrs. LCMS showed 3-cyclopropylbenzimidazole-5-carbonitrile was consumed and only one peak with the desired MS was detected. The mixture was filtered, the filtrate was concentrated to give a residue. The residue was purified by prep-HPLC (column: Waters Xbridge Prep OBD C18 150*40 mm*10 μm; mobile phase: [water (0.04% NH3H2O+10 mM NH4HCO3)-ACN]; B %: 1%-15%, 10 min) to give (3-cyclopropylbenzimidazol-5-yl)methanamine (100 mg, 534.07 umol, 69.89% yield) as a colorless oil. ESI [M+H]=188.1.

$^1$H-NMR (400 MHz, METHANOL-d4) δ 8.17 (s, 1H), 7.72 (s, 1H), 7.63 (d, J=8.3 Hz, 1H), 7.31 (dd, J=1.0, 8.3 Hz, 1H), 4.06 (s, 2H), 3.53-3.46 (m, 1H), 1.24-1.16 (m, 2H), 1.11-1.05 (m, 2H).

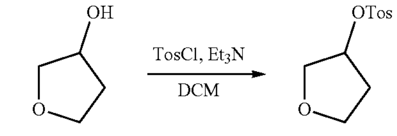

1 2

To a mixture of tetrahydrofuran-3-ol (30 g, 340.50 mmol, 27.52 mL, 1 eq) and $Et_3N$ (51.68 g, 510.76 mmol, 71.09 mL, 1.5 eq) in DCM (300 mL) was added TosCl (71.41 g, 374.55 mmol, 1.1 eq), the mixture was stirred at 15° C. for 48 hrs. TLC (PE:EtOAc=1:1) showed most of tetrahydrofuran-3-ol was consumed and one major new spot with lower polarity was detected. The mixture was concentrated to give a residue. The residue was purified by column chromatography ($SiO_2$, Petroleum ether/Ethyl acetate=1/0 to 3/1) to give tetrahydrofuran-3-yl 4-methylbenzenesulfonate (67 g, 276.53 mmol, 81.21% yield) as a light brown oil.

$^1$H-NMR (400 MHz, CHLOROFORM-d) δ 7.72 (d, J=8.1 Hz, 2H), 7.29 (d, J=8.1 Hz, 2H), 5.04 (br d, J=2.4 Hz, 1H), 3.86-3.70 (m, 4H), 2.39 (s, 3H), 2.08-1.97 (m, 2H).

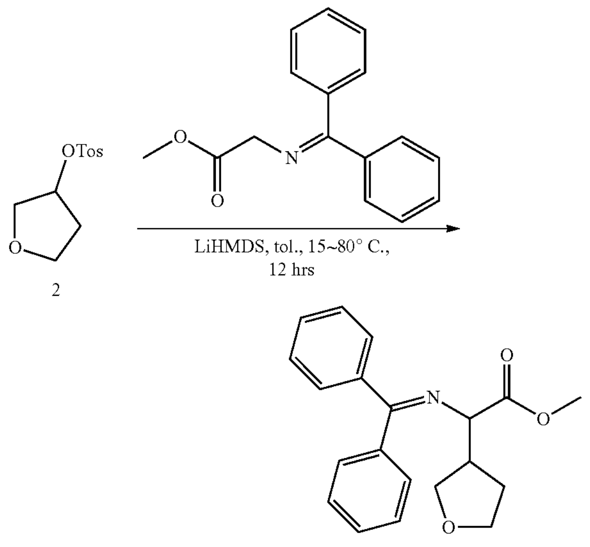

2 3

To a 15° C. stirred mixture of tetrahydrofuran-3-yl 4-methylbenzenesulfonate (15 g, 61.91 mmol, 1.2 eq) and methyl 2-(benzhydrylideneamino)acetate (13.07 g, 51.59 mmol, 1 eq) in Tol. (150 mL) was added LiHMDS (1 M, 61.91 mL, 1.2 eq) (in THF) dropwise, the resulting mixture was stirred at 80° C. for 12 hrs. LCMS showed the desired MS was detected. TLC (PE:EtOAc=3:1) showed most of methyl 2-(benzhydrylideneamino)acetate was consumed and the desired spots were detected. The reaction mixture was concentrated under reduced pressure to remove Tol. To the residue was added $H_2O$ (100 mL) and extracted with EtOAc (100 mL*3). The combined organic layers were washed with brine (100 mL), dried over $Na_2SO_4$, filtered and concentrated under reduced pressure to give a residue. The residue was purified by column chromatography ($SiO_2$, Petroleum ether/Ethyl acetate=1/0 to 10/1) to give methyl 2-(benzhydrylideneamino)-2-tetrahydrofuran-3-yl-acetate (12 g, 37.11 mmol, 71.93% yield) as a brown oil. ESI [M+H]=324.1.

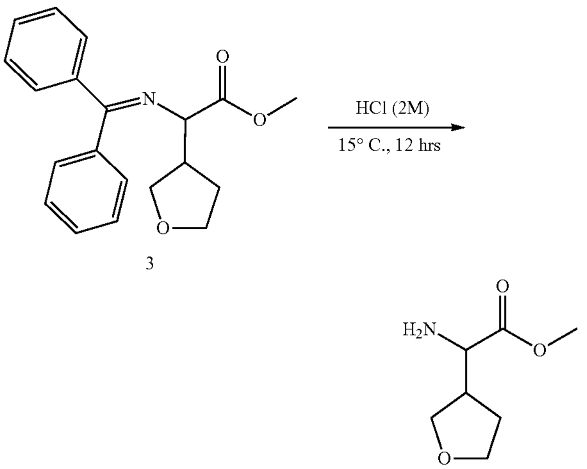

3 4

To a solution of methyl 2-(benzhydrylideneamino)-2-tetrahydrofuran-3-yl-acetate (12 g, 37.11 mmol, 1 eq) in THF (100 mL) was added HCl (2 M, 37.11 mL, 2 eq) dropwise at 15° C., the mixture was stirred at 15° C. for 12 hrs. TLC (PE:EtOAc=2:1) showed methyl 2-(benzhydrylideneamino)-2-tetrahydrofuran-3-yl-acetate was consumed. The reaction mixture was concentrated to remove THF. The residue was extracted with MTBE (30 mL*3). The aqueous layer was adjusted to pH=8~9 by $Na_2CO_3$ solid, methyl 2-amino-2-tetrahydrofuran-3-yl-acetate (5 g, crude) was obtained as a brown oil and then it was used directly to the next step.

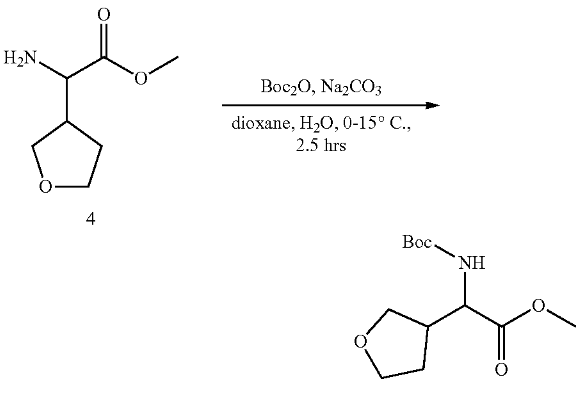

4 5

To a mixture of methyl 2-amino-2-tetrahydrofuran-3-yl-acetate (5.00 g, 31.41 mmol, 1 eq) and $Na_2CO_3$ (3.33 g, 31.41 mmol, 1 eq) in dioxane (30 mL) and $H_2O$ (30 mL) (pH-8) was added $Boc_2O$ (8.23 g, 37.69 mmol, 8.66 mL, 1.2 eq) at 0° C. The resulting mixture was stirred at 15° C. for 2.5 hrs. LCMS showed methyl 2-amino-2-tetrahydrofuran-3-yl-acetate was consumed and the desired MS was detected. TLC (PE:EtOAc=3:1) showed two major new spots with lower polarity were detected. To the reaction mixture was added $H_2O$ (20 mL) and extracted with DCM (20 mL*3). The combined organic layers were dried over $Na_2SO_4$, filtered and concentrated under reduced pressure to give a residue. The residue was purified by column chromatography ($SiO_2$, Petroleum ether/Ethyl acetate=1/0 to 5/1) to give methyl 2-(tert-butoxycarbonylamino)-2-tetrahydrofuran-3-yl-acetate (5.8 g, 22.37 mmol, 71.21% yield) as a colorless oil. ESI [1/2M+H]=160.2, [M−56+H]=204.2, [M+H]=260.2.

$^1$H-NMR (400 MHz, CHLOROFORM-d) δ 5.16 (br d, J=7.5 Hz, 1H), 4.34-4.15 (m, 1H), 3.76-3.59 (m, 7H), 2.69-2.53 (m, 1H), 2.08-1.73 (m, 2H), 1.43 (d, J=1.1 Hz, 9H).

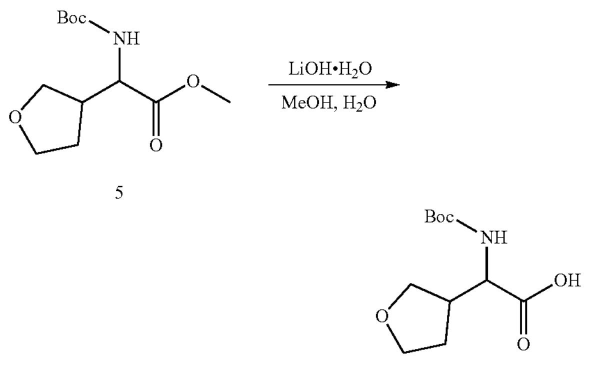

5

6

To a solution of methyl 2-(tert-butoxycarbonylamino)-2-tetrahydrofuran-3-yl-acetate (5.8 g, 22.37 mmol, 1 eq) in MeOH (60 mL) and $H_2O$ (20 mL) was added LiOH·$H_2O$ (1.88 g, 44.74 mmol, 2.0 eq), the resulting mixture was stirred at 15° C. for 12 hrs. LCMS showed methyl 2-(tert-butoxycarbonylamino)-2-tetrahydrofuran-3-yl-acetate was consumed and the desired MS was detected. The mixture was concentrated to give a residue. To the residue was added $H_2O$ (20 mL), acidified to Ph=5-4 by 1M HCl solution and extracted with ethyl acetate/THF (3:1, 20 mL*5). The combined organic phase was washed with brine (20 mL*2), dried over anhydrous $Na_2SO_4$, filtered and concentrated in vacuum to give 2-(tert-butoxycarbonylamino)-2-tetrahydrofuran-3-yl-acetic acid (5.4 g, 22.02 mmol, 98.43% yield) as a brown oil. ESI [1/2M+H]=146.0, [M−56+H]=190.0, [M+23]=268.1.

$^1$H-NMR (400 MHz, CHLOROFORM-d) δ 10.15 (br s, 1H), 5.25 (br dd, J=8.4, 14.6 Hz, 1H), 4.26 (br d, J=6.4 Hz, 1H), 3.92-3.77 (m, 1H), 3.74-3.57 (m, 2H), 2.64 (br d, J=7.2 Hz, 1H), 2.09-1.89 (m, 2H), 1.87-1.67 (m, 1H), 1.38 (s, 9H).

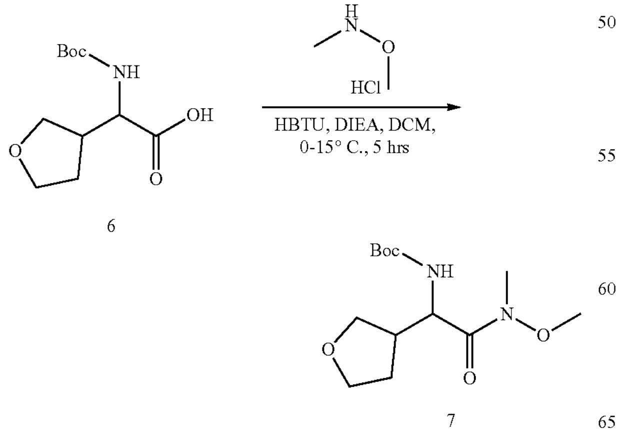

6

7

To a 0° C. stirred solution of 2-(tert-butoxycarbonylamino)-2-tetrahydrofuran-3-yl-acetic acid (5.40 g, 22.02 mmol, 1 eq) in DCM (60 mL) was added HBTU (10.02 g, 26.42 mmol, 1.2 eq) and DIPEA (5.69 g, 44.03 mmol, 7.67 mL, 2 eq), the mixture was stirred at 0° C. for 10 mins, then N-methoxymethanamine; hydrochloride (2.58 g, 26.42 mmol, 1.2 eq) was added. The resulting mixture was stirred at 15° C. for 5 hrs. LCMS showed 2-(tert-butoxycarbonylamino)-2-tetrahydrofuran-3-yl-acetic acid was consumed and the desired MS was detected. To the reaction mixture was added $H_2O$ (40 mL), extracted with DCM (20 mL*3). The combined organic layers were dried over $Na_2SO_4$, filtered and concentrated under reduced pressure to give a residue. The residue was purified by column chromatography ($SiO_2$, Petroleum ether/Ethyl acetate=1/0 to 10/1) to give tert-butyl N-[2-[methoxy(methyl)amino]-2-oxo-1-tetrahydrofuran-3-yl-ethyl]carbamate (6.15 g, 20.81 mmol, 94.52% yield) as a white solid. ESI [1/2M+H]=189.1, [M−56+H]=233.1, [M+H]=289.1.

$^1$H-NMR (400 MHz, CHLOROFORM-d) δ 5.27 (br s, 1H), 4.78 (br s, 1H), 3.93-3.52 (m, 7H), 3.22 (s, 3H), 2.65-2.49 (m, 1H), 2.05-1.74 (m, 2H), 1.43 (s, 9H).

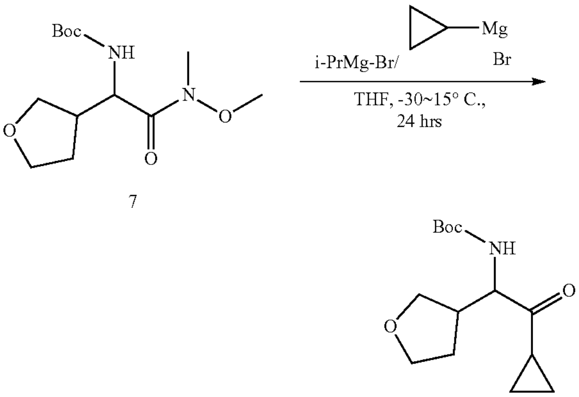

7

8

To a −30° C. stirred solution of tert-butyl N-[2-[methoxy(methyl)amino]-2-oxo-1-tetrahydrofuran-3-yl-ethyl]carbamate (1 g, 3.47 mmol, 1 eq) in THF (20 mL) was added i-PrMgCl (2 M, 1.65 mL, 0.95 eq) (in THF) dropwise. Then the mixture was warmed to 10° C. and bromo(cyclopropyl)magnesium (0.5 M, 10.40 mL, 1.5 eq) (in THF) was added dropwise and the resulting mixture was stirred at 15° C. for 12 hrs. LCMS and HPLC showed about ⅖ of tert-butyl N-[2-[methoxy(methyl)amino]-2-oxo-1-tetrahydrofuran-3-yl-ethyl]carbamate was remained and ⅗ of the desired product was detected. So to the mixture was added bromo(cyclopropyl)magnesium (0.5 M, 3.47 mL, 0.5 eq) at 15° C. under N2, and the mixture was stirred at 15° C. for 12 hrs. HPLC showed 1/3 of tert-butyl N-[2-[methoxy(methyl)amino]-2-oxo-1-tetrahydrofuran-3-yl-ethyl]carbamate was still remained and 2/3 of the desired product was detected. The reaction mixture was quenched by addition saturated aq·$NH_4Cl$ (50 mL), and extracted with EtOAc (20 mL*3). The combined organic layers were washed with brine (10 mL*2), dried over $Na_2SO_4$, filtered and concentrated under reduced pressure to give a residue. The residue was purified by prep-HPLC (column: Nano-micro Kromasil C18 100*30 mm 5 um; mobile phase: [water (0.1% TFA)-ACN]; B %: 25%-45%, 10 min) to give tert-butyl N-(2-cyclopropyl-2-oxo-1-tetrahydrofuran-3-yl-ethyl)carbamate (450 mg, 1.67 mmol, 48.18% yield) as a white solid. ESI [1/2M+H]=170.2, [M−56+H]=214.2, [M+H]=270.2.

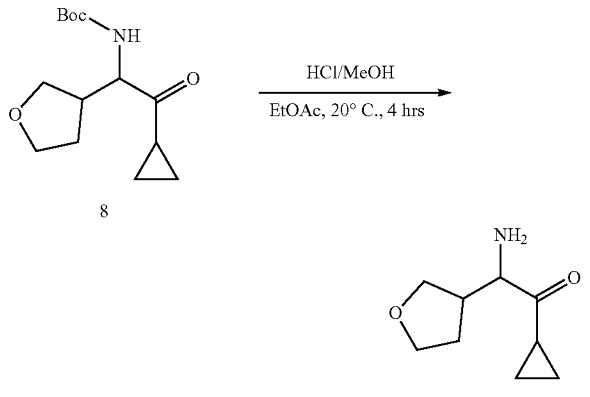

8

9

To a solution of tert-butyl N-(2-cyclopropyl-2-oxo-1-tetrahydrofuran-3-yl-ethyl)carbamate (450 mg, 1.67 mmol, 1 eq) in EtOAc (10 mL) was added HCl/MeOH (4 M, 4 mL, 9.58 eq). The resulting mixture was stirred at 20° C. for 4 hrs. LCMS showed tert-butyl N-(2-cyclopropyl-2-oxo-1-tetrahydrofuran-3-yl-ethyl)carbamate was consumed and the main peak with the desired MS was detected. The reaction mixture was concentrated under reduced pressure to give 2-amino-1-cyclopropyl-2-tetrahydrofuran-3-yl-ethanone (340 mg, crude, HCl) as a colorless oil. ESI [M+H]=170.1

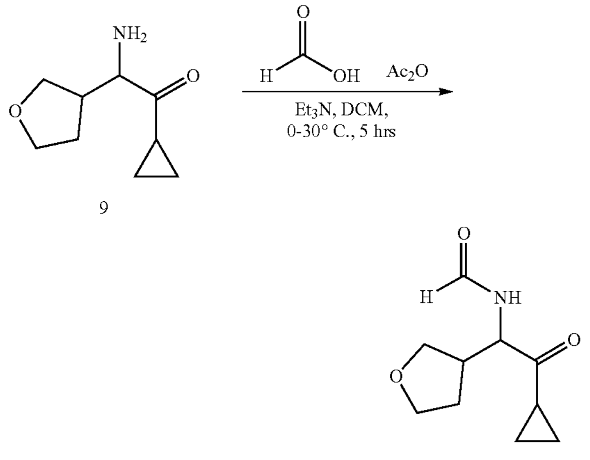

9

10

A mixture of formic acid (167.38 mg, 3.64 mmol, 137.20 μL, 2.2 eq) and acetyl acetate (185.63 mg, 1.82 mmol, 170.30 uL, 1.1 eq) was stirred at 15° C. for 1 hr. Then this mixture was added to a mixture of 2-amino-1-cyclopropyl-2-tetrahydrofuran-3-yl-ethanone (340 mg, 1.65 mmol, 1 eq, HCl) and $Et_3N$ (1.67 g, 16.53 mmol, 2.30 mL, 10 eq) in DCM (20 mL) at 0° C. The resulting mixture was stirred at 30° C. for 4 hrs. LCMS showed 2-amino-1-cyclopropyl-2-tetrahydrofuran-3-yl-ethanone was consumed and the desired MS was detected. To the reaction mixture was added $H_2O$ (10 mL) and extracted with DCM (10 mL*5). The combined organic layers were dried over $Na_2SO_4$, filtered and concentrated under reduced pressure to give a residue. The residue was purified by prep-HPLC (column: Waters Xbridge BEH C18 100*30 mm*10 μm; mobile phase: [water (0.04% $NH_3H_2O$+10 mM $NH_4HCO_3$)-ACN]; B %: 1%-20%, 10 min) to give N-(2-cyclopropyl-2-oxo-1-tetrahydrofuran-3-yl-ethyl)formamide (175 mg, 887.29 umol, 53.68% yield) as a colorless oil. ESI [M+H]=198.1.

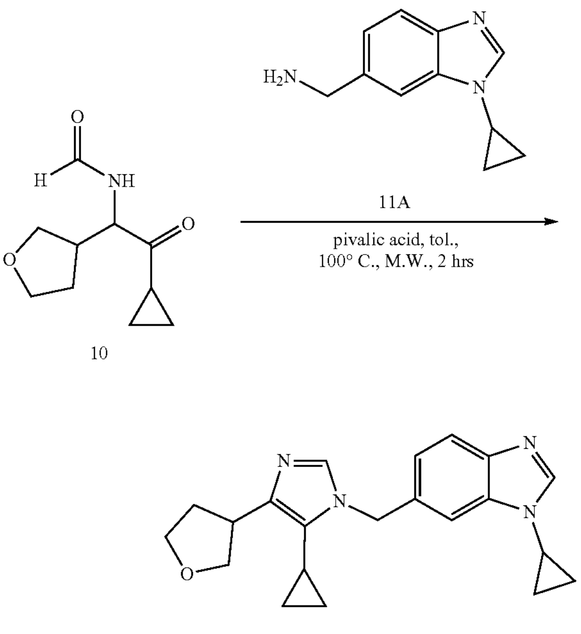

10

Bax-131 RS

N-(2-cyclopropyl-2-oxo-1-tetrahydrofuran-3-yl-ethyl) formamide (70 mg, 354.91 umol, 1 eq), (3-cyclopropylbenzimidazol-5-yl)methanamine (66.45 mg, 354.91 umol, 1 eq), PIVALIC ACID (181.24 mg, 1.77 mmol, 203.87 uL, 5 eq) and 4 A Molecular sieves were taken up into a microwave tube in Tol. (1 mL). The sealed tube was heated at 100° C. for 2 hrs under microwave. The reaction mixture was concentrated under reduced pressure to remove tol. The residue was dissolved in EtOAc (10 mL) and adjusted to pH=8 by saturated aq·$Na_2CO_3$ solution, extracted with EtOAc (10 mL*3). The combined organic layers were washed with brine (10 mL), dried over $Na_2SO_4$, filtered and concentrated under reduced pressure to give a residue. The residue was purified by prep-HPLC (column: Phenomenex Luna C18 100*30 mm*5 um; mobile phase: [water (0.2% FA)-ACN]; B %: 3%-20%, 10 min) to give the crude product, it was re-purified by prep-HPLC (column: Waters Xbridge BEH C18 100*30 mm*10 μm; mobile phase: [water (10 mM $NH_4HCO_3$)-ACN]; B %: 25%-50%, 10 min) to give 1-cyclopropyl-6-[(5-cyclopropyl-4-tetrahydrofuran-3-yl-imidazol-1-yl)methyl]benzimidazole (7.25 mg, 20.81 umol, 5.86% yield, 100.000% purity) as a white solid. ESI [M+H]=349.1.

$^1$H-NMR (400 MHz, METHANOL-d4) δ 8.20 (s, 1H), 7.69-7.63 (m, 2H), 7.47 (s, 1H), 7.17 (d, J=8.4 Hz, 1H), 5.44 (s, 2H), 4.09-4.01 (m, 2H), 3.91 (q, J=7.9 Hz, 1H), 3.75-3.68 (m, 1H), 3.68-3.58 (m, 1H), 3.49 (tt, J=3.7, 7.1 Hz, 1H), 2.25-2.13 (m, 2H), 1.45-1.34 (m, 1H), 1.22-1.15 (m, 2H), 1.09-1.02 (m, 2H), 0.98-0.92 (m, 2H), 0.64-0.57 (m, 2H).

Example 50

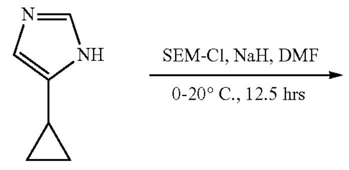

1A

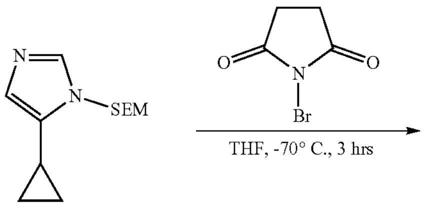

2A

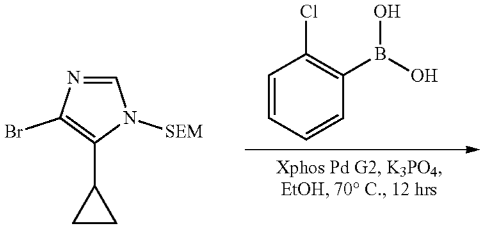

3A

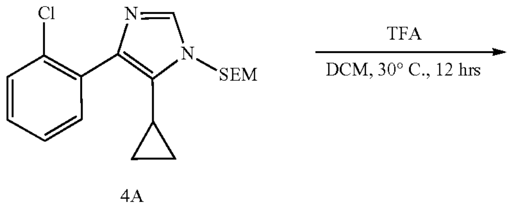

4A

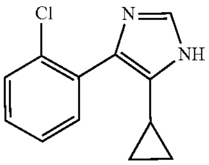

5A

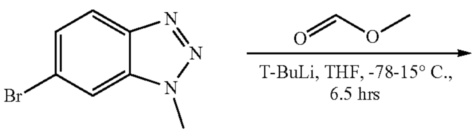

1

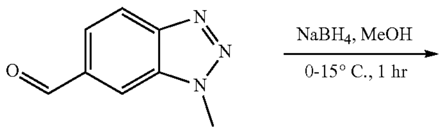

2

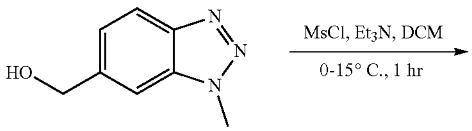

3

-continued

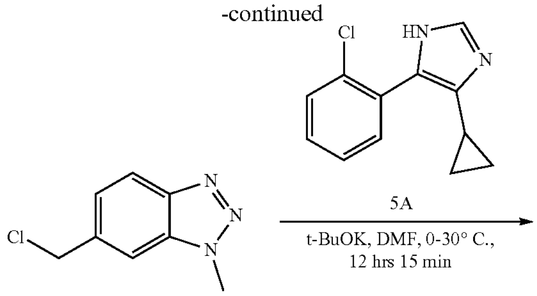

4

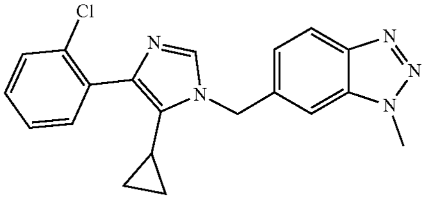

Bax-132

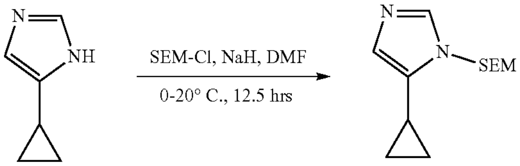

1A

2A

To a 0° C. stirred solution of 5-cyclopropyl-1H-imidazole (9 g, 83.22 mmol, 1 eq) in DMF (100 mL) was added NaH (3.33 g, 83.22 mmol, 60% purity, 1 eq) in portions. The mixture was stirred at 0° C. for 0.5 hr, then 2-(chloromethoxy)ethyl-trimethyl-silane (15.26 g, 91.55 mmol, 16.20 mL, 1.1 eq) was added dropwise. The resulting mixture was stirred at 20° C. for 12 hrs. The reaction mixture was quenched by saturated aq·$NH_4Cl$ (300 mL) at 0° C. and then diluted with EtOAc (100 mL). The aqueous phase was extracted with ethyl acetate (200 mL*3). The combined organic phase was washed with brine (200 mL*2), dried over anhydrous $Na_2SO_4$, filtered and concentrated in vacuum to give a residue. The residue was purified by column chromatography ($SiO_2$, Petroleum ether/Ethyl acetate=1/0 to 0/1, according to Plate 1) to give 2-[(5-cyclopropylimidazol-1-yl)methoxy]ethyl-trimethyl-silane (total 11 g) was obtained as a yellow oil. ESI [M+H]=239.2.

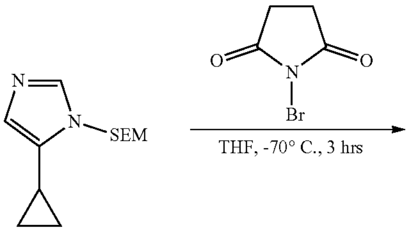

2A

-continued

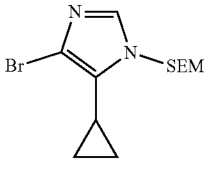

3A

To a −70° C. stirred solution of 2-[(5-cyclopropylimidazol-1-yl)methoxy]ethyl-trimethyl-silane (total 10 g, 41.95 mmol, 1 eq) in THF (200 mL) was added 1-bromopyrrolidine-2,5-dione (7.84 g, 44.04 mmol, 1.05 eq) in portions. The resulting mixture was stirred at −70° C. for 3 hrs. The reaction mixture was quenched by addition $H_2O$ (200 mL) at −70° C., and then diluted with EtOAc (100 mL) and extracted with EtOAc (200 mL*3). The combined organic layers were washed with brine (100 mL*2), dried over $Na_2SO_4$, filtered and concentrated under reduced pressure to give a residue. The residue was purified by column chromatography ($SiO_2$, Petroleum ether/Ethyl acetate=1/0 to 10/1) to give 2-[(4-bromo-5-cyclopropyl-imidazol-1-yl)methoxy]ethyl-trimethyl-silane (total 6.5 g) was obtained as a brown oil. ESI [M+H and M+3H]=317.0 and 319.0.

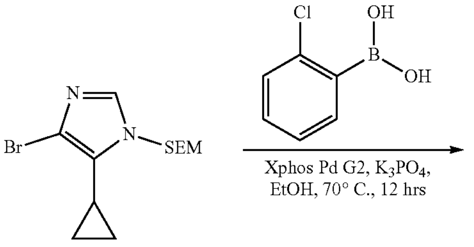

3A

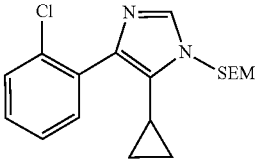

4A

To a solution of 2-[(4-bromo-5-cyclopropyl-imidazol-1-yl)methoxy]ethyl-trimethyl-silane (250 mg, 630.32 umol, 1 eq), (2-chlorophenyl)boronic acid (184.81 mg, 1.18 mmol, 1.5 eq) and $K_3PO_4$ (0.5 M, 3.15 mL, 2 eq) in EtOH (4 mL) was added [2-(2-aminophenyl)phenyl]-chloro-palladium; bis(1-adamantyl)-butyl-phosphane (52.68 mg, 78.79 μmol, 0.1 eq). The mixture was stirred at 70° C. for 12 hrs under N2. The reaction was add water (20 mL) extracted with EtOAc (30 mL*4). The organic phase dried over drying $Na_2SO_4$, and then concentrated in vacuo. The residue was purified by prep-TLC ($SiO_2$, Petroleum ether:Ethyl acetate=0/1) to give 2-[[4-(2-chlorophenyl)-5-cyclopropyl-imidazol-1-yl]methoxy]ethyl-trimethyl-silane was total 180 mg as a yellow oil. ESI [M+H]=349.1.

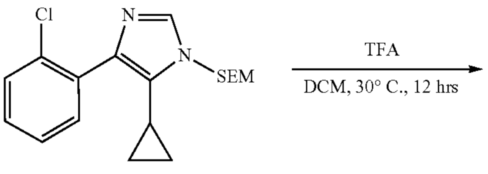

4A

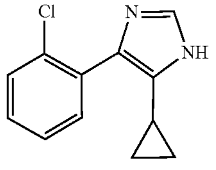

5A

To a solution of 2-[[4-(2-chlorophenyl)-5-cyclopropyl-imidazol-1-yl]methoxy]ethyl-trimethyl-silane (total 180 mg) in DCM (1.8 mL) was added TFA (924.00 mg, 8.10 mmol, 0.6 mL, 15.71 eq). The mixture was stirred at 30° C. for 12 hrs. The reaction was concentrated in vacuo. The reaction mixture was adjusted to pH=8 with saturated aq·$Na_2CO_3$ and extracted with DCM (20 mL*3). The organic phase was dried over drying $Na_2SO_4$, and then concentrated in vacuo. The residue was purified by prep-TLC ($SiO_2$, Ethyl acetate:Methanol=10:1) to give 4-(2-chlorophenyl)-5-cyclopropyl-1H-imidazole (90 mg, 411.56 umol, 79.78% yield) was obtained as a yellow solid.

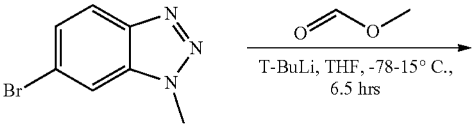

1

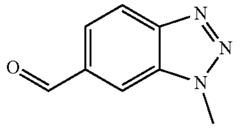

2

To a −78° C. stirred solution of 6-bromo-1-methyl-benzotriazole (300 mg, 1.41 mmol, 1 eq) in THF (5 mL) was added t-BuLi (1.3 M, 1.31 mL, 1.2 eq) (in hexane) dropwise, the mixture was stirred at −78° C. for 1 hr. Then methyl formate (424.80 mg, 7.07 mmol, 429.09 uL, 5 eq) was added at −78° C. dropwise. The mixture was stirred at −78° C. for 0.5 hr and then allowed to warm to 15° C. for 5 hrs. The reaction mixture was quenched by addition saturated aq·$NH_4Cl$ (5 mL), adjusted to pH=3 by 2N HCl, and extracted with EtOAc (5 mL*3). The combined organic layers were washed with brine (5 mL*2), dried over $Na_2SO_4$, filtered and concentrated under reduced pressure to give a residue to give 3-methylbenzotriazole-5-carbaldehyde (200 mg, crude) was obtained as a brown oil. ESI [M+H]=162.1.

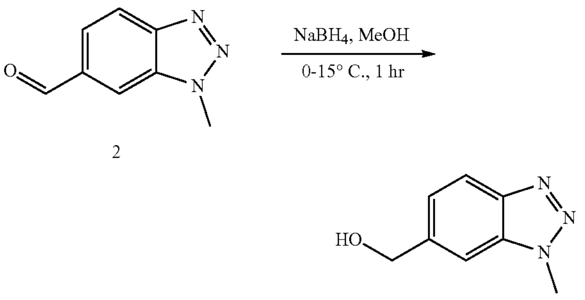

2

3

To a 0° C. stirred solution of 3-methylbenzotriazole-5-carbaldehyde (200 mg, 1.24 mmol, 1 eq) in MeOH (5 mL) was added $NaBH_4$ (46.95 mg, 1.24 mmol, 1 eq) in portions, the mixture was stirred at 15° C. for 1 hr. The reaction mixture was quenched by $H_2O$ (2 mL), and extracted with EtOAc (5 mL*3). The combined organic layers were washed with brine (5 mL*2), dried over $Na_2SO_4$, filtered and concentrated under reduced pressure to give a residue. The residue was purified by prep-TLC ($SiO_2$, PE:EtOAc=0:1) to give (3-methyl benzotriazol-5-yl)methanol (110 mg, 674.12 umol, 54.32% yield) was obtained as a brown oil. ESI [M+H]=164.0.

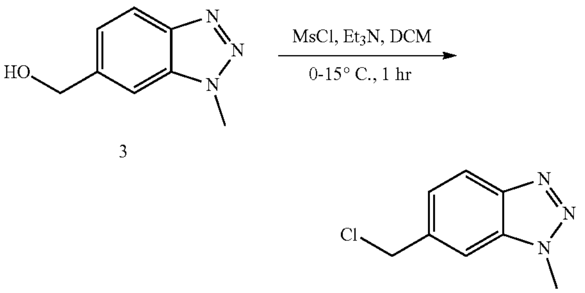

3

4

To a 0° C. stirred solution of (3-methylbenzotriazol-5-yl) methanol (110 mg, 674.12 umol, 1 eq) and $Et_3N$ (136.43 mg, 1.35 mmol, 187.66 uL, 2 eq) in DCM (2 mL) was added MsCl (115.83 mg, 1.01 mmol, 78.26 uL, 1.5 eq) in portions, the mixture was stirred at 15° C. for 1 hr. The reaction mixture was concentrated under reduced pressure to give a residue to give 6-(chloromethyl)-1-methyl-benzotriazole (100 mg, crude) was obtained as a yellow oil.

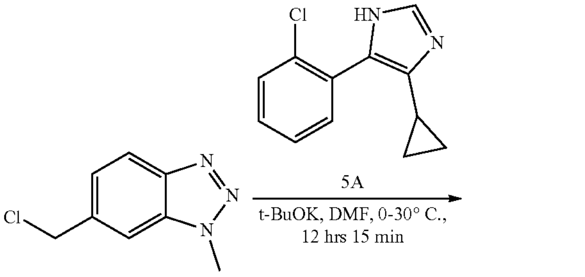

4

-continued

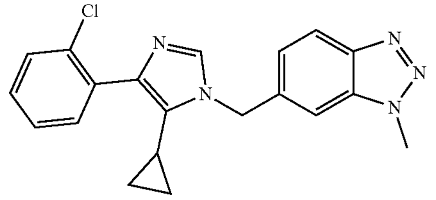

Bax-132

To a solution of t-BuOK (1 M, 330.36 μL, 1.5 eq) in DMF (1 mL) under N2 was added dropwise ethyl 2-methyl-3-oxo-butanoate (48.16 mg, 220.24 umol, 47.22 μL, 1 eq) in DMF (1 mL) at 0° C. under N2. After 15 min, 6-(chloromethyl)-1-methyl-benzotriazole (40 mg, 220.24 umol, 1 eq) in DMF (1 mL) was added at 0° C. under N2. The mixture was stirred at 30° C. for 12 hrs. To the reaction mixture was added water (15 mL) and extracted with EtOAc (20 mL*5). The organic phase was dried over drying $Na_2SO_4$, filtered and the filtrate was concentrated in vacuo to give a residue. The residue was purified by prep-HPLC (column: Waters Xbridge BEH C18 100*25 mm*5 μm; mobile phase: [water (10 mM $NH_4HCO_3$)-ACN]; B %: 30%-60%, 8 min) to give 6-[[4-(2-chlorophenyl)-5-cyclopropyl-imidazol-1-yl] methyl]-1-methyl-benzotriazole (6.09 mg, 15.13 umol, 6.87% yield, 90.407% purity) was obtained as a white solid. ESI [M+H]=364.2.

$^1H$ NMR (400 MHz, METHANOL-d4) δ 7.80 (d, J=8.6 Hz, 1H), 7.65-7.63 (m, 1H), 7.35 (s, 1H), 7.29-7.25 (m, 1H), 7.23-7.18 (m, 2H), 7.17-7.09 (m, 2H), 5.39 (s, 2H), 4.11 (s, 3H), 1.33 (tt, J=5.3, 8.2 Hz, 1H), 0.48-0.44 (m, 2H), 0.03-0.06 (m, 2H).

Example 51

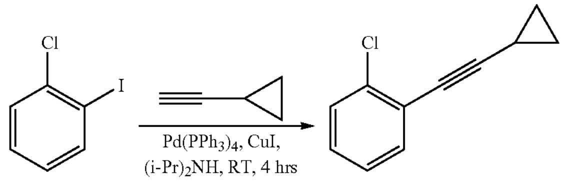

1A 1B

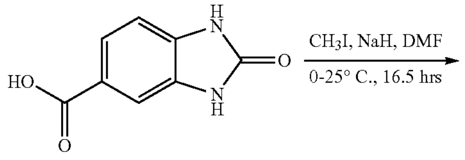

1

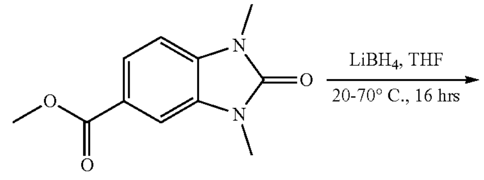

2

-continued

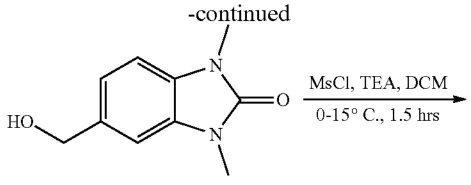

3

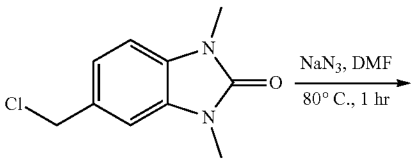

4

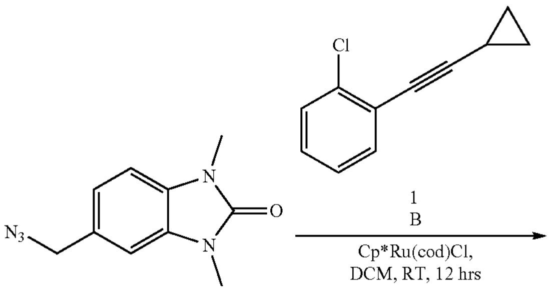

5

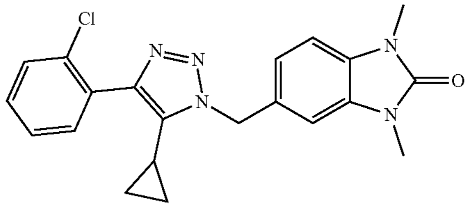

Bax-133

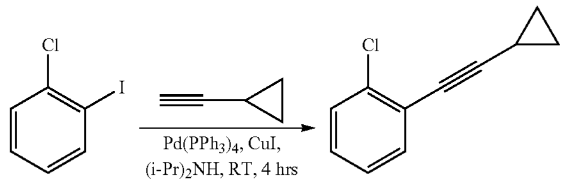

1A 1B

A mixture of 1-chloro-2-iodo-benzene (500 mg, 2.10 mmol, 1 eq), ethynylcyclopropane (166.32 mg, 2.52 mmol, 208.69 uL, 1.2 eq), $Pd(PPh_3)_4$ (242.30 mg, 209.69 umol, 0.1 eq) and CuI (79.87 mg, 419.37 umol, 0.2 eq) in i-$Pr_2NH$ (5 mL) was stirred at 25° C. for 4 hrs under N2. The reaction mixture was quenched by addition $H_2O$ (20 mL), diluted with EtOAc (10 mL), and then filtered, the filtrate was extracted with EtOAc (10 mL*3). The combined organic layers were washed with brine (20 mL*2), dried over $Na_2SO_4$, filtered and concentrated under reduced pressure to give a residue. The residue was purified by column chromatography ($SiO_2$, Petroleum ether/Ethyl acetate=1/0 to 10/1) to give 1-chloro-2-(2-cyclopropylethynyl)benzene (60 mg, 339.67 umol, 16.20% yield) was obtained as a colorless oil.

$^1$H-NMR (400 MHz, CHLOROFORM-d) δ 7.44-7.31 (m, 2H), 7.21-7.11 (m, 2H), 1.56-1.46 (m, 1H), 0.96-0.82 (m, 3H), 0.96-0.82 (m, 1H).

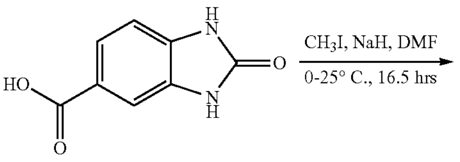

1

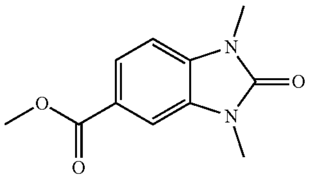

2

To a solution of 2-oxo-1,3-dihydrobenzimidazole-5-carboxylic acid (5 g, 28.07 mmol, 1 eq) in DMF (120 mL) was added NaH (3.93 g, 98.23 mmol, 60% purity, 3.5 eq) at 0° C. After 30 min, MeI (13.94 g, 98.23 mmol, 6.12 mL, 3.5 eq) was added at 0° C. Then the mixture was stirred at 25° C. for 16 hrs. The reaction was quenched with sat.aq.$NH_4Cl$ (500 mL) and extracted with EtOAc (200 mL*3). The organic layer was washed with brine (500 mL*2), dried over $MgSO_4$ and concentrated in vacuo. The residue was triturated with PE/MTBE (50 mL/5 mL), and solid precipitate was collected via filtration, dried in vacuo to give methyl 1,3-dimethyl-2-oxo-benzimidazole-5-carboxylate (5.5 g, 24.97 mmol, 88.98% yield) was obtained as a brown solid. ESI [M+H]=221.1.

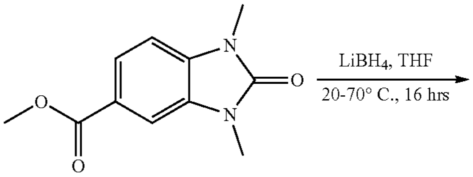

2

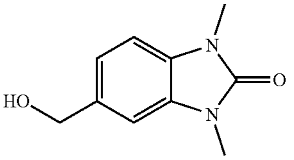

3

To a solution of methyl 1,3-dimethyl-2-oxo-benzimidazole-5-carboxylate (5.5 g, 24.97 mmol, 1 eq) in THF (100 mL) was added $LiBH_4$ (1.09 g, 49.95 mmol, 2 eq) at 20° C. Then the mixture was stirred at 70° C. for 16 hrs. The reaction was quenched with cold sat.aq.$NH_4Cl$ (200 mL), extracted with EtOAc (100 mL*3). The organic layer was washed with brine (200 mL), dried over $MgSO_4$ and concentrated in vacuo. The residue was triturated with EtOAc/MTBE (1:1, 50 mL) to give 5-(hydroxymethyl)-1,3-dimethyl-benzimidazol-2-one (4.5 g, 23.41 mmol, 93.74% yield) was obtained as a light red solid. ESI [M+H]=193.1.

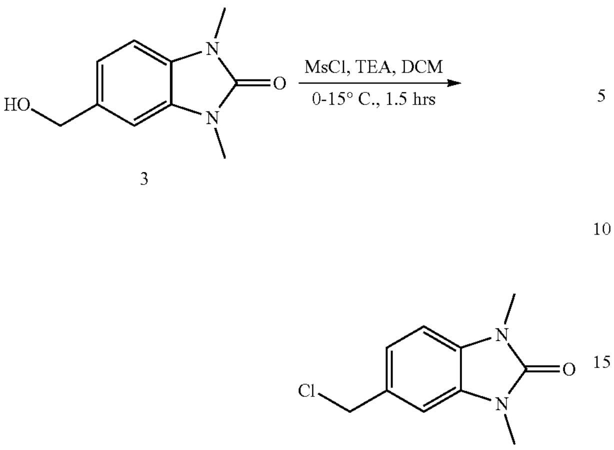

3
4

To a solution of 5-(hydroxymethyl)-1,3-dimethyl-benzimidazol-2-one (420 mg, 2.19 mmol, 1 eq) in DCM (8 mL) was added TEA (221.11 mg, 2.19 mmol, 304.14 μL, 1 eq), and methanesulfonyl chloride (375.45 mg, 3.28 mmol, 253.68 uL, 1.5 eq) at 0° C. under N2. The mixture was stirred at 15° C. for 1.5 hrs. The reaction was concentrated in vacuo. The residue was purified by column chromatography ($SiO_2$, Petroleum ether/Ethyl acetate=20/1 to 1/1) to give 5-(chloromethyl)-1,3-dimethyl-benzimidazol-2-one (417 mg, 1.98 mmol, 90.59% yield) was obtained as a white solid.

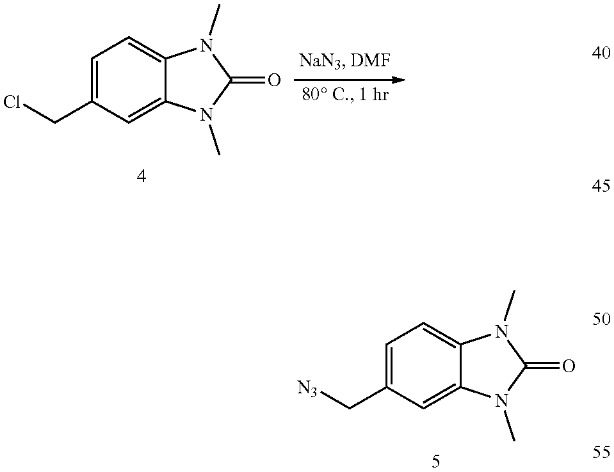

4
5

To a solution of 5-(chloromethyl)-1,3-dimethyl-benzimidazol-2-one (410 mg, 1.95 mmol, 1 eq) in DMF (5 mL) was added $NaN_3$ (139.18 mg, 2.14 mmol, 1.1 eq). The mixture was stirred at 80° C. for 1 hr. The reaction mixture was quenched by addition cold water (20 mL), and extracted with (40 mL*5). The combined organic layers was washed with brine (20 mL), dried over drying $Na_2SO_4$, filtered and blow-dried by N2 to give 5-(azidomethyl)-1,3-di methyl-benzimidazol-2-one (400 mg, 1.84 mmol, 94.61% yield) was obtained as a white solid. ESI [M+H]=218.0.

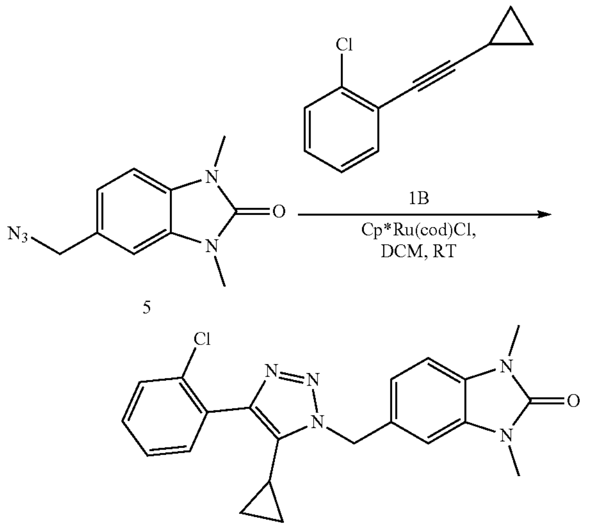

5
Bax-133

A mixture of 5-(azidomethyl)-1,3-dimethyl-benzimidazol-2-one (25 mg, 115.09 umol, 1 eq), 1-chloro-2-(2-cyclopropylethynyl)benzene (40.66 mg, 230.17 μmol, 2 eq), chlororuthenium; (1Z,5Z)-cycloocta-1,5-diene; 1,2,3,4,5-pentamethylcyclopentane (4.43 mg, 11.51 umol, 0.1 eq) in DCM (1 mL) was stirred at 20° C. for 12 hrs under N2 atmosphere. The reaction was concentrated in vacuo. The residue was purified by prep-HPLC (column: Phenomenex Luna C18 150*30 mm*5 um; mobile phase: [water (0.04% HCl)-ACN]; B %: 35%-65%, 10 min) to give 5-[[4-(2-chlorophenyl)-5-cyclopropyl-triazol-1-yl]methyl]-1,3-dimethyl-benzimidazol-2-one (11 mg, 27.93 umol, 24.27% yield, 100% purity) was obtained as a white solid. ESI [M+H]=394.1.

$^1$H NMR (400 MHz, METHANOL-d4) δ 7.59-7.54 (m, 1H), 7.53-7.48 (m, 1H), 7.48-7.43 (m, 1H), 7.48-7.41 (m, 1H), 7.18 (s, 3H), 5.84 (s, 2H), 3.45-3.43 (m, 3H), 3.34-3.32 (m, 3H), 1.85-1.75 (m, 1H), 0.91-0.83 (m, 2H), 0.38-0.30 (m, 2H).

Example 52

Experimental Procedure: Bax-134

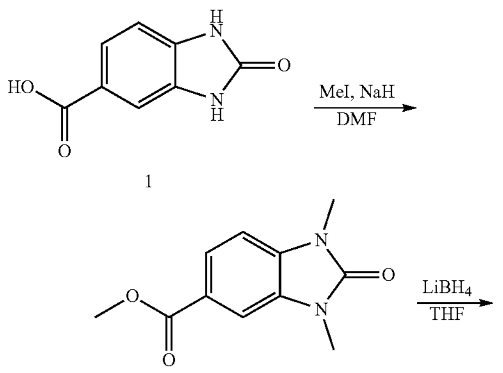

1
2

-continued

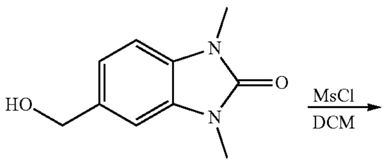

3

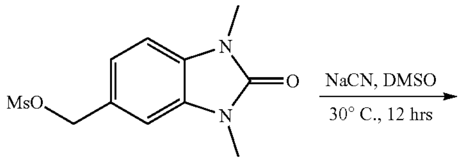

4

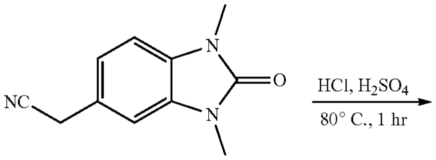

5

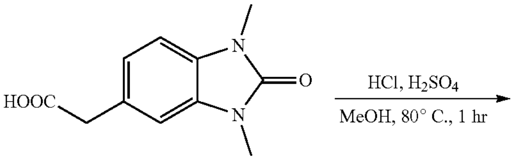

6

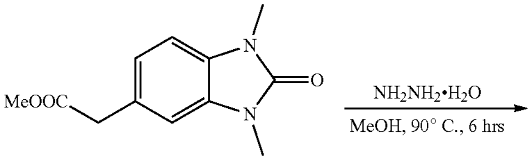

7

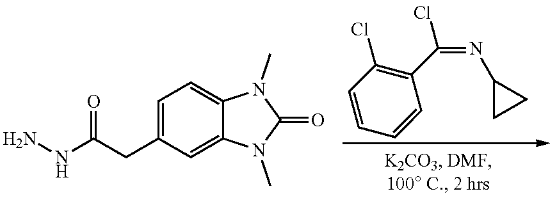

8

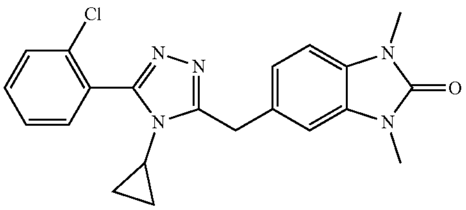

Bax-134

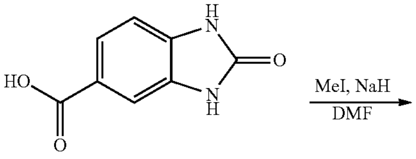

1

-continued

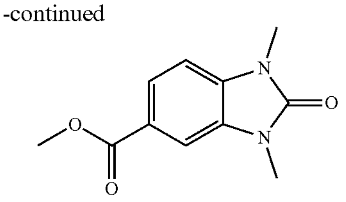

2

To a 0° C. stirred solution of 2-oxo-1,3-dihydrobenzimidazole-5-carboxylic acid (11 g, 61.75 mmol, 1 eq) in DMF (500 mL) was added NaH (8.64 g, 216.12 mmol, 60% purity, 3.5 eq) in portions, after 30 mins, MeI (30.68 g, 216.12 mmol, 13.45 mL, 3.5 eq) was added dropwise at 0° C. The resulting mixture was stirred at 15° C. for 36 hrs. The reaction was quenched with sat.aq.$NH_4Cl$ (600 mL) and extracted with EtOAc (300 mL*3). The organic layer was washed with brine (500 mL*2), dried over $Na_2SO_4$ and concentrated in vacuo to give a residue. The residue was triturated with PE/MTBE (100 mL/10 mL), and the solid precipitate was collected via filtration, dried in vacuo to give methyl 1,3-dimethyl-2-oxo-benzimidazo-le-5-carboxylate (11.5 g, 52.22 mmol, 84.57% yield) as a light pink solid. ESI [M+H]=221.1.

$^1$H NMR (400 MHz, CHLOROFORM-d) δ 7.88 (dd, J=1.4, 8.3 Hz, 1H), 7.66 (s, 1H), 6.99 (d, J=8.2 Hz, 1H), 3.93 (s, 3H), 3.46 (d, J=4.0 Hz, 6H).

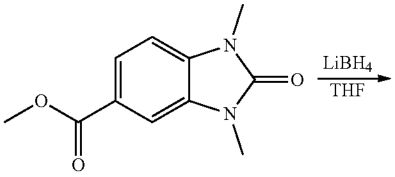

2

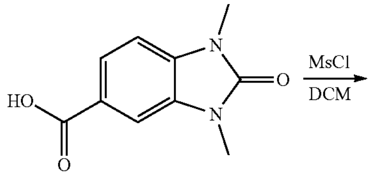

3

To a solution of methyl 1,3-dimethyl-2-oxo-benzimidazole-5-carboxylate (11 g, 49.95 mmol, 1 eq) in THF (200 mL) was added $LiBH_4$ (4.35 g, 199.80 mmol, 4 eq) at 15° C. The mixture was stirred at 80° C. for 24 hrs. The reaction mixture was poured into the stirring saturated sat.aq.$NH_4Cl$ (200 mL) at 0° C., and extracted with EtOAc (100 mL*5). The organic layer was dried over $MgSO_4$ and concentrated in vacuo to give 5-(hydroxymethyl)-1,3-dimethyl-benzimidazol-2-one (9 g, crude) was obtained as a yellow solid. ESI [M+H]=193.0.

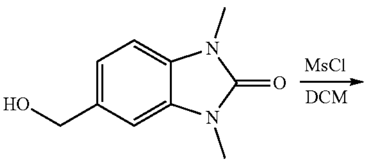

3

-continued

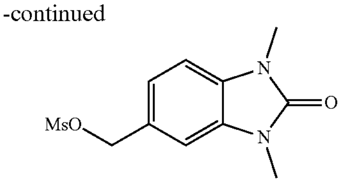

4

To a solution of 5-(hydroxymethyl)-1,3-dimethyl-benzimidazol-2-one (1 g, 5.20 mmol, 1 eq) in DCM (25 mL) was added TEA (526.44 mg, 5.20 mmol, 724.13 μL, 1 eq), and methanesulfonyl chloride (893.93 mg, 7.80 mmol, 604.01 uL, 1.5 eq) at 0° C. under N2. The mixture was stirred at 15° C. for 1.5 hrs. The reaction was concentrated in vacuo to give the crude product 5-(chloromethyl)-1,3-dimethyl-benzimidazol-2-one (2.5 g, crude) as a yellow solid.

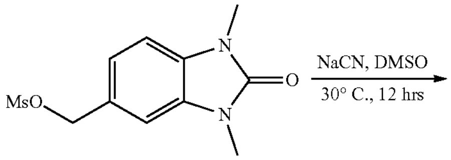

4

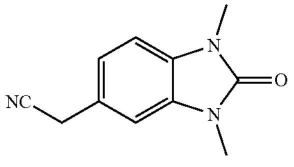

5

To a solution of 5-(chloromethyl)-1,3-dimethyl-benzimidazol-2-one (1.1 g, 5.22 mmol, 1 eq) in DMSO (20 mL) was added NaCN (1.28 g, 26.11 mmol, 5 eq). The mixture was stirred at 30° C. for 12 hrs. The reaction was added water (30 mL) and extracted with EtOAc (30 mL*3). The organic layer was washed with $H_2O$ (20 mL*2), dried over $MgSO_4$ and concentrated in vacuo. The residue was purified by prep-HPLC (column: Welch Xtimate C18 250*50 mm*10 μm; mobile phase: [water (10 mM $NH_4HCO_3$)-ACN]; B %: 15%-40%, 10 min) to give 2-(1,3-dimethyl-2-oxo-benzimidazol-5-yl)acetonitrile (0.5 g, 2.48 mmol, 47.59% yield) as a white solid. ESI [M+H]=202.1.

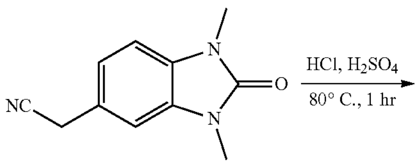

5

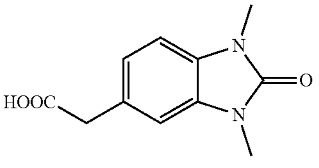

6

To a solution of 2-(1,3-dimethyl-2-oxo-benzimidazol-5-yl)acetonitrile (250 mg, 1.24 mmol, 1 eq) in HCl (2 mL) (12 M) was added $H_2SO_4$ (0.2 mL) (98%). The mixture was stirred at 80° C. for 50 min. The reaction solution was used into the next step without further purification. ESI [M+H]=235.0.

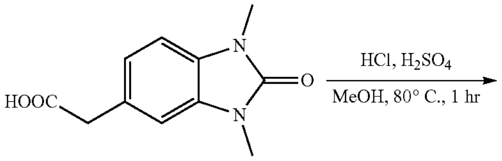

6

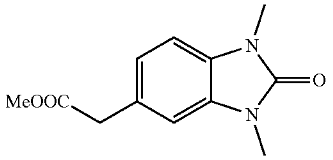

7

A mixture of 2-(1,3-dimethyl-2-oxo-benzimidazol-5-yl) acetic acid (270 mg, 1.23 mmol, 1 eq), HCl (2 mL), $H_2SO_4$ (0.2 mL), MeOH (10 mL) was stirred at 80° C. for 4 hrs. The reaction mixture was adjusted to pH=8 with sat.aq $Na_2CO_3$ and extracted with EtOAc (20 mL*4). The combined organic layers were dried over drying $Na_2SO_4$, filtered and concentrated under reduced pressure to give methyl 2-(1,3-dimethyl-2-oxo-benzimidazol-5-yl)acetate (200 mg, 853.79 μmol, 69.41% yield) as a white solid. ESI [M+H]=235.0.

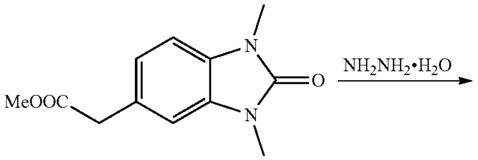

7

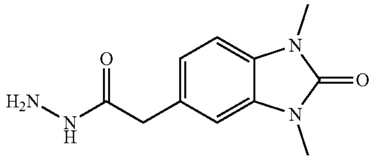

8

To a solution of methyl 2-(1,3-dimethyl-2-oxo-benzimidazol-5-yl)acetate (130 mg, 554.96 umol, 1 eq) in MeOH (3 mL) was added hydrazine; hydrate (198.44 mg, 3.88 mmol, 192.66 μL, 98% purity, 7 eq). The mixture was stirred at 90° C. for 6 hrs. The reaction was concentrated in vacuo to give 2-(1,3-dimethyl-2-oxo-benzimidazol-5-yl)acetohydrazide (120 mg, 512.26 μmol, 92.31% yield) as a white solid. ESI [M+H]=235.1.

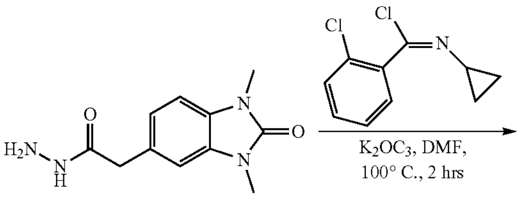

8

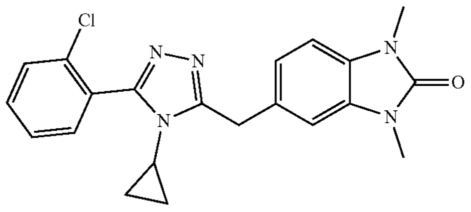

Bax-134

A mixture of 2-(1,3-dimethyl-2-oxo-benzimidazol-5-yl) acetohydrazide (50 mg, 213.44 μmol, 1 eq), (1E)-2-chloro-N-cyclopropyl-benzimidoyl chloride (91.39 mg, 426.89 umol, 2 eq) and $K_2CO_3$ (29.50 mg, 213.44 umol, 1 eq) in DMF (2 mL) was stirred at 100° C. for 1 hr. The reaction mixture was concentrated in vacuo to give a residue. The residue was purified by prep-HPLC (column: Phenomenex Luna C18 150*30 mm*5 μm; mobile phase: [water (0.04% HCl)-ACN]; B %: 20%-50%, 10 min) to give 5-[[5-(2-chlorophenyl)-4-cyclopropyl-1,2,4-triazol-3-yl]methyl]-1, 3-dimethyl-benzimidazol-2-one (20.26 mg, 50.82 umol, 23.81% yield, 98.79% purity) as a white solid. ESI [M+H]=353.2.

$^1$H NMR (400 MHz, METHANOL-d4) δ 7.78-7.74 (m, 2H), 7.73-7.70 (m, 1H), 7.66-7.60 (m, 1H), 7.28-7.26 (m, 1H), 7.25-7.20 (m, 2H), 4.68 (s, 2H), 3.51-3.48 (m, 1H), 3.48-3.47 (m, 4H), 3.46-3.46 (m, 2H), 3.45-3.45 (m, 1H), 1.09-1.01 (m, 2H), 0.92-0.85 (m, 2H).

Example 53

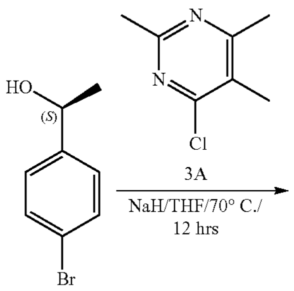

3A

1

-continued

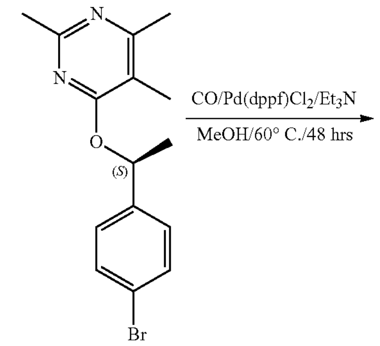

2

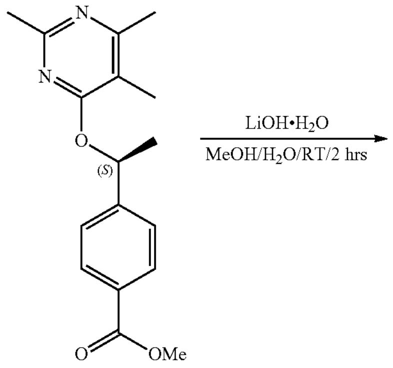

3

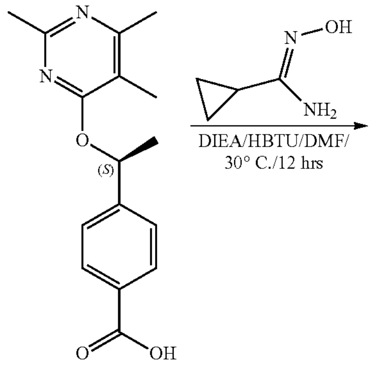

4

-continued

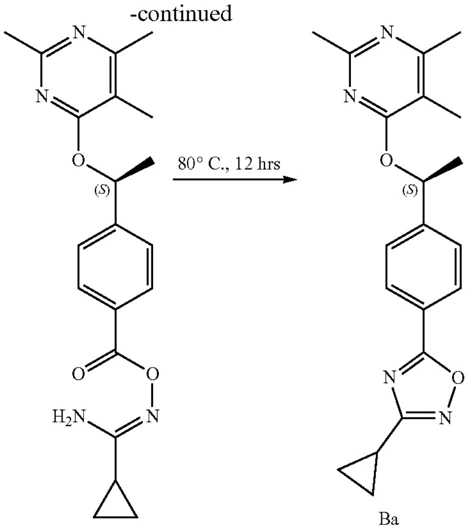

5

Bax-137S

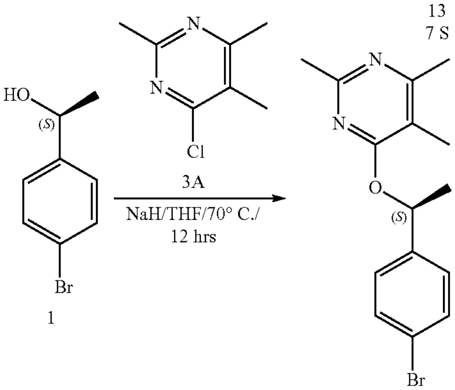

1

2

To a 0° C. stirred mixture of (1S)-1-(4-bromophenyl) ethanol (1 g, 4.97 mmol, 1 eq) and 4-chloro-2,5,6-trimethyl-pyrimidine (934.72 mg, 5.97 mmol, 1.2 eq) in THF (15 mL) was added NaH (397.89 mg, 9.95 mmol, 60% purity, 2.0 eq), then the mixture was stirred at 70° C. for 5 hrs. The mixture was quenched by addition saturated aq. $NH_4Cl$ (100 mL) and extracted with EtOAc (50 mL*3). The combined organic layers were washed with brine (20 mL*2), dried over $Na_2SO_4$, filtered and concentrated under reduced pressure to give 4-[(1S)-1-(4-bromophenyl)ethoxy]-2,5,6-trimethyl-pyrimidine (1.58 g, 4.92 mmol, 98.90% yield) was obtained as a yellow oil. ESI [M+H and M+3H]=321.0 and 323.0.

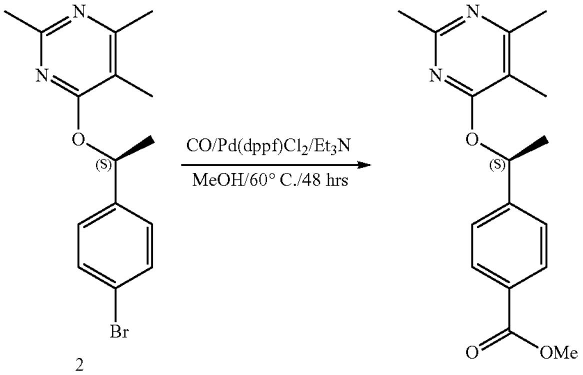

2

3

To a solution of 4-[(1S)-1-(4-bromophenyl)ethoxy]-2,5,6-trimethyl-pyrimidine (1 g, 3.11 mmol, 1 eq) and Et3N (1.58 g, 15.57 mmol, 2.17 mL, 5 eq) in MeOH (20 mL) was added Pd(dppf)$Cl_2$ (455.59 mg, 622.64 umol, 0.2 eq) under N2. The suspension was degassed under vacuum and purged with CO several times. The mixture was stirred under CO (50 psi) at 60° C. for 60 hrs. The reaction mixture was filtered, the filtrate was concentrated to give a residue. The residue was purified by column chromatography ($SiO_2$, Petroleum ether/Ethyl acetate=1/0 to 3/1) to give methyl 4-[(1S)-1-(2,5,6-trimethylpyrimidin-4-yl)oxyethyl]benzoate (500 mg, 1.66 mmol, 53.47% yield) as a light yellow oil. ESI [M+H]=301.1.

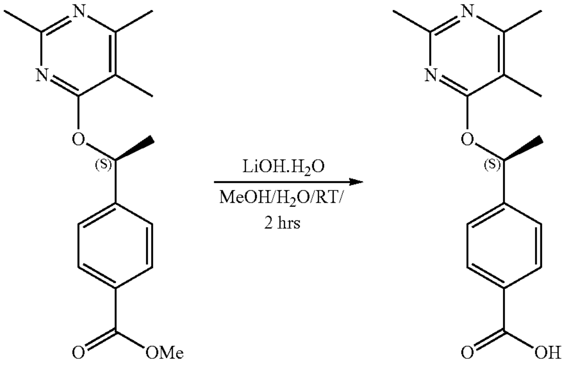

3

4

To a solution of methyl 4-[(1S)-1-(2,5,6-trimethylpyrimidin-4-yl)oxyethyl]benzoate (500 mg, 1.66 mmol, 1 eq) in MeOH (10 mL) and $H_2O$ (3 mL) was added LiOH·$H_2O$ (209.57 mg, 4.99 mmol, 3 eq). The mixture was stirred at 25° C. for 2 hrs. To the solution was added $H_2O$ 10 mL, and then washed with MTBE (10 mL*2). The aqueous phase was added sat.aq.1N HCl adjusted pH=3 and then extracted with DCM/i-PrOH=3:1 (20 ml*5), dried over $Na_2SO_4$, filtered and concentrated under reduced pressure to give 4-[(1S)-1-(2,5,6-trimethylpyrimidin-4-yl)oxyethyl]benzoic acid (437 mg, 1.53 mmol, 91.68% yield) as a white solid. ESI [M+H]=287.1.

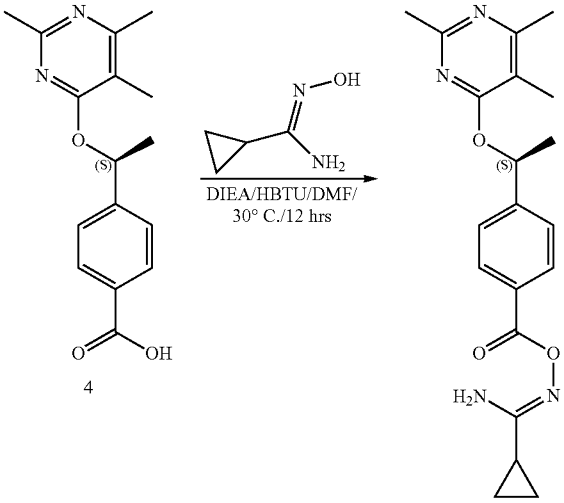

4

5

To a solution of 4-[(1S)-1-(2,5,6-trimethylpyrimidin-4-yl) oxyethyl]benzoic acid (200 mg, 698.51 umol, 1 eq) in DMF (4 mL) was added N'-hydroxycyclopropanecarboxamidine (174.83 mg, 1.75 mmol, 2.5 eq) and DIEA (270.83 mg, 2.10 mmol, 365.00 uL, 3 eq) and the last was added HBTU (397.35 mg, 1.05 mmol, 1.5 eq). The mixture was stirred at 25° C. for 12 hrs. The reaction mixture was concentrated under reduced pressure to remove DMF to give [(Z)-[amino (cyclopropyl)methylene]amino]4-[(1S)-1-(2,5,6-trimethylpyrimidin-4-yl)oxyethyl]benzoate (120 mg, 325.71 umol, 46.63% yield) as a white solid. ESI [M+H]=369.1.

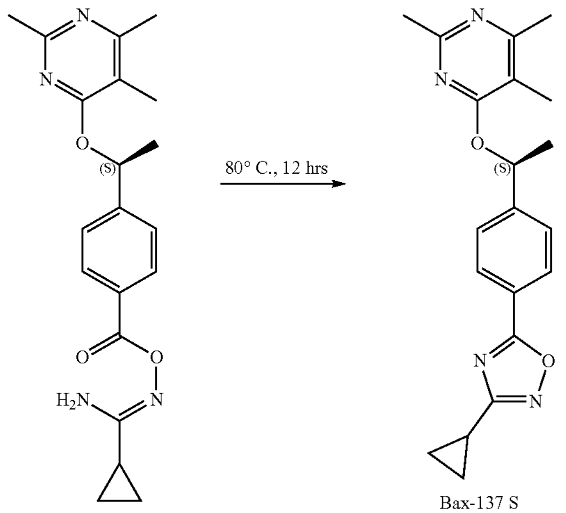

5

Bax-137 S

To a solution of [(Z)-[amino(cyclopropyl)methylene] amino] 4-[(1S)-1-(2,5,6-trimethylpyrimidin-4-yl)oxyethyl] benzoate (100.00 mg, 271.42 umol, 1 eq) in DMF (3 mL). The mixture was stirred at 80° C. for 12 hrs. The reaction mixture was concentrated under reduced pressure to remove DMF. The residue was purified by prep-HPLC (column: Nano-micro Kromasil C18 100*40 mm 3 μm; mobile phase: [water (0.1% TFA)-ACN]; B %: 25%-55%, 8 min) to give 3-cyclopropyl-5-[4-[(1S)-1-(2,5,6-trimethylpyrimidin-4-yl) oxyethyl]phenyl]-1,2,4-oxadiazole (29 mg, 78.55 umol, 28.94% yield, 94.913% purity) as a colourless oil. ESI [M+H]=351.2.

$^1$H NMR (400 MHz, METHANOL-d4) δ=8.24-8.03 (m, 2H), 7.67 (s, 2H), 6.59-6.50 (m, 1H), 2.78-2.49 (m, 6H), 2.37-2.29 (m, 3H), 2.22-2.10 (m, 1H), 1.91-1.64 (m, 3H), 1.21-1.04 (m, 4H)

Example 54

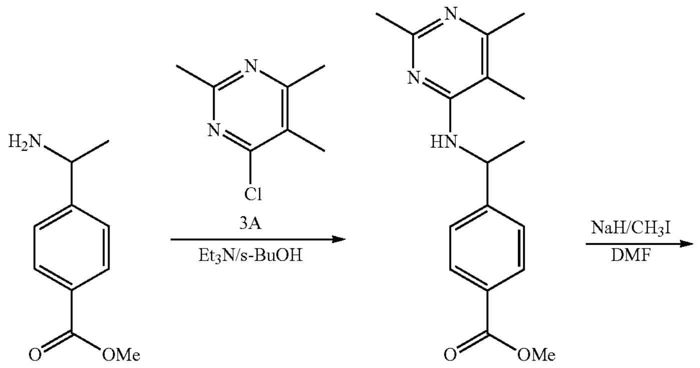

1 2

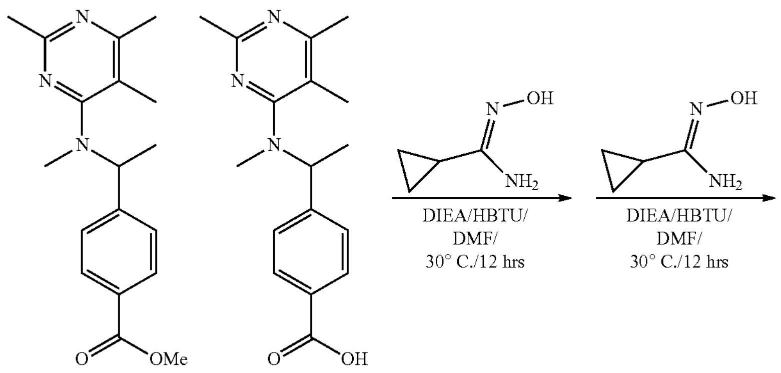

3 4

-continued

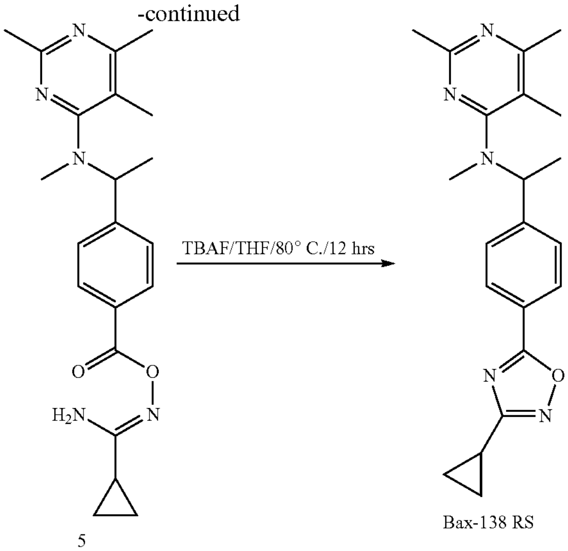

5

Bax-138 RS

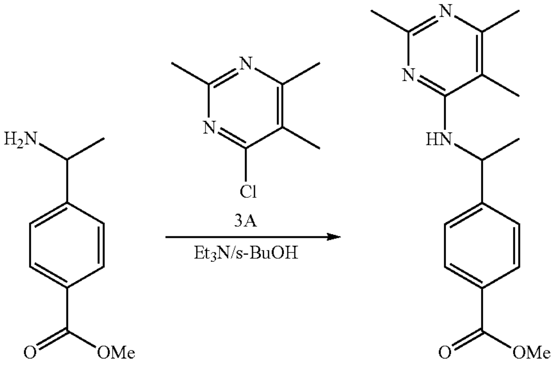

1

2

A mixture of methyl 4-(1-aminoethyl)benzoate (200.00 mg, 1.12 mmol, 1 eq), 4-chloro-2,5,6-trimethyl-pyrimidine (227.21 mg, 1.45 mmol, 1.3 eq) and $Et_3N$ (338.78 mg, 3.35 mmol, 465.99 μL, 3 eq) in butan-2-ol (5 mL) was stirred at 120° C. for 12 hrs. The mixture was concentrated in reduced pressure to give a residue. The residue was purified by prep-TLC ($SiO_2$, Petroleum ether/Ethyl acetate=0/1) to give methyl 4-[1-[(2,5,6-trimethylpyrimidin-4-yl)amino]ethyl] benzoate (140 mg, 467.65 umol, 41.91% yield) as a light brown oil. ESI [M+H]=300.1.

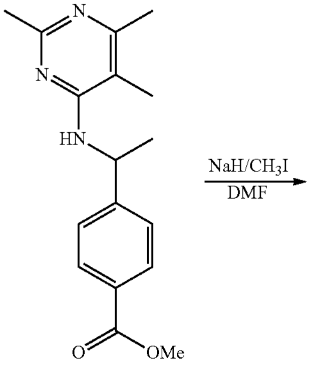

2

-continued

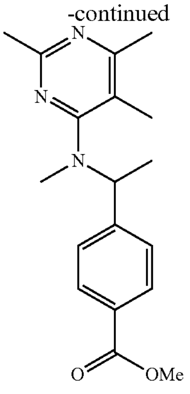

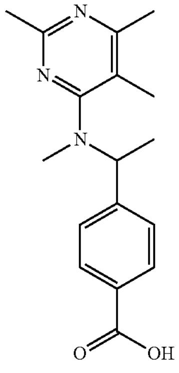

3 4

To a solution of methyl 4-[1-[(2,5,6-trimethylpyrimidin-4-yl)amino]ethyl]benzoate (120 mg, 400.85 umol, 1 eq) in DMF (2 mL) was added NaH (32.07 mg, 801.69 umol, 60% purity, 2 eq) at 15° C. The mixture was stirred at 15° C. for 10 mins, then $CH_3I$ (85.34 mg, 601.27 umol, 37.43 uL, 1.5 eq) was added. The mixture was stirred at 30° C. for 12 hrs. The reaction mixture was concentrated to give a residue. To the residue was added $H_2O$ (10 mL), and extracted with DCM/i-PrOH (3/1, 5 mL*10). The combined organic layers were dried over $Na_2SO_4$, filtered and concentrated under reduced pressure to give methyl 4-[1-[methyl-(2,5,6-trimethylpyrimidin-4-yl)amino]ethyl]benzoate (50 mg, crude) and 4-[1-[methyl-(2,5,6-trimethylpyrimidin-4-yl)amino]ethyl]benzoic acid (50 mg, crude) (mixture, total 100 mg) as a light brown solid. ESI [M+H]=300.1.

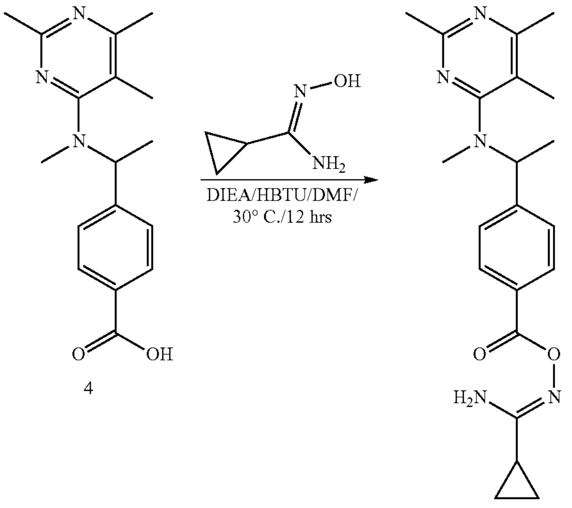

4

5

To a solution of 4-[1-[methyl-(2,5,6-trimethylpyrimidin-4-yl)amino]ethyl]benzoic acid (50 mg, 167.02 μmol, 1 eq) in DMF (2 mL) was added DIPEA (64.76 mg, 501.06 umol, 87.27 uL, 3 eq), N'-hydroxycyclopropanecarboxamidine (25.08 mg, 250.53 μmol, 1.5 eq) and HBTU (76.01 mg, 200.42 umol, 1.2 eq). The mixture was stirred at 30° C. for 12 hrs. The reaction mixture was concentrated to give a residue. The residue was purified by prep-HPLC (column: Welch Ultimate AQ-C18 150*30 mm*5 μm; mobile phase: [water (0.1% TFA)-ACN]; B %: 20%-50%, 12 min) to give [(Z)-[amino(cyclopropyl)methylene]amino] 4-[1-[methyl-(2,5,6-trimethylpyrimidin-4-yl)amino]ethyl]benzoate (15 mg, 30.27 umol, 18.13% yield, TFA) as a white solid. ESI [M+H]=382.2.

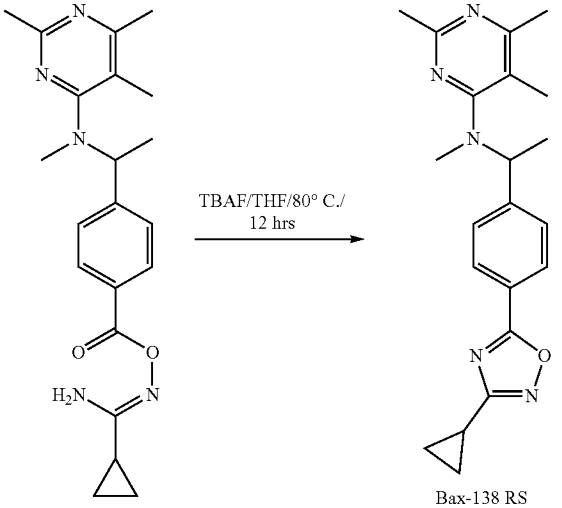

5

Bax-138 RS

To a solution of [(Z)-[amino(cyclopropyl)methylene]amino] 4-[1-[methyl-(2,5,6-trimethylpyrimidin-4-yl)amino]

ethyl]benzoate (15 mg, 30.27 umol, 1 eq, TFA) in THF (2 mL) was added TBAF (1 M, 151.36 uL, 5 eq), the mixture was stirred at 80° C. for 12 hrs. The mixture was concentrated to give a residue. The residue was purified by prep-TLC (EtOAc:MeOH=10:1) and prep-HPLC (column: Phenomenex Luna C18 150*30 mm*5 μm; mobile phase: [water (0.04% HCl)-ACN]; B %: 35%-65%, 10 min) to give N-[1-[4-(3-cyclopropyl-1,2,4-oxadiazol-5-yl)phenyl]ethyl]-N,2,5,6-tetramethyl-pyrimidin-4-amine (5.13 mg, 13.07 umol, 43.16% yield, 92.566% purity) as a white solid. ESI [M+H]=364.2.

$^1$H-NMR (400 MHz, METHANOL-d4) δ 8.13 (d, J=8.2 Hz, 2H), 7.60 (d, J=8.2 Hz, 2H), 6.24 (br d, J=6.0 Hz, 1H), 3.07 (s, 3H), 2.58 (s, 3H), 2.50 (s, 3H), 2.32 (s, 3H), 2.22-2.13 (m, 1H), 1.77 (d, J=7.0 Hz, 3H), 1.18-1.04 (m, 4H).

Example 55

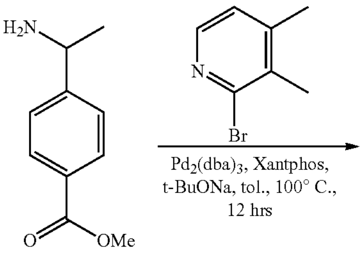

1

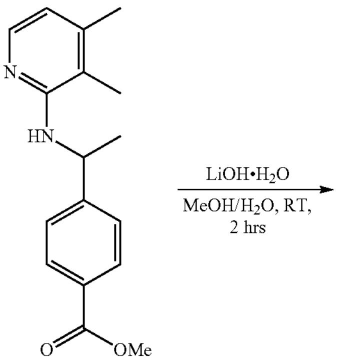

2

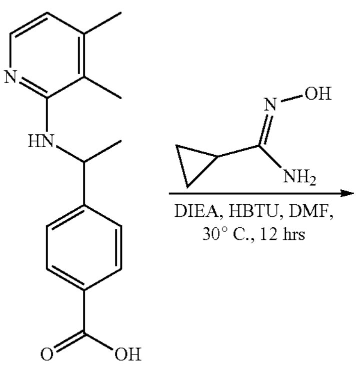

3

-continued

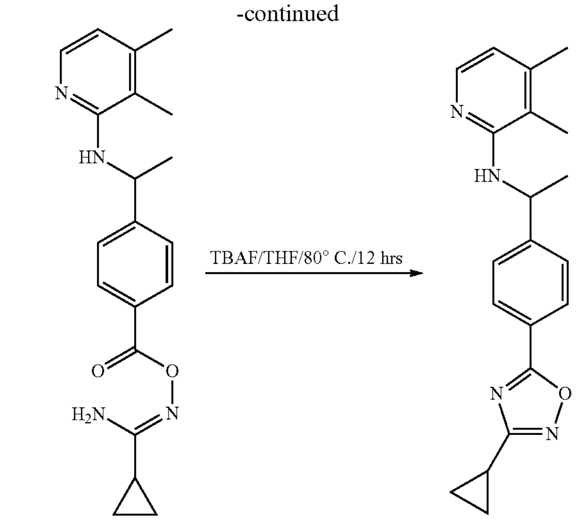

4 Bax-139 RS

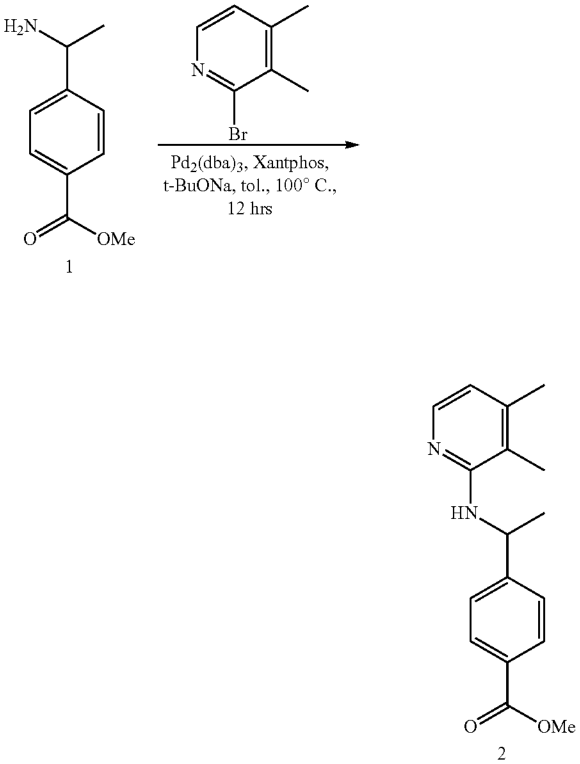

1

2

To a solution of methyl 4-(1-aminoethyl)benzoate (250 mg, 1.39 mmol, 1 eq) in Tol. (8 mL) was added 2-bromo-3,4-dimethyl-pyridine (319.23 mg, 1.72 mmol, 1.23 eq), t-BuONa (268.12 mg, 2.79 mmol, 2 eq) and Xantphos (80.72 mg, 139.50 μmol, 0.1 eq) and $Pd_2(dba)_3$ (127.74 mg, 139.50 μmol, 0.1 eq). The mixture was stirred at 100° C. for 12 hrs under N2. The reaction was concentrated in vacuo. The residue was purified by prep-TLC ($SiO_2$, Petroleum ether:Ethyl acetate=5:1) to give methyl 4-[1-[(3,4-dimethyl-2-pyridyl)amino]-ethyl]benzoate (340 mg, 1.20 mmol, 85.72% yield) as a yellow oil. ESI [M+H]=285.2.

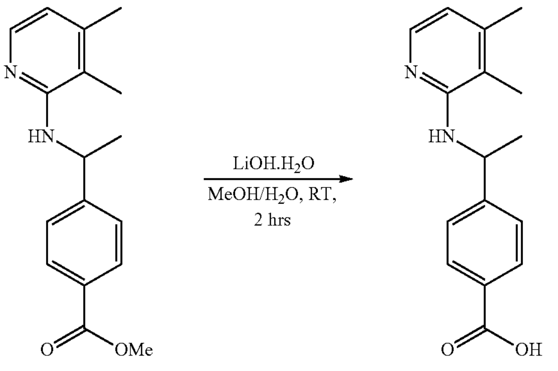

2 3

To a solution of methyl 4-[1-[(3,4-dimethyl-2-pyridyl)amino]ethyl]benzoate (340 mg, 1.20 mmol, 1 eq) in MeOH (3 mL) and $H_2O$ (1 mL) was added $LiOH{\cdot}H_2O$ (200.69 mg, 4.78 mmol, 4 eq). The mixture was stirred at 30° C. for 12 hrs. MeOH was removed, the aqueous layer was diluted with $H_2O$ 15 mL and extracted with MTBE (20 mL*2). Then the aqueous layer was adjusted to pH=2 with 1N HCl, and extracted with DCM/i-PrOH (3/1, 20 mL*8). The organic layer was dried over $Na_2SO_4$ and concentrated in vacuo to give 4-[1-[(3,4-dimethyl-2-pyridyl)amino]ethyl]benzoic acid (149 mg, crude) as a yellow oil. ESI [M+H]=371.1.

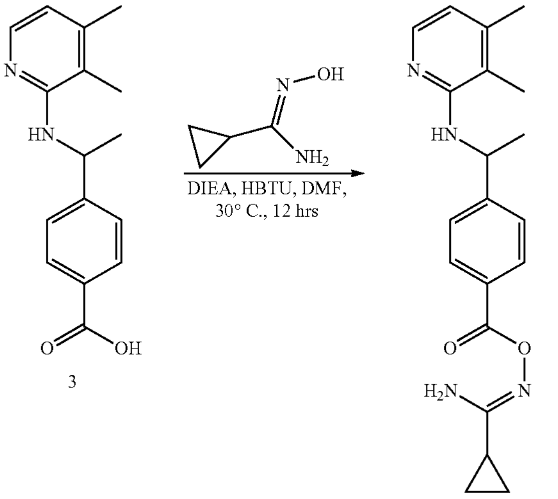

3

4

To a solution of 4-[1-[(3,4-dimethyl-2-pyridyl)amino]ethyl]benzoic acid (120 mg, 443.91 μmol, 1 eq) in DMF (3 mL) was added DIEA (172.11 mg, 1.33 mmol, 231.96 μL, 3 eq), N'-hydroxycyclopropanecarboxamidine (66.67 mg, 665.86 umol, 1.5 eq) and HBTU (202.02 mg, 532.69 umol, 1.2 eq). The mixture was stirred at 30° C. for 12 hrs. To the reaction mixture was added water (20 mL) and extracted with DCM/i-PrOH (3/1, 20 mL*4). The organic layer was washed with brine (20 mL*2), dried over $MgSO_4$, filtered and concentrated in vacuo to give [(Z)-[amino(cyclopropyl)methylene]amino] 4-[1-[(3,4-dimethyl-2-pyridyl)amino]ethyl]benzoate (200 mg, crude) as a brown oil. ESI [M+H]=353.2.

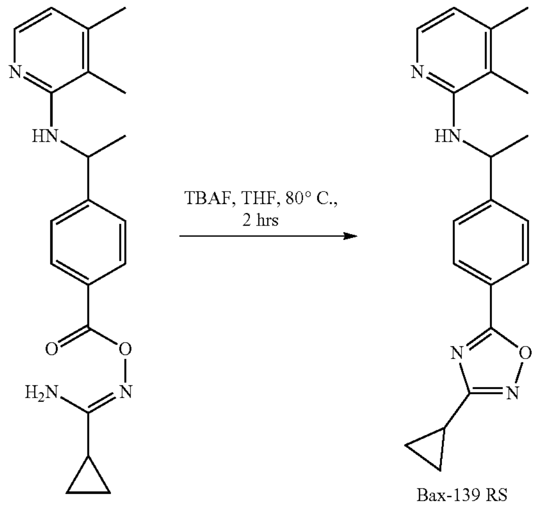

4
Bax-139 RS

To a solution of [(Z)-[amino(cyclopropyl)methylene] amino] 4-[1-[(3,4-dimethyl-2-pyridyl)amino]ethyl]benzoate (130 mg, 368.87 umol, 1 eq) in THF (2 mL) was added TBAF (1 M, 1.11 mL, 3 eq) (in THF). The mixture was stirred at 80° C. for 2 hrs. The reaction mixture was concentrated in vacuo to give a residue. The residue was purified by prep-TLC ($SiO_2$, EtOAc/PE=2:1). Then the residue was purified again by prep-HPLC (column: Phenomenex Luna C18 150*30 mm*5 μm; mobile phase: [water (0.04% HCl)-ACN]; B %: 20%-50%, 10 min) to give N-[l-[4-(3-cyclopropyl-1,2,4-oxadiazol-5-yl)phenyl]ethyl]-3,4-dimethyl-pyridin-2-amine (44.8 mg, 120.80 umol, 32.75% yield, 100% purity, HCl) as a white solid. ESI [M+H]=335.2.

$^1$H NMR (400 MHz, METHANOL-d4) δ 8.09 (d, J=8.3 Hz, 2H), 7.67 (d, J=8.3 Hz, 2H), 7.64-7.58 (m, 1H), 6.88 (d, J=6.6 Hz, 1H), 5.23 (q, J=6.4 Hz, 1H), 2.50-2.44 (m, 3H), 2.40-2.34 (m, 3H), 2.20-2.09 (m, 1H), 1.83-1.74 (m, 3H), 1.16-1.09 (m, 2H), 1.09-1.04 (m, 2H)

Example 56

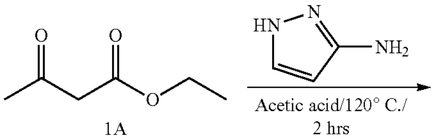

1A

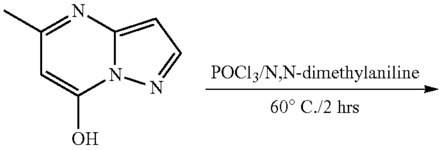

2A

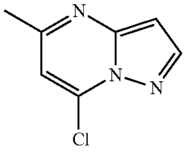
3A

-continued

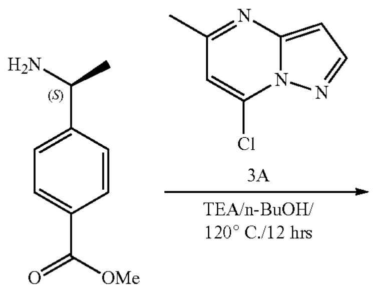

1

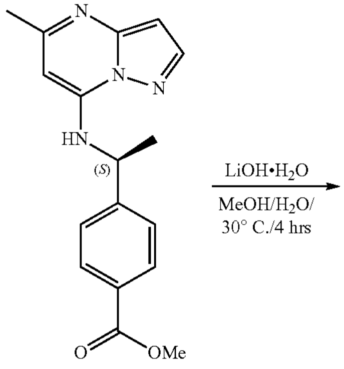

2

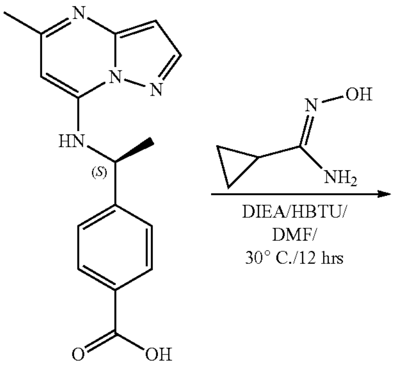

3

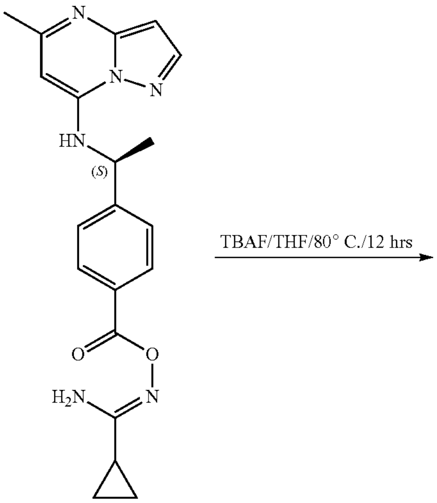

4

-continued

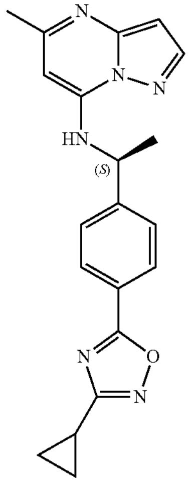

Bax-140 S

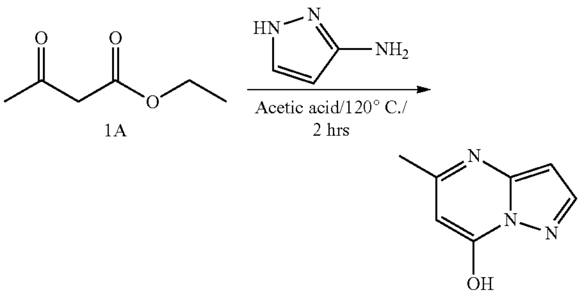

1A

2A

A mixture of ethyl 3-oxobutanoate (5 g, 38.42 mmol, 4.85 mL, 1 eq) and 1H-pyrazol-3-amine (3.19 g, 38.42 mmol, 1 eq) in AcOH (30 mL) was stirred at 120° C. for 2 hrs. The reaction mixture was cooled to RT and filtered. The filtered cake was washed by EtOAc (10 mL*2), and concentrated to give 5-methylpyrazolo[1,5-a]pyrimidin-7-ol (5 g, 33.52 mmol, 87.26% yield) as a white solid. ESI [M+H]=150.1.

$^1$H-NMR (400 MHz, DMSO-d6) δ 12.27 (br s, 1H), 7.82 (d, J=1.8 Hz, 1H), 6.09 (d, J=1.8 Hz, 1H1), 5.57 (s, 1H1), 2.29 (s, 3H).

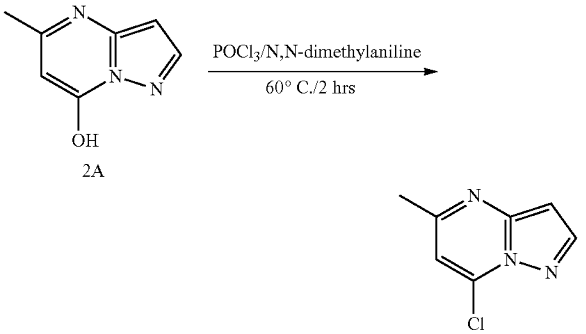

2A

3A

A mixture of 5-methylpyrazolo[1,5-a]pyrimidin-7-ol (3 g, 20.11 mmol, 1 eq) in $POCl_3$ (24.67 g, 160.91 mmol, 14.95 mL, 8 eq) and N,N-DIMETHYLANILINE (9.75 g, 80.46 mmol, 10.20 mL, 4 eq) was stirred at 60° C. for 2 hrs. The reaction mixture was poured into a stirring ice water (200 mL), and adjusted to pH=7 by saturated aq. $NaHCO_3$, filtered, the filtrate was extracted with DCM (100 mL*3), dried over $Na_2SO_4$, filtered and concentrated to give the crude product. The crude product was purified by column chromatography ($SiO_2$, Petroleum ether/Ethyl acetate=1/0 to 10/1) to give 7-chloro-5-methyl-pyrazolo[1,5-a]pyrimidine (2.5 g, 14.92 mmol, 74.16% yield) as a light green oil.

$^1$H-NMR (400 MHz, CHLOROFORM-d) δ 8.09 (d, J=2.1 Hz, 1H), 6.79 (s, 1H), 6.60 (d, J=2.2 Hz, 11H), 2.54 (s, 3H1).

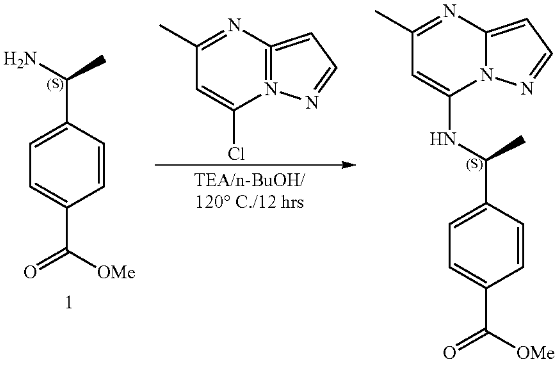

1

2

A mixture of methyl 4-[(1S)-1-aminoethyl]benzoate (300 mg, 1.67 mmol, 1 eq), 7-chloro-5-methyl-pyrazolo[1,5-a]pyrimidine (336.66 mg, 2.01 mmol, 1.2 eq) and $Et_3N$ (338.78 mg, 3.35 mmol, 465.99 uL, 2 eq) in n-BuOH (8 mL) was stirred at 120° C. for 12 hrs. The mixture was concentrated in reduced pressure to give a residue. The residue was purified by column chromatography ($SiO_2$, Petroleum ether/Ethyl acetate=1/0 to 1/1) to give methyl 4-[(1S)-1-[(5-methylpyrazolo[1,5-a]pyrimidin-7-yl)amino]ethyl]benzoate (500 mg, 1.61 mmol, 96.24% yield) as a light brown oil. ESI [M+H]=311.1.

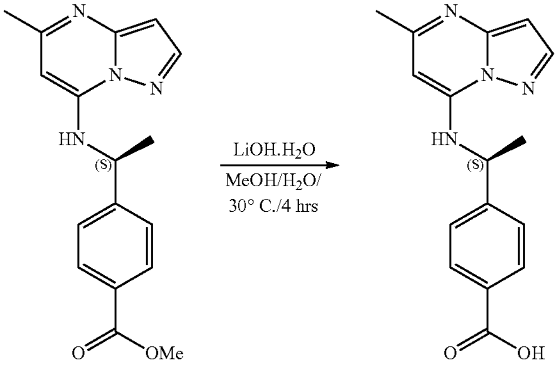

2

3

To a solution of methyl 4-[(1S)-1-[(5-methylpyrazolo[1,5-a]pyrimidin-7-yl)amino]ethyl]benzoate (500 mg, 1.61 mmol, 1 eq) in MeOH (5 mL) and $H_2O$ (1 mL) was added $LiOH{\cdot}H_2O$ (135.21 mg, 3.22 mmol, 2 eq). The resulting mixture was stirred at 30° C. for 4 hrs. The reaction mixture was concentrated to give a residue. To the residue was added $H_2O$ (10 mL), extracted with MTBE (5 mL*2), the aqueous layer was acidified to pH=2, and extracted with DCM/i-PrOH (3/1, 5 mL*10). The combined organic layers were dried over $Na_2SO_4$, filtered and concentrated under reduced pressure to give 4-[(1S)-1-[(5-methylpyrazolo[1,5-a]pyrimidin-7-yl)amino]ethyl]benzoic acid (470 mg, 1.59 mmol, 98.45% yield) as a light brown solid. ESI [M+H]=297.1.

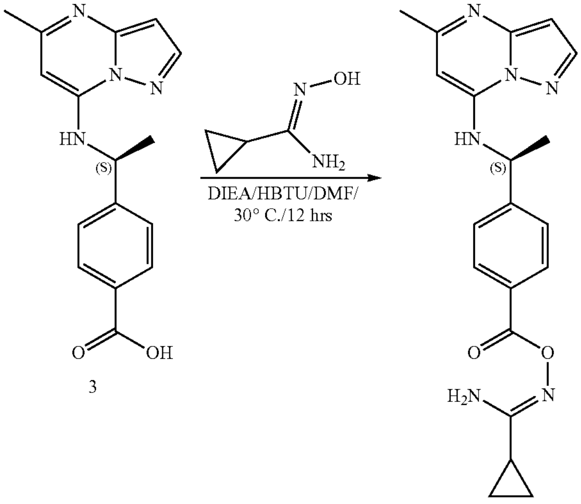

3

4

To a solution of 4-[(1S)-1-[(5-methylpyrazolo[1,5-a]pyrimidin-7-yl)amino]ethyl]benzoic acid (470 mg, 1.59 mmol, 1 eq) in DMF (4 mL) was added DIPEA (614.98 mg, 4.76 mmol, 828.81 uL, 3 eq), N'-hydroxycyclopropanecarboxamidine (238.20 mg, 2.38 mmol, 1.5 eq) and HBTU (721.82 mg, 1.90 mmol, 1.2 eq). The mixture was stirred at 30° C. for 12 hrs. The reaction mixture was concentrated to give a residue. The residue was purified by column chromatography ($SiO_2$, Petroleum ether/Ethyl acetate=10/1 to 1/1) to give [(Z)-[amino(cyclopropyl)methylene]amino] 4-[(1S)-1-[(5-methylpyrazolo[1,5-a]pyrimidin-7-yl)amino]ethyl]benzoate (600 mg, crude) as a brown solid. ESI [M+H]=379.1.

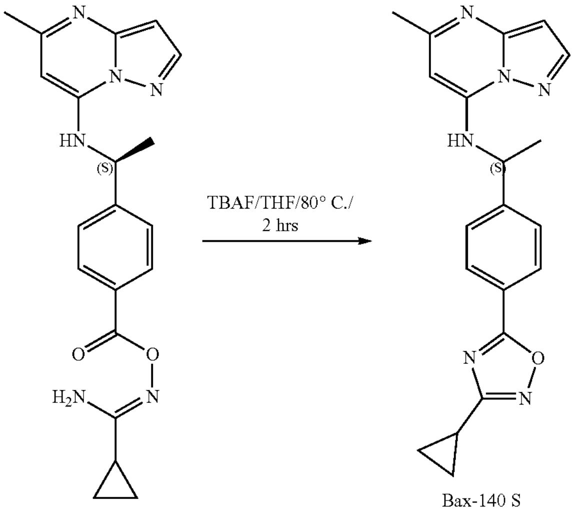

4

Bax-140 S

To a solution of [(Z)-[amino(cyclopropyl)methylene] amino] 4-[(1S)-1-[(5-methylpyrazolo[1,5-a]pyrimidin-7-yl) amino]ethyl]benzoate (200 mg, 528.50 umol, 1 eq) in THF (3 mL) was added TBAF (1 M, 2.11 mL, 4 eq), the mixture was stirred at 80° C. for 2 hrs. The mixture was concentrated to give a residue. The residue was purified by prep-TLC (EtOAc:MeOH=10:1) and prep-HPLC (column: Phenomenex Luna C18 150*30 mm*5 um; mobile phase: [water (0.04% HCl)-ACN]; B %: 25%-55%, 10 min) to give N-[(1S)-1-[4-(3-cyclopropyl-1,2,4-oxadiazol-5-yl)phenyl] ethyl]-5-methyl-pyrazolo[1,5-a]pyrimidin-7-amine (63.3 mg, 159.50 umol, 30.18% yield, 100.000% purity, HCl) as a white solid. ESI [M+H]=361.1.

$^1$H-NMR (400 MHz, METHANOL-d4) δ 8.27 (d, J=1.8 Hz, 1H), 8.13 (br d, J=8.3 Hz, 2H), 7.72 (br d, J=8.2 Hz, 2H), 6.54 (d, J=2.0 Hz, 1H), 6.42 (s, 1H), 5.37 (q, J=6.5 Hz, 1H), 2.58 (s, 3H), 2.22-2.11 (m, 1H), 1.84 (d, J=6.8 Hz, 3H), 1.17-1.05 (m, 4H).

Example 57

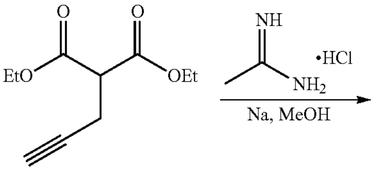

1

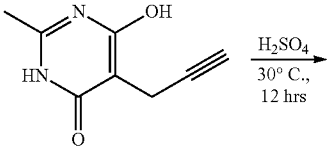

2

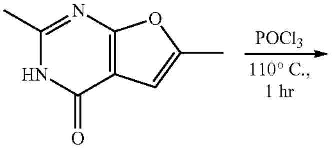

3

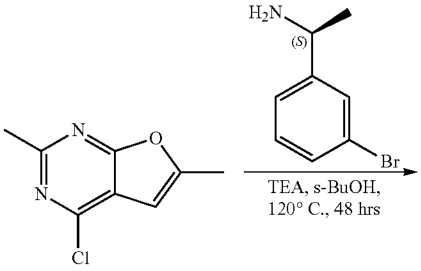

4

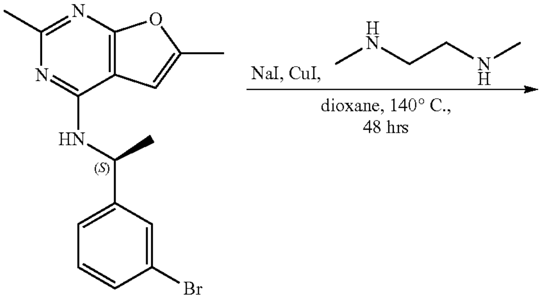

5

-continued

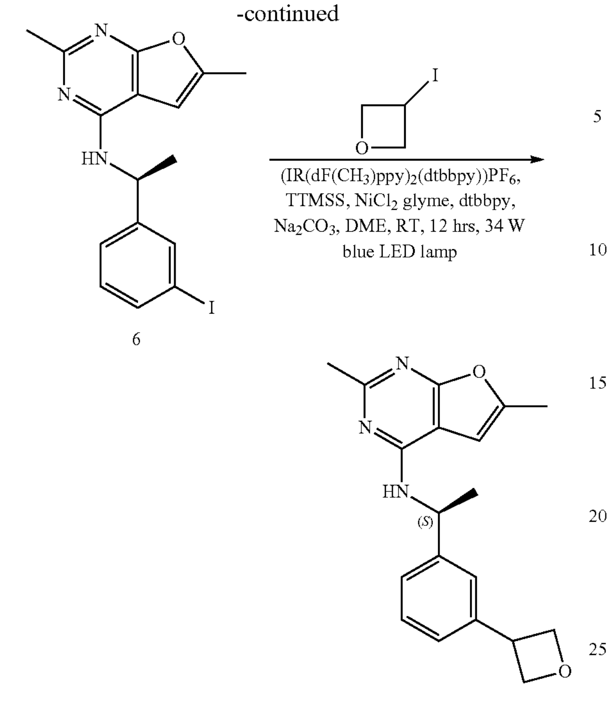

6

Bax-144 S

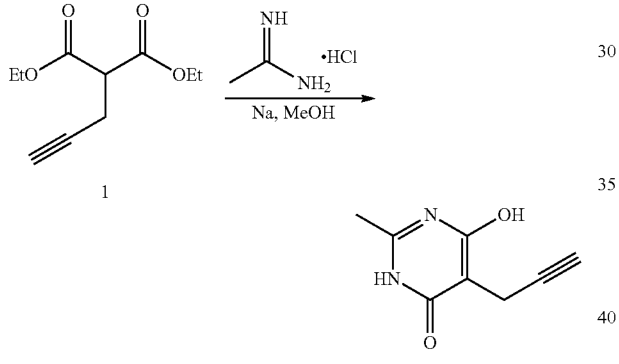

1

2

A solution of Na (1.16 g, 50.45 mmol, 1.20 mL, 1 eq) in MeOH (200 mL) was stirred 20 min, then diethyl 2-prop-2-ynylpropanedioate (10 g, 50.45 mmol, 1 eq) and acetamidine; hydrochloride (4.77 g, 50.45 mmol, 1 eq) was added. The mixture was stirred at 70° C. for 12 hrs. The precipitate was formed and collected by filtration and dissolved in 20 mL of water. This solution was adjusted to pH=3 with 1N HCl, and then the mixture was filtered and collection of filter cake to give 4-hydroxy-2-methyl-5-prop-2-ynyl-1H-pyrimidin-6-one (1.1 g, 6.70 mmol, 13.28% yield) as a white solid. ESI [M+H]=165.1.

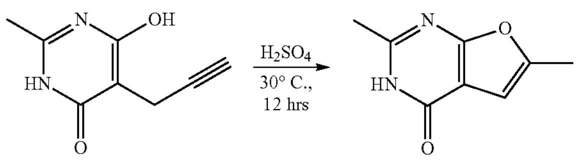

2

3

A solution of 4-hydroxy-2-methyl-5-prop-2-ynyl-1H-pyrimidin-6-one (1.1 g, 6.70 mmol, 1 eq) in $H_2SO_4$ (12 mL) was stirred at 30° C. for 12 hrs. The reaction mixture was quenched by addition to cold water (30 mL), and extracted with DCM (30 mL*4). The organic layer was dried over $MgSO_4$ and concentrated in vacuo to give 2,6-dimethyl-3H-furo[2,3-d]pyrimidin-4-one (820 mg, crude) as a white solid. ESI [M+H]=165.1.

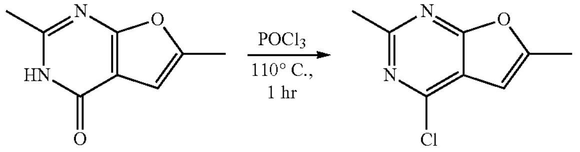

3

4

A solution of 2,6-dimethyl-3H-furo[2,3-d]pyrimidin-4-one (820 mg, 5.00 mmol, 1 eq) in $POCl_3$ (12 mL) was stirred at 110° C. for 1 hr. The reaction mixture was concentrated in vacuo to give 4-chloro-2,6-dimethyl-furo[2,3-d]pyrimidine (1.5 g, crude) as a brown oil. ESI [M+H and M+3H]=183.1 and 185.1.

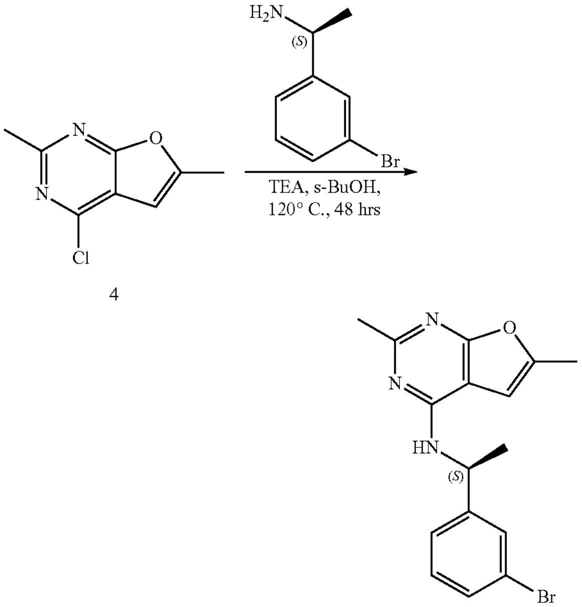

4

5

A mixture of 4-chloro-2,6-dimethyl-furo[2,3-d]pyrimidine (200 mg, 1.10 mmol, 1 eq), (1S)-1-(3-bromophenyl)ethanamine (219.13 mg, 1.10 mmol, 1 eq) and TEA (443.31 mg, 4.38 mmol, 609.78 uL, 4 eq) in s-BuOH (4 mL) was stirred at 120° C. for 48 hrs. The reaction mixture was concentrated under reduced pressure to give a residue. The residue was purified by prep-HPLC (column: Phenomenex Luna C18 150*30 mm*5 µm; mobile phase: [water (0.04% HCl)-ACN]; B %: 30%-60%, 10 min) to give N-[(1S)-1-(3-bromophenyl)ethyl]-2,6-dimethyl-furo[2,3-d]pyrimidin-4-amine (80 mg, 231.07 umol, 21.10% yield) as a white solid. ESI [M+H and M+3H]=346.0 and 348.0.

$^1$H-NMR (400 MHz, DMSO-d6) δ 8.65 (s, 1H), 7.65 (s, 1H), 7.45 (d, J=5.4 Hz, 2H), 7.35-7.27 (m, 1H), 6.80 (s, 1H), 5.54 (s, 1H), 2.44 (s, 3H), 2.42-2.38 (m, 3H), 1.54 (d, J=6.9 Hz, 3H).

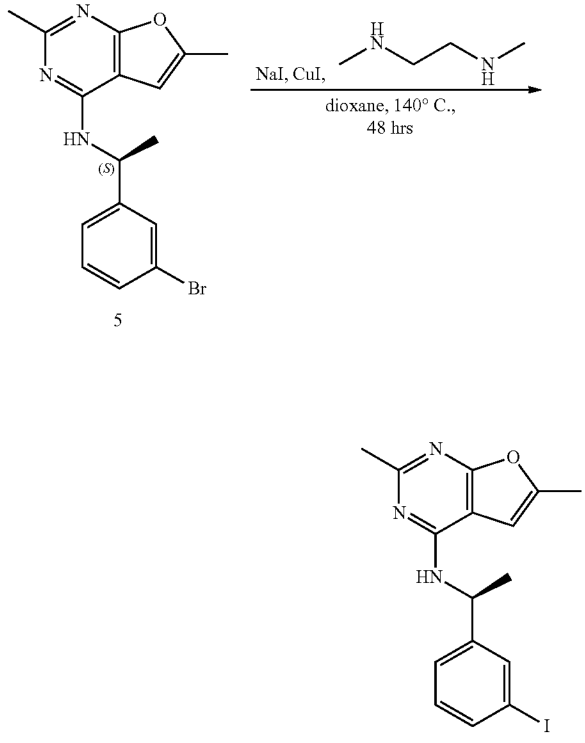

5

6

To a solution of N-[(1S)-1-(3-bromophenyl)ethyl]-2,6-dimethyl-furo[2,3-d]pyrimidin-4-amine (60 mg, 173.30 umol, 1 eq) in dioxane (4 mL) was added NaI (77.93 mg, 519.90 umol, 3 eq), CuI (3.30 mg, 17.33 umol, 0.1 eq) and N,N'-dimethylethane-1,2-diamine (3.82 mg, 43.32 umol, 4.66 uL, 0.25 eq) under N2. The mixture was stirred at 140° C. for 48 hrs in a 30 mL of sealed tube. The reaction was concentrated in vacuo to give a residue. The residue was purified by prep-TLC ($SiO_2$, Petroleum ether:Ethyl acetate=2:1) to give N-[(1S)-1-(3-iodophenyl)ethyl]-2,6-dimethyl-furo[2,3-d]pyrimidin-4-amine (65 mg, 165.30 umol, 95.38% yield) as a yellow oil. ESI [M+H]=394.0.

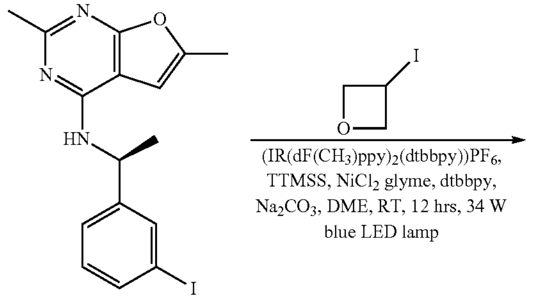

6

-continued

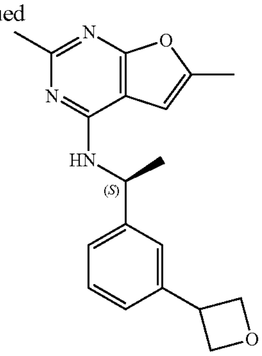

Bax-144 S

A mixture of N-[(1S)-1-(3-iodophenyl)ethyl]-2,6-dimethyl-furo[2,3-d]pyrimidin-4-amine (60 mg, 152.59 umol, 1 eq), 3-iodooxetane (126.32 mg, 686.64 umol, 4.5 eq), TTMSS (37.94 mg, 152.59 umol, 47.07 uL, 1 eq), $Na_2CO_3$ (32.35 mg, 305.17 umol, 2 eq), dichloronickel; 1,2 dimethoxyethane (8.38 mg, 38.15 umol, 0.25 eq), 4-tert-butyl-2-(4-tert-butyl-2-pyridyl)pyridine (12.29 mg, 45.78 umol, 0.3 eq) and $(IR(dF(CH3)ppy)_2(dtbbpy))PF_6$ (30.95 mg, 30.52 umol, 0.2 eq) in DME (5 mL) was stirred and irradiated with a 34 W blue LED lamp at 20° C. for 12 hrs under N2. The reaction mixture was added $H_2O$ (10 mL) and extracted with EtOAc (10 mL*3). The combined organic layers were dried over $Na_2SO_4$, filtered and concentrated under reduced pressure to give a residue. The residue was purified by prep-HPLC (column: Waters Xbridge BEH C18 100*30 mm*10 um; mobile phase: [water (10 mM NH4HCO3)-ACN]; B %: 33%-63%, 10 min) to give 2,6-dimethyl-N-[(1S)-1-[3-(oxetan-3-yl)phenyl]ethyl]furo[2,3-d]pyrimidin-4-amine (11.23 mg, 34.73 umol, 22.76% yield, 100% purity) as a white solid. ESI [M+H]=324.1.

$^1H$ NMR (400 MHz, METHANOL-d4) δ 7.36 (s, 1H), 7.24-7.19 (m, 2H), 7.19-7.12 (m, 1H), 6.41 (s, 1H), 5.49-5.30 (m, 1H), 4.96 (dd, J=5.9, 8.4 Hz, 2H), 4.66-4.50 (m, 2H), 4.22-4.06 (m, 1H), 2.32-2.30 (m, 3H), 2.28-2.22 (m, 3H), 1.48 (d, J=7.0 Hz, 3H)

Example 58

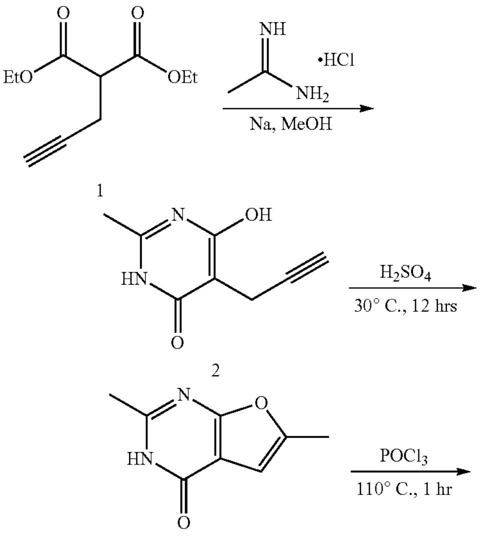

1

2

3

-continued

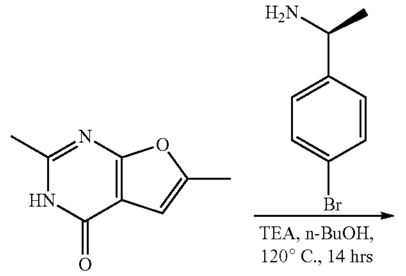

3

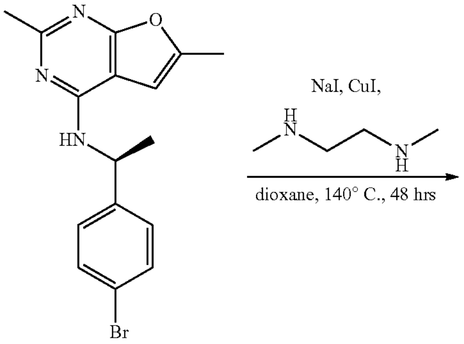

5

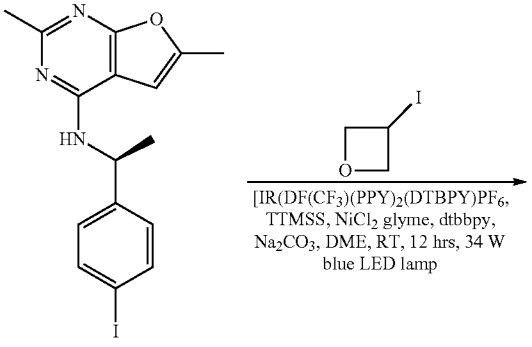

6

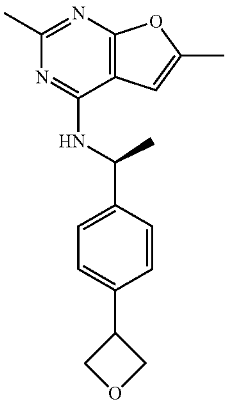

Bax-145 S

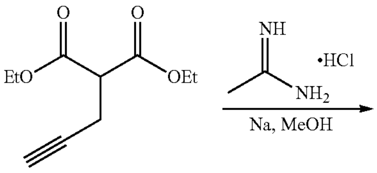

1

-continued

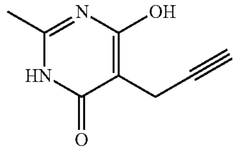

2

A solution of Na (1.16 g, 50.45 mmol, 1.20 mL, 1 eq) in MeOH (200 mL) was stirred 20 min, then diethyl 2-prop-2-ynylpropanedioate (10 g, 50.45 mmol, 1 eq) and acetamidine; hydrochloride (4.77 g, 50.45 mmol, 1 eq) was added. The mixture was stirred at 70° C. for 12 hrs. The precipitate was formed and collected by filtration and dissolved in 20 mL of water. This solution was adjusted to pH=3 with 1N HCl, and then the mixture was filtered and collection of filter cake to give 4-hydroxy-2-methyl-5-prop-2-ynyl-1H-pyrimidin-6-one (1.1 g, 6.70 mmol, 13.28% yield) as a white solid. ESI [M+H]=165.1.

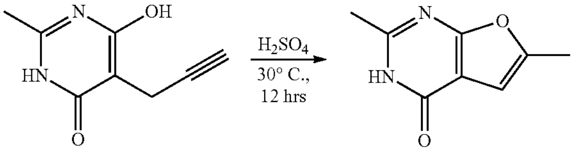

2 3

A solution of 4-hydroxy-2-methyl-5-prop-2-ynyl-1H-pyrimidin-6-one (1.1 g, 6.70 mmol, 1 eq) in $H_2SO_4$ (12 mL) was stirred at 30° C. for 12 hrs. The reaction mixture was quenched by addition to cold water (30 mL), and extracted with DCM (30 mL*4). The organic layer was dried over $MgSO_4$ and concentrated in vacuo to give 2,6-dimethyl-3H-furo[2,3-d]pyrimidin-4-one (820 mg crude) as a white solid. ESI [M+H]=165.1.

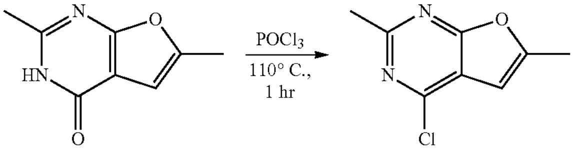

3 4

A solution of 2,6-dimethyl-3H-furo[2,3-d]pyrimidin-4-one (820 mg, 5.00 mmol, 1 eq) in $POCl_3$ (12 mL) was stirred at 110° C. for 1 hr. The reaction mixture was concentrated in vacuo to give 4-chloro-2,6-dimethyl-furo[2,3-d]pyrimidine (1.5 g, crude) as a brown oil. ESI [M+H and M+3H]=183.1 and 185.1.

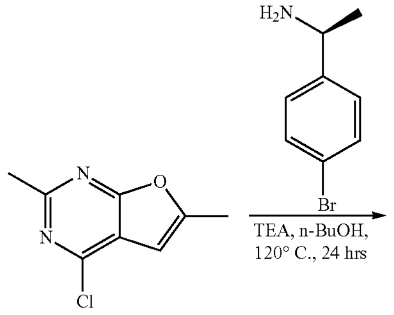

4

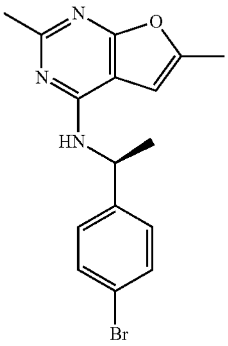

5

To a solution of 4-chloro-2,6-dimethyl-furo[2,3-d]pyrimidine (300 mg, 1.64 mmol, 1 eq) in 2-BuOH (7 mL) was added TEA (831.21 mg, 8.21 mmol, 1.14 mL, 5 eq) and (1S)-1-(4-bromophenyl)ethanamine (493.05 mg, 2.46 mmol, 354.71 μL, 1.5 eq). The mixture was stirred at 110° C. for 12 hrs. The reaction mixture was concentrated under reduced pressure to give a residue. The residue was purified by column chromatography ($SiO_2$, Petroleum ether/Ethyl acetate=20/1 to 3/1). Then the residue was purified again by prep-HPLC (column: Waters Xbridge BEH C18 100*30 mm*10 μm; mobile phase: [water (10 mM $NH_4HCO_3$)-ACN]; B %: 45%-75%, 10 min) to give N-[(1S)-1-(4-bromophenyl)ethyl]-2,6-di-methyl-furo[2,3-d]pyrimidin-4-amine (150 mg, 433.25 umol, 26.37% yield) as a white solid. ESI [M+H and M+3H1]=346.0 and 348.0.

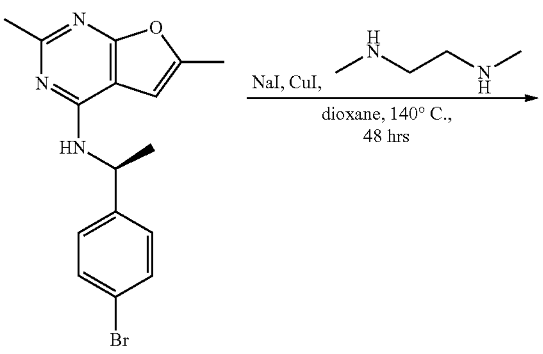

5

-continued

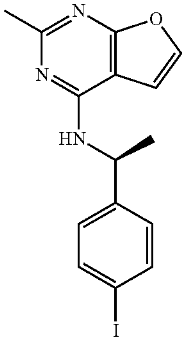

6

To a solution of N-[(1S)-1-(4-bromophenyl)ethyl]-2,6-dimethyl-furo[2,3-d]pyrimidin-4-amine (140 mg, 404.37 umol, 1 eq) in dioxane (6 mL) was added NaI (181.84 mg, 1.21 mmol, 3 eq), CuI (7.70 mg, 40.44 umol, 0.1 eq) and N,N'-dimethylethane-1,2-diamine (8.91 mg, 101.09 μmol, 10.88 uL, 0.25 eq) under N2. The mixture was stirred at 140° C. for 48 hrs in a 30 mL of sealed tube. The reaction was concentrated in vacuo to give a residue. The residue was purified by prep-TLC ($SiO_2$, Petroleum ether:Ethyl acetate=2:1) to give N-[(1S)-1-(4-iodophenyl)ethyl]-2,6-di-methyl-furo[2,3-d]pyrimidin-4-amine (155 mg, 394.18 μmol, 97.48% yield) as a yellow solid. ESI [M+H and M+3H]=394.0.

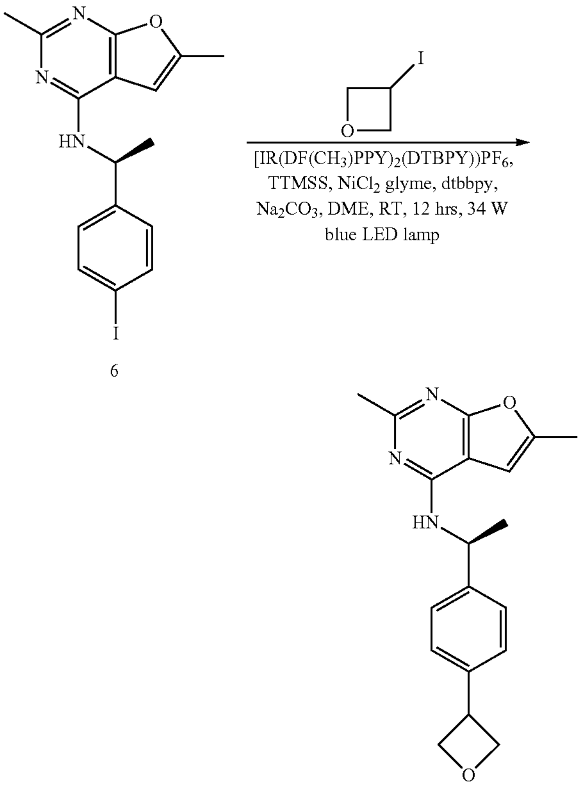

6

Bax-145 S

A mixture of N-[(1S)-1-(4-iodophenyl)ethyl]-2,6-dimethyl-furo[2,3-d]pyrimidin-4-amine (111 mg, 282.28 umol, 1 eq), 3-iodooxetane (207.73 mg, 1.13 mmol, 4 eq), TTMSS (70.19 mg, 282.28 umol, 87.09 uL, 1 eq), $Na_2CO_3$ (59.84 mg, 564.57 umol, 2 eq), dichloronickel; 1,2-dimethoxyethane (15.51 mg, 70.57 umol, 0.25 eq), 4-tert-butyl-2-(4-tert-butyl-2-pyridyl)pyridine (22.73 mg, 84.69 umol, 0.3 eq) and $(IR(dF(CH_3)ppy)_2(dtbbpy))PF_6$ (57.26 mg, 56.46 umol, 0.2 eq) in DME (3 mL) was stirred and irradiated with a 34 W blue LED lamp at 30° C. for 12 hrs under N2. To the reaction mixture was added water 10 mL, and extracted with EtOAc (15 mL*3). The organic layer was dried over $Na_2SO_4$ and concentrated in vacuo to give a residue. The residue was purified by prep-HPLC (column: Waters Xbridge Prep OBD C18 150*40 mm*10 μm; mobile phase: [water (10 mM $NH_4HCO_3$)-ACN]; B %: 30%-60%, 8 min) to give 2,6-dimethyl-N-[(1S)-1-[4-(oxetan-3-yl)phenyl]ethyl]furo[2,3-d]pyrimidin-4-amine (13.05 mg, 40.21 μmol, 14.24% yield, 99.631% purity) as a white solid. ESI [M+H]=324.1.

$^1H$ NMR (400 MHz, METHANOL-d4) δ 7.53-7.26 (m, 4H), 6.58 (s, 1H), 5.60-5.38 (m, 1H), 5.09 (dd, J=5.9, 8.3 Hz, 2H), 4.88-4.86 (m, 1H), 4.81-4.63 (m, 2H), 4.35-4.16 (m, 1H), 2.46 (s, 3H), 2.42 (s, 3H), 1.61 (d, J=7.0 Hz, 3H)

Example 59

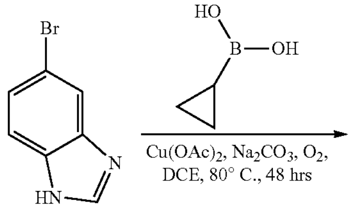

1

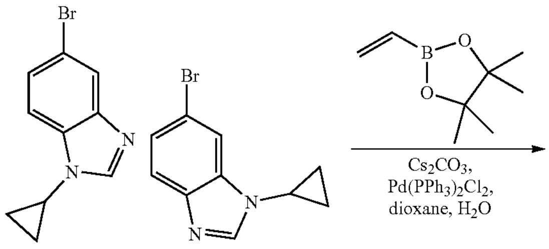

2 2A

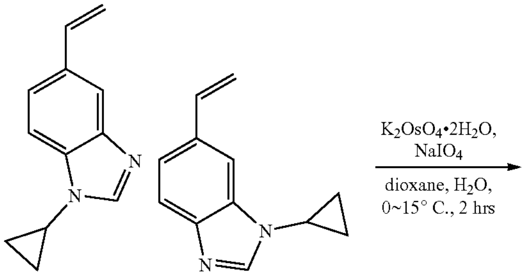

3 3A

-continued

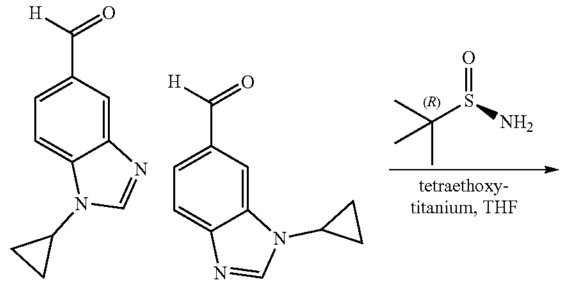

4 4A

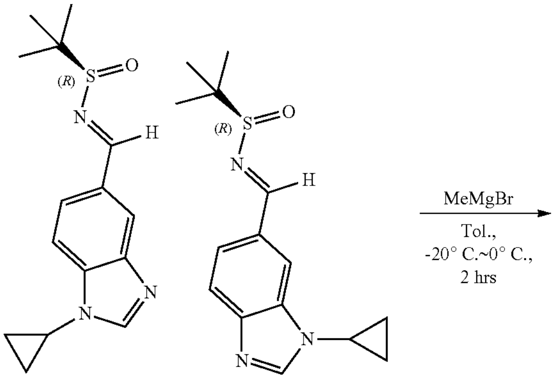

5 5A

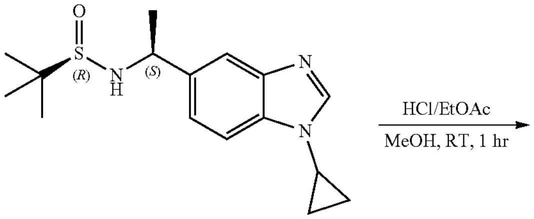

6

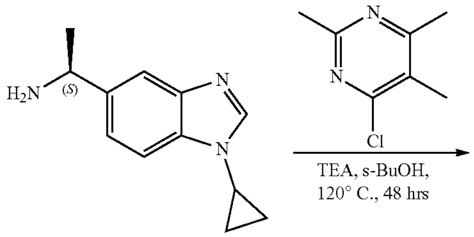

7

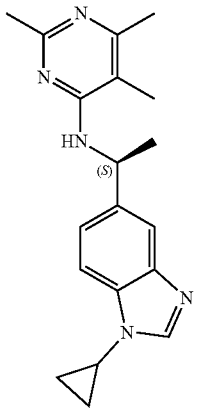

Bax-146 s

-continued

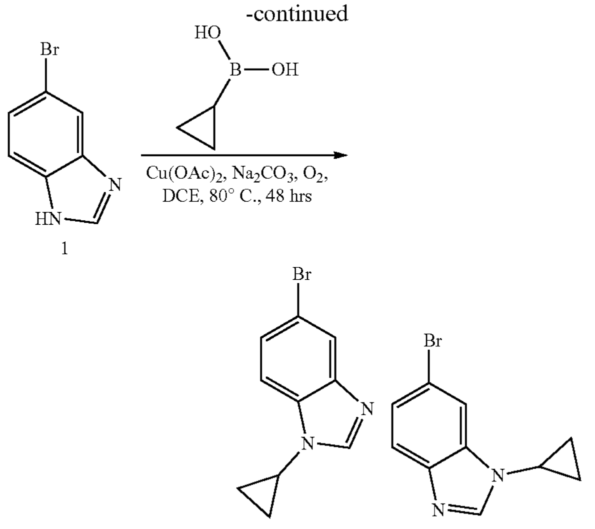

1

2

2A

A mixture of 6-bromo-1H-benzimidazole (4 g, 20.30 mmol, 1 eq), cyclopropylboronic acid (4.36 g, 50.75 mmol, 2.5 eq), $Cu(OAc)_2$ (3.69 g, 20.30 mmol, 1 eq), 2-(2-pyridyl) pyridine (3.17 g, 20.30 mmol, 1 eq) and $Na_2CO_3$ (6.46 g, 60.90 mmol, 3 eq) in DCE (120 mL) was stirred at 80° C. for 48 hrs under 02 (15 psi). The reaction mixture was filtered and the filtrate was concentrated to give a residue. The residue was purified by column chromatography ($SiO_2$, Petroleum ether/Ethyl acetate=1/0 to 0/1) to give 6-bromo-1-cyclopropyl-benzimidazole (1.2 g, 5.06 mmol, 49.86% yield) and 5-bromo-1-cyclopropyl-benzimidazole (1.2 g, 5.06 mmol, 49.86% yield) (regio-mixture total 2.4 g) as a brown oil. ESI [M+H and M+3H]=236.9 and 238.9.

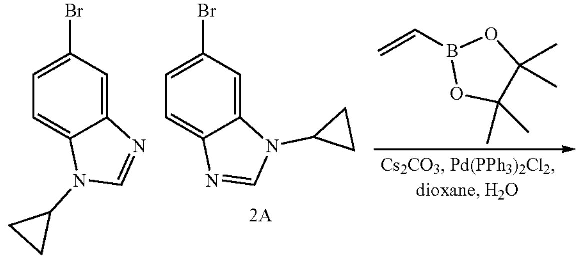

2

2A

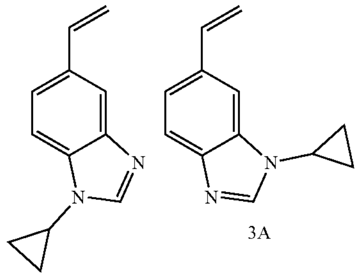

3

3A

A mixture of 5-bromo-1-cyclopropyl-benzimidazole (1.2 g, 5.06 mmol, 0.5 eq), 6-bromo-1-cyclopropyl-benzimidazole (1.20 g, 5.06 mmol, 0.5 eq) (regio-mixture, total 2.4 g), 4,4,5,5-tetramethyl-2-vinyl-1,3,2-dioxaborolane (3.90 g, 25.31 mmol, 4.29 mL, 2.5 eq), $Cs_2CO_3$ (8.25 g, 25.31 mmol, 2.5 eq) and Pd(PPh3)2Cl2 (355.25 mg, 506.13 umol, 0.05 eq) in dioxane (40 mL) and $H_2O$ (10 mL) was stirred at 80° C. for 16 hrs. The mixture was concentrated to give a residue. To the residue was added $H_2O$ (20 mL) and extracted with EtOAc (20 mL*5). The combined organic layers were washed with brine (10 mL*2), dried over $Na_2SO_4$, filtered and concentrated under reduced pressure to give the crude product. The crude product was purified by column chromatography ($SiO_2$, Petroleum ether/Ethyl acetate=1/0 to 0/1) 1-cyclopropyl-5-vinyl-benzimidazole (0.8 g, 4.34 mmol, 85.79% yield) and 1-cyclopropyl-6-vinyl-benzimidazole (0.8 g, 4.34 mmol, 85.79% yield) (regio-mixture) total 1.6 g was obtained as a yellow oil. ESI [M+H]=185.1.

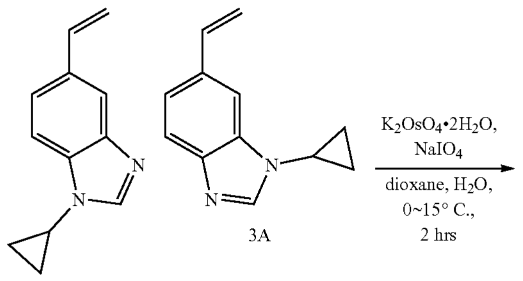

3

3A

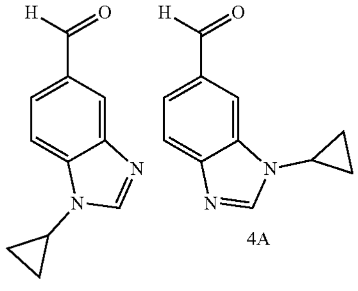

4

4A

To a 0° C. stirred solution of 1-cyclopropyl-5-vinyl-benzimidazole (0.8 g, 4.34 mmol, 0.5 eq), 1-cyclopropyl-6-vinyl-benzimidazole (800.00 mg, 4.34 mmol, 0.5 eq) (regio-mixture, total 1.6 g) in dioxane (30 mL) and $H_2O$ (10 mL) was added $NaIO_4$ (3.72 g, 17.37 mmol, 962.45 uL, 2.0 eq) and dipotassium; dioxido(dioxo)osmium; dihydrate (479.98 mg, 1.30 mmol, 0.15 eq). The resulting mixture was stirred at 15° C. for 2 hrs. The mixture was concentrated to give a residue. To the residue was added $H_2O$ (20 mL) and then quenched with saturated aq·$Na_2SO_3$ (30 mL), extracted with EtOAc/THF (3:1, 30 mL*3), dried over $Na_2SO_4$, filtered and concentrated under reduced pressure to give 1-cyclopropylbenzimidazole-5-carbaldehyde (800 mg, crude) and 3-cyclopropylbenzimidazole-5-carbaldehyde (800 mg, crude) (regio-mixture, total 1.6 g, crude) as a brown oil. ESI [M+H]=187.0.

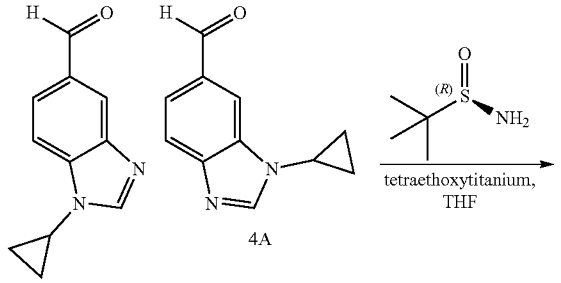

4

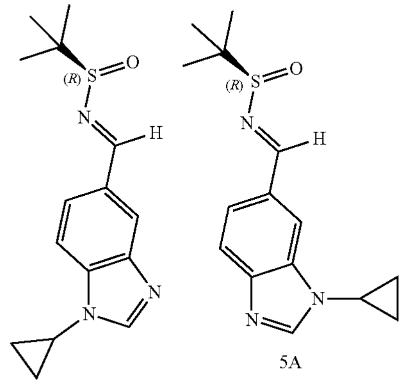

5

To a 15° C. stirred mixture of 1-cyclopropylbenzimidazole-5-carbaldehyde (0.8 g, 4.30 mmol, 0.5 eq), 3-cyclopropylbenzimidazole-5-carbaldehyde (800.00 mg, 4.30 mmol, 0.5 eq) (regio-mixture 1.6 g) and 2-methylpropane-2-sulfinamide (2.29 g, 18.90 mmol, 2.2 eq) in THF (30 mL) was added tetraethoxytitanium (3.92 g, 17.18 mmol, 3.56 mL, 2.0 eq), and the resulting mixture was stirred at 70° C. for 12 hrs under N2. To the reaction mixture was added $H_2O$ (20 mL), then filtered, the filtrate was concentrated to give a residue. The residue was purified by prep-HPLC (column: Waters Xbridge Prep OBD C18 150*40 mm*10 μm; mobile phase: [water (10 mM $NH_4HCO_3$)-ACN]; B %: 30%-50%, 8 min) to give (NE)-N-[(3-cyclopropylbenzimidazol-5-yl) methylene]-2-methyl-propane-2-sulfinamide (720 mg, 2.49 mmol, 57.96% yield) and (NE)-N-[(1-cyclopropylbenzimidazol-5-yl)methylene]-2-methyl-propane-2-sulfinamide (620 mg, 2.14 mmol, 49.81% yield) as light brown oil. ESI [M+H]=290.1.

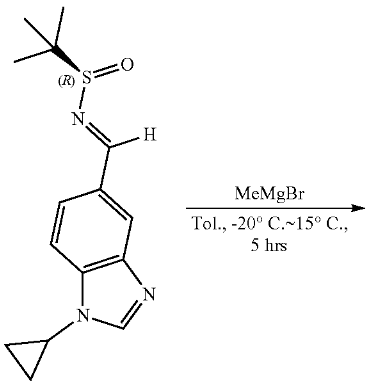

5

-continued

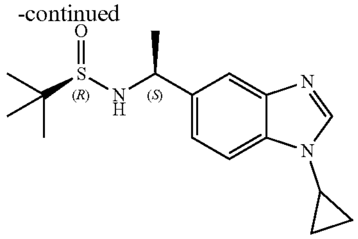

6

To a −20° C. stirred mixture of (NE)-N-[(1-cyclopropylbenzimidazol-5-yl)methylene]-2-methyl-propane-2-sulfinamide (620 mg, 2.14 mmol, 1 eq) in Tol. (20 mL) was added MeMgBr (3 M, 1.79 mL, 2.5 eq) (in ether) dropwise. The mixture was stirred at −20° C.~0° C. for 3 hrs. LCMS showed about ½ of the starting materials were remained and the desired MS was detected. So to the mixture was added MeMgBr (3 M, 2.14 mL, 3.0 eq) (in ether) dropwise at −20° C. under N2 and the mixture was stirred at 0° C.~15° C. for 2 hrs. The reaction mixture was concentrated under reduced pressure to remove tol. To the residue was added saturated aq·$NH_4Cl$ (10 mL) and $H_2O$ (10 mL), extracted with EtOAc (20 mL*3). The combined organic layers were washed with brine (10 mL*2), dried over $Na_2SO_4$, filtered and concentrated under reduced pressure to give a residue. The residue was purified by prep-HPLC (column: Nano-micro Kromasil C18 100*30 mm 5 um; mobile phase: [water (0.1% TFA)-ACN]; B %: 12%-28%, 10 min) to give N-[(1S)-1-(1-cyclopropylbenzimidazol-5-yl)ethyl]-2-methyl-propane-2-sulfinamide (500 mg, 1.64 mmol, 76.41% yield) as a white solid. ESI [M+H]=306.05.

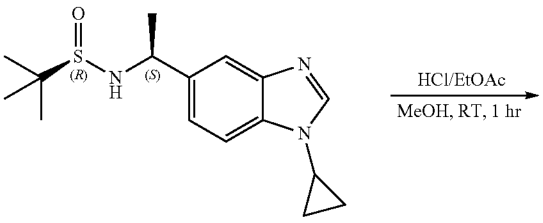

6

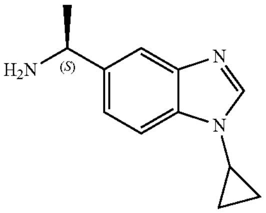

7

To a solution of N-[(1S)-1-(1-cyclopropylbenzimidazol-5-yl)ethyl]-2-methyl-propane-2-sulfinamide (500 mg, 1.64 mmol, 1 eq) in EtOAc (10 mL) and MeOH (10 mL) was added HCl/EtOAc (4 M, 5 mL, 12.22 eq). The resulting mixture was stirred at 10° C. for 1 hr. The reaction mixture was concentrated to give (1S)-1-(1-cyclopropylbenzimidazol-5-yl)ethanamine (380 mg, 1.60 mmol, 97.65% yield, HCl) as a white solid. ESI [M+H]=202.2.

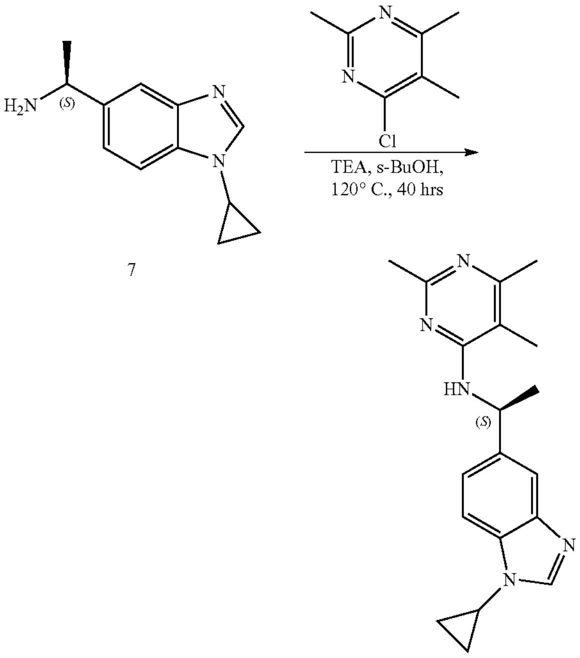

7

Bax-146 S

To a solution of 4-chloro-2,5,6-trimethyl-pyrimidine (79.05 mg, 504.78 μmol, 1.2 eq) in butan-2-ol (3 mL) was added $Et_3N$ (212.83 mg, 2.10 mmol, 292.75 μL, 5 eq), the mixture was stirred at 10° C. for 5 mins, then (1S)-1-(1-cyclopropylbenzimidazol-5-yl)ethanamine (100 mg, 420.65 umol, 1 eq, HCl) was added, the resulting mixture was stirred at 120° C. for 16 hrs. LCMS and HPLC showed about 60% of the starting materials were remained and a peak with the desired MS was detected. So the mixture was stirred at 120° C. for another 24 hrs. The reaction mixture was concentrated to give a residue. The residue was purified by prep-HPLC (column: Phenomenex Luna C18 150*30 mm*5 μm; mobile phase: [water (0.04% HCl)-ACN]; B %: 5%-30%, 10 min) to give the crude product, it was re-purified by prep-HPLC (column: Welch Xtimate C18 150*25 mm*5 μm; mobile phase: [water (10 mM NH4HCO3)-ACN]; B %: 30%-55%, 10 min) to give N-[(1S)-1-(1-cyclopropylbenzimidazol-5-yl)ethyl]-2,5,6-trimethyl-pyrimidin-4-amine (24 mg, 74.45 umol, 17.70% yield, 99.712% purity) as a white solid. ESI [M+H]=534.3.

$^1$H-NMR (400 MHz, METHANOL-d4) δ 8.07 (s, 1H), 7.66 (s, 1H), 7.56 (d, J=8.4 Hz, 1H), 7.40 (d, J=8.4 Hz, 1H), 5.57 (q, J=7.0 Hz, 1H), 3.42 (tt, J=3.6, 7.0 Hz, 1H), 2.27 (d, J=15.4 Hz, 6H), 2.04 (s, 3H), 1.60 (d, J=7.1 Hz, 3H), 1.16-1.08 (m, 2H), 1.05-0.94 (m, 2H).

Example 60

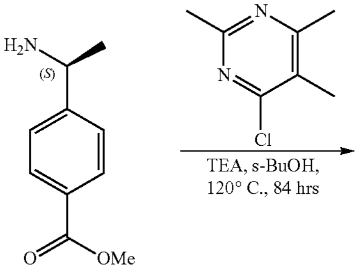

1

-continued

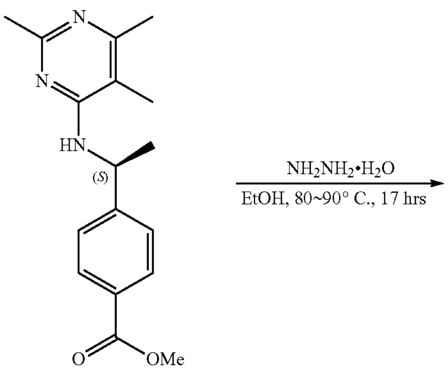

2

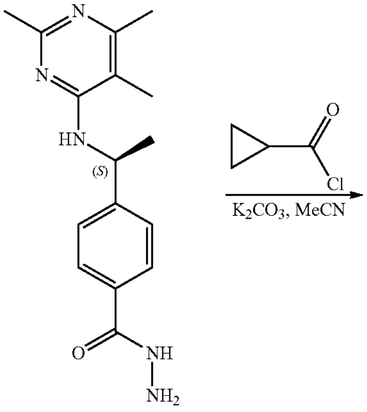

3

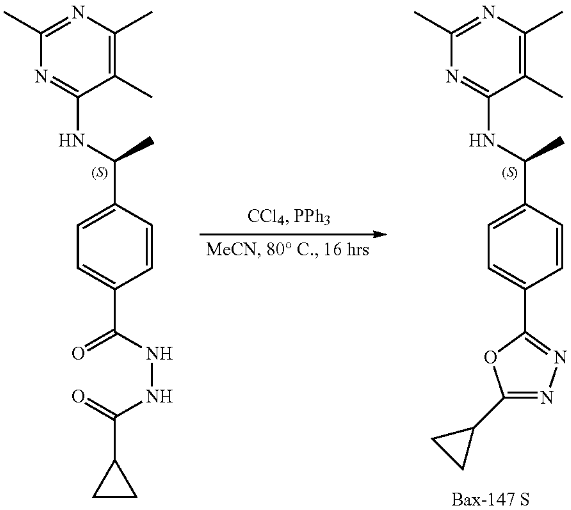

4

Bax-147 S

-continued

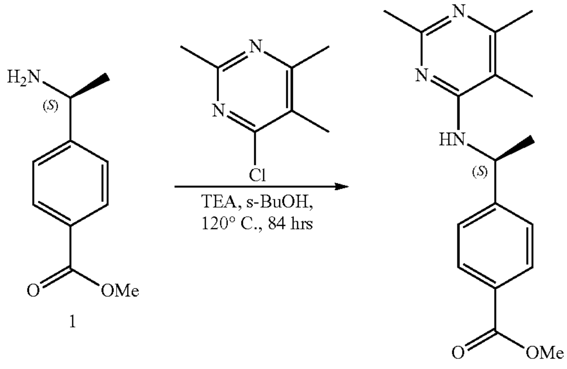

1

2

To a 15° C. stirred solution of 4-chloro-2,5,6-trimethylpyrimidine (314.60 mg, 2.01 mmol, 1.2 eq) in butan-2-ol (4 mL) was added $Et_3N$ (677.55 mg, 6.70 mmol, 931.99 uL, 4 eq), then methyl 4-[(1S)-1-aminoethyl]benzoate (300 mg, 1.67 mmol, 1 eq) was added. The resulting mixture was stirred at 120° C. for 36 hrs. LCMS and HPLC showed about 60% of the starting materials were remained, and a peak with the desired MS was detected. So the mixture was stirred at 120° C. for another 48 hrs. The reaction mixture was concentrated under reduced pressure to give a residue. The residue was purified by prep-HPLC (column: Nano-micro Kromasil C18 100*30 mm 5 μm; mobile phase: [water (0.1% TFA)-ACN]; B %: 18%-40%, 10 min) to give methyl 4-[(1S)-1-[(2,5,6-trimethylpyrimidin-4-yl)amino]ethyl]benzoate (300 mg, 725.71 umol, 43.35% yield, TFA) as a brown oil. ESI [M+H]=300.1.

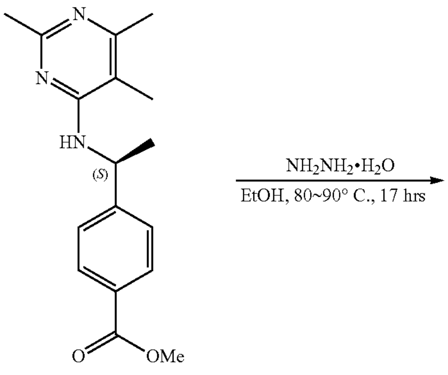

2

-continued

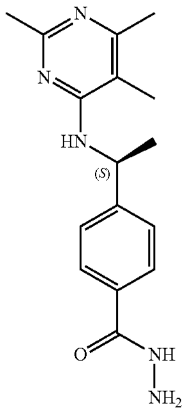

3

To a solution of methyl 4-[(1S)-1-[(2,5,6-trimethylpyrimidin-4-yl)amino]ethyl]benzoate (300 mg, 725.71 umol, 1 eq, TFA) in EtOH (3 mL) was added $NH_2NH_2 \cdot H_2O$ (259.49 mg, 5.08 mmol, 251.94 uL, 7 eq), the resulting mixture was stirred at 80° C. for 12 hrs. LCMS showed a part of 2 was remained, so to the mixture was added $NH_2NH_2 \cdot H_2O$ (111.21 mg, 2.18 mmol, 107.97 μL, 3 eq) and the mixture was stirred at 90° C. for 5 hrs. The mixture was concentrated to give a residue. To the residue was added $H_2O$ (5 mL) and extracted with EtOAc/THF (10 mL*3). The combined organic layers were washed with brine (5 mL), dried over $Na_2SO_4$, filtered and concentrated under reduced pressure to give 4-[(1S)-1-[(2,5,6-trimethylpyrimidin-4-yl)amino]ethyl]benzohydrazide (150 mg, 501.05 umol, 69.04% yield) as a colorless oil. ESI [M+H]=368.1.

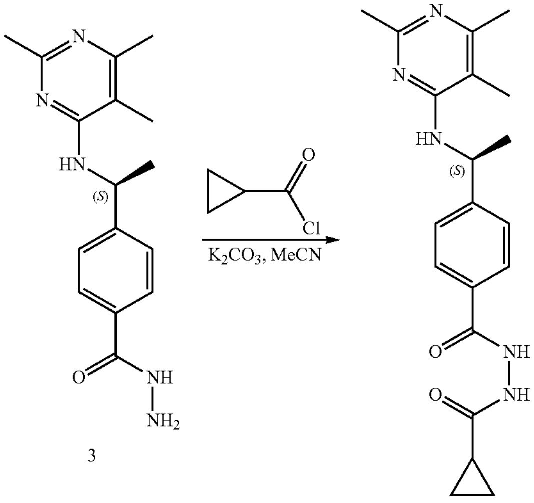

3

4

To a 0° C. stirred mixture of 4-[(1S)-1-[(2,5,6-trimethylpyrimidin-4-yl)amino]ethyl]benzohydrazide (150 mg, 501.05 μmol, 1 eq) and $K_2CO_3$ (103.88 mg, 751.58 umol, 1.5 eq) in MeCN (10 mL) was added cyclopropanecarbonyl chloride (57.62 mg, 551.16 umol, 50.10 uL, 1.1 eq) dropwise, the resulting mixture was stirred at 20° C. for 4 hrs. LCMS showed about 20% of 3 was remained and 60% of desired product was detected. So to the mixture was added $K_2CO_3$ (34.62 mg, 250.53 μmol, 0.5 eq) and cyclopropanecarbonyl chloride (26.19 mg, 250.53 umol, 22.77 uL, 0.5 eq), the resulting mixture was stirred at 20° C. for 2 hrs. The reaction mixture was concentrated under reduced pressure to remove MeCN. The residue was diluted with $H_2O$ (10 mL) and extracted with EtOAc/THF (5:1, 10 mL*3). The combined organic layers were washed with brine (10 mL*2), dried over $Na_2SO_4$, filtered and concentrated under reduced pressure to give N'-(cyclopropanecarbonyl)-4-[(1S)-1-[(2,5,6-trimethylpyrimidin-4-yl)amino]ethyl]benzohydrazide (180 mg, crude) as a white solid. ESI [M+H]=368.1.

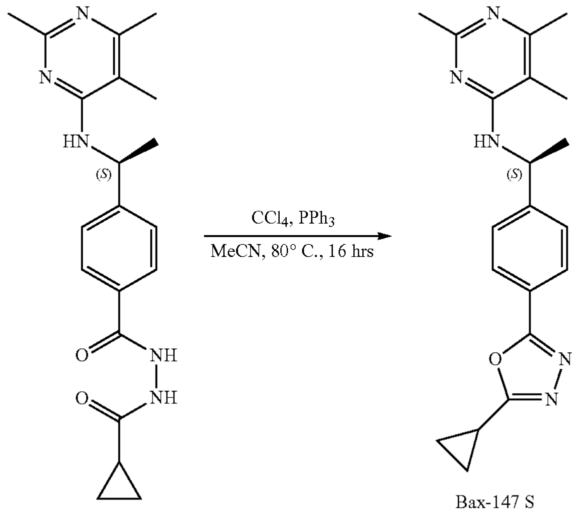

4

Bax-147 S

A mixture of N'-(cyclopropanecarbonyl)-4-[(1S)-1-[(2,5,6-trimethylpyrimidin-4-yl)amino]ethyl]benzohydrazide (180 mg, 489.87 μmol, 1 eq), $PPh_3$ (256.98 mg, 979.74 umol, 2 eq) and $CCl_4$ (75.35 mg, 489.87 μmol, 47.09 μL, 1 eq) in MeCN (2 mL) was stirred at 80° C. for 16 hrs under $N_2$. The mixture was concentrated to give a residue. The residue was purified by prep-HPLC (column: Phenomenex Luna C18 150*30 mm*5 μm; mobile phase: [water (0.04% HCl)-ACN]; B %: 20%-52%, 10 min) to give the crude product, it was re-purified by prep-HPLC (column: Waters Xbridge BEH C18 100*25 mm*5 μm; mobile phase: [water (10 mM $NH_4HCO_3$)-ACN]; B %: 20%-50%, 8 min) and then it was purified by prep-HPLC (column: Waters Xbridge Prep OBD C18 150*40 mm*10 um; mobile phase: [water (0.04% $NH_3H_2O$+10 mM $NH_4HCO_3$)-MeOH]; B %: 40%-70%, 10 min) to give N-[(1S)-1-[4-(5-cyclopropyl-1,3,4-oxadiazol-2-yl)phenyl]ethyl]-2,5,6-trimethyl-pyrimidin-4-amine (18.50 mg, 52.94 umol, 10.81% yield, 100.000% purity) as a brown solid. ESI [M+H]=350.1.

$^1$H-NMR (400 MHz, METHANOL-d4) δ 7.92 (d, J=8.2 Hz, 2H), 7.57 (d, J=8.2 Hz, 2H), 5.50 (br d, J=7.1 Hz, 1H), 2.29 (d, J=4.4 Hz, 6H), 2.28-2.23 (m, 1H), 2.10 (s, 3H), 1.60 (d, J=7.0 Hz, 3H), 1.30-1.15 (m, 4H).

Example 61

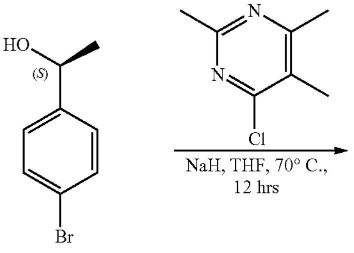

1

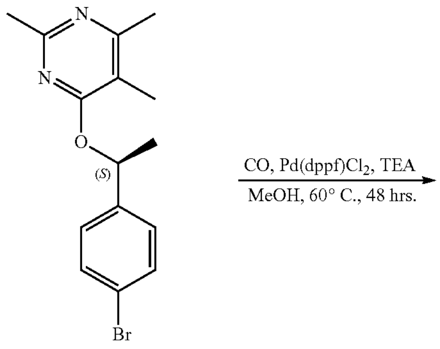

2

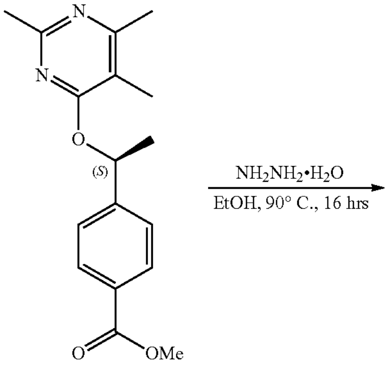

3

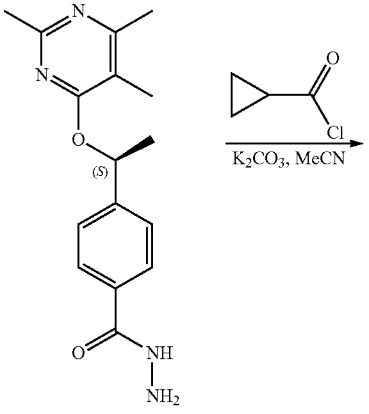

4

-continued

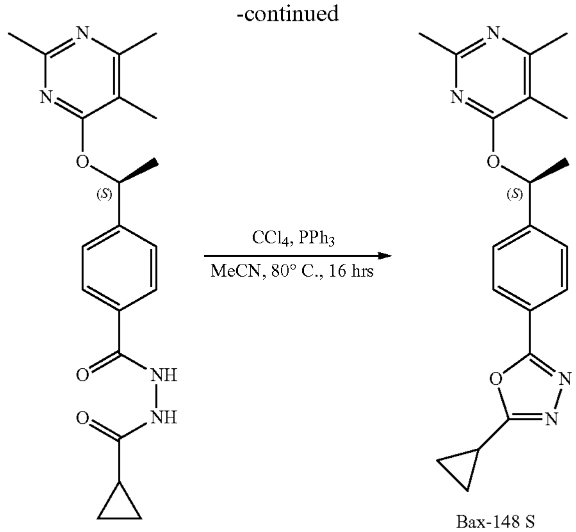

5

Bax-148 S

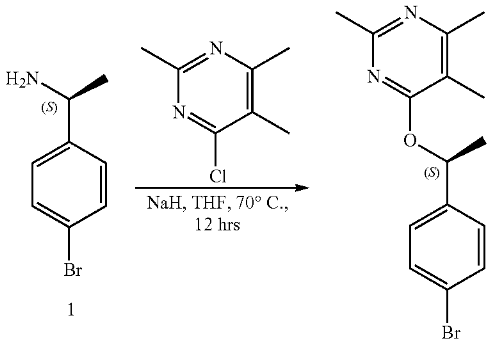

1

2

To a solution of (1S)-1-(4-bromophenyl)ethanol (1.8 g, 8.95 mmol, 1 eq) and 4-chloro-2,5,6-trimethyl-pyrimidine (1.68 g, 10.74 mmol, 1.2 eq) in THF (80 mL) was added NaH (1.79 g, 44.76 mmol, 60% purity, 5 eq) at 0° C. The reaction mixture was heated at 70° C. for 12 hrs. To the reaction mixture was added $H_2O$ (20 mL) and extracted with EtOAc (40 mL*3). The combined organic layers were dried over $Na_2SO_4$, filtered and concentrated under reduced pressure to give 4-[(1S)-1-(4-bromophenyl)ethoxy]-2,5,6-trimethyl-pyrimidine (3.5 g, crude) as a yellow oil. ESI [M+H and M+3H]=321.0 and 323.0.

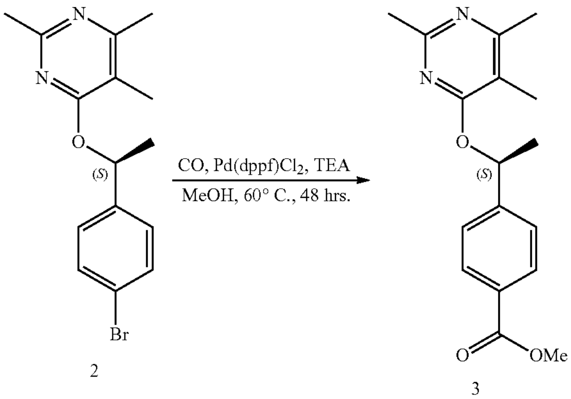

2

3

To a solution of 4-[(1S)-1-(4-bromophenyl)ethoxy]-2,5,6-trimethyl-pyrimidine (500 mg, 1.56 mmol, 1 eq) and $Et_3N$ (787.56 mg, 7.78 mmol, 1.08 mL, 5 eq) in MeOH (15 mL) was added Pd(dppf)$Cl_2$ (227.80 mg, 311.32 umol, 0.2 eq) under N2. The suspension was degassed under vacuum and purged with CO several times. The mixture was stirred under CO (50 psi) at 60° C. for 48 hrs. The reaction mixture was filtered, the filtrate was concentrated to give a residue. The residue was purified by column chromatography ($SiO_2$, Petroleum ether/Ethyl acetate=1/0 to 3/1) to give methyl 4-[(1S)-1-(2,5,6-trimethylpyrimidin-4-yl)oxyethyl]benzoate (170 mg, 566.00 μmol, 36.36% yield) as a light yellow oil. ESI [M+H]=301.2.

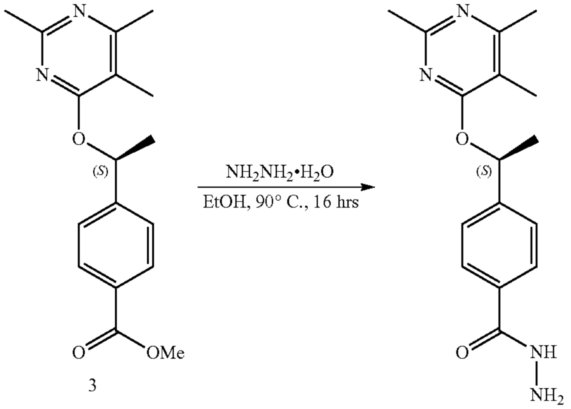

3

4

To a solution of methyl 4-[(1S)-1-(2,5,6-trimethylpyrimidin-4-yl)oxyethyl]benzoate (170 mg, 566.00 umol, 1 eq) in EtOH (3 mL) was added $NH_2NH_2·H_2O$ (289.12 mg, 5.66 mmol, 280.70 μL, 10 eq), the resulting mixture was stirred at 90° C. for 16 hrs. The mixture was concentrated to give a residue. To the residue was added $H_2O$ (5 mL) and extracted with EtOAc/THF (3:1, 5 mL*5). The combined organic layers were washed with brine (5 mL), dried over $Na_2SO_4$, filtered and concentrated under reduced pressure to give 4-[(1S)-1-(2,5,6-trimethylpyrimidin-4-yl)oxyethyl] benzohydrazide (120 mg, crude) as a colorless oil. ESI [M+H]=301.2.

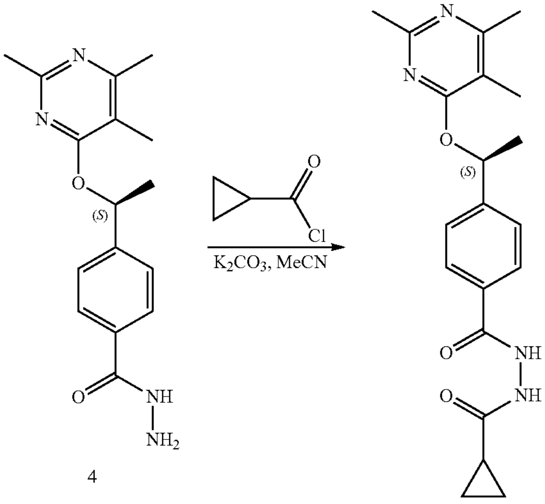

4

5

To a 0° C. stirred mixture of 4-[(1S)-1-(2,5,6-trimethylpyrimidin-4-yl)oxyethyl]benzohydrazide (120 mg, 399.53 umol, 1 eq) and $K_2CO_3$ (110.44 mg, 799.05 umol, 2.0 eq) in MeCN (3 mL) was added cyclopropanecarbonyl chloride (62.65 mg, 599.29 umol, 54.48 μL, 1.5 eq) dropwise, the resulting mixture was stirred at 20° C. for 12 hrs. The reaction mixture was concentrated under reduced pressure to remove MeCN. The residue was diluted with $H_2O$ (5 mL) and extracted with EtOAc/THF (5:1, 5 mL*5). The combined organic layers were washed with brine (5 mL*2), dried over $Na_2SO_4$, filtered and concentrated under reduced pressure to give a residue. The residue was purified by prep-TLC (EtOAc:MeOH=10:1) to give N'-(cyclopropanecarbonyl)-4-[(1S)-1-(2,5,6-trimethylpyrimidin-4-yl)oxyethyl]benzohydrazide (130 mg, 352.85 umol, 88.32% yield) as a light brown solid. ESI [M+H]=369.2.

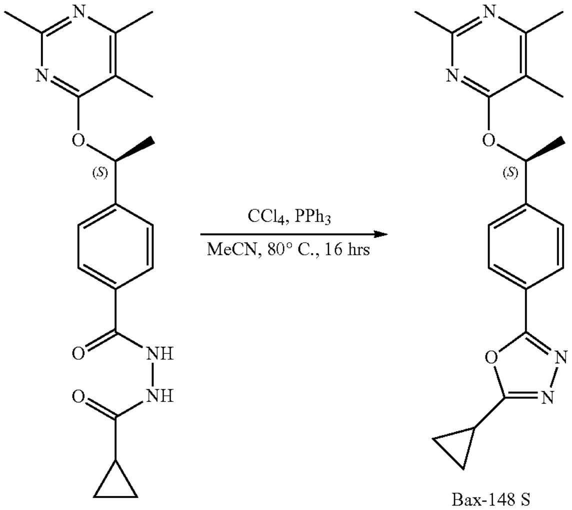

5

Bax-148 S

A mixture of N'-(cyclopropanecarbonyl)-4-[(1S)-1-(2,5,6-trimethylpyrimidin-4-yl)oxyethyl]benzohydrazide (120 mg, 325.71 μmol, 1 eq), $PPh_3$ (170.86 mg, 651.42 μmol, 2 eq) and $CCl_4$ (50.10 mg, 325.71 umol, 31.31 μL, 1 eq) in DCE (2 mL) was stirred at 80° C. for 16 hrs under N2. The mixture was concentrated to give a residue. The residue was purified by prep-TLC (PE:EtOAc=1:1) to give the crude product, it was re-purified by prep-HPLC (column: Waters Xbridge Prep OBD C18 150*40 mm*10 μm; mobile phase: [water (0.04% NH3H2O+10 mM NH4HCO3)-ACN]; B %: 30%-60%, 10 min) to give 2-cyclopropyl-5-[4-[(1S)-1-(2,5,6-trimethylpyrimidin-4-yl)oxyethyl]phenyl]-1,3,4-oxadiazole (11.53 mg, 32.90 umol, 10.10% yield, 100.000% purity) as a brown gum. ESI [M+H]=351.1.

$^1$H-NMR (400 MHz, METHANOL-d4) δ 7.96 (d, J=8.4 Hz, 2H), 7.60 (d, J=8.3 Hz, 2H), 6.35 (q, J=6.6 Hz, 1H), 2.40 (s, 3H), 2.37 (s, 3H), 2.32-2.23 (m, 1H), 2.18 (s, 3H), 1.66 (d, J=6.6 Hz, 3H), 1.27-1.15 (m, 4H).

Example 62

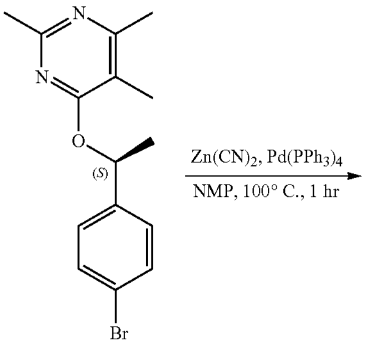

2

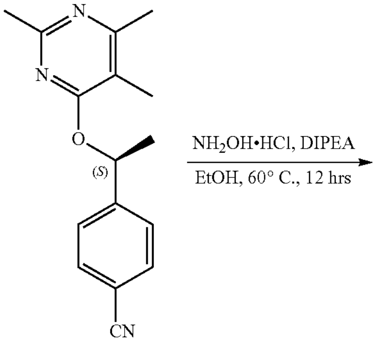

3

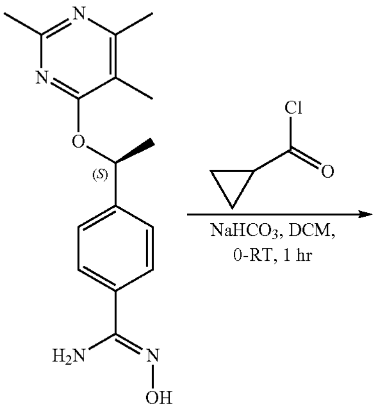

4

-continued

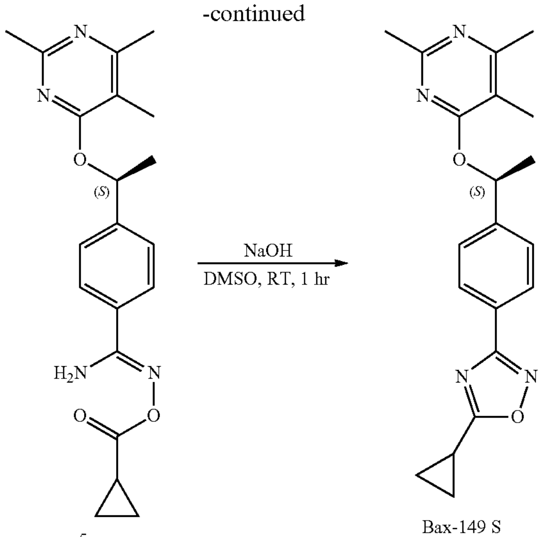

5

Bax-149 S

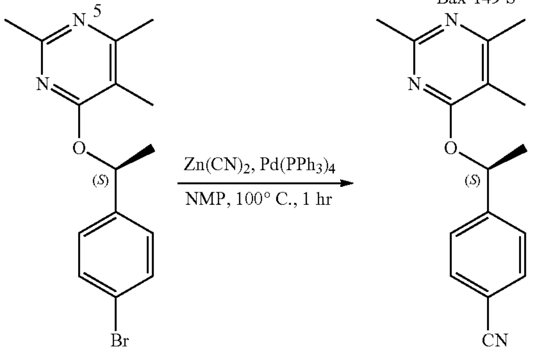

2

3

A mixture of 4-[(1S)-1-(4-bromophenyl)ethoxy]-2,5,6-trimethyl-pyrimidine (400 mg, 1.25 mmol, 1 eq), $Zn(CN)_2$ (160.85 mg, 1.37 mmol, 86.95 uL, 1.1 eq), $Pd(PPh_3)_4$ (143.90 mg, 124.53 μmol, 0.1 eq) in NMP (10 mL) was stirred at 100° C. for 1 hr under N2 atmosphere. To the reaction mixture was added water (20 mL) and extracted with EtOAc (30 mL*3). The organic layer was washed with brine (20 mL*2), dried over $MgSO_4$, filtered and concentrated under reduced pressure to give a residue. The residue was purified by column chromatography ($SiO_2$, Petroleum ether/Ethyl acetate=20/1 to 1/1) to give 4-[(1S)-1-(2,5,6-trimethylpyrimidin-4-yl)oxyethyl]benzonitrile (300 mg, 1.12 mmol, 90.12% yield) was obtained as a yellow oil. ESI [M+H]=268.1.

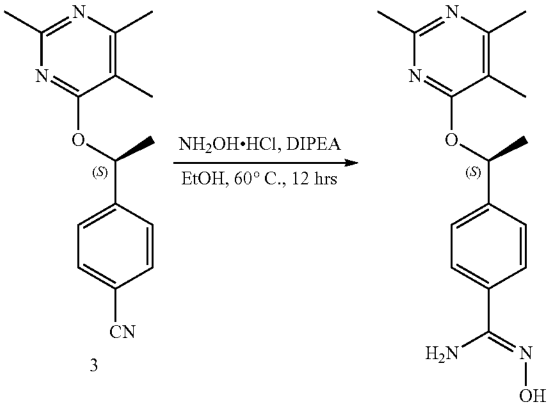

3

4

A mixture of $NH_2OH$·HCl (207.96 mg, 2.99 mmol, 4 eq) and DIPEA (483.47 mg, 3.74 mmol, 651.57 μL, 5 eq) in EtOH (3 mL) was stirred at 15° C. for 30 mins, then 4-[(1S)-1-(2,5,6-trimethylpyrimidin-4-yl)oxyethyl]benzonitrile (200 mg, 748.15 μmol, 1 eq) was added, the resulting mixture was stirred at 60° C. for 12 hrs. The reaction mixture was concentrated under reduced pressure to remove EtOH. The residue was diluted with $H_2O$ (5 mL) and extracted with EtOAc/THF (5:1, 5 mL*5). The combined organic layers were washed with brine (5 mL*2), dried over $Na_2SO_4$, filtered and concentrated under reduced pressure to give N'-hydroxy-4-[(1S)-1-(2,5,6-trimethylpyrimidin-4-yl)oxyethyl]benzamidine (150 mg, crude) as a colorless oil. ESI [M+H]=301.2.

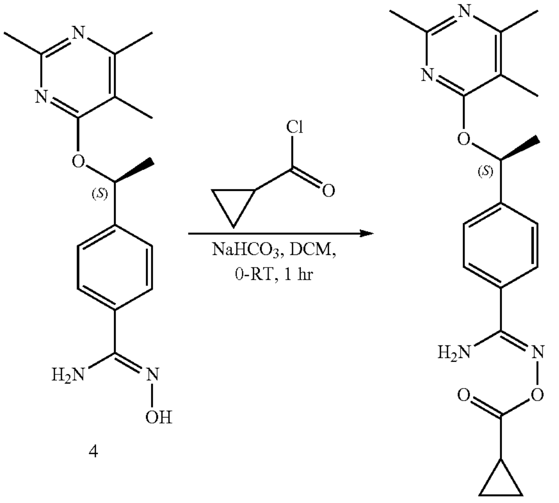

4

5

To a 0° C. stirred mixture of N'-hydroxy-4-[(1S)-1-(2,5,6-trimethylpyrimidin-4-yl)oxyethyl]benzamidine (80.00 mg, 266.35 μmol, 1 eq) and $NaHCO_3$ (44.75 mg, 532.70 umol, 20.72 μL, 2 eq) in DCM (2 mL) was added cyclopropanecarbonyl chloride (33.41 mg, 319.62 umol, 29.05 μL, 1.2 eq) in DCM (0.1 mL) dropwise. The mixture was stirred at 20° C. for 1 hr. The reaction mixture was concentrated under reduced pressure to remove DCM. The residue was diluted with $H_2O$ (2 mL) and extracted with EtOAc (2 mL*3). The combined organic layers were washed with brine (2 mL*2), dried over $Na_2SO_4$, filtered and concentrated under reduced pressure to give [(Z)-[amino-[4-[(1S)-1-(2,5,6-trimethylpyrimidin-4-yl)oxyethyl]phenyl]methylene]amino]cyclopropanecarboxylate (90 mg, 244.28 μmol, 91.71% yield) as a colorless oil.

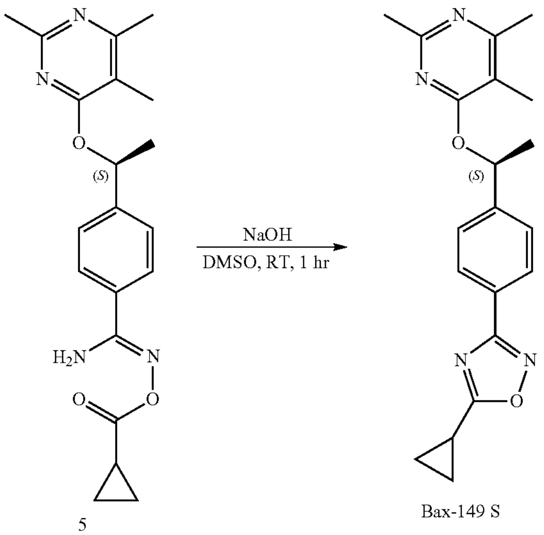

5

Bax-149 S

A mixture of [(Z)-[amino-[4-[(1S)-1-(2,5,6-trimethylpyrimidin-4-yl)oxyethyl]phenyl]methylene]amino]cyclopropanecarboxylate (90 mg, 244.28 umol, 1 eq) and NaOH (9.77 mg, 244.28 umol, 1 eq) in DMSO (1 mL) was stirred at 20° C. for 1 hr. The reaction mixture was filtered and concentrated under reduced pressure to give a residue. The residue was purified by prep-HPLC (column: Waters Xbridge Prep OBD C18 150*40 mm*10 μm; mobile phase: [water (0.04% NH3H2O+10 mM NH4HCO3)-ACN]; B %: 45%-75%, 10 min) to give 5-cyclopropyl-3-[4-[(1S)-1-(2,5,6-trimethylpyrimidin-4-yl)oxyethyl]phenyl]-1,2,4-oxadiazole (58.46 mg, 166.48 μmol, 68.15% yield, 99.787% purity) as a brown gum. ESI [M+H]=351.1.

$^{1}$H-NMR (400 MHz, METHANOL-d4) δ 7.94 (d, J=8.4 Hz, 2H), 7.51 (d, J=8.3 Hz, 2H), 6.31 (q, J=6.5 Hz, 1H), 2.39 (s, 3H), 2.34 (s, 3H), 2.31-2.24 (m, 1H), 2.14 (s, 3H), 1.63 (d, J=6.5 Hz, 3H), 1.29-1.19 (m, 4H).

Example 63

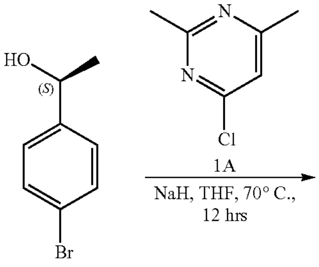

1

-continued

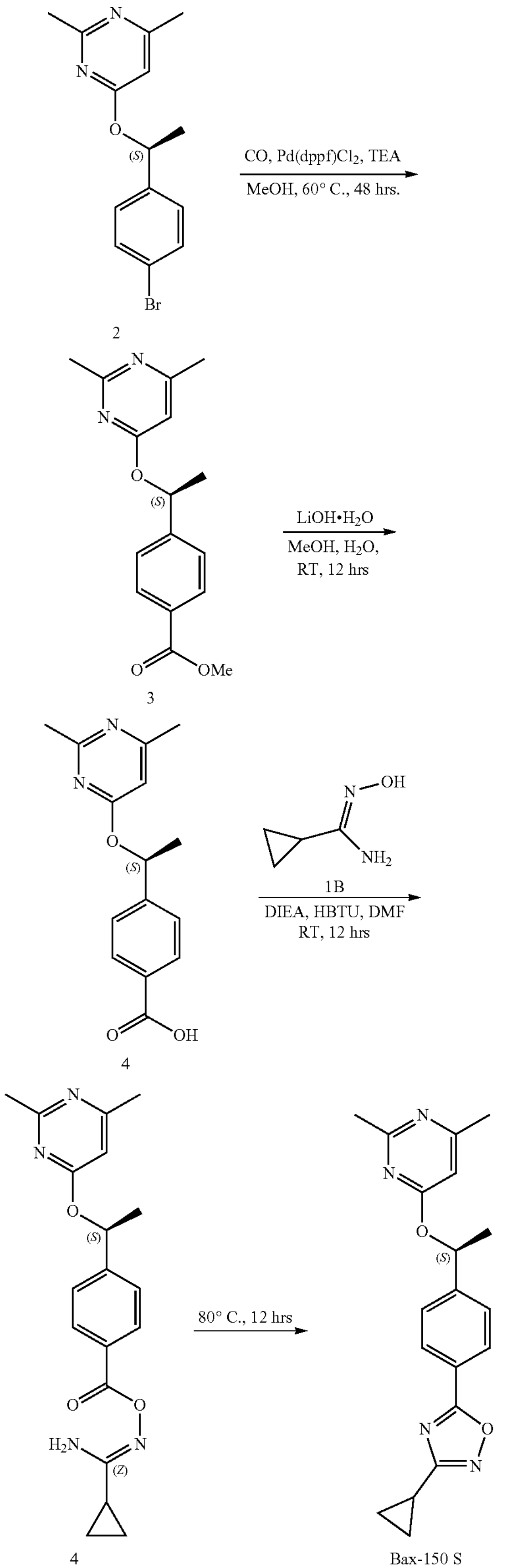

2

3

4

4

Bax-150 S

-continued

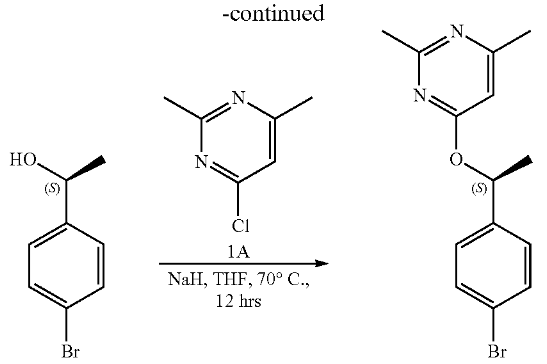

1 2

To a solution of (1S)-1-(4-bromophenyl)ethanol (1 g, 4.97 mmol, 143.88 μL, 1 eq) and 4-chloro-2,6-dimethyl-pyrimidine (851.01 mg, 5.97 mmol, 1.2 eq) in THF (50 mL) was added NaH (994.63 mg, 24.87 mmol, 60% purity, 5 eq) at 0° C. The reaction mixture was heated to 70° C. and stirred for 12 hrs. The reaction mixture was quenched by addition saturated aq·$NH_4Cl$ (20 mL), and then diluted with EtOAc (20 mL) and extracted with EtOAc (10 mL*3). The combined organic layers were washed with brine (10 mL*2), dried over $Na_2SO_4$, filtered and concentrated under reduced pressure to give a residue. The residue was purified by column chromatography ($SiO_2$, Petroleum ether/Ethyl acetate=0/1 to 5:1) to give 4-[(1S)-1-(4-bromophenyl) ethoxy]-2,6-dimethyl-pyrimidine (1.5 g, 4.88 mmol, 98.18% yield) as a light yellow oil. ESI [M+H and M+3H]=307.1 and 309.0.

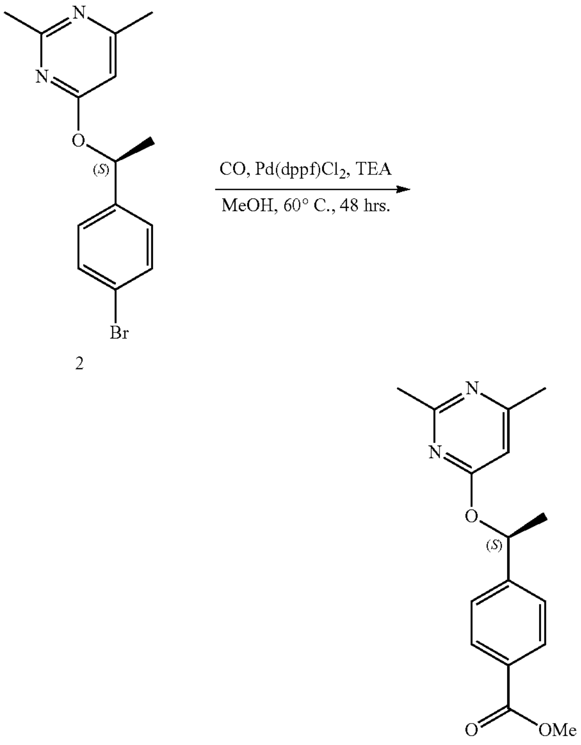

2

3

To a solution of 4-[(1S)-1-(4-bromophenyl)ethoxy]-2,6-dimethyl-pyrimidine (600 mg, 1.95 mmol, 1 eq) and $Et_3N$ (988.23 mg, 9.77 mmol, 1.36 mL, 5 eq) in MeOH (15 mL) was added Pd(dppf)$Cl_2$ (285.84 mg, 390.64 umol, 0.2 eq) under N2. The suspension was degassed under vacuum and purged with CO several times. The mixture was stirred under CO (50 psi) at 60° C. for 48 hrs. The reaction mixture was filtered, the filtrate was concentrated to give a residue. The residue was purified by column chromatography ($SiO_2$, Petroleum ether/Ethyl acetate=1/0 to 3/1) to give methyl 4-[(1S)-1-(2,6-dimethylpyrimidin-4-yl)oxyethyl]benzoate (200 mg, 698.51 μmol, 35.76% yield) as a light yellow oil. ESI [M+H]=287.2.

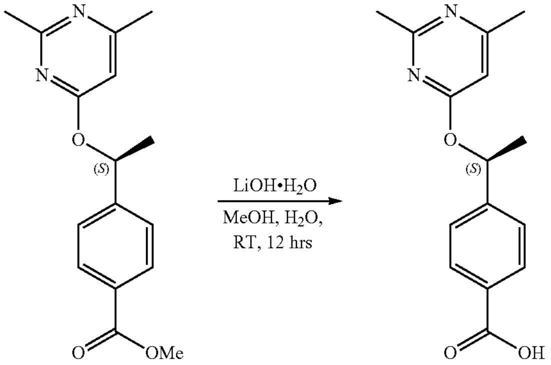

3 4

To a solution of methyl 4-[(1S)-1-(2,6-dimethylpyrimidin-4-yl)oxyethyl]benzoate (200 mg, 698.51 umol, 1 eq) in MeOH (5 mL) and $H_2O$ (1 mL) was added LiOH·$H_2O$ (87.93 mg, 2.10 mmol, 3 eq). The resulting mixture was stirred at 20° C. for 12 hrs. The reaction mixture was concentrated to give a residue. To the residue was added $H_2O$ (50 mL), extracted with MTBE (5 mL*2), the aqueous layer was acidified to pH=2, and extracted with DCM/i-PrOH (3/1, 5 mL*5). The combined organic layers were dried over $Na_2SO_4$, filtered and concentrated under reduced pressure to give 4-[(1S)-1-(2,6-dimethylpyrimidin-4-yl) oxyethyl]benzoic acid (120 mg, 440.69 μmol, 63.09% yield) as a white solid. ESI [M+H]=273.1.

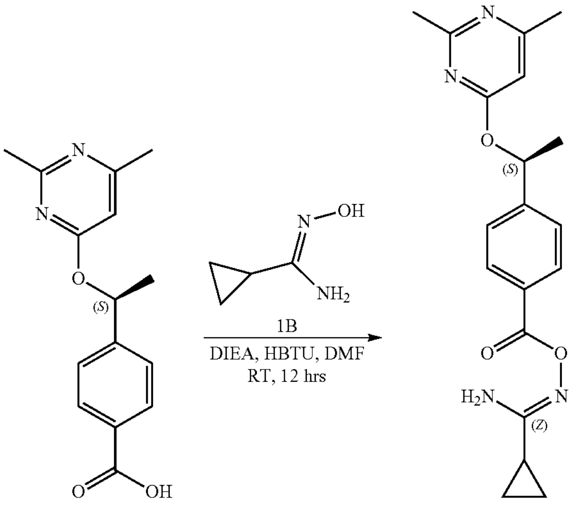

4 5

To a solution of 4-[(1S)-1-(2,6-dimethylpyrimidin-4-yl)oxyethyl]benzoic acid (120 mg, 440.69 umol, 1 eq) in DMF (3 mL) was added N'-hydroxycyclopropanecarboxamidine (66.18 mg, 661.04 umol, 1.5 eq), DIPEA (227.82 mg, 1.76 mmol, 307.04 uL, 4 eq) and HBTU (200.55 mg, 528.83 umol, 1.2 eq). The mixture was stirred at 20° C. for 12 hrs. According the conversion rate of LCMS, about 60 mg of 5 was obtained, and the reaction mixture was used directly to the next step without purification. ESI [M+H]=355.2.

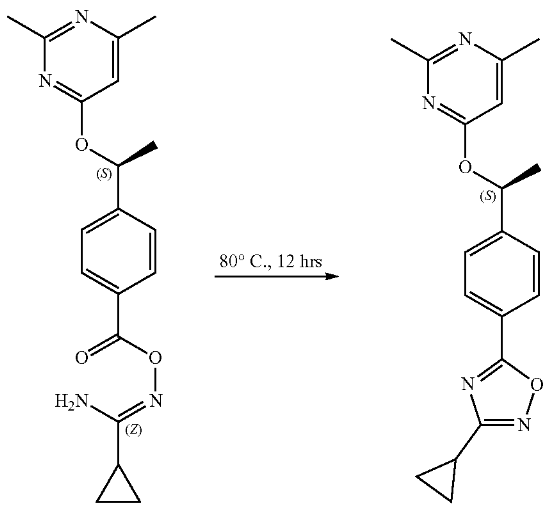

4 Bax-150 S

A mixture of [(Z)-[amino(cyclopropyl)methylene]amino] 4-[(1S)-1-(2,6-dimethylpyrimidin-4-yl)oxyethyl]benzoate (60 mg, 169.30 umol, 1 eq) in DMF (1 mL) was stirred at 80° C. for 12 hrs (This reaction mixture was the previous step reaction mixture). The reaction mixture was filtered, the filtrate was concentrated to give a residue. The residue was purified by prep-HPLC (column: Waters Xbridge Prep OBD C18 150*40 mm*10 μm; mobile phase: [water (10 mM $NH_4HCO_3$)-ACN]; B %: 20%-90%, 8 min) to give 3-cyclopropyl-5-[4-[(1S)-1-(2,6-dimethylpyrimidin-4-yl)oxyethyl]phenyl]-1,2,4-oxadiazole (28.48 mg, 83.74 umol, 49.46% yield, 98.910% purity) as a light brown gum. ESI [M+H]=337.2.

$^1$H-NMR (400 MHz, METHANOL-d4) δ 8.06 (d, J=8.4 Hz, 2H), 7.62 (d, J=8.3 Hz, 2H), 6.61 (s, 1H), 6.34 (q, J=6.5 Hz, 1H), 2.46 (s, 3H), 2.38 (s, 3H), 2.19-2.11 (m, 1H), 1.66 (d, J=6.6 Hz, 3H), 1.16-1.04 (m, 4H).

Example 64

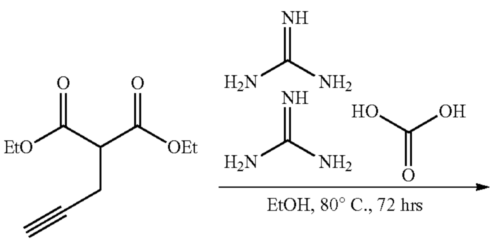

1

-continued

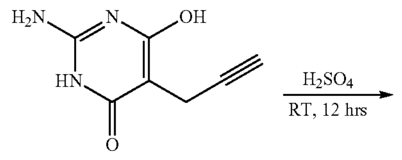

2

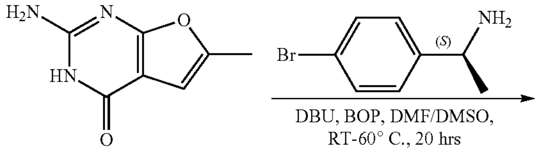

3

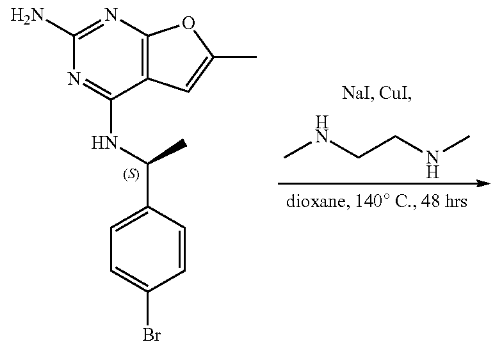

4

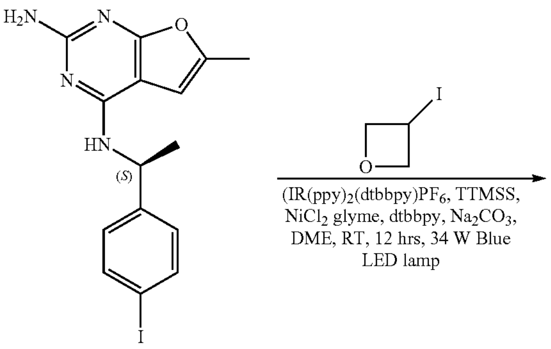

5

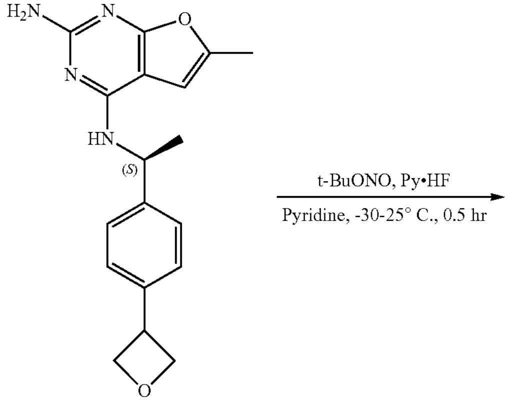

6

-continued

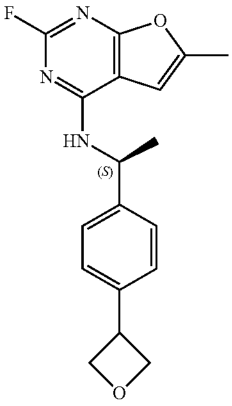

Bax-151 S

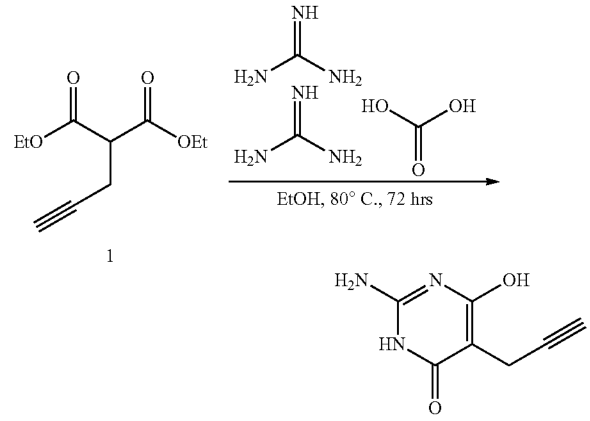

1

2

A mixture of diethyl 2-prop-2-ynylpropanedioate (10 g, 50.45 mmol, 1 eq) and carbonic acid; guanidine (5.00 g, 27.75 mmol, 0.55 eq) in EtOH (100 mL) was stirred at 80° C. for 72 hrs under N2. The reaction was cooled to 15° C., filtered, the filter cake was collected and then dissolved in water (10 mL). The aqueous layer was adjusted to pH=3 with 1M HCl, the precipitate was formed, and filtered, the filter cake was collected and concentrated in vacuo to give 2-amino-4-hydroxy-5-prop-2-ynyl-1H-pyrimidin-6-one (1.5 g, 9.08 mmol, 18.00% yield) as a light pink solid. ESI [M+H]=166.0.

$^1$H-NMR (400 MHz, DMSO-d6) δ 10.49 (br s, 2H), 6.53 (br s, 2H), 2.96 (d, J=2.6 Hz, 2H), 2.46 (t, J=2.5 Hz, 1H)

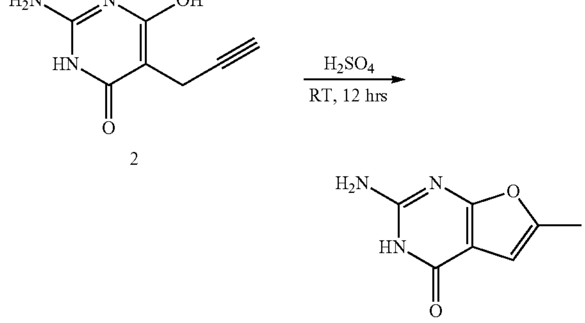

2

3

A solution of 2-amino-4-hydroxy-5-prop-2-ynyl-1H-pyrimidin-6-one (1.5 g, 9.08 mmol, 1 eq) in conc.$H_2SO_4$ (10 mL) was stirred at 25° C. for 12 hrs. The reaction mixture was added dropwise to cold water (100 mL). Then the mixture was basified to pH~8 by 5N NaOH solution, extracted with EtOAc/THF (3:1, 50 mL*4). The combined organic layers were washed with brine (50 mL*2), dried over $Na_2SO_4$, filtered and concentrated under reduced pressure to give 2-amino-6-methyl-3H-furo[2,3-d]pyrimidin-4-one (400 mg, 2.42 mmol, 26.67% yield) as a yellow solid. ESI [M+H]=166.1.

$^1$H-NMR (400 MHz, DMSO-d6) δ 10.69 (br s, 1H), 6.54 (br s, 2H), 6.24 (d, J=1.1 Hz, 1H), 2.22 (d, J=0.9 Hz, 3H).

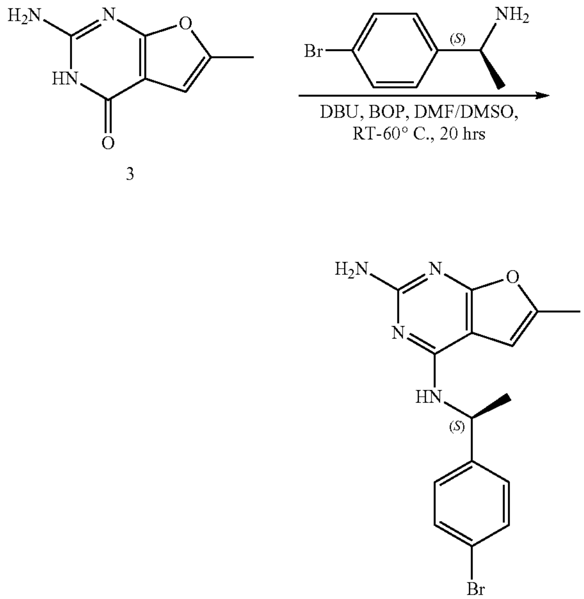

3

4

To a mixture of 2-amino-6-methyl-3H-furo[2,3-d]pyrimidin-4-one (380 mg, 2.30 mmol, 1 eq), DBU (700.58 mg, 4.60 mmol, 693.64 μL, 2 eq) and BOP (1.22 g, 2.76 mmol, 1.2 eq) in DMF (10 mL) and DMSO (10 mL) was added (1S)-1-(4-bromophenyl)ethanamine (920.73 mg, 4.60 mmol, 662.39 uL, 2 eq), and the mixture was stirred at 25° C. for 8 hrs. Then the mixture was heated to 60° C. for 12 hrs. To the mixture was added $H_2O$ (5 mL) and extracted with EtOAc (5 mL*5). The combined organic layers were washed with brine (5 mL*2), dried over $Na_2SO_4$, filtered and concentrated under reduced pressure to give a residue. The residue was purified by prep-HPLC (column: Welch Xtimate C18 250*50 mm*10 μm; mobile phase: [water (10 mM $NH_4HCO_3$)-ACN]; B %: 40%-70%, 10 min) to give N4-[(1S)-1-(4-bromophenyl)ethyl]-6-methyl-furo[2,3-d]pyrimidine-2,4-diamine (265 mg, 763.23 umol, 33.17% yield) as light yellow solid. ESI [M+H and M+3H]=347.1 and 349.1.

$^1$H-NMR (400 MHz, CHLOROFORM-d) δ 7.41-7.34 (m, 2H), 7.17 (d, J=8.4 Hz, 2H), 5.92 (d, J=0.9 Hz, 1H), 5.18 (br t, J=6.9 Hz, 1H), 4.95 (br d, J=5.3 Hz, 1H), 4.61 (br s, 2H), 2.23 (d, J=1.0 Hz, 3H), 1.49 (d, J=6.9 Hz, 3H).

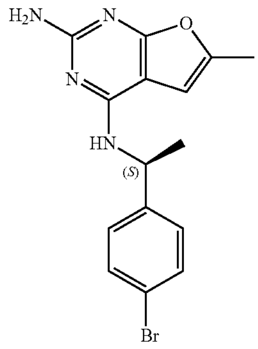
4

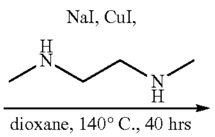

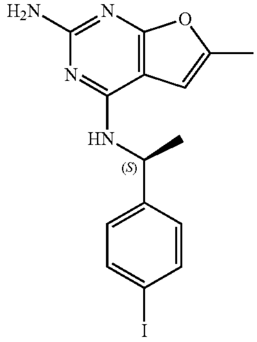
5

To a solution of N4-[(1S)-1-(4-bromophenyl)ethyl]-6-methyl-furo[2,3-d]pyrimidine-2,4-diamine (240.00 mg, 691.23 umol, 1 eq) in dioxane (10 mL) was added NaI (310.83 mg, 2.07 mmol, 3 eq), CuI (26.33 mg, 138.25 μmol, 0.2 eq) and N,N'-dimethylethane-1,2-diamine (15.23 mg, 172.81 μmol, 18.60 uL, 0.25 eq) under N2. The mixture was stirred at 140° C. for 40 hrs. The reaction mixture was filtered and the filtrate was concentrated in vacuo to give a residue. The residue was purified by prep-TLC ($SiO_2$, Petroleum ether:Ethyl acetate=1:1) to give N4-[(1S)-1-(4-iodophenyl)ethyl]-6-methyl-furo[2,3-d]pyrimidine-2,4-diamine (220 mg, 558.08 umol, 80.74% yield) as a white solid. ESI [M+H]=395.0.

-continued

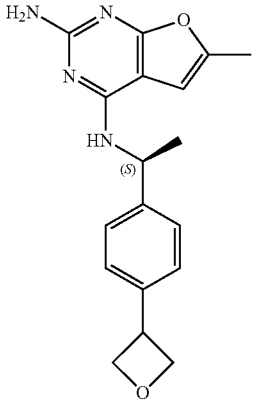
6

A mixture of N4-[(1S)-1-(4-iodophenyl)ethyl]-6-methyl-furo[2,3-d]pyrimidine-2,4-diamine (100 mg, 253.67 μmol, 1 eq), 3-iodooxetane (233.35 mg, 1.27 mmol, 5 eq), 4-tert-butyl-2-(4-tert-butyl-2-pyridyl)pyridine (3.40 mg, 12.68 umol, 0.05 eq), $Na_2CO_3$ (53.77 mg, 507.34 umol, 2 eq), TTMSS (63.08 mg, 253.67 umol, 78.26 uL, 1 eq), bis[2-(2-pyridyl)phenyl]iridium(1+); 4-tert-butyl-2-(4-tert-butyl-2-pyridyl)pyridine; hexafluorophosphate (23.18 mg, 25.37 umol, 0.1 eq) and dichloronickel; 1,2-dimethoxyethane (2.79 mg, 12.68 umol, 0.05 eq) in DME (2 mL) was stirred and irradiated with a 34 W blue LED lamp at 30° C. for 12 hrs under argon. The reaction mixture was concentrated under reduced pressure to remove solvent. The residue was diluted with $H_2O$ (10 mL) and extracted with DCM (10 mL*3). The combined organic layers were washed with brine (10 mL*2), dried over $Na_2SO_4$, filtered and concentrated under reduced pressure to give a residue. The residue was purified by prep-HPLC (column: Waters Xbridge Prep OBD C18 150*40 mm*10 μm; mobile phase: [water (0.04% $NH_3H_2O$+10 mM $NH_4HCO_3$)-ACN]; B %: 25%-70%, 8 min) to give 6-methyl-N4-[(1S)-1-[4-(oxetan-3-yl)phenyl]ethyl]furo[2,3-d]pyrimidine-2,4-diamine (18 mg, 55.49 μmol, 10.94% yield) as a white solid. ESI [M+H]=325.3.

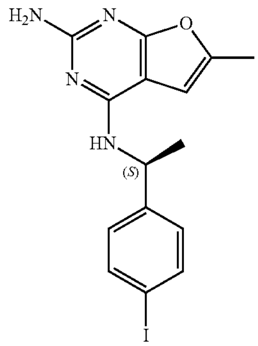
5

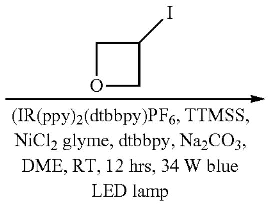

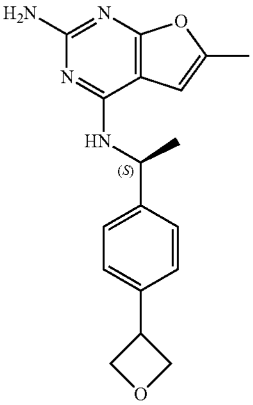
6

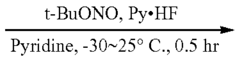

-continued

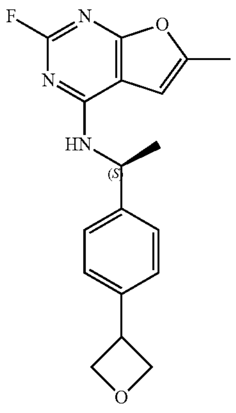

Bax-151 S

To a −30° C. stirred solution of 6-methyl-N4-[(1S)-1-[4-(oxetan-3-yl)phenyl]ethyl]furo[2,3-d]pyrimidine-2,4-diamine (16 mg, 49.33 umol, 1 eq) in PYRIDINE (0.1 mL) was added the mixture of PYRIDINE (0.1 mL) and pyridine; hydrofluoride (330.00 mg, 3.33 mmol, 0.3 mL, 67.51 eq) under N2, after 10 mins, tert-butyl nitrite (25.43 mg, 246.63 umol, 29.33 uL, 5 eq) was added at −20° C. The mixture was stirred at −10-25° C. for 20 mins. Cold water (2 mL) was added, then the reaction mixture was adjusted to pH=8 with sat.aq $Na_2CO_3$ and extracted with DCM (3 mL*4). The combined organic layers were dried over drying $Na_2SO_4$, filtered and concentrated under reduced pressure to give a residue. The residue was purified by prep-HPLC (column: Waters Xbridge BEH C18 100*25 mm*5 um; mobile phase: [water (10 mM NH4HCO3)-ACN]; B %: 30%-65%, 8 min) to give 2-fluoro-6-methyl-N-[(1S)-1-[4-(oxetan-3-yl)phenyl]ethyl]furo[2,3-d]pyrimidin-4-amine (5.13 mg, 15.56 μmol, 31.54% yield, 99.278% purity) as white gum.

$^1$H-NMR (400 MHz, METHANOL-d4) δ 7.41 (q, J=8.3 Hz, 4H), 6.60 (br s, 1H), 5.40 (br d, J=6.0 Hz, 1H), 5.08 (dd, J=5.9, 8.3 Hz, 2H), 4.75 (dt, J=2.6, 6.3 Hz, 2H), 4.32-4.17 (m, 1H), 2.40 (s, 3H), 1.60 (d, J=7.0 Hz, 3H). ESI [M+H]=328.2.

Example 65

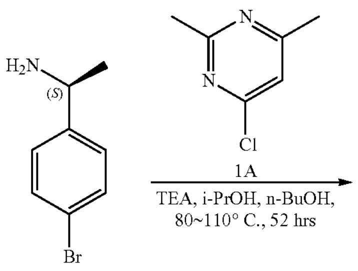

1

-continued

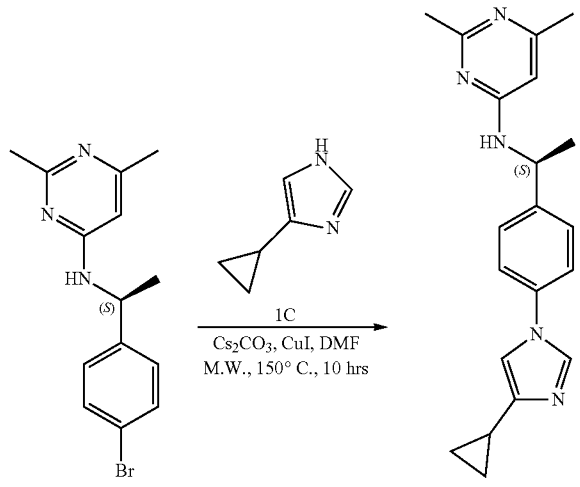

2

Bax-152 S

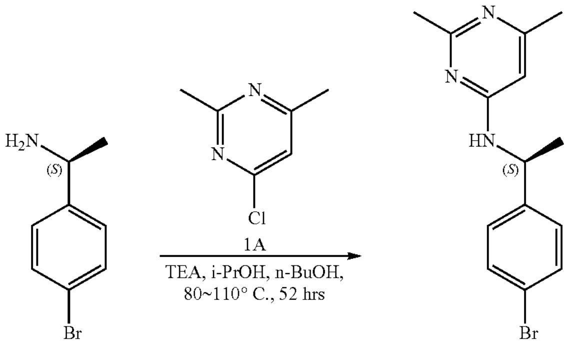

1

2

To a mixture of 4-chloro-2,6-dimethyl-pyrimidine (171.04 mg, 1.20 mmol, 1.2 eq) and $Et_3N$ (404.61 mg, 4.00 mmol, 556.54 uL, 4 eq) in i-PrOH (2 mL) was added (1S)-1-(4-bromophenyl)ethanamine (200 mg, 999.62 umol, 143.88 uL, 1 eq). The resulting mixture was stirred at 80° C. for 12 hrs. LCMS showed most of starting materials were remained, so the mixture was stirred at 80° C. for 24 hrs. HPLC showed about 70% of the starting materials were remained and 30% of the desired product was detected. So to the mixture was added $Et_3N$ (202.30 mg, 2.00 mmol, 278.27 μL, 2 eq) and n-BuOH (2 mL), the mixture was stirred at 110° C. for 16 hrs. HPLC showed about 40% of the starting materials were remained, and about 60% of the desired product was detected. The reaction mixture was concentrated under reduced pressure to give a residue. The residue was purified by prep-TLC (PE:EtOAc=0:1) to give N-[(1S)-1-(4-bromophenyl)ethyl]-2,6-dimethyl-pyrimidin-4-amine (130 mg, 424.56 umol, 42.47% yield) as a colorless oil. ESI [M+H and M+3H1]=183.0 and 184.9.

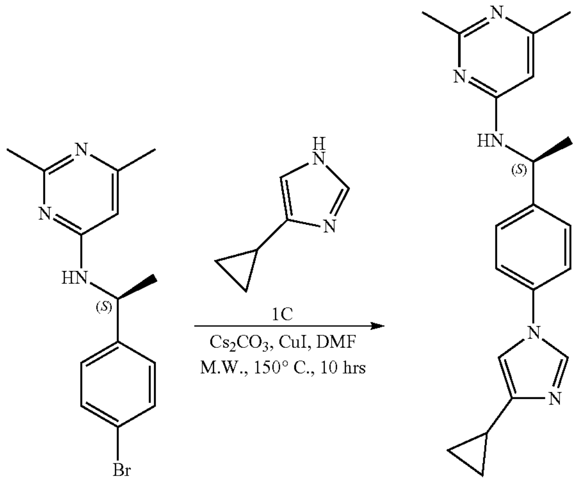

2

Bax-152 S

N-[(1S)-1-(4-bromophenyl)ethyl]-2,6-dimethyl-pyrimidin-4-amine (120 mg, 391.90 umol, 1 eq), 4-cyclopropyl-1H-imidazole (63.57 mg, 587.85 μmol, 1.5 eq), $Cs_2CO_3$ (255.38 mg, 783.80 umol, 2 eq) and CuI (14.93 mg, 78.38 umol, 0.2 eq) were taken up into a microwave tube in DMF (2 mL). The sealed tube was heated at 150° C. for 10 hrs under microwave under N2. The reaction mixture was diluted with $H_2O$ (5 mL) and extracted with EtOAc (5 mL*3). The combined organic layers were dried over $Na_2SO_4$, filtered and concentrated under reduced pressure to give a residue. The residue was purified by prep-HPLC (column: Waters Xbridge Prep OBD C18 150*40 mm*10 μm; mobile phase: [water (0.04% $NH_3H_2O$+10 mM $NH_4HCO_3$)-ACN]; B %: 20%-45%, 10 min) to give N-[(1S)-1-[4-(4-cyclopropylimidazol-1-yl)phenyl]ethyl]-2,6-dimethyl-pyrimidin-4-amine (45.02 mg, 134.62 umol, 34.35% yield, 99.701% purity) as a light brown gum. ESI [M+H]=334.2.

$^1$H-NMR (400 MHz, METHANOL-d4) δ 7.95 (br s, 1H), 7.53-7.45 (m, 4H), 7.27 (br s, 1H), 6.15 (br s, 1H), 5.39-4.96 (m, 1H), 2.35 (s, 3H), 2.22 (s, 3H), 1.94-1.84 (m, 1H), 1.54 (d, J=7.0 Hz, 3H), 0.92-0.85 (m, 2H), 0.77-0.70 (m, 2H).

Example 66

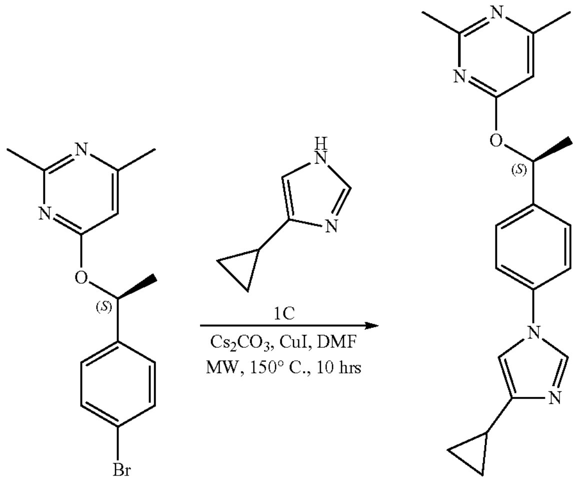

2

Bax-153 S

-continued

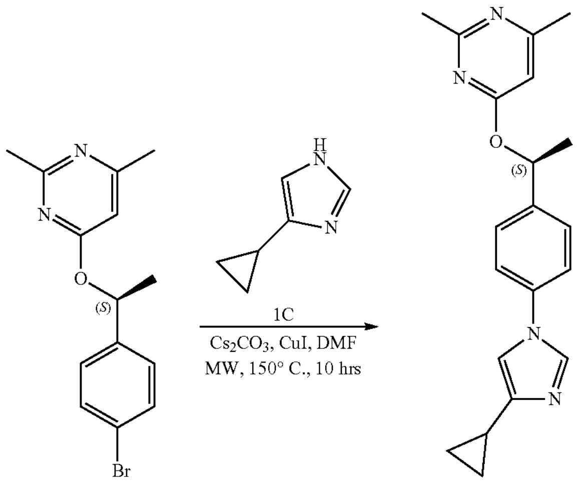

2

Bax-153 S

4-[(1S)-1-(4-bromophenyl)ethoxy]-2,6-dimethyl-pyrimidine (100 mg, 325.54 umol, 1 eq), 4-cyclopropyl-1H-imidazole (52.81 mg, 488.30 umol, 1.5 eq), $Cs_2CO_3$ (212.13 mg, 651.07 umol, 2 eq) and CuI (12.40 mg, 65.11 μmol, 0.2 eq) were taken up into a microwave tube in DMF (2 mL). The sealed tube was heated at 150° C. for 10 hrs under microwave under N2. The reaction mixture was diluted with $H_2O$ (5 mL) and extracted with EtOAc (5 mL*3). The combined organic layers were dried over $Na_2SO_4$, filtered and concentrated under reduced pressure to give a residue. The residue was purified by prep-HPLC (column: Welch Xtimate C18 150*40 mm*10 μm; mobile phase: [water (10 mM NH4HCO3)-ACN]; B %: 40%-50%, 8 min) to give 4-[(1S)-1-[4-(4-cyclopropylimidazol-1-yl)phenyl]ethoxy]-2,6-dimethyl-pyrimidine (35.81 mg, 105.85 μmol, 32.51% yield, 98.845% purity) as a light brown gum. ESI [M+H]=335.1.

$^1$H-NMR (400 MHz, METHANOL-d4) δ 7.95 (d, J=1.3 Hz, 1H), 7.60-7.54 (m, 2H), 7.53-7.47 (m, 2H), 7.26 (d, J=1.1 Hz, 1H), 6.58 (s, 1H), 6.31 (d, J=6.5 Hz, 1H), 2.48 (s, 3H), 2.37 (s, 3H), 1.88 (tt, J=5.0, 8.4 Hz, 1H), 1.65 (d, J=6.6 Hz, 3H), 0.91-0.84 (m, 2H), 0.77-0.71 (m, 2H).

Example 67

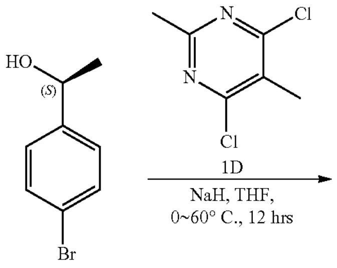

1

-continued

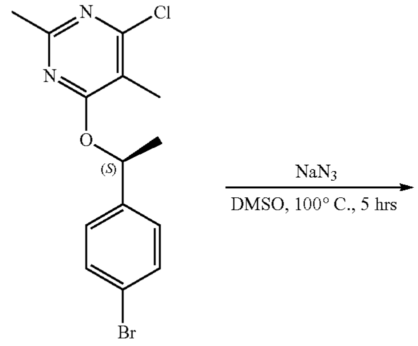

2

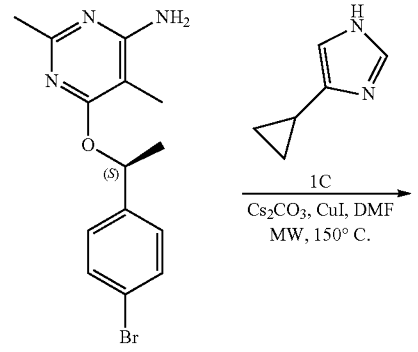

3

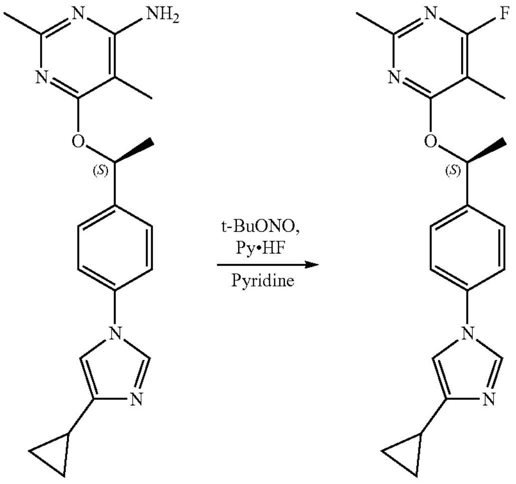

4 Bax-154 S

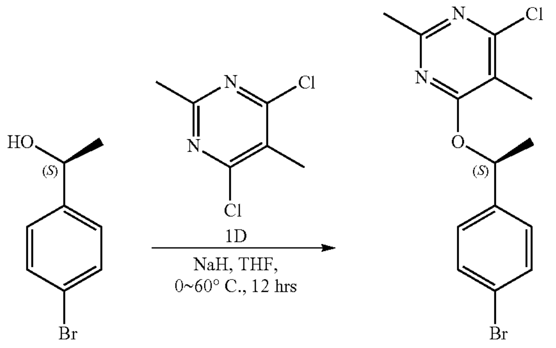

1 2

To a solution of (1S)-1-(4-bromophenyl)ethanol (1 g, 4.97 mmol, 143.88 uL, 1 eq) and 4,6-dichloro-2,5-dimethyl-pyrimidine (880.49 mg, 4.97 mmol, 1 eq) in THF (150 mL) was added NaH (994.73 mg, 24.87 mmol, 60% purity, 5 eq) at 0° C. The reaction mixture was heated to 60° C. and stirred for 12 hrs. The reaction mixture was poured into saturated aq·$NH_4Cl$ (50 mL) at 0° C., and then diluted with EtOAc (20 mL) and extracted with EtOAc (20 mL*3). The combined organic layers were washed with saturated aq·$NH_4Cl$ (10 mL*2), dried over $Na_2SO_4$, filtered and concentrated under reduced pressure to give 4-[(1S)-1-(4-bromophenyl)ethoxy]-6-chloro-2,5-dimethyl-pyrimidine (1.92 g, crude) as a light yellow oil. ESI [M+H and M+3H]=341.0 and 343.0.

$^1$H-NMR (400 MHz, CHLOROFORM-d) δ 7.40 (d, J=8.4 Hz, 2H), 7.22 (d, J=8.4 Hz, 2H), 6.17 (q, J=6.5 Hz, 1H), 2.42 (s, 3H), 2.15 (s, 3H), 1.55 (d, J=6.5 Hz, 3H).

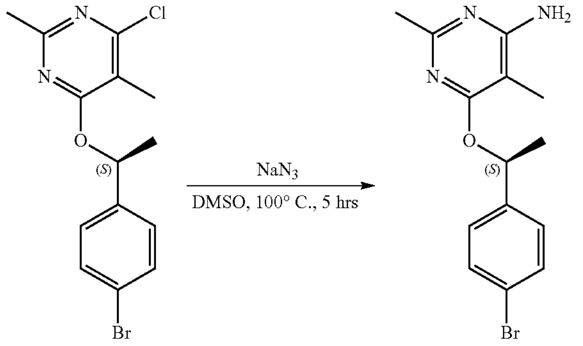

2 3

A mixture of 4-[(1S)-1-(4-bromophenyl)ethoxy]-6-chloro-2,5-dimethyl-pyrimidine (1.9 g, 5.56 mmol, 1 eq) and $NaN_3$ (433.87 mg, 6.67 mmol, 1.2 eq) in DMSO (20 mL) was stirred at 110° C. for 12 hrs. To the reaction mixture was added $H_2O$ (20 mL), then it was basified to pH=10 by 2M NaOH solution, and extracted with EtOAc (20 mL*3). The combined organic layers were washed with brine (5 mL*2), dried over $Na_2SO_4$, filtered and concentrated under reduced pressure to remove EtOAc. The aqueous layer was quenched by NaClO (20 mL), and then discarded. The residue was purified by prep-HPLC (column: Kromasil C18 (250*50 mm*10 μm); mobile phase: [water (10 mM $NH_4HCO_3$)-ACN]; B %: 45%-75%, 10 min) to give 6-[(1S)-1-(4-bromophenyl)ethoxy]-2,5-dimethyl-pyrimidin-4-amine (210 mg, 651.77 μmol, 11.72% yield) as a brown solid. ESI [M+H and M+3H]=322.1 and 324.0.

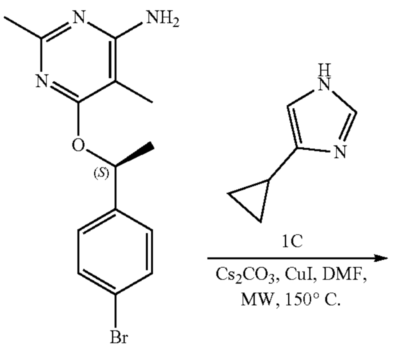

3

-continued

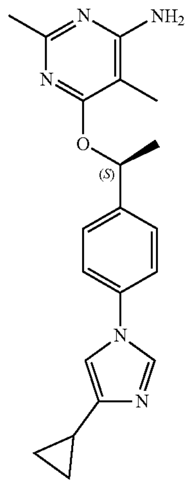

4

6-[(1S)-1-(4-bromophenyl)ethoxy]-2,5-dimethyl-pyrimidin-4-amine (50 mg, 155.18 μmol, 1 eq), 4-cyclopropyl-1H-imidazole (50.34 mg, 465.55 umol, 3 eq), $Cs_2CO_3$ (151.69 mg, 465.55 μmol, 3 eq) and CuI (118.22 mg, 620.73 μmol, 4 eq) were taken up into a microwave tube in DMF (3 mL). The sealed tube was heated at 150° C. for 25 hrs under microwave under N2. The reaction mixture was filtered, the filtrate was concentrated under reduced pressure to give a residue. The residue was purified by prep-HPLC (column: Waters Xbridge BEH C18 100*25 mm*5 μm; mobile phase: [water (10 mM $NH_4HCO_3$)-ACN]; B %: 30%-55%, 8 min) to give 6-[(1S)-1-[4-(4-cyclopropylimidazol-1-yl)phenyl]ethoxy]-2,5-dimethyl-pyrimidin-4-amine (22 mg, 62.96 umol, 20.29% yield) as a white solid. ESI [M+H]=350.1.

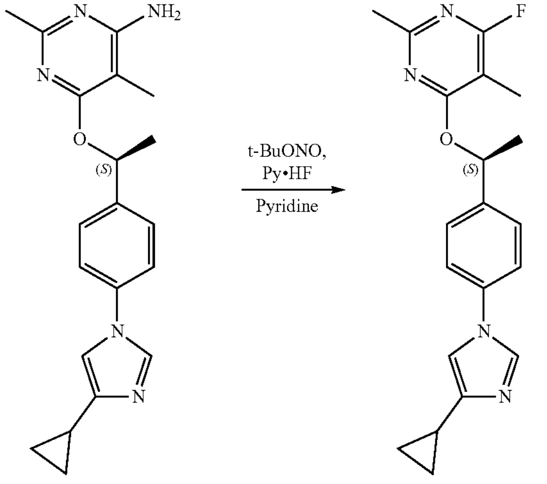

4

Bax-154 S

To a −40° C. stirred solution of 6-[(1S)-1-[4-(4-cyclopropylimidazol-1-yl)phenyl]ethoxy]-2,5-dimethyl-pyrimidin-4-amine (20 mg, 57.24 umol, 1 eq) in PYRIDINE (0.05 mL) was added pyridine; hydrofluoride (330.00 mg, 3.33 mmol, 0.3 mL, 58.18 eq) (mixed solvent, v/v=1/3) under N2, then tert-butyl nitrite (17.71 mg, 171.71 μmol, 20.42 μL, 3 eq) was added at −20° C. The resulting mixture was stirred at −10-25° C. for 30 mins. Cold water (5 mL) was added, then the reaction mixture was adjusted to pH=8 with sat.aq $NaHCO_3$ and extracted with DCM (5 mL*4). The combined organic layers were dried over drying $Na_2SO_4$, filtered and concentrated under reduced pressure to give a residue. The residue was purified by prep-HPLC (column: Waters Xbridge BEH C18 100*30 mm*10 μm; mobile phase: [water (10 mM $NH_4HCO_3$)-ACN]; B %: 40%-65%, 10 min) to give 4-[(1S)-1-[4-(4-cyclopropylimidazol-1-yl)phenyl]ethoxy]-6-fluoro-2,5-dimethyl-pyrimidine (8.31 mg, 23.41 umol, 40.91% yield, 99.292% purity) as a white solid. ESI [M+H]=353.2.

$^1$H-NMR (400 MHz, METHANOL-d4) δ 7.97 (d, J=1.3 Hz, 1H), 7.64-7.56 (m, 2H), 7.55-7.48 (m, 2H), 7.28 (d, J=0.9 Hz, 1H), 6.38 (q, J=6.5 Hz, 1H), 2.44 (s, 3H), 2.12 (s, 3H), 1.95-1.83 (m, 1H), 1.69 (d, J=6.5 Hz, 3H), 0.97-0.84 (m, 2H), 0.81-0.64 (m, 2H).

Example 68

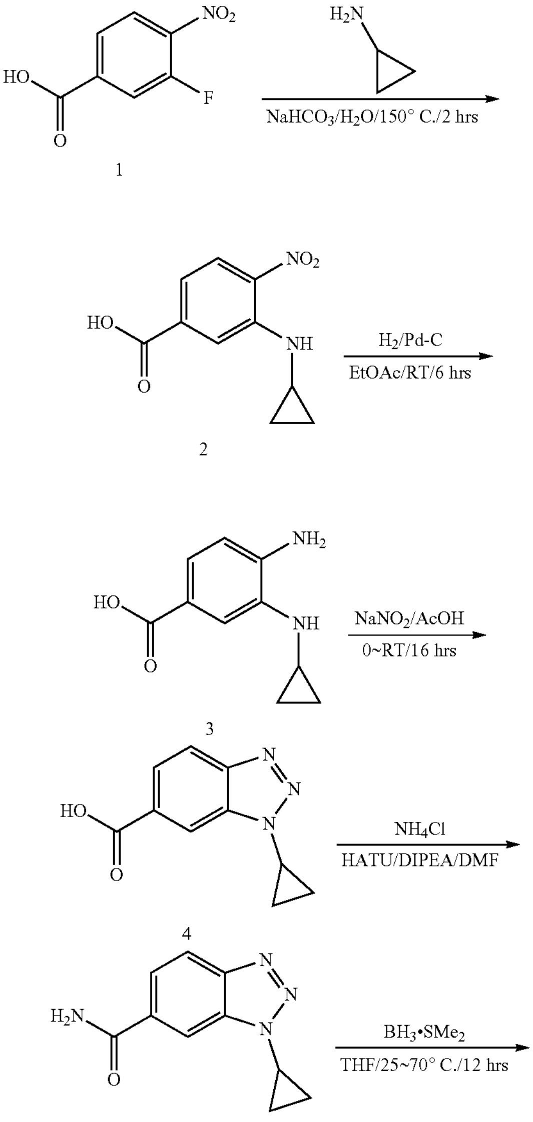

-continued
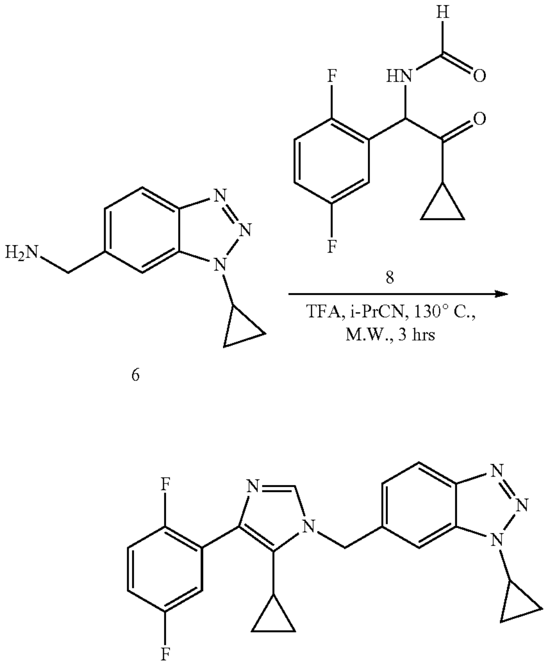
Bax-158
ESI [M+H] = 534.3
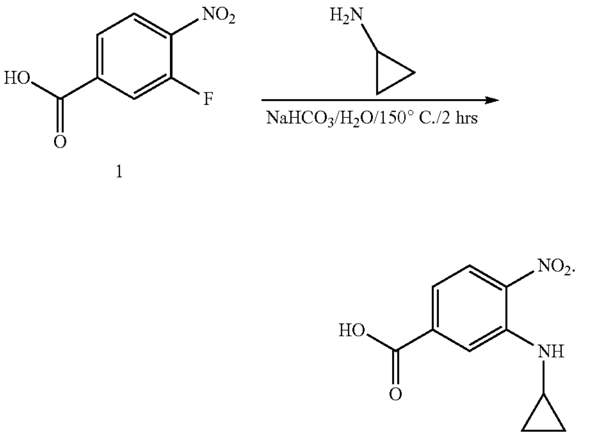
2
ESI [M+H] = 534.3
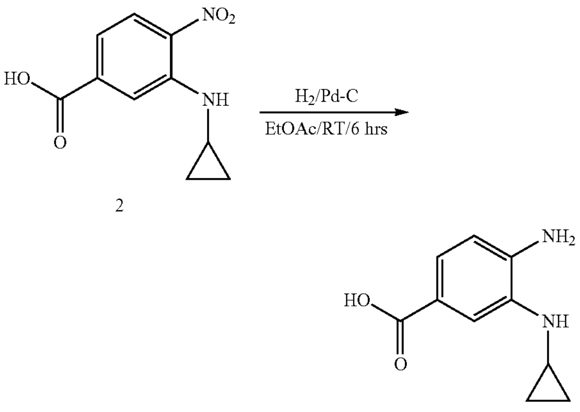
3
-continued
ESI [M+H] = 534.3
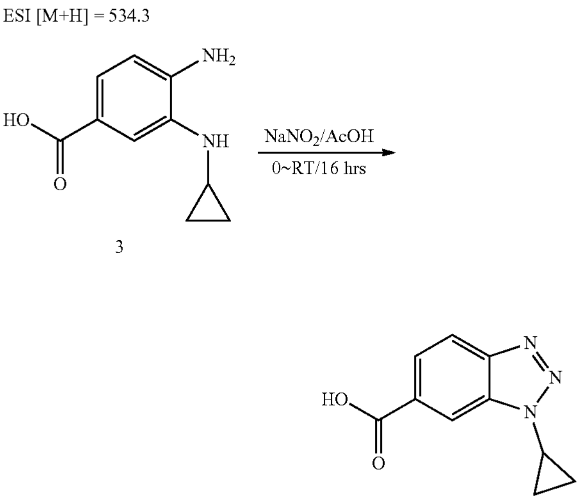
4
ESI [M+H] = 534.3
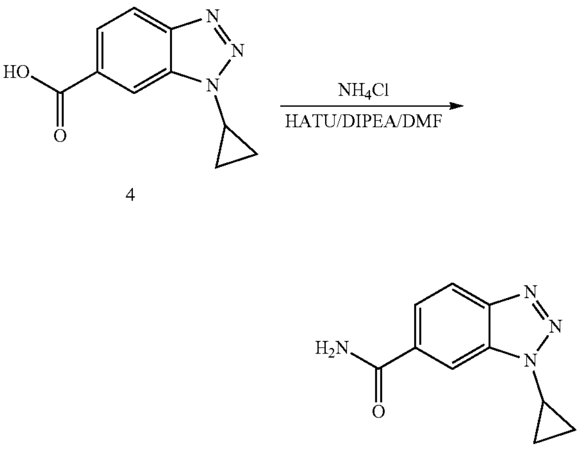
5
ESI [M+H] = 534.3
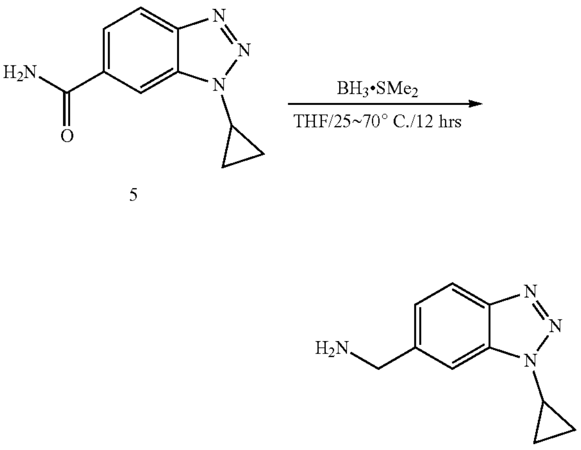
6

-continued
ESI [M+H] = 534.3
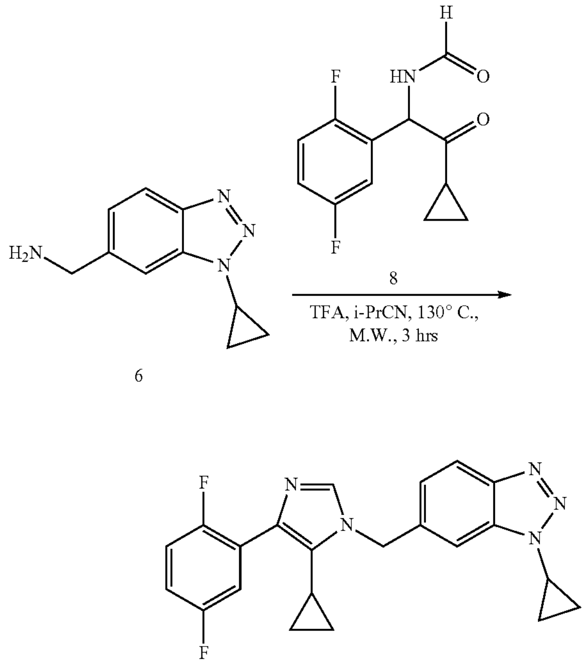
8
6
Bax-158
Example 69
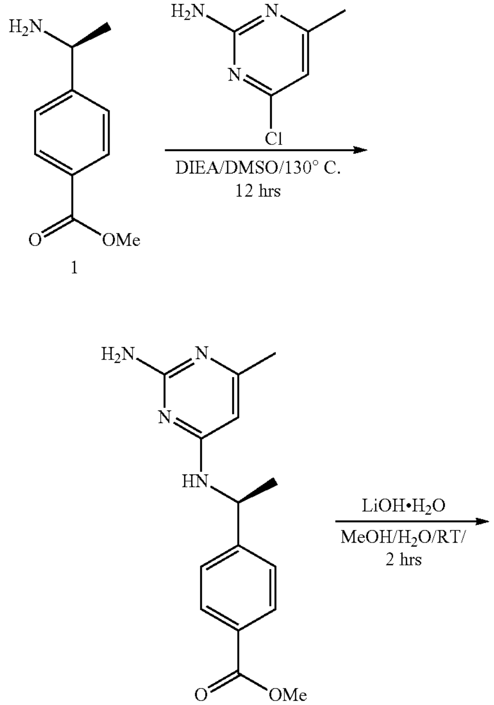
1
2
-continued
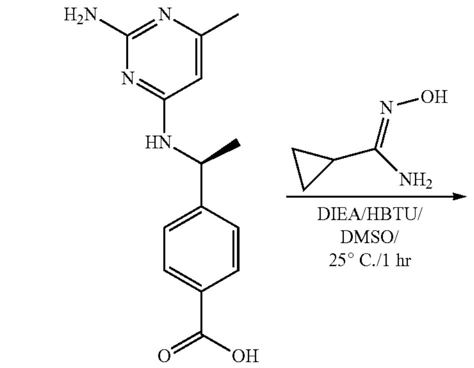
3
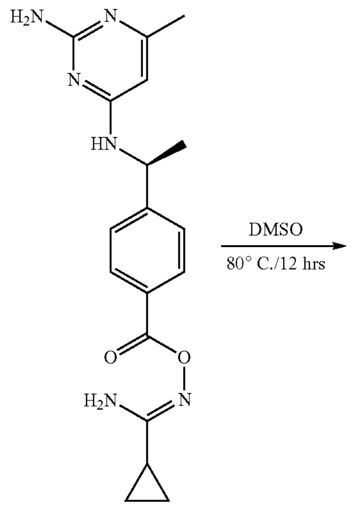
5
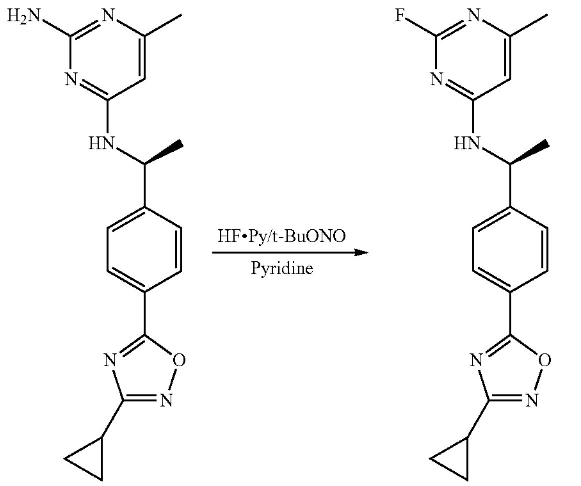
5
Bax-159 S -continued

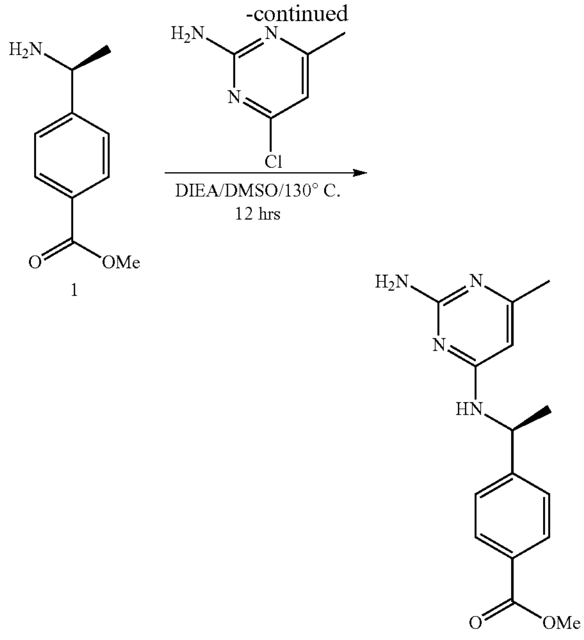

1

2

To a solution of methyl 4-[(1S)-1-aminoethyl]benzoate (2 g, 11.16 mmol, 1 eq) in DMSO (30 mL) was added DIEA (4.33 g, 33.48 mmol, 5.83 mL, 3 eq) and 4-chloro-6-methyl-pyrimidin-2-amine (2.08 g, 14.51 mmol, 1.3 eq). The mixture was stirred at 130° C. for 12 hrs. The reaction mixture was concentrated under reduced pressure to give a residue. The residue was purified by column chromatography on silica gel (PE:EtOAc=3:1/0:1) to give methyl 4-[(1S)-1-[(2-amino-6-methyl-pyrimidin-4-yl)amino]ethyl]benzoate (4.4 g, crude) was obtained as a yellow oil. ESI [M+H]=287.1.

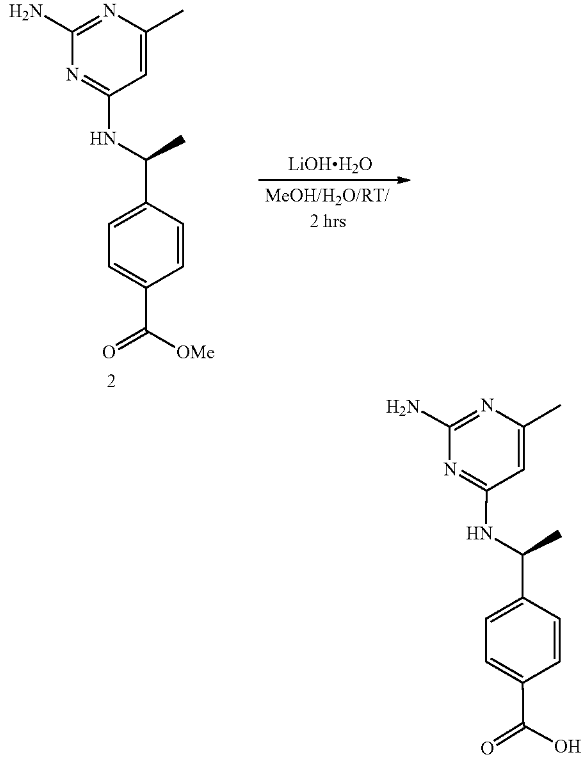

2

3

To a solution of methyl 4-[(1S)-1-[(2-amino-6-methyl-pyrimidin-4-yl)amino]ethyl]benzoate (2.8 g, 9.78 mmol, 1 eq) in MeOH (20 mL) and $H_2O$ (6 mL) was added $LiOH{\cdot}H_2O$ (1.23 g, 29.34 mmol, 3 eq). The mixture was stirred at 25° C. for 2 hrs. The reaction mixture was concentrated under reduced pressure to remove MeOH. The residue was diluted with $H_2O$ 30 mL and then adjusted with 1 M HCl to pH 6-7. Then the mixture was filtered and collected filter cake. The filtrate was purified by reversed-phase HPLC (0.1% $NH_3{\cdot}H_2O$) to give 4-[(1S)-1-[(2-amino-6-methyl-pyrimidin-4-yl)amino]ethyl]benzoic acid (520 mg, 1.91 mmol, 19.53% yield) was obtained as a white solid. ESI [M+H]=273.2.

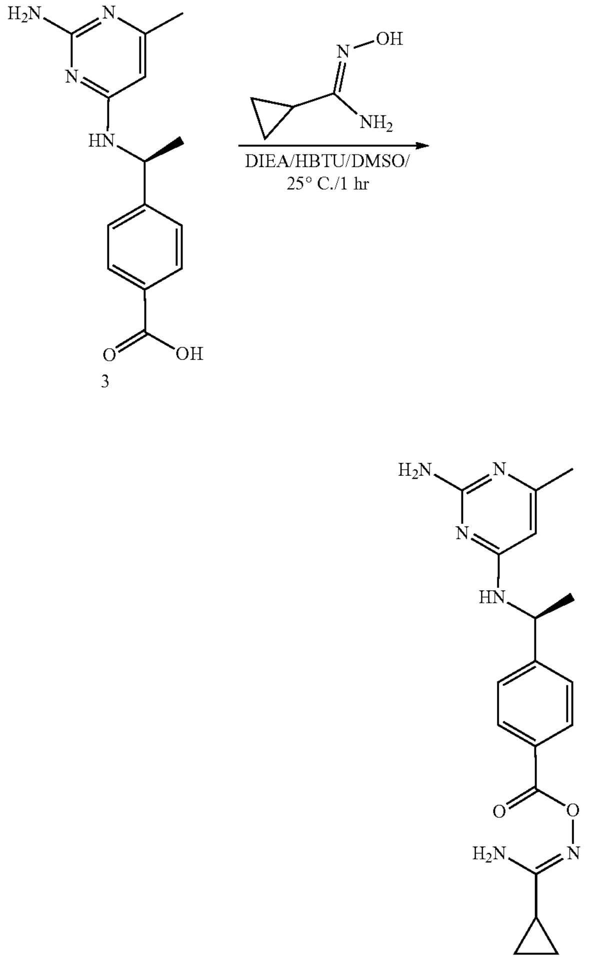

3

4

To a solution of 4-[(1S)-1-[(2-amino-6-methyl-pyrimidin-4-yl)amino]ethyl]benzoic acid (500 mg, 1.84 mmol, 1 eq) in DMSO (8 mL) was added N'-hydroxycyclopropanecarboxamidine (551.51 mg, 5.51 mmol, 3 eq), DIEA (1.42 g, 11.02 mmol, 1.92 mL, 6 eq) and HBTU (1.04 g, 2.75 mmol, 1.5 eq). The mixture was stirred at 25° C. for 1 hr. The reaction mixture was concentrated under reduced pressure to give a residue to give [(Z)-[amino (cyclopropyl) methylene]amino] 4-[(1S)-1-[(2-amino-6-methyl-pyrimidin-4-yl)amino]ethyl] benzoate (300 mg, crude) was obtained as a brown oil. ESI [M+H]=355.3.

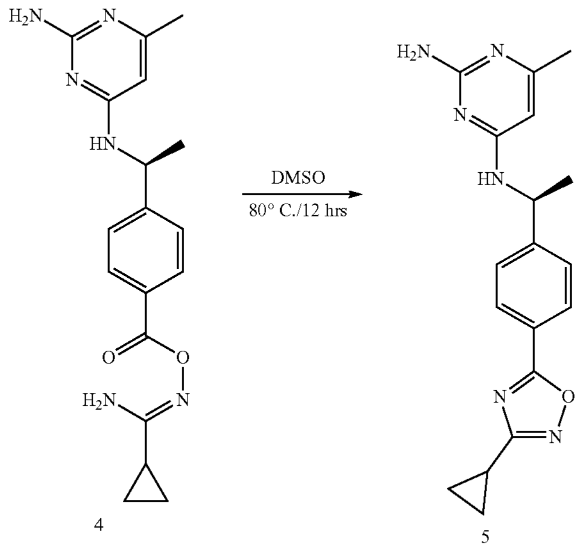 [SMILES: Cc1cc(N[C@@H](C)c2ccc(C(=O)O/N=C(\N)C3CC3)cc2)nc(N)n1 ; Cc1cc(N[C@@H](C)c2ccc(-c3nc(C4CC4)no3)cc2)nc(N)n1]

4

5

A mixture of [(Z)-[amino(cyclopropyl)methylene]amino] 4-[(1S)-1-[(2-amino-6-methyl-pyrimidin-4-yl)amino]ethyl] benzoate (300 mg, 846.49 umol, 1 eq) in DMSO (8 mL), and then the mixture was stirred at 80° C. for 12 hrs. The reaction mixture was concentrated under reduced pressure to give a residue. The residue was purified by prep-HPLC (column: Phenomenex Gemini-NX C18 75*30 mm*3 μm; mobile phase: [water (0.04% $NH_3H_2O$+10 mM $NH_4HCO_3$)-ACN]; B %: 20%-50%, 10 min) to give N4-[(1S)-1-[4-(3-cyclopropyl-1,2,4-oxa diazol-5-yl)phenyl]ethyl]-6-methyl-pyrimidine-2,4-diamine (148 mg, 439.97 μmol, 51.98% yield) was obtained as a brown solid. ESI [M+H]=337.1.

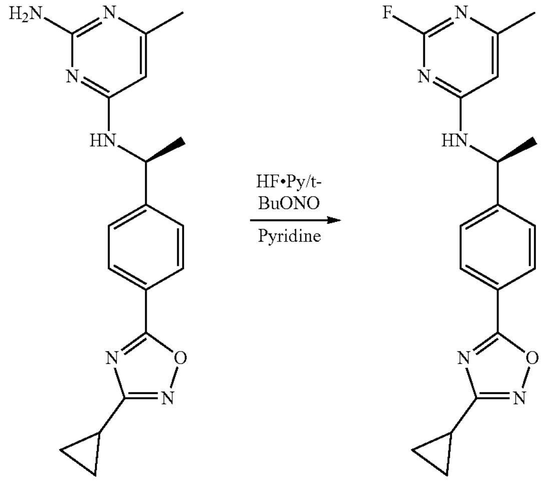

5

Bax-159 S

To a solution of N4-[(1S)-1-[4-(3-cyclopropyl-1,2,4-oxadiazol-5-yl)phenyl]ethyl]-6-methyl-pyrimidine-2,4-diamine (60 mg, 178.36 umol, 1 eq) in Py (0.3 mL) was added pyridine; hydrofluoride (990.00 mg, 9.99 mmol, 0.9 mL, 56.00 eq) at −50° C., the mixture was stirred at −25° C. for 15 min. Then tert-butyl nitrite (36.79 mg, 356.73 μmol, 42.43 μL, 2 eq) was added at −25° C. The mixture was stirred at 15° C. for 1 hr. Cold water (15 mL) was added, then the reaction mixture was adjusted to pH=8 with sat.aq $NaHCO_3$ and extracted with DCM (15 mL*4). The combined organic layers were dried over drying $Na_2SO_4$, filtered and concentrated under reduced pressure to give a residue. The residue was purified by prep-HPLC (column: Waters Xbridge BEH C18 100*25 mm*5 μm; mobile phase: [water (10 mM $NH_4HCO_3$)-ACN]; B %: 30%-60%, 10 min) to give N-[(1S)-1-[4-(3-cyclopropyl-1,2,4-oxadiazol-5-yl)phenyl] ethyl]-2-fluoro-6-methyl-pyrimidin-4-amine (15.14 mg, 42.92 umol, 24.06% yield, 96.2% purity) was obtained as white solid. ESI [M+H]=340.2.

$^1H$ NMR (400 MHz, DMSO-d6) δ 8.41 (d, J=7.5 Hz, 1H), 8.02 (d, J=7.9 Hz, 2H), 7.56 (d, J=7.1 Hz, 2H), 6.34 (s, 1H), 5.26-4.69 (m, 1H), 2.27-1.99 (m, 4H), 1.47 (d, J=7.0 Hz, 3H1), 1.18-0.88 (m, 4H1).

Example 70

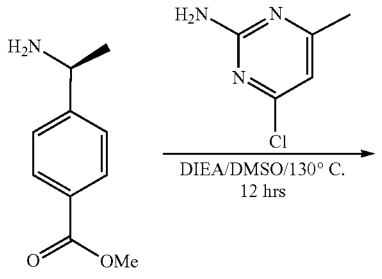

1

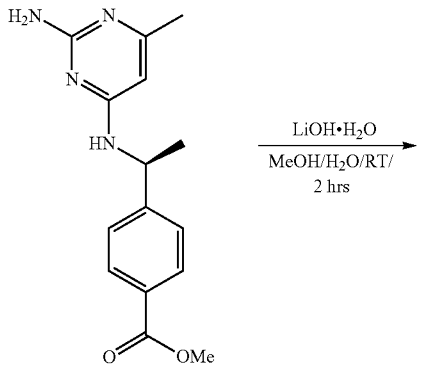

2

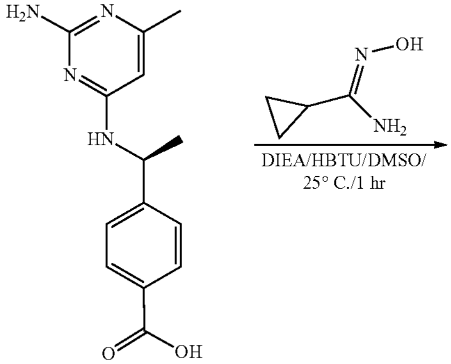

3

-continued

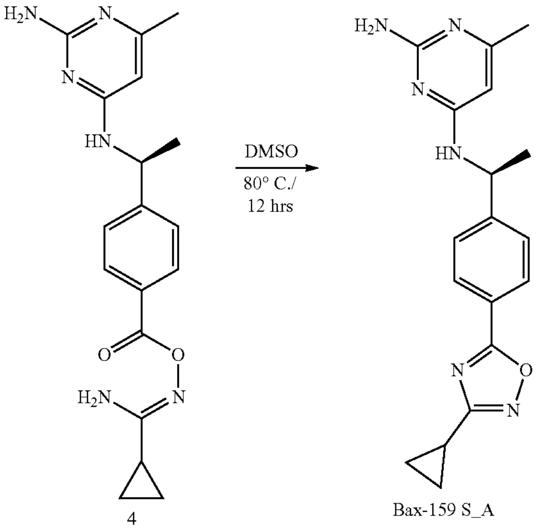

4

Bax-159 S_A

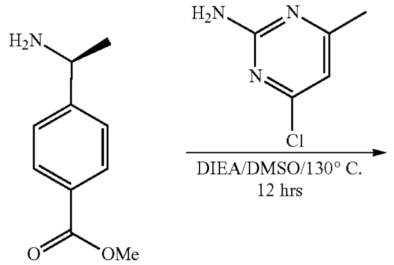

1

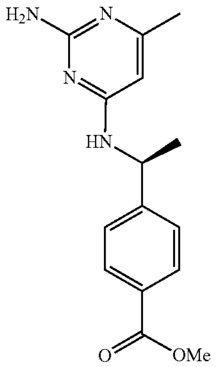

2

To a solution of methyl 4-[(1S)-1-aminoethyl]benzoate (2 g, 11.16 mmol, 1 eq) in DMSO (30 mL) was added DIEA (4.33 g, 33.48 mmol, 5.83 mL, 3 eq) and 4-chloro-6-methyl-pyrimidin-2-amine (2.08 g, 14.51 mmol, 1.3 eq). The mixture was stirred at 130° C. for 12 hrs. The reaction mixture was concentrated under reduced pressure to give a residue. The residue was purified by column chromatography on silica gel (PE:EtOAc=3:1/0:1) to give methyl 4-[(1S)-1-[(2-amino-6-methyl-pyrimidin-4-yl)amino]ethyl]benzoate (4.4 g, crude) was obtained as a yellow oil. ESI [M+H]=287.1.

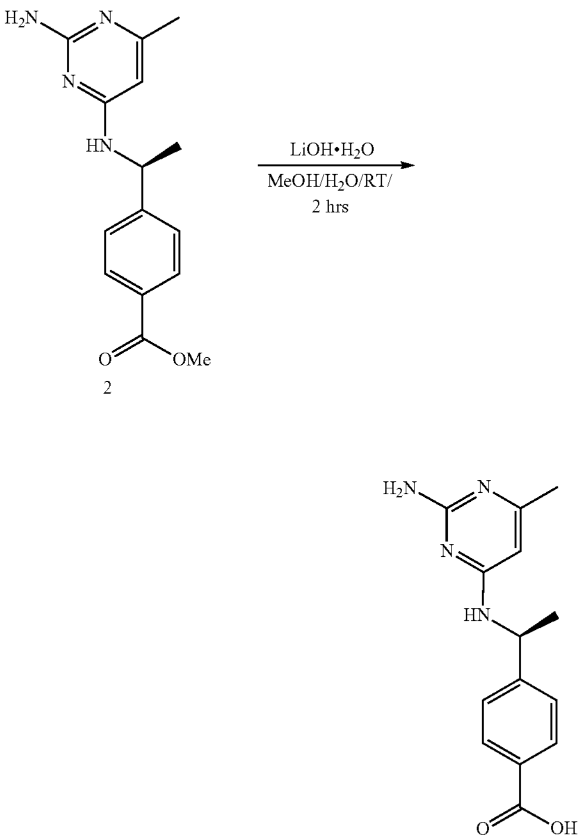

2

3

To a solution of methyl 4-[(1S)-1-[(2-amino-6-methyl-pyrimidin-4-yl)amino]ethyl]benzoate (2.8 g, 9.78 mmol, 1 eq) in MeOH (20 mL) and $H_2O$ (6 mL) was added LiOH·$H_2O$ (1.23 g, 29.34 mmol, 3 eq). The mixture was stirred at 25° C. for 2 hrs. The reaction mixture was concentrated under reduced pressure to remove MeOH. The residue was diluted with $H_2O$ 30 mL and then adjusted with 1 M HCl to pH 6-7. Then the mixture was filtered and collected filter cake. The filtrate was purified by reversed-phase HPLC (0.1% $NH_3$·$H_2O$) to give 4-[(1S)-1-[(2-amino-6-methyl-pyrimidin-4-yl)amino]ethyl]benzoic acid (520 mg, 1.91 mmol, 19.53% yield) was obtained as a white solid. ESI [M+H]=273.2.

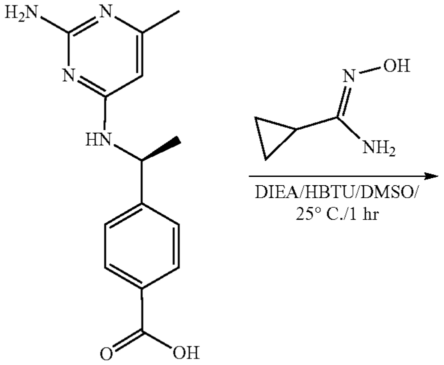

3

-continued

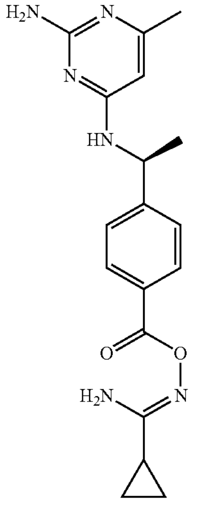

4

To a solution of 4-[(1S)-1-[(2-amino-6-methyl-pyrimidin-4-yl)amino]ethyl]benzoic acid (500 mg, 1.84 mmol, 1 eq) in DMSO (8 mL) was added N'-hydroxycyclopropanecarboxamidine (551.51 mg, 5.51 mmol, 3 eq), DIEA (1.42 g, 11.02 mmol, 1.92 mL, 6 eq) and HBTU (1.04 g, 2.75 mmol, 1.5 eq). The mixture was stirred at 25° C. for 1 hr. The reaction mixture was concentrated under reduced pressure to give a residue to give [(Z)-[amino (cyclopropyl) methylene]amino] 4-[(1S)-1-[(2-amino-6-methyl-pyrimidin-4-yl)amino]ethyl] benzoate (300 mg, crude) was obtained as a brown oil. ESI [M+H]=355.3.

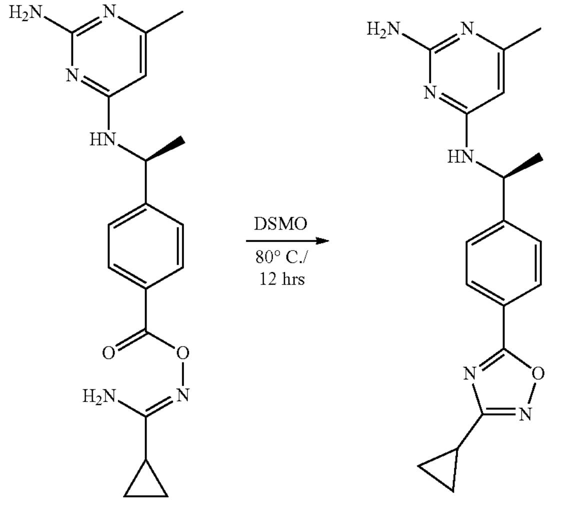

4 Bax-159 S_A

A mixture of [(Z)-[amino(cyclopropyl)methylene]amino] 4-[(1S)-1-[(2-amino-6-methyl-pyrimidin-4-yl)amino]ethyl] benzoate (300 mg, 846.49 umol, 1 eq) in DMSO (8 mL), and then the mixture was stirred at 80° C. for 12 hrs. The reaction mixture was concentrated under reduced pressure to give a residue. The residue was purified by prep-HPLC (column: Phenomenex Gemini-NX C18 75*30 mm*3 μm; mobile phase: [water (0.04% $NH_3H_2O$+10 mM $NH_4HCO_3$)-ACN]; B %: 20%-50%, 10 min) to give N4-[(1S)-1-[4-(3-cyclopropyl-1,2,4-oxa diazol-5-yl)phenyl]ethyl]-6-methyl-pyrimidine-2,4-diamine (15.77 mg, 45.16 umol, 96.33% yield, 96.330% purity) was obtained as yellow solid. ESI [M+H]=337.2.

$^1$H NMR (400 MHz, METHANOL-d4) δ 8.00 (d, J=8.2 Hz, 2H), 7.52 (d, J=8.2 Hz, 2H), 4.89 (s, 4H), 3.39-3.25 (m, 1H), 2.16-2.01 (m, 4H), 1.49 (d, J=6.8 Hz, 3H), 1.16-0.93 (m, 4H).

Example 71

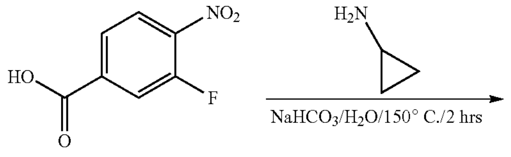

1

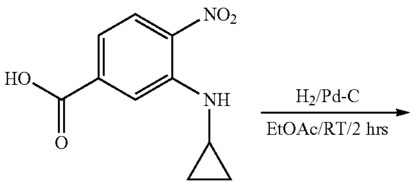

2

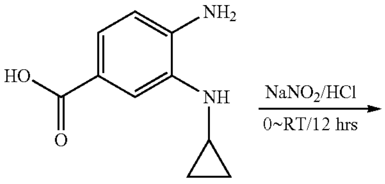

3

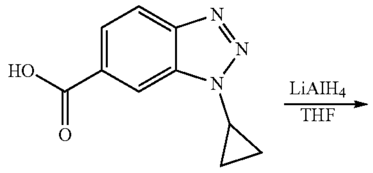

4

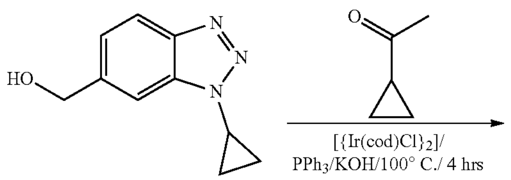

5

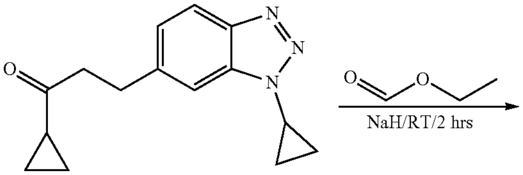

6

-continued

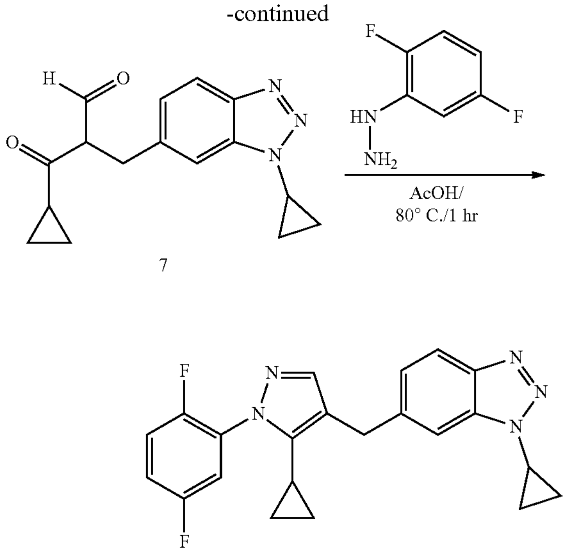

7

Bax-168

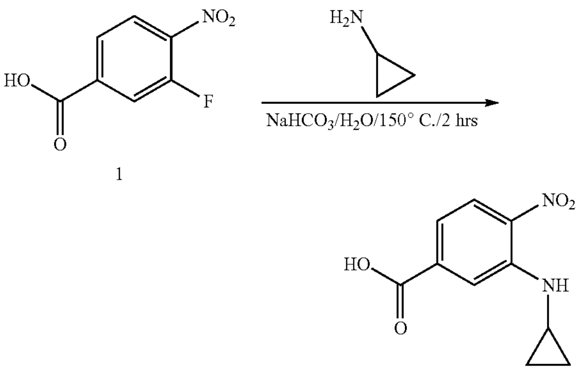

1

2

A mixture of 3-fluoro-4-nitro-benzoic acid (5 g, 27.01 mmol, 1 eq), cyclopropanamine (2.31 g, 40.52 mmol, 2.81 mL, 1.5 eq) and $NaHCO_3$ (3.63 g, 43.22 mmol, 1.68 mL, 1.6 eq) in $H_2O$ (40 mL) was stirred at 150° C. for 2 hrs. The reaction mixture was cooled to 20° C. and it was acidified to pH=2~3 by 1N HCl until the yellow precipitate was formed. Then it was filtered and the filter cake was washed by $H_2O$ (20 mL*3), and concentrated to give a residue to give 3-(cyclopropylamino)-4-nitro-benzoic acid (5.9 g, 26.55 mmol, 98.30% yield) as a yellow solid. ESI [M+H]=223.0.

$^1$H NMR (400 MHz, CHLOROFORM-d) δ 8.26 (d, J=8.8 Hz, 1H), 8.19-7.98 (m, 2H), 7.38 (dd, J=1.7, 8.8 Hz, 1H), 2.69 (dd, J=3.6, 5.4 Hz, 1H), 1.28 (s, 1H), 1.12-0.92 (m, 2H), 0.80-0.58 (m, 2H).

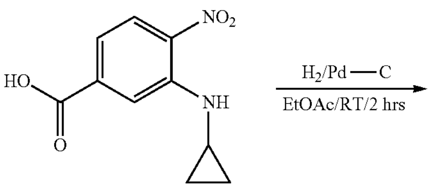

2

-continued

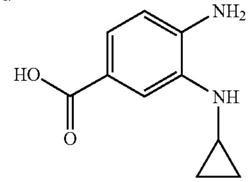

3

To a solution of 3-(cyclopropylamino)-4-nitro-benzoic acid (5.9 g, 26.55 mmol, 1 eq) in EtOAc (150 mL) was added Pd/C (2.0 g, 10% purity) under Argon. The suspension was degassed under vacuum and purged with $H_2$ several times. The mixture was stirred under $H_2$ (15 psi) at 25° C. for 2 hrs. The reaction mixture was filtered and the filtrate was concentrated to give 4-amino-3-(cyclopropylamino) benzoic acid (6.5 g, crude) as a purple solid. ESI [M+H]=193.1.

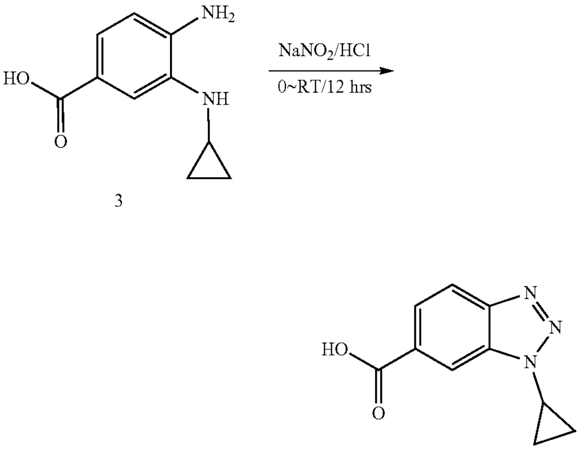

3

4

To a 0° C. stirred mixture of 4-amino-3-(cyclopropylamino)benzoic acid (6.3 g, 32.78 mmol, 1 eq) in 6N HCl (50 mL) was added $NaNO_2$ (3.39 g, 49.16 mmol, 1.5 eq) in $H_2O$ (5 mL) dropwise. The mixture was stirred at 25° C. for 12 hrs. The reaction mixture was diluted with $H_2O$ (20 mL) and extracted with EtOAc (50 mL*3). The combined organic layers were dried over $MgSO_4$, filtered and concentrated under reduced pressure to give a residue. The residue was purified by column chromatography ($SiO_2$, Ethyl acetate/Methanol=1/0 to 3/1) to give 3-cyclopropylbenzotriazole-5-carboxylic acid (3.5 g, 17.22 mmol, 52.55% yield) as a yellow solid. ESI [M+H]=204.0.

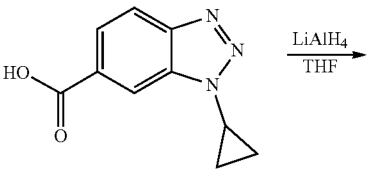

4

-continued

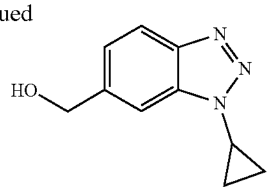

5

To a 0° C. mixture of 3-cyclopropylbenzotriazole-5-carboxylic acid (3.49 g, 17.18 mmol, 1 eq) in THF (35 mL) was added $LiAlH_4$ (977.82 mg, 25.76 mmol, 1.5 eq), and then the mixture was stirred at 25° C. for 2 hrs. The reaction mixture was quenched by 15% NaOH solution (2 mL) and $H_2O$ (5 mL) at 0° C. and concentrated under reduced pressure to give a residue to give (3-cyclopropylbenzotriazol-5-yl) methanol (1.68 g, 8.88 mmol, 51.70% yield) as a yellow oil. ESI [M+H]=190.1.

$^1H$ NMR (400 MHz, DMSO-d6) δ 7.96 (d, J=8.6 Hz, 1H), 7.84-7.65 (m, 1H), 7.34 (dd, J=1.2, 8.6 Hz, 1H), 5.47 (s, 1H), 4.71 (d, J=3.5 Hz, 2H), 4.15-3.88 (m, 1H), 1.32-1.19 (m, 4H).

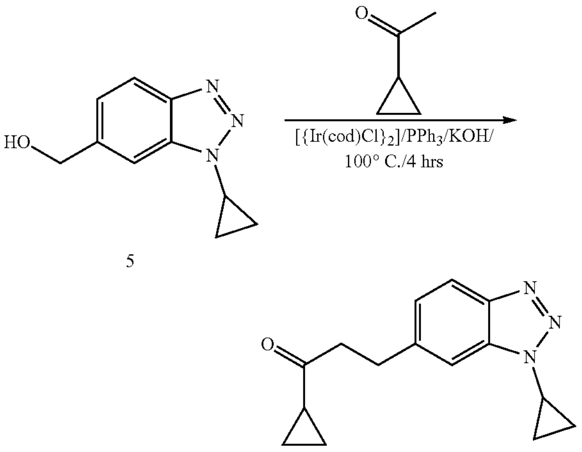

5

6

(3-cyclopropylbenzotriazol-5-yl)methanol (400 mg, 2.11 mmol, 1 eq) was reacted with 1-cyclopropylethanone (106.69 mg, 1.27 mmol, 125.67 µL, 0.6 eq) in the presence of chloroiridium; (1Z,5Z)-cycloocta-1,5-diene (7.10 mg, 10.57 µmol, 0.005 eq), $PPh_3$ (27.72 mg, 105.70 µmol, 0.05 eq) and KOH (2.37 mg, 42.28 µmol, 0.02 eq) at 100° C. for 4 hrs under N2 atmosphere without solvent. The reaction mixture was concentrated under reduced pressure to give a residue. The residue was purified by prep-TLC (PE:EtOAc=3:1) to give 1-cyclopropyl-3-(3-cyclopropylbenzotriazol-5-yl)propan-1-one (52 mg, 203.67 µmol, 9.63% yield) as a brown solid. ESI[M+H]=256.1

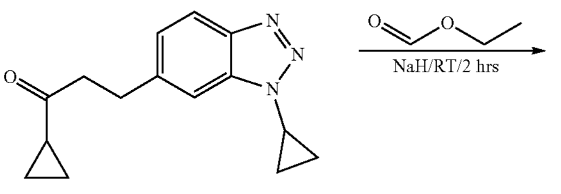

6

-continued

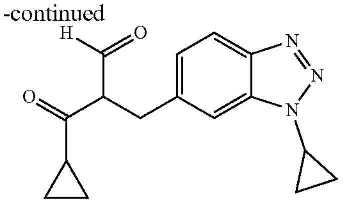

7

To a 0° C. mixture of 1-cyclopropyl-3-(3-cyclopropylbenzotriazol-5-yl)propan-1-one (42 mg, 164.50 µmol, 1 eq) and ethyl formate (243.72 mg, 3.29 mmol, 264.63 µL, 20 eq) in DMF (3 mL) was added NaH (13.16 mg, 329.01 µmol, 60% purity, 2 eq), and then the mixture was stirred at 25° C. for 2 hrs. The mixture was quenched by addition saturated aq. $NH_4Cl$ (10 mL) and extracted with ethyl acetate (10 mL*3). The combined organic phase was washed with brine (10 mL*2), dried over anhydrous $Na_2SO_4$, filtered and concentrated in vacuum to give 3-cyclopropyl-2-[(3-cyclopropylbenzotriazol-5-yl)methyl]-3-oxo-propanal (50 mg, crude) as a yellow oil. ESI[M+H]=284.1

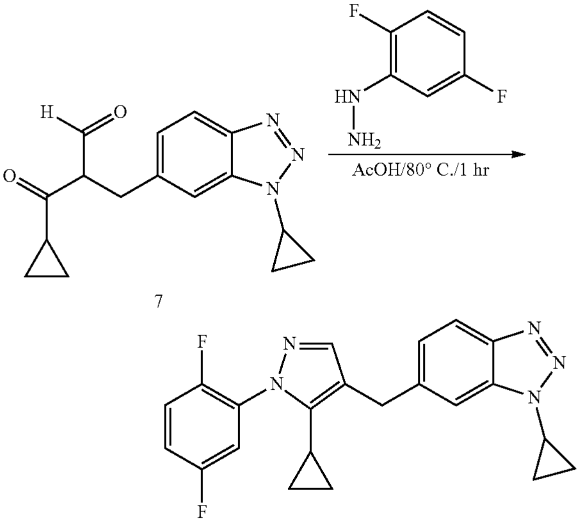

7

Bax-168

A mixture of 3-cyclopropyl-2-[(3-cyclopropylbenzotriazol-5-yl)methyl]-3-oxo-propanal (40 mg, 141.18 umol, 1 eq) and (2,5-difluorophenyl)hydrazine (40.69 mg, 282.36 umol, 2 eq) in $CH_3COOH$ (4 mL) was stirred at 80° C. for 1 hr. The reaction mixture was diluted with $H_2O$ (5 mL) and extracted with EtOAc (10 mL*3). The combined organic layers were dried over $Na_2SO_4$, filtered and concentrated under reduced pressure to give a residue. The residue was purified by prep-HPLC (column: Waters Xbridge BEH C18 100*25 mm*5 µm; mobile phase: [water (10 mM $NH_4HCO_3$)-ACN]; B %: 40%-70%, 10 min) to give 1-cyclopropyl-6-[[5-cyclopropyl-1-(2,5-difluorophenyl)pyrazol-4-yl]methyl]benzotriazole (15.15 mg, 38.53 umol, 27.29% yield, 99.554% purity) as a white solid. ESI [M+H]=392.2

$^1H$ NMR (400 MHz, METHANOL-d4) δ 7.89 (d, J=8.7 Hz, 1H), 7.64 (s, 1H), 7.52 (s, 1H), 7.44-7.27 (m, 4H), 4.16 (s, 2H), 3.90 (quin, J=5.3 Hz, 1H), 1.77-1.60 (m, 1H), 1.41-1.28 (m, 4H), 0.81-0.65 (m, 2H), 0.51-0.37 (m, 2H)

Example 72
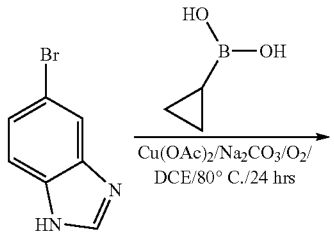
1
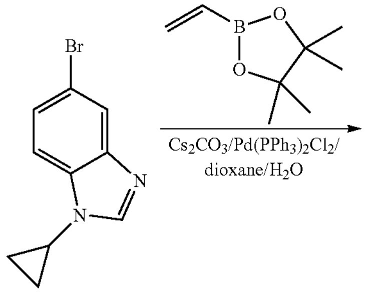
2
mixture
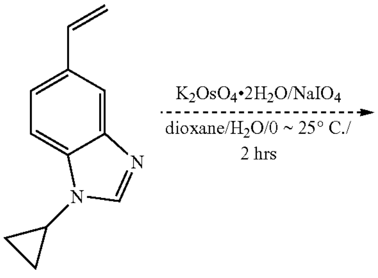
3
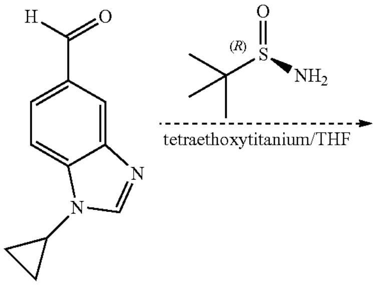
4
-continued
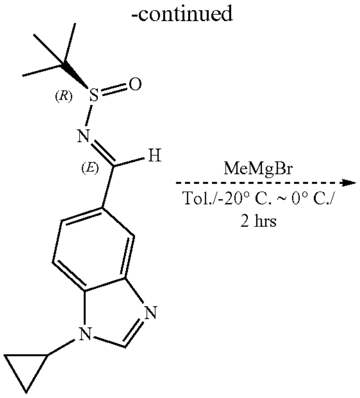
5
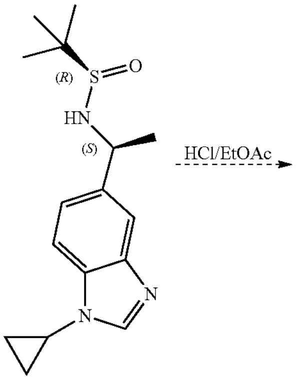
6
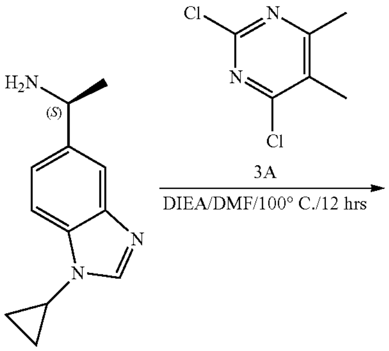
7
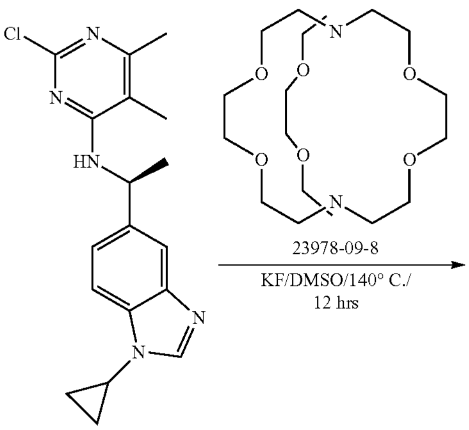
8

-continued

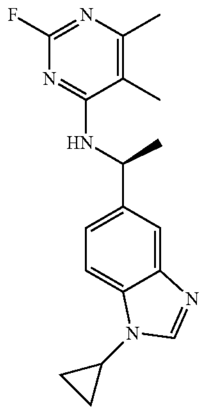

Bax-170 S

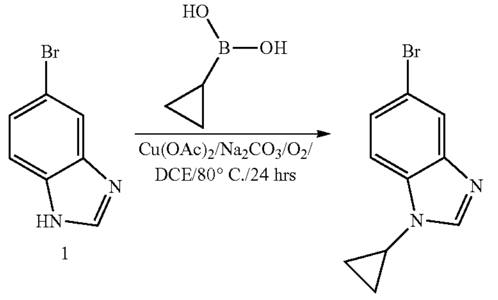

1

2
mixture

A mixture of 6-bromo-1H-benzimidazole (4 g, 20.30 mmol, 1 eq), cyclopropylboronic acid (4.36 g, 50.75 mmol, 2.5 eq), $Cu(OAc)_2$ (3.69 g, 20.30 mmol, 1 eq), 2-(2-pyridyl) pyridine (3.17 g, 20.30 mmol, 1 eq) and $Na_2CO_3$ (6.46 g, 60.90 mmol, 3 eq) in DCE (120 mL) was stirred at 80° C. for 48 hrs under 02 (15 psi). The reaction mixture was filtered and the filtrate was concentrated to give a residue. The residue was purified by column chromatography ($SiO_2$, PE/EtOAc=1/0 to 0/1) to give 6-bromo-1-cyclopropyl-benzimidazole (1.2 g, 5.06 mmol, 49.86% yield) and 5-bromo-1-cyclopropyl-benzimidazole (1.2 g, 5.06 mmol, 49.86% yield) (regio-mixture total 2.4) as a brown oil. ESI [M+H and M+3H]=236.9 and 238.9.

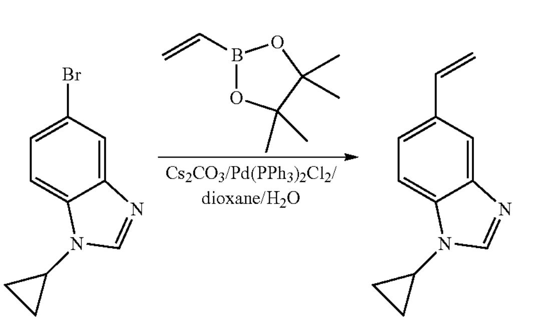

2

3

A mixture of 5-bromo-1-cyclopropyl-benzimidazole (1.2 g, 5.06 mmol, 0.5 eq), 6-bromo-1-cyclopropyl-benzimidazole (1.20 g, 5.06 mmol, 0.5 eq) (regio-mixture, total 2.4 g), 4,4,5,5-tetramethyl-2-vinyl-1,3,2-dioxaborolane (3.90 g, 25.31 mmol, 4.29 mL, 2.5 eq), $Cs_2CO_3$ (8.25 g, 25.31 mmol, 2.5 eq) and $Pd(PPh_3)_2Cl_2$ (355.25 mg, 506.13 umol, 0.05 eq) in dioxane (40 mL) and $H_2O$ (10 mL) was stirred at 80° C. for 16 hrs. The mixture was concentrated to give a residue. To the residue was added $H_2O$ (20 mL) and extracted with EtOAc (20 mL*5). The combined organic layers were washed with brine (10 mL*2), dried over $Na_2SO_4$, filtered and concentrated under reduced pressure to give the crude product. The crude product was purified by column chromatography ($SiO_2$, Petroleum ether/Ethyl acetate=1/0 to 0/1) to give 1-cyclopropyl-5-vinyl-benzimidazole (0.8 g, 4.34 mmol, 85.79% yield) and 1-cyclopropyl-6-vinyl-benzimidazole (0.8 g, 4.34 mmol, 85.79% yield) (regio-mixture) total 1.6 g as a yellow oil. ESI [M+H]=185.1.

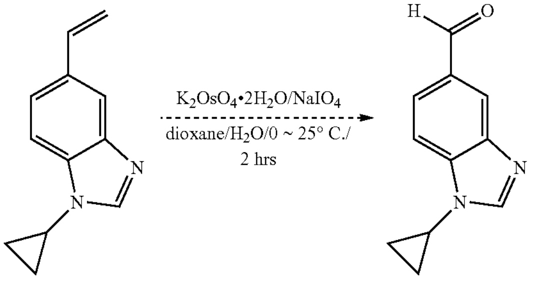

3

4

To a 0° C. stirred solution of 1-cyclopropyl-5-vinyl-benzimidazole (0.8 g, 4.34 mmol, 0.5 eq), 1-cyclopropyl-6-vinyl-benzimidazole (800.00 mg, 4.34 mmol, 0.5 eq) (regio-mixture, total 1.6 g) in dioxane (30 mL) and $H_2O$ (10 mL) was added $NaIO_4$ (3.72 g, 17.37 mmol, 962.45 uL, 2.0 eq) and dipotassium; dioxido(dioxo)osmium; dihydrate (479.98 mg, 1.30 mmol, 0.15 eq). The resulting mixture was stirred at 15° C. for 2 hrs. The mixture was concentrated to give a residue. To the residue was added $H_2O$ (20 mL) and then quenched with saturated aq·$Na_2SO_3$ (30 mL), extracted with EtOAc/THF (3:1, 30 mL*3), dried over $Na_2SO_4$, filtered and concentrated under reduced pressure to give a residue to give 1-cyclopropylbenzimidazole-5-carbaldehyde (800 mg, crude) and 3-cyclopropylbenzimidazole-5-carbaldehyde (800 mg, crude) (regio-mixture, total 1.6 g, crude) as a brown oil. ESI [M+H]=187.0.

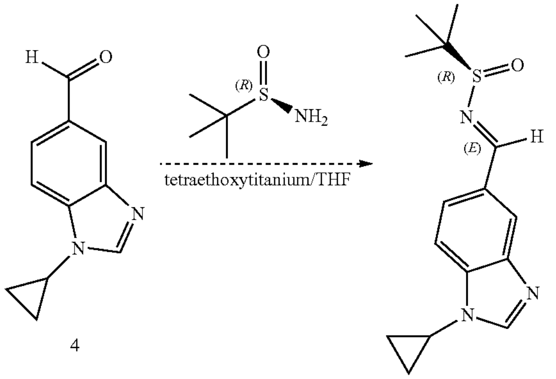

4

5

To a 15° C. stirred mixture of 1-cyclopropylbenzimidazole-5-carbaldehyde (0.8 g, 4.30 mmol, 0.5 eq), 3-cyclopropylbenzimidazole-5-carbaldehyde (800.00 mg, 4.30 mmol, 0.5 eq) (regio-mixture 1.6 g) and 2-methylpropane-2-sulfinamide (2.29 g, 18.90 mmol, 2.2 eq) in THF (30 mL) was added tetraethoxytitanium (3.92 g, 17.18 mmol, 3.56 mL, 2.0 eq), and the resulting mixture was stirred at 70° C. for 12 hrs under N2. To the reaction mixture was added $H_2O$ (20 mL), then filtered, the filtrate was concentrated to give a residue. The residue was purified by prep-HPLC (column: Waters Xbridge Prep OBD C18 150*40 mm*10 μm; mobile phase: [water (10 mM $NH_4HCO_3$)-ACN]; B %: 30%-50%, 8 min) to give (NE)-N-[(3-cyclopropylbenzimidazol-5-yl) methylene]-2-methyl-propane-2-sulfinamide (720 mg, 2.49 mmol, 57.96% yield) and (NE)-N-[(1-cyclopropylbenzimidazol-5-yl)methylene]-2-methyl-propane-2-sulfinamide (620 mg, 2.14 mmol, 49.81% yield) as light brown oil. ESI [M+H]=290.1.

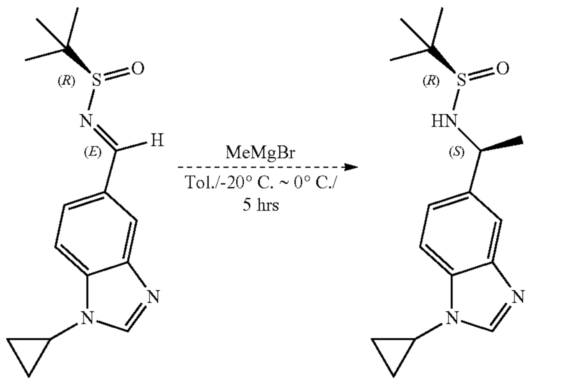

5 6

To a −20° C. stirred mixture of (NE)-N-[(1-cyclopropylbenzimidazol-5-yl)methylene]-2-methyl-propane-2-sulfinamide (620 mg, 2.14 mmol, 1 eq) in Tol. (20 mL) was added MeMgBr (3 M, 3.93 mL, 2.5 eq) (in ether) dropwise. The mixture was stirred at −20° C.~0° C. for 5 hrs. The reaction mixture was concentrated under reduced pressure to remove Tol. To the residue was added saturated aq·$NH_4Cl$ (10 mL) and $H_2O$ (10 mL), extracted with EtOAc (20 mL*3). The combined organic layers were washed with brine (10 mL*2), dried over $Na_2SO_4$, filtered and concentrated under reduced pressure to give a residue. The residue was purified by prep-HPLC (column: Nano-micro Kromasil C18 100*30 mm 5 μm; mobile phase: [water (0.1% TFA)-ACN]; B %: 12%-28%, 10 min) to give N-[(1S)-1-(1-cyclopropylbenzimidazol-5-yl)ethyl]-2-methyl-propane-2-sulfinamide (500 mg, 1.64 mmol, 76.41% yield) as a white solid. ESI [M+H]=306.05.

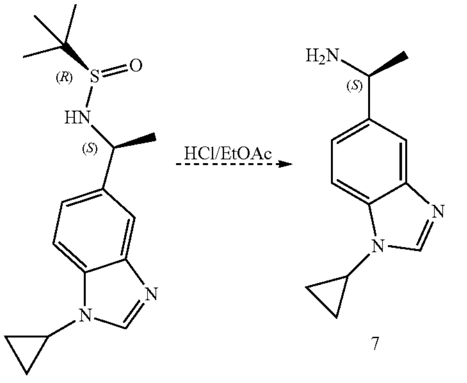

7

6

To a solution of N-[(1S)-1-(1-cyclopropylbenzimidazol-5-yl)ethyl]-2-methyl-propane-2-sulfinamide (500 mg, 1.64 mmol, 1 eq) in EtOAc (10 mL) and MeOH (10 mL) was added HCl/EtOAc (4 M, 5 mL, 12.22 eq). The resulting mixture was stirred at 10° C. for 1 hr. The reaction mixture was concentrated to give (1S)-1-(1-cyclopropylbenzimidazol-5-yl)ethanamethanamine (380 mg, 1.60 mmol, 97.65% yield, HCl) as a white solid. ESI [M+H]=202.2.

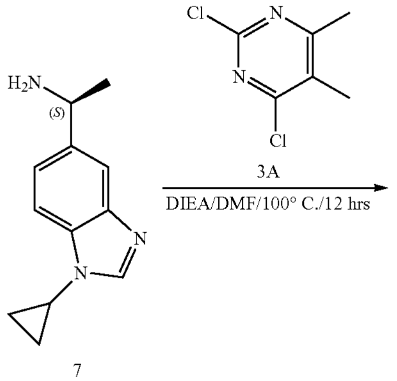

7

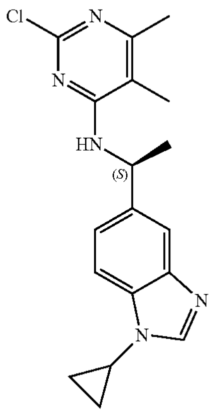

8

To a mixture of (1S)-1-(1-cyclopropylbenzimidazol-5-yl) ethanamine (60 mg, 252.39 umol, 1 eq, HCl) DIEA (130.48 mg, 1.01 mmol, 175.85 uL, 4 eq) in DMF (5 mL) was added 2,4-dichloro-5,6-dimethyl-pyrimidine (44.68 mg, 252.39 umol, 1 eq) and then the mixture was stirred at 100° C. for 18 hrs. The reaction mixture was filtered, the filtrate was concentrated to give the crude product. The residue was purified by prep-HPLC (column: Waters Xbridge Prep OBD C18 150*40 mm*10 μm; mobile phase: [water (0.05% $NH_3H_2O$+10 mM $NH_4HCO_3$)-ACN]; B %: 25%-55%, 8 min) to give 2-chloro-N-[(1S)-1-(1-cyclopropylbenzimidazol-5-yl)ethyl]-5,6-dimethyl-pyrimidin-4-amine (47 mg, 116.87 umol, 46.30% yield, 85% purity) as a white solid. ESI [M+H and M+3H]=342.1 and 344.1.

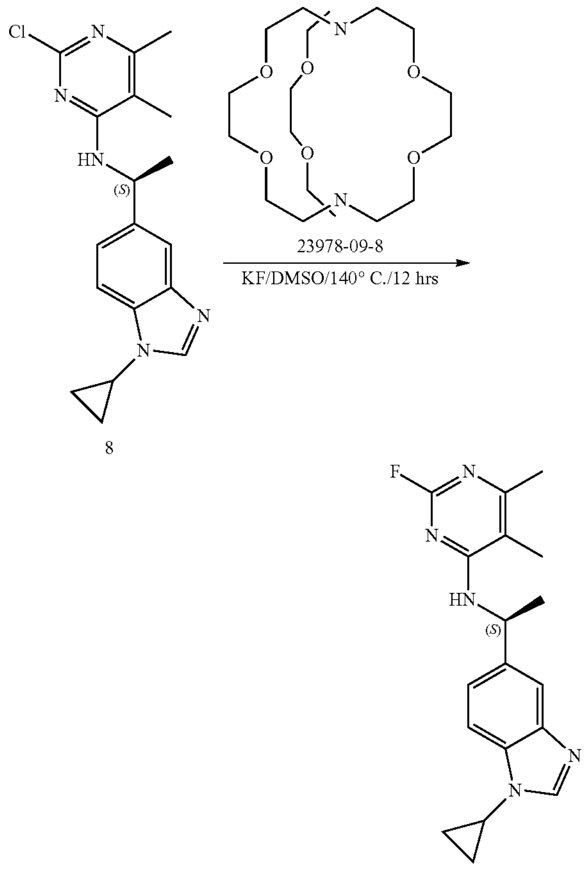

8

Bax-170 S

A mixture of 2-chloro-N-[(1S)-1-(1-cyclopropylbenzimidazol-5-yl)ethyl]-5,6-dimethyl-pyrimidin-4-amine (32 mg, 79.57 umol, 1 eq), KF (46.23 mg, 795.70 μmol, 18.64 μL, 10 eq) and 4,7,13,16,21,24-hexaoxa-1,10-diazabicyclo[8.8.8]hexacosane (44.94 mg, 119.36 umol, 1.5 eq) in DMSO (1 mL) was stirred at 140° C. for 12 hrs. The residue was purified by prep-HPLC (column: Waters Xbridge Prep OBD C18 150*40 mm*10 μm; mobile phase: [water (10 mM $NH_4HCO_3$)-ACN]; B %: 25%-40%, 8 min) to give N-[(1S)-1-(1-cyclopropylbenzimidazol-5-yl)ethyl]-2-fluoro-5,6-dimethyl-pyrimidin-4-amine (14 mg, 43.03 μmol, 54.07% yield, 100% purity) as a white solid. ESI [M+H]=326.3.

$^1$H NMR (400 MHz, CHLOROFORM-d) δ 7.94 (s, 1H), 7.78 (s, 1H), 7.55 (d, J=8.3 Hz, 1H), 7.37 (d, J=8.3 Hz, 1H), 5.51 (quin, J=7.0 Hz, 1H), 5.00 (d, J=6.8 Hz, 1H), 3.47-3.42 (m, 1H), 3.38 (tt, J=3.6, 6.9 Hz, 1H), 2.34 (s, 3H), 1.99 (s, 3H), 1.66 (d, J=6.7 Hz, 4H), 1.22-1.10 (m, 2H), 1.10-0.92 (m, 2H)

Example 73

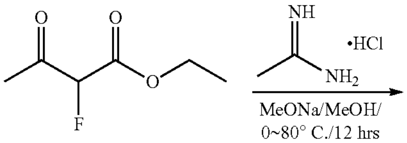

1A

-continued

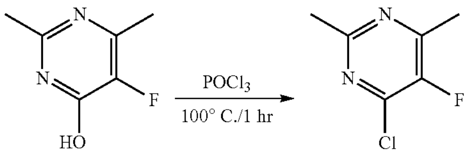

2A

3A

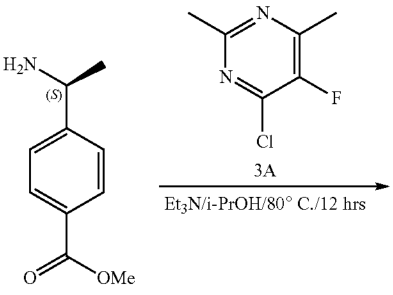

3A

1

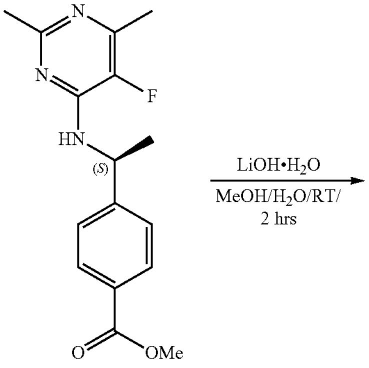

2

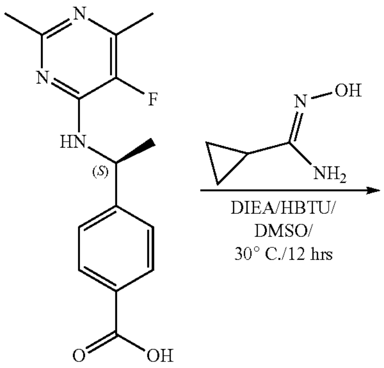

3

-continued

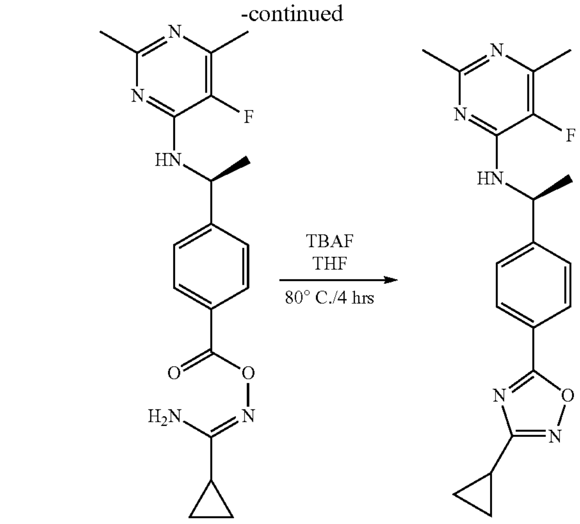

4

Bax-171 S

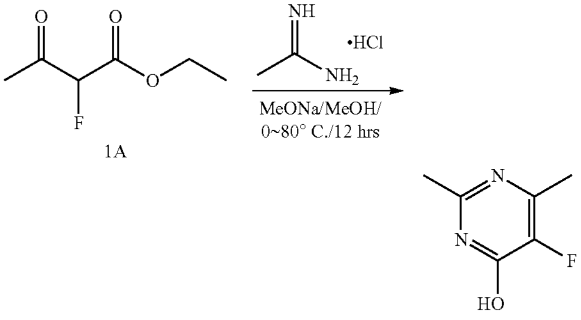

1A

2A

To a 0° C. stirred mixture of acetamidine; hydrochloride (3.51 g, 37.13 mmol, 1.1 eq) and NaOMe (5 M, 13.50 mL, 30% purity, 2 eq) (30% in MeOH) in MeOH (50 mL) was added ethyl 2-fluoro-3-oxo-butanoate (5 g, 33.75 mmol, 4.24 mL, 1 eq) dropwith. The resulting mixture was heated to 80° C. and stirred for 12 hrs. The reaction mixture was concentrated in vacuo. To the residue was added water (100 mL) and adjusted to pH=6 with 1N HCl, extracted with DCM/i-PrOH (3/1, 50 mL*10). The organic layer was dried over $Na_2SO_4$ and concentrated in vacuo to give 5-fluoro-2,6-dimethyl-pyrimidin-4-ol (3 g, 21.11 mmol, 62.53% yield) was obtained as a light brown solid. ESI [M+H]=143.1.

$^1H$ NMR (400 MHz, DMSO-d6) δ=12.76 (s, 1H), 2.23 (s, 3H), 2.15 (d, J=3.5 Hz, 3H)

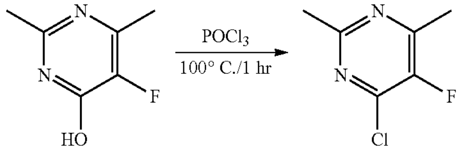

2A

3A

A solution of 5-fluoro-2,6-dimethyl-pyrimidin-4-ol (3 g, 21.11 mmol, 1 eq) in $POCl_3$ (60 mL) was stirred at 100° C. for 1 hr. The reaction mixture was concentrated under reduced pressure to give a residue. The residue was dissolved in DCM (20 mL), and basified to pH=7 by saturated aq·$Na_2CO_3$ solution, extracted with DCM (20 mL*3). The combined organic layers were washed with brine (20 mL*2), dried over $Na_2SO_4$, filtered and concentrated under reduced pressure to give 4-chloro-5-fluoro-2,6-dimethyl-pyrimidine (3 g, 18.68 mmol, 88.51% yield) was obtained as a brown oil. ESI [M+H]=161.0.

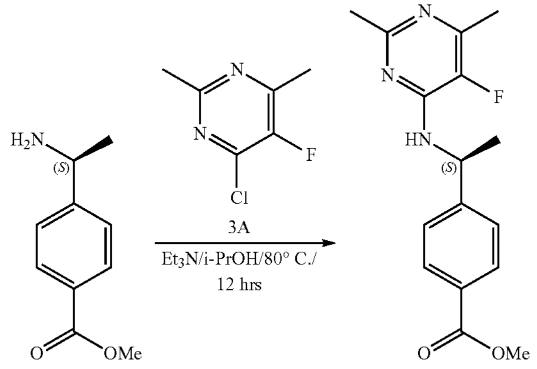

1

2

A mixture of methyl 4-[(1S)-1-aminoethyl]benzoate (300 mg, 1.67 mmol, 1 eq), 4-chloro-5-fluoro-2,6-dimethyl-pyrimidine (376.32 mg, 2.34 mmol, 1.4 eq) and $Et_3N$ (677.55 mg, 6.70 mmol, 931.98 uL, 4 eq) in i-PrOH (5 mL) was stirred at 80° C. for 12 hrs. The mixture was concentrated to give a residue. The residue was purified by prep-TLC ($SiO_2$, EtOAc, plate 1) to give methyl 4-[(1S)-1-[(5-fluoro-2,6-dimethyl-pyrimidin-4-yl)amino]ethyl]benzoate (330 mg, 1.09 mmol, 64.99% yield) was obtained as light yellow solid. ESI [M+H]=304.1.

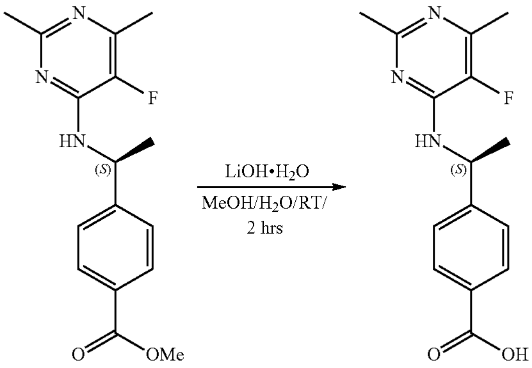

2

3

To a solution of methyl 4-[(1S)-1-[(5-fluoro-2,6-dimethyl-pyrimidin-4-yl)amino]ethyl]benzoate (330 mg, 1.09 mmol, 1 eq) in MeOH (10 mL) and $H_2O$ (3 mL) was added LiOH·$H_2O$ (136.96 mg, 3.26 mmol, 3 eq). The mixture was stirred at 25° C. for 2 hrs. To the solution was added $H_2O$ 10 mL, and then washed with MTBE (10 mL*2). The aqueous phase was adjusted with 1M HCl to pH 2-3 and then extracted with DCM:i-PrOH=3:1 (60 ml*5), dried over $Na_2SO_4$, filtered and concentrated under reduced pressure to give 4-(1S)-1-[(5-fluoro-2,6-dimethyl-pyrimidin-4-yl) amino]ethyl]benzoic acid (250 mg, 864.14 umol, 79.43% yield) was obtained as a white solid. ESI [M+H]=290.1.

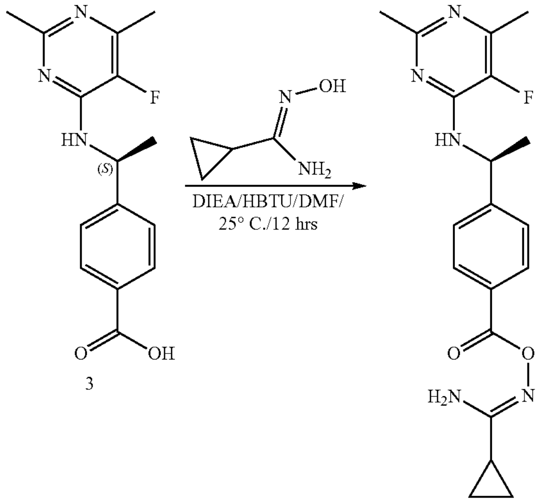

3

4

To a solution of 4-[(1S)-1-[(5-fluoro-2,6-dimethyl-pyrimidin-4-yl)amino]ethyl]benzoic acid (93 mg, 321.46 umol, 1 eq) in DMF (2.5 mL) was added N'-hydroxycyclopropanecarboxamidine (96.55 mg, 964.38 μmol, 3 eq), DIEA (124.64 mg, 964.38 umol, 167.98 uL, 3 eq) and HBTU (182.87 mg, 482.19 umol, 1.5 eq). The mixture was stirred at 25° C. for 12 hrs. The reaction mixture was diluted with $H_2O$ 10 mL and extracted with EtOAc 15 mL (5 mL*3). The combined organic layers were washed with brine 10 mL (5 mL*2), dried over $Na_2SO_4$, filtered and concentrated under reduced pressure to give [(Z)-[amino(cyclopropyl) methylene]amino] 4-[(1S)-1-[(5-fluoro-2,6-dimethyl-pyrimidin-4-yl)amino]ethyl]benzoate (360 mg, crude) was obtained as a brown oil. ESI [M+H]=372.1.

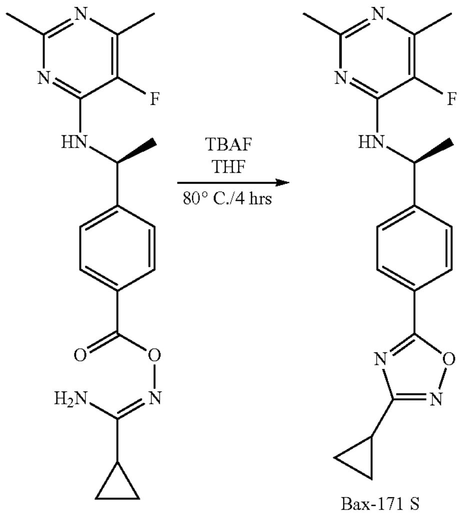

4

Bax-171 S

A mixture of [(Z)-[amino(cyclopropyl)methylene]amino] 4-[(1S)-1-[(5-fluoro-2,6-dimethyl-pyrimidin-4-yl)amino] ethyl]benzoate (360 mg, 969.28 μmol, 1 eq), TBAF (1 M, 3.88 mL, 4 eq), in THF (5 mL), and then the mixture was stirred at 80° C. for 4 hrs. The reaction mixture was concentrated under reduced pressure to give a residue. The residue was purified by prep-TLC (PE:EtOAc=0:1) to remove TBAF. Then the residue was purified by prep-HPLC (column: Nano-micro Kromasil C18 100*40 mm 3 um; mobile phase: [water (0.1% TFA)-ACN]; B %: 23%-53%, 8 min) to give N-[(1S)-1-[4-(3-cyclopropyl-1,2,4-oxadiazol-5-yl)phenyl]ethyl]-5-fluoro-2,6-dimethyl-pyrimidin-4-amine (52.35 mg, 146.65 umol, 15.13% yield, 99% purity) was obtained as white solid. ESI [M+H]=354.2.

$^1H$ NMR (400 MHz, DMSO-d6) δ 9.48 (s, 1H), 8.01 (d, J=8.2 Hz, 2H), 7.61 (d, J=8.2 Hz, 2H), 5.54-5.43 (m, 1H), 2.40 (s, 3H), 2.32 (d, J=2.4 Hz, 3H), 2.21-2.10 (m, 1H), 1.56 (d, J=7.1 Hz, 3H), 1.19-1.03 (m, 2H1), 0.97-0.89 (m, 2H1).

Example 74

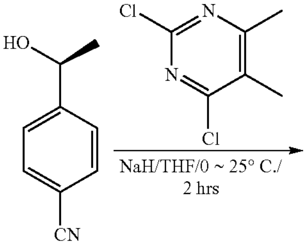

1

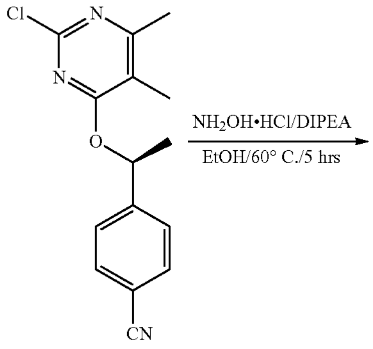

2

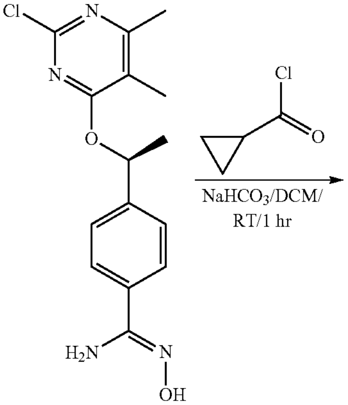

3

-continued

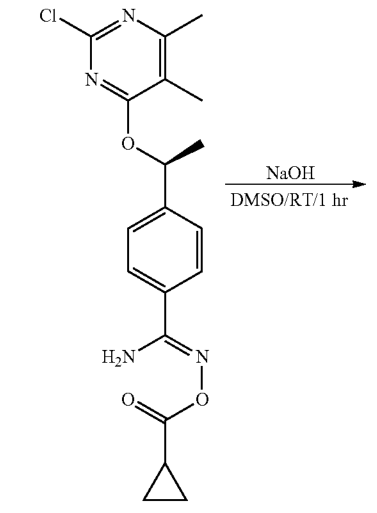

4

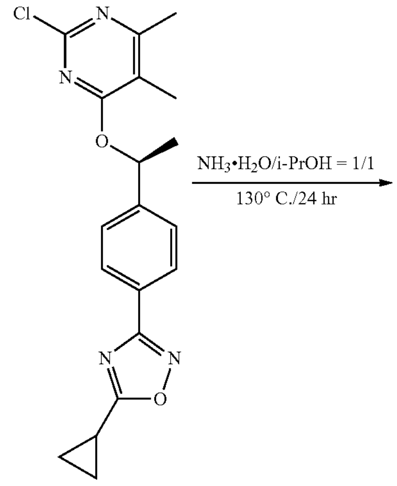

5

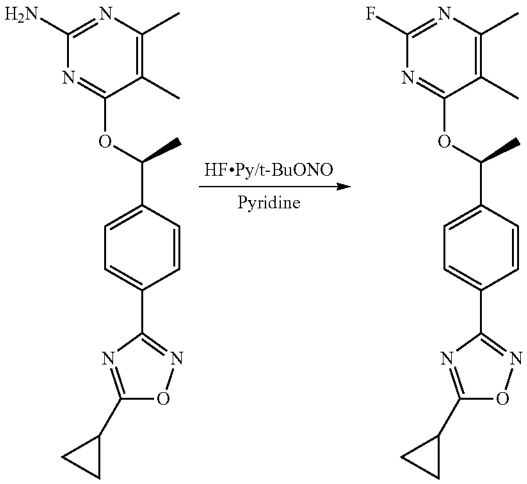

6

Bax-172 S

-continued

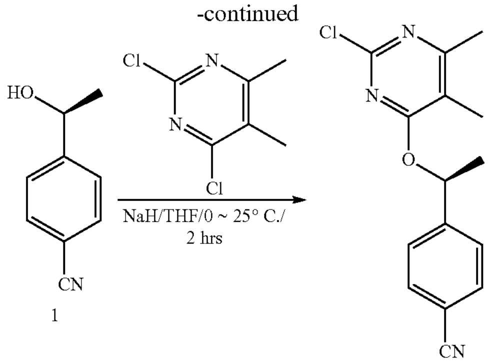

1

2

To a 0° C. mixture of 4-[(1S)-1-hydroxyethyl]benzonitrile (500 mg, 3.40 mmol, 1 eq) and 2,4-dichloro-5,6-dimethyl-pyrimidine (601.44 mg, 3.40 mmol, 1 eq) in THF (15 mL) was added NaH (271.76 mg, 6.79 mmol, 60% purity, 2 eq), and then the mixture was stirred at 25° C. for 2 hrs. The mixture was quenched by addition saturated aq·$NH_4Cl$ (30 mL) and extracted with EtOAc (20 mL*3). The combined organic phase was washed with brine (10 mL*2), dried over $Na_2SO_4$, filtered and concentrated in vacuum to give 4-[(1S)-1-(2-chloro-5,6-dimethyl-pyrimidin-4-yl)oxyethyl] benzonitrile (1.12 g, crude) was obtained as a yellow oil. ESI [M+H]=288.1.

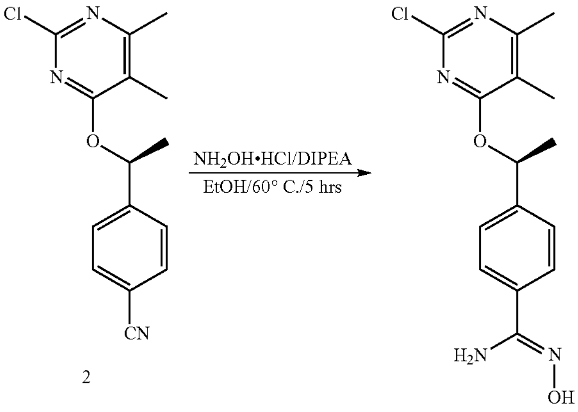

2

3

A mixture of 4-[(1S)-1-(2-chloro-5,6-dimethyl-pyrimidin-4-yl)oxyethyl]benzonitrile (1.1 g, 3.82 mmol, 1 eq), $NH_2OH{\cdot}HCl$ (1.06 g, 15.29 mmol, 4 eq), DIPEA (2.47 g, 19.11 mmol, 3.33 mL, 5 eq) in EtOH (10 mL), and then the mixture was stirred a 60° C. for 5 hrs. The reaction mixture was concentrated under reduced pressure to remove EtOH. The residue was diluted with $H_2O$ (30 mL) and extracted with EtOAc/THF (5:1, 20 mL*3). The combined organic layers were washed with brine (15 mL*2), dried over $Na_2SO_4$, filtered and concentrated under reduced pressure to give a residue to give 4-[(1S)-1-(2-chloro-5,6-dimethyl-pyrimidin-4-yl)oxyethyl]-N'-hydroxy-benzamidine (1.18 g, 3.68 mmol, 96.23% yield) was obtained as a yellow gum. ESI [M+H]=321.0.

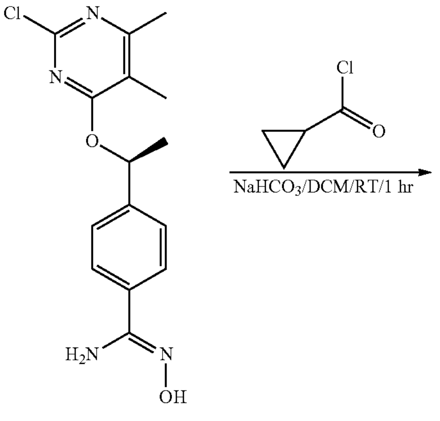

3

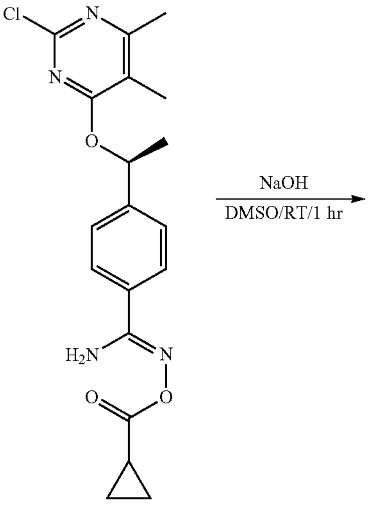

4

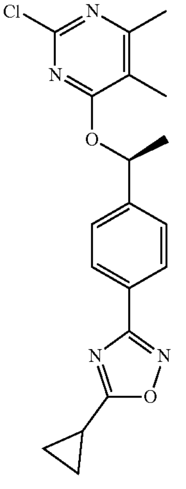

5

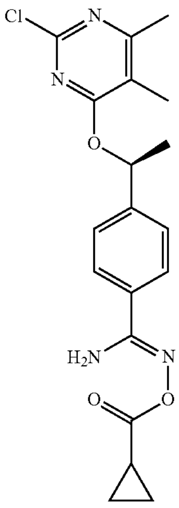

4

To a solution of 4-[(1S)-1-(2-chloro-5,6-dimethyl-pyrimidin-4-yl)oxyethyl]-N'-hydroxy-benz amidine (1.18 g, 3.68 mmol, 1 eq) in DCM (10 mL) was added $NaHCO_3$ (618.05 mg, 7.36 mmol, 286.14 uL, 2 eq) and cyclopropanecarbonyl chloride (461.45 mg, 4.41 mmol, 401.26 μL, 1.2 eq). The mixture was stirred at 25° C. for 1 hr. The reaction mixture was concentrated under reduced pressure to remove DCM. The residue was diluted with $H_2O$ (30 mL) and extracted with DCM/isopropyl alcohol (4:1, 20 mL*3). The combined organic layers were dried over $Na_2SO_4$, filtered and concentrated under reduced pressure to give a residue to give [(Z)-[amino-[4-[(1S)-1-(2-chloro-5,6-dimethyl-pyrimidin-4-yl)oxyethyl]phenyl]methylene]amino]cyclopropanecarboxylate (1.36 g, 3.50 mmol, 95.08% yield) was obtained as a yellow gum. ESI [M+H]=389.1.

A mixture of [(Z)-[amino-[4-[(1S)-1-(2-chloro-5,6-dimethyl-pyrimidin-4-yl)oxyethyl]phenyl]methylene]amino] cyclopropanecarboxylate (1.36 g, 3.50 mmol, 1 eq) and NaOH (139.89 mg, 3.50 mmol, 1 eq) in DMSO (10 mL), and then the mixture was stirred at 25° C. for 1 hr. The reaction mixture was diluted with $H_2O$ (15 mL) and extracted with EtOAc (10 mL*3). The combined organic layers were washed with brine (10 mL*2), dried over $Na_2SO_4$, filtered and concentrated under reduced pressure to give a residue. The residue was purified by prep-HPLC (column: Kromasil C18 (250*50 mm*10 μm); mobile phase: [water (10 mM $NH_4HCO_3$)-ACN]; B %: 60%-90%, 10 min) to give 3-[4-[(1S)-1-(2-chloro-5,6-dimethyl-pyrimidin-4-yl)oxyethyl] phenyl]-5-cyclopropyl-1,2,4-oxadiazole (450 mg, 1.21 mmol, 34.70% yield) was obtained as a brown gum. ESI [M+H]=371.1.

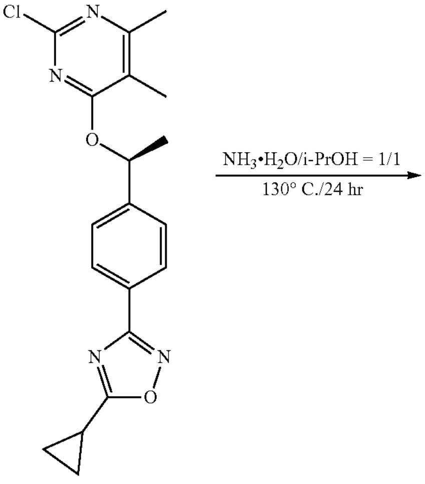

5

-continued

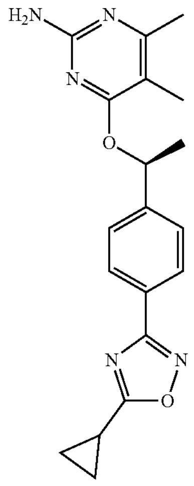

6

A solution of 3-[4-[(1S)-1-(2-chloro-5,6-dimethyl-pyrimidin-4-yl)oxyethyl]phenyl]-5-cyclopropyl-1,2,4-oxadiazole (200 mg, 539.33 μmol, 1 eq) in i-PrOH (3 mL) saturated with $NH_3 \cdot H_2O$ (2.73 g, 19.47 mmol, 3 mL, 25% purity, 36.11 eq) was stirred at 130° C. for 24 hrs in a 30 mL of autoclave. The reaction mixture was concentrated under reduced pressure to give a residue. The residue was purified by prep-HPLC (column: Waters Xbridge BEH C18 100*30 mm*10 μm; mobile phase: [water (10 mM $NH_4HCO_3$)-ACN]; B %: 40%-70%, 8 min) to give 4-[(1S)-1-[4-(5-cyclopropyl-1,2,4-oxadiazol-3-yl)phenyl]ethoxy]-5,6-dimethyl-pyrimidin-2-amine (60 mg, 170.74 umol, 31.66% yield) was obtained as a white solid. ESI [M+H]=352.2.

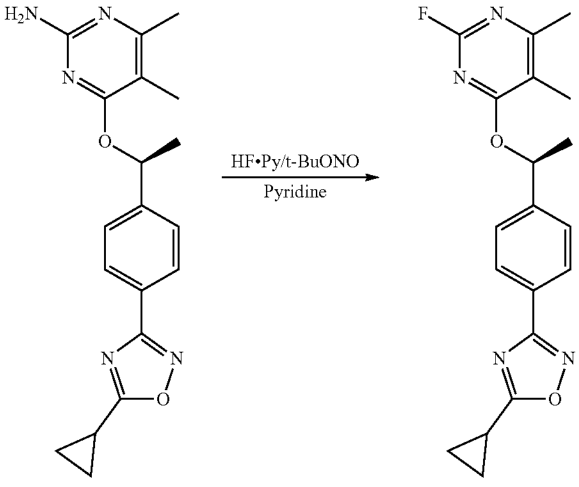

6 Bax-172 S

To a solution of 4-[(1S)-1-[4-(5-cyclopropyl-1,2,4-oxadiazol-3-yl)phenyl]ethoxy]-5,6-dimethyl-pyrimidin-2-amine (40 mg, 113.83 μmol, 1 eq) in Py (0.5 mL) was added pyridine; hydrofluoride (1.10 g, 11.10 mmol, 1 mL, 97.51 eq) at −50° C., the mixture was stirred at −25° C. for 15 min. Then tert-butyl nitrite (23.48 mg, 227.66 umol, 27.08 uL, 2 eq) was added at −25° C. The mixture was stirred at 15° C. for 1 hr. Cold water (15 mL) was added, then the reaction mixture was adjusted to pH=8 with saturated aq.$NaHCO_3$ and extracted with DCM (15 mL*4). The combined organic layers were dried over drying $Na_2SO_4$, filtered and concentrated under reduced pressure to give a residue. The residue was purified by prep-HPLC (column: Waters Xbridge BEH C18 100*25 mm*5 μm; mobile phase: [water (10 mM $NH_4HCO_3$)-ACN]; B %: 50%-85%, 10 min) to give 5-cyclopropyl-3-[4-[(1S)-1-(2-fluoro-5,6-dimethyl-pyrimidin-4-yl)oxyethyl]phenyl]-1,2,4-oxadiazole (3.88 mg, 10.63 umol, 9.34% yield, 97.12% purity) was obtained as yellow gum. ESI [M+H]=355.2.

1H NMR (400 MHz, METHANOL-d4) δ 7.99 (d, J=8.2 Hz, 2H), 7.56 (d, J=8.4 Hz, 2H), 6.26 (q, J=6.4 Hz, 1H), 2.39 (s, 3H), 2.35-2.26 (m, 1H), 2.19 (s, 3H), 1.68 (d, J=6.6 Hz, 3H), 1.43-1.07 (m, 4H).

Example 75

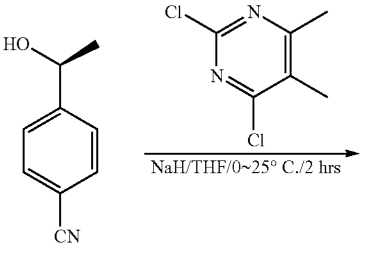

1

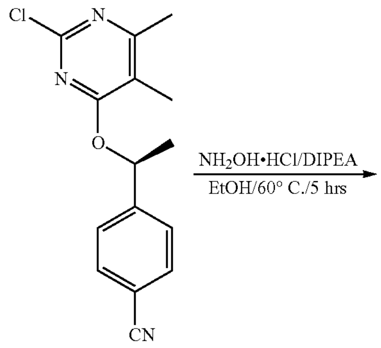

2

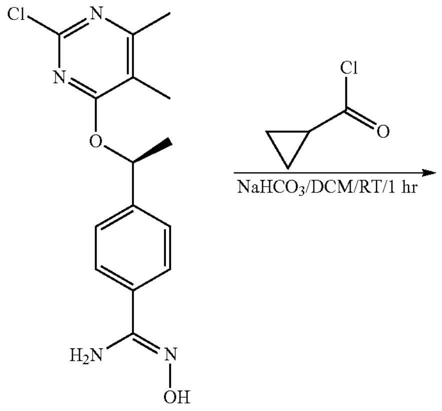

3

-continued

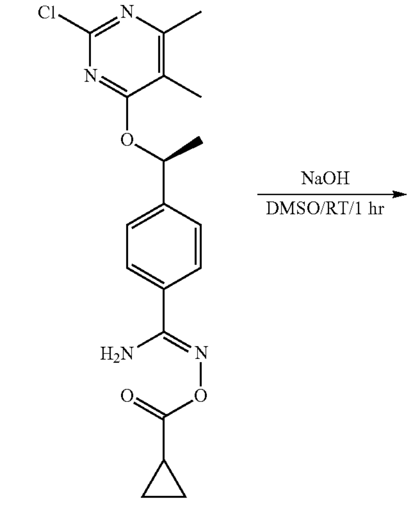

4

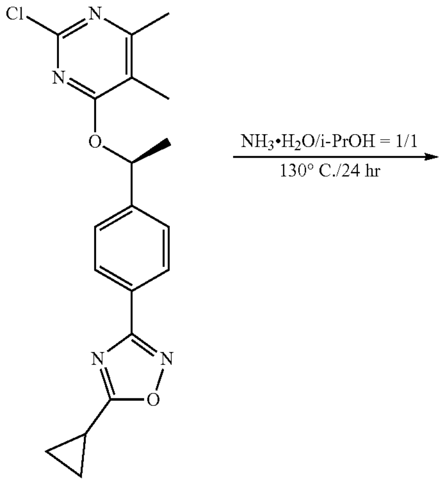

5

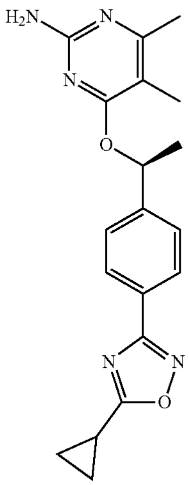

Bax-172 S_A

-continued

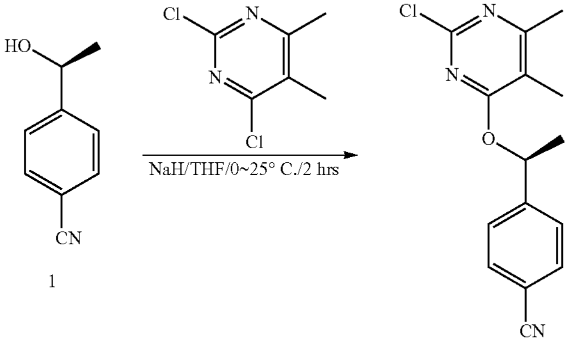

1

2

To a 0° C. mixture of 4-[(1S)-1-hydroxyethyl]benzonitrile (500 mg, 3.40 mmol, 1 eq) and 2,4-dichloro-5,6-dimethyl-pyrimidine (601.44 mg, 3.40 mmol, 1 eq) in THF (15 mL) was added NaH (271.76 mg, 6.79 mmol, 60% purity, 2 eq), and then the mixture was stirred at 25° C. for 2 hrs. The mixture was quenched by addition saturated aq·$NH_4Cl$ (30 mL) and extracted with EtOAc (20 mL*3). The combined organic phase was washed with brine (10 mL*2), dried over $Na_2SO_4$, filtered and concentrated in vacuum to give 4-[(1S)-1-(2-chloro-5,6-dimethyl-pyrimidin-4-yl)oxyethyl] benzonitrile (1.12 g, crude) was obtained as a yellow oil. ESI [M+H]=288.1.

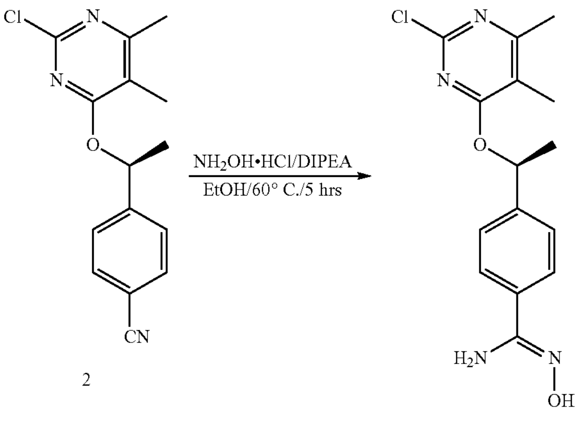

2

3

A mixture of 4-[(1S)-1-(2-chloro-5,6-dimethyl-pyrimidin-4-yl)oxyethyl]benzonitrile (1.1 g, 3.82 mmol, 1 eq), $NH_2OH$·HCl (1.06 g, 15.29 mmol, 4 eq), DIPEA (2.47 g, 19.11 mmol, 3.33 mL, 5 eq) in EtOH (10 mL), and then the mixture was stirred at 60° C. for 5 hrs. The reaction mixture was concentrated under reduced pressure to remove EtOH. The residue was diluted with $H_2O$ (30 mL) and extracted with EtOAc/THF (5:1, 20 mL*3). The combined organic layers were washed with brine (15 mL*2), dried over $Na_2SO_4$, filtered and concentrated under reduced pressure to give a residue to give 4-[(1S)-1-(2-chloro-5,6-dimethyl-pyrimidin-4-yl)oxyethyl]-N'-hydroxy-benzamidine (1.18 g, 3.68 mmol, 96.23% yield) was obtained as a yellow gum. ESI [M+H]=321.0.

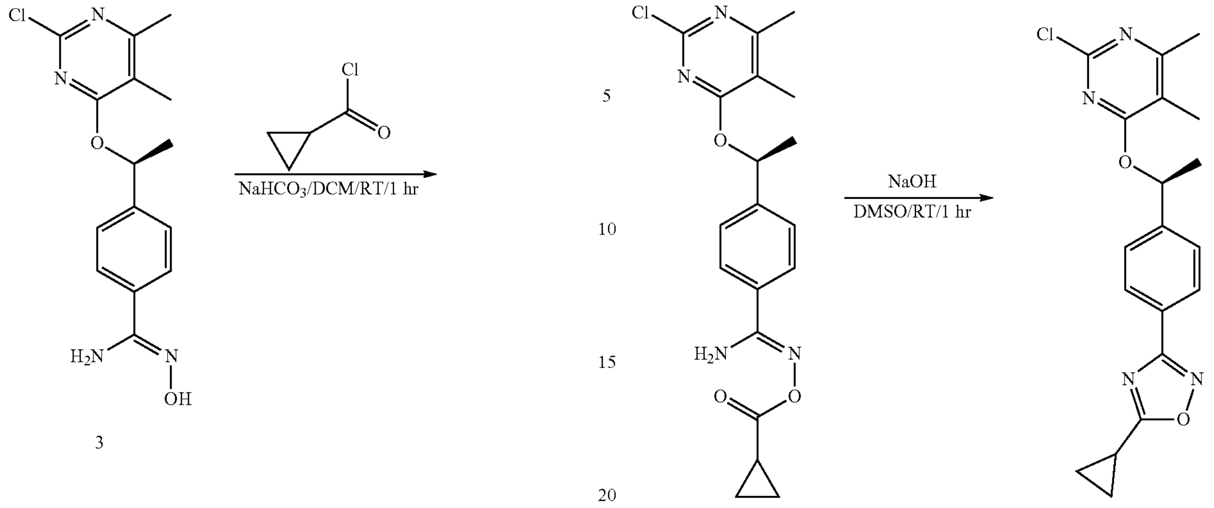

3 4 5

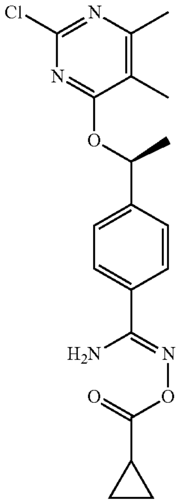

4

To a solution of 4-[(1S)-1-(2-chloro-5,6-dimethyl-pyrimidin-4-yl)oxyethyl]-N'-hydroxy-benz amidine (1.18 g, 3.68 mmol, 1 eq) in DCM (10 mL) was added $NaHCO_3$ (618.05 mg, 7.36 mmol, 286.14 uL, 2 eq) and cyclopropanecarbonyl chloride (461.45 mg, 4.41 mmol, 401.26 uL, 1.2 eq). The mixture was stirred at 25° C. for 1 hr. The reaction mixture was concentrated under reduced pressure to remove DCM. The residue was diluted with $H_2O$ (30 mL) and extracted with DCM/isopropyl alcohol (4:1, 20 mL*3). The combined organic layers were dried over $Na_2SO_4$, filtered and concentrated under reduced pressure to give a residue to give [(Z)-[amino-[4-[(1S)-1-(2-chloro-5,6-dimethyl-pyrimidin-4-yl)oxyethyl]phenyl]methylene]amino]cyclopropanecarboxylate (1.36 g, 3.50 mmol, 95.08% yield) was obtained as a yellow gum. ESI [M+H]=389.1.

A mixture of [(Z)-[amino-[4-[(1S)-1-(2-chloro-5,6-dimethyl-pyrimidin-4-yl)oxyethyl]phenyl]methylene]amino] cyclopropanecarboxylate (1.36 g, 3.50 mmol, 1 eq) and NaOH (139.89 mg, 3.50 mmol, 1 eq) in DMSO (10 mL), and then the mixture was stirred at 25° C. for 1 hr. The reaction mixture was diluted with $H_2O$ (15 mL) and extracted with EtOAc (10 mL*3). The combined organic layers were washed with brine (10 mL*2), dried over $Na_2SO_4$, filtered and concentrated under reduced pressure to give a residue. The residue was purified by prep-HPLC (column: Kromasil C18 (250*50 mm*10 μm); mobile phase: [water (10 mM $NH_4HCO_3$)-ACN]; B %: 60%-90%, 10 min) to give 3-[4-[(1S)-1-(2-chloro-5,6-dimethyl-pyrimidin-4-yl)oxyethyl] phenyl]-5-cyclopropyl-1,2,4-oxadiazole (450 mg, 1.21 mmol, 34.70% yield) was obtained as a brown gum. ESI [M+H]=371.1.

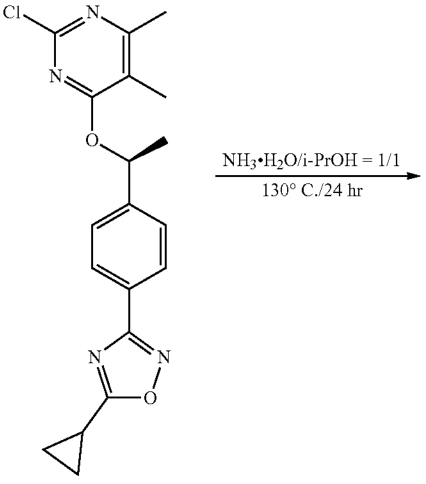

5

-continued

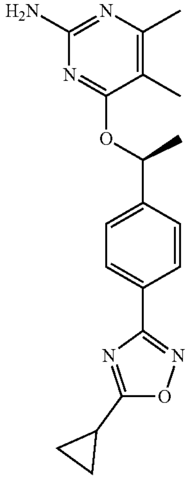

Bax-172S_A

A solution of 3-[4-[(1S)-1-(2-chloro-5,6-dimethyl-pyrimidin-4-yl)oxyethyl]phenyl]-5-cyclopropyl-1,2,4-oxadiazole (200 mg, 539.33 μmol, 1 eq) in i-PrOH (3 mL) saturated with $NH_3 \cdot H_2O$ (2.73 g, 19.47 mmol, 3 mL, 25% purity, 36.11 eq) was stirred at 130° C. for 24 hrs in a 30 mL of autoclave. The reaction mixture was concentrated under reduced pressure to give a residue. The residue was purified by prep-HPLC (column: Waters Xbridge BEH C18 100*30 mm*10 μm; mobile phase: [water (10 mM $NH_4HCO_3$)-ACN]; B %: 40%-70%, 8 min) to give 4-[(1S)-1-[4-(5-cyclopropyl-1,2,4-oxadiazol-3-yl)phenyl]ethoxy]-5,6-dimethyl-pyrimidin-2-amine (60 mg, 170.74 μmol, 31.66% yield) was obtained as a white solid. ESI [M+H]=352.2.

$^1$H NMR (400 MHz, DMSO-d6) δ 7.95 (d, J=7.9 Hz, 2H), 7.57 (d, J=7.9 Hz, 2H), 6.23 (q, J=6.2 Hz, 1H), 6.08 (s, 2H), 5.76 (s, 1H), 2.16 (s, 3H), 1.98 (s, 3H), 1.57 (d, J=6.4 Hz, 3H1), 1.33-1.13 (m, 4H).

Example 76

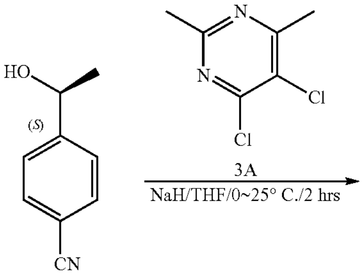

1

-continued

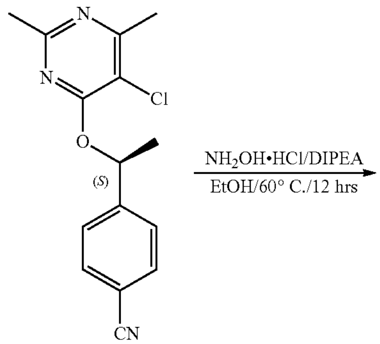

2

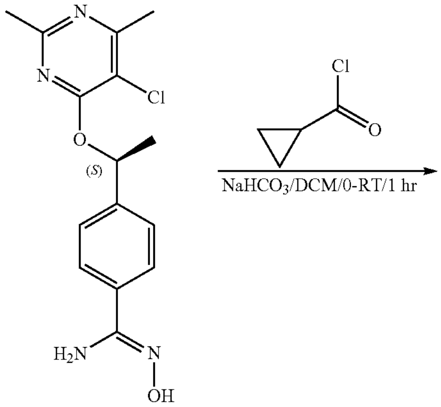

3

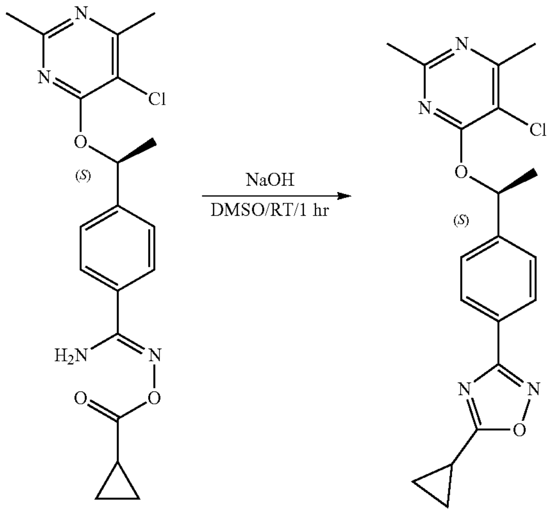

4

Bax-173 S

-continued

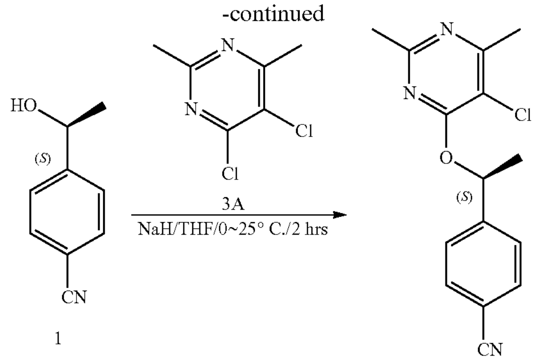

1

2

To a 0° C. stirred mixture of 4-[(1S)-1-hydroxyethyl]benzonitrile (500 mg, 3.40 mmol, 1 eq) and 4,5-dichloro-2,6-dimethyl-pyrimidine (721.72 mg, 4.08 mmol, 1.2 eq) in THF (15 mL) was added NaH (271.76 mg, 6.79 mmol, 60% purity, 2 eq), then the mixture was stirred at 25° C. for 2 hrs. The reaction mixture was quenched by saturated aq·$NH_4Cl$ (30 mL) and extracted with EtOAc (20 mL*3). The combined organic layers were washed with brine (10 mL*2), dried over $Na_2SO_4$, filtered and concentrated under reduced pressure to give 4-[(1S)-1-(5-chloro-2,6-dimethyl-pyrimidin-4-yl)oxyethyl]benzonitrile (1.2 g, 3.04 mmol, 89.61% yield, 73% purity) as a yellow oil. ESI [M+H and M+3H]=288.0 and 290.0.

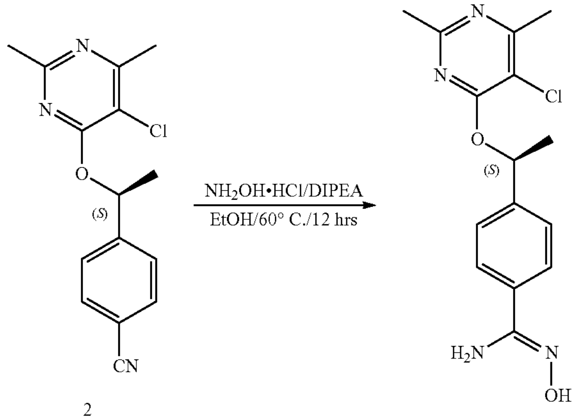

2

3

A mixture of 4-[(1S)-1-(5-chloro-2,6-dimethyl-pyrimidin-4-yl)oxyethyl]benzonitrile (300 mg, 761.09 umol, 1 eq), $NH_2OH$·HCl (211.56 mg, 3.04 mmol, 4 eq) and DIPEA (491.83 mg, 3.81 mmol, 662.84 μL, 5 eq) in EtOH (10 mL) was stirred at 60° C. for 12 hrs. The reaction mixture was concentrated under reduced pressure to remove EtOH. The residue was diluted with $H_2O$ (20 mL) and extracted with EtOAc/THF (5:1, 20 mL*3). The combined organic layers were washed with brine (20 mL*2), dried over $Na_2SO_4$, filtered and concentrated under reduced pressure to give 4-[(1S)-1-(5-chloro-2,6-dimethyl-pyrimidin-4-yl)oxyethyl]-N'-hydroxy-benzamidine (275 mg, 747.57 umol, 98.22% yield, 87.2% purity) as a yellow gum. ESI [M+H and M+3H]=321.0 and 323.0.

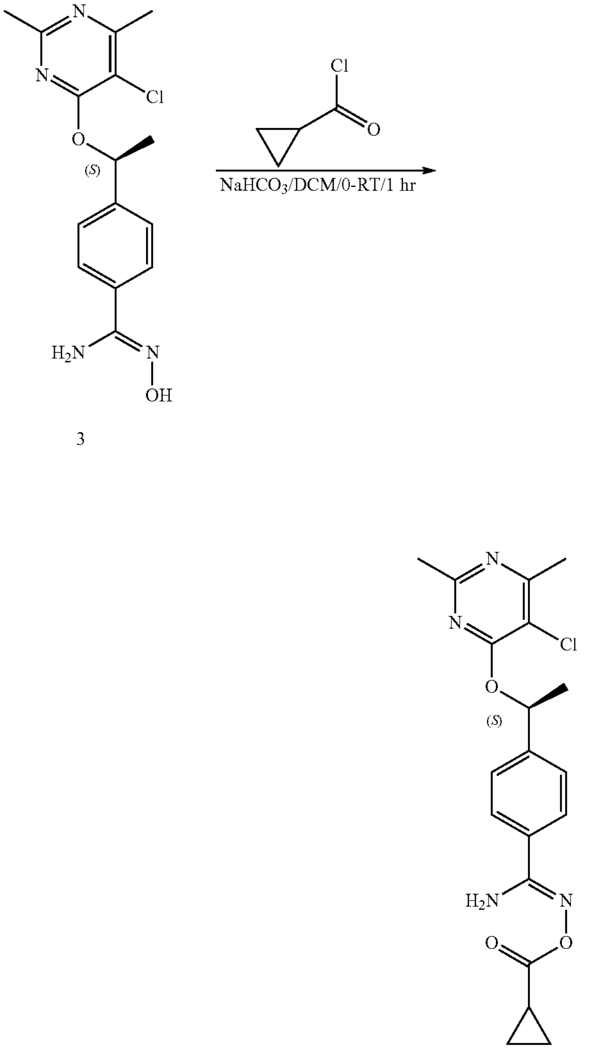

3

4

To a 0° C. stirred mixture of 4-[(1S)-1-(5-chloro-2,6-dimethyl-pyrimidin-4-yl)oxyethyl]-N'-hydroxy-benzamidine (255 mg, 693.20 umol, 1 eq) and $NaHCO_3$ (116.47 mg, 1.39 mmol, 53.92 uL, 2 eq) in DCM (10 mL) was added cyclopropanecarbonyl chloride (86.96 mg, 831.84 umol, 75.61 uL, 1.2 eq) in DCM (1 mL) dropwise. The mixture was stirred at 20° C. for 1 hr. The reaction mixture was concentrated under reduced pressure to remove DCM. The residue was diluted with $H_2O$ (10 mL) and extracted with DCM/i-PrOH (4:1, 10 mL*3). The combined organic layers were dried over $Na_2SO_4$, filtered and concentrated under reduced pressure to give [(Z)-[amino-[4-[(1S)-1-(5-chloro-2,6-dimethyl-pyrimidin-4-yl)oxyethyl]phenyl]methylene]amino]cyclopropanecarboxylate (250 mg, 642.93 μmol, 92.75% yield) as a yellow gum. ESI [M+H and M+3H]=389.1 and 391.1.

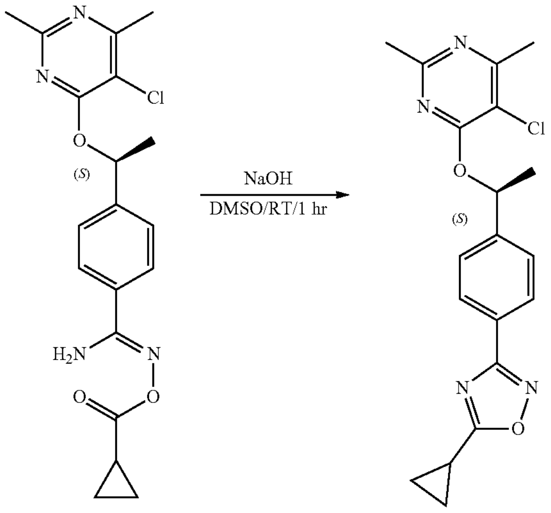

4

Bax-173 S

A mixture of [(Z)-[amino-[4-[(1S)-1-(5-chloro-2,6-dimethyl-pyrimidin-4-yl)oxyethyl]phenyl]-methylene]amino] cyclopropanecarboxylate (100 mg, 257.17 μmol, 1 eq) and NaOH (10.29 mg, 257.17 μmol, 1 eq) in DMSO (8 mL) was stirred at 25° C. for 1 hr. The reaction mixture was diluted with $H_2O$ (5 mL) and extracted with EtOAc (15 mL*3). The combined organic layers were washed with brine (15 mL*2), dried over $Na_2SO_4$, filtered and concentrated under reduced pressure to give a residue. The residue was purified by prep-HPLC (column: Waters Xbridge BEH C18 100*30 mm*10 um; mobile phase: [water (10 mM $NH_4HCO_3$)-ACN]; B %: 65%-95%, 8 min) to give 3-[4-[(1S)-1-(5-chloro-2,6-dimethyl-pyrimidin-4-yl)oxyethyl]phenyl]-5-cyclopropyl-1,2,4-oxadiazole (29.9 mg, 80.63 μmol, 31.35% yield, 100% purity) as a yellow gum. ESI [M+H and M+3H]=371.0 and 373.0.

$^1$H-NMR (400 MHz, CHLOROFORM-d) δ 8.02 (d, J=8.3 Hz, 2H), 7.54 (d, J=8.4 Hz, 2H), 6.34 (q, J=6.5 Hz, 1H), 2.49 (d, J=4.3 Hz, 6H), 2.32-2.12 (m, 1H), 1.69 (d, J=6.6 Hz, 3H1), 1.38-1.17 (m, 4H1).

Example 77

FIG. 1 is a graph illustrating Bax inhibiting compounds described herein (i.e., Bax41S (BBI5/6 analog) and Bax-11 (BBI7 analog)) protected Mouse Embryonic Fibroblasts (MEFs) from Bax-induced cell death at the concentration of 1 and 10 nM, respectively. Bax inhibitors reported by others (DAN004, Compound 22, Inception Bax inhibitor, iMAC2) require at least 200 nM to show protective activities.

Figure 2:
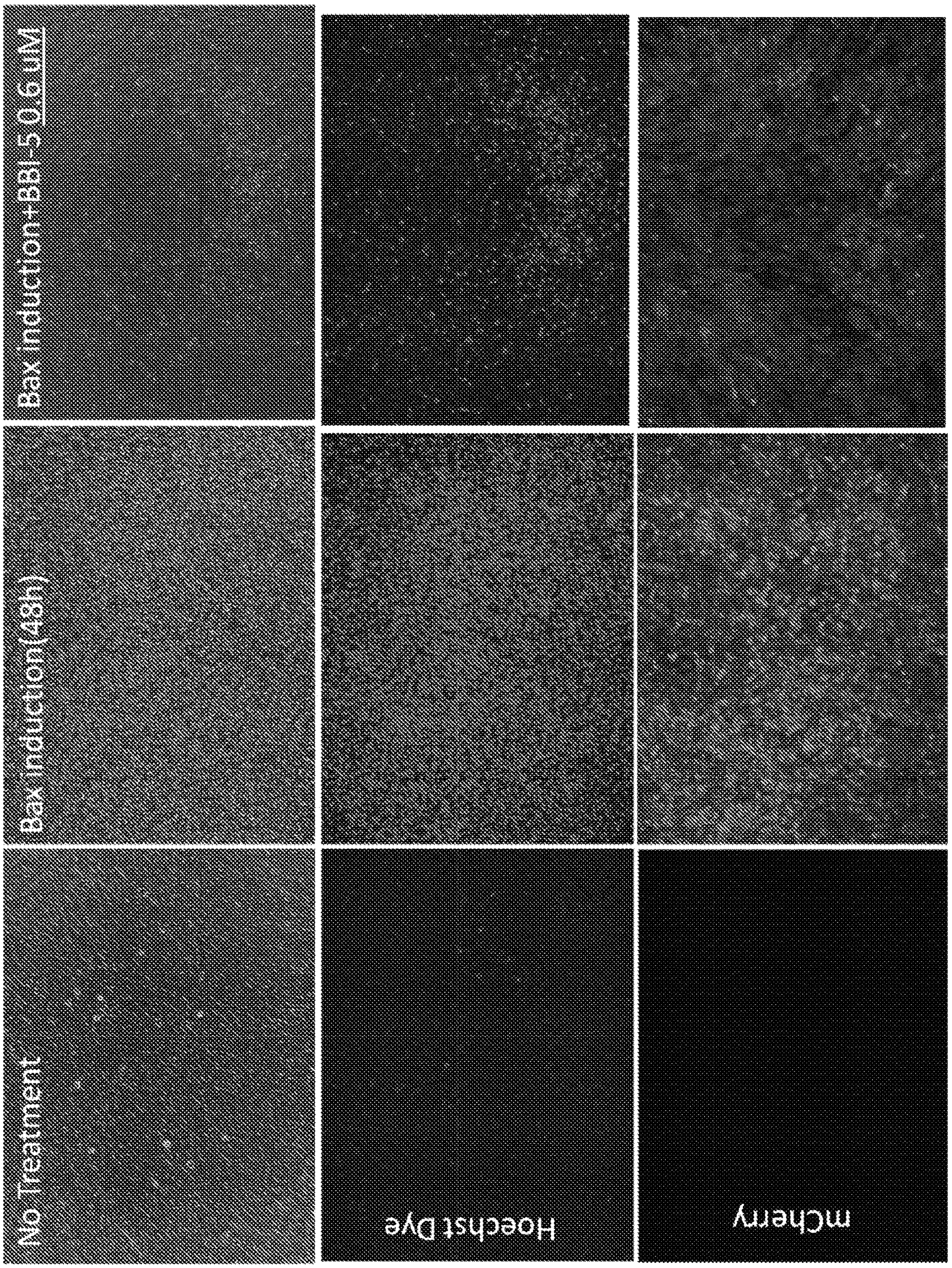
FIG. 2 illustrates images showing a Bax inhibiting compound described herein protected mouse embryonic fibroblast (MEF) cells from Bax induced cell death.

FIG. 2 illustrates images showing a Bax inhibiting compound described herein protected mouse embryonic fibroblast (MEF) cells from Bax induced cell death.

Figure 3:
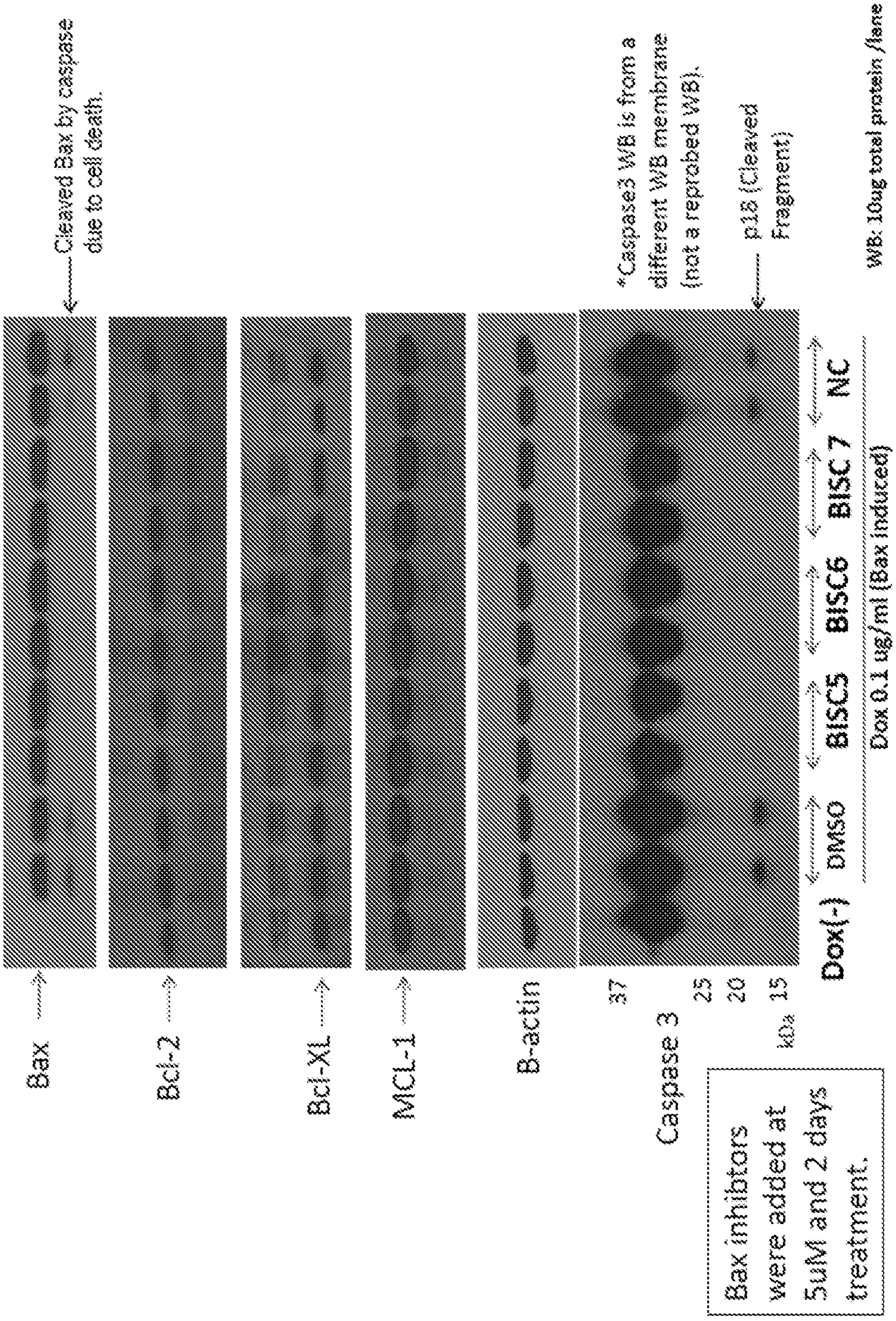
FIG. 3 illustrates images showing a Bax inhibiting compound described herein inhibited Bax-induced apoptosis without significant impact on expression levels of Bax, Bcl-2, Bcl-XL and Mcl-1.

FIG. 3 illustrates images showing a Bax inhibiting compound described herein inhibited Bax-induced apoptosis without significant impact on expression levels of Bax, Bcl-2, Bcl-XL and Mcl-1.

Figure 4A:
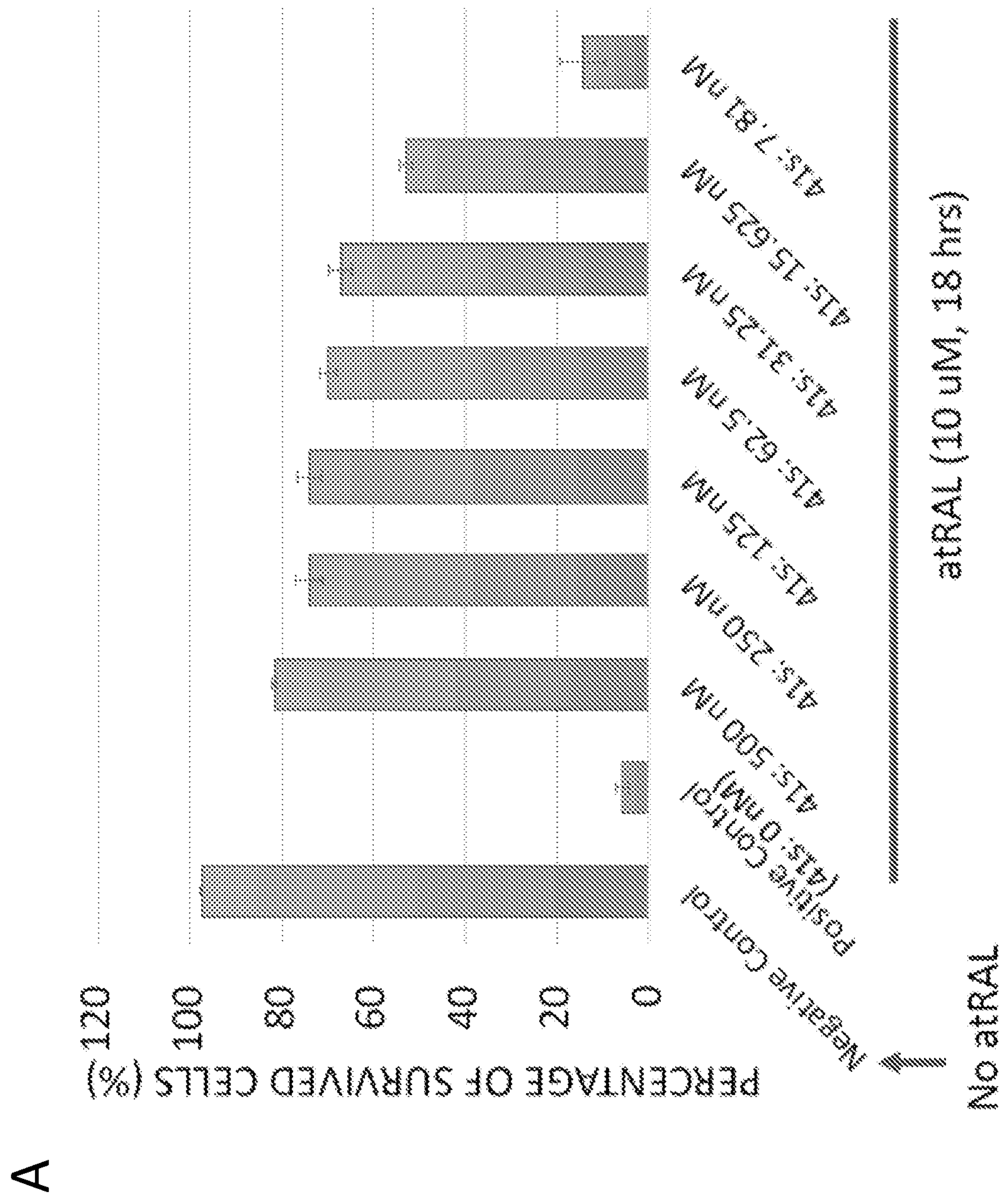
FIG. 4 illustrates the results showing Bax inhibiting compound described herein protected ARPE19 (Human Retinal cells) cells from atRAL induced cell death (FIG. 4A) and mouse retina from the bright light-induced cell death in vivo (Stargadrdt's disease mouse model) (FIG. 4B,C).
Figure 4B:
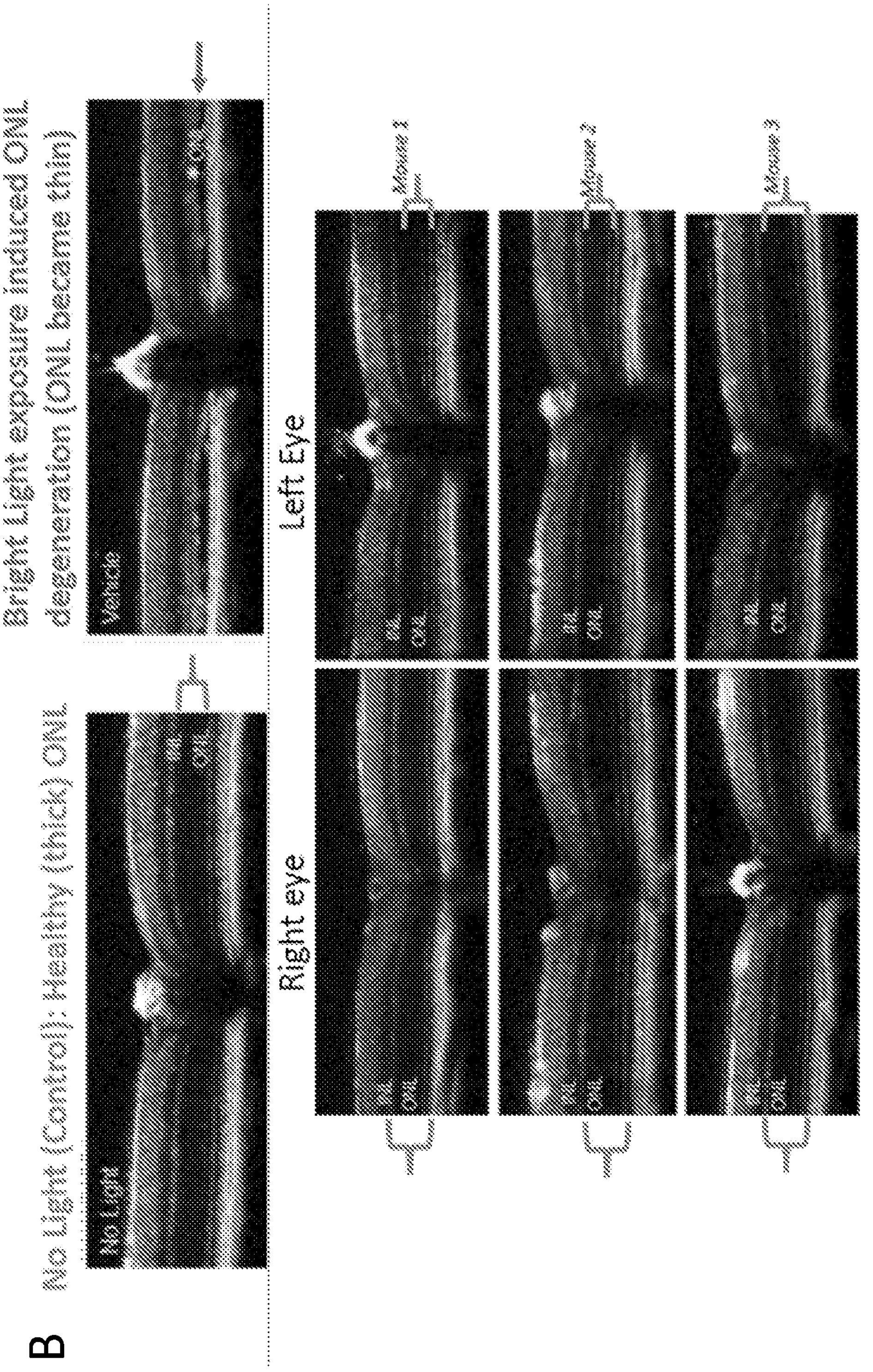
Figure 4C:
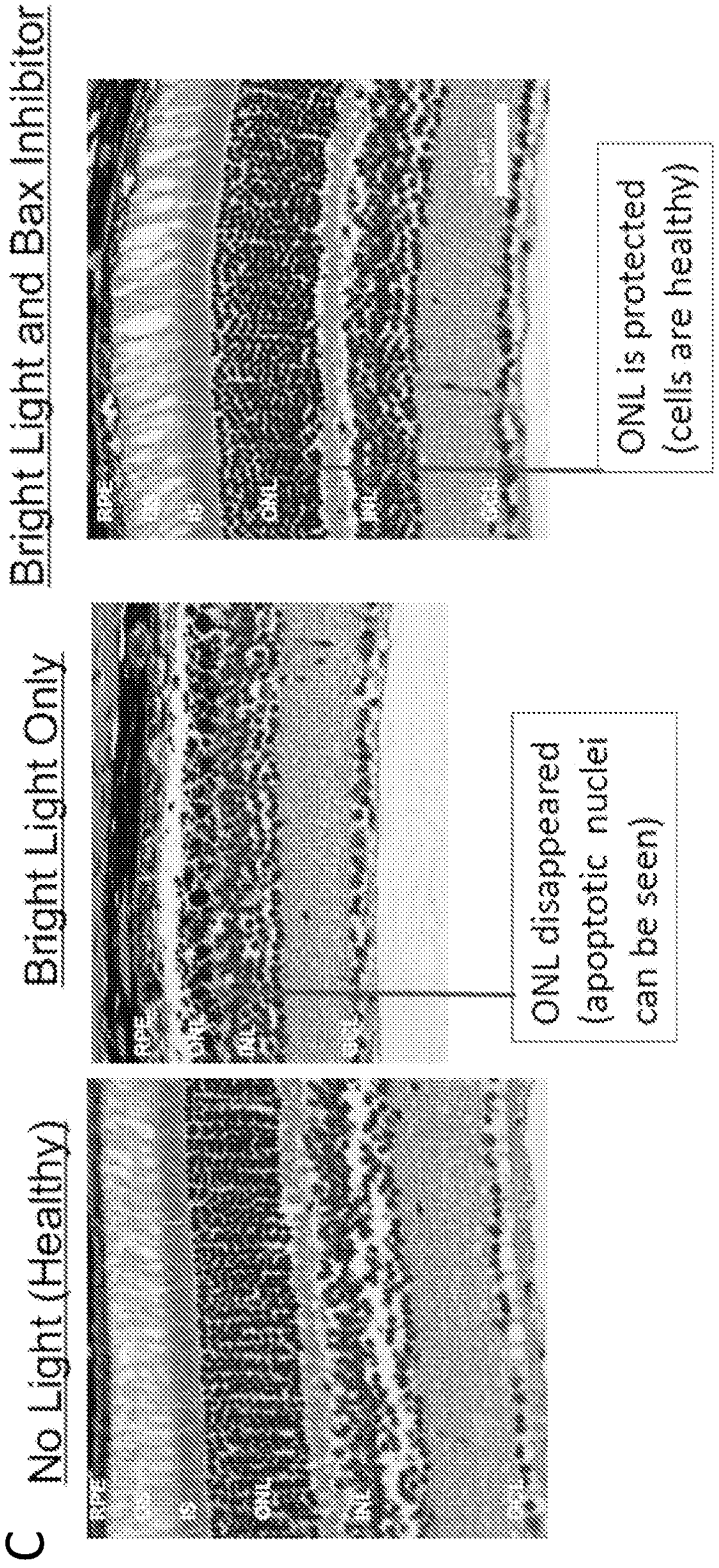

FIG. 4 illustrates the results showing Bax inhibiting compound described herein protected ARPE19 (Human Retinal cells) cells from atRAL induced cell death (FIG. 4A) and mouse retina from the bright light-induced cell death in vivo (Stargadrdt's disease mouse model) (FIG. 4B,C). FIG. 4A shows Bax inhibiting compound (41S) protected human retinal cells (ARPE19) from atRAL-induced cell death. FIG. 4B illustrates images bright light-induced retinal cell degeneration (the degeneration of Outer Nuclear Layer (ONL)) was protected by Bax Inhibiting Small Compound in Stargardt's disease mouse model (abca4$^{-/-}$ rdh8$^{-/-}$ mice). Bax inhibitor (109) treatment included 10 mg/kg/oral, 24 h and 1 h before the light exposure (10K lux 45 min)+24 H and 48 h after the light. ONL protection was confirmed in both eyes of all 3 mice tested. FIG. 4C shows Bax inhibiting Small Compound protected retinal cells from bright light induced apoptosis in Stargardt's disease model (abca4$^{-/-}$dh8$^{-/-}$): Outer Nuclear Layer (ONL) consisted from retinal cells protected by Bax Inhibitor.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A compound including the following formula (I):

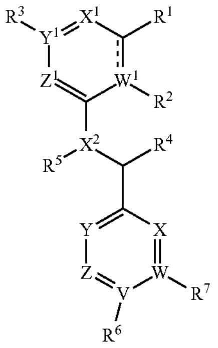

(I)

or a pharmaceutically acceptable salt, tautomer, or solvate thereof, wherein:

$R^1$ and $R^2$ are each independently —H, alkyl, —F, —CN, —O-alkyl, cycloalkyl, oxetanyl, or tetrahydrofuranyl, or $R^1$ together with $R^2$ forms a phenyl ring optionally substituted with one or two $R^8$ groups, or $R^1$ together with $R^2$ forms a five or six-membered heteroaromatic ring containing one or two heteroatoms chosen from N, O and S, optionally substituted with one or two $R^8$ groups;

$R^8$ is halo, alkyl, cycloalkyl, oxetanyl, tetrahydrofuranyl, —CN, —O-alkyl, —O-cycloalkyl, —$SO_2$-alkyl, or —$CH_2SO_2$-alkyl;

$R^3$ is absent, —H, —D, —F, —Cl, —$CF_3$, -alkyl, cyclopropyl-O-alkyl, or —CN;

$R^4$ is —H, alkyl, cyclopropyl, or —$CF_3$;

$R^5$ is absent, —H, or alkyl;

alternatively, $R^5$ and the nitrogen atom to which it is attached may be replaced by an oxygen atom;

V and W are each independently C or N;

X, Y and Z are each independently —CH, or N;

$X^1$ and $Z^1$ are each independently —CH or N;

$W^1$ and $Y^1$ are each independently C or N, and when $Y^1$ is N, $R^3$ is absent;

$X^2$ is O or N, when $X^2$ is O, $R^5$ is absent;

$\overline{\underline{---}}$ represents a single or double bond;

$R^6$ is selected from the group consisting of:

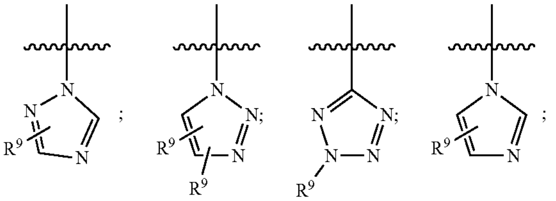

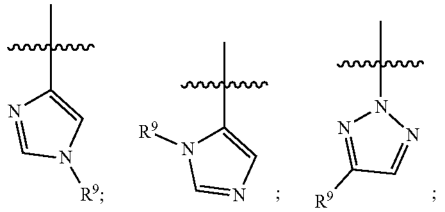

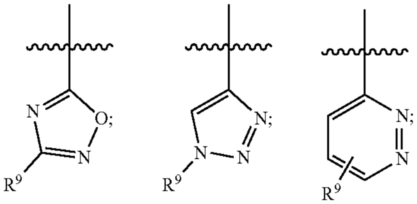

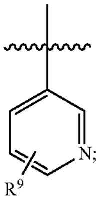 and 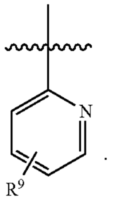 .

$R^7$ is —H, halo, alkyl, cycloalkyl, —CN, —O-alkyl, —O-cycloalkyl, —O-heterocyclyl, —$SO_2$-alkyl, —$CH_2SO_2$-alkyl, —$CONH_2$, —CONH-alkyl, or —CON(alkyl)$_2$;

alternatively, $R^7$ can be an aryl optionally substituted with one or two $R^9$ groups;

alternatively, $R^7$ can be a 4-6 membered ring heterocycle containing one or two heteroatoms chosen from the group consisting of N, O and S, and optionally substituted with one or two $R^9$ groups, excluding unstable heterocycles;

alternatively, $R^7$ can be a 5-6 membered ring heteroaryl group containing one to four heteroatoms chosen from the group consisting of N, O and S, and optionally substituted with one or two $R^9$ groups, excluding unstable heterocycles;

$R^9$ is H, halo, alkyl, cycloalkyl, alkyl-CO—, oxetanyl, 3-tetrahydrofuranyl, —CN, —O-alkyl, —O-cycloalkyl, —$CONH_2$, —CONH-alkyl, or —CON (alkyl)$_2$; or alternatively, $R^6$ together with $R^7$ and the phenyl ring or heteroaryl ring to which they are attached, may be benzotriazole ring, azaindole ring, or azaindazole, with N of the rings bearing an optional substituent $R^{10}$, and with Cs of the rings optionally substituted with $R^{11}$;

$R^{10}$ is —H, alkyl, or cycloalkyl; and $R^{11}$ is —H, alkyl, or cycloalkyl.

2. A compound including the following formula:

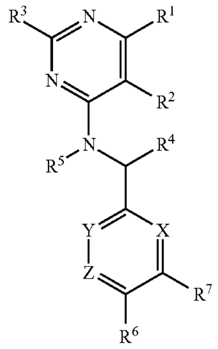

or a pharmaceutically acceptable salt, tautomer, or solvate thereof, wherein:

$R^1$ and $R^2$ are each independently —H, $C_1$-$C_6$-alkyl, —F, —CN, —O—$C_1$-$C_6$-alkyl, $C_3$-$C_7$-cycloalkyl, 3-oxetanyl, or 3-tetrahydrofuranyl, or $R^1$ together with $R^2$ forms a phenyl ring optionally substituted with one or two $R^8$ groups, or $R^1$ together with $R^2$ forms a five or six-membered heteroaromatic ring containing one or two heteroatoms chosen from N, O and S, optionally substituted with one or two $R^8$ groups;

$R^8$ is halo, $C_1$-$C_6$-alkyl, $C_3$-$C_7$-cycloalkyl, 3-oxetanyl, 3-tetrahydrofuranyl, —CN, —O—$C_1$-$C_6$-alkyl, —O—$C_3$-$C_7$-cycloalkyl, —$SO_2$—$C_1$-$C_6$-alkyl, or —$CH_2SO_2$—$C_1$-$C_6$-alkyl;

$R^3$ is —H, -D, —F, —Cl, —$CF_3$, —$C_1$-$C_6$-alkyl, cyclopropyl-O—$C_1$-$C_6$-alkyl, or —CN;

$R^4$ is —H, —$C_1$-$C_6$-alkyl,-cyclopropyl, or —$CF_3$;

$R^5$ is —H, or —$C_1$-$C_6$-alkyl;

alternatively, $R^5$ and the nitrogen atom to which it is attached may be replaced by an oxygen atom;

X, Y and Z are each independently-CH, or N;

$\overline{\overline{---}}$ represents a single or double bond;

$R^6$ is selected from the group consisting of:

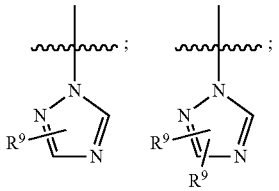

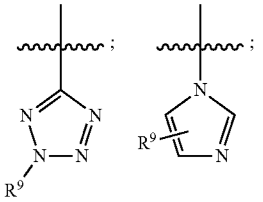

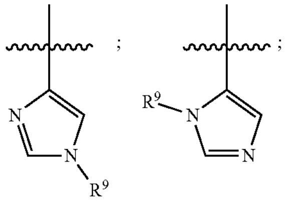

-continued

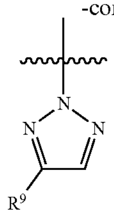 ; 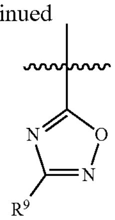 ;

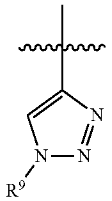 ; 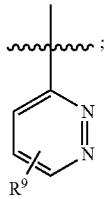 ;

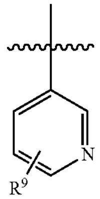 ; and 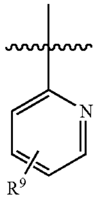 ;

$R^7$ is —H, halo, $C_1$-$C_6$-alkyl, $C_3$-$C_7$-cycloalkyl, —CN, —O—$C_1$-$C_6$-alkyl, —O—$C_3$-$C_7$-cycloalkyl, —O-heterocyclyl, —$SO_2$—$C_1$-$C^6$-alkyl, —$CH_2SO_2$—$C_1$-$C_6$-alkyl, —$CONH_2$, —CONH—$C_1$-$C_6$-alkyl, or —CON($C_1$-$C_6$-alkyl)$_2$;

alternatively, $R^7$ can be an aryl optionally substituted with one or two $R^9$ groups;

alternatively, $R^7$ can be a 4-6 membered ring heterocycle containing one or two heteroatoms chosen from the group consisting of N, O and S, and optionally substituted with one or two $R^9$ groups, excluding unstable heterocycles;

alternatively, $R^7$ can be a 5-6 membered ring heteroaryl group containing one to four heteroatoms chosen from the group consisting of N, O and S, and optionally substituted with one or two $R^9$ groups, excluding unstable heterocycles;

$R^9$ is halo, $C_1$-$C_6$-alkyl, $C_3$-$C_7$-cycloalkyl, $C_1$-$C_5$-alkyl-CO—, 3-oxetanyl, 3-tetrahydrofuranyl, —CN, —O—$C_1$-$C_6$-alkyl, —O—$C_3$-$C_7$-cycloalkyl, —$CONH_2$, —CONH-alkyl, or —CON(alkyl)$_2$; or alternatively, $R^6$ together with $R^7$ and the phenyl ring or heteroaryl ring to which they are attached, may be a benzotriazole ring, azaindole ring, or azaindazole, with N of the rings bearing an optional substituent $R^{10}$, and with Cs of the rings optionally substituted with $R^{11}$;

$R^{10}$ is —H, $C_1$-$C_6$-alkyl, or $C_3$-$C_7$-cycloalkyl; and $R^{11}$ is —H, $C_1$-$C_6$-alkyl, or $C_3$-$C_7$-cycloalkyl.

3. The compound of claim 1, wherein $R^1$ together with $R^2$ forms a phenyl ring optionally substituted with one or two $R^8$ groups, or $R^1$ together with $R^2$ forms a five or six-membered heteroaromatic ring containing one or two heteroatoms chosen from N, O and S, optionally substituted with one or two $R^8$ groups.

4. The compound of claim 1, wherein $R^4$ is —$C_1$-$C_6$-alkyl or —$CF_3$, and $R^5$ is —H.

5. The compound of claim 1, wherein X, Y, and Z are each independently CH.

6. The compound of claim 1, wherein $R^7$ is a 4-6 membered ring heterocycle containing one or two heteroatoms chosen from the group consisting of N, O and S, and optionally substituted with one or two $R^9$ groups, excluding unstable heterocycles or $R^7$ is a 5-6 membered ring heteroaryl group containing one to four heteroatoms chosen from the group consisting of N, O and S, and optionally substituted with one or two $R^9$ groups, excluding unstable heterocycles.

7. A compound selected from the group consisting of:

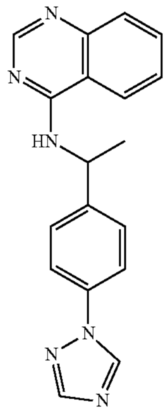 ; 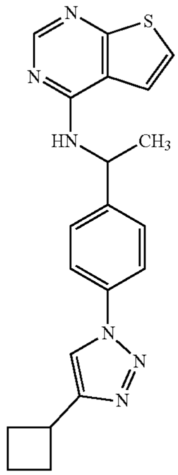 ;

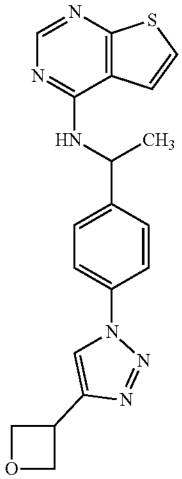 ; 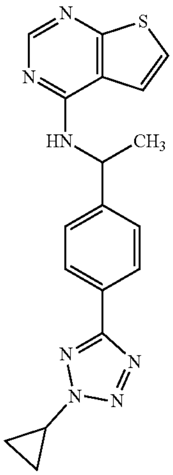 ;

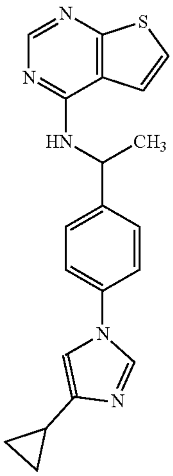 ; 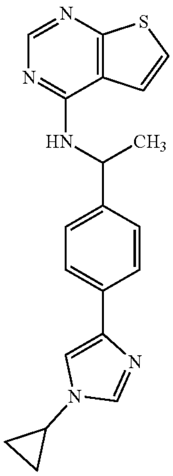 ;

-continued
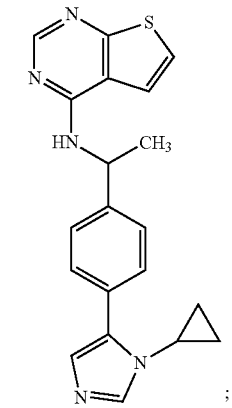
;
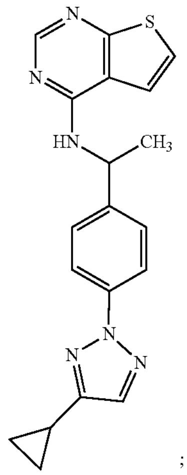
;
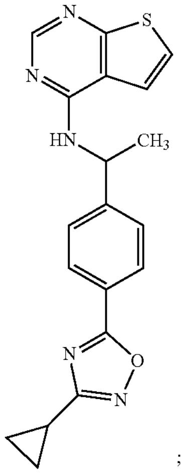
;
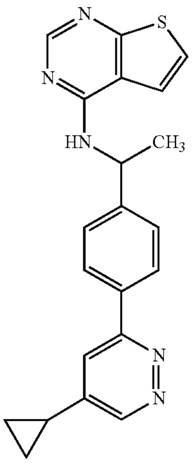
;
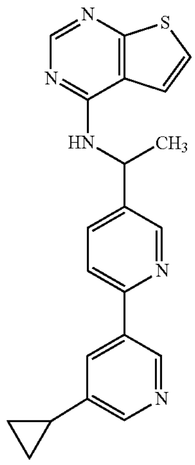
;
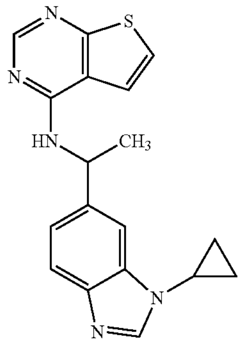
;
-continued
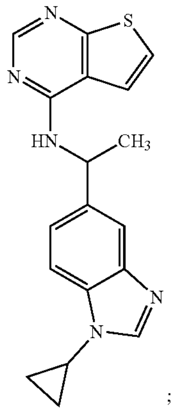
;
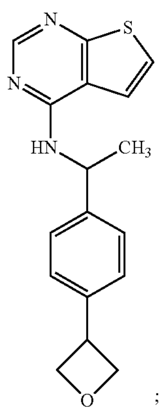
;
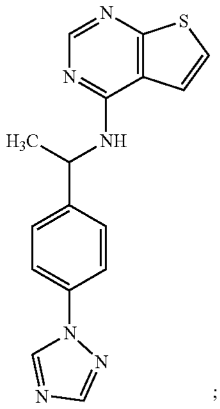
;
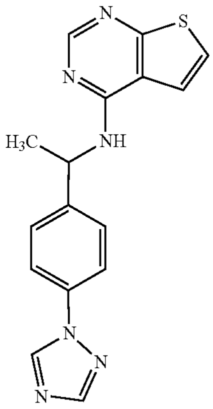
;
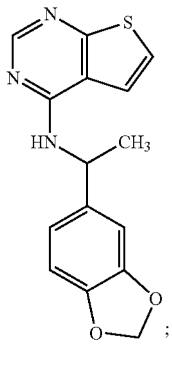
;
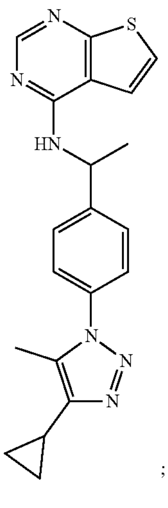
;

-continued
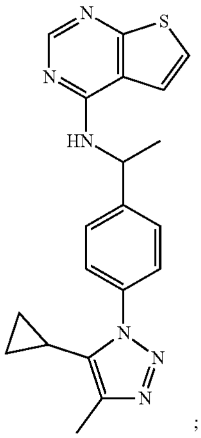
;
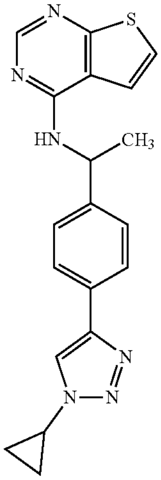
;
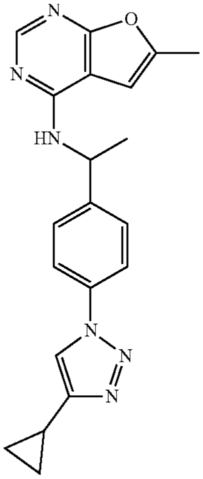
;
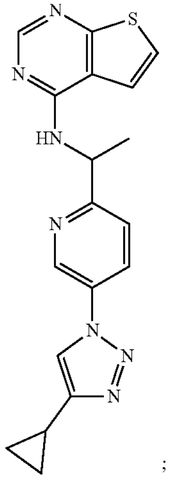
;
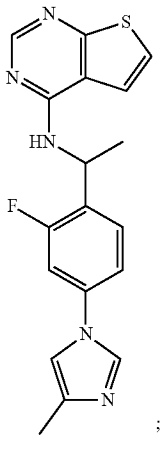
;
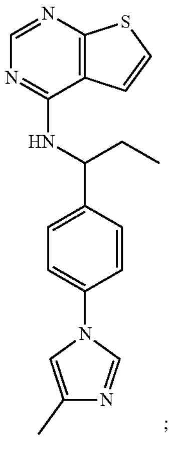
;
-continued
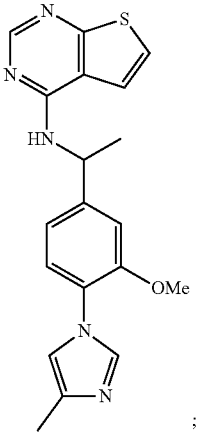
;
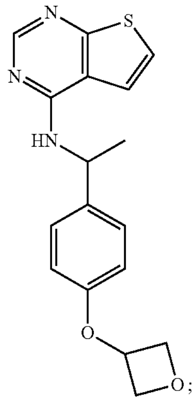
;
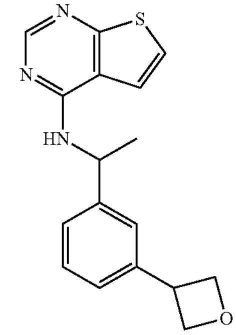
;
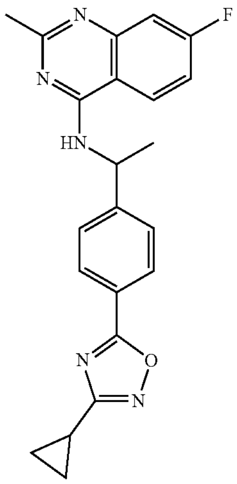
;
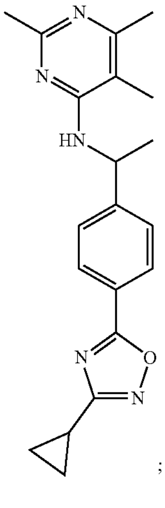
;
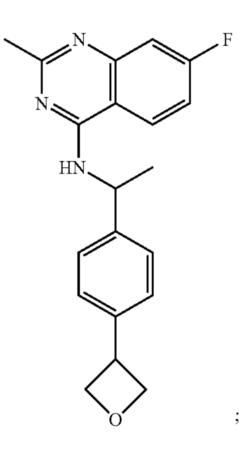
;

-continued
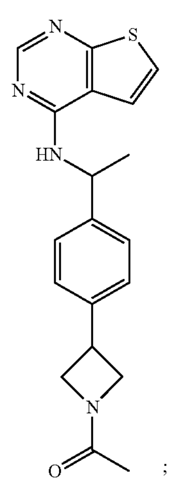
;
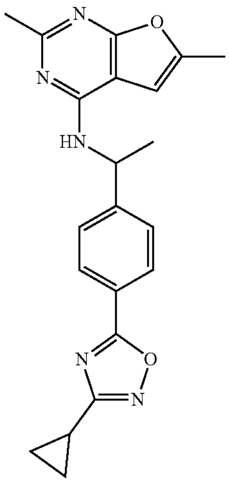
;
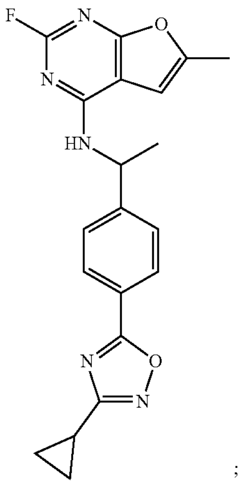
;
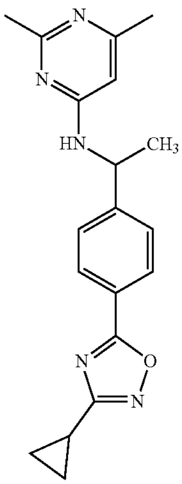
;
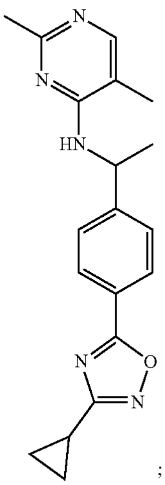
;
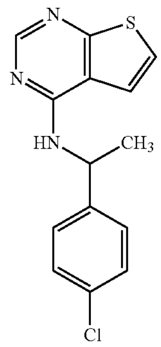
;
-continued
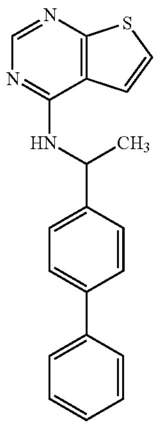
;
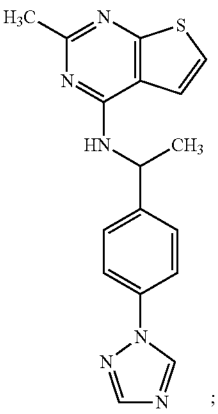
;
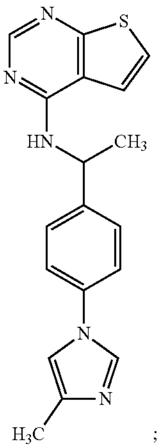
;
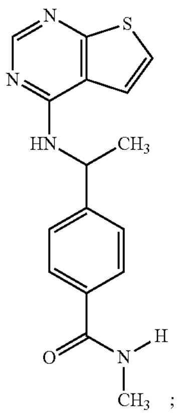
;
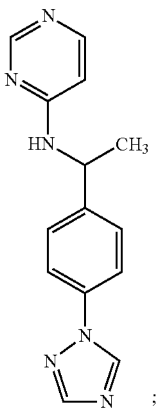
;
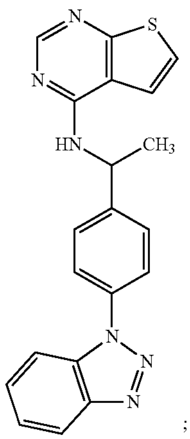
;

-continued
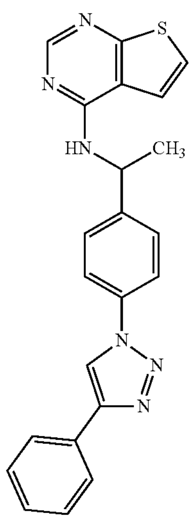
;
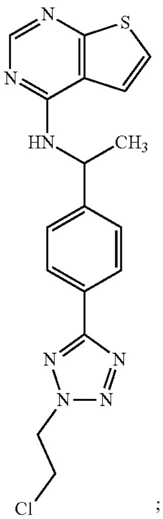
;
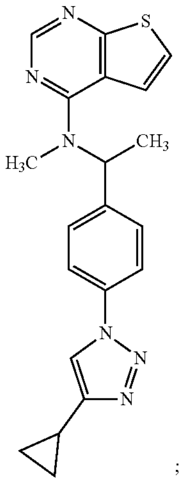
;
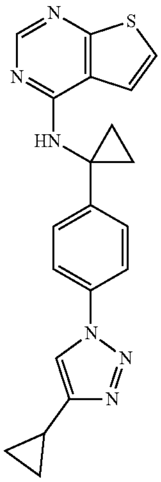
;
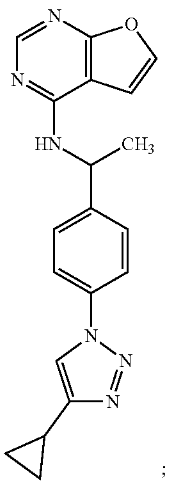
;
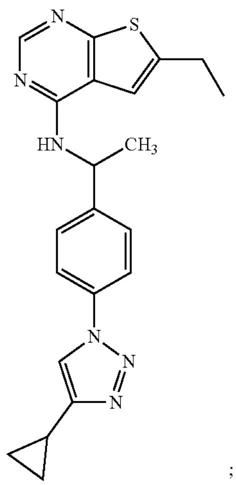
;
-continued
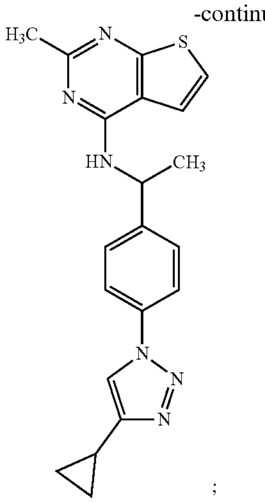
;
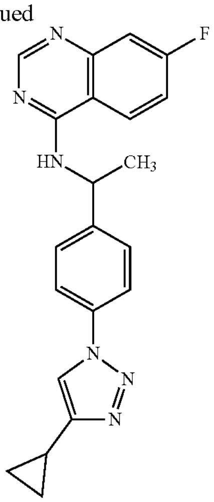
;
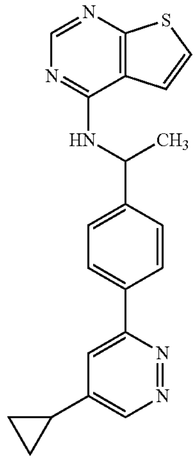
;
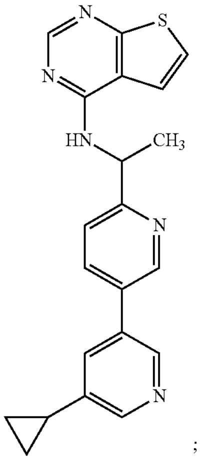
;
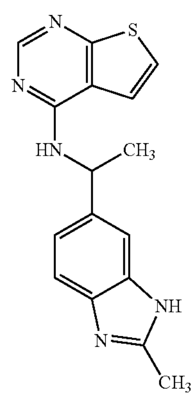
;
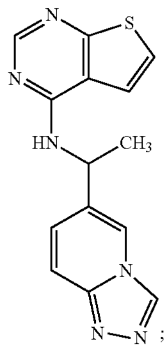
;

-continued
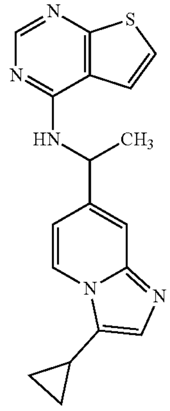
;
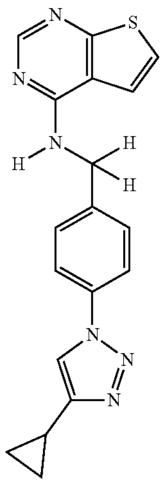
;
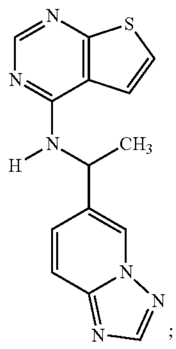
;
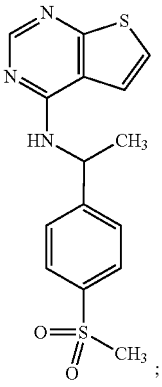
;
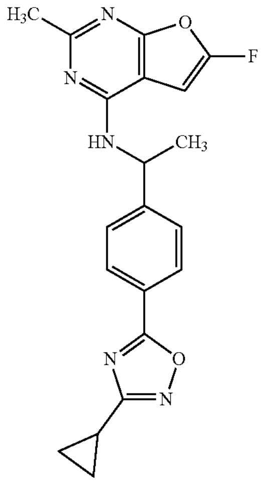
;
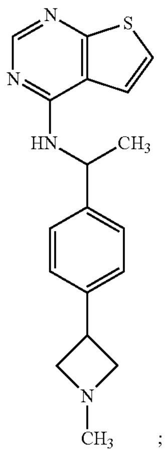
;
-continued
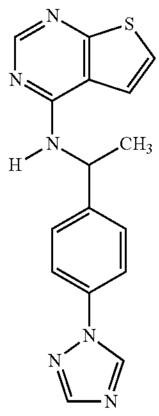
;
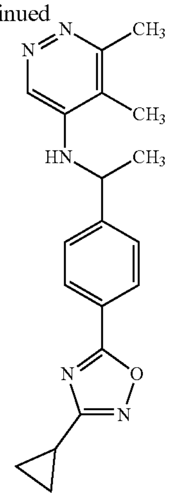
;
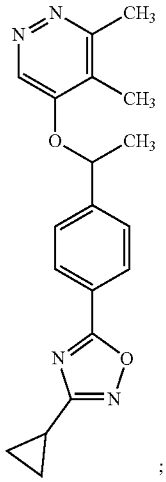
;
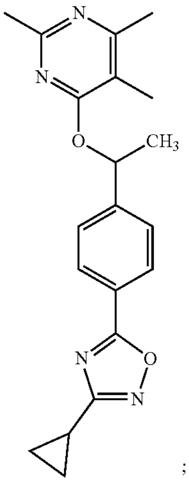
;
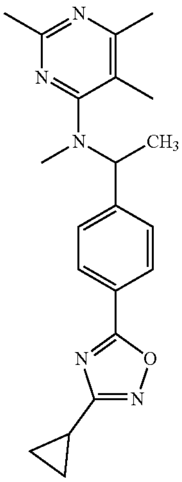
;
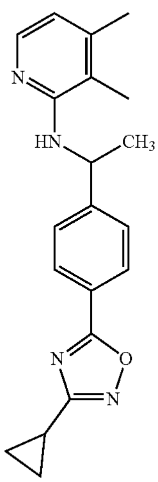
;

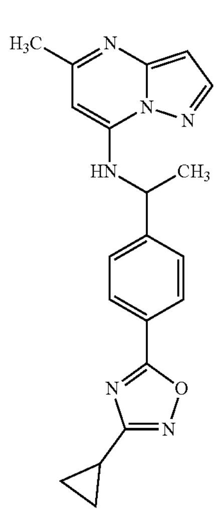
;
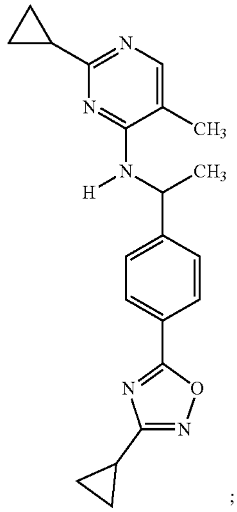
;
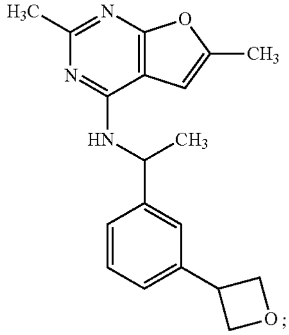
;
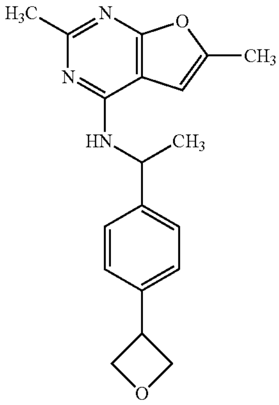
;
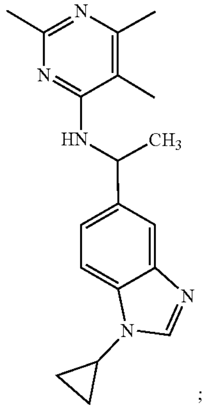
;
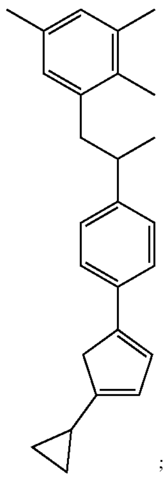
;
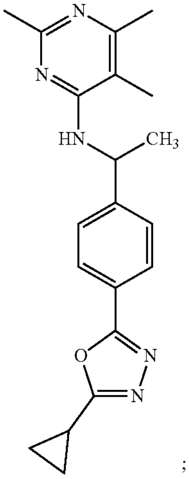
;
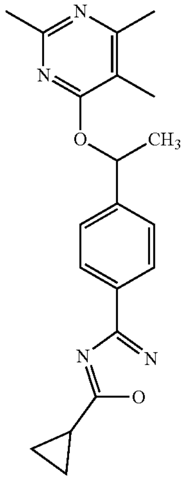
;
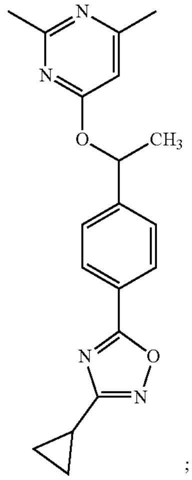
;
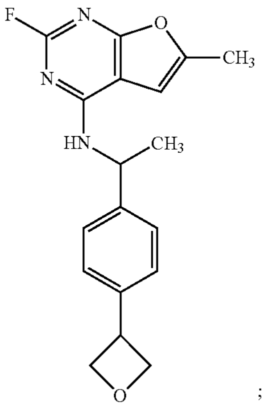
;
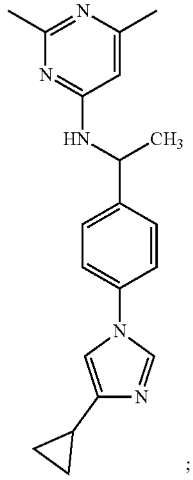
;
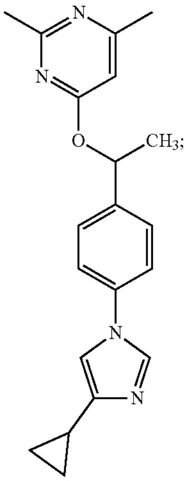
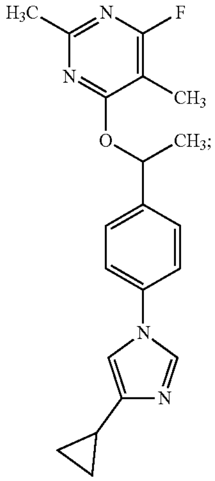

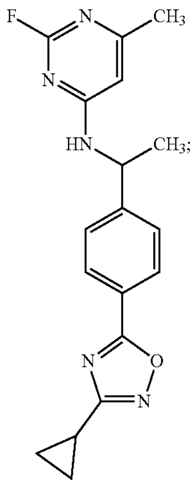
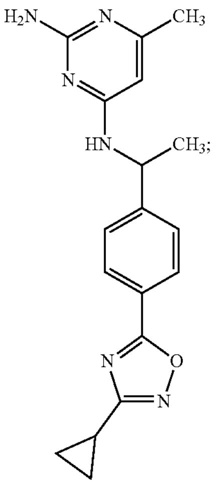
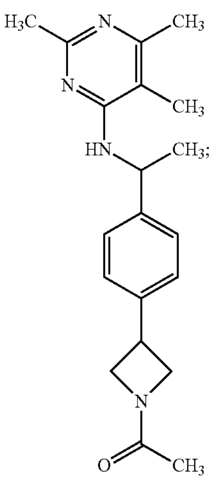
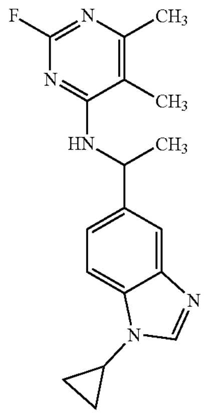
;
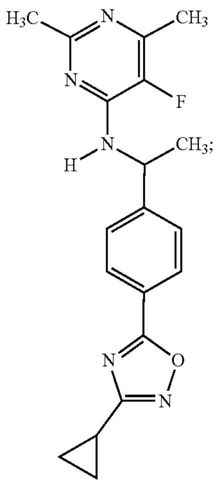
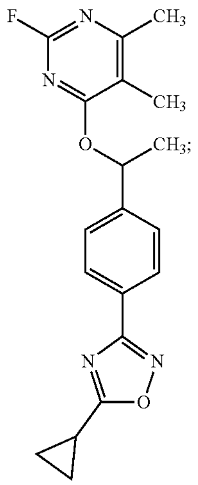
-continued
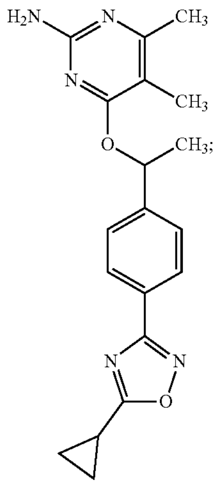
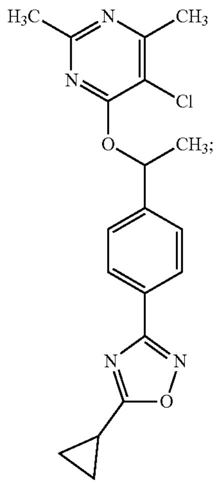
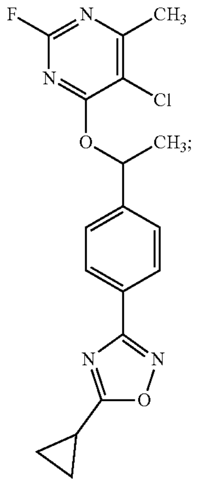
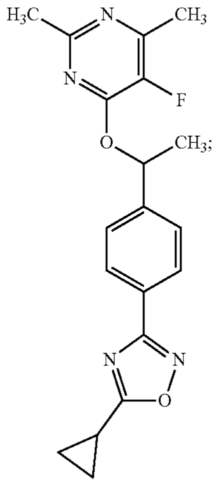
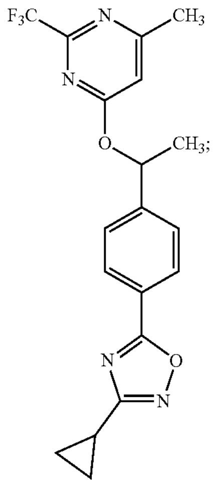
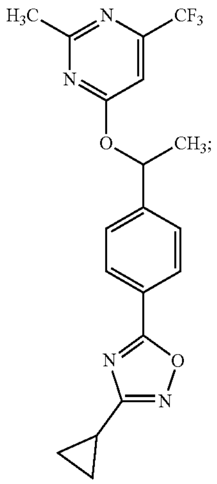

-continued
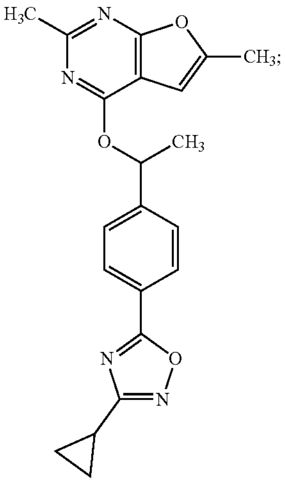
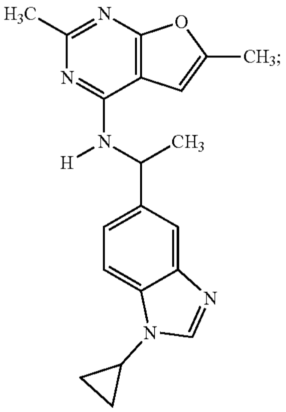
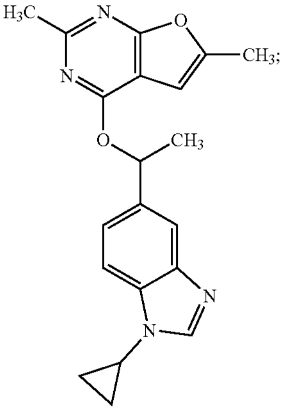
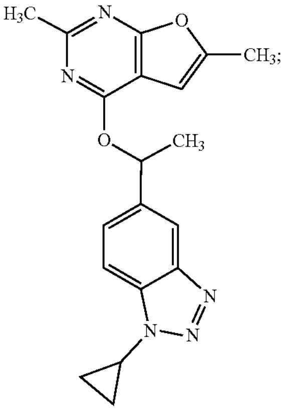
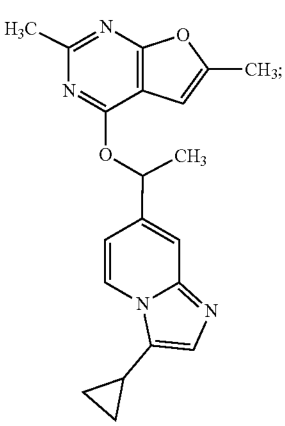
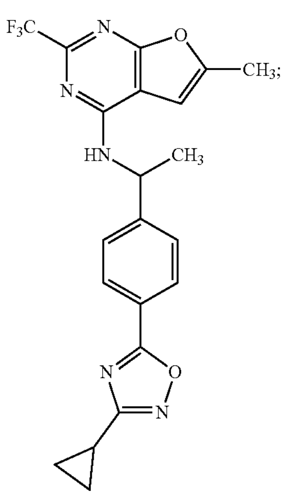
-continued
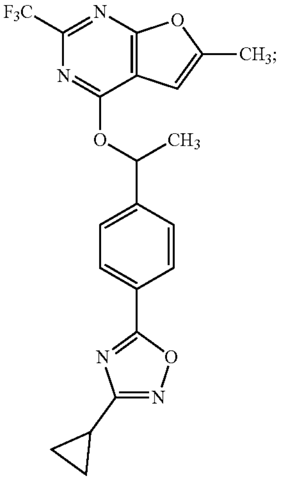
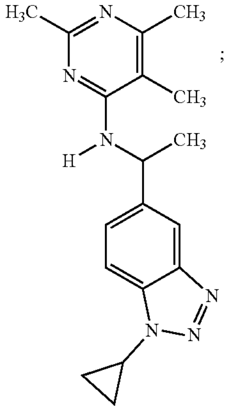
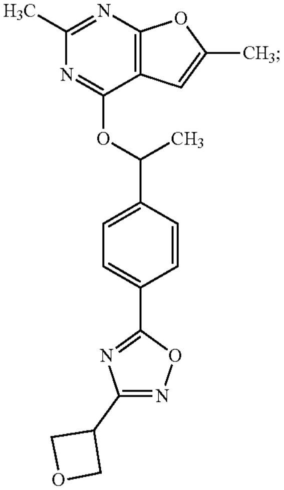
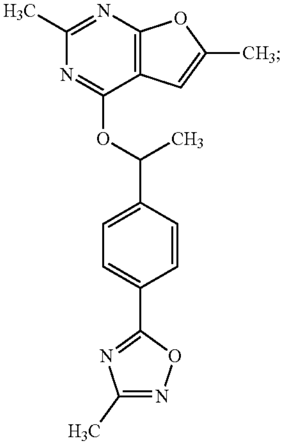
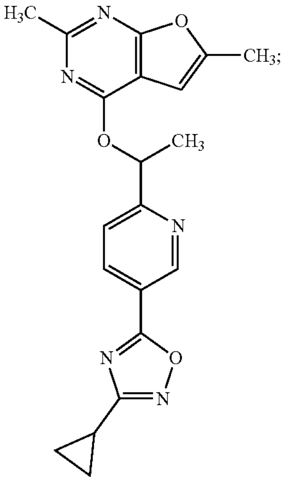
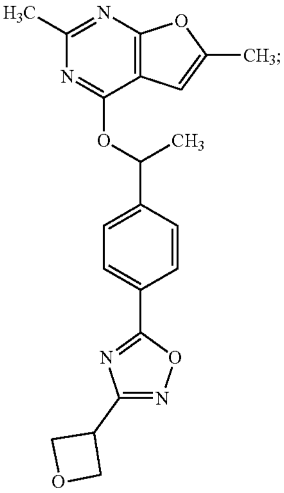

-continued
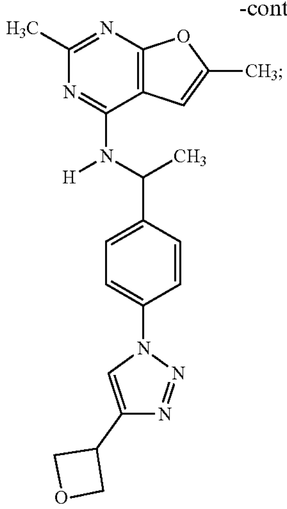
;
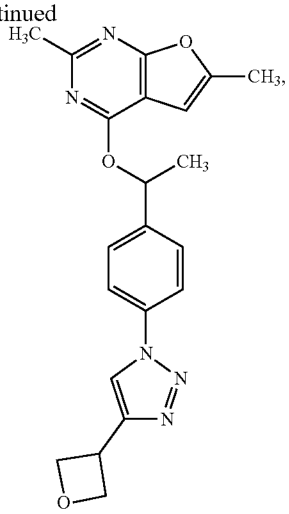
,
and pharmaceutically acceptable salts thereof.
8. A pharmaceutical composition comprising a compound of claim 1, and a pharmaceutically acceptable excipient or a carrier.
* * * * *